(12) United States Patent
Wang et al.

(10) Patent No.: US 9,321,756 B2
(45) Date of Patent: *Apr. 26, 2016

(54) AZOLE COMPOUNDS AS PIM INHIBITORS

(75) Inventors: Hui-Ling Wang, Thousand Oaks, CA (US); Victor J. Cee, Thousand Oaks, CA (US); Bradley J. Herberich, Newbury Park, CA (US); Claire L. M. Jackson, Thousand Oaks, CA (US); Brian Alan Lanman, Woodland Hills, CA (US); Thomas Nixey, Newbury Park, CA (US); Liping H. Pettus, Thousand Oaks, CA (US); Anthony B. Reed, Newbury Park, CA (US); Bin Wu, Thousand Oaks, CA (US); Ryan Wurz, Newbury Park, CA (US); Andrew Tasker, Simi Valley, CA (US)

(73) Assignee: AMGEN INC., Thousand Oaks, CA (US)

( * ) Notice: Subject to any disclaimer, the term of this patent is extended or adjusted under 35 U.S.C. 154(b) by 83 days.

This patent is subject to a terminal disclaimer.

(21) Appl. No.: 14/006,285

(22) PCT Filed: Mar. 21, 2012

(86) PCT No.: PCT/US2012/029997
§ 371 (c)(1),
(2), (4) Date: Feb. 12, 2014

(87) PCT Pub. No.: WO2012/129338
PCT Pub. Date: Sep. 27, 2012

(65) Prior Publication Data
US 2014/0187553 A1    Jul. 3, 2014

Related U.S. Application Data

(60) Provisional application No. 61/466,410, filed on Mar. 22, 2011.

(51) Int. Cl.
| | | |
|---|---|---|
| *C07D 413/14* | (2006.01) | |
| *C07D 487/04* | (2006.01) | |
| *C07D 417/04* | (2006.01) | |
| *C07D 471/04* | (2006.01) | |
| *C07D 417/14* | (2006.01) | |
| *A61P 35/00* | (2006.01) | |
| *A61P 35/02* | (2006.01) | |
| *A61P 35/04* | (2006.01) | |

(52) U.S. Cl.
CPC ............ *C07D 413/14* (2013.01); *C07D 417/04* (2013.01); *C07D 417/14* (2013.01); *C07D 471/04* (2013.01); *C07D 487/04* (2013.01)

(58) Field of Classification Search
CPC .. C07D 413/14; C07D 417/04; C07D 417/14; C07D 487/04; C07D 471/04
See application file for complete search history.

(56) References Cited

U.S. PATENT DOCUMENTS

| 5,744,488 A | 4/1998 | Cross et al. |
|---|---|---|
| 6,180,643 B1 | 1/2001 | Zablocki et al. |
| 6,184,238 B1 | 2/2001 | Takano et al. |
| 6,358,972 B1 | 3/2002 | Filla et al. |
| 6,998,399 B2 | 2/2006 | Galli et al. |
| 7,399,780 B2 | 7/2008 | Berg et al. |
| 2004/0127536 A1 | 7/2004 | Bhagwat et al. |
| 2004/0127538 A1 | 7/2004 | Oinuma et al. |
| 2005/0090529 A1 | 4/2005 | McAlpine et al. |
| 2005/0137201 A1 | 6/2005 | Aronov et al. |
| 2005/0153987 A1 | 7/2005 | Berg et al. |
| 2005/0282880 A1 | 12/2005 | Oinuma et al. |
| 2007/0043048 A1 | 2/2007 | Bollbuck et al. |
| 2007/0191604 A1 | 8/2007 | Cooper et al. |
| 2008/0039462 A1* | 2/2008 | Dunn et al. ................ 514/235.2 |
| 2008/0113988 A1 | 5/2008 | Andres-Gil et al. |
| 2008/0176833 A1 | 7/2008 | Adler et al. |
| 2009/0118284 A1 | 5/2009 | Cooper et al. |
| 2009/0203690 A1 | 8/2009 | Akritopoulou-Zanze et al. |
| 2009/0203691 A1 | 8/2009 | Oinuma et al. |
| 2009/0318446 A1 | 12/2009 | Fischer et al. |
| 2010/0160287 A1 | 6/2010 | Wannamaker et al. |
| 2010/0267707 A1 | 10/2010 | Kozina et al. |
| 2011/0033417 A1 | 2/2011 | Anilkumar et al. |
| 2011/0086834 A1 | 4/2011 | Chen et al. |
| 2011/0104110 A1 | 5/2011 | Anikumar et al. |
| 2011/0130384 A1 | 6/2011 | Setoh et al. |

(Continued)

FOREIGN PATENT DOCUMENTS

| WO | 00/00487 A1 | 1/2000 |
|---|---|---|
| WO | 00/43393 A1 | 7/2000 |

(Continued)

OTHER PUBLICATIONS

International Search Report for parent PCT Application No. PCT/US2012/02997, mailed on Aug. 2, 2012.
International Preliminary Report on Patentability for parent PCT Application No. PCT/US2012/02997, dated Sep. 24, 2013.
Tonsiengsom, F. et al., "Reduction of 2,5-Bis(3'-indolyl)pyrazines to 2,5-Bis(3'-indolyl)piperazines: Synthesis of Bisindolylpiperazine Marine Alkaloids Dragmacidin A, B, and C", Synthesis 2006, No. 01, pp. 49-54.
Pfoertner, K-H et al., "Herstellung der 1H-Indazole durch Photolyse von 2-Aminophenylketon-O-(äthoxycarbonyl)oximen und von 3,1,4-Benzoxadiazepin-2(1H)-onen" Helvetica Chimica Acta, vol. 65, No. 3, May 5, 1982 pp. 798-806.
Akue-Gedu, R. et al., "Synthesis and biological activities of aminopyrimidyl-indoles structurally related to meridianins" Bioorganic & Medicinal Chemistry, vol. 17, No. 13, Jul. 1, 2009, pp. 4420-4424.
Chemical Abstract No: 1176535-07-1, (copyright 2014).

(Continued)

Primary Examiner — Susanna Moore
(74) Attorney, Agent, or Firm — Bernard P. Friedrichsen

(57) ABSTRACT

The invention relates to bicyclic compounds of formulas I and Ia, and salts thereof. In some embodiments, the invention relates to inhibitors or modulators of Pim-1 and/or Pim-2, and/or Pim-3 protein kinase activity or enzyme function. In still further embodiments, the invention relates to pharmaceutical compositions comprising compounds disclosed herein, and their use in the prevention and treatment of Pim kinase related conditions and diseases, preferably cancer.

16 Claims, No Drawings

(56) References Cited

U.S. PATENT DOCUMENTS

| | | |
|---|---|---|
| 2011/0172221 A1 | 7/2011 | Michels et al. |
| 2014/0031360 A1 | 1/2014 | Wang et al. |

FOREIGN PATENT DOCUMENTS

| | | |
|---|---|---|
| WO | 01/53268 A2 | 7/2001 |
| WO | 02/10137 A2 | 2/2002 |
| WO | 03/044020 A1 | 5/2003 |
| WO | 2005/009997 A1 | 2/2005 |
| WO | 2007/098418 A1 | 8/2007 |
| WO | 2008/058096 A2 | 5/2008 |
| WO | 2009/011871 A2 | 1/2009 |
| WO | 2009/067579 A1 | 5/2009 |
| WO | 2009/071577 A1 | 6/2009 |
| WO | 2009/149836 A1 | 12/2009 |
| WO | 2009/150138 A1 | 12/2009 |
| WO | 2010/002933 A1 | 1/2010 |
| WO | 2010/094405 A1 | 8/2010 |
| WO | 2012/078777 A1 | 6/2012 |

OTHER PUBLICATIONS

Lamattina, J. L. et al., "Antiulcer Agents. 4-Substituted 2-Guanidinothiazoles: Reversible, Competitive, and Selective Inhibitors of Gastric H+, K+-ATPase", Journal of Medicinal Chemistry, vol. 33, No. 2, Feb. 1, 1990, pp. 543-552.

Matzen L et al., "5-HT Reuptake Inhibitors with 5-HT$_{1B/1D}$ Antagonistic Activity: A New Approach toward Efficient Antidepressants", Journal of Medicinal Chemistry, American Chemical Society, US, vol. 43, Jan. 1, 2000, pp. 1149-1157.

Gamo, F-J et al., "Thousands of chemical starting points for antimalarial lead identification", Nature, Nature Publishing Group, United Kingdom, vol. 465, No. 7296 May 20, 2010, pp. 305-310.

Nishiguchi, G.A. et al., "Discovery of Novel 3,5-Disubstituted Indole Derivatives as Potent Inhibitors of Pim-1, Pim-2, and Pim-3 Protein Kinases," Bioorganic & Medicinal Chemistry Letters, vol. 21 (2011), pp. 6366-6369.

Vachhani, D. D. et al., "Pd/Cu-Catalyzed C—H Arylation of 1,3,4-Thiadiazoles with (Hetero)aryl Iodides, Bromides, and Triflates," Journal of Organic Chemistry, vol. 77 (2012), pp. 8768-8774.

* cited by examiner

AZOLE COMPOUNDS AS PIM INHIBITORS

FIELD OF THE INVENTION

The present invention relates to certain azole and diazole compounds that are Pim inhibitors, pharmaceutical compositions containing such compounds, and processes for preparing such compounds. Provided herein also are methods of treating disorders or diseases treatable by inhibition of Pims, such as cancer, and the like.

BACKGROUND

The role of Pim serine/threonine kinases in the pathogenesis and therapy of hematological malignancies and solid cancers is of interest to the medical community. Pim proteins are constitutively active and are over-expressed in a subset of human cancers, many of hematological origin. Pim kinases also regulate aspects of transformation and drug resistance in hematological malignancies such as DLBCL, MM, and AML where they are overexpressed or mutated. Aberrant expression of Pim-1 or Pim-2 promotes tumor development in mouse models of lymphoma and prostate cancer. Elevated Pim-1 levels correlate with poor prognosis in DLBCL and mantle cell lymphoma. Pims play a role in some solid tumors (prostate cancer, and head and neck cancer). Whereas elevated levels of Pim-1 and Pim-2 were mostly found in hematological malignancies and prostate cancer, increased Pim-3 expression was observed in different solid tumors. Pim kinases are constitutively active and their activity supports in vitro and in vivo tumour cell growth and survival through modification of an increasing number of common as well as isoform-specific substrates including several cell cycle regulators and apoptosis mediators. Pim-1 but not Pim-2 mediates homing and migration of normal and malignant hematopoietic cells by regulating chemokine receptor surface expression. Knockdown experiments by RNA interference or dominant-negative acting mutants suggested that Pim kinases are important for maintenance of a transformed phenotype and therefore potential therapeutic targets.

There exists a need for compounds that inhibit the growth of tumors, treat cancer, modulate cell cycle arrest, and/or inhibit molecules such as Pim-1, Pim-2, or Pim-3 and pharmaceutical formulations and medicaments that contain such compounds.

SUMMARY OF THE INVENTION

The present invention comprises a new class of azole and diazole compounds useful in the treatment of diseases, such as Pim-mediated diseases, for example cancer. Accordingly, the invention also comprises pharmaceutical compositions comprising the compounds, methods for the treatment of Pim-mediated diseases and other maladies, such as treatment of hematological malignancies and of solid tumors, for example prostate cancer, and head and neck cancer, using the compounds and compositions of the invention, and intermediates and processes useful for the preparation of the compounds of the invention.

The compounds of the invention are represented by the following general structure:

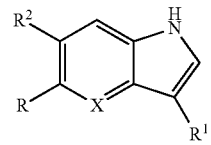

and a pharmaceutically acceptable salt thereof; wherein X; R; and $R^1$ are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION OF THE INVENTION

One aspect of the current invention relates to compounds having the general structure of formula (I):

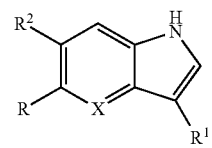

wherein X is CH or N;
wherein R is optionally substituted oxazolyl, optionally substituted thiazolyl, optionally substituted thiadiazolyl or optionally substituted oxadiazolyl;
wherein $R^1$ is optionally substituted phenyl, optionally substituted 5-membered heterocyclyl, optionally substituted 6-membered heterocyclyl, optionally substituted 9 membered heterocyclyl or optionally substituted 10 membered heterocyclyl;
wherein $R^2$ is H or halo;
and a pharmaceutically acceptable salt thereof.

In another embodiment, X is CH; and a pharmaceutically acceptable salt thereof.

In another embodiment, X is N; and a pharmaceutically acceptable salt thereof.

In another embodiment, R is oxadiazolyl optionally substituted with amino, $C_{1-6}$ alkylamino, $C_{1-6}$ haloalkylamino, cyano-$C_{1-6}$ alkylamino, amino-$C_{1-6}$ alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$alkylamino, optionally substituted 9-10-membered nitrogen containing heterocyclyl substituted amino, optionally substituted 9-10-membered nitrogen containing heterocyclyl-$C_{1-4}$alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

In another embodiment, R is thiadiazolyl optionally substituted with amino, $C_{1-6}$ alkylamino, $C_{1-6}$ haloalkylamino, cyano-$C_{1-6}$ alkylamino, amino-$C_{1-6}$ alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$alkylamino, optionally substituted 9-10-membered nitrogen containing heterocyclyl substituted amino, optionally substituted 9-10-membered nitrogen containing heterocyclyl-$C_{1-4}$alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

In another embodiment, R is thiazolyl optionally substituted with amino, $C_{1-6}$ alkylamino, $C_{1-6}$ haloalkylamino, cyano-$C_{1-6}$ alkylamino, amino-$C_{1-6}$-alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$ alkylamino, optionally substituted 9-10-membered nitrogen containing heterocyclyl substituted amino, optionally substituted 9-10-membered nitrogen containing heterocyclyl-$C_{1-4}$ alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

In another embodiment, R is oxazolyl optionally substituted with amino, $C_{1-6}$ alkylamino, $C_{1-6}$ haloalkylamino, cyano-$C_{1-6}$ alkylamino, amino-$C_{1-6}$-alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$ alkylamino, optionally substituted 9-10-membered nitrogen containing heterocyclyl substituted amino, optionally substituted 9-10-membered nitrogen containing heterocyclyl-$C_{1-4}$ alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

In another embodiment, R is substituted with H, amino, methylamino, propylamino, isopropylamino, tert-butylamino, cyanomethylamino, aminopropylamino, 1,1,1-trifluoroethylamino, methylcarbonylamino, hydroxy, methoxy, ethoxy, propoxy, isopropoxy, butoxy, isobutoxy, tert-butoxy, hexyloxy, methylthio, bromo, methyl, ethyl, n-propyl, isopropyl, n-butyl, isobutyl, sec-butyl, tert-butyl, pentyl, isoamyl, hexyl, cyclopropyl, cyclobutyl, cyclopentyl, cyclohexyl, aminocarbonyl, cyclopropylamino, piperidylamino, piperidylmethylamino, piperidylethylamino, indolylmethylamino, 2,3-dimethylaminoindolymethylamino, phenylamino, 3-fluorophenylamino, benzylamino, 3-(methylcarbonylamino)benzylamino, 3-(methylamino)benzylamino, 3-(methoxymethylcarbonylamino)benzylamino, 4-(methylcarbonylamino)benzylamino, 2-methyl-2-phenylethylamino, phenyl, pyrrolidinyl, 3-amino-1-pyrrolidinyl, piperidyl, 4-amino-1-piperidyl, pyrazolyl, morpholinyl, 2-methylmorpholinyl, 3-methylmorpholinyl, 3,3-dimethylmorpholinyl, 3-ethylmorpholinyl, piperazinyl, oxetanyl, or azetidinyl; and a pharmaceutically acceptable salt thereof.

In another embodiment, $R^1$ is unsubstituted or substituted phenyl or unsubstituted or substituted biphenyl; and a pharmaceutically acceptable salt thereof.

In another embodiment, $R^1$ is unsubstituted or substituted pyrazinyl, unsubstituted or substituted pyridyl, unsubstituted or substituted pyrimidinyl or unsubstituted or substituted pyridazinyl; and a pharmaceutically acceptable salt thereof.

In another embodiment, $R^1$ is unsubstituted or substituted quinolyl, unsubstituted or substituted dihydrobenzofuryl, unsubstituted or substituted quinoxalinyl, unsubstituted or substituted indazolyl, or unsubstituted or substituted 6,7-dihydro-5H-pyrrolo[2,3-b]pyrazinyl; and a pharmaceutically acceptable salt thereof.

In another embodiment, $R^1$ is unsubstituted or substituted triazolyl, unsubstituted or substituted dihydro-2H-pyranyl, unsubstituted or substituted thiazolyl, unsubstituted or substituted pyrazolyl, or unsubstituted or substituted thienyl; and a pharmaceutically acceptable salt thereof.

In another embodiment, $R^1$ is unsubstituted or substituted with one or more amino, halo, cyano, hydroxy, $C_{1-6}$ alkyl, $C_{1-3}$ haloalkyl, $C_{1-6}$ alkylamino, (optionally substituted 5-6-membered nitrogen containing heterocyclyl)amino, phenylamino, $C_{3-6}$ cycloalkyl-$C_{1-3}$-alkylamino, $C_{3-6}$ cycloalkylamino, carboxy, aminocarbonyl, phenylaminocarbonyl, optionally substituted 5-6-membered nitrogen containing heterocyclyl)carbonyl, $C_{1-6}$ alkoxy, $C_{1-6}$ haloalkoxy, $C_{3-6}$ cycloalkoxy, optionally substituted phenyloxy, (optionally substituted 5-6-membered nitrogen containing heterocyclyl)oxy, optionally substituted phenyl, optionally substituted 6-membered nitrogen containing heterocyclyl, optionally substituted 5-membered nitrogen containing heterocyclyl, optionally substituted 9-10-membered nitrogen containing heterocyclyl, or $C_{3-6}$ cycloalkyl; and a pharmaceutically acceptable salt thereof.

In another embodiment, $R^2$ is H or fluoro; and a pharmaceutically acceptable salt thereof.

Another aspect of the current invention relates to compounds having the general structure of formula II:

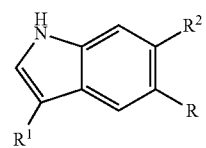

II wherein R is optionally substituted thiadiazolyl or optionally substituted oxadiazolyl;

wherein $R^1$ is optionally substituted phenyl or optionally substituted 5-membered heterocyclyl, optionally substituted 6-membered heterocyclyl, optionally substituted 9 membered heterocyclyl or optionally substituted 10 membered heterocyclyl; and wherein $R^2$ is H or halo;

and a pharmaceutically acceptable salt thereof.

In another embodiment, $R^1$ is unsubstituted or substituted phenyl, unsubstituted or substituted biphenyl, unsubstituted or substituted pyrazinyl, unsubstituted or substituted pyridyl, unsubstituted or substituted pyrimidinyl, unsubstituted or substituted pyridazinyl, unsubstituted or substituted quinolyl, unsubstituted or substituted dihydrobenzofuryl, unsubstituted or substituted quinoxalinyl, unsubstituted or substituted indazolyl, unsubstituted or substituted 6,7-dihydro-5H-pyrrolo[2,3-b]pyrazinyl, unsubstituted or substituted triazolyl, unsubstituted or substituted dihydro-2H-pyranyl, unsubstituted or substituted thiazolyl, unsubstituted or substituted pyrazolyl, or unsubstituted or substituted thienyl; and a pharmaceutically acceptable salt thereof.

In another embodiment, R is oxadiazolyl optionally substituted with amino, $C_{1-6}$ alkylamino, $C_{1-6}$ haloalkylamino, cyano-$C_{1-6}$ alkylamino, amino-$C_{1-6}$-alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$ alkylamino, optionally substituted 9-10-membered nitrogen containing heterocyclyl substituted amino, optionally substituted 9-10-membered nitrogen containing heterocyclyl-$C_{1-4}$ alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

In another embodiment, R is thiadiazolyl optionally substituted with amino, $C_{1-6}$ alkylamino, $C_{1-6}$ haloalkylamino, cyano-$C_{1-6}$ alkylamino, amino-$C_{1-6}$-alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$ alkylamino, optionally substituted 9-10-membered nitrogen containing heterocyclyl substituted amino, optionally substituted 9-10-membered nitrogen containing heterocyclyl-$C_{1-4}$ alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

In another embodiment, wherein R is

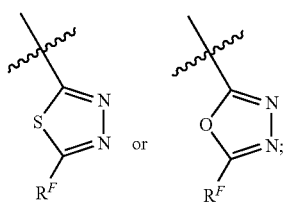

wherein $R^F$ is H, amino, methylamino, propylamino, isopropylamino, tert-butylamino, cyanomethylamino, aminopropylamino, 1,1,1-trifluoroethylamino, methylcarbonylamino, hydroxy, methoxy, ethoxy, propoxy, isopropoxy, butoxy, isobutoxy, tert-butoxy, hexyloxy, methylthio, bromo, methyl, ethyl, n-propyl, isopropyl, n-butyl, isobutyl, sec-butyl, tert-butyl, pentyl, isoamyl, hexyl, cyclopropyl, cyclobutyl, cyclopentyl, cyclohexyl, aminocarbonyl, cyclopropylamino, piperidylamino, piperidylmethylamino, piperidylethylamino, indolylmethylamino, 2,3-dimethylaminoindolymethylamino, phenylamino, 3-fluorophenylamino, benzylamino, 3-(methylcarbonylamino)benzylamino, 3-(methylamino)benzylamino, 3-(methoxymethylcarbonylamino)benzylamino, 4-(methylcarbonylamino)benzylamino, 2-methyl-2-phenylethylamino, phenyl, pyrrolidinyl, 3-amino-1-pyrrolidinyl, piperidyl, 4-amino-1-piperidyl, pyrazolyl, morpholinyl, 2-methylmorpholinyl, 3-methylmorpholinyl, 3,3-dimethylmorpholinyl, 3-ethylmorpholinyl, piperazinyl, oxetanyl, or azetidinyl; and a pharmaceutically acceptable salt thereof.

In another embodiment, $R^1$ is unsubstituted or substituted phenyl or unsubstituted or substituted biphenyl; and a pharmaceutically acceptable salt thereof.

In another embodiment, $R^1$ is unsubstituted or substituted pyrazinyl, unsubstituted or substituted pyridyl, unsubstituted or substituted pyrimidinyl or unsubstituted or substituted pyridazinyl; and a pharmaceutically acceptable salt thereof.

In another embodiment, $R^1$ is unsubstituted or substituted quinolyl, unsubstituted or substituted dihydrobenzofuryl, unsubstituted or substituted quinoxalinyl, unsubstituted or substituted indazolyl, or unsubstituted or substituted 6,7-dihydro-5H-pyrrolo[2,3-b]pyrazinyl; and a pharmaceutically acceptable salt thereof.

In another embodiment, $R^1$ is unsubstituted or substituted triazolyl, unsubstituted or substituted dihydro-2H-pyranyl, unsubstituted or substituted thiazolyl, unsubstituted or substituted pyrazolyl, or unsubstituted or substituted thienyl; and a pharmaceutically acceptable salt thereof.

In another embodiment, $R^1$ is pyrimidinyl unsubstituted or substituted with one or more amino, halo, cyano, hydroxy, $C_{1-6}$ alkyl, $C_{1-3}$ haloalkyl, $C_{1-6}$ alkylamino, (optionally substituted 5-6-membered nitrogen containing heterocyclyl)amino, phenylamino, $C_{3-6}$ cycloalkyl-$C_{1-3}$-alkylamino, $C_{3-6}$ cycloalkylamino, carboxy, aminocarbonyl, phenylaminocarbonyl, optionally substituted 5-6-membered nitrogen containing heterocyclyl)carbonyl, $C_{1-6}$ alkoxy, $C_{1-6}$ haloalkoxy, $C_{3-6}$ cycloalkoxy, optionally substituted phenyloxy, (optionally substituted 5-6-membered nitrogen containing heterocyclyl)oxy, optionally substituted phenyl, optionally substituted 6-membered nitrogen containing heterocyclyl, optionally substituted 5-membered nitrogen containing heterocyclyl, optionally substituted 9-10-membered nitrogen containing heterocyclyl, or $C_{3-6}$ cycloalkyl, pyrazinyl unsubstituted or substituted with one or more amino, halo, cyano, hydroxy, $C_{1-6}$ alkyl, $C_{1-3}$ haloalkyl, $C_{1-6}$ alkylamino, (optionally substituted 5-6-membered nitrogen containing heterocyclyl)amino, phenylamino, $C_{3-6}$ cycloalkyl-$C_{1-3}$-alkylamino, $C_{3-6}$ cycloalkylamino, carboxy, aminocarbonyl, phenylaminocarbonyl, optionally substituted 5-6-membered nitrogen containing heterocyclyl)carbonyl, $C_{1-6}$ alkoxy, $C_{1-6}$ haloalkoxy, $C_{3-6}$ cycloalkoxy, optionally substituted phenyloxy, (optionally substituted 5-6-membered nitrogen containing heterocyclyl)oxy, optionally substituted phenyl, optionally substituted 6-membered nitrogen containing heterocyclyl, optionally substituted 5-membered nitrogen containing heterocyclyl, optionally substituted 9-10-membered nitrogen containing heterocyclyl, or $C_{3-6}$ cycloalkyl, pyridinyl unsubstituted or substituted with one or more amino, halo, cyano, hydroxy, $C_{1-6}$ alkyl, $C_{1-3}$ haloalkyl, $C_{1-6}$ alkylamino, (optionally substituted 5-6-membered nitrogen containing heterocyclyl)amino, phenylamino, $C_{3-6}$ cycloalkyl-$C_{1-3}$-alkylamino, $C_{3-6}$ cycloalkylamino, carboxy, aminocarbonyl, phenylaminocarbonyl, optionally substituted 5-6-membered nitrogen containing heterocyclyl)carbonyl, $C_{1-6}$ alkoxy, $C_{1-6}$ haloalkoxy, $C_{3-6}$ cycloalkoxy, optionally substituted phenyloxy, (optionally substituted 5-6-membered nitrogen containing heterocyclyl)oxy, optionally substituted phenyl, optionally substituted 6-membered nitrogen containing heterocyclyl, optionally substituted 5-membered nitrogen containing heterocyclyl, optionally substituted 9-10-membered nitrogen containing heterocyclyl, or $C_{3-6}$ cycloalkyl, phenyl unsubstituted or substituted with one or more amino, halo, cyano, hydroxy, $C_{1-6}$ alkyl, $C_{1-3}$ haloalkyl, $C_{1-6}$ alkylamino, (optionally substituted 5-6-membered nitrogen containing heterocyclyl)amino, phenylamino, $C_{3-6}$ cycloalkyl-$C_{1-3}$-alkylamino, $C_{3-6}$ cycloalkylamino, carboxy, aminocarbonyl, phenylaminocarbonyl, optionally substituted 5-6-membered nitrogen containing heterocyclyl)carbonyl, $C_{1-6}$ alkoxy, $C_{1-6}$ haloalkoxy, $C_{3-6}$ cycloalkoxy, optionally substituted phenyloxy, (optionally substituted 5-6-membered nitrogen containing heterocyclyl)oxy, optionally substituted phenyl, optionally substituted 6-membered nitrogen containing heterocyclyl, optionally substituted 5-membered nitrogen containing heterocyclyl, optionally substituted 9-10-membered nitrogen containing heterocyclyl, or $C_{3-6}$ cycloalkyl, 3-quinolinyl, 1H-indazolyl, 2,2-dimethyl-2,3-dihydro-1-benzofuranyl, 6-quinoxalinyl, 7,7-dimethyl-6,7-dihydro-5H-pyrrolo[2,3-b]pyrazinyl, thiazolyl unsubstituted or substituted with optionally substituted 5-6-membered nitrogen containing heterocyclyl, triazolyl unsubstituted or substituted with $C_{3-6}$ cycloalkyl, dihydro-2H-pyranyl, pyrazolyl unsubstituted or substituted with $C_{1-6}$ alkyl or optionally substituted 5-6-membered nitrogen containing heterocyclyl, or thiophenyl unsubstituted or substituted with optionally substituted 5-6-membered nitrogen containing heterocyclyl, and a pharmaceutically acceptable salt thereof.

In another embodiment, $R^1$ is 2-pyrimidinyl, 4-methyl-2-pyrimidinyl, 4-ethyl-5-fluoro-6-methyl-2-pyrimidinyl, 4-amino-6-methyl-2-pyrimidinyl, 4-isopropyl-2-pyrimidinyl, 4-trifluoromethyl-6-pyrimidinyl, 4-trifluoromethyl-2-pyrimidinyl, 4-trifluoromethoxy-2-pyrimidinyl, 4-(1-methylethylamino)-2-pyrimidinyl, 4-(1-methyl-3-piperidinyl)amino-2-pyrimidinyl, 4-methoxy-2-pyrimidinyl, 4-isopropoxy-2-pyrimidinyl, 2,4-dimethoxy-6-pyrimidinyl, 6-methoxy-2-(1-methylethoxy)-4-pyrimidinyl, 5-fluoro-4-methoxy-2-pyrimidinyl, 5-fluoro-4-ethoxy-2-pyrimidinyl, 5-fluoro-4-methoxy-2-pyrimidinyl, 4-phenyloxy-2-pyrimidinyl, 4-(1-methyl-3-piperidinyl)oxy-2-pyrimidinyl, 4-phenylamino-2-pyrimidinyl, 4-carboxy-6-cyclopropyl-2-pyrimidinyl, 4-aminocarbonyl-2-pyrimidinyl, 2-(4-morpholinyl)-4-pyrimidinyl, 4-(4-morpholinyl)-2-pyrimidinyl, 4-(3-methyl-4-morpholinyl)-2-pyrimidinyl, 4-(1-piperidinyl)-2-pyrimidinyl, 4-(2-methyl-1-piperidinyl)-2-pyrimidinyl, 4-(1-methyl-3-piperidinyl)-2-pyrimidinyl, 4-(3-methyl-1-piperidinyl)-2-pyrimidinyl, 4-(3-amino-1-piperidinyl)-2-pyrimidinyl, 4-(3-dimethylamino-1-piperidinyl)-2-pyrimidinyl, 4-(3-hydroxy-1-piperidinyl)-2-pyrimidinyl, 4-(2-methyl-1-pyrrolidinyl)-2-pyrimidinyl, 4-(2-methoxymethyl-1-pyrrolidinyl)-2-pyrimidinyl, 4-(2-methoxy-1-pyrrolidinyl)-2-pyrimidinyl, 4-(4-methyl-1-piperazinyl)-2-pyrimidinyl, 4-(4-methyl-3-oxo-1-piperazinyl)-2-pyrimidinyl, 4-(3-amino-piperidinyl)-2-pyrimidinyl, 4-(1-methyl-3-piperidinyl)oxy-2-pyrimidinyl, 4-cyclopropyl-2-pyrimidinyl, 5-fluoro-4-cyclopropyl-2-pyrimidinyl, 4-(2-chlorophenyl)-2-pyrimidinyl, 4-(2-fluorophenyl)-2-pyrimidinyl, 4-(2-methylphenyl)-2-pyrimidinyl, 4-phenyl-2-pyrimidinyl, 2-pyrazinyl, 6-amino-2-pyrazinyl, 6-chloro-2-pyrazinyl, 6-methyl-2-pyrazinyl, 6-cyclopropylmethylamino-2-pyrazinyl, 6-(1-methylethylamino)-2-pyrazinyl, 5-(N-ethyl-N-methyl-amino)-2-pyrazinyl, 2-(N,N-dimethylamino)-6-pyrazinyl, 6-(N,N-diethylamino)-2-pyrazinyl, 6-cyclopropylamino-2-pyrazinyl, 6-cyclopentylamino-2-pyrazinyl, 6-cyclohexylamino-2-pyrazinyl, 5-ethoxy-2-pyrazinyl, 6-(2,2,2-trifluoro-1-methylethoxy)-2-pyrazinyl, 6-methoxy-2-pyrazinyl, 6-ethoxy-2-pyrazinyl, 5-(1-methylethoxy)-2-pyrazinyl, 6-(1-methylethoxy)-2-pyrazinyl, 5-butoxy-2-pyrazinyl, 6-(cyclopentyloxy)-2-pyrazinyl, 5-(cyclopentyloxy)-2-pyrazinyl, 6-(phenyloxy)-2-pyrazinyl, 6-(3-piperidinyloxy)-2-pyrazinyl, 5-(1-pyrrolidinyl)-2-pyrazinyl, 6-(1-pyrrolidinyl)-2-pyrazinyl, 5-(2-oxo-1-pyrrolidinyl)-2-pyrazinyl, 6-(3,3-difluoro-1-pyrrolidinyl)-2-pyrazinyl, 4-(1-methyl-2-oxo-piperazinyl)-2-pyrazinyl, 5-(4-methyl-1-piperazinyl)-2-pyrazinyl, 6-(1-piperidinyl)-2-pyrazinyl, 6-(2-methyl-1-piperidinyl)-2-pyrazinyl, 6-(4,4-difluoro-1-piperidinyl)-2-pyrazinyl, 6-(4-methyl-1-piperidinyl)-2-pyrazinyl, 6-(4-morpholinyl)-2-pyrazinyl, 5-(4-morpholinyl)-2-pyrazinyl, 6-(1-methyl-1H-pyrazol-4-yl)-2-pyrazinyl, 5-(3-methyl-1H-pyrazol-1-yl)-2-pyrazinyl, 6-cyclopropyl-2-pyrazinyl, 6-phenyl-2-pyrazinyl, 6-(4-fluorophenyl)-2-pyrazinyl, 6-(3-fluorophenyl)-2-pyrazinyl, 6-(2-fluorophenyl)-2-pyrazinyl, 6-(3-chlorophenyl)-2-pyrazinyl, 6-(2-chlorophenyl)-2-pyrazinyl, 6-(4-chlorophenyl)-2-pyrazinyl, 2-pyridinyl, 4-pyridinyl, 3-pyridinyl, 6-amino-2-pyridinyl, 5-amino-4-pyridinyl, 6-(1-methylethylamino)-2-pyridinyl, 6-(cyclopropylmethylamino)-2-pyridinyl, 6-cyclopentylamino-2-pyridinyl, 6-(cyclohexylamino)-2-pyridinyl, 6-trifluoromethyl-2-pyridinyl, 5-fluoro-6-methyl-2-pyridinyl, 6-fluoro-2-pyridinyl, 6-cyano-2-pyridinyl, 6-hydroxy-2-pyridinyl, 5,6-dimethoxy-2-pyridinyl, 5-methoxy-3-pyridinyl, 6-ethoxy-2-pyridinyl, 6-propoxy-2-pyridinyl, 6-(1-methylethoxy)-2-pyridinyl, 6-(cyclobutyloxy)-2-pyridinyl, 6-(cyclopentyloxy)-2-pyridinyl, 6-(cyclohexyloxy)-2-pyridinyl, 5-(4-morpholinylcarbonyl)-3-pyridinyl, 6-(1-pyrrolidinyl)-2-pyridinyl, 6-(2-oxo-1-pyrrolidinyl)-2-pyridinyl, 6-(4-methyl-1-piperazinyl)-2-pyridinyl, 4-(1-methyl-2-oxo-piperazinyl)-2-pyridinyl, 6-(4-morpholinyl)-2-pyridinyl, 6-(1-piperidinyl)-2-pyridinyl, 6-(3-methylpiperidin-1-yl)pyridin-2-yl, 6-(4-methyl-1-piperidinyl)-2-pyridinyl, 6-(2-methylpiperidin-1-yl)pyridin-2-yl, 6-(3-amino-piperidinyl)-2-pyridinyl, 6-(2-oxo-1-piperidinyl)-2-pyridinyl, 6-(2-methyl-1H-imidazol-1-yl)-2-pyridinyl, 6-(4-methyl-1H-imidazol-1-yl)-2-pyridinyl, 6-(1H-pyrazol-1-yl)-2-pyridinyl, 6-(3-methyl-1H-pyrazol-1-yl)-2-pyridinyl, 6-(2-oxo-1-pyridinyl)-2-pyridinyl, 6-(3-methyl-5,6-dihydro[1,2,4]triazolo[4,3-a]pyrazin-7(8H)-yl)-2-pyridinyl, 6-phenyl-2-pyridinyl, 6-(4-chlorophenyl)-2-pyridinyl, phenyl, 2-fluorophenyl, 2,3-difluorophenyl, 2,4-difluorophenyl, 2,6-difluorophenyl, 2-fluoro-5-(1-methylethoxy)phenyl, 3-(1-methylethoxy)phenyl, 3-fluoro-5-(1-methylethoxy)phenyl, 2-fluoro-5-(N-phenyl-aminocarbonyl)phenyl, 3-aminophenyl, 3-(trifluoromethyl)phenyl, 3-(trifluoromethoxy)phenyl, 3-methoxyphenyl, 3-biphenyl, 3-quinolinyl, 1H-indazol-6-yl, 2,2-dimethyl-2,3-dihydro-1-benzofuran-6-yl, 6-quinoxalinyl, 7,7-dimethyl-6,7-dihydro-5H-pyrrolo[2,3-b]pyrazin-2-yl, 2-(4-methyl-1H-imidazol-1-yl)-1,3-thiazol-4-yl, 2-(2-oxo-1-pyridinyl)-1,3-thiazol-4-yl, 2-(3-furyl)-1,3-thiazol-4-yl, 2-(2-methylpiperidin-1-yl)thiazol-4-yl, 1H-pyrazol-4-yl, 1H-pyrazol-5-yl, 1-(2-methylpropyl)-1H-pyrazol-4-yl, 1-(2-

(4-morpholinyl)ethyl)-1H-pyrazol-4-yl, 3-cyclopropyl-1H-1,2,4-triazol-5-yl, 3,6-dihydro-2H-pyran-4-yl or 2,2'-bithiophen-5-yl; and a pharmaceutically acceptable salt thereof.

In another embodiment, $R^2$ is H or fluoro; and a pharmaceutically acceptable salt thereof.

Another aspect of the current invention relates to compounds having the general structure of formula Ia

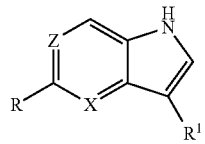

Ia wherein X is CH or N;
wherein Z is $CR^2$ or N;
wherein R is optionally substituted oxazolyl, optionally substituted thiazolyl, optionally substituted thiadiazolyl or optionally substituted oxadiazolyl;
wherein $R^1$ is —NH(C=O)—$R^a$, —(C=O)—NH$R^a$, optionally substituted phenyl, optionally substituted 5-membered heterocyclyl, optionally substituted 6-membered heterocyclyl, optionally substituted 9 membered heterocyclyl or optionally substituted 10 membered heterocyclyl;
wherein $R^a$ is alkyl, optionally substituted cycloalkyl, optionally substituted phenyl, optionally substituted 5-membered heterocyclyl, or optionally substituted 6-membered heterocyclyl; and
wherein $R^2$ is H or halo;
and a pharmaceutically acceptable salt thereof.

In another embodiment, X is CH and Z is $CR^2$; and a pharmaceutically acceptable salt thereof.

In another embodiment, X is N and Z is $CR^2$; and a pharmaceutically acceptable salt thereof.

In another embodiment, X is CH and Z is N; and a pharmaceutically acceptable salt thereof.

In another embodiment, R is oxadiazolyl optionally substituted with amino, $C_{1-6}$ alkylamino, $C_{1-6}$ haloalkylamino, cyano-$C_{1-6}$ alkylamino, amino-$C_{1-6}$ alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$alkylamino, optionally substituted 9-10-membered nitrogen containing heterocyclyl substituted amino, optionally substituted 9-10-membered nitrogen containing heterocyclyl-$C_{1-4}$alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

In another embodiment, R is thiadiazolyl optionally substituted with amino, $C_{1-6}$ alkylamino, $C_{1-6}$ haloalkylamino, cyano-$C_{1-6}$ alkylamino, amino-$C_{1-6}$ alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$alkylamino, optionally substituted 9-10-membered nitrogen containing heterocyclyl substituted amino, optionally substituted 9-10-membered nitrogen containing heterocyclyl-$C_{1-4}$alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

In another embodiment, R is thiazolyl optionally substituted with amino, $C_{1-6}$ alkylamino, $C_{1-6}$ haloalkylamino, cyano-$C_{1-6}$ alkylamino, amino-$C_{1-6}$ alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$alkylamino, optionally substituted 9-10-membered nitrogen containing heterocyclyl substituted amino, optionally substituted 9-10-membered nitrogen containing heterocyclyl-$C_{1-4}$alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

In another embodiment, R is oxazolyl optionally substituted with amino, $C_{1-6}$ alkylamino, $C_{1-6}$ haloalkylamino, cyano-$C_{1-6}$ alkylamino, amino-$C_{1-6}$ alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$alkylamino, optionally substituted 9-10-membered nitrogen containing heterocyclyl substituted amino, optionally substituted 9-10-membered nitrogen containing heterocyclyl-$C_{1-4}$alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

In another embodiment, R is substituted with H, amino, methylamino, propylamino, isopropylamino, tert-butylamino, cyanomethylamino, aminopropylamino, 1,1,1-trifluoroethylamino, methylcarbonylamino, hydroxy, methoxy, ethoxy, propoxy, isopropoxy, butoxy, isobutoxy, tert-butoxy, hexyloxy, methylthio, bromo, methyl, ethyl, n-propyl, isopropyl, n-butyl, isobutyl, sec-butyl, tert-butyl, pentyl, isoamyl, hexyl, cyclopropyl, cyclobutyl, cyclopentyl, cyclohexyl, aminocarbonyl, cyclopropylamino, piperidylamino, piperidylmethylamino, piperidylethylamino, indolylmethylamino, 2,3-dimethylaminoindolymethylamino, phenylamino, 3-fluorophenylamino, benzylamino, 3-(methylcarbonylamino)benzylamino, 3-(methylamino)benzylamino, 3-(methoxymethylcarbonylamino)benzylamino, 4-(methylcarbonylamino)benzylamino, 2-methyl-2-phenylethylamino, phenyl, pyrrolidinyl, 3-amino-1-pyrrolidinyl, piperidyl, 4-amino-1-piperidyl, pyrazolyl, morpholinyl, 2-methylmorpholinyl, 3-methylmorpholinyl, 3,3-dimethylmorpholinyl, 3-ethylmorpholinyl, piperazinyl, oxetanyl, or azetidinyl; and a pharmaceutically acceptable salt thereof.

In another embodiment, $R^1$ is optionally substituted phenyl or optionally substituted biphenyl; and a pharmaceutically acceptable salt thereof.

In another embodiment, $R^1$ is optionally substituted pyrazinyl, optionally substituted pyridyl, or optionally substituted pyrimidinyl, or optionally substituted pyridazinyl; and a pharmaceutically acceptable salt thereof.

In another embodiment, $R^1$ is optionally substituted quinolyl, optionally substituted dihydrobenzofuryl, optionally substituted quinoxalinyl, optionally substituted indazolyl, or optionally substituted 6,7-dihydro-5H-pyrrolo[2,3-b]pyrazinyl; and a pharmaceutically acceptable salt thereof.

In another embodiment, $R^1$ is unsubstituted or substituted triazolyl, unsubstituted or substituted dihydro-2H-pyranyl, unsubstituted or substituted thiazolyl, unsubstituted or substituted pyrazolyl, or unsubstituted or substituted thienyl; and a pharmaceutically acceptable salt thereof.

In another embodiment, $R^2$ is H or fluoro; and a pharmaceutically acceptable salt thereof.

In another embodiment, $R^a$ is $C_{1-6}$ alkyl, optionally substituted $C_{3-6}$ cycloalkyl, optionally substituted phenyl, optionally substituted 5-membered heterocyclyl, or optionally substituted 6-membered heterocyclyl; and a pharmaceutically acceptable salt thereof.

Another aspect of the current invention relates to compounds having the general structure of formula IIa

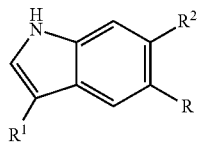

IIa wherein R is optionally substituted thiadiazolyl or optionally substituted oxadiazolyl;
wherein $R^1$ is $C_{3-6}$ cycloalkylcarbonylamino, optionally substituted 6-membered heterocyclylcarbonylamino, optionally substituted phenyl or optionally substituted 5-membered heterocyclyl, optionally substituted 6-membered heterocyclyl, optionally substituted 9 membered heterocyclyl or optionally substituted 10 membered heterocyclyl; and
wherein $R^2$ is H or halo;
and a pharmaceutically acceptable salt thereof.

In another embodiment, $R^1$ is unsubstituted or substituted phenyl, unsubstituted or substituted biphenyl, unsubstituted or substituted pyrazinyl, unsubstituted or substituted pyridyl, unsubstituted or substituted pyrimidinyl, unsubstituted or substituted pyridazinyl, unsubstituted or substituted quinolyl, unsubstituted or substituted dihydrobenzofuryl, unsubstituted or substituted quinoxalinyl, unsubstituted or substituted indazolyl, unsubstituted or substituted 6,7-dihydro-5H-pyrrolo[2,3-b]pyrazinyl, unsubstituted or substituted triazolyl, unsubstituted or substituted dihydro-2H-pyranyl, unsubstituted or substituted thiazolyl, unsubstituted or substituted pyrazolyl, or unsubstituted or substituted thienyl and a pharmaceutically acceptable salt thereof.

In another embodiment, R is oxadiazolyl optionally substituted with amino, $C_{1-6}$ alkylamino, $C_{1-6}$ haloalkylamino, cyano-$C_{1-6}$ alkylamino, amino-$C_{1-6}$ alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$alkylamino, optionally substituted 9-10-membered nitrogen containing heterocyclyl substituted amino, optionally substituted 9-10-membered nitrogen containing heterocyclyl-$C_{1-4}$alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

In another embodiment, R is thiadiazolyl optionally substituted with amino, $C_{1-6}$ alkylamino, $C_{1-6}$ haloalkylamino, cyano-$C_{1-6}$ alkylamino, amino-$C_{1-6}$ alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$alkylamino, optionally substituted 9-10-membered nitrogen containing heterocyclyl substituted amino, optionally substituted 9-10-membered nitrogen containing heterocyclyl-$C_{1-4}$alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

In another embodiment, R is

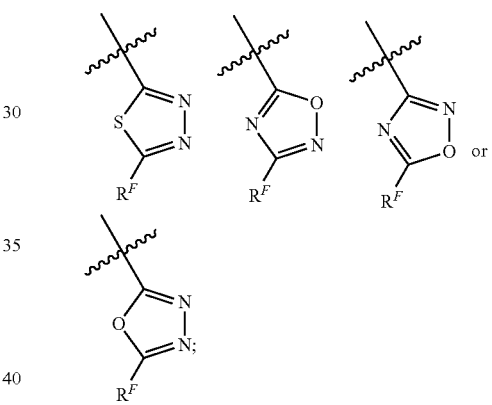

wherein $R^F$ is H, amino, methylamino, propylamino, isopropylamino, tert-butylamino, cyanomethylamino, aminopropylamino, 1,1,1-trifluoroethylamino, methylcarbonylamino, hydroxy, methoxy, ethoxy, propoxy, isopropoxy, butoxy, isobutoxy, tert-butoxy, hexyloxy, methylthio, bromo, methyl, ethyl, n-propyl, isopropyl, n-butyl, isobutyl, sec-butyl, tert-butyl, pentyl, isoamyl, hexyl, cyclopropyl, cyclobutyl, cyclopentyl, cyclohexyl, aminocarbonyl, cyclopropylamino, piperidylamino, piperidylmethylamino, piperidylethylamino, indolylmethylamino, 2,3-dimethylaminoindolymethylamino, phenylamino, 3-fluorophenylamino, benzylamino, 3-(methylcarbonylamino)benzylamino, 3-(methylamino)benzylamino, 3-(methoxymethylcarbonylamino)benzylamino, 4-(methylcarbonylamino)benzylamino, 2-methyl-2-phenylethylamino, phenyl, pyrrolidinyl, 3-amino-1-pyrrolidinyl, piperidyl, 4-amino-1-piperidyl, pyrazolyl, morpholinyl, 2-methylmorpholinyl, 3-methylmorpholinyl, 3,3-dimethylmorpholinyl, 3-ethylmorpholinyl, piperazinyl, oxetanyl, or azetidinyl; and a pharmaceutically acceptable salt thereof.

In another embodiment, $R^1$ is optionally substituted phenyl or optionally substituted biphenyl; and a pharmaceutically acceptable salt thereof.

In another embodiment, $R^1$ is optionally substituted pyrazinyl, optionally substituted pyridyl, or optionally substituted pyrimidinyl, or optionally substituted pyridazinyl; and a pharmaceutically acceptable salt thereof.

In another embodiment, $R^1$ is optionally substituted quinolyl, optionally substituted dihydrobenzofuryl, optionally substituted quinoxalinyl, optionally substituted indazolyl, or optionally substituted 6,7-dihydro-5H-pyrrolo[2,3-b]pyrazinyl; and a pharmaceutically acceptable salt thereof.

In another embodiment, $R^1$ is unsubstituted or substituted triazolyl, unsubstituted or substituted dihydro-2H-pyranyl, unsubstituted or substituted thiazolyl, unsubstituted or substituted pyrazolyl, or unsubstituted or substituted thienyl; and a pharmaceutically acceptable salt thereof.

In another embodiment, $R^1$ is
pyrimidinyl unsubstituted or substituted with one or more amino, halo, cyano, hydroxy, oxo, $C_{1-6}$ alkyl, $C_{1-3}$ haloalkyl, $C_{1-6}$ alkylamino, (optionally substituted 5-6-membered nitrogen containing heterocyclyl)amino, phenylamino, $C_{3-6}$ cycloalkyl-$C_{1-3}$-alkylamino, $C_{3-6}$ cycloalkylamino, carboxy, aminocarbonyl, $C_{1-6}$ alkylaminocarbonyl, $C_{3-6}$ cycloalkylaminocarbonyl, phenylaminocarbonyl, optionally substituted 5-6-membered nitrogen containing heterocyclyl)carbonyl, $C_{1-6}$ alkoxy, $C_{1-6}$ haloalkoxy, $C_{3-6}$ cycloalkoxy, optionally substituted phenyloxy, (optionally substituted 5-6-membered nitrogen containing heterocyclyl)oxy, optionally substituted phenyl, optionally substituted 6-membered nitrogen containing heterocyclyl, optionally substituted 5-membered nitrogen containing heterocyclyl, optionally substituted 9-10-membered nitrogen containing heterocyclyl, or $C_{3-6}$ cycloalkyl,
pyrazinyl unsubstituted or substituted with one or more amino, halo, cyano, hydroxy, $C_{1-6}$ alkyl, $C_{1-3}$ haloalkyl, $C_{1-6}$ alkylamino, (optionally substituted 5-6-membered nitrogen containing heterocyclyl)amino, phenylamino, $C_{3-6}$ cycloalkyl-$C_{1-3}$-alkylamino, $C_{3-6}$ cycloalkylamino, carboxy, aminocarbonyl, phenylaminocarbonyl, $C_{3-6}$ cycloalkylaminocarbonyl, optionally substituted 5-6-membered nitrogen containing heterocyclyl)carbonyl, $C_{1-6}$ alkoxy, $C_{1-6}$ haloalkoxy, $C_{3-6}$ cycloalkoxy, optionally substituted phenyloxy, (optionally substituted 5-6-membered nitrogen containing heterocyclyl)oxy, optionally substituted phenyl, optionally substituted 6-membered nitrogen containing heterocyclyl, optionally substituted 5-membered nitrogen containing heterocyclyl, optionally substituted 9-10-membered nitrogen containing heterocyclyl, or $C_{3-6}$ cycloalkyl,
pyridinyl unsubstituted or substituted with one or more amino, halo, cyano, hydroxy, oxo, $C_{1-6}$ alkyl, $C_{1-3}$ haloalkyl, $C_{1-6}$ alkylamino, (optionally substituted 5-6-membered nitrogen containing heterocyclyl)amino, phenylamino, $C_{3-6}$ cycloalkyl-$C_{1-3}$-alkylamino, $C_{3-6}$ cycloalkylamino, carboxy, aminocarbonyl, $C_{1-6}$ alkylaminocarbonyl, $C_{3-6}$ cycloalkylaminocarbonyl, phenylaminocarbonyl, (optionally substituted 5-6-membered nitrogen containing heterocyclyl)carbonyl, $C_{1-6}$ alkylsulfonyl, $C_{1-6}$ alkoxy, $C_{1-6}$ haloalkoxy, $C_{3-6}$ cycloalkoxy, optionally substituted phenyloxy, (optionally substituted 5-6-membered nitrogen containing heterocyclyl)oxy, optionally substituted phenyl, optionally substituted 6-membered nitrogen containing heterocyclyl, optionally substituted 5-membered nitrogen containing heterocyclyl, optionally substituted 9-10-membered nitrogen containing heterocyclyl, or $C_{3-6}$ cycloalkyl,
phenyl unsubstituted or substituted with one or more amino, halo, cyano, hydroxy, $C_{1-6}$ alkyl, $C_{1-3}$ haloalkyl, $C_{1-6}$ alkylamino, (optionally substituted 5-6-membered nitrogen containing heterocyclyl)amino, phenylamino, $C_{3-6}$ cycloalkyl-$C_{1-3}$-alkylamino, $C_{3-6}$ cycloalkylamino, carboxy, aminocarbonyl, $C_{1-6}$ alkylaminocarbonyl, phenylaminocarbonyl, optionally substituted 5-6-membered nitrogen containing heterocyclyl)carbonyl, $C_{1-6}$ alkoxy, $C_{1-6}$ haloalkoxy, $C_{3-6}$ cycloalkoxy, optionally substituted phenyloxy, (optionally substituted 5-6-membered nitrogen containing heterocyclyl)oxy, optionally substituted phenyl, optionally substituted 6-membered nitrogen containing heterocyclyl, optionally substituted 5-membered nitrogen containing heterocyclyl, optionally substituted 9-10-membered nitrogen containing heterocyclyl, or $C_{3-6}$ cycloalkyl,
3-quinolinyl, 1H-indazolyl, 2,2-dimethyl-2,3-dihydro-1-benzofuranyl, 6-quinoxalinyl, 7,7-dimethyl-6,7-dihydro-5H-pyrrolo[2,3-b]pyrazinyl,
thiazolyl unsubstituted or substituted with aminocarbonyl, $C_{3-6}$ cycloalkylaminocarbonyl, 4-methyl-1H-imidazolyl, 2-oxo-pyridinyl, furyl, or methylpiperidinyl,
triazolyl unsubstituted or substituted with $C_{3-6}$ cyclopropyl, dihydro-2H-pyranyl,
pyrazolyl unsubstituted or substituted with 2-methylpropyl, or 2-(4-morpholinyl)ethyl, or
thiophenyl unsubstituted or substituted with thienyl;
and a pharmaceutically acceptable salt thereof.

In another embodiment, $R^1$ is
2-pyrimidinyl, 4-methyl-2-pyrimidinyl, 4-ethyl-5-fluoro-6-methyl-2-pyrimidinyl, 4-methoxy-5-fluoro-6-methyl-2-pyrimidinyl, 4-amino-6-methyl-2-pyrimidinyl, 4-isopropyl-2-pyrimidinyl, 4-trifluoromethyl-6-pyrimidinyl, 4-trifluoromethyl-2-pyrimidinyl, 4-trifluoromethoxy-2-pyrimidinyl, 4-(1-methylethylamino)-2-pyrimidinyl, 2-isopropylamino-4-pyrimidinyl, 4-(1-methyl-3-piperidinyl)amino-2-pyrimidinyl, 4-methoxy-2-pyrimidinyl, 2-methoxy-4-pyrimidinyl, 4-isopropoxy-2-pyrimidinyl, 2,4-dimethoxy-6-pyrimidinyl, 6-methoxy-2-(1-methylethoxy)-4-pyrimidinyl, 5-fluoro-4-methoxy-2-pyrimidinyl, 4-ethoxy-5-fluoro-2-pyrimidinyl, 5-fluoro-4-methoxy-2-pyrimidinyl, 4-phenyloxy-2-pyrimidinyl, 4-(1-methyl-3-piperidinyl)oxy-2-pyrimidinyl, 4-phenylamino-2-pyrimidinyl, 4-cyclopropyl-2-pyrimidinyl, 4-carboxy-6-cyclopropyl-2-pyrimidinyl, 5-aminocarbonyl-4-cyclopropyl-2-pyrimidinyl, 4-aminocarbonyl-2-pyrimidinyl, 4-methylaminocarbonyl-2-pyrimidinyl, 4-cyclopropylaminocarbonyl-2-pyrimidinyl, 2-(4-morpholinyl)-4-pyrimidinyl, 4-(4-morpholinyl)-2-pyrimidinyl, 4-(3-methyl-4-morpholinyl)-2-pyrimidinyl, 4-(1-piperidinyl)-2-pyrimidinyl, 4-(2-methyl-1-piperidinyl)-2-pyrimidinyl, 4-(1-methyl-3-piperidinyl)-2-pyrimidinyl, 4-(3-methyl-1-piperidinyl)-2-pyrimidinyl, 4-(3-amino-1-piperidinyl)-2-pyrimidinyl, 4-(3-dimethyl-amino-1-piperidinyl)-2-pyrimidinyl, 4-(3-hydroxy-1-piperidinyl)-2-pyrimidinyl, 4-(2-methyl-1-pyrrolidinyl)-2-pyrimidinyl, 4-(2-methoxymethyl-1-pyrrolidinyl)-2-pyrimidinyl, 4-(2-methoxy-1-pyrrolidinyl)-2-pyrimidinyl, 4-(4-methyl-1-piperazinyl)-2-pyrimidinyl, 4-(4-methyl-3-oxo-1-piperazinyl)-2-pyrimidinyl, 4-(3-amino-piperidinyl)-2-pyrimidinyl, 4-(1-methyl-3-piperidinyl)oxy-2-pyrimidinyl, 4-cyclopropyl-2-pyrimidinyl, 2-cyclopropyl-4-pyrimidinyl, 5-fluoro-4-cyclopropyl-2-pyrimidinyl, 4-(2-chlorophenyl)-2-pyrimidinyl, 4-(2-fluorophenyl)-2-pyrimidinyl, 4-(2-methylphenyl)-2-pyrimidinyl, 4-phenyl-2-pyrimidinyl, 2-isopropylamino-4-oxo-6-pyrimidinyl, 2-cyclopropyl-4-oxo-6-pyrimidinyl, 2-methoxy-4-oxo-6-pyrimidinyl, 2-cyclopropyl-4-oxo-6-pyrimidinyl,
2-pyrazinyl, 6-amino-2-pyrazinyl, 6-chloro-2-pyrazinyl, 6-methyl-2-pyrazinyl, 6-cyclopropylmethyl-amino-2-pyrazinyl, 6-(1-methylethylamino)-2-pyrazinyl, 5-(N- ethyl-N-methyl-amino)-2-pyrazinyl, 2-(N,N-dimethylamino)-6-pyrazinyl, 6-(N,N-diethylamino)-2-pyrazinyl, 6-cyclopropyl-amino-2-pyrazinyl, 6-cyclopentylamino-2-pyrazinyl, 6-cyclohexylamino-2-pyrazinyl, 5-ethoxy-2-pyrazinyl, 2-isopropoxy-6-pyrazinyl, 6-(2,2,2-trifluoro-1-methylethoxy)-2-pyrazinyl, 6-methoxy-2-pyrazinyl, 6-ethoxy-2-pyrazinyl, 5-(1-methylethoxy)-2-pyrazinyl, 6-(1-methylethoxy)-2-pyrazinyl, 5-butoxy-2-pyrazinyl, 6-(cyclopentyloxy)-2-pyrazinyl, 5-(cyclopentyloxy)-2-pyrazinyl, 6-(phenyloxy)-2-pyrazinyl, 6-(3-piperidinyloxy)-2-pyrazinyl, 5-(1-pyrrolidinyl)-2-pyrazinyl, 6-(1-pyrrolidinyl)-2-pyrazinyl, 5-(2-oxo-1-pyrrolidinyl)-2-pyrazinyl, 6-(3,3-difluoro-1-pyrrolidinyl)-2-pyrazinyl, 4-(1-methyl-2-oxo-piperazinyl)-2-pyrazinyl, 5-(4-methyl-1-piperazinyl)-2-pyrazinyl, 6-(1-piperidinyl)-2-pyrazinyl, 6-(2-methyl-1-piperidinyl)-2-pyrazinyl, 6-(4,4-difluoro-1-piperidinyl)-2-pyrazinyl, 6-(4-methyl-1-piperidinyl)-2-pyrazinyl, 6-(4-morpholinyl)-2-pyrazinyl, 5-(4-morpholinyl)-2-pyrazinyl, 6-(1-methyl-1H-pyrazol-4-yl)-2-pyrazinyl, 5-(3-methyl-1H-pyrazol-1-yl)-2-pyrazinyl, 6-cyclopropyl-2-pyrazinyl, 6-phenyl-2-pyrazinyl, 6-(4-fluorophenyl)-2-pyrazinyl, 6-(3-fluorophenyl)-2-pyrazinyl, 6-(2-fluorophenyl)-2-pyrazinyl, 6-(3-chlorophenyl)-2-pyrazinyl, 6-(2-chlorophenyl)-2-pyrazinyl, 6-(4-chlorophenyl)-2-pyrazinyl, 2-pyridinyl, 4-pyridinyl, 3-pyridinyl, 2-amino-4-pyridinyl, 6-amino-2-pyridinyl, 5-amino-4-pyridinyl, 6-(1-methylethyl-amino)-2-pyridinyl, 6-(cyclopropylmethylamino)-2-pyridinyl, 6-cyclopentylamino-2-pyridinyl, 6-(cyclohexylamino)-2-pyridinyl, 6-trifluoromethyl-2-pyridinyl, 5-fluoro-6-methyl-2-pyridinyl, 6-fluoro-2-pyridinyl, 6-cyano-2-pyridinyl, 6-hydroxy-2-pyridinyl, 3-methylsulphonyl-6-pyridinyl, 5,6-dimethoxy-2-pyridinyl, 5-methoxy-3-pyridinyl, 6-ethoxy-2-pyridinyl, 6-propoxy-2-pyridinyl, 2-(1-methylethoxy)-6-pyridinyl, 6-(cyclobutyloxy)-2-pyridinyl, 6-(cyclopentyloxy)-2-pyridinyl, 6-(cyclohexyloxy)-2-pyridinyl, 3-aminocarbonylpyridin-6-yl, 2-methylaminocarbonylpyridin-6-yl, 3-methylaminocarbonylpyridin-6-yl, 3-(N,N-dimethylamino)carbonylpyridin-5-yl, 2-(N,N-dimethylamino)carbonylpyridin-6-yl, 3-methylaminocarbonylpyridin-5-yl, 3-isopropylaminocarbonylpyridin-5-yl, 2-isopropylaminocarbonylpyridin-6-yl, 3-cyclopropylaminocarbonylpyridin-5-yl, 2-cyclopropylaminocarbonylpyridin-6-yl, 5-(4-morpholinylcarbonyl)-3-pyridinyl, 3-(4-morpholinylcarbonyl)-6-pyridinyl, 6-(1-pyrrolidinyl)-2-pyridinyl, 6-(2-oxo-1-pyrrolidinyl)-2-pyridinyl, 6-(4-methyl-1-piperazinyl)-2-pyridinyl, 4-(1-methyl-2-oxo-piperazinyl)-2-pyridinyl, 6-(4-morpholinyl)-2-pyridinyl, 6-(1-piperidinyl)-2-pyridinyl, 6-(3-methylpiperidin-1-yl)pyridin-2-yl, 6-(4-methyl-1-piperidinyl)-2-pyridinyl, 6-(2-methylpiperidin-1-yl)pyridin-2-yl, 6-(3-amino-piperidinyl)-2-pyridinyl, 6-(2-oxo-1-piperidinyl)-2-pyridinyl, 6-(2-methyl-1H-imidazol-1-yl)-2-pyridinyl, 6-(4-methyl-1H-imidazol-1-yl)-2-pyridinyl, 6-(1H-pyrazol-1-yl)-2-pyridinyl, 6-(3-methyl-1H-pyrazol-1-yl)-2-pyridinyl, 6-(2-oxo-1-pyridinyl)-2-pyridinyl, 6-(3-methyl-5,6-dihydro[1,2,4]triazolo[4,3-a]pyrazin-7(8H)-yl)-2-pyridinyl, 6-phenyl-2-pyridinyl, 6-(4-chlorophenyl)-2-pyridinyl, phenyl, 2-fluorophenyl, 2,3-difluorophenyl, 2,4-difluorophenyl, 2,6-difluorophenyl, 2-fluoro-5-(1-methylethoxy)phenyl, 3-(1-methylethoxy)phenyl, 3-fluoro-5-(1-methylethoxy)phenyl, 2-fluoro-5-(N-phenyl-aminocarbonyl)phenyl, 2-fluoro-5-(N,N-dimethyl-aminocarbonyl)phenyl, 2-fluoro-5-(N-methylaminocarbonyl)phenyl, 4-aminocarbonyl-2-fluorophenyl, 3-aminophenyl, 3-(trifluoromethyl)phenyl, 3-(trifluoromethoxy)phenyl, 3-methoxyphenyl, 3-quinolinyl, 3-biphenyl, 1H-indazol-6-yl, 2,2-dimethyl-2,3-dihydro-1-benzofuran-6-yl, 6-quinoxalinyl, 7,7-dimethyl-6,7-dihydro-5H-pyrrolo[2,3-b]pyrazin-2-yl, 5-aminocarbonyl-1,3-thiazol-2-yl, 4-cyclopropylaminocarbonyl-1,3-thiazol-2-yl, 5-cyclopropylaminocarbonyl-1,3-thiazol-2-yl, 2-(4-methyl-1H-imidazol-1-yl)-1,3-thiazol-4-yl, 2-(2-oxo-1-pyridinyl)-1,3-thiazol-4-yl, 2-(3-furyl)-1,3-thiazol-4-yl, 2-(2-methylpiperidin-1-yl)thiazol-4-yl, 1H-pyrazol-4-yl, 1H-pyrazol-5-yl, 1-(2-methylpropyl)-1H-pyrazol-4-yl, 1-(2-(4-morpholinyl)ethyl)-1H-pyrazol-4-yl, 3-cyclopropyl-1H-1,2,4-triazol-5-yl, 3,6-dihydro-2H-pyran-4-yl or 2,2'-bi-thiophen-5-yl;

and a pharmaceutically acceptable salt thereof.

In another embodiment, $R^2$ is H or fluoro; and a pharmaceutically acceptable salt thereof.

In another embodiment, $R^1$ is cyclopropylcarbonylamino, cyclobutylcarbonylamino, pyrmindinylcarbonylamino, or pyridylcarbonylamino; and a pharmaceutically acceptable salt thereof.

A family of specific compounds of particular interest within Formula I and Ia consists of compounds and pharmaceutically-acceptable derivatives thereof as follows:

5-(3-(4-cyclopropyl-2-pyrimidinyl)-1H-indol-5-yl)-N-(2,2,2-trifluoroethyl)-1,3,4-oxadiazol-2-amine;

5-(3-(4-cyclopropyl-2-pyrimidinyl)-1H-indol-5-yl)-1,3,4-oxadiazol-2-amine;

6-cyclopropyl-2-(4-(5-(((1-methylethyl)amino)-1,3,4-oxadiazol-2-yl)-1H-indol-3-yl)-4-pyrimidinecarboxamide;

5-(3-(4-cyclopropyl-2-pyrimidinyl)-1H-indol-5-yl)-N-(1-methylethyl)-1,3,4-oxadiazol-2-amine;

((5-(3-(4-(1-methylethyl)-2-pyrimidinyl)-1H-indol-5-yl)-1,3,4-oxadiazol-2-yl)amino)acetonitrile;

5-(3-(6-cyclopropyl-2-pyrazinyl)-1H-indol-5-yl)-N-(1-methylethyl)-1,3,4-oxadiazol-2-amine;

N-tert-butyl-5-(3-(4-cyclopropyl-2-pyrimidinyl)-1H-indol-5-yl)-1,3,4-oxadiazol-2-amine;

N-cyclopropyl-5-(3-(4-cyclopropyl-2-pyrimidinyl)-1H-indol-5-yl)-1,3,4-oxadiazol-2-amine;

5-(3-(4-cyclopropyl-2-pyrimidinyl)-6-fluoro-1H-indol-5-yl)-N-(1-methylethyl)-1,3,4-oxadiazol-2-amine;

5-(3-(6-cyclopropyl-2-pyrazinyl)-1H-indol-5-yl)-1,3,4-oxadiazol-2-amine;

5-(3-(2-cyclopropyl-4-pyrimidinyl)-1H-indol-5-yl)-N-(1-methylethyl)-1,3,4-oxadiazol-2-amine;

5-(3-(6-(1-methylethoxy)-2-pyrazinyl)-1H-indol-5-yl)-1,3,4-oxadiazol-2-amine;

2-(5-(5-(tert-butylamino)-1,3,4-oxadiazol-2-yl)-1H-indol-3-yl)-4-pyrimidinecarboxamide;

4-cyclopropyl-2-(5-(5-(((1-methylethyl)amino)-1,3,4-oxadiazol-2-yl)-1H-indol-3-yl)-5-pyrimidinecarboxamide;

5-(3-(4-(2-methyl-1-piperidinyl)-2-pyrimidinyl)-1H-indol-5-yl)-1,3,4-oxadiazol-2-amine;

5-(3-(4-(2-methyl-1-pyrrolidinyl)-2-pyrimidinyl)-1H-indol-5-yl)-1,3,4-oxadiazol-2-amine;

6-(5-(5-amino-1,3,4-oxadiazol-2-yl)-1H-indol-3-yl)-N-cyclopentyl-2-pyrazinamine;

5-(3-(6-(4,4-difluoro-1-piperidinyl)-2-pyrazinyl)-1H-indol-5-yl)-1,3,4-oxadiazol-2-amine;

5-(3-(6-(2-methyl-1-piperidinyl)-2-pyrazinyl)-1H-indol-5-yl)-1,3,4-oxadiazol-2-amine;

5-(3-(6-(3,3-difluoro-1-pyrrolidinyl)-2-pyrazinyl)-1H-indol-5-yl)-1,3,4-oxadiazol-2-amine;

6-(5-(5-amino-1,3,4-oxadiazol-2-yl)-1H-indol-3-yl)-N-(cyclopropylmethyl)-2-pyrazinamine;

5-(3-(4-cyclopropyl-2-pyrimidinyl)-1H-indol-5-yl)-N-3-oxetanyl-1,3,4-oxadiazol-2-amine;

6-(5-(5-amino-1,3,4-oxadiazol-2-yl)-1H-indol-3-yl)-N-(1-methylethyl)-2-pyrazinamine;

5-(3-(6-(1-piperidinyl)-2-pyrazinyl)-1H-indol-5-yl)-1,3,4-oxadiazol-2-amine; and 5-(3-(4-phenyl-2-pyrimidinyl)-1H-indol-5-yl)-1,3,4-oxadiazol-2-amine; and a pharmaceutically acceptable salt thereof.

A family of specific compounds of particular interest within Formula I and Ia consists of compounds and pharmaceutically-acceptable derivatives thereof as follows:

5-(3-(6-(2-methyl-1-piperidinyl)-2-pyrazinyl)-1H-indol-5-yl)-1,3,4-oxadiazol-2-amine;

5-(3-(6-(4,4-difluoro-1-piperidinyl)-2-pyrazinyl)-1H-indol-5-yl)-1,3,4-oxadiazol-2-amine;

5-(3-(4-(2-methyl-1-piperidinyl)-2-pyrimidinyl)-1H-indol-5-yl)-1,3,4-oxadiazol-2-amine;

6-(5-(5-amino-1,3,4-oxadiazol-2-yl)-1H-indol-3-yl)-N-cyclopentyl-2-pyrazinamine;

2-(5-(5-amino-1,3,4-oxadiazol-2-yl)-1H-indol-3-yl)-N-(1-methylethyl)-4-pyrimidinamine;

5-(3-(6-(4-morpholinyl)-2-pyridinyl)-1H-indol-5-yl)-1,3,4-oxadiazol-2-amine;

5-(3-(6-(3-fluorophenyl)-2-pyrazinyl)-1H-indol-5-yl)-1,3,4-oxadiazol-2-amine;

5-(3-(4-(2-fluorophenyl)-2-pyrimidinyl)-1H-indol-5-yl)-1,3,4-oxadiazol-2-amine;

5-(3-(2-fluorophenyl)-1H-pyrrolo[3,2-b]pyridin-5-yl)-1,3,4-oxadiazol-2-amine;

5-(3-(5-methoxy-3-pyridinyl)-1H-pyrrolo[3,2-b]pyridin-5-yl)-1,3,4-oxadiazol-2-amine;

5-(3-(4-(4-morpholinyl)-2-pyrimidinyl)-1H-indol-5-yl)-1,3,4-thiadiazol-2-amine;

N-(5-(3-(2-fluorophenyl)-1H-indol-5-yl)-1,3,4-thiadiazol-2-yl)-1,3-propanediamine;

5-(3-(6-(4-methyl-1-piperazinyl)-2-pyridinyl)-1H-indol-5-yl)-1,3,4-thiadiazol-2-amine;

5-(3-(6-(1-pyrrolidinyl)-2-pyrazinyl)-1H-indol-5-yl)-1,3,4-thiadiazol-2-amine;

6-(5-(5-amino-1,3,4-thiadiazol-2-yl)-1H-indol-3-yl)-N-cyclopropyl-2-pyrazinamine;

6-(5-(5-amino-1,3,4-thiadiazol-2-yl)-1H-indol-3-yl)-N-cyclopentyl-2-pyridinamine;

6-(5-(5-amino-1,3,4-thiadiazol-2-yl)-1H-indol-3-yl)-N-cyclopentyl-2-pyrazinamine;

4-(6-(5-(5-amino-1,3,4-thiadiazol-2-yl)-1H-indol-3-yl)-2-pyrazinyl)-1-methyl-2-piperazinone;

5-(3-(6-ethoxy-2-pyrazinyl)-1H-indol-5-yl)-1,3,4-thiadiazol-2-amine;

5-(3-(3-quinolinyl)-1H-indol-5-yl)-1,3-thiazol-2-amine;

5-(3-(3-quinolinyl)-1H-indol-5-yl)-1,3,4-thiadiazol-2-amine;

5-(3-(3-biphenylyl)-1H-indol-5-yl)-N-methyl-1,3,4-thiadiazol-2-amine;

5-(3-(2,4-difluorophenyl)-1H-indol-5-yl)-N-methyl-1,3,4-thiadiazol-2-amine;

5-(3-(6-(4-morpholinyl)-2-pyridinyl)-1H-indol-5-yl)-1,3,4-thiadiazol-2-amine;

5-(3-(6-(3-methyl-5,6-dihydro[1,2,4]triazolo[4,3-a]pyrazin-7(8H)-yl)-2-pyridinyl)-1H-indol-5-yl)-1,3,4-thiadiazol-2-amine;

5-(3-(2,4-difluorophenyl)-1H-indol-5-yl)-1,3,4-thiadiazol-2-ol;

5-(5-bromo-1,3,4-thiadiazol-2-yl)-3-(6-(4-morpholinyl)-2-pyridinyl)-1H-indole;

3-(6-(4-morpholinyl)-2-pyridinyl)-5-(1,3,4-thiadiazol-2-yl)-1H-indole;

5-(3-(6-(4-morpholinyl)-2-pyridinyl)-1H-indol-5-yl)-1,3,4-thiadiazol-2-ol;

4-(6-(5-(5-amino-1,3,4-thiadiazol-2-yl)-1H-indol-3-yl)-2-pyridinyl)-1-methyl-2-piperazinone;

5-(3-(6-(4-chlorophenyl)-2-pyridinyl)-1H-indol-5-yl)-1,3,4-thiadiazol-2-amine;

N-methyl-5-(3-(6-(1-methylethoxy)-2-pyridinyl)-1H-indol-5-yl)-1,3,4-oxadiazol-2-amine;

3-(6-(1-methylethoxy)-2-pyridinyl)-5-(5-methyl-1,3,4-oxadiazol-2-yl)-1H-indole;

5-(3-(2-fluoro-5-(1-methylethoxy)phenyl)-1H-pyrrolo[3,2-b]pyridin-5-yl)-1,3,4-oxadiazol-2-amine;

5-(3-(3-(1-methylethoxy)phenyl)-1H-pyrrolo[3,2-b]pyridin-5-yl)-1,3,4-oxadiazol-2-amine;

5-(3-(6-(4-methyl-1-piperazinyl)-2-pyridinyl)-1H-indol-5-yl)-1,3,4-oxadiazol-2-amine;

5-(3-(6-(1-methylethoxy)-2-pyrazinyl)-1H-indol-5-yl)-1,3,4-oxadiazol-2-amine;

5-(3-(4-(2-methyl-1-pyrrolidinyl)-2-pyrimidinyl)-1H-indol-5-yl)-1,3,4-oxadiazol-2-amine;

5-(3-(6-(1H-pyrazol-1-yl)-2-pyridinyl)-1H-indol-5-yl)-1,3,4-oxadiazol-2-amine;

3-(6-(1-methylethoxy)-2-pyridinyl)-5-(1,3,4-oxadiazol-2-yl)-1H-indole;

5-(3-(2,3-difluorophenyl)-1H-indol-5-yl)-1,3,4-oxadiazol-2-amine;

5-(3-(3-fluoro-5-(1-methylethoxy)phenyl)-1H-indol-5-yl)-1,3,4-oxadiazol-2-amine;

(3S)-1-(6-(5-(5-amino-1,3,4-thiadiazol-2-yl)-1H-indol-3-yl)-2-pyridinyl)-3-piperidinamine;

(3S)-1-(2-(5-(5-(methylamino)-1,3,4-thiadiazol-2-yl)-1H-indol-3-yl)-4-pyrimidinyl)-3-piperidinamine;

N-methyl-5-(3-(2-(4-morpholinyl)-4-pyrimidinyl)-1H-indol-5-yl)-1,3,4-thiadiazol-2-amine;

5-(3-(6-phenyl-2-pyridinyl)-1H-indol-5-yl)-1,3,4-thiadiazol-2-amine;

5-(3-(2-fluorophenyl)-1H-indol-5-yl)-1,3,4-thiadiazol-2-amine;

N-methyl-5-(3-(4-phenyl-2-pyrimidinyl)-1H-indol-5-yl)-1,3,4-thiadiazol-2-amine;

3-(5-(5-amino-1,3,4-thiadiazol-2-yl)-1H-indol-3-yl)-4-fluoro-N-phenylbenzamide;

5-(3-(2,6-difluorophenyl)-1H-indol-5-yl)-1,3,4-thiadiazol-2-amine;

5-(3-(6-(2-methylpiperidin-1-yl)pyrazin-2-yl)-1H-indol-5-yl)-1,3,4-thiadiazol-2-amine;

6-(5-(5-amino-1,3,4-thiadiazol-2-yl)-1H-indol-3-yl)-N,N-diethyl-2-pyrazinamine;

5-(3-(6-(4-methyl-1H-imidazol-1-yl)-2-pyridinyl)-1H-indol-5-yl)-1,3,4-thiadiazol-2-amine;

N-methyl-5-(3-(6-(1-piperidinyl)-2-pyrazinyl)-1H-indol-5-yl)-1,3,4-thiadiazol-2-amine;

5-(3-(6-(4-morpholinyl)-2-pyrazinyl)-1H-indol-5-yl)-1,3,4-thiadiazol-2-amine;

5-(3-(6-(1-methylethoxy)-2-pyridinyl)-1H-indol-5-yl)-1,3,4-thiadiazol-2-amine;

6-(5-(5-amino-1,3,4-thiadiazol-2-yl)-1H-indol-3-yl)-N,N-dimethyl-2-pyrazinamine;

5-(3-(6-(1-methylethoxy)-2-pyrazinyl)-1H-indol-5-yl)-1,3,4-thiadiazol-2-amine;

5-(3-(6-(cyclopentyloxy)-2-pyrazinyl)-1H-indol-5-yl)-1,3,4-thiadiazol-2-amine;

5-(3-(6-(cyclobutyloxy)-2-pyridinyl)-1H-indol-5-yl)-1,3,4-thiadiazol-2-amine;

5-(3-(6-(4-methyl-1-piperidinyl)-2-pyrazinyl)-1H-indol-5-yl)-1,3,4-thiadiazol-2-amine;

N-methyl-5-(3-(6-(4-methyl-1H-imidazol-1-yl)-2-pyridinyl)-1H-indol-5-yl)-1,3,4-thiadiazol-2-amine;

5-(3-(6-(cyclopentyloxy)-2-pyridinyl)-1H-indol-5-yl)-1,3,4-thiadiazol-2-amine;

5-(3-(6-ethoxy-2-pyridinyl)-1H-indol-5-yl)-1,3,4-thiadiazol-2-amine;

5-(3-(6-propoxy-2-pyridinyl)-1H-indol-5-yl)-1,3,4-thiadiazol-2-amine;

1-(6-(5-(5-amino-1,3,4-thiadiazol-2-yl)-1H-indol-3-yl)-2-pyridinyl)-2-pyrrolidinone;

5-(3-(6-(2-methylpiperidin-1-yl)pyridin-2-yl)-1H-indol-5-yl)-1,3,4-thiadiazol-2-amine;

5-(3-(5,6-dimethoxy-2-pyridinyl)-1H-indol-5-yl)-1,3,4-thiadiazol-2-amine;

5-(3-(6-(2-methyl-1H-imidazol-1-yl)-2-pyridinyl)-1H-indol-5-yl)-1,3,4-thiadiazol-2-amine;

1-(6-(5-(5-(methylamino)-1,3,4-thiadiazol-2-yl)-1H-indol-3-yl)-2-pyridinyl)-2-pyrrolidinone;

(3R)—N-(5-(3-(2-fluorophenyl)-1H-indol-5-yl)-1,3,4-thiadiazol-2-yl)-3-piperidinamine;

5-(3-(6-ethoxy-2-pyridinyl)-1H-indol-5-yl)-N-methyl-1,3,4-thiadiazol-2-amine;

5-(3-(2-(4-methyl-1H-imidazol-1-yl)-1,3-thiazol-4-yl)-1H-indol-5-yl)-1,3,4-thiadiazol-2-amine;

5-(3-(1H-indazol-6-yl)-1H-indol-5-yl)-1,3,4-thiadiazol-2-amine;

N,N-dimethyl-6-(5-(5-(methylamino)-1,3,4-thiadiazol-2-yl)-1H-indol-3-yl)-2-pyrazinamine;

5-(3-(6-(1-piperidinyl)-2-pyridinyl)-1H-indol-5-yl)-1,3,4-thiadiazol-2-amine;

5-(3-(6-(cyclohexyloxy)-2-pyridinyl)-1H-indol-5-yl)-1,3,4-thiadiazol-2-amine;

5-(3-(6-(3-methylpiperidin-1-yl)pyridin-2-yl)-1H-indol-5-yl)-1,3,4-thiadiazol-2-amine;

5-(3-(6-(4-methyl-1-piperidinyl)-2-pyridinyl)-1H-indol-5-yl)-1,3,4-thiadiazol-2-amine;

5-(3-(6-(1-pyrrolidinyl)-2-pyridinyl)-1H-indol-5-yl)-1,3,4-thiadiazol-2-amine;

1-(4-(5-(5-amino-1,3,4-thiadiazol-2-yl)-1H-indol-3-yl)-1,3-thiazol-2-yl)-2(1H)-pyridinone;

5-(3-(6-(cyclobutyloxy)-2-pyridinyl)-1H-indol-5-yl)-N-methyl-1,3,4-thiadiazol-2-amine;

5-(3-(5-(4-methyl-1-piperazinyl)-2-pyrazinyl)-1H-indol-5-yl)-1,3,4-thiadiazol-2-amine;

1-(5-(3-(2-fluorophenyl)-1H-indol-5-yl)-1,3,4-thiadiazol-2-yl)pyrrolidin-3-amine;

5-(3-(2-fluorophenyl)-1H-indol-5-yl)-N-(2-(piperidin-2-yl)ethyl)-1,3,4-thiadiazol-2-amine;

5-(3-(6-(3-methyl-1H-pyrazol-1-yl)-2-pyridinyl)-1H-indol-5-yl)-1,3,4-thiadiazol-2-amine;

5-(3-(6-(1H-pyrazol-1-yl)-2-pyridinyl)-1H-indol-5-yl)-1,3,4-thiadiazol-2-amine;

1-(6-(5-(5-amino-1,3,4-thiadiazol-2-yl)-1H-indol-3-yl)-2-pyridinyl)-2-piperidinone;

N-methyl-5-(3-(2-(4-methyl-1H-imidazol-1-yl)-1,3-thiazol-4-yl)-1H-indol-5-yl)-1,3,4-thiadiazol-2-amine;

N-methyl-5-(3-(6-(2-methyl-1H-imidazol-1-yl)-2-pyridinyl)-1H-indol-5-yl)-1,3,4-thiadiazol-2-amine;

5-(3-(2-fluorophenyl)-1H-indol-5-yl)-N-(1H-indol-5-ylmethyl)-1,3,4-thiadiazol-2-amine;

5-(3-(6-(trifluoromethyl)-2-pyridinyl)-1H-indol-5-yl)-1,3,4-thiadiazol-2-amine;

5-(3-(2-fluorophenyl)-1H-indol-5-yl)-N-(1H-indol-4-ylmethyl)-1,3,4-thiadiazol-2-amine;

6-(5-(5-amino-1,3,4-thiadiazol-2-yl)-1H-indol-3-yl)-2-pyridinecarbonitrile;

5-(3-(2-(2-methylpiperidin-1-yl)thiazol-4-yl)-1H-indol-5-yl)-1,3,4-thiadiazol-2-amine;

5-(3-(2,2-dimethyl-2,3-dihydro-1-benzofuran-6-yl)-1H-indol-5-yl)-N-methyl-1,3,4-thiadiazol-2-amine;

6'-(5-(5-amino-1,3,4-thiadiazol-2-yl)-1H-indol-3-yl)-2H-1,2'-bipyridin-2-one;

5-(3-(2-fluorophenyl)-1H-indol-5-yl)-N-methyl-1,3,4-thiadiazol-2-amine;

N-methyl-5-(3-(3-quinolinyl)-1H-indol-5-yl)-1,3,4-thiadiazol-2-amine;

N-methyl-5-(3-(1H-pyrazol-4-yl)-1H-indol-5-yl)-1,3,4-thiadiazol-2-amine;

4-(5-(5-amino-1,3,4-thiadiazol-2-yl)-1H-indol-3-yl)-2-pyridinamine;

1-(5-(3-(2-fluorophenyl)-1H-indol-5-yl)-1,3,4-thiadiazol-2-yl)-4-piperidinamine;

5-(3-(5-(1-methylethoxy)-2-pyrazinyl)-1H-indol-5-yl)-1,3,4-thiadiazol-2-amine;

N-(3-(((5-(3-(2-fluorophenyl)-1H-indol-5-yl)-1,3,4-thiadiazol-2-yl)amino)methyl)phenyl)acetamide;

1-(6-(5-(5-(methylamino)-1,3,4-thiadiazol-2-yl)-1H-indol-3-yl)-2-pyridinyl)-2-piperidinone;

N-(3-(((5-(3-(2-fluorophenyl)-1H-indol-5-yl)-1,3,4-thiadiazol-2-yl)amino)methyl)phenyl)-2-methoxyacetamide;

5-(5-(5-amino-1,3,4-thiadiazol-2-yl)-1H-indol-3-yl)-N-ethyl-N-methyl-2-pyrazinamine;

5-(3-(2,4-difluorophenyl)-1H-indol-5-yl)-N-((2,3-dimethyl-1H-indol-5-yl)methyl)-1,3,4-thiadiazol-2-amine;

5-(3-(2,6-difluorophenyl)-1H-indol-5-yl)-N-methyl-1,3,4-thiadiazol-2-amine;

N-methyl-5-(3-(4-pyridinyl)-1H-indol-5-yl)-1,3,4-thiadiazol-2-amine;

5-(3-(5-(1-pyrrolidinyl)-2-pyrazinyl)-1H-indol-5-yl)-1,3,4-thiadiazol-2-amine;

N-methyl-5-(3-(3-pyridinyl)-1H-indol-5-yl)-1,3,4-thiadiazol-2-amine;

6-(5-(5-amino-1,3,4-thiadiazol-2-yl)-1H-indol-3-yl)-2-pyridinamine;

6'-(5-(5-(methylamino)-1,3,4-thiadiazol-2-yl)-1H-indol-3-yl)-2H-1,2'-bipyridin-2-one;

5-(3-(3-aminophenyl)-1H-indol-5-yl)-N-methyl-1,3,4-thiadiazol-2-amine;

N-(4-(((5-(3-(2,4-difluorophenyl)-1H-indol-5-yl)-1,3,4-thiadiazol-2-yl)amino)methyl)phenyl)acetamide;

5-(3-(5-fluoro-6-methyl-2-pyridinyl)-1H-indol-5-yl)-1,3,4-thiadiazol-2-amine;

5-(3-(5-(4-morpholinyl)-2-pyrazinyl)-1H-indol-5-yl)-1,3,4-thiadiazol-2-amine;

5-(3-(5-butoxy-2-pyrazinyl)-1H-indol-5-yl)-1,3,4-thiadiazol-2-amine;

1-(5-(5-(5-amino-1,3,4-thiadiazol-2-yl)-1H-indol-3-yl)-2-pyrazinyl)-2-pyrrolidinone;

5-(3-(5-(cyclopentyloxy)-2-pyrazinyl)-1H-indol-5-yl)-1,3,4-thiadiazol-2-amine;

N-methyl-5-(3-(1H-pyrazol-5-yl)-1H-indol-5-yl)-1,3,4-thiadiazol-2-amine;

5-(3-(6-fluoro-2-pyridinyl)-1H-indol-5-yl)-N-methyl-1,3,4-thiadiazol-2-amine;

N-benzyl-5-(3-(2-fluorophenyl)-1H-indol-5-yl)-1,3,4-thiadiazol-2-amine;

N-methyl-5-(3-phenyl-1H-indol-5-yl)-1,3,4-thiadiazol-2-amine;

5-(3-(2,4-difluorophenyl)-1H-indol-5-yl)-N-(3-(methylamino)benzyl)-1,3,4-thiadiazol-2-amine;
5-(3-(2-(3-furanyl)-1,3-thiazol-4-yl)-1H-indol-5-yl)-N-methyl-1,3,4-thiadiazol-2-amine;
N-methyl-5-(3-(3-(trifluoromethyl)phenyl)-1H-indol-5-yl)-1,3,4-thiadiazol-2-amine;
6-(5-(5-amino-1,3,4-thiadiazol-2-yl)-1H-indol-3-yl)-2-pyridinol;
5-(3-(2,2'-bithiophen-5-yl)-1H-indol-5-yl)-N-methyl-1,3,4-thiadiazol-2-amine;
5-(3-(5-(3-methyl-1H-pyrazol-1-yl)-2-pyrazinyl)-1H-indol-5-yl)-1,3,4-thiadiazol-2-amine;
N-methyl-5-(3-(3-(trifluoromethoxy)phenyl)-1H-indol-5-yl)-1,3,4-thiadiazol-2-amine;
5-(3-(3-methoxyphenyl)-1H-indol-5-yl)-N-methyl-1,3,4-thiadiazol-2-amine;
5-(3-(6-(1-piperidinyl)-2-pyrazinyl)-1H-indol-5-yl)-1,3,4-thiadiazol-2-amine;
5-(3-(6-(3,3-difluoro-1-pyrrolidinyl)-2-pyrazinyl)-1H-indol-5-yl)-1,3,4-oxadiazol-2-amine;
5-(3-(1-(2-methylpropyl)-1H-pyrazol-4-yl)-1H-indol-5-yl)-1,3,4-oxadiazol-2-amine;
5-(3-(1-(2-(4-morpholinyl)ethyl)-1H-pyrazol-4-yl)-1H-indol-5-yl)-1,3,4-oxadiazol-2-amine;
5-(3-(1-(2-methylpropyl)-1H-pyrazol-4-yl)-1H-pyrrolo[3,2-b]pyridin-5-yl)-1,3,4-oxadiazol-2-amine;
5-(3-(6-(4-morpholinyl)-2-pyridinyl)-1H-indol-5-yl)-1,3,4-thiadiazole-2-carboxamide;
5-(3-(5-(4-morpholinylcarbonyl)-3-pyridinyl)-1H-indol-5-yl)-1,3,4-oxadiazol-2-amine;
N-methyl-5-(3-(4-(4-methyl-1-piperazinyl)-2-pyrimidinyl)-1H-indol-5-yl)-1,3,4-thiadiazol-2-amine;
5-(3-(2-(4-morpholinyl)-4-pyrimidinyl)-1H-indol-5-yl)-1,3,4-thiadiazol-2-amine;
N-methyl-5-(3-(6-(4-morpholinyl)-2-pyridinyl)-1H-indol-5-yl)-1,3,4-thiadiazol-2-amine;
N-methyl-5-(3-(4-(4-morpholinyl)-2-pyrimidinyl)-1H-indol-5-yl)-1,3,4-thiadiazol-2-amine;
N-methyl-5-(3-(4-(1-piperidinyl)-2-pyrimidinyl)-1H-indol-5-yl)-1,3,4-thiadiazol-2-amine;
5-(3-(6-quinoxalinyl)-1H-indol-5-yl)-1,3,4-thiadiazol-2-amine;
5-(5-(methylsulfonyl)-1,3,4-thiadiazol-2-yl)-3-(6-(4-morpholinyl)-2-pyridinyl)-1H-indole;
5-(5-(methylsulfanyl)-1,3,4-thiadiazol-2-yl)-3-(6-(4-morpholinyl)-2-pyridinyl)-1H-indole;
5-(3-(6-(4-fluorophenyl)-2-pyrazinyl)-1H-indol-5-yl)-1,3,4-oxadiazol-2-amine;
5-(3-(6-(3-chlorophenyl)-2-pyrazinyl)-1H-indol-5-yl)-1,3,4-oxadiazol-2-amine;
5-(3-(6-(4-morpholinyl)-2-pyridinyl)-1H-indol-5-yl)-1,3-thiazol-2-amine;
6-(5-(5-amino-1,3,4-thiadiazol-2-yl)-1H-indol-3-yl)-N-(1-methylethyl)-2-pyrazinamine;
6-(5-(5-amino-1,3,4-thiadiazol-2-yl)-1H-indol-3-yl)-N-(cyclopropylmethyl)-2-pyrazinamine;
5-(3-(6-(1-piperidinyl)-2-pyrazinyl)-1H-indol-5-yl)-1,3,4-oxadiazol-2-amine;
6-(5-(5-amino-1,3,4-thiadiazol-2-yl)-1H-indol-3-yl)-N-cyclohexyl-2-pyrazinamine;
5-(3-(6-(4-morpholinyl)-2-pyrazinyl)-1H-indol-5-yl)-1,3,4-oxadiazol-2-amine;
5-(3-(6-methoxy-2-(1-methylethoxy)-4-pyrimidinyl)-1H-indol-5-yl)-1,3,4-thiadiazol-2-amine;
5-(3-(7,7-dimethyl-6,7-dihydro-5H-pyrrolo[2,3-b]pyrazin-2-yl)-1H-indol-5-yl)-1,3,4-thiadiazol-2-amine;
6-(5-(5-amino-1,3,4-thiadiazol-2-yl)-1H-indol-3-yl)-N-(1-methylethyl)-2-pyridinamine;
5-(3-(6-(2,2,2-trifluoro-1-methylethoxy)-2-pyrazinyl)-1H-indol-5-yl)-1,3,4-thiadiazol-2-amine;
5-(3-(6-methoxy-2-pyrazinyl)-1H-indol-5-yl)-1,3,4-thiadiazol-2-amine;
5-(3-(2,6-dimethoxy-4-pyrimidinyl)-1H-indol-5-yl)-1,3,4-thiadiazol-2-amine;
6-(5-(5-amino-1,3,4-thiadiazol-2-yl)-1H-indol-3-yl)-N-(cyclopropylmethyl)-2-pyridinamine;
6-(5-(5-amino-1,3,4-thiadiazol-2-yl)-1H-indol-3-yl)-N-cyclohexyl-2-pyridinamine;
5-(3-(5-methoxy-3-pyridinyl)-1H-indol-5-yl)-1,3,4-thiadiazol-2-amine;
5-(3-(6-fluoro-2-pyridinyl)-1H-indol-5-yl)-1,3,4-thiadiazol-2-amine;
6-(5-(5-amino-1,3,4-thiadiazol-2-yl)-1H-indol-3-yl)-2-pyrazinamine;
6-(5-(5-amino-1,3,4-oxadiazol-2-yl)-1H-indol-3-yl)-N-(cyclopropylmethyl)-2-pyrazinamine;
6-(5-(5-amino-1,3,4-oxadiazol-2-yl)-1H-indol-3-yl)-N-(1-methylethyl)-2-pyrazinamine;
5-(3-(6-cyclopropyl-2-pyrazinyl)-1H-indol-5-yl)-1,3,4-oxadiazol-2-amine;
5-(3-(6-((3R)-3-piperidinyloxy)-2-pyrazinyl)-1H-indol-5-yl)-1,3,4-oxadiazol-2-amine;
5-(3-(6-(1-methyl-1H-pyrazol-4-yl)-2-pyrazinyl)-1H-indol-5-yl)-1,3,4-oxadiazol-2-amine;
5-(3-(2-fluoro-5-(1-methylethoxy)phenyl)-1H-indol-5-yl)-1,3,4-oxadiazol-2-amine;
5-(3-(2-fluorophenyl)-1H-indol-5-yl)-1,3,4-oxadiazol-2-amine;
5-(3-(6-chloro-2-pyrazinyl)-1H-indol-5-yl)-1,3,4-oxadiazol-2-amine;
5-(3-(3-(1-methylethoxy)phenyl)-1H-indol-5-yl)-1,3,4-oxadiazol-2-amine;
5-(3-(5-ethoxy-2-pyrazinyl)-1H-indol-5-yl)-1,3,4-oxadiazol-2-amine; or
5-(3-(6-(1-methylethoxy)-2-pyridinyl)-1H-indol-5-yl)-1,3,4-oxadiazol-2-amine.

Another aspect of the invention relates to a pharmaceutical composition comprising a compound of formula I and Ia and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of cancer.

The compounds of this invention may have in general several asymmetric centers and are typically depicted in the form of racemic mixtures. This invention is intended to encompass racemic mixtures, partially racemic mixtures and separate enantiomers and diasteromers.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2H$ and $^3H$, carbon, such as $^{11}C$, $^{13}C$ and $^{14}C$, chlorine, such as $^{38}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the present invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof, Unless otherwise specified, the following definitions apply to terms found in the specification and claims:

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3, 4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

"Heterocycle" means a ring comprising at least one carbon atom and at least one other atom selected from N, O and S. Examples of heterocycles that may be found in the claims include, but are not limited to, the following:

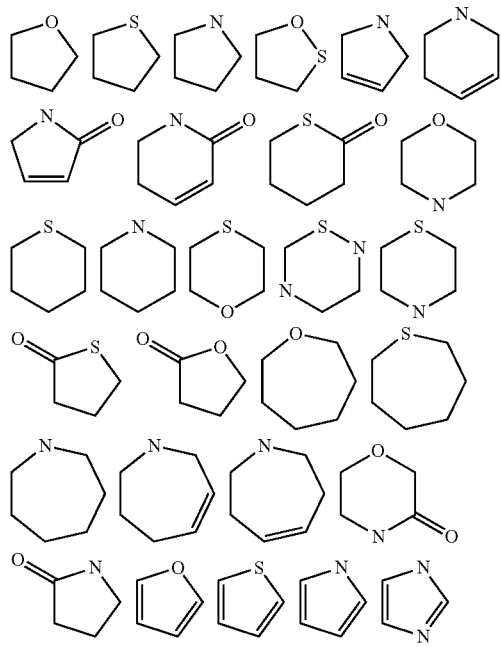

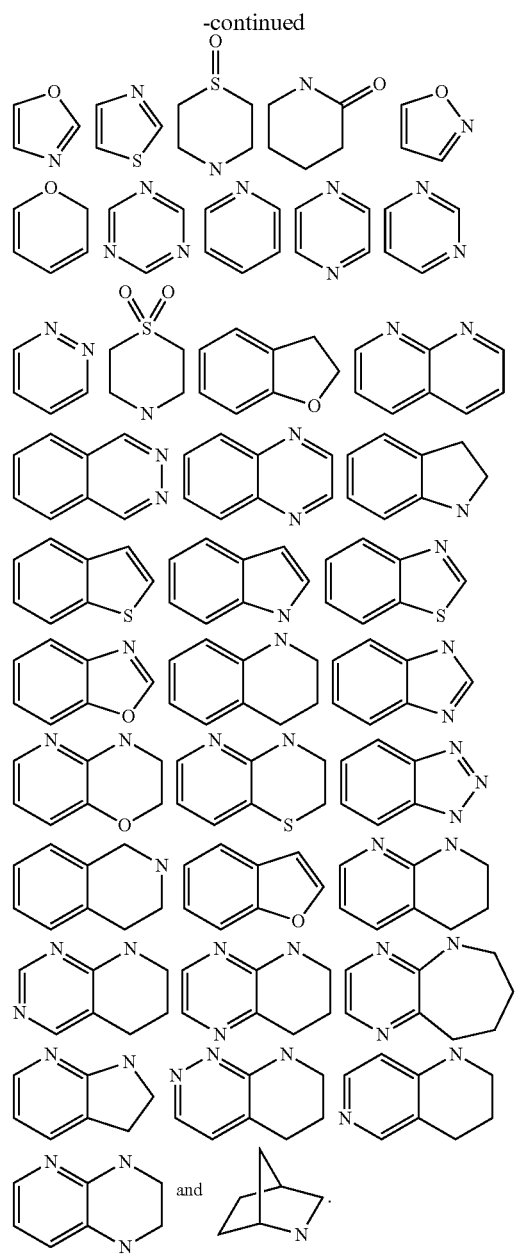

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "alkoxycarbonyl" denotes an ester group, containing an alkoxy substituted carbonyl.

The term "aminocarbonyl" denotes an amide group of the formula —C(=O)NH$_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical. More preferred are phenylaminocarbonyl and substituted phenylaminocarbonyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylamino" embraces "N-alkylamino" and "N,N-dialkylamino" where amino groups are substituted with one alkyl radical and with two independent alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The arylamino radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "cycloalkylamino" denotes amino groups which have been substituted with one or two cycloalkyl radicals, such as N-cyclohexylamino. The cycloalkylamino radicals may be further substituted on the cycloalkyl ring portion of the radical.

The term "cycloalkylalkylamino" denotes amino groups which have been substituted with one or two cycloalkylalkyl radicals, such as N-cyclopropylamino. The cycloalkylalkylamino radicals may be further substituted on the cycloalkyl ring portion of the radical.

The term "aralkylamino" denotes amino groups which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups which have been substituted with one aralkyl and one alkyl radical, or one aryl and one alkyl radical, respectively, to an amino group.

The term "alkylcarbonylamino" denotes amino radicals independently substituted with an alkylcarbonyl radicals, respectively. More preferred are "lower alkylcarbonylamino" having lower alkyl radicals as described above attached to an carbonylamino radical.

The term "arylcarbonylamino" denotes amino radicals independently substituted with an arylcarbonyl radicals, respectively. More preferred are "phenylcarbonylamino".

The term "aralkylcarbonylamino" denotes amino radicals independently substituted with an aralkylcarbonyl radicals, respectively. More preferred are "lower aralkylcarbonylamino" having lower alkyl radicals as described above attached to an carbonylamino radical. More preferred are benzylcarbonylamino radicals.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

"Benzo group", alone or in combination, means the divalent radical $C_4H_4$=, one representation of which is —CH=CH—CH=CH—, that when vicinally attached to another ring forms a benzene-like ring—for example tetrahydronaphthylene, indole and the like.

The term "oxo" represents the groups =O (as in carbonyl).

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups, and the like, for example as illustrated in the following examples:

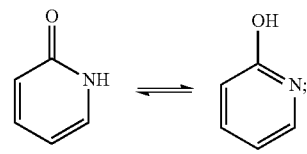 [SMILES: O=c1cccc[nH]1 ; Oc1ccccn1]

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Utility and Methods of Use

An aspect of the present invention is a method for inhibiting Pim kinase activity in a cell, comprising contacting the cell with an effective amount of a compound of Formulas I-II and Ia-IIa.

Another aspect of the present invention provides a method for treating a condition by modulation of Pim kinase activity comprising administering to a patient in need of such treatment an effective amount of a compound of Formulas I-II and Ia-IIa.

Another embodiment of the present invention provides a method for treating a cancer disorder in a patient, comprising administering to the patient a composition comprising an amount of a compound of Formulas I-II and Ia-IIa effective to inhibit Pim kinase activity in the patient.

Another embodiment of the present invention provides a method for treating a cancer disorder in a patient, wherein the cancer is prostate, head and neck or lymphoma, comprising administering to the patient a composition comprising an amount of a compound of Formulas I-II and Ia-IIa effective to inhibit Pim kinase activity in the patient.

Another aspect of the present invention provides the use of any one of the compounds of Formulas I-II and Ia-IIa in the manufacture of a medicament for the treatment of cancer.

Administration and Pharmaceutical Compositions

In general, the compounds of this invention can be administered in a therapeutically effective amount by any of the accepted modes of administration for agents that serve similar utilities. The actual amount of a compound of this invention, i.e., the active ingredient, depends upon numerous factors, such as the severity of the disease to be treated, the age and relative health of the subject, the potency of the compound used, the route and form of administration, and other factors.

Therapeutically effective amounts of compounds of formulas I-II and Ia-IIa may range from approximately 0.1-1000 mg per day.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors, such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compounds of the present invention in combination with at least one pharmaceutically acceptable excipient. Acceptable excipients are non-toxic, aid administration, and do not adversely affect the therapeutic benefit of the compounds of the present invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, Gennaro, A. R. (Mack Publishing Company, 18th ed., 1995).

The level of the compound in a formulation can vary within the full range employed by those skilled in the art. Typically, the formulation contains, on a weight percent (wt %) basis, from about 0.01-99.99 wt % of a compounds of the present invention based on the total formulation, with the balance being one or more suitable pharmaceutical excipients. Preferably, the compound is present at a level of about 1-80 wt %.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formulas I-II and Ia-IIa may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other agents, such as other kinase inhibitors including CDK inhibitors, mTor inhibitors, Pi3k inhibitors, and Aurora kinase inhibitors.

Synthetic Methods

The compounds of the invention can be prepared according to the following procedures of Schemes 1-10, wherein the substituents are as defined for Formulas I-II and Ia-IIa, above, except where noted.

The following abbreviations may be used herein:
Ac$_2$O acetic anhydride
ACN, MeCN acetonitrile
A-phos bis[(di-tert-butylphenyl phosphine)]palladium dichloride
Amphos (2-diphenylphosphinoethyl)trimethylammonium nitrate
aq aqueous
ATP adenosine 5'-triphosphate
BOP (1H-benzo[d][1,2,3]triazol-1-yloxy)tris(dimethylamino)-phosphonium hexafluorophosphate(V)
nBuLi n-butyllithium
Calcd or Calc'd calculated
CDI 1,1'-carbonyldiimidazole
CDCl$_3$ chloroform-deuterated
CHCl$_3$ chloroform
Conc. concentrated
Cs$_2$CO$_3$ cesium carbonate
CuI copper (I) iodide
DCM dichloromethane DIPEA diisopropylethyl amine
DMAP dimethyl aminopyridine
DME dimethoxyl ethyl ether
DMF N,N-dimethylformamide
DMSO dimethyl sulfoxide
DMSO-d6 deuterated dimethyl sulfoxide
dppf 1,1'-bis(diphenylphosphino)ferrocene
DTT dithiothreitol
EDC, EDC-HCl N1-((ethylimino)methylene)-N3,N3-dimethylpropane-1,3-diamine hydrochloride
ESI electrospray ionization
$Et_2O$ diethyl ether
$Et_3N$ triethylamine
EtOAc ethyl acetate
EtOH ethyl alcohol
FBS fetal bovine serum
g grams
h hour
HBTU-2-(1H-benzotriazole-1-yl)-1,1,3,3-tetramethylaminium hexafluorophosphate
HATU O-(7-azobenzotriazol-1-yl)-1,1,3,3-tetramethyluronium hexafluorophosphate
HCl hydrochloric acid
$HCO_2H$ formic acid
$H_2NNH_2$ hydrazine
$H_2O$ water
$H_2O_2$ hydrogen peroxide
Hex hexanes
HOAc acetic acid
HOBt 1-hydroxybenzotriazole
HPLC high pressure liquid chromatography
$I_2$ iodine
IPA or iPrOH or iPr isopropyl alcohol
$iPr_2NEt$ N-ethyl diisopropylamine
KF potassium fluoride
KOAc potassium hydroxyacetate
KOH potassium hydroxide
$K_2CO_3$ potassium carbonate
$K_3PO_4$ potassium phosphate tribasic
L liter
LCMS, LC-MS or LC/MS liquid chromatography mass spectroscopy
LDA lithium diisopropylamide
m/z mass divided by charge
Me- methyl
MTBE methyl tert-butyl ether
$(Me_3Sn)_2$ hexamethylditin
MeI iodomethane
$Me_2SO_4$ dimethyl sulphate
MeOH methyl alcohol
MeOH-d deuterated methanol
mg milligrams
min minutes
mL milliliters
$MgSO_4$ magnesium sulfate
MS mass spectra
MsCl mesylchloride
$N_2$ nitrogen
$NH_3$ ammonia
$NH_2NH_2$ hydrazine, hydrazine hydrate
$NH_4OH$ ammonium hydroxide
$NH_4Cl$ ammonium chloride
NaH sodium hydride
NaOH sodium hydroxide
$Na_2CO_3$ sodium carbonate
$NaHCO_3$ sodium bicarbonate
$Na_2SO_4$ sodium sulfate $NaWO_4$ sodium tungstate
NBS N-bromosuccinimide
NMP 1-methyl-2-pyrrolidinone
NMR nuclear magnetic resonance
$Pd(PPh_3)_4$ tetrakistriphenylphosphinepalladium (0)
$Pd_2(dba)_3$ tris(dibenzylideneacetone)dipalladium (0)
$Pd(dppf)Cl_2$ [(1,1-bis(diphenylphosphino)ferrocene]dichloropalladium(II)
$PdCl_2$ palladium chloride
P protecting group
Pos. ion positive ion
py or pyr pyridine
PyBOP (benzotriazol-1-yloxy)tripyrrolidinophosphonium hexafluorophosphate
rt or RT room temperature
Sat. saturated
TFA trifluoroacetic acid
TFAA trifluoroacetic anhydride
THF tetrahydrofuran
THP tetrahydropyran
TMS tetramethylsilane
Ts or tosyl para-toluene sulfonyl
TSA p-toluenesulfonic acid
TsCl para-toluene sulfonyl chloride
wt weight
Xantphos 9,9-dimethyl-4,5-bis(diphenylphosphino)xanthene
Xphos 2-dicyclohexylphosphino-2',4',6'-triisopropylbiphenyl

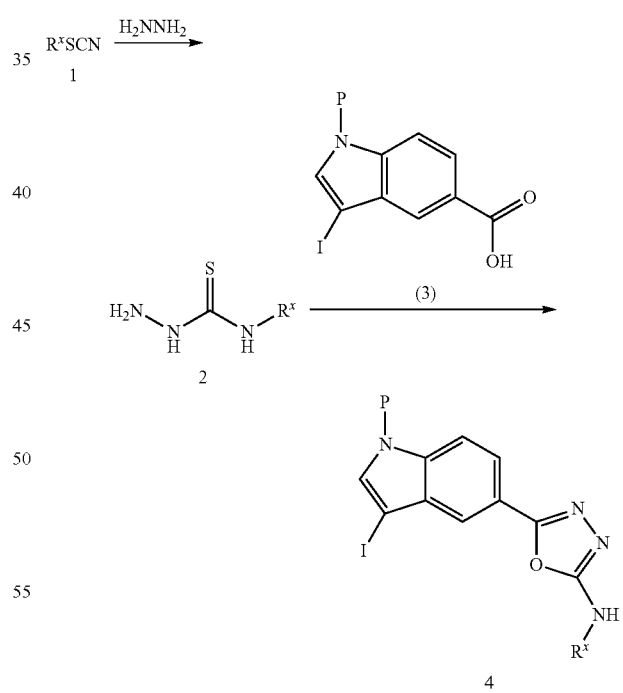

Scheme 1

Oxadiazole substituted indoles 4 (where P is a protecting group such as Tosyl or Boc) can be prepared according to the general method set out in Scheme 1. Treatment of a substituted isothiocyanate 1 with a hydrazine provides the corresponding substituted thioamide 2. The reaction is maintained in an appropriate solvent, such as EtOH. The reaction is maintained at a temperature of about RT. Reaction of the thioamide 2 with a protected indole carboxylic acid 3 in the presence of a coupling reagent, such as EDCI, provides the oxadiazole substituted indoles 4. The reaction is maintained in an appropriate solvent, such as DMF. The reaction is maintained at a temperature above RT, preferably above about 50° C., more preferably at about 80-90° C.

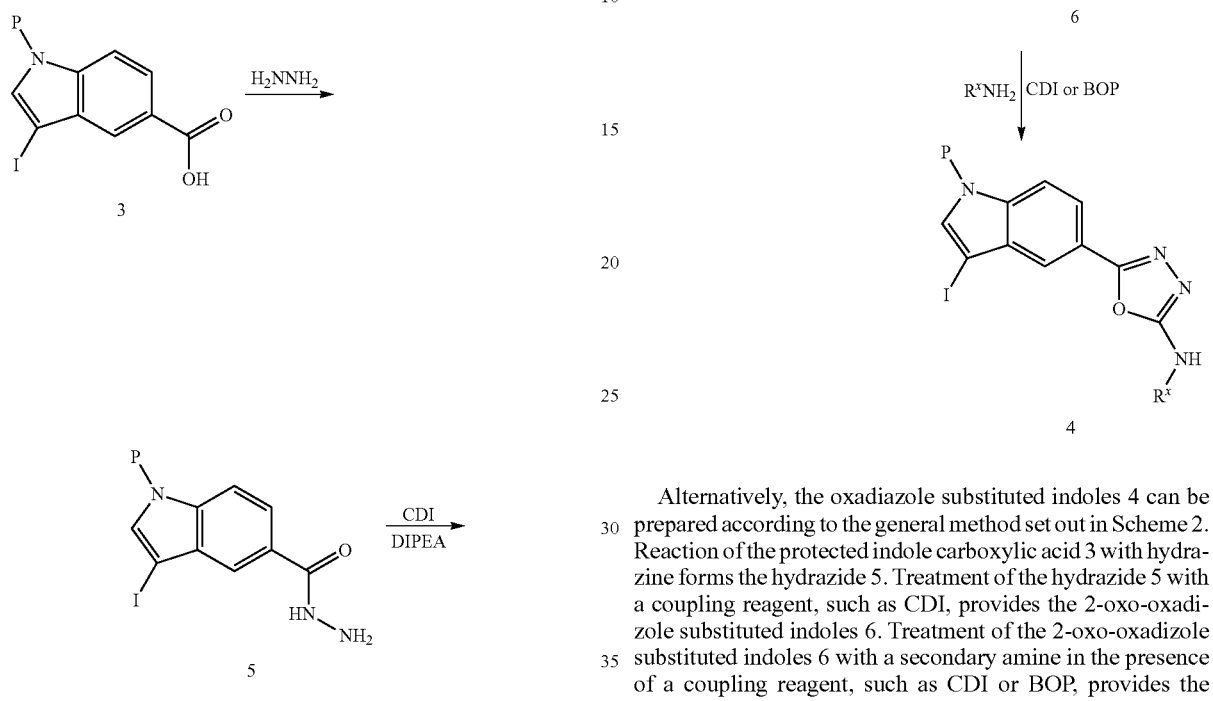

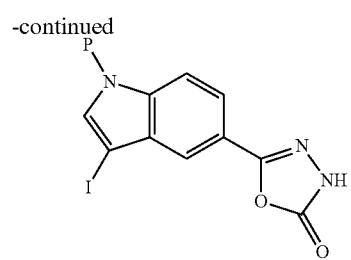

Alternatively, the oxadiazole substituted indoles 4 can be prepared according to the general method set out in Scheme 2. Reaction of the protected indole carboxylic acid 3 with hydrazine forms the hydrazide 5. Treatment of the hydrazide 5 with a coupling reagent, such as CDI, provides the 2-oxo-oxadizole substituted indoles 6. Treatment of the 2-oxo-oxadizole substituted indoles 6 with a secondary amine in the presence of a coupling reagent, such as CDI or BOP, provides the oxadiazole substituted indoles 4.

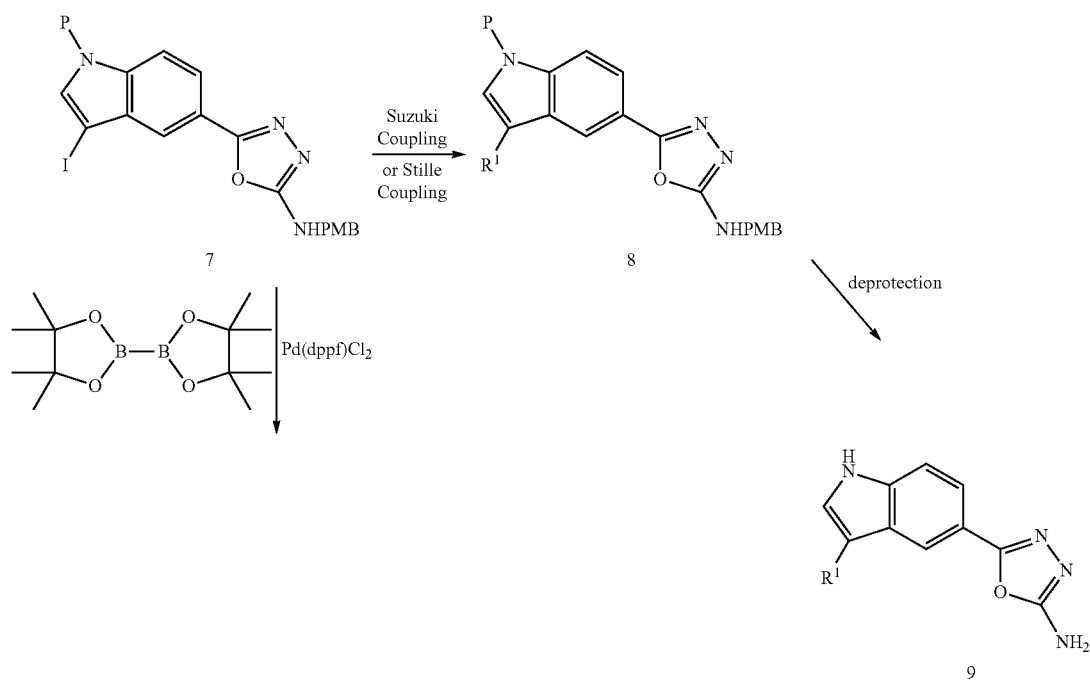

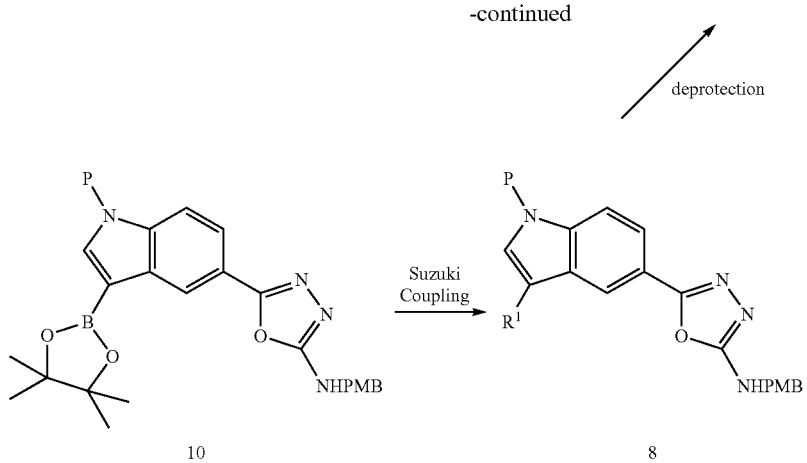

Di-substituted indoles 9 (where R¹ is aryl or heteroaryl) can be prepared according to the general method set out in Scheme 3. Treatment of the protected amine substituted oxadiazole substituted indole 7 with bis(pinacolato)diboron, base such as potassium acetate, and a palladium compound such as Pd(dppf)Cl$_2$, DMF, provides the boronic ester intermediate 10. The reaction was maintained at a temperature above RT, preferably above about 50° C., more preferably at about 90° C. Subsequent Suzuki coupling with aryl halides or heteroaryl halides provides the protected di-substituted indoles 8. Deptrotection provides the di-substituted indoles 9. Alternatively, the protected di-substituted indoles 8 are prepared directly from the protected amine substituted oxadiazole substituted indole 7 through Suzuki coupling or Stille coupling.

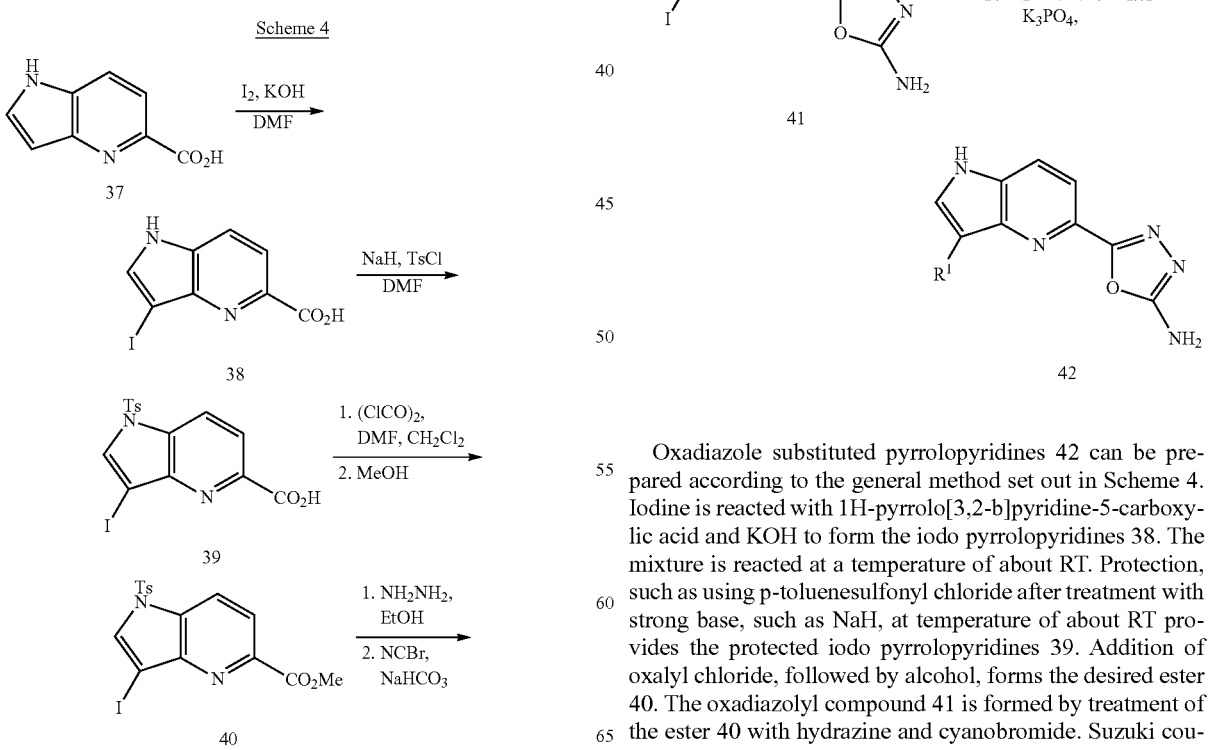

Oxadiazole substituted pyrrolopyridines 42 can be prepared according to the general method set out in Scheme 4. Iodine is reacted with 1H-pyrrolo[3,2-b]pyridine-5-carboxylic acid and KOH to form the iodo pyrrolopyridines 38. The mixture is reacted at a temperature of about RT. Protection, such as using p-toluenesulfonyl chloride after treatment with strong base, such as NaH, at temperature of about RT provides the protected iodo pyrrolopyridines 39. Addition of oxalyl chloride, followed by alcohol, forms the desired ester 40. The oxadiazolyl compound 41 is formed by treatment of the ester 40 with hydrazine and cyanobromide. Suzuki coupling of pyrrolopyridines 41 and R—B(OH)$_2$ provides the desired disubstituted compound 42.

Scheme 5

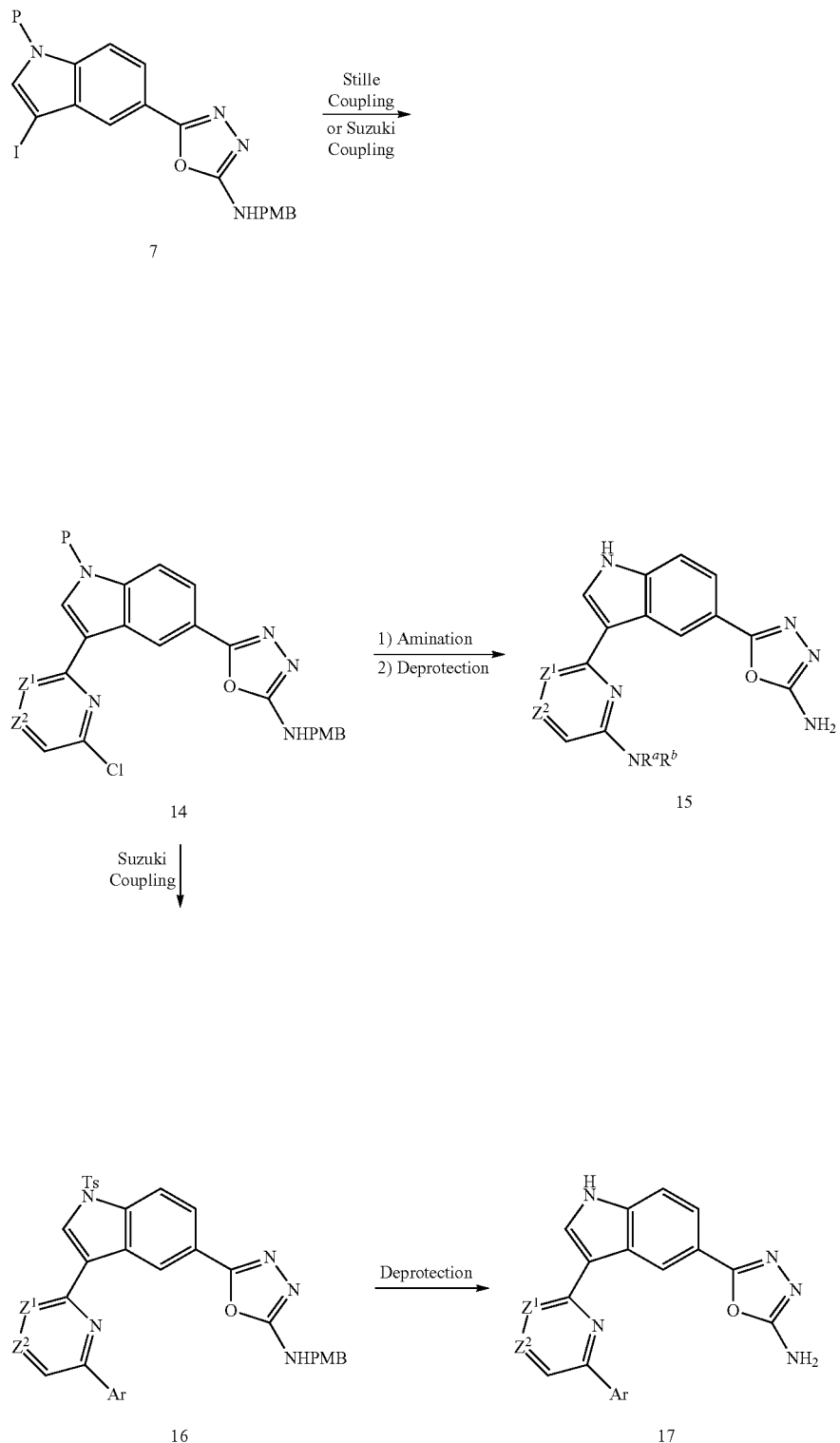

5-(2-Amino-oxadiazol-5-yl)-substituted indoles 15 and 17 can be prepared according to the general method set out in Scheme 5. The protected di-substituted indoles 14 are prepared from the protected amine substituted oxadiazole substituted indole 7 through Suzuki coupling or Stille coupling ($Z^1=Z^2=CH$ or $Z^1=CH$ and $Z^2=N$ or $Z^1=N$ and $Z^2=CH$). Amination followed by deprotection provides the pyridyl, pyrimidinyl and pyrazinyl compounds 15. Alternatively, Suzuki coupling of 14 followed by deprotection provides the pyridyl, pyrimidinyl and pyrazinyl compounds 17.

Scheme 6

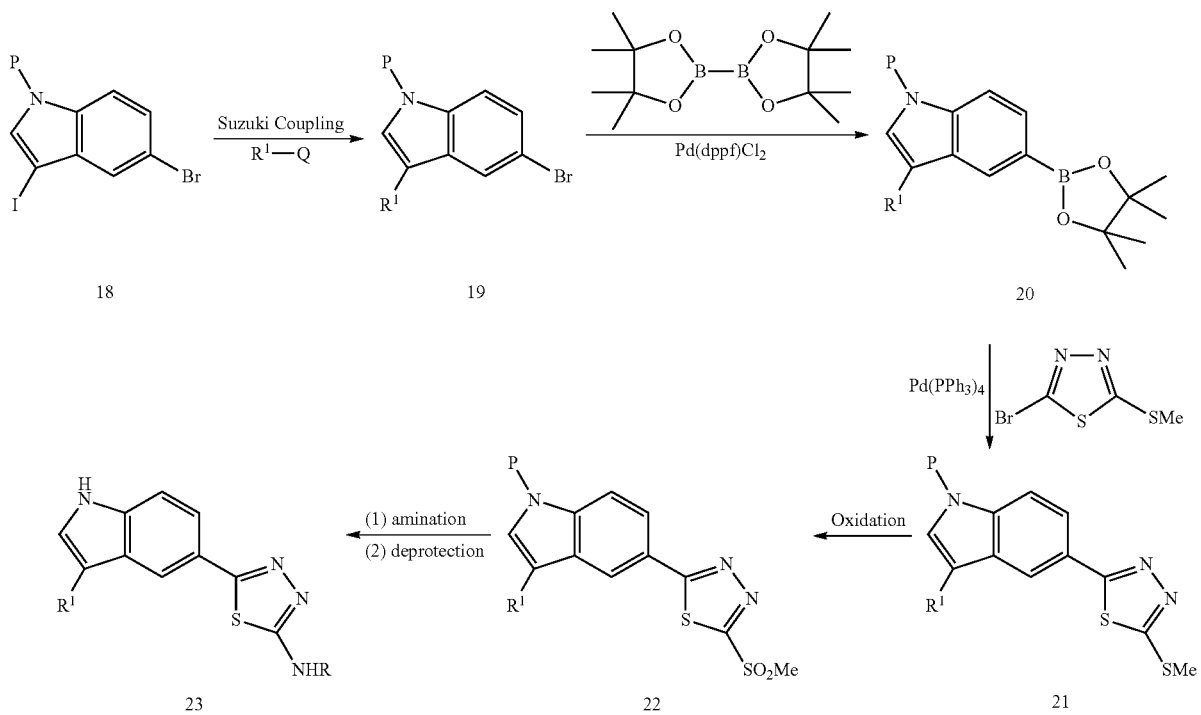

Optionally substituted 5-(2-thiadiazol-5-yl)-indoles can be prepared according to the general method set out in Scheme 6. Suzuki coupling of 3,5-dihalo-indole 18 with aryl boronic acids or esters and heteroaryl boronic acids or esters provides the 3-substituted-indole 19. The boronic ester 20 made following a procedure similar to that described in Scheme 3, is reacted with a halo-thiadiazole to form the 3-aryl-5-(5-methylthio)thiadiazol-2-yl indole 21. Deprotection provides the 5-(5-methylthio)thiadiazol-2-yl indoles of the invention. Oxidation yields the methylsulfonyl compound 22. Deprotection provides the 5-(5-methylsulfonyl)thiadiazol-2-yl indoles of the invention Amination of the methylsulfonyl compound 22, followed by deprotection yields the substituted 5-(2-amino-thiadiazol-5-yl)indoles 23.

Protected indoles 26 can be prepared by the following method shown in Scheme 7. Treatment of a boronic ester 24 with RQ (where Q is bromo), together with a palladium catalyst, such as Pd(dppf)Cl$_2$ and a base, e.g. Na$_2$CO$_3$, in a solvent such as toluene, at a temperature of over 50° C., preferably over about 100° C., and more preferably at about 125° C. provides the desired intermediate 25. Iodination, such as with iodine and NaOH and protection, such as with TsCl, and a base such as NaH, provides the desired protected 3-iodo indoles 26 (P=tosyl).

Scheme 7

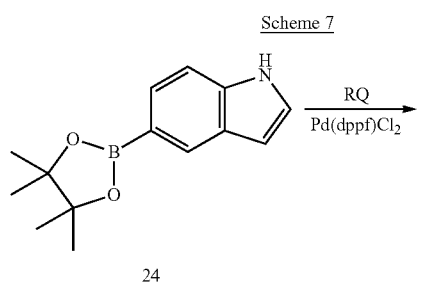

Scheme 8

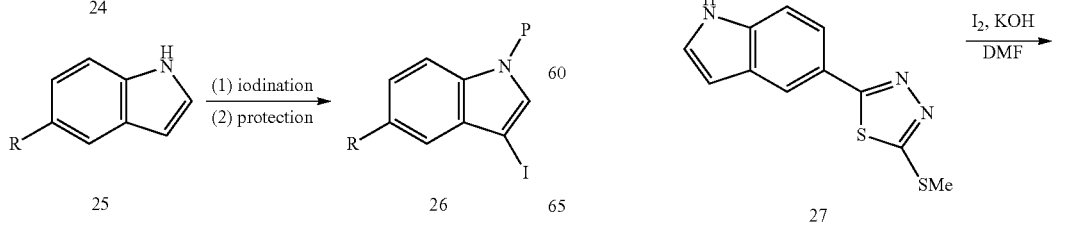

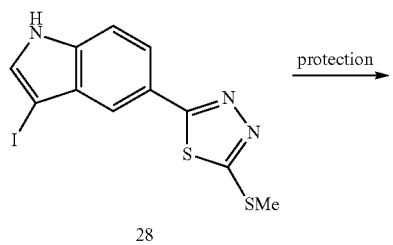

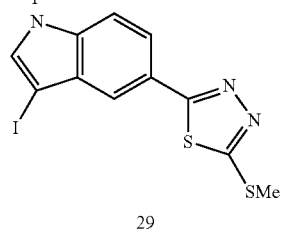

Protected 3-iodo-5-thiadiazole indoles 29 can be prepared by the following method shown in Scheme 8. Treatment of a boronic ester 24 with a bromothiadiazole, together with a palladium catalyst, such as Pd(PPh$_3$)$_4$ and a base, e.g. K$_2$CO$_3$, in a solvent such as toluene, at a temperature of over 50° C., preferably over about 100° C., and more preferably at about 125° C. provides the desired intermediate 27. Iodination and protection, such as with TsCl, and a base such as NaH, provides the desired protected 3-iodo indoles 29 (P=tosyl).

Scheme 9

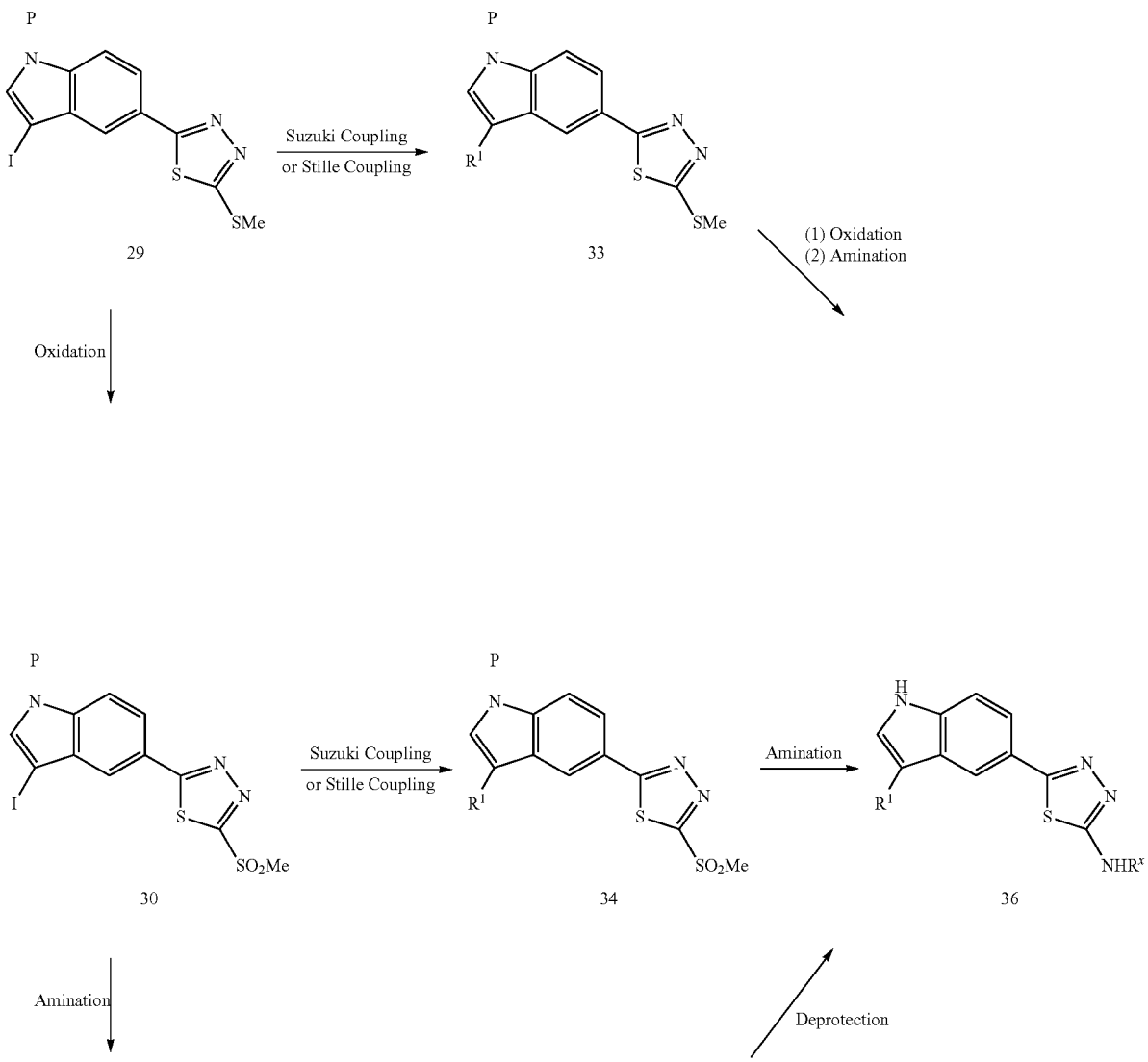

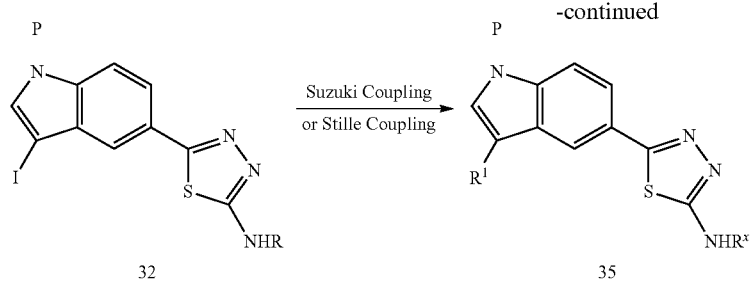

Scheme 9 indicates that the compounds 36 can be prepared from the 3-iodo-indole 29 via several alternative methods. One can first couple with an aryl boronic acids or esters or heteroaryl boronic acids or esters to form the 3-aryl derivative 33. The methylthio function can be converted to an amine 36 through oxidation and amination. Alternatively, the methylthio function of the 3-iodo-indole 29 can be oxidized to the sulfonyl derivative 30 before coupling with an aryl boronic acids or esters or heteroaryl boronic acids or esters and amination to form compound 36. Finally, the sulfonyl derivative 30 can be converted to an amine 32 before coupling with an aryl boronic acids or esters or heteroaryl boronic acids or esters and deprotection to form the desired compound 36.

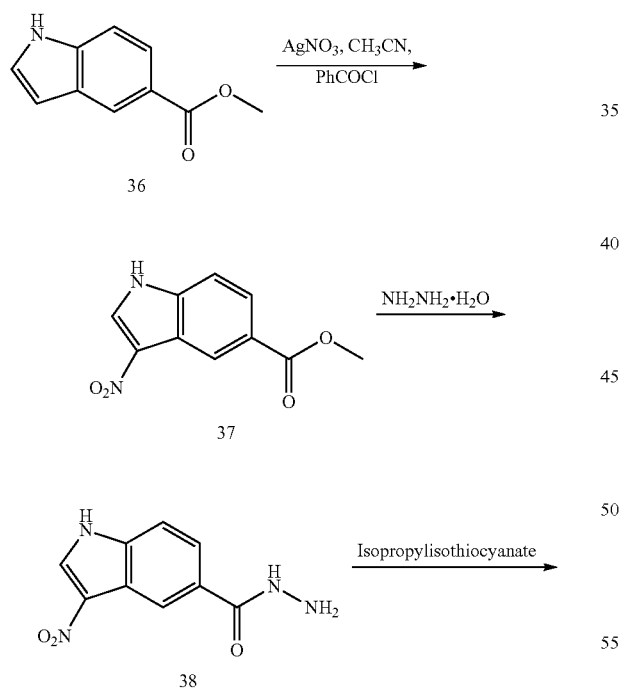

Amide substituted indoles can be prepared as described in Scheme 10. The 1H-indole-5-carboxylic acid methyl ester 36 is added to a solution of AgNO$_3$ and benzoyl chloride at a temperature of about RT to form the nitro derivative 37. The oxadiazole derivative 40 is formed similar to that described in Scheme 1-2. Hydrogenation of the nitro group, such as with Raney-Ni, followed by addition of NH$_2$NH$_2$ at RT affords the amino compound 41. Treatment of the amino group with substituted carboxylic acids together with a coupling reagent, such as EDC.HCl and HOBt at RT gives the desired amides 42.

The starting compounds defined in Schemes 1-10 may also be present with functional groups in protected form if necessary and/or in the form of salts, provided a salt-forming group is present and the reaction in salt form is possible. If so desired, one compound of formulas I-II and Ia-IIa can be converted into another compound of formulas I-II and Ia-IIa or a N-oxide thereof; a compound of formulas I-II and Ia-IIa can be converted into a salt; a salt of a compound of formulas I-II and Ia-IIa can be converted into the free compound or another salt; and/or a mixture of isomeric compounds of formulas I-II and Ia-IIa can be separated into the individual isomers.

N-Oxides can be obtained in a known manner by reacting a compound of formulas I-II and Ia-IIa with hydrogen peroxide or a peracid, e.g. 3-chloroperoxy-benzoic acid, in an inert solvent, e.g. dichloromethane, at a temperature between about −10-35° C., such as about 0° C.-RT.

If one or more other functional groups, for example carboxy, hydroxy, amino, or mercapto, are or need to be protected in a compound of formulas I-II and Ia-IIa or in the synthesis of a compound of formulas I-II and Ia-IIa, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide and Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formulas I-II and Ia-IIa with a salt-forming group may be prepared in a manner known per se. Acid addition salts of compounds of formulas I-II and Ia-IIa may thus be obtained by treatment with an acid or with a suitable anion exchange reagent. A salt with two acid molecules (for example a dihalogenide of a compound of formulas I-II and Ia-IIa) may also be converted into a salt with one acid molecule per compound (for example a monohalogenide); this may be done by heating to a melt, or for example by heating as a solid under a high vacuum at elevated temperature, for example from about 130° C. to about 170° C., one molecule of the acid being expelled per molecule of a compound of formulas I-II and Ia-IIa.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., ethyl acetate, ethers, typically aliphatic ethers, e.g., diethylether, or cyclic ethers, e.g., THF, liquid aromatic hydrocarbons, typically benzene or toluene, alcohols, typically MeOH, EtOH or 1-propanol, 2-propanol, nitriles, typically $CH_3CN$, halogenated hydrocarbons, typically DCM, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formulas I-II and Ia-IIa, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); A. Katritzky and A. Pozharski, Handbook of Heterocyclic Chemistry, $2^{nd}$ Ed. (2001); M. Bodanszky, A. Bodanszky: *The practice of Peptide Synthesis* Springer-Verlag, Berlin Heidelberg 1984; J. Seyden-Penne: *Reductions by the Alumino- and Borohydrides in Organic Synthesis*, $2^{nd}$ Ed., Wiley-VCH, 1997; and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formulas I-II. These detailed descriptions fall within the scope, and serve to exemplify, the above described General Synthetic Procedures which form part of the invention. These detailed descriptions are presented for illustrative purposes only and are not intended as a restriction on the scope of the invention.

EXPERIMENTAL

Unless otherwise noted, all materials were obtained from commercial suppliers and used without further purification. All parts are by weight and temperatures are in degrees centigrade unless otherwise indicated. All microwave assisted reactions were conducted with a Smith Synthesizer™ from Biotage™. All compounds showed NMR spectra consistent with their assigned structures. Melting points were determined on a Buchi apparatus and are uncorrected. MS data was determined by electrospray ionization technique. All examples were purified to >90% purity as determined by high-performance liquid chromatography. Unless otherwise stated, reactions were run at RT.

Analytical Methods:

Unless otherwise indicated, HPLC analyses were run on an Agilent Model 1100 system with an Agilent Technologies Zorbax SB-$C_8$ (5µ) reverse phase column (4.6×150 mm) run at 30° C. with a flow rate of about 1.50 mL/min (Agilent Technologies, Santa Clara, Calif.). The mobile phase used solvent A ($H_2O$/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

LC-MS Methods:

Unless otherwise indicated, samples were run on an Agilent model-1100 LC-MSD system with an Agilent Technologies XDB-$C_8$ (3.5μ) reverse phase column (4.6×75 mm) at 30° C. The flow rate was constant and ranged from about 0.75 mL/min to about 1.0 mL/min. The mobile phase used a mixture of solvent A ($H_2O$/0.1% $HCO_2H$ or TFA) and solvent B (ACN/0.1% $HCO_2H$ or TFA) with a 5 to for a gradient from 10% to 90% solvent B. The gradient was followed by a 0.5 min period 9 min time period to return to 10% solvent B and a 2.5 min 10% solvent B re-equilibration (flush) of the column Preparative HPLC Methods:

Where indicated, compounds of the present invention were purified via reverse phase HPLC using a Gilson (Gilson, Middleton, Wis.) or Shimadzu (Columbia, Md.) workstation utilizing one of the following two protocols: (A) Using a 50×100 mm column (Waters, Externa, C18, 5μ) (Waters, Milford, Mass.) at 50 mL/min. The mobile phase used was a mixture of solvent A ($H_2O$/10 mM ammonium carbonate at pH about 10, adjusted with conc. $NH_4OH$) and solvent B (85:15 ACN/water, 10 mM ammonium carbonate at pH of about 10 adjusted with conc. $NH_4OH$). Each purification run utilized a ≥10 min gradient from 40% to 100% solvent B followed by a 5 min flow of 100% solvent B. The gradient was followed by a 2 min return to 40% solvent B; or (B) Using a Waters 20×50 mm column at 20 mL/min or Phenomenex Gemni 5μ, C18 100×30 mm (Phenomenex, Torrance, Calif.). The mobile phase used was a mixture of solvent A ($H_2O$/0.1% TFA) and solvent B (ACN/0.1% TFA) with a ≥10 min gradient from 5% to 100% solvent B. The gradient is followed by a 2 min return to 5% ACN.

Mass Spectra (MS)

Unless otherwise indicated, all mass spectral data for starting materials, intermediates and/or exemplary compounds are reported as mass/charge (m/z), having an (M+H$^+$) or (M−H$^−$) molecular ion, depending on the inonization mode (positive or negative). The molecular ion reported was obtained by electrospray detection method. Compounds having an isotopic atom, such as bromine and the like, are reported according to the detected isotopic pattern, as appreciated by those skilled in the art.

Example 1

5-(3-(6-(2-methylpiperidin-1-yl)pyrazin-2-yl)-1H-indol-5-yl)-1,3,4-oxadiazol-2-amine

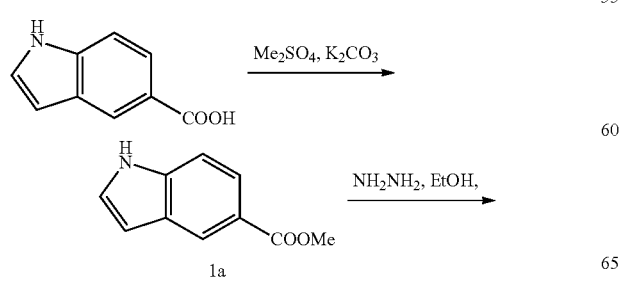

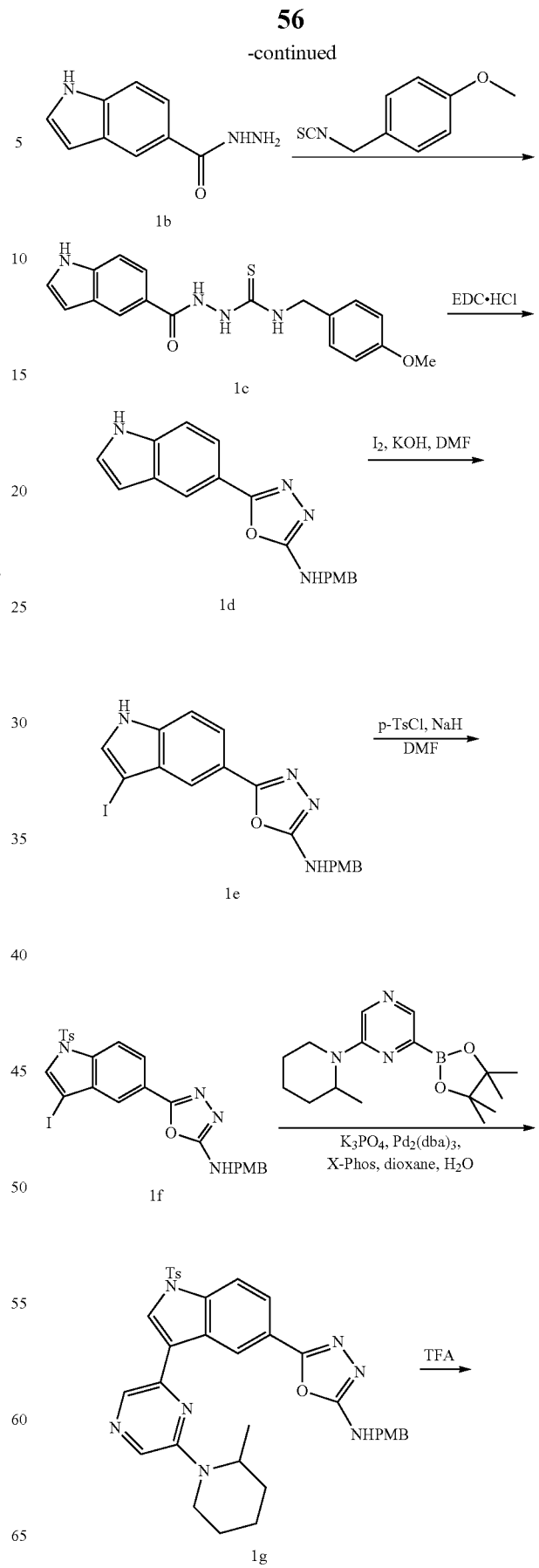

-continued

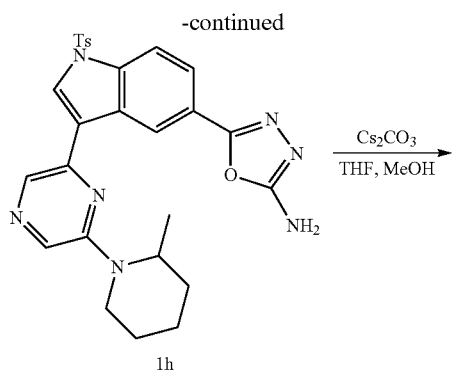

1h

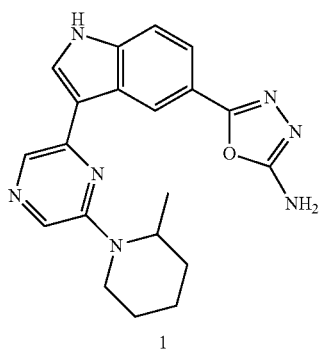

1

Preparation of compound 1a: methyl 1H-indole-5-carboxylate

The solution of 1H-indole-5-carboxylic acid (1.0 g, 6.2 mmol, Aldrich) and $K_2CO_3$ (0.939 g, 6.8 mmol) in DMF (10 mL) was heated to 65° C., and $Me_2SO_4$ (0.78 g, 6.2 mmol) was added dropwise between 65-70° C. over 15 min. The reaction was stirred for 1 h at 80° C. then the mixture was poured into ice/water. The resulting precipitate was collected by filtration and dried in vacuo to give methyl 1H-indole-5-carboxylate (0.91 g, 5.2 mmol, 85.8%). MS (ESI, pos. ion) m/z: 176 (M+1).

Preparation of compound 1b: 1H-indole-5-carbohydrazide

To a solution of methyl 1H-indole-5-carboxylate (0.9 g, 5.142 mmol) in EtOH (10 mL) was added $NH_2NH_2$ (1.8 mL, 38.11 mmol). The reaction was heated at reflux for 12 h. The solvent was removed in vacuo to give a yellow solid, which was recrystallized with 60% EtOAc in n-hexane (10 mL) to afford 1H-indole-5-carbohydrazide (0.7 g, 3.98 mmol, 77.8%). MS (ESI, pos. ion) m/z: 176 (M+1).

Preparation of compound 1c: 2-(1H-indole-5-carbonyl)-N-(4-methoxybenzyl)hydrazinecarbothioamide A solution of 1H-indole-5-carbohydrazide (0.7 g, 3.98 mmol) and 1-isothiocyanatomethyl-4-methoxy-benzene (1.0 g, 5.56 mmol) in EtOH (10 mL) was heated to reflux for 2 h. The solvent was then removed in vacuo and the residue was triturated with EtOH (5 mL) to give 2-(1H-indole-5-carbonyl)-N-(4-methoxybenzyl)-hydrazinecarbothioamide (0.7 g, 2.0 mmol, 51%) as a white solid. MS (ESI, pos. ion) m/z: 355 (M+1).

Preparation of compound 1d: 5-(1H-indol-5-yl)-N-(4-methoxybenzyl)-1,3,4-oxadiazol-2-amine A solution of 2-(1H-indole-5-carbonyl)-N-(4-methoxybenzyl)hydrazinecarbothioamide (0.1 g, 0.284 mmol) and EDC.HCl (0.109 g, 0.586 mmol) in toluene (10 mL) was heated to reflux for 12 h. The mixture was cooled to RT. The supernatant layer was decanted and the sticky material in the bottom was dissolved in EtOAc (20 mL). The organic layer was washed with water, brine, dried, filtered and concentrated to give the crude material. MS (ESI, pos. ion) m/z: 321 (M+1).

Preparation of compound 1e: 5-(3-iodo-1H-indol-5-yl)-N-(4-methoxybenzyl)-1,3,4-oxadiazol-2-amine To a solution of 5-(1H-indol-5-yl)-N-(4-methoxybenzyl)-1,3,4-oxadiazol-2-amine (28.0 g, 87.5 mmol) in DMF (270 mL) was added $I_2$ (24.42 g, 96.25 mmol) followed by KOH (12.27 g, 218.75 mmol). The mixture was stirred at RT for 1 h, then poured into ice with 5% sodium bisulfite. The aqueous layer was extracted with DCM and the combined organic layers were washed with water, dried, filtered and concentrated. The residue was purified with silica gel chromatography (eluting with 2-3% MeOH in DCM) to give 5-(3-iodo-1H-indol-5-yl)-N-(4-methoxybenzyl)-1,3,4-oxadiazol-2-amine (23.2 g, 52.0 mmol, 59.44%). MS (ESI, pos. ion) m/z: 447.0 (M+1); $^1$H-NMR (DMSO-$d_6$) δ 11.87 (s, 1H), 8.22 (t, 1H), 7.69-7.65 (m, 2H), 7.44 (d, J=9 Hz, 2H), 7.34 (s, 1H), 6.92 (d, J=9 Hz, 2H), 5.76 (s, 1H), 4.38 (d, 2H), 3.73 (s, 3H).

Preparation of compound 1f: 5-(3-iodo-1-tosyl-1H-indol-5-yl)-N-(4-methoxybenzyl)-1,3,4-oxadiazol-2-amine To a solution of 5-(3-iodo-1H-indol-5-yl)-N-(4-methoxybenzyl)-1,3,4-oxadiazol-2-amine (0.5 g, 1.12 mmol) in DMF (5 mL) at −25° C. was added NaH (0.059 g, 50% in mineral oil, 1.23 mmol) portion wise. The mixture was stirred for 5 min at −25° C. then a solution of 4-methyl benzene sulfonyl chloride (0.235 g, 1.23 mmol) in DMF (1 mL) was added at same temperature dropwise. The reaction was stirred at −25° C. for 10 min. The mixture was poured into ice cold water and a white solid precipitated out which was collected by filtration and recrystallized by triturating it with 1:3 volume of EtOH (2 mL) and $CHCl_3$ (6 mL) to give 5-(3-iodo-1-tosyl-1H-indol-5-yl)-N-(4-methoxybenzyl)-1,3,4-oxadiazol-2-amine (0.450 g, 0.75 mmol, 66.96%). MS (ESI, pos. ion) m/z: 601.1 (M+1); $^1$H-NMR (DMSO-$d_6$) δ8.312 (s, 1H), 8.21 (s, 1H), 8.13 (s, 1H), 7.9-7.90 (m, 3H), 7.68 (s, 1H), 7.44 (d, J=9 Hz, 2H), 7.33 (d, J=9 Hz, 2H), 6.92 (d, J=9 Hz, 2H), 4.38 (d, J=6 Hz, 2H), 3.73 (s, 3H), 2.33 (s, 3H).

Preparation of compound 1g: N-(4-methoxybenzyl)-5-(3-(6-(2-methylpiperidin-1-yl)pyrazin-2-yl)-1-tosyl-1H-indol-5-yl)-1,3,4-oxadiazol-2-amine $K_3PO_4$ (327 mg, 1.539 mmol) (Reidel-de Haen), XPhos (14.67 mg, 0.031 mmol) (Strem), $Pd_2(dba)_3$ (14.09 mg, 0.015 mmol) (Strem), 2-(2-methylpiperidin-1-yl)-6-(4,4,5,5-tetramethyl-1,3,2-dioxaborolan-2-yl)pyrazine (194 mg, 0.641 mmol) (CombiPhos Catalysts Inc.) and 5-(3-iodo-1-tosyl-1H-indol-5-yl)-N-(4-methoxybenzyl)-1,3,4-oxadiazol-2-amine (308 mg, 0.513 mmol) were weighed into a 5 mL glass microwave tube. The tube was purged with argon and the contents were treated with dioxane (3.0 mL) and water (0.5 mL). The tube was sealed and the suspension was heated at 120° C. for 10 min in an Initiator microwave reactor (Personal Chemistry, Biotage AB, Inc., Uppsala, Sweden). An additional 50 mg of the boronic ester were added, the tube was sealed and the mixture was heated at 120° C. for an additional 10 min. The mixture was treated with 1N NaOH and extracted with EtOAc (50 mL). The organic layer was dried over MgSO$_4$, filtered and concentrated. Purification by flash chromatography (eluent: 20% MeOH in DCM) afforded N-(4-methoxybenzyl)-5-(3-(6-(2-methylpiperidin-1-yl)pyrazin-2-yl)-1-tosyl-1H-indol-5-yl)-1,3,4-oxadiazol-2-amine (177 mg, 0.272 mmol, 53.1%) as a dark yellow solid. MS (ESI, pos. ion) m/z: 650.0 (M+1).

Preparation of compound 1h: 5-(3-(6-(2-methylpiperidin-1-yl)pyrazin-2-yl)-1-tosyl-1H-indol-5-yl)-1,3,4-oxadiazol-2-amine N-(4-Methoxybenzyl)-5-(3-(6-(2-methylpiperidin-1-yl)pyrazin-2-yl)-1-tosyl-1H-indol-5-yl)-1,3,4-oxadiazol-2-amine (177 mg, 0.272 mmol) was weighed into a 5 mL glass microwave tube. The material was dissolved in TFA (1.5 mL) (Aldrich). The tube was sealed and the solution was heated at 120° C. for 10 min in an Initiator microwave reactor (Personal Chemistry, Biotage AB, Inc., Uppsala, Sweden). The excess TFA was removed in vacuo, the crude residue was treated with 1N NaOH and extracted with EtOAc. The organic layer was dried over MgSO$_4$, filtered and concentrated. The material was used in the next step without purification. MS (ESI, pos. ion) m/z 530.0 (M+1).

Preparation of compound 1: 5-(3-(6-(2-methylpiperidin-1-yl)pyrazin-2-yl)-1H-indol-5-yl)-1,3,4-oxadiazol-2-amine 5-(3-(6-(2-Methylpiperidin-1-yl)pyrazin-2-yl)-1-tosyl-1H-indol-5-yl)-1,3,4-oxadiazol-2-amine (99.1 mg, 0.187 mmol) in a round bottomed flask was dissolved in MeOH (0.75 mL) and THF (1.5 mL). Cs$_2$CO$_3$ (183 mg, 0.561 mmol) was added, the flask was fitted with a reflux condenser and the contents were heated at 45° C. for 15 min. Water (20 mL) was added and the mixture was extracted with EtOAc (50 mL), DCM (50 mL) and EtOAc again (50 mL). The combined organic layers were dried over MgSO$_4$, filtered and concentrated. The crude material was dissolved in DMSO (6 mL). Purification by reverse phase HPLC (10-90% MeCN in H$_2$O with 0.01% TFA as additive to each solvent by volume) afforded 5-(3-(6-(2-methylpiperidin-1-yl)pyrazin-2-yl)-1H-indol-5-yl)-1,3,4-oxadiazol-2-amine 2,2,2-trifluoroacetate (17 mg, 0.035 mmol, 18.56%) as a bright yellow solid. MS (ESI, pos. ion) m/z 376.1 (M+1). $^1$H NMR (400 MHz, MeOH-d$_4$) δ ppm 9.07 (s, 1H), 8.24 (s, 2H), 7.91 (s, 1H), 7.77 (dd, J=8.6, 1.4 Hz, 1H), 7.62 (d, J=8.6 Hz, 1H), 4.92 (dd, J=9.9, 3.6 Hz, 2H), 4.32-4.43 (m, 1H), 1.78-2.01 (m, 4H), 1.59-1.78 (m, 2H), 1.40 (d, J=6.8 Hz, 3H).

Example 2

5-(3-(6-(4,4-difluoropiperidin-1-yl)pyrazin-2-yl)-1H-indol-5-yl)-1,3,4-oxadiazol-2-amine

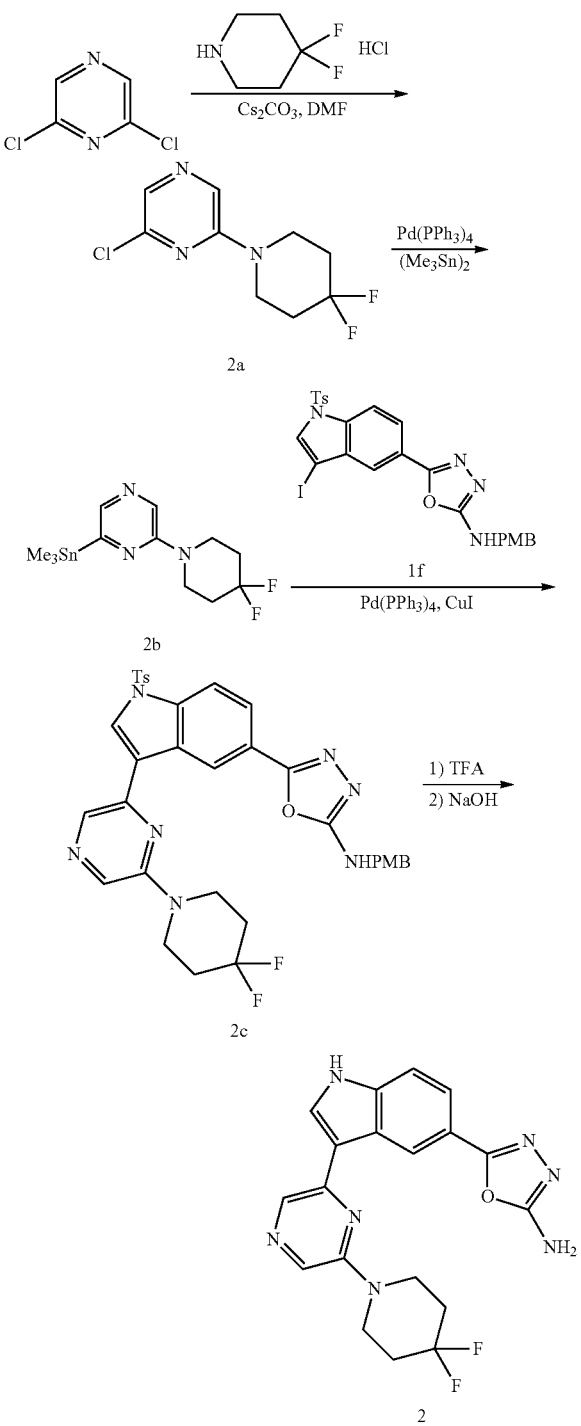

Preparation of compound 2a: 2-chloro-6-(4,4-difluoropiperidin-1-yl)pyrazine

A mixture of 4,4-difluoropiperidine hydrochloride (598 mg, 3.79 mmol), $Cs_2CO_3$ (2471 mg, 7.58 mmol) and 2,6-dichloropyrazine (538 mg, 3.61 mmol) in DMF (5 mL) was heated in a microwave at 100° C. for 35 min. The mixture was diluted with EtOAc (50 mL) and washed with 2×5 mL of $H_2O$. The organic layer was dried, filtered and concentrated. The residue was purified on a silica gel column (eluting with 25-35% EtOAc in Hex) to give 2-chloro-6-(4,4-difluoropiperidin-1-yl)pyrazine (717 mg, 85%) as a brown amorphous solid. MS (ESI, pos. ion) m/z 234.1 (M+1); $^1$H NMR (400 MHz, DMSO-$d_6$) δ ppm 8.39 (s, 1H), 7.89 (s, 1H), 3.75 (t, J=5.7 Hz, 4H), 2.06 (m, 4H).

Preparation of compound 2c: 5-(3-(6-(4,4-difluoropiperidin-1-yl)pyrazin-2-yl)-1-tosyl-1H-indol-5-yl)-N-(4-methoxybenzyl)-1,3,4-oxadiazol-2-amine A glass microwave reaction vessel was charged with 2-chloro-6-(4,4-difluoropiperidin-1-yl)pyrazine (300 mg, 1.28 mmol) and $(Me_3Sn)_2$ (0.32 mL, 1.54 mmol) in p-dioxane (2.5 mL) followed by $Pd(PPh_3)_4$ (60 mg, 0.05 mmol). The reaction was heated in a microwave reactor (Personal Chemistry, Biotage AB, Inc., Uppsala, Sweden) at 125° C. for 30 min. The mixture was cooled to RT and 5-(3-iodo-1-tosyl-1H-indol-5-yl)-N-(4-methoxybenzyl)-1,3,4-oxadiazol-2-amine (0.615 g, 1.024 mmol) was added followed by DMF (1 mL), CuI (244 mg, 1.28 mmol) and $Pd(PPh_3)_4$ (59 mg, 0.05 mmol). The reaction was heated in a microwave reactor (Personal Chemistry, Biotage AB, Inc., Uppsala, Sweden) at 125° C. for 0.5 h. It was diluted with 5 mL of acetone and 10 mL of EtOAc, filtered through a pad of Celite. The filtrate was concentrated. The residue was loaded on a silica gel column and eluted with 50% EtOAc in DCM followed by 10-20% MeOH in EtOAc to give 5-(3-(6-(4,4-difluoropiperidin-1-yl)pyrazin-2-yl)-1-tosyl-1H-indol-5-yl)-N-(4-methoxybenzyl)-1,3,4-oxadiazol-2-amine (590 mg) as a brown amorphous solid that was used in the next step without further purification. MS (ESI, pos. ion) m/z 672.0 (M+1).

Preparation of compound 2: 5-(3-(6-(4,4-difluoropiperidin-1-yl)pyrazin-2-yl)-1H-indol-5-yl)-1,3,4-oxadiazol-2-amine A solution of 5-(3-(6-(4,4-difluoropiperidin-1-yl)pyrazin-2-yl)-1-tosyl-1H-indol-5-yl)-N-(4-methoxybenzyl)-1,3,4-oxadiazol-2-amine (590 mg) in TFA (5 mL) was heated in a microwave reactor (Personal Chemistry, Biotage AB, Inc., Uppsala, Sweden) at 110° C. for 20 min. The volatiles were removed under reduced pressure. The brown residue was diluted with EtOAc and washed with 0.5 N NaOH. The EtOAc layer was concentrated. The off white solid was stirred with 5 mL $Et_2O$, filtered, rinsed with 2×5 ml of $Et_2O$ to give 350 mg of crude material of 5-(3-(6-(4,4-difluoropiperidin-1-yl)pyrazin-2-yl)-1-tosyl-1H-indol-5-yl)-1,3,4-oxadiazol-2-amine that was used without further purification. A glass microwave reaction vessel was charged with the above obtained 5-(3-(6-(4,4-difluoropiperidin-1-yl)pyrazin-2-yl)-1-tosyl-1H-indol-5-yl)-1,3,4-oxadiazol-2-amine (350 mg) in p-dioxane (3 mL) followed by 1 N NaOH (2 mL). The reaction was heated in a microwave reactor (Personal Chemistry, Biotage AB, Inc., Uppsala, Sweden) at 105° C. for 20 min. The mixture was partitioned between 5 mL of $H_2O$ and 50 mL of EtOAc. The EtOAc layer was concentrated and the residue purified on a reverse phase HPLC, using a gradient of 10-90% [0.1% TFA in MeCN] in [0.1% TFA in $H_2O$]. The desired fractions were collected, concentrated, the residue was extracted with EtOAc and washed with 0.5 N NaOH to give 5-(3-(6-(4,4-difluoropiperidin-1-yl)pyrazin-2-yl)-1H-indol-5-yl)-1,3,4-oxadiazol-2-amine (20 mg, 5%) as an off white crystalline solid. MS (ESI, pos. ion) 398.1 (M+1); $^1$H NMR (400 MHz, DMSO-$d_6$) δ ppm 11.93 (1H, br. s.), 8.85 (1H, d, J=1.2 Hz), 8.45 (1H, s), 8.29 (1H, s), 8.19 (1H, s), 7.67 (1H, m), 8.57 (1H, d, J=8.6 Hz), 7.06 (2H, br. s.), 3.89 (4H, t, J=5.6 Hz), 2.12 (4H, m).

Example 3

5-(3-(4-(2-methylpiperidin-1-yl)pyrimidin-2-yl)-1H-indol-5-yl)-1,3,4-oxadiazol-2-amine

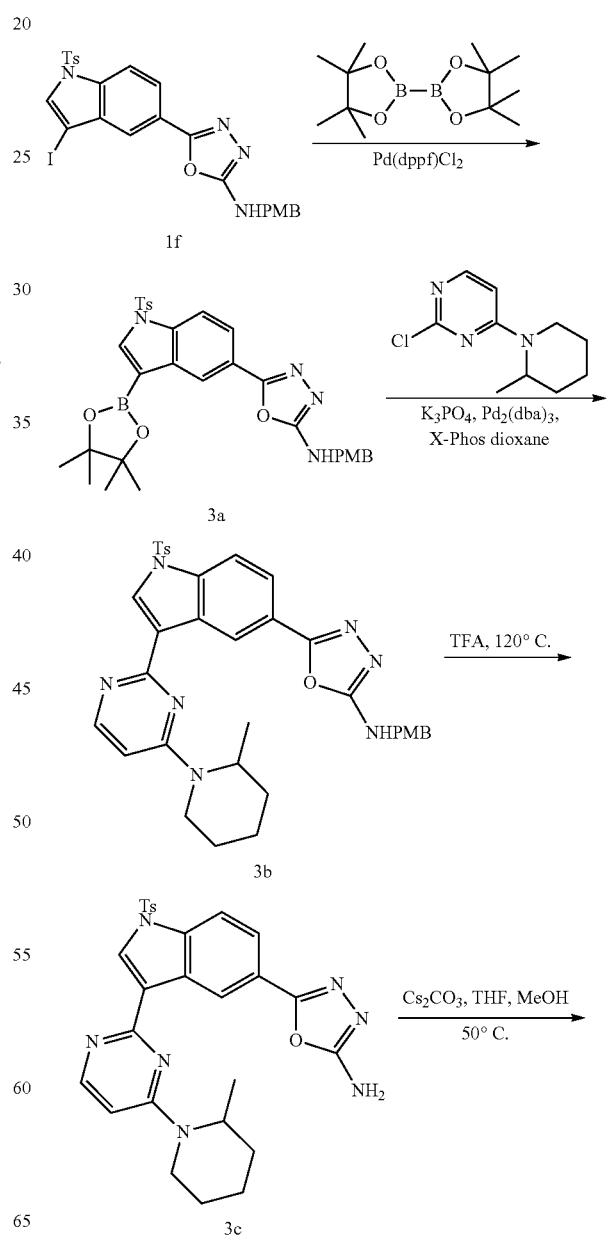

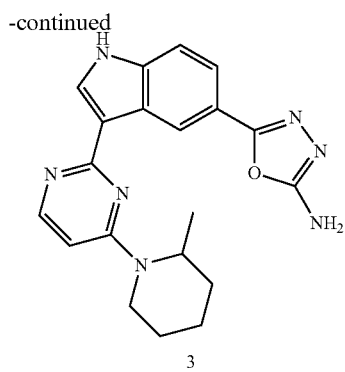

3

Preparation of compound 3a: N-(4-methoxybenzyl)-5-(3-(4,4,5,5-tetramethyl-1,3,2-dioxaborolan-2-yl)-1-tosyl-1H-indol-5-yl)-1,3,4-oxadiazol-2-amine 5-(3-Iodo-1-tosyl-1H-indol-5-yl)-N-(4-methoxybenzyl)-1,3,4-oxadiazol-2-amine (508 mg, 0.846 mmol), bis(pinacolato)diboron (645 mg, 2.54 mmol) (Aldrich, Catalog#473294-100G, Batch#21899MJ), potassium acetate (415 mg, 4.23 mmol) (Aldrich, Catalog#236497-100G, Batch#12621PA), and [1,1'-bis(diphenylphosphino)ferrocene]-dichloropalladium(ii), complex with dichloromethane (104 mg, 0.127 mmol) (Strem, Catalog#46-0450, Batch#B3015095) were weighed into a 20 mL glass microwave tube. The tube was purged with argon, the contents were treated with DMF (3.5 mL), the tube was sealed, and the contents were heated in an oil bath with stirring at 90° C. for 1 hour. The mixture was treated with H$_2$O and extracted with EtOAc (2×100 mL). The combined organic layers were washed with brine (75 mL), dried over MgSO$_4$, filtered and concentrated to give the crude material. MS (ESI, pos ion) m/z 601.2 (M+1).

Preparation of compound 3b: N-(4-methoxybenzyl)-5-(3-(4-(2-methylpiperidin-1-yl)pyrimidin-2-yl)-1-tosyl-1H-indol-5-yl)-1,3,4-oxadiazol-2-amine 2-Chloro-4-(2-methylpiperidin-1-yl)pyrimidine (102 mg, 0.482 mmol), dicyclohexyl(2',4',6'-triisopropylbiphenyl-2-yl)phosphine (13.80 mg, 0.029 mmol) (Strem), Pd$_2$(dba)$_3$ (13.25 mg, 0.014 mmol) (Strem), and K$_3$PO$_4$ (307 mg, 1.447 mmol) (Reidel-de Haen) were weighed into a 20 mL glass microwave tube. The tube was purged with argon, the contents were treated with dioxane (4.00 mL) and H$_2$O (0.400 mL) and the tube was sealed. The contents were heated in Initiator microwave reactor (Personal Chemistry, Biotage AB, Inc., Uppsala, Sweden) at 120° C. for 20 min. Additional catalyst and ligand (ca. 7 mg each) were added, the tube was sealed, and the contents were heated in the microwave reactor at 120° C. for an additional 20 min. The mixture was treated with H$_2$O and extracted with EtOAc (20 mL). The organic layer was dried over MgSO$_4$, filtered and concentrated to give the crude material. MS (ESI, pos ion) m/z 650.2 (M+1).

Preparation of compound 3c: 5-(3-(4-(2-methylpiperidin-1-yl)pyrimidin-2-yl)-1-tosyl-1H-indol-5-yl)-1,3,4-oxadiazol-2-amine N-(4-Methoxybenzyl)-5-(3-(4-(2-methylpiperidin-1-yl)pyrimidin-2-yl)-1-tosyl-1H-indol-5-yl)-1,3,4-oxadiazol-2-amine (313 mg, 0.482 mmol) in a 20 mL glass microwave tube was dissolved in TFA (3.00 mL). The tube was sealed, and the solution was heated in an Initiator microwave reactor (Personal Chemistry, Biotage AB, Inc., Uppsala, Sweden) at 120° C. for 20 min. The excess TFA was removed, the crude residue treated with 1N NaOH and extracted with EtOAc (2×50 mL). The combined organic layers were dried over MgSO$_4$, filtered and concentrated to give the crude material: MS (ESI, pos ion) m/z 530.2 (M+1).

Preparation of compound 3: 5-(3-(4-(2-methylpiperidin-1-yl)pyrimidin-2-yl)-1H-indol-5-yl)-1,3,4-oxadiazol-2-amine 5-(3-(4-(2-Methylpiperidin-1-yl)pyrimidin-2-yl)-1-tosyl-1H-indol-5-yl)-1,3,4-oxadiazol-2-amine (255 mg, 0.481 mmol) in a round bottomed flask was dissolved in MeOH (2.0 mL) and THF (4.0 mL). Cs$_2$CO$_3$ (471 mg, 1.444 mmol) (Aldrich) was added, the flask was fitted with a reflux condenser and the contents of the flask were heated at 50° C. for 15 min. H$_2$O (20 mL) was added and the mixture was extracted with EtOAc (2×50 mL). The organic layer was dried over MgSO$_4$, filtered and concentrated. The residue was purified with RP-HPLC to give 5-(3-(4-(2-methylpiperidin-1-yl)pyrimidin-2-yl)-1H-indol-5-yl)-1,3,4-oxadiazol-2-amine 2,2,2-trifluoroacetate (37.4 mg, 0.076 mmol, 15.87%) as a light yellow amorphous solid. MS (ESI, pos ion) m/z 376.3 (M+1); $^1$H NMR (400 MHz, DMSO-d$_6$) δ ppm 12.63 (d, J=2.7 Hz, 1H), 8.85 (s, 1H), 8.62 (d, J=3.1 Hz, 1H), 8.26 (d, J=7.4 Hz, 1H), 7.67-7.80 (m, 2H), 7.27 (br. s., 1H), 7.01 (d, J=7.8 Hz, 1H), 3.25-3.45 (m, 1H), 1.26-2.08 (m, 11H).

Example 4

5-(3-(6-(cyclopentylamino)pyrazin-2-yl)-1H-indol-5-yl)-1,3,4-oxadiazol-2-amine

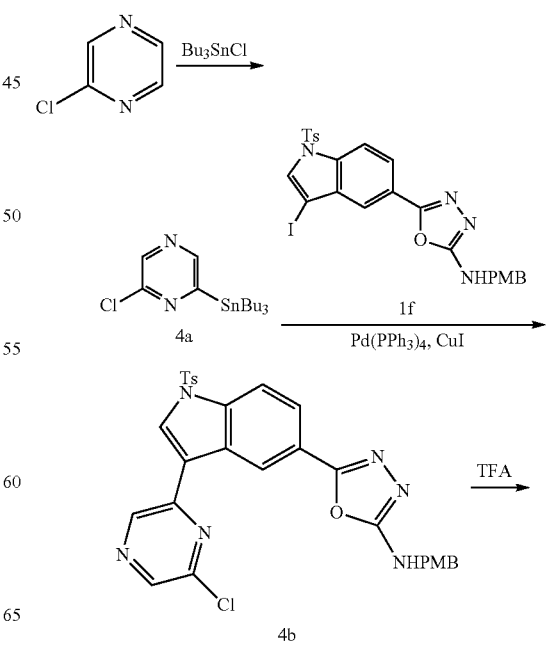

-continued

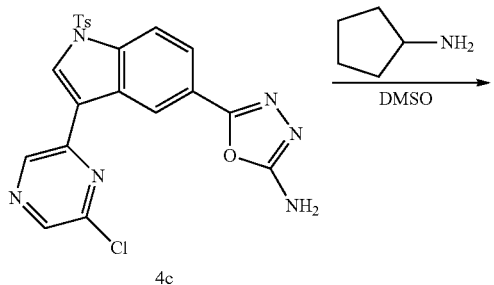

4c

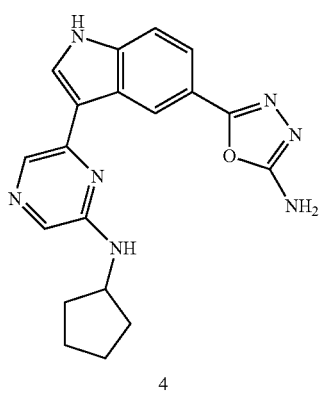

4

Preparation of compound 4a:
2-chloro-6-(tributylstannyl)pyrazine

To a solution of nBuLi, 1.6 m in hexane (21.49 mL, 34.4 mmol) in THF (80 mL) at −50° C. was added 2,2,6,6-tetramethylpiperidine (5.80 mL, 34.4 mmol). The mixture was warmed to 0° C. and stirred for 20 min. The mixture was then cooled to −78° C. In another flask, 2-chloropyrazine (0.974 mL, 10.91 mmol) and tributyltin chloride (2.96 mL, 10.91 mmol) were dissolved in THF (50 mL) and cooled to −78° C. The cooled solution was transferred to lithium solution through cannula and the resulting orange mixture was slowly warmed up to −40° C. in 3 h, and was quenched with sat. HCl:EtOH:THF (1:4:5, 50 mL) and warmed to RT. The mixture was neutralized with sat. NaHCO₃ and the volatiles were removed. The residue was diluted in H₂O and extracted with DCM. The combined organic layers were dried, filtered and concentrated. The residue was purified with silica gel chromatography (eluting with 0-30% DCM in Hex) to give 2-chloro-6-(tributylstannyl)pyrazine (3.15 g, 7.81 mmol, 71.5%) as a clear oil. MS (ESI, pos. ion) m/z: 405 (M+1). $^1$H NMR (400 MHz, CDCl₃) δ ppm 8.42 (1H, s), 8.38 (1H, s), 1.50-1.62 (6H, m), 1.27-1.41 (6H, m), 1.14-1.22 (6H, m), 0.89 (9H, t, J=7.3 Hz)

Preparation of compound 4b: 5-(3-(6-chloropyrazin-2-yl)-1-tosyl-1H-indol-5-yl)-N-(4-methoxybenzyl)-1,3,4-oxadiazol-2-amine In a 20 mL glass microwave tube, 2-chloro-6-(tributylstannyl)pyrazine (0.807 g, 1.999 mmol), 5-(3-iodo-1-tosyl-1H-indol-5-yl)-N-(4-methoxybenzyl)-1,3,4-oxadiazol-2-amine (1.00 g, 1.665 mmol), CuI (0.381 g, 1.999 mmol), Pd(PPh₃)₄ (0.096 g, 0.083 mmol) was purged with argon and treated with DMF (15 mL). The tube was heated in an Initiator microwave reactor (Personal Chemistry, Biotage AB, Inc., Uppsala, Sweden) at 100° C. for 1 h. The crude mixture was then diluted with DCM and washed with water. The organic layer was dried, filtered and concentrated and the residue was purified with flash chromatography to give 5-(3-(6-chloropyrazin-2-yl)-1-tosyl-1H-indol-5-yl)-N-(4-methoxybenzyl)-1,3,4-oxadiazol-2-amine (0.48 g, 0.818 mmol, 49%) as a light yellow amorphous solid. MS (ESI, pos. ion) m/z: 586.9 (M+1). $^1$H NMR (400 MHz, DMSO-d₆) δ ppm 9.44 (1H, s), 9.02 (1H, s), 8.85 (1H, s), 8.71 (1H, s), 8.28-8.36 (1H, m), 8.18 (1H, d, J=8.8 Hz), 8.03 (1H, m, J=8.4 Hz), 7.95 (1H, s), 7.88-7.95 (1H, m), 7.45 (1H, m, J=8.2 Hz), 7.33 (2H, m, J=8.6 Hz), 6.90 (2H, m, J=8.6 Hz), 4.37 (2H, d, J=6.1 Hz), 3.72 (3H, s), 2.33 (3H, s).

Preparation of compound 4c: 5-(3-(6-chloropyrazin-2-yl)-1-tosyl-1H-indol-5-yl)-1,3,4-oxadiazol-2-amine A glass microwave reaction vessel was charged with 5-(3-(6-chloropyrazin-2-yl)-1-tosyl-1H-indol-5-yl)-N-(4-methoxybenzyl)-1,3,4-oxadiazol-2-amine (480 mg, 0.818 mmol) and TFA (2.0 mL). The mixture was stirred and heated in an Initiator microwave reactor (Personal Chemistry, Biotage AB, Inc., Uppsala, Sweden) at 120° C. for 20 min then the solvent was removed. The crude residue was treated with 1N NaOH and the resulting precipitate was collected to give 5-(3-(6-chloropyrazin-2-yl)-1-tosyl-1H-indol-5-yl)-1,3,4-oxadiazol-2-amine (340 mg, 0.728 mmol, 89%) as a light yellow amorphous solid. MS (ESI, pos. ion) m/z: 466.9 (M+1). $^1$H NMR (400 MHz, DMSO-d₆) δ ppm 9.43 (1H, s), 9.01 (1H, s), 8.84 (1H, s), 8.71 (1H, s), 8.18 (1H, d, J=8.8 Hz), 8.03 (2H, m, J=8.4 Hz), 7.85-7.93 (1H, m), 7.45 (2H, m, J=8.2 Hz), 7.28 (2H, s), 2.34 (3H, s).

Preparation of compound 4: 5-(3-(6-(cyclopentylamino)pyrazin-2-yl)-1H-indol-5-yl)-1,3,4-oxadiazol-2-amine In a 5 mL glass microwave tube 5-(3-(6-chloropyrazin-2-yl)-1-tosyl-1H-indol-5-yl)-1,3,4-oxadiazol-2-amine (80 mg, 0.171 mmol) was treated with cyclopentanamine (219 mg, 2.57 mmol) and DMSO (0.50 mL). The tube was sealed and heated in an Initiator microwave reactor (Personal Chemistry, Biotage AB, Inc., Uppsala, Sweden) at 165° C. for 45 min. The crude material was treated with water and extracted with EtOAc. The combined organic layers were dried, filtered and concentrated. The residue was purified with RP-HPLC (10-90% AcCN in 0.1% TFA/H₂O) to give 5-(3-(6-(cyclopentylamino)pyrazin-2-yl)-1H-indol-5-yl)-1,3,4-oxadiazol-2-amine 2,2,2-trifluoroacetate (25.1 mg, 0.053 mmol, 31%) as a yellow, amorphous solid. MS (ESI, pos. ion) m/z: 362.0 (M+1). $^1$H NMR (400 MHz, MeOH) δ ppm 9.20 (1H, s), 8.24-8.28 (1H, m), 8.17 (1H, s), 7.75 (1H, dd, J=8.6, 1.4 Hz), 7.63 (1H, d, J=8.6 Hz), 7.55 (1H, s), 4.44-4.55 (1H, m), 2.21-2.32 (2H, m), 1.74-1.90 (5H, m), 1.60-1.74 (3H, m).

Example 5

5-(3-(4-(isopropylamino)pyrimidin-2-yl)-1H-indol-5-yl)-1,3,4-oxadiazol-2-amine

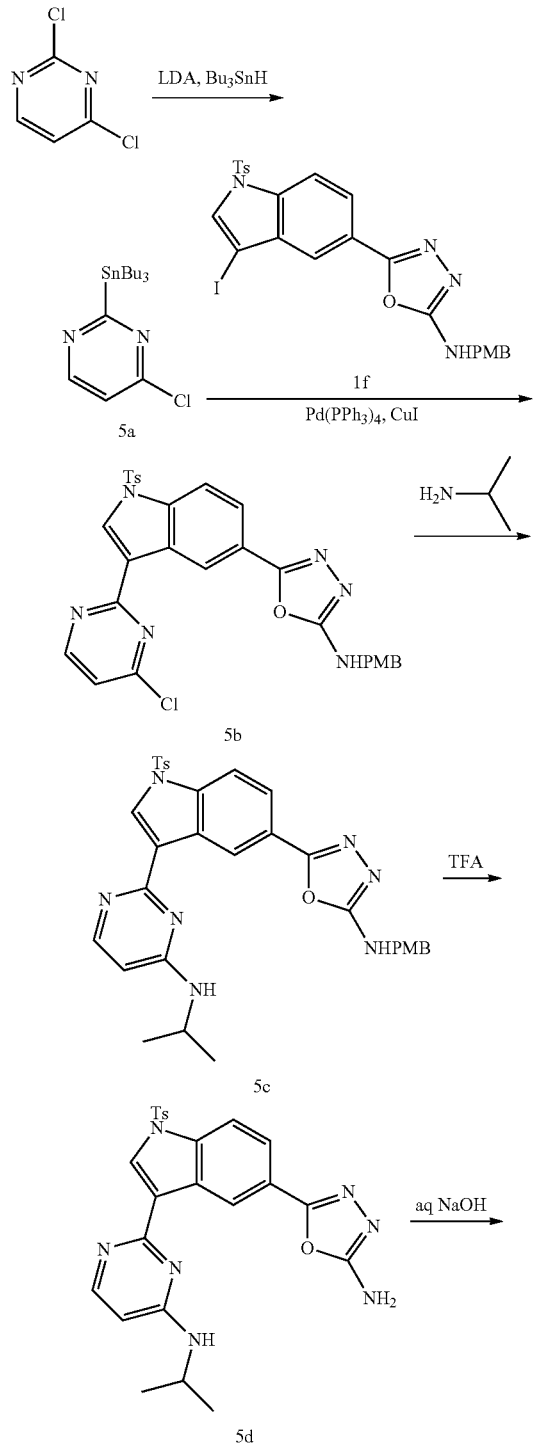

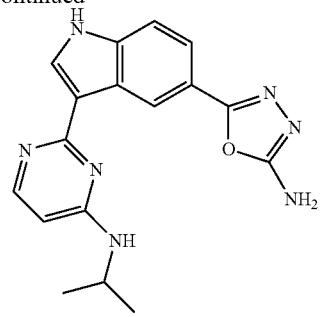

Preparation of compound 5a: 4-chloro-2-(tributylstannyl)pyrimidine

To a solution of LDA (251 ml, 502 mmol) in THF (650 mL) at −20° C. was added SnBu$_3$H (108.5 ml, 402 mmol) dropwise. The mixture was maintained at −20° C. for 15 min, then cooled to −78° C. 2,4-dichloro pyrimidine (50 g, 335 mmol) was added and the reaction was stirred at −78° C. for 5 h. The cooling bath was removed and the reaction was slowly warmed to 0° C. within 30 min. The mixture was poured into 10% NH$_4$Cl at 0° C., and the aqueous layer was extracted with Et$_2$O. The combined organic layers were washed with brine, dried, filtered and concentrated. The residue was purified with silica gel chromatography (eluting with 1% EtOAc in Hex) to give 4-chloro-2-(tributylstannyl)pyrimidine (18.5 g, 24%) as a pale yellow color syrup. MS (ESI, pos. ion) m/z: 405.1 (M+1); $^1$H-NMR (400 MHz, CDCl$_3$): δ 8.54 (d, J=8 Hz, 1H), 7.17 (d, J=8 Hz, 1H), 1.61-1.54 (m, 6H), 1.37-1.28 (m, 6H), 1.21-1.17 (m, 6H), 0.90 (m, 9H).

Preparation of compound 5b: 5-(3-(4-chloropyrimidin-2-yl)-1-tosyl-1H-indol-5-yl)-N-(4-methoxybenzyl)-1,3,4-oxadiazol-2-amine A solution of 5-(3-iodo-1-tosyl-1H-indol-5-yl)-N-(4-methoxybenzyl)-1,3,4-oxadiazol-2-amine (3.0 g, 5.20 mmol) and 4-chloro-2-(tributylstannyl)pyrimidine (2.5 g, 6.00 mmol) in DMF was bubbled with N$_2$ for 15 min. To the above mixture was added CuI (476 mg; 2.50 mmol) and Pd(PPh$_3$)$_4$ (577 mg, 0.52 mmol) and N$_2$ gas was bubbled for another 15 min. The reaction was heated at 80° C. for 1 h. The reaction was quenched with H$_2$O and the resulting precipitate was filtered, washed with H$_2$O and dried. The crude material was purified with silica gel chromatography (eluting with 30% EtOAc in Hex) to give 5-(3-(4-chloropyrimidin-2-yl)-1-tosyl-1H-indol-5-yl)-N-(4-methoxybenzyl)-1,3,4-oxadiazol-2-amine (1.6 g, 53.3%). MS (ESI, pos. ion) m/z: 586.6 (M+1); $^1$H-NMR (400 MHz, DMSO-d$_6$): δ 8.96 (s, 1H), 8.91 (d, J=4 Hz, 1H), 8.62 (s, 1H), 8.35 (m, 1H), 8.17 (d, J=8 Hz, 1H), 8.10 (d, J=8 Hz, 2H), 7.91 (d, J=8 Hz, 1H), 7.65-7.62 (m, 2H), 7.45-7.43 (m, 6H), 7.33 (d, J=8 Hz, 2H), 6.90 (d, J=8 Hz, 2H), 4.38 (d, J=5.6 Hz, 2H), 3.72 (s, 3H), 2.33 (s, 3H).

Preparation of compound 5c: 5-(3-(4-(isopropylamino)pyrimidin-2-yl)-1-tosyl-1H-indol-5-yl)-N-(4-methoxybenzyl)-1,3,4-oxadiazol-2-amine To a solution of 5-(3-(4-chloropyrimidin-2-yl)-1-tosyl-1H-indol-5-yl)-N-(4-methoxybenzyl)-1,3,4-oxadiazol-2-amine (500 mg, 0.85 mmol) in DMSO (5 mL) was added isopropylamine (60 mg, 1.02 mmol). The mixture was stirred at 110° C. for 12 h. The reaction was quenched with ice cold H₂O and was extracted with EtOAc. The combined organic layers were dried, filtered and concentrated. The residue was purified with flash chromatography (basic alumina, eluting with 30-40% EtOAc in Hex) to give 5-(3-(4-(isopropylamino)pyrimidin-2-yl)-1-tosyl-1H-indol-5-yl)-N-(4-methoxybenzyl)-1,3,4-oxadiazol-2-amine (220 mg, 52%). MS (ESI, pos. ion) m/z: 609.6 (M+1); ¹H-NMR (400 MHz, DMSO-d₆): δ 9.07 (s, 1H), 8.39 (s, 1H), 8.23 (m, 1H), 8.12 (d, J=8 Hz, 1H), 8.00 (d, J=8 Hz, 2H), 7.85 (d, J=8.4 Hz, 1H), 7.79-7.57 (m, 5H), 7.43 (d, J=8 Hz, 2H), 7.312 (d, J=8 Hz, 3H), 6.90 (d, J=8 Hz, 2H), 4.38 (m, 3H), 3.72 (s, 3H), 2.32 (s, 3H), 1.17 (d, J=6.4 Hz, 6H).

Preparation of compound 5d: 5-(3-(4-(isopropylamino)pyrimidin-2-yl)-1-tosyl-1H-indol-5-yl)-1,3,4-oxadiazol-2-amine A solution of 5-(3-(4-(isopropylamino)pyrimidin-2-yl)-1-tosyl-1H-indol-5-yl)-N-(4-methoxybenzyl)-1,3,4-oxadiazol-2-amine (220 mg, 0.36 mmol) in TFA (1.1 mL) was heated at 100° C. in a microwave for 30 min. The mixture was cooled to RT and TFA was removed in vacuo. The residue was washed with Et₂O to give the crude material (150 mg, 85%). MS (ESI, pos. ion) m/z: 489.7 (M+1).

Preparation of compound 5: 5-(3-(4-(isopropylamino)pyrimidin-2-yl)-1H-indol-5-yl)-1,3,4-oxadiazol-2-amine To a solution of 5-(3-(4-(isopropylamino)pyrimidin-2-yl)-1-tosyl-1H-indol-5-yl)-1,3,4-oxadiazol-2-amine (400 mg, 0.817 mmol) in p-dioxane (4 mL) was added aq. 10% NaOH (2 mL). The mixture was heated at 100° C. for 2 h. The reaction was quenched with ice cold H₂O and the resulting precipitate was filtered, washed with ice cold H₂O and dried. The residue was purified with RP-HPLC to 5-(3-(4-(isopropylamino)pyrimidin-2-yl)-1H-indol-5-yl)-1,3,4-oxadiazol-2-amine (60 mg, 22%) as an off-yellow solid. MS (ESI, pos. ion) m/z: 335.9 (M+1); ¹H-NMR (400 MHz, DMSO-d₆): δ 11.77 (d, J=2 Hz, 1H), 9.02 (s, 1H), 8.14-8.07 (m, 2H), 7.65 (dd, J=2, 8.8 Hz, 1H), 7.55 (d, J=8 Hz, 1H), 7.11-7.06 (m, 3H), 6.24 (d, J=8 Hz, 1H), 4.33 (brs, 1H), 1.26 (d, J=6.8 Hz, 6H).

Example 6

5-(3-(6-morpholinopyridin-2-yl)-1H-indol-5-yl)-1,3,4-oxadiazol-2-amine

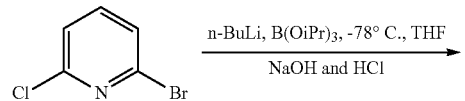

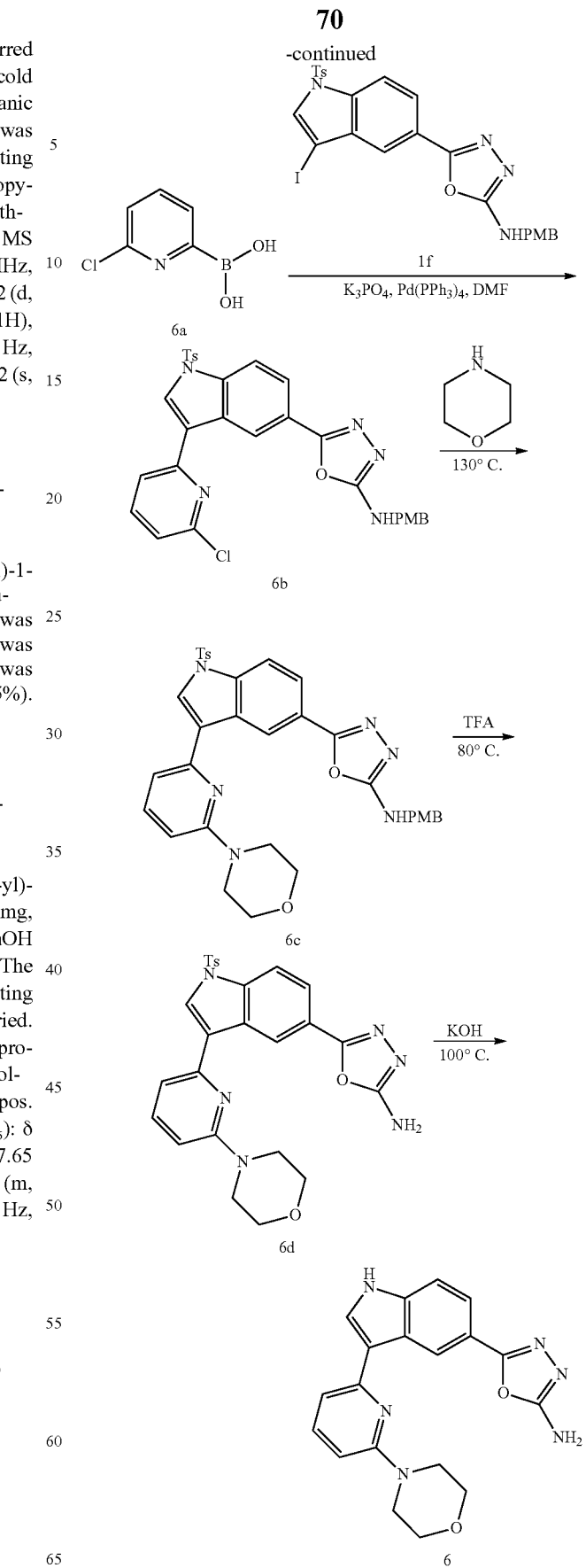

Preparation of compound 6a: 6-chloropyridin-2-ylboronic acid

A solution of n-BuLi (2.5 M, 24.91 mL, 62.3 mmol) in freshly distilled THF (100 mL) was cooled to −78° C., followed by the addition of a solution of 2-bromo-6-chloropyridine (10.0 g, 51.96 mmol) in 10 mL THF. The resulting dark colored mixture was stirred at this temperature for 45 min. A solution of triisopropylborate (11.72 g, 62.3 mmol) was added and the mixture was stirred at −78° C. for 2 h, and warmed to RT and stirred for an additional 1 h. The mixture was quenched by slow addition of 3% aq NaOH solution (400 mL). The resulting aqueous layer was collected and acidified down to pH 5-6 by dropwise addition of 3N HCl (180 mL), keeping the internal temperature below 5° C. The mixture was extracted with EtOAc and the combined organic layers were dried, filtered and concentrated. The residue was recrystallized from Et$_2$O to give 6-chloropyridin-2-ylboronic acid (6 g, 73.6%) as a white solid. MS (ESI, pos. ion) m/z: 158 (M+1); $^1$H NMR (DMSO-d$_6$, 300 MHz): δ ppm 8.51 (brs, 1H), 7.84 (m, 2H), 7.51-7.48 (m, 1H).

Preparation of compound 6b: 5-(3-(6-chloropyridin-2-yl)-1-tosyl-1H-indol-5-yl)-N-(4-methoxybenzyl)-1,3,4-oxadiazol-2-amine To the solution of 5-(3-iodo-1-tosyl-1H-indol-5-yl)-N-(4-methoxybenzyl)-1,3,4-oxadiazol-2-amine (1.0 g, 1.66 mmol) and 6-chloropyridin-2-ylboronic acid (0.392 g, 2.49 mmol) in DMF (10 mL) was added K$_3$PO$_4$ (0.704 g, 3.32 mmol) and this solution was purged under N$_2$ for 15 min. Then Pd(PPh$_3$)$_4$ (0.176 g, 0.152 mmol) was added and the reaction was heated at 85° C. for 5 h. The solution was poured in ice cold water (50 mL) and extracted with EtOAc. The combined organic layers were washed with H$_2$O, dried, filtered and concentrated. The residue was purified with silica gel chromatography (eluting with 15% EtOAc in Hex) to give 5-(3-(6-chloropyridin-2-yl)-1-tosyl-1H-indol-5-yl)-N-(4-methoxybenzyl)-1,3,4-oxadiazol-2-amine (0.52 g, 53.3%) as a brown solid. MS (ESI, pos. ion) m/z: 586 (M+1); $^1$H NMR (DMSO-d$_6$, 300 MHz): δ ppm 8.94 (s, 1H), 8.79 (s, 1H), 8.16-8.14 (m, 2H), 8.03-7.97 (m, 4H), 7.67-7.55 (m, 1H), 7.49-7.42 (m, 3H), 7.34 (d, J=8.4 Hz, 2H), 6.9 (d, J=8.1 Hz, 2H), 4.38 (s, 2H), 3.72 (s, 3H), 2.32 (s, 3H).

Preparation of compound 6c: N-(4-methoxybenzyl)-5-(3-(6-morpholinopyridin-2-yl)-1-tosyl-1H-indol-5-yl)-1,3,4-oxadiazol-2-amine The solution of 5-(3-(6-chloropyridin-2-yl)-1-tosyl-1H-indol-5-yl)-N-(4-methoxybenzyl)-1,3,4-oxadiazol-2-amine (1.0 g, 1.70 mmol) and morpholine (0.178 g, 2.05 mmol) was taken in sealed tube and heated at 130° C. for 5 h, then cooled to RT and poured in cooled ice water (5 mL) and extracted with EtOAc. The combined organic layers were washed with brine, dried, filtered and concentrated to give N-(4-methoxybenzyl)-5-(3-(6-morpholinopyridin-2-yl)-1-tosyl-1H-indol-5-yl)-1,3,4-oxadiazol-2-amine (0.52 g, 48%) as an off-white solid. MS (ESI, pos. ion) m/z: 637 (M+1); $^1$H NMR (DMSO-d$_6$, 400 MHz): δ ppm 8.95 (s, 1H), 8.51 (s, 1H), 8.14 (d, J=8.8 Hz, 1H), 7.99 (d, J=8.4 Hz, 2H), 7.85-7.82 (m, 1H), 7.72-7.64 (m, 2H), 7.42-7.39 (m, 3H), 7.32 (d, J=8.4 Hz, 2H), 6.9 (d, J=8.8 Hz, 2H), 6.83 (d, J=8.8 Hz, 1H), 4.3 (s, 2H), 3.75 (m, 8H), 3.56 (s, 3H), 2.31 (s, 3H).

Preparation of compound 6d: 5-(3-(6-morpholinopyridin-2-yl)-1-tosyl-1H-indol-5-yl)-1,3,4-oxadiazol-2-amine The solution of N-(4-methoxybenzyl)-5-(3-(6-morpholinopyridin-2-yl)-1-tosyl-1H-indol-5-yl)-1,3,4-oxadiazol-2-amine (0.21 g, 0.33 mmol) in CHCl$_3$ (2 mL) and TFA (2 mL) was heated at 80° C. for 12 h. Then the reaction mass was evaporated to dryness and ice cold H$_2$O (10 mL) was added and basified with saturated NaHCO$_3$ solution to pH 8. A white colored solid precipitated out which was collected by filtration and dried under vacuum to give 5-(3-(6-morpholinopyridin-2-yl)-1-tosyl-1H-indol-5-yl)-1,3,4-oxadiazol-2-amine (0.075 g, 44.1%). MS (ESI, pos. ion) m/z: 517 (M+1); $^1$H NMR (DMSO-d$_6$, 400 MHz): δ ppm 8.94 (s, 1H), 8.51 (s, 1H), 8.14 (d, J=8.8 Hz, 1H), 7.99 (d, J=8.4 Hz, 2H), 7.84 (d, J=8.8 Hz, 1H), 7.68-7.64 (m, 1H), 7.42-7.36 (m, 3H), 7.18 (s, 1H), 6.82 (d, J=8.8 Hz, 1H), 3.77-3.75 (m, 4H), 3.57-3.56 (m, 4H), 2.3 (s, 3H).

Preparation of compound 6: 5-(3-(6-morpholinopyridin-2-yl)-1H-indol-5-yl)-1,3,4-oxadiazol-2-amine The solution of 5-(3-(6-morpholinopyridin-2-yl)-1-tosyl-1H-indol-5-yl)-1,3,4-oxadiazol-2-amine (0.07 g, 0.135 mmol) in 10% KOH (0.7 mL) and THF (0.7 mL) was heated at 100° C. for 5 h. Then the reaction mass was evaporated to dryness and ice cold H$_2$O (5 mL) was added and extracted with EtOAc. The combined organic layers were washed with brine, dried, filtered and concentrated. The crude product was recrystallized with 10% MeOH in CHCl$_3$ to give 5-(3-(6-morpholinopyridin-2-yl)-1H-indol-5-yl)-1,3,4-oxadiazol-2-amine (0.02 g, 40.8%) as a pale yellow solid. MS (ESI, pos. ion) m/z: 363 (M+1); $^1$H NMR (DMSO-d$_6$, 400 MHz): δ 11.74 (s, 1H), 8.91 (s, 1H), 8.11 (s, 1H), 7.64-7.52 (m, 3H), 7.19 (d, J=7.6 Hz, 1H), 7.04 (s, 2H), 6.65 (d, J=8.4 Hz, 1H), 3.79 (s, 4H), 3.58 (s, 4H).

Example 7

5-(3-(6-(4-fluorophenyl)pyrazin-2-yl)-1H-indol-5-yl)-1,3,4-oxadiazol-2-amine

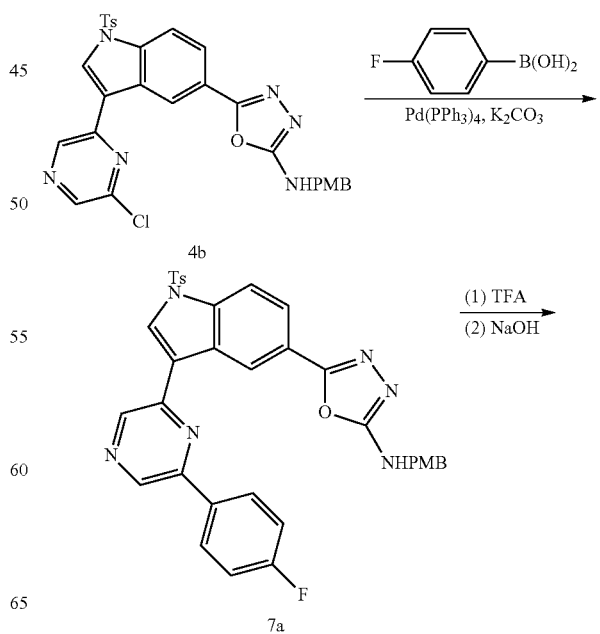

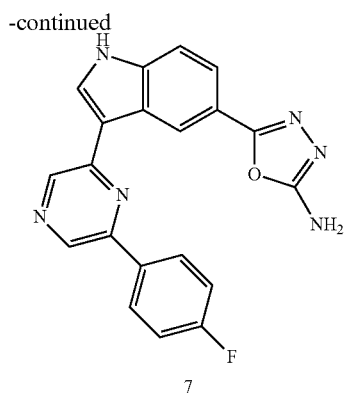

7

Preparation of compound 7a: 5-(3-(6-(4-fluorophenyl)pyrazin-2-yl)-1-tosyl-1H-indol-5-yl)-N-(4-methoxybenzyl)-1,3,4-oxadiazol-2-amine To a solution of 5-(3-(6-chloropyrazin-2-yl)-1-tosyl-1H-indol-5-yl)-N-(4-methoxybenzyl)-1,3,4-oxadiazol-2-amine (500 mg, 0.853 mmol) and 4-fluorophenylboronic acid (143.5 mg, 1.02 mmol) in 1,4-dioxane/$H_2O$ (3:1, 15 mL), was added $K_2CO_3$ (235.5 mg, 1.71 mmol) and $Pd(PPh_3)_4$ (49 mg, 0.0427 mmol). The reaction was heated at reflux for 24 h then quenched with $H_2O$ and extracted with EtOAc. The organic layer was dried, filtered and concentrated. The residue was purified with silica gel chromatography (eluting with 50% EtOAc in Hex) to give 5-(3-(6-(4-fluorophenyl)pyrazin-2-yl)-1-tosyl-1H-indol-5-yl)-N-(4-methoxybenzyl)-1,3,4-oxadiazol-2-amine (200 mg, 36.5%). MS (ESI, pos. ion) m/z: 647.1 (M+1); $^1$H-NMR (400 MHz DMSO-$d_6$): δ 12.11 (s, 1H), 9.18 (s, 1H), 9.08-8.98 (m, 2H), 8.52 (d, J=2.8 Hz, 1H), 8.36-8.33 (m, 2H), 8.14-8.03 (m, 1H), 7.74 (d, J=8 Hz, 1H), 7.65-7.55 (m, 2H), 7.46-7.7.28 (m, 4H), 6.92-6.88 (m, 2H), 4.41 (m, 2H), 3.73 (s, 3H), 2.24 (s, 3H).

Preparation of compound 7: 5-(3-(6-(4-fluorophenyl)pyrazin-2-yl)-1H-indol-5-yl)-1,3,4-oxadiazol-2-amine A solution of 5-(3-(6-(4-fluorophenyl)pyrazin-2-yl)-1-tosyl-1H-indol-5-yl)-N-(4-methoxybenzyl)-1,3,4-oxadiazol-2-amine (200 mg, 0.309 mmol) in TFA (1 ml) was heated to 100° C. in microwave for 30 min. The mixture was cooled to RT and TFA was removed in vacuo to give the crude material (130 mg, 80%). MS (ESI, pos. ion) m/z: 527 (M+1). To a solution of crude 5-(3-(6-(4-fluorophenyl)pyrazin-2-yl)-1-tosyl-1H-indol-5-yl)-1,3,4-oxadiazol-2-amine (130 mg, 0.247 mmol) in p-dioxane (1.3 mL) was added aq 10% NaOH (0.65 mL). The mixture was heated at 100° C. for 2 h and quenched with ice cold $H_2O$. The resulting precipitate was filtered and washed with $H_2O$. The crude was recrystallized with 10% MeOH/$CHCl_3$ to give 5-(3-(6-(4-fluorophenyl)pyrazin-2-yl)-1H-indol-5-yl)-1,3,4-oxadiazol-2-amine (25 mg, 27.3%) as an off-yellow solid. MS (ESI, pos. ion) m/z: 374.0 (M+1); $^1$H-NMR (400 MHz, DMSO-$d_6$): δ 12.11 (s, 1H), 9.17 (s, 1H), 9.06 (s, 1H), 9.00 (s, 1H), 8.53 (m, 1H), 8.37-8.34 (m, 2H), 8.75-8.73 (m, 1H), 7.64 (d, J=8 Hz, 1H), 7.49 (m, 2H), 7.12 (s, 2H).

Example 8

5-(3-(4-(2-fluorophenyl)pyrimidin-2-yl)-1H-indol-5-yl)-1,3,4-oxadiazol-2-amine

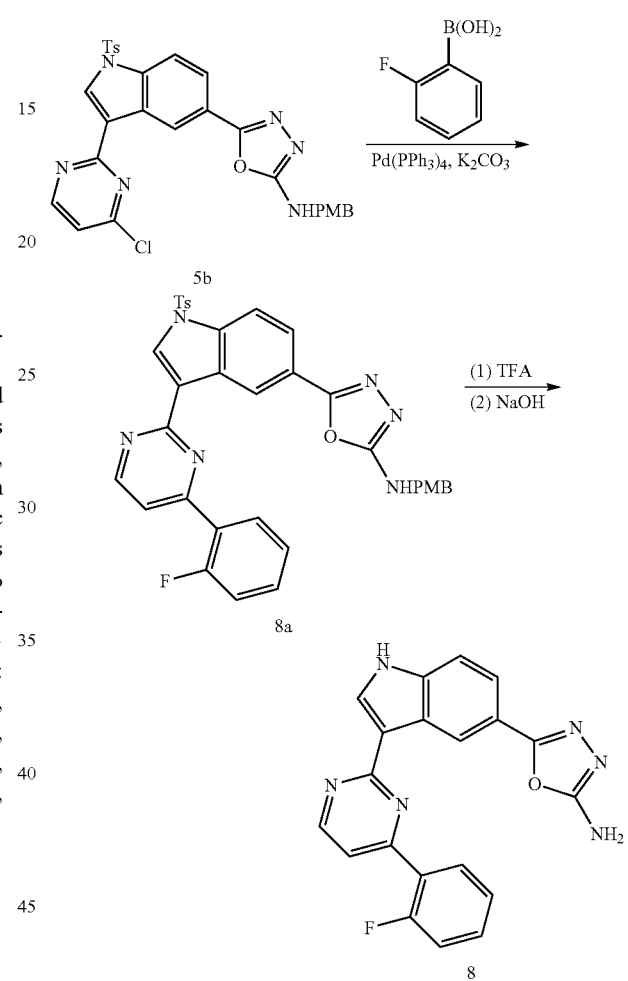

Preparation of compound 8a: 5-(3-(4-(2-fluorophenyl)pyrimidin-2-yl)-1-tosyl-1H-indol-5-yl)-N-(4-methoxybenzyl)-1,3,4-oxadiazol-2-amine To a solution of 5-(3-(4-chloropyrimidin-2-yl)-1-tosyl-1H-indol-5-yl)-N-(4-methoxybenzyl)-1,3,4-oxadiazol-2-amine (500 mg, 0.85 mmol) and 2-fluorophenylboronic acid (143.5 mg, 1.02 mmol) in p-dioxane/$H_2O$ (3:1, 15 mL) was added $K_2CO_3$ (235.5 mg, 1.71 mmol) and $Pd(PPh_3)_4$ (49 mg, 0.0427 mmol). The reaction was heated at reflux for 24 h, quenched with $H_2O$ and extracted with EtOAc. The combined organic layers were dried, filtered and concentrated. The residue was purified with silica gel chromatography (eluting with 50% EtOAc in Hex) to give to 5-(3-(4-(2-fluorophenyl)pyrimidin-2-yl)-1-tosyl-1H-indol-5-yl)-N-(4-methoxybenzyl)-1,3,4-oxadiazol-2-amine (400 mg, 72.8%). MS (ESI, pos. ion) m/z: 647.1 (M+1); $^1$H-NMR (400 MHz, DMSO-$d_6$): δ

9.43 (s, 1H), 9.06-8.97 (m, 2H), 8.42-8.17 (m, 2H), 8.12-8.03 (m, 3H), 7.91 (dd, J=8, 1.6 Hz, 1H), 7.65-7.53 (m, 5H), 7.46-7.40 (m, 4H), 7.28 (m, 2H), 6.88 (d, J=8 Hz, 2H), 4.35 (d, J=8 Hz, 2H), 3.72 (s, 3H), 2.33 (s, 3H).

Preparation of compound 8: 5-(3-(4-(2-fluorophenyl) pyrimidin-2-yl)-1H-indol-5-yl)-1,3,4-oxadiazol-2-amine To a solution of 5-(3-(4-(2-fluorophenyl)pyrimidin-2-yl)-1-tosyl-1H-indol-5-yl)-N-(4-methoxybenzyl)-1,3,4-oxadiazol-2-amine (250 mg, 0.38 mmol) in TFA (1.25 mL) was heated to 100° C. in a microwave for 30 min. The mixture was cooled to RT and TFA was removed in vacuo to give the crude material after washing with Et$_2$O. MS (ESI, pos. ion) m/z: 527 (M+1). To a solution of crude 5-(3-(4-(2-fluorophenyl) pyrimidin-2-yl)-1-tosyl-1H-indol-5-yl)-1,3,4-oxadiazol-2-amine (250 mg, 0.47 mmol) in p-dioxane (2.5 mL) was added aq. 10% NaOH (1.25 mL) and the reaction was heated at 100° C. for 2 h. The reaction was quenched with ice cold H$_2$O and the resulting precipitate was filtered, washed with ice cold H$_2$O and dried. The crude product was recrystallized with 10% MeOH/CHCl$_3$ to give 5-(3-(4-(2-fluorophenyl)pyrimidin-2-yl)-1H-indol-5-yl)-1,3,4-oxadiazol-2-amine (40 mg, 23%) as an off yellow solid. MS (ESI, pos. ion) m/z: 373.1 (M+1); $^1$H-NMR (400 MHz, DMSO-d$_6$): δ 12.13 (s, 1H), 9.08 (s, 1H), 8.92 (m, 1H) 8.47 (d, J=2.8 Hz, 1H) 8.33-8.30 (m, 1H), 7.72-7.76 (m, 6H), 7.51-7.53 (m, 3H).

Example 9

5-(3-(2-fluorophenyl)-1H-pyrrolo[3,2-b]pyridin-5-yl)-1,3,4-oxadiazol-2-amine

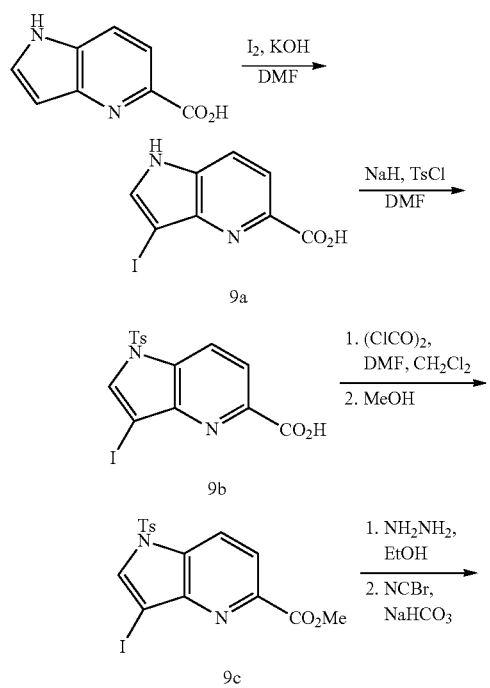

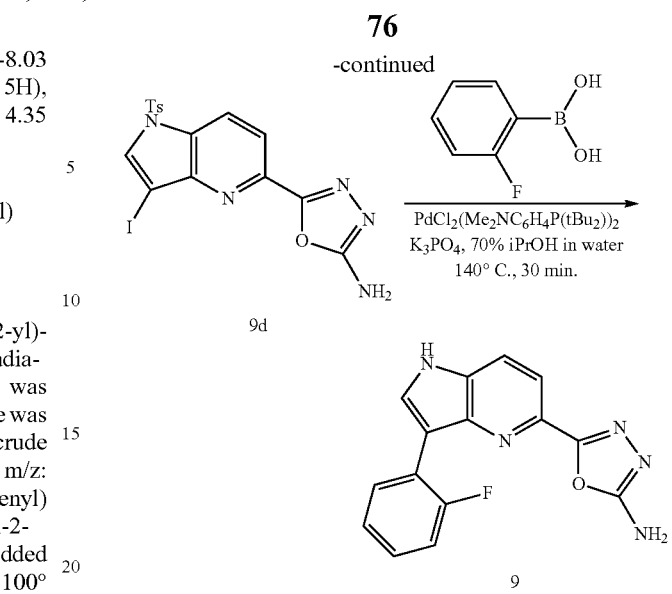

Preparation of compound 9a: 3-iodo-1H-pyrrolo[3,2-b]pyridine-5-carboxylic acid

To a solution of 1H-pyrrolo[3,2-b]pyridine-5-carboxylic acid (0.400 g, 2.467 mmol, Adesis, New Castle, Del.) in DMF (4.9 mL) was added I$_2$ (0.626 g, 2.467 mmol) and KOH (0.346 g, 6.17 mmol). The mixture was stirred at RT for 1 h. The mixture was poured into ice and H$_2$O (30 mL) containing sodium bisulfite (0.257 g, 2.467 mmol). The reaction was acidified with 5 M HCl. A yellow solid precipitated out and was collected by filtration, washed with H$_2$O and dried overnight in a vacuum oven to give 3-iodo-1H-pyrrolo[3,2-b] pyridine-5-carboxylic acid (0.516 g, 1.791 mmol, 72.6%). MS (ESI, pos. ion) m/z: 289.0 (M+1). $^1$H NMR (400 MHz, DMSO-d$_6$) δ ppm 7.91 (2H, s), 8.01 (1H, d, J=2.74 Hz), 12.03-12.11 (1H, m).

Preparation of compound 9b: 3-iodo-1-tosyl-1H-pyrrolo[3,2-b]pyridine-5-carboxylic acid To a solution of 3-iodo-1H-pyrrolo[3,2-b]pyridine-5-carboxylic acid (0.549 g, 1.906 mmol) in DMF (9.5 mL) at 0° C. was added NaH (60% in mineral oil, 0.191 g, 4.76 mmol). After 30 min at 0° C., p-toluenesulfonyl chloride (0.436 g, 2.287 mmol) was added and the reaction was warmed to RT. After 1 h at RT, the mixture was poured into H$_2$O and the mixture was acidified with 5 M HCl (aq.). The precipitate was collected by filtration, washed with H$_2$O and dried in a vacuum oven overnight to afford 3-iodo-1-((4-methylphenyl) sulfonyl)-1H-pyrrolo[3,2-b]pyridine-5-carboxylic acid. (0.663 g, 1.499 mmol, 79%) as a tan solid. MS (ESI, pos. ion) m/z: 442.9 (M+1). $^1$H NMR (400 MHz, DMSO-d$_6$) δ ppm 2.35 (3H, br s), 7.44 (2H, d, J=8.22 Hz), 7.96-8.01 (2H, m), 8.10 (1H, d, J=8.80 Hz), 8.47 (1H, d, J=8.80 Hz), 8.54 (1H, s).

Preparation of compound 9c: methyl 3-iodo-1-tosyl-1H-pyrrolo[3,2-b]pyridine-5-carboxylate To a suspension of 3-iodo-1-((4-methylphenyl)sulfonyl)-1H-pyrrolo[3,2-b]pyridine-5-carboxylic acid (0.750 g, 1.696 mmol) in DCM (8.5 mL) and a few drops of DMF was added oxalyl chloride (0.259 mL, 2.97 mmol) at RT. After 30 min, the reaction was cooled to 0° C., MeOH was added and the mixture was stirred for 30 min. The mixture was then concentrated. To the yellow solid was added H$_2$O and the mixture was extracted with DCM (3×). The combined organic layers were dried over anhydrous Na$_2$SO$_4$, filtered and concentrated to give methyl 3-iodo-1-((4-methylphenyl)sulfonyl)-1H-pyrrolo[3,2-b]pyridine-5-carboxylate (0.700 g, 1.534 mmol, 90%) as a pale yellow solid. MS (ESI, pos. ion) m/z: 457.0 (M+1). $^1$H NMR (400 MHz, CDCl$_3$) δ ppm 2.38 (3H, s), 4.01 (3H, s), 7.27-7.32 (2H, m), 7.75-7.81 (2H, m), 8.02 (1H, s), 8.18 (1H, d, J=8.80 Hz), 8.34 (1H, d, J=8.61 Hz).

Preparation of compound 9d: 5-(3-iodo-1-tosyl-1H-pyrrolo[3,2-b]pyridin-5-yl)-1,3,4-oxadiazol-2-amine A mixture of methyl 3-iodo-1-((4-methylphenyl)sulfonyl)-1H-pyrrolo[3,2-b]pyridine-5-carboxylate (1.080 g, 2.367 mmol) and hydrazine monohydrate (2.16 mL, 35.5 mmol) in EtOH (11.8 mL) was stirred at reflux for 30 min. After cooling to RT, the residue was partitioned between EtOAc and H$_2$O. The layers were separated and the organic phase was washed with H$_2$O, brine, dried over Na$_2$SO$_4$, filtered and concentrated to afford 790 mg of an off-white solid. The material was placed in 25 mL of a 3/2 dioxane/DCM solvent system and 1 M NaHCO$_3$ (aq.) (2.60 mL, 2.60 mmol) was added followed by a dropwise addition of cyanogen bromide (3.0 M solution in DCM, 0.868 mL, 2.60 mmol) at RT. The heterogenous solution was stirred for 30 min. Saturated NaHCO$_3$ (aq.) was added and the mixture was extracted with 10/1 DCM/MeOH (3×). The combined organic layers were dried over anhydrous Na$_2$SO$_4$, filtered and concentrated to give 790 mg of material. The yellow solid was suspended in MeOH and filtered. The filtrate contained the desired product and it was concentrated to afford 5-(3-iodo-1-((4-methylphenyl)sulfonyl)-1H-pyrrolo[3,2-b]pyridin-5-yl)-1,3,4-oxadiazol-2-amine (0.523 g, 1.087 mmol, 45.9%) as a pale yellow solid. MS (ESI, pos. ion) m/z: 481.9 (M+1). $^1$H NMR (400 MHz, DMSO-d$_6$) δ ppm 2.34 (3H, s), 7.44 (2H, d, J=8.22 Hz), 7.50 (2H, s), 8.00 (2H, d, J=8.41 Hz), 8.06 (1H, d, J=8.61 Hz), 8.46-8.52 (2H, m).

Preparation of compound 9: 5-(3-(2-fluorophenyl)-1H-pyrrolo[3,2-b]pyridin-5-yl)-1,3,4-oxadiazol-2-amine A glass microwave reaction vessel was charged with 5-(3-iodo-1-((4-methylphenyl)sulfonyl)-1H-pyrrolo[3,2-b]pyridin-5-yl)-1,3,4-oxadiazol-2-amine (0.050 g, 0.104 mmol), 2-fluorophenylboronic acid (0.020 g, 0.145 mmol, Sigma-Aldrich), bis-(di-tert-butyl(4-dimethylaminophenyl)phosphine)dichloropalladium(II) (3.68 mg, 5.19 µmol) and K$_3$PO$_4$ (0.066 g, 0.312 mmol) in 70% i-PrOH in water (1.00 mL). The mixture was stirred and heated in an Initiator microwave reactor (Personal Chemistry, Biotage AB, Inc., Uppsala, Sweden) at 140° C. for 30 min. The layers were separated and the reaction vessel washed with MeOH. The organic washes were combined, filtered and purified by RP-HPLC (5-100% MeCN in H$_2$O with 0.1% TFA over 20 min). Saturated NaHCO$_3$ (aq.) was added to the tubes that contained the desired product. The mixture was extracted with 3/1 CHCl$_3$/i-PrOH and the combined organic layers were dried over anhydrous Na$_2$SO$_4$, filtered and concentrated to give 5-(3-(2-fluorophenyl)-1H-pyrrolo[3,2-b]pyridin-5-yl)-1,3,4-oxadiazol-2-amine (0.005 g, 0.017 mmol, 16.30%). MS (ESI, pos. ion) m/z: 296.1 (M+1). $^1$H NMR (400 MHz, CD$_3$OD) δ ppm 7.02-7.10 (m, 1H), 7.11-7.19 (m, 2H), 7.77-7.86 (m, 2H), 7.99 (d, J=2.93 Hz, 1H), 8.81-8.91 (m, 1H).

Example 10

5-(3-(5-methoxypyridin-3-yl)-1H-pyrrolo[3,2-b]pyridin-5-yl)-1,3,4-oxadiazol-2-amine

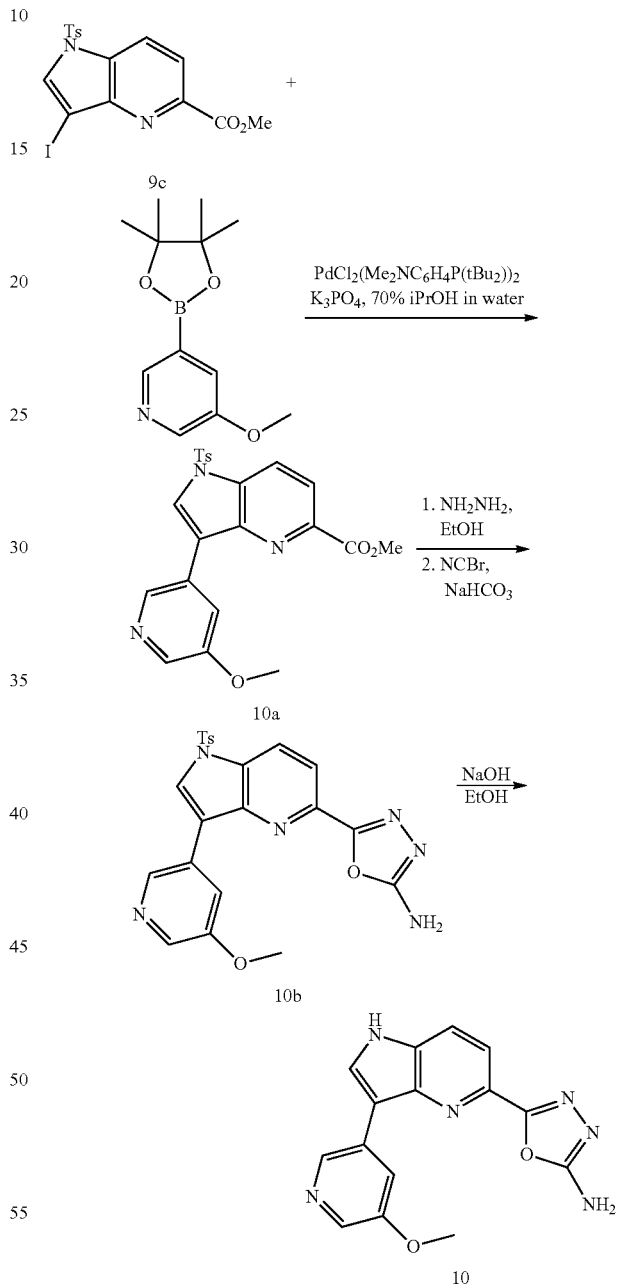

Preparation of compound 10a: methyl 3-(5-methoxypyridin-3-yl)-1-tosyl-1H-pyrrolo[3,2-b]pyridine-5-carboxylate A glass microwave reaction vessel was charged with methyl 3-iodo-1-((4-methylphenyl)sulfonyl)-1H-pyrrolo[3,2-b]pyridine-5-carboxylate (0.300 g, 0.658 mmol), 5-methoxy-3-pyridineboronic acid pinacol ester (0.216 g, 0.921 mmol, Sigma-Aldrich), and K₃PO₄ (0.419 g, 1.973 mmol) in 70% i-PrOH in H₂O (3.30 mL). The reaction was stirred and heated in an Initiator microwave reactor (Personal Chemistry, Biotage AB, Inc., Uppsala, Sweden) at 100° C. for 10 min. 2 M HCl (aq.) was added and the mixture was extracted with DCM (3×). The combined organic layers were dried over anhydrous Na₂SO₄, filtered and concentrated. The crude material was absorbed onto a plug of silica gel and purified by column chromatography (eluting with 0-10% MeOH in DCM) to provide methyl 3-(5-methoxy-3-pyridinyl)-1-((4-methylphenyl)sulfonyl)-1H-pyrrolo[3,2-b]pyridine-5-carboxylate (0.170 g, 0.389 mmol, 59.1%) as a pale yellow solid. MS (ESI, pos. ion) m/z: 438.0 (M+1). ¹H NMR (400 MHz, CDCl₃) δ ppm 2.37 (3H, s), 3.96 (3H, s), 4.00 (3H, s), 7.29 (2H, d, J=8.22 Hz), 7.79-7.85 (2H, m), 8.16-8.21 (2H, m), 8.27-8.34 (2H, m), 8.42 (1H, d, J=8.61 Hz), 8.81 (1H, d, J=1.56 Hz).

Preparation of compound 10b: 5-(3-(5-methoxypyridin-3-yl)-1-tosyl-1H-pyrrolo[3,2-b]pyridin-5-yl)-1,3,4-oxadiazol-2-amine A mixture of methyl 3-(5-methoxypyridin-3-yl)-1-((4-methylphenyl)sulfonyl)-1H-pyrrolo[3,2-b]pyridine-5-carboxylate (0.170 g, 0.389 mmol) and hydrazine monohydrate (0.283 mL, 5.83 mmol) in EtOH (3.90 mL) was stirred at reflux for 30 min. After cooling to RT, the mixture was filtered and the gray solid was washed with EtOAc to give 130 mg of material. This solid was placed in 5 mL of 3/2 dioxane/DCM and 1 M NaHCO₃ (0.427 mL, 0.427 mmol) was added followed by a dropwise addition of cyanogen bromide (3.0 M solution in DCM, 0.142 mL, 0.427 mmol) dropwise at RT. The heterogenous solution was stirred for 90 min, then more cyanogen bromide (0.070 mL) and more 1 M NaHCO₃ (aq., 0.200 mL) were added. The reaction was stirred for another 2 h. Saturated NaHCO₃ was added and the mixture was extracted with DCM (3×). The crude material was adsorbed onto a plug of silica gel and purified by column chromatography (eluting with 0-10% MeOH in DCM) to provide 5-(3-(5-methoxypyridin-3-yl)-1-((4-methylphenyl)sulfonyl)-1H-pyrrolo[3,2-b]pyridin-5-yl)-1,3,4-oxadiazol-2-amine (0.022 g, 0.048 mmol, 12.24%) as a yellow solid. MS (ESI, pos. ion) m/z: 463.1 (M+1). ¹H NMR (400 MHz, CD₃OD) δ ppm 2.37 (3H, s), 4.00 (3H, s), 7.40 (2H, d, J=8.22 Hz), 7.99 (2H, d, J=8.41 Hz), 8.10 (1H, d, J=8.80 Hz), 8.21 (1H, d, J=2.74 Hz), 8.34-8.40 (1H, m), 8.55 (1H, d, J=8.80 Hz), 8.67 (1H, s), 9.05 (1H, d, J=1.56 Hz).

Preparation of compound 10: 5-(3-(5-methoxypyridin-3-yl)-1H-pyrrolo[3,2-b]pyridin-5-yl)-1,3,4-oxadiazol-2-amine A mixture of 5-(3-(5-methoxypyridin-3-yl)-1-((4-methylphenyl)sulfonyl)-1H-pyrrolo[3,2-b]pyridin-5-yl)-1,3,4-oxadiazol-2-amine (0.022 g, 0.048 mmol) and 1 M NaOH (aq.) (0.095 mL, 0.095 mmol) in 4 mL of EtOH was stirred overnight at RT. The reaction was then concentrated and the residue taken up in H₂O and EtOAc. The EtOAc layer was put aside and the aqueous layer was acidified with 2 M HCl (aq.) and extracted with DCM and 3/1 CHCl₃/i-PrOH (2×). The aqueous layer was concentrated to give an orange solid, which was washed with MeOH and the MeOH washes were dried over Na₂SO₄, filtered and concentrated to give an orange solid. The solid was triturated with DCM and the orange solid (20 mg) was collected by filtration. This material was purified by reverse phase HPLC (5-100% MeCN in H₂O with 0.1% TFA) followed by silica gel chromatography (0-10% MeOH in DCM) to afford 5-(3-(5-methoxypyridin-3-yl)-1H-pyrrolo[3,2-b]pyridin-5-yl)-1,3,4-oxadiazol-2-amine (0.0022 g, 7.14 μmol, 15.00%) as a white solid. MS (ESI, pos. ion) m/z: 309.0 (M+1). ¹H NMR (400 MHz, CD₃OD) δ ppm 4.01 (3H, s), 7.92-7.99 (2H, m), 8.11 (1H, d, J=2.93 Hz), 8.23 (1H, s), 8.43-8.47 (1H, m), 9.03 (1H, d, J=1.76 Hz).

Example 11

5-(3-(2-fluorophenyl)-1H-pyrrolo[3,2-b]pyridin-5-yl)-1,3,4-oxadiazol-2-amine

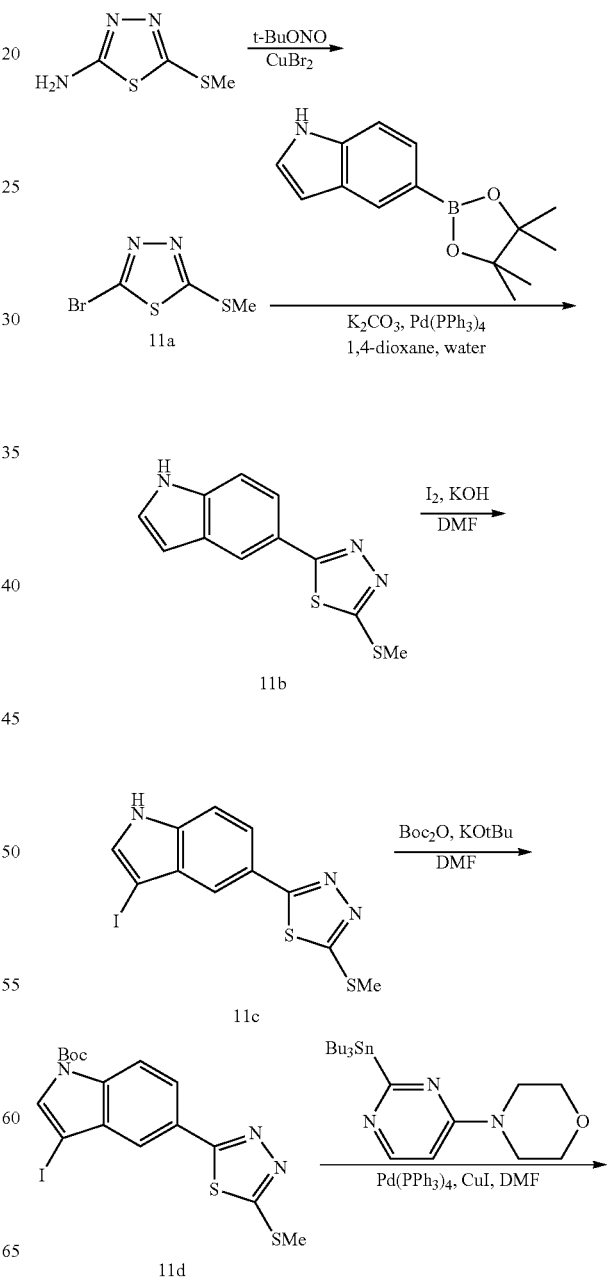

-continued

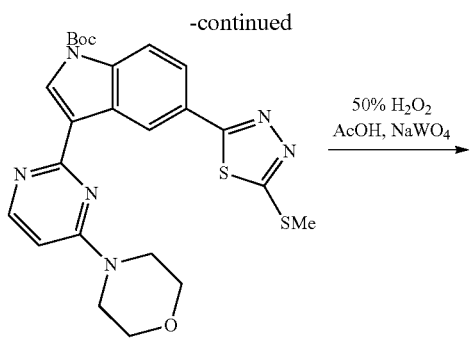

11e

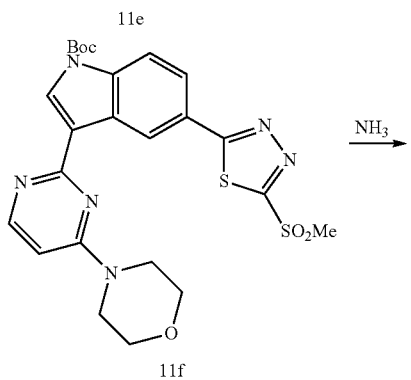

11f

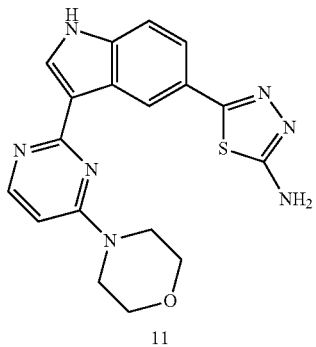 [SMILES: Nc1nnc(-c2ccc3[nH]cc(-c4cccc(N5CCOCC5)n4)c3c2)o1]

11

Preparation of compound 11a: 2-bromo-5-(methylthio)-1,3,4-thiadiazole

To a solution of MeCN (350 mL) was added CuBr$_2$ (67 g, 300 mmol) at RT. The mixture was cooled to 0-5° C. and tert-butyl nitrite (72.5 mL, 535 mmol) was added dropwise. The mixture was stirred for 5 min and 2-amino-5-(methylthio)-1,3,4-thiadiazole 1a (35 g, 238 mmol) was added. The reaction was stirred at RT for 2 h. EtOAc (525 mL) was added to the mixture and the reaction was quenched with 10% aq. NH$_4$Cl (350 mL) and 2% aq.NH$_3$ (175 mL) solution. The layers were separated and the aqueous layer was extracted with EtOAc. The combined organic layers were dried, filtered and concentrated. The residue was purified with silica gel chromatography (eluting with 5% EtOAc in Hex) to give 2-bromo-5-(methylthio)-1,3,4-thiadiazole (35 g, 70%) as a yellow solid. MS (ESI, pos. ion) m/z: 212.8 (M+1).

Preparation of compound 11b: 2-(1H-indol-5-yl)-5-(methylthio)-1,3,4-thiadiazole To a solution of 2-bromo-5-(methylthio)-1,3,4-thiadiazole (18.5 g, 87 mmol) and 5-(4,4,5,5-tetramethyl-1,3,2-dioxaborolan-2-yl)-1H-indole (21 g, 86 mmol) in p-dioxane (5 mL)/H$_2$O (5 mL) was added Pd(PPh$_3$)$_4$ (15.1 g, 13 mmol) followed by K$_2$CO$_3$ (48.2 g, 349 mmol). The reaction was heated under argon atmosphere at 110° C. for 4 h, then cooled to RT. The mixture was diluted with EtOAc and H$_2$O, and the two layers were separated. The aqueous layer was extracted with EtOAc. The combined organic layers were dried, filtered and concentrated. The crude material was recrystallized in EtOH to give 2-(1H-indol-5-yl)-5-(methylthio)-1,3,4-thiadiazole (10 g, 50%) as an off-white solid. MS (ESI, pos. ion) m/z: 247.8 (M+1). $^1$H-NMR (DMSO-d$_6$, 300 MHz): 2.8 (s, 3H), 6.6 (d, 1H), 7.5 (t, 1H), 7.55 (dd, 1H), 8.1 (s, 1H), 11.5 (s, 1H).

Preparation of compound 11c: 2-(3-iodo-1H-indol-5-yl)-5-(methylthio)-1,3,4-thiadiazole To a solution of 2-(1H-indol-5-yl)-5-(methylthio)-1,3,4-thiadiazole (18.5 g, 74.8 mmol) in DMF (190 mL) was added KOH (16.2 g, 299 mmol) followed by I$_2$ (38 g, 149.7 mmol). The reaction was stirred at RT for 2 h, and was quenched with 10% aq sodium bisulphate solution. The resulting precipitate was filtered and washed with H$_2$O to give 2-(3-iodo-1H-indol-5-yl)-5-(methylthio)-1,3,4-thiadiazole (21 g, 75%). MS (ESI, pos. ion) m/z: 373.8 (M+1). $^1$HNMR (DMSO-d$_6$, 300 MHz): 2.8 (s, 3H), 7.5 (d, 1H), 7.7 (m, 2H), 12.0 (s, 1H).

Preparation of compound 11d: tert-butyl 3-iodo-5-(5-(methylthio)-1,3,4-thiadiazol-2-yl)-1H-indole-1-carboxylate To a solution of 2-(3-iodo-1H-indol-5-yl)-5-(methylthio)-1,3,4-thiadiazole (21 g, 56.3 mmol) in DMF (210 mL) was added potassium tert-butoxide (12.6 g, 112.6 mol) and followed by di-tert-butyl-di-cabonate (24.5 g, 112.6 mmol). The reaction was stirred at RT for 2 h, and ice/H$_2$O was added. The resulting precipitate was filtered and washed with H$_2$O to give tert-butyl 3-iodo-5-(5-(methylthio)-1,3,4-thiadiazol-2-yl)-1H-indole-1-carboxylate (20 g, 75%). MS (ESI, pos. ion) m/z: 473.8 (M+1). $^1$HNMR (DMSO-d$_6$, 300 MHz): δ 2.8 (s, 3H), 7.5 (d, 1H), 7.7 (m, 2H), 12.0 (s, 1H).

Preparation of compound 11e: tert-butyl 5-(5-(methylthio)-1,3,4-thiadiazol-2-yl)-3-(4-morpholinopyrimidin-2-yl)-1H-indole-1-carboxylate To a solution of tert-butyl 3-iodo-5-(5-(methylthio)-1,3,4-thiadiazol-2-yl)-1H-indole-1-carboxylate (1.2 g, 2.5 mmol) and 4-(2-(tributylstannyl)pyrimidin-4-yl)morpholine (1.38 g, 4.0 mmol) in DMF (10 mL) was added CuI (0.62 g, 3.2 mmol) and Pd(PPh$_3$)$_4$ (0.29 g, 0.25 mmol). The mixture was purged with Ar for 5 min then heated at 90° C. for 1 h. The mixture was poured into H$_2$O and the aqueous layer was extracted with Et$_2$O. The combined organic layers were dried, filtered and concentrated. The residue was purified with flash chromatography to give tert-butyl 5-(5-(methylthio)-1,3,4-thiadiazol-2-yl)-3-(4-morpholinopyrimidin-2-yl)-1H-indole-1-carboxylate (255 mg, 20%). MS (ESI, pos. ion) m/z: 511.1 (M+1). $^1$H-NMR (DMSO-d$_6$, 300 MHz) δ: 9.12 (1H, d), 8.39 (2H, brs), 8.25 (1H, d), 7.9 (1H, dd), 6.79 (1H, d). 3.7-3.85 (8H, brs), 2.85 (3H, s), 1.65 (9H, s).

Preparation of compound 11f: tert-butyl 5-(5-(methylsulfonyl)-1,3,4-thiadiazol-2-yl)-3-(4-morpholinopyrimidin-2-yl)-1H-indole-1-carboxylate A mixture of tert-butyl 5-(5-(methylthio)-1,3,4-thiadiazol-2-yl)-3-(4-morpholinopyrimidin-2-yl)-1H-indole-1-carboxylate (1.7 g, 3.3 mmol), AcOH (15 mL), Na₂WO₄ (0.209 g, 0.6 mmol), and H₂O₂ (50%, 2.3 mL, 6.6 mmol) was stirred at RT overnight. Then the solvent was removed in vacuo and ice/H₂O was added to the residue. The mixture was extracted with DCM. The combined organic layers were dried, filtered and concentrated. The residue was purified with silica gel chromatography to give tert-butyl 5-(5-(methylsulfonyl)-1,3,4-thiadiazol-2-yl)-3-(4-morpholinopyrimidin-2-yl)-1H-indole-1-carboxylate (1.65 g, 90%). MS (ESI, pos. ion) m/z: 543.1 (M+1).

Preparation of compound 11: 5-(3-(4-morpholinopyrimidin-2-yl)-1H-indol-5-yl)-1,3,4-thiadiazol-2-amine A sealed tube was charged with tert-butyl 5-(5-(methylsulfonyl)-1,3,4-thiadiazol-2-yl)-3-(4-morpholinopyrimidin-2-yl)-1H-indole-1-carboxylate (1.7 g, 3.3 mmol) in DMSO (17 mL) saturated with NH₃. The reaction was heated at 110° C. for 7 h, then the mixture was poured into H₂O. The mixture was extracted with EtOAc and the combined organic layers were dried, filtered and concentrated. The residue was purified with silica gel chromatography to give 5-(3-(4-morpholinopyrimidin-2-yl)-1H-indol-5-yl)-1,3,4-thiadiazol-2-amine (65 mg, 5%). MS (ESI, pos. ion) m/z: 380.1 (M+1). ¹H-NMR (DMSO-d₆, 300 MHz) δ: 11.89 (1H, s), 8.79 (1H, s), 8.28 (1H, d, J=6.3 Hz), 8.24 (1H, d, J=2.4 Hz), 7.75 (1H, dd, J=8.4, 1.5 Hz), 7.52 (1H, d, J=8.7 Hz), 7.32 (2H, s), 6.66 (1H, d, J=6.3 Hz), 3.81 (8H, brs).

Example 12

N-(5-(3-(2-fluorophenyl)-1H-indol-5-yl)-1,3,4-thiadiazol-2-yl)propane-1,3-diamine

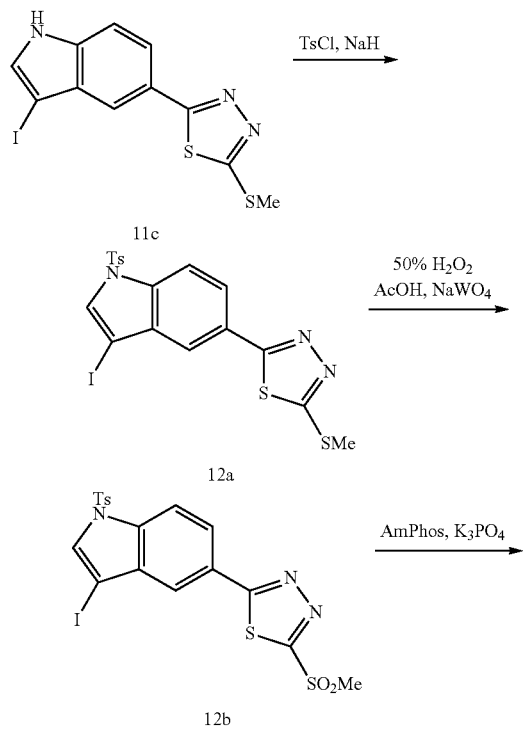

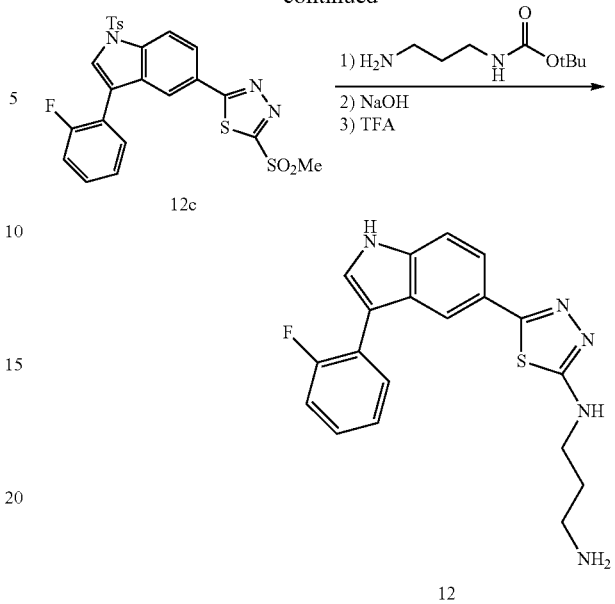

Preparation of compound 12a: 2-(3-iodo-1-tosyl-1H-indol-5-yl)-5-(methylthio)-1,3,4-thiadiazole To a solution of 2-(3-iodo-1H-indol-5-yl)-5-(methylthio)-1,3,4-thiadiazole (7.0 g, 18.7 mmol) in DMF (70 mL) was added NaH 60% in mineral oil (1.5 g, 37.4 mmol) followed by TsCl (5.3 g, 28.1 mmol). The reaction was stirred at RT for 8 h, and the mixture was then poured into ice/H₂O. The resulting precipitate was filtered, washed with water and dried to give 2-(3-iodo-1-tosyl-1H-indol-5-yl)-5-(methylthio)-1,3,4-thiadiazole (7.7 g, 78%). MS (ESI, pos. ion) m/z: 528 (M+1); ¹H-NMR (DMSO-d₆, 300 MHz): 2.3 (s, 3H), 2.8 (s, 3H), 7.4 (d, 2H) 7.8 (d, 1H) 7.95 (m, 3H), 8.1 (d, 1H), 8.25 (s, 1H).

Preparation of compound 12b: 2-(3-iodo-1-tosyl-1H-indol-5-yl)-5-(methylsulfonyl)-1,3,4-thiadiazole To a stirred solution of 2-(3-iodo-1-tosyl-1H-indol-5-yl)-5-(methylthio)-1,3,4-thiadiazole (500 mg, 0.948 mmol) in HOAc (3.0 ml) was added NaWO₄ (13.93 mg, 0.047 mmol) and dropwise H₂O₂, 35 wt. % solution in H₂O (1.0 mL) and the mixture was stirred at RT for 3 days. The resulting suspension mixture was diluted with H₂O and extracted with DCM. The organic layer was separated, washed with saturated NaHCO₃ aq solution, dried over Na₂SO₄, filtered, and concentrated to afford a yellow solid (474 mg) which is a mixture of 2-(3-iodo-1-tosyl-1H-indol-5-yl)-5-(methylsulfonyl)-1,3,4-thiadiazole [MS (ESI, pos. ion) m/z: 560 (M+1)] and 2-(3-iodo-1-tosyl-1H-indol-5-yl)-5-(methylsulfinyl)-1,3,4-thiadiazole MS (ESI, pos. ion) m/z: 544 (M+1).

Preparation of compound 12c: 2-(3-(2-fluorophenyl)-1-tosyl-1H-indol-5-yl)-5-(methylsulfonyl)-1,3,4-thiadiazole To a mixture of 2-(2-fluorophenyl)-4,4,5,5-tetramethyl-1,3,2-dioxaborolane (0.639 g, 2.88 mmol), 2-(3-iodo-1-tosyl-1H-indol-5-yl)-5-(methylsulfonyl)-1,3,4-thiadiazole (1.150 g, 2.056 mmol) in 70% IPA/H₂O (18 mL) was added potassium phosphate (1.309 g, 6.17 mmol), and AmPhos (0.073 g, 0.103 mmol). The reaction was heated at 100° C. for 5 min.

The aq. layer was removed and the organic layer was evaporated. The residue was purified with prep HPLC to give 2-(3-(2-fluorophenyl)-1-tosyl-1H-indol-5-yl)-5-(methylsulfonyl)-1,3,4-thiadiazole (0.487 g, 0.923 mmol, 44.9%) as a light brown solid. MS (ESI, pos. ion) m/z: 528 (M+1).

Preparation of compound 12: N-(5-(3-(2-fluorophenyl)-1H-indol-5-yl)-1,3,4-thiadiazol-2-yl)propane-1,3-diamine To a solution of 2-(3-(2-fluorophenyl)-1-tosyl-1H-indol-5-yl)-5-(methylsulfonyl)-1,3,4-thiadiazole (0.053 g, 0.10 mmol) in p-dioxane (1 mL) was added tert-butyl 3-aminopropylcarbamate (88 mg, 0.50 mmol, Aldrich), and the reaction was heated at 90° C. for 8 h. The residue was then purified with RP-HPLC. The purified material was dissolved in dioxane (1 mL) and aq. NaOH (1M, 0.1 mL) was added. The solution was heated in a microwave at 120° C. for 10 min. The solution was concentrated under reduced pressure and the resulting oil was stirred with 4M HCl/dioxane for 30 min, then evaporated under reduced pressure. The residue was purified by preparative HPLC to give N-(5-(3-(2-fluorophenyl)-1H-indol-5-yl)-1,3,4-thiadiazol-2-yl)-1,3-propanediamine (32 mg, 61.4%). MS (ESI, pos. ion) m/z: 368 (M+1). $^1$H NMR (400 MHz, CD$_3$OD) δ ppm 8.10 (1H, s), 7.66-7.72 (1H, m), 7.62-7.66 (1H, m), 7.59 (1H, d, J=1.6 Hz), 7.53-7.57 (1H, m), 7.17-7.35 (3H, m), 3.57 (2H, t, J=6.7 Hz), 3.03-3.10 (2H, m), 2.04-2.11 (2H, m).

Example 13

5-(3-(2-fluorophenyl)-1H-pyrrolo[3,2-b]pyridin-5-yl)-1,3,4-oxadiazol-2-amine

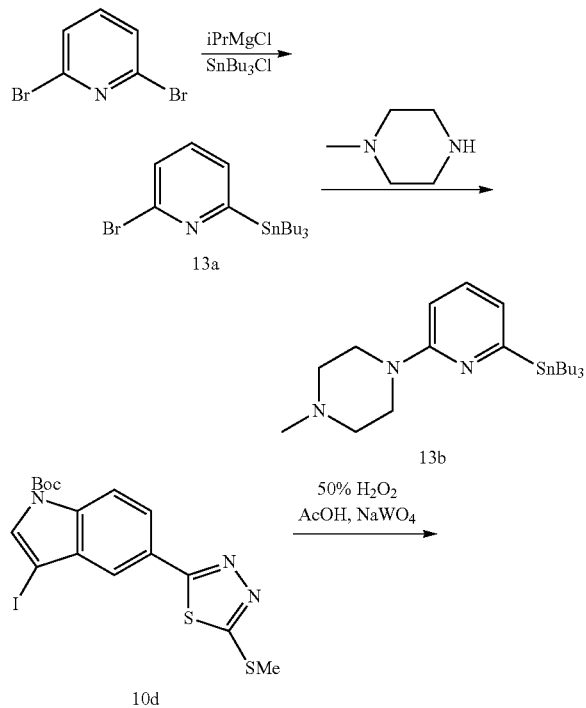

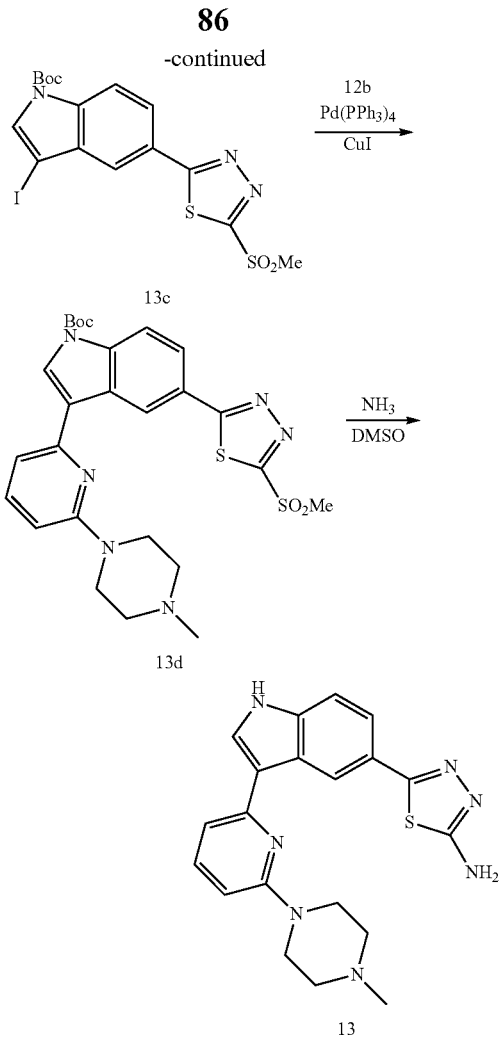

Preparation of compound 13a:
2-bromo-6-(tributylstannyl)pyridine

To a solution of 2.6-dibromopyridine (5.0 g, 21.1 mmol) in dry THF (50 ml) at 0° C. was added iso-propyl magnesium chloride (11.6 ml, 23.21 mmol) dropwise for 20 min. The reaction was stirred at RT for 2 h, then cooled to 0° C. Tri-butyl tin chloride (7.55 g, 23.21 mmol) was added dropwise in 15 min. The mixture was stirred at RT for 12 h. The reaction was quenched with 10% NH$_4$Cl solution and was extracted with EtOAc. The combined organic layers were washed with brine, dried, and concentrated. The residue was purified with silica gel chromatography to give 2-bromo-6-(tributylstannyl)pyridine (3.7 g, 40.3%). MS (ESI, pos. ion) m/z: 448 (M+1); $^1$H-NMR (CDCl$_3$, 300 MHz) δ 7.3-7.5 (3H, m), 1.5-1.7 (6H, m), 1.3-1.4 (6H, m), 1.1-1.25 (6H, q), 0.7-0.9 (9H, q).

Preparation of compound 13b: 1-methyl-4-(6-(tributylstannyl)pyridin-2-yl)piperazine To a solution of 2-bromo-6-(tributylstannyl)pyridine (2.0 g, 4.47 mmol) in Et$_3$N (3.12 mL, 22.37 mmol) and was added 1-methyl piperazine (2 ml, 17.89 mmol). The reaction was heated at 100° C. for 24 h then cooled to RT, diluted with water, and extracted with EtOAc. The combined organic layer were washed with brine, dried and concentrated. The residue was purified with silica gel chromatography to give 1-methyl-4-(6-(tributylstannyl)pyridin-2-yl)piperazine (1.4 g, 70.3%). MS (ESI, pos. ion) m/z: 466.2 (M+1); $^1$H-NMR (CDCl$_3$, 300 MHz) δ 7.3 (1H, t), 6.8 (1H, d), 6.5 (1H, d), 3.6 (4H, t), 2.5 (4H, t), 2.4 (3H, s), 1.5-1.7 (6H, m), 1.2-1.5 (6H, m), 1.0-1.2 (6H, q), 0.8-0.9 (9H, q).

Preparation of compound 13c: tert-butyl 3-iodo-5-(5-(methylsulfonyl)-1,3,4-thiadiazol-2-yl)-1H-indole-1-carboxylate tert-Butyl 3-iodo-5-(5-(methylthio)-1,3,4-thiadiazol-2-yl)-1H-indole-1-carboxylate (1 g, 2.11 mmol) was dissolved in HOAc (10 mL). To the solution was added NaWO$_4$ (35 mg, 0.1057 mmol) and 50% H$_2$O$_2$ (0.36 ml, 10.57 mmol). The reaction was stirred for 12 h at RT. Work up was carried by quenching ice H$_2$O (20 mL) solution. The solid precipitate was filtered and washed with H$_2$O and dried under vacuum to give tert-butyl 3-iodo-5-(5-(methylsulfonyl)-1,3,4-thiadiazol-2-yl)-1H-indole-1-carboxylate (800 mg, 80%). MS (ESI, pos. ion) m/z: 505.8 (M+1); $^1$HNMR (CDCl$_3$, 300 MHz): δ 8.4 (1H, d), 8.0-8.2 (2H, dd), 7.7 (1H, s), 3.5 (3H, s), 1.7 (9H, s).

Preparation of compound 13d: tert-butyl 3-(6-(4-methylpiperazin-1-yl)pyridin-2-yl)-5-(5-(methylsulfonyl)-1,3,4-thiadiazol-2-yl)-1H-indole-1-carboxylate A solution of tert-butyl 3-iodo-5-(5-(methylsulfonyl)-1,3,4-thiadiazol-2-yl)-1H-indole-1-carboxylate (650 mg, 1.146 mmol) and 1-methyl-4-(6-(tributylstannyl)pyridin-2-yl)piperazine (596 mg, 1.146 mmol) DMF (10 mL) was purged the Argon gas for 5 min. To the solution was added CuI (327.5 mg, 1.71 mmol), Pd(PPh$_3$)$_4$ (159 mg, 0.137 mmol) and again the mixture was purged the Argon gas for 5 min. The mixture was stirred at RT for 2 h, then at 90° C. for 1 h. The mixture was poured into H$_2$O and was extracted with EtOAc. The combined organic layer was dried, filtered and concentrated. The residue was purified with silica gel chromatography to give tert-butyl 3-(6-(4-methylpiperazin-1-yl)pyridin-2-yl)-5-(5-(methylsulfonyl)-1,3,4-thiadiazol-2-yl)-1H-indole-1-carboxylate (400 mg, 53.5%). MS (ESI, pos. ion) m/z: 555.1 (M+1); $^1$H-NMR (DMSO-d$_6$, 300 MHz) δ: 9.245 (1H, s), 8.45 (1H, s), 8.35 (1H, d), 8.07 (1H, d), 7.65 (1H, m), 7.4 (1H, d), 6.85 (1H, d), 3.7-3.8 (3H, s), 3.7 (2H, brs), 2.3 (3H, s), 1.75 (9H, s), 1.2-1.3 (6H, m).

Preparation of compound 13: 5-(3-(6-(4-methylpiperazin-1-yl)pyridin-2-yl)-1H-indol-5-yl)-1,3,4-thiadiazol-2-amine A sealed tube was charged with tert-butyl 3-(6-(4-methylpiperazin-1-yl)pyridin-2-yl)-5-(5-(methylsulfonyl)-1,3,4-thiadiazol-2-yl)-1H-indole-1-carboxylate (300 mg, 0.541 mmol) followed by ammonia in DMSO (10 mL). The reaction was heated at 120° C. for 4 h. Ice/H$_2$O and EtOAc were added to the mixture. The organic layer was separated and the aqueous layer was extracted with EtOAc. The combined organic layer was dried, filtered and concentrated. The residue was purified with RP-HPLC to give 5-(3-(6-(4-methylpiperazin-1-yl)pyridin-2-yl)-1H-indol-5-yl)-1,3,4-thiadiazol-2-amine (40 mg, 19%). MS (ESI, pos. ion) m/z: 392.1 (M+1); $^1$H-NMR (DMSO-d$_6$, 300 MHz) δ 11.76 (1H, s), 10 (1H, brs), 8.8 (1H, s), 8.16 (1H, s), 7.5-7.67 (4H, m), 7.28-7.3 (1H, d), 6.75-6.79 (1H, d), 4.54-4.57 (2H, d), 3.6-3.65 (2H, d), 3.17-3.24 (4H, m), 2.91 (3H, s).

Example 14

5-(3-(6-(pyrrolidin-1-yl)pyridin-2-yl)-1H-indol-5-yl)-1,3,4-thiadiazol-2-amine

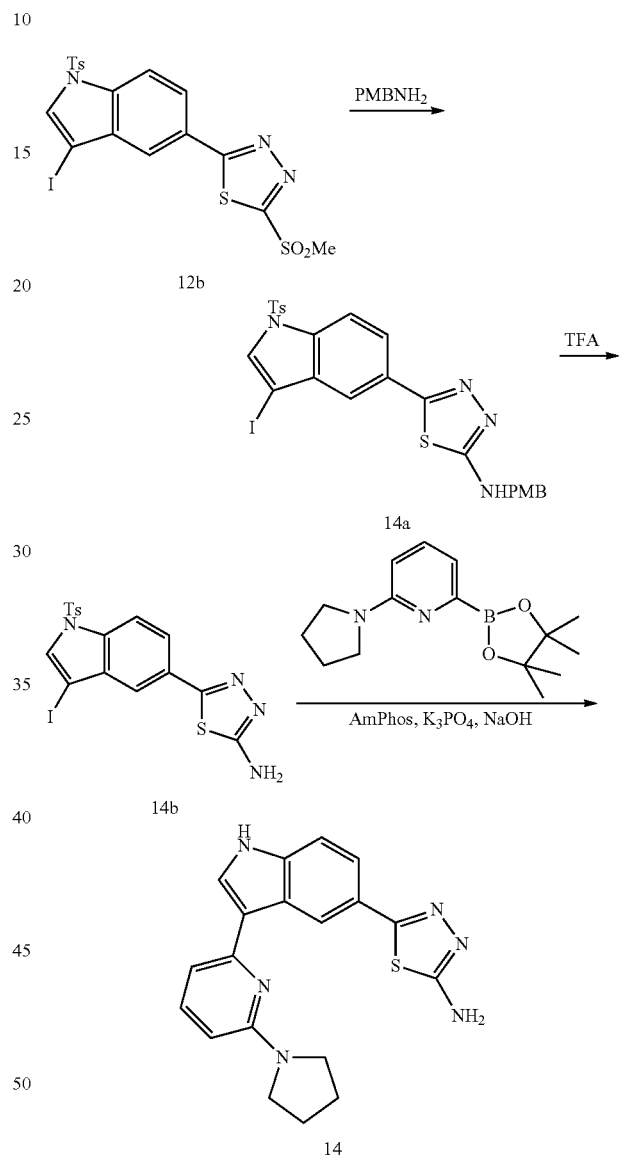

Preparation of compound 14a: 5-(3-iodo-1-tosyl-1H-indol-5-yl)-N-(4-methoxybenzyl)-1,3,4-thiadiazol-2-amine To a mixture of 2-(3-iodo-1-tosyl-1H-indol-5-yl)-5-(methylsulfinyl)-1,3,4-thiadiazole (423 mg, 0.757 mmol) in dioxane (3.0 mL) was added 4-methoxybenzylamine (0.294 mL, 2.268 mmol) at RT. The reaction was heated at 100° C. for 24 h. The solvent was removed and the residue was sonicated in MeOH and filtered. The filtrate was concentrated and the residue was purified with flash chromatography (eluting with 0-50% EtOAc in DCM) to give 5-(3-iodo-1-tosyl-1H-indol- 5-yl)-N-(4-methoxybenzyl)-1,3,4-thiadiazol-2-amine (245 mg, 0.397 mmol, 47%). MS (ESI, pos. ion) m/z: 617 (M+1); $^1$H NMR (400 MHz, DMSO-d$_6$) δ ppm 8.40 (t, J=5.67 Hz, 1H), 8.16 (s, 1H), 8.03 (d, J=8.61 Hz, 1H), 7.94 (d, J=8.41 Hz, 2H), 7.79 (dd, J=8.71, 1.66 Hz, 1H), 7.62 (d, J=1.56 Hz, 1H), 7.42 (d, J=8.41 Hz, 2H), 7.32 (d, J=8.61 Hz, 2H), 6.92 (d, J=8.61 Hz, 2H), 4.46 (d, J=5.67 Hz, 2H), 3.73 (s, 3H), 2.33 (s, 3H).

Preparation of compound 14b: 5-(3-iodo-1-tosyl-1H-indol-5-yl)-1,3,4-thiadiazol-2-amine A solution of 5-(3-iodo-1-tosyl-1H-indol-5-yl)-N-(4-methoxybenzyl)-1,3,4-thiadiazol-2-amine (0.50 g, 0.811 mmol) and TFA (2.0 mL, 26.9 mmol) was heated in a microwave at 100° C. for 8 min. The solvent was removed in vacuo and the residue was dissolved in DCM and washed with sat. NaHCO$_3$. The organic layer was dried, filtered and concentrated to give the crude material. MS (ESI, pos. ion) m/z: 497 (M+1).

Preparation of compound 14: 5-(3-(6-(pyrrolidin-1-yl)pyridin-2-yl)-1H-indol-5-yl)-1,3,4-thiadiazol-2-amine A glass microwave reaction vessel was charged with 2-(pyrrolidin-1-yl)-6-(4,4,5,5-tetramethyl-1,3,2-dioxaborolan-2-yl)pyridine (46 mg, 0.17 mmol, CombiPhos Catalysts, Inc.) and 5-(3-iodo-1-tosyl-1H-indol-5-yl)-1,3,4-thiadiazol-2-amine (060 g, 0.12 mmol) in 66% IPA in H$_2$O (1 mL) followed by Amphos (4 mg, 6 μmol), potassium phosphate (0.077 g, 0.36 mmol). The mixture was stirred and heated in a Initiator microwave reactor (Personal Chemistry, Biotage AB, Inc., Uppsala, Sweden) at 100° C. for 10 min. The aqueous layer was removed and the resulting mixture was concentrated in vacuo and purified by preparative HPLC. The product was dissolved in p-dioxane (1 mL) and aq. NaOH (1 M, 0.1 mL) was added. The solution was heated in a microwave at 100° C. for 10 min, and purified by preparative HPLC to give 5-(3-(6-(1-pyrrolidinyl)-2-pyridinyl)-1H-indol-5-yl)-1,3,4-thiadiazol-2-amine (3 mg, 8%). MS (ESI, pos. ion) m/z: 364 (M+1). $^1$H NMR (400 MHz, CD$_3$OD) δ ppm 8.23 (1H, s), 8.00 (1H, s), 7.91 (1H, dd, J=9.0, 7.6 Hz), 7.65 (1H, d, J=8.6 Hz), 7.58 (1H, d, J=8.6 Hz), 7.09 (1H, d, J=7.2 Hz), 6.85 (1H, d, J=9.0 Hz), 3.60-3.68 (4H, m), 2.06-2.14 (4H, m).

Example 15

5-(3-(6-(pyrrolidin-1-yl)pyridin-2-yl)-1H-indol-5-yl)-1,3,4-thiadiazol-2-amine

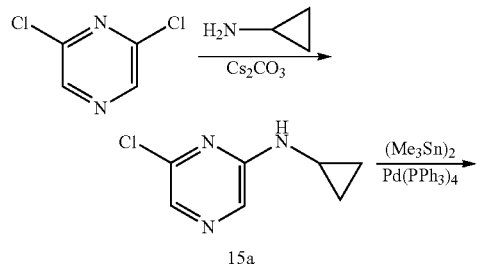

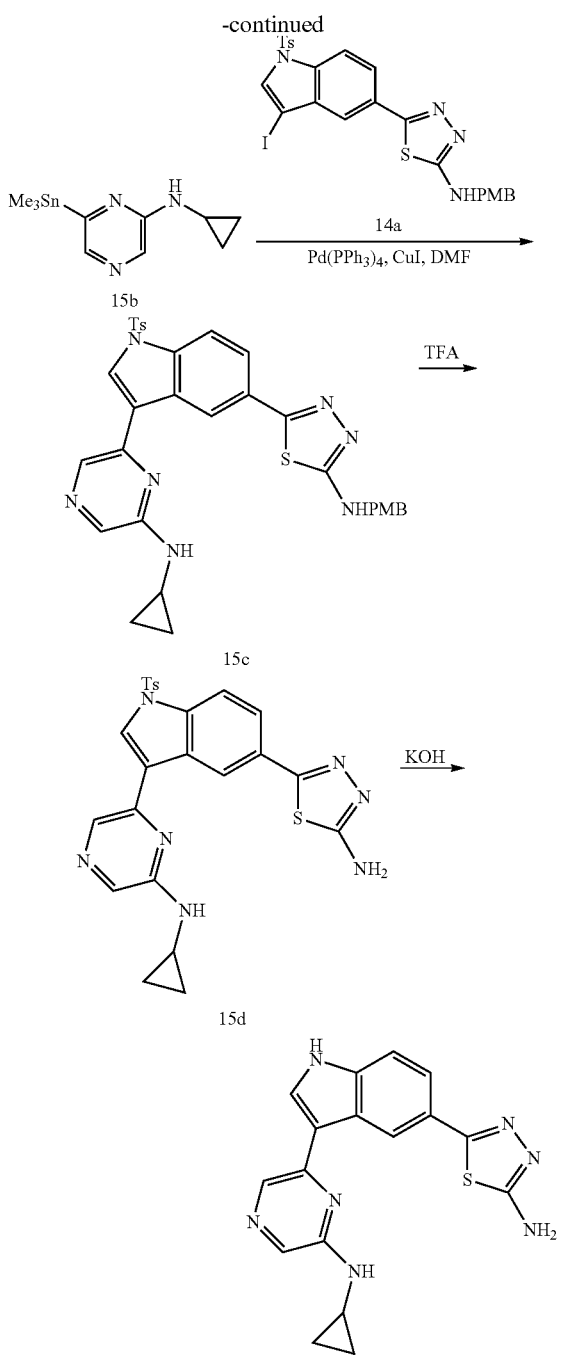

Preparation of compound 15a: 6-chloro-N-cyclopropylpyrazin-2-amine

A glass microwave reaction vessel was charged with 2,6-dichloropyrazine (1.0 g, 6.71 mmol) and cyclopropanamine (0.383 g, 6.71 mmol) in DMF (4 mL) followed by cesium carbonate (2.187 g, 6.71 mmol). The reaction was stirred and heated in an oil bath at 100° C. for 15 h, then cooled to RT. The mixture was diluted with DCM and washed with H$_2$O. The organic layer was dried, filtered and concentrated. The residue was purified with silica gel chromatography (eluting with 5-10% EtOAc in Hex) to give 6-chloro-N-cyclopropylpyrazin-2-amine (0.87 g, 5.13 mmol, 76%) as a yellow solid. MS (ESI, pos. ion) m/z: 170 (M+1).

Preparation of compound 15b: N-cyclopropyl-6-(trimethylstannyl)pyrazin-2-amine

A glass microwave reaction vessel was charged with 6-chloro-N-cyclopropylpyrazin-2-amine (200 mg, 1.179 mmol) and Pd(PPh$_3$)$_4$ (68 mg, 0.059 mmol) in p-dioxane (2 mL) followed by hexamethylditin (367 µL, 1.769 mmol). The reaction was stirred and heated in a Initiator microwave reactor (Personal Chemistry, Biotage AB, Inc., Uppsala, Sweden) at 100° C. for 2 h, the solvent was removed and the crude material was used in the next step without further purification. MS (ESI, pos. ion) m/z: 300 (M+1).

Preparation of compound 15c: 5-(3-(6-(cyclopropylamino)pyrazin-2-yl)-1-tosyl-1H-indol-5-yl)-N-(4-methoxybenzyl)-1,3,4-thiadiazol-2-amine A glass microwave reaction vessel was charged with 5-(3-iodo-1-tosyl-1H-indol-5-yl)-N-(4-methoxybenzyl)-1,3,4-thiadiazol-2-amine (543 mg, 0.881 mmol) and N-cyclopropyl-6-(trimethylstannyl)pyrazin-2-amine (350 mg, 1.175 mmol) in DMF (3 mL) followed by copper(i) iodide (223 mg, 1.175 mmol) and Pd(PPh$_3$)$_4$ (67.9 mg, 0.059 mmol). The reaction was stirred and heated in a Initiator microwave reactor (Personal Chemistry, Biotage AB, Inc., Uppsala, Sweden) at 100° C. for 1 h, then diluted with DCM and washed with H$_2$O. The organic layer was dried, filtered and concentrated. The residue was purified with silica gel chromatography (eluting with 20-60% EtOAc in Hex) to give 5-(3-(6-(cyclopropylamino)pyrazin-2-yl)-1-tosyl-1H-indol-5-yl)-N-(4-methoxybenzyl)-1,3,4-thiadiazol-2-amine (130 mg, 0.208 mmol, 17.74% for two steps). MS (ESI, pos. ion) m/z: 624 (M+1).

Preparation of compound 15d: 5-(3-(6-(cyclopropylamino)pyrazin-2-yl)-1-tosyl-1H-indol-5-yl)-1,3,4-thiadiazol-2-amine A glass microwave reaction vessel was charged with 5-(3-(6-(cyclopropylamino)pyrazin-2-yl)-1-tosyl-1H-indol-5-yl)-N-(4-methoxybenzyl)-1,3,4-thiadiazol-2-amine (120 mg, 0.192 mmol) in TFA (1.5 mL). The reaction was stirred and heated in a Initiator microwave reactor (Personal Chemistry, Biotage AB, Inc., Uppsala, Sweden) at 120° C. for 15 min. Then the solvent was removed. The residue was diluted with DCM and washed with sat. NaHCO$_3$, dried, filtered and concentrated to give the crude material, which was used in the next step without further purification. MS (ESI, pos. ion) m/z: 504 (M+1).

Preparation of compound 15: 5-(3-(6-(cyclopropylamino)pyrazin-2-yl)-1H-indol-5-yl)-1,3,4-thiadiazol-2-amine A glass microwave reaction vessel was charged with 5-(3-(6-(cyclopropylamino)pyrazin-2-yl)-1-tosyl-1H-indol-5-yl)-1,3,4-thiadiazol-2-amine (97 mg, 0.193 mmol) in p-dioxane (2 mL) followed by 1 M KOH (0.8 mL). The reaction was stirred and heated in a Initiator microwave reactor (Personal Chemistry, Biotage AB, Inc., Uppsala, Sweden) at 100° C. for 15 min, then solvent was removed. The residue was purified with RP-HPLC (5-40% ACN in H$_2$O with 0.1% TFA) to give 5-(3-(6-(cyclopropylamino)pyrazin-2-yl)-1H-indol-5-yl)-1,3,4-thiadiazol-2-amine (12.5 mg, 18.6%) as a solid. MS (ESI, pos. ion) m/z: 350 (M+1); $^1$H NMR (400 MHz, DMSO-d$_6$) δ ppm 11.80 (1H, br. s.), 8.97 (1H, s), 8.31 (1H, s), 8.22 (1H, d, J=2.7 Hz), 7.62-7.76 (2H, m), 7.52 (2H, d, J=8.4 Hz), 7.27 (1H, br. s.), 2.83 (1H, dt, J=6.9, 3.2 Hz), 0.88-1.00 (2H, m), 0.49-0.60 (2H, m)

Example 16

5-(3-(6-(cyclopentylamino)pyridin-2-yl)-1H-indol-5-yl)-1,3,4-thiadiazol-2-amine

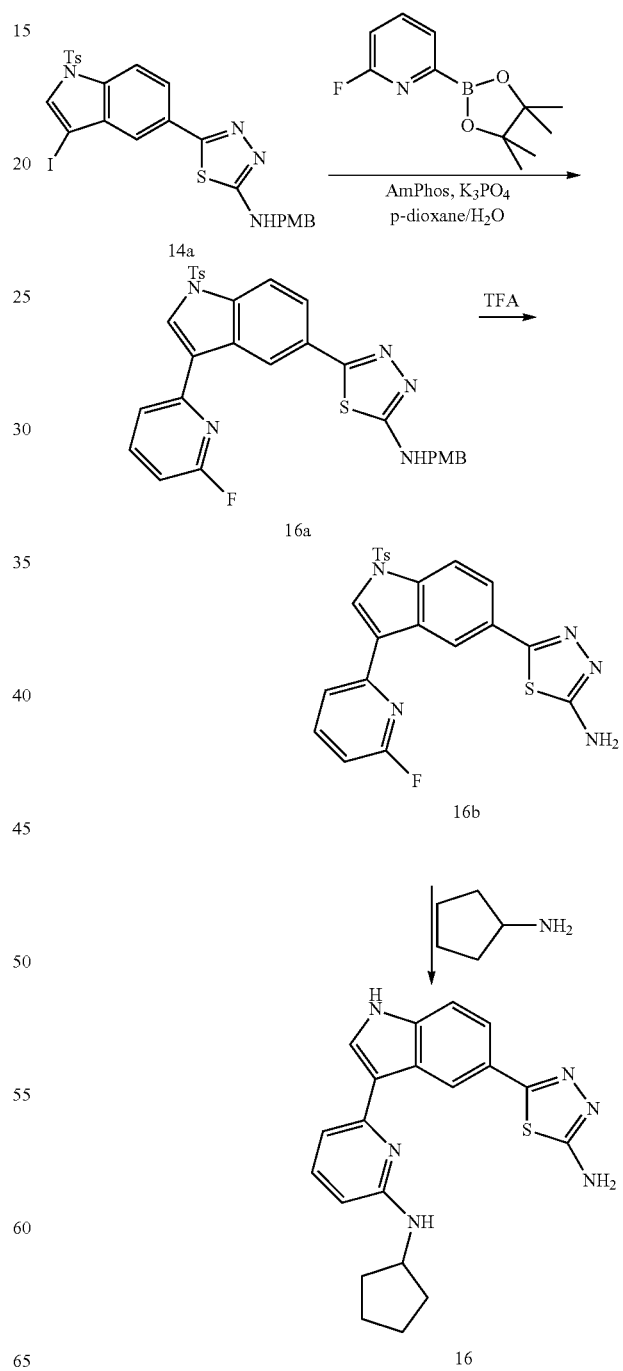

Preparation of compound 16a: 5-(3-(6-fluoropyridin-2-yl)-1-tosyl-1H-indol-5-yl)-N-(4-methoxybenzyl)-1,3,4-thiadiazol-2-amine A glass microwave reaction vessel was charged with 5-(3-iodo-1-tosyl-1H-indol-5-yl)-N-(4-methoxybenzyl)-1,3,4-thiadiazol-2-amine (500 mg, 0.811 mmol) and 6-fluoropyridine-2-boronic acid pinacol ester (226 mg, 1.014 mmol) in p-dioxane/H$_2$O (4:1, 7.5 mL) followed by potassium phosphate (430 mg, 2.028 mmol) and bis(di-tert-butyl(4-dimethylaminophenyl)phosphine)dichloropalladium(II) (28.7 mg, 0.041 mmol). The reaction was stirred and heated in a Initiator microwave reactor (Personal Chemistry, Biotage AB, Inc., Uppsala, Sweden) at 105° C. for 30 min. The mixture was diluted with DCM and washed with H$_2$O. The organic layer was dried, filtered and concentrated. The residue was purified with silica gel chromatography (eluting with 5-15% EtOAc in DCM with 1% MeOH) to give 5-(3-(6-fluoropyridin-2-yl)-1-tosyl-1H-indol-5-yl)-N-(4-methoxybenzyl)-1,3,4-thiadiazol-2-amine (418 mg, 0.714 mmol, 88%) as a yellow solid. MS (ESI, pos. ion) m/z: 378 (M+1).

Preparation of compound 16b: 5-(3-(6-fluoropyridin-2-yl)-1-tosyl-1H-indol-5-yl)-1,3,4-thiadiazol-2-amine A glass microwave reaction vessel was charged with 5-(3-(6-fluoropyridin-2-yl)-1-tosyl-1H-indol-5-yl)-N-(4-methoxybenzyl)-1,3,4-thiadiazol-2-amine (400 mg, 0.683 mmol) in TFA (0.5 mL). The reaction was stirred and heated in a Initiator microwave reactor (Personal Chemistry, Biotage AB, Inc., Uppsala, Sweden) at 120° C. for 30 min. The solvent was removed and the residue was diluted with DCM and washed with sat. NaHCO$_3$. The organic layer was dried, filtered and concentrated. The residue was purified with silica gel chromatography (eluting with 10-25% EtOAc in DCM with 1% MeOH) to give 5-(3-(6-fluoropyridin-2-yl)-1-tosyl-1H-indol-5-yl)-1,3,4-thiadiazol-2-amine (250 mg, 0.537 mmol, 79%) as a white solid. MS (ESI, pos. ion) m/z: 466 (M+1).

Preparation of compound 16: 5-(3-(6-(cyclopentylamino)pyridin-2-yl)-1H-indol-5-yl)-1,3,4-thiadiazol-2-amine 2,2,2-trifluoroacetate A glass microwave reaction vessel was charged with 5-(3-(6-fluoropyridin-2-yl)-1-tosyl-1H-indol-5-yl)-1,3,4-thiadiazol-2-amine (50 mg, 0.107 mmol) and aminocyclopentane (0.1 mL, 1.01 mmol) in DMSO (0.8 mL). The reaction was stirred and heated in a Initiator microwave reactor (Personal Chemistry, Biotage AB, Inc., Uppsala, Sweden) at 150° C. for 3 h, then the mixture was purified with RP-HPLC to give 5-(3-(6-(cyclopentylamino)pyridin-2-yl)-1H-indol-5-yl)-1,3,4-thiadiazol-2-amine 2,2,2-trifluoroacetate (18.0 mg, 34%) as a yellow solid (TFA salt). MS (ESI, pos. ion) m/z: 377 (M+1). $^1$H NMR (400 MHz, DMSO-d$_6$) δ ppm 12.19 (1H, br. s.), 8.10 (1H, br. s.), 7.54-7.75 (2H, m), 7.42 (2H, br. s.), 7.14 (1H, br. s.), 1.98-2.18 (2H, m), 1.44-1.85 (5H, m).

Example 17

5-(3-(6-(cyclopentylamino)pyrazin-2-yl)-1H-indol-5-yl)-1,3,4-thiadiazol-2-amine

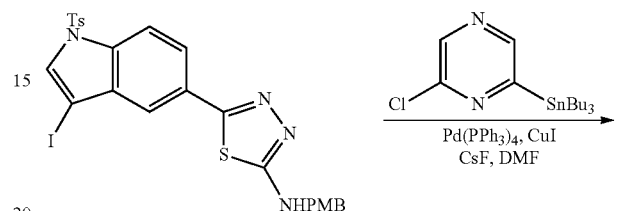

14a

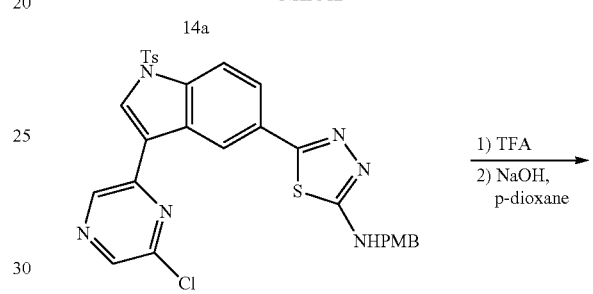

17a

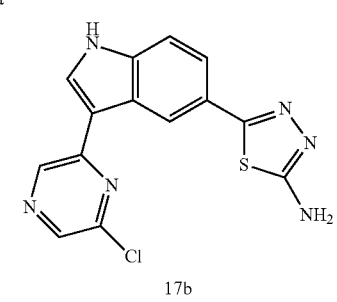

17b

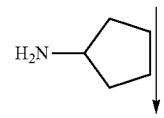

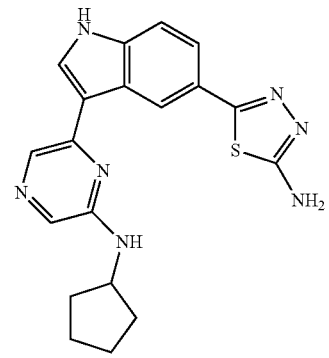

17

Preparation of compound 17a: 5-(3-(6-fluoropyridin-2-yl)-1-tosyl-1H-indol-5-yl)-N-(4-methoxybenzyl)-1,3,4-thiadiazol-2-amine A glass microwave reaction vessel was charged with 5-(3-iodo-1-tosyl-1H-indol-5-yl)-N-(4-methoxybenzyl)-1,3,4-thiadiazol-2-amine (1.50 g, 2.433 mmol) and 2-chloro-6-(tributylstannyl)pyrazine (1.473 g, 3.65 mmol) in DMF (20 mL) followed by cesium fluoride (555 mg, 3.65 mmol), CuI (46 mg, 0.243 mmol) and Pd(PPh$_3$)$_4$ (0.281 g, 0.243 mmol). The reaction was stirred and heated in a Initiator microwave reactor (Personal Chemistry, Biotage AB, Inc., Uppsala, Sweden) at 100° C. for 1 h, then the mixture was diluted with DCM and washed with H$_2$O. The organic layer was dried (MgSO$_4$), filtered and concentrated in vacuo. The residue was purified silica gel chromatography (eluting with 20-60% EtOAc in Hex) to give 5-(3-(6-chloropyrazin-2-yl)-1-tosyl-1H-indol-5-yl)-N-(4-methoxybenzyl)-1,3,4-thiadiazol-2-amine (1.0 g, 68.2%) as a solid. MS (ESI, pos. ion) m/z: 603 (M+1).

Preparation of compound 17b: 5-(3-(6-chloropyrazin-2-yl)-1H-indol-5-yl)-1,3,4-thiadiazol-2-amine A glass microwave reaction vessel was charged with 5-(3-(6-chloropyrazin-2-yl)-1-tosyl-1H-indol-5-yl)-N-(4-methoxybenzyl)-1,3,4-thiadiazol-2-amine (400 mg, 0.663 mmol) in TFA (1.5 mL). The mixture was stirred and heated in a Initiator microwave reactor (Personal Chemistry, Biotage AB, Inc., Uppsala, Sweden) at 120° C. for 15 min, then cooled to RT. The solvent was removed in vacuo and the residue was diluted with p-dioxane (2 mL) and aq. NaOH (5 M, 0.8 mL) and the mixture was heated in a microwave at 100° C. for 15 min. The mixture was cooled to RT, diluted with water and extracted with CHCl$_3$/iPrOH (4:1). The combined organic layers were dried, filtered and concentrated to give the crude material. MS (ESI, pos. ion) m/z: 329 (M+1).

Preparation of compound 17: 5-(3-(6-(cyclopentylamino)pyrazin-2-yl)-1H-indol-5-yl)-1,3,4-thiadiazol-2-amine 2,2,2-trifluoroacetate A glass microwave reaction vessel was charged with 5-(3-(6-chloropyrazin-2-yl)-1H-indol-5-yl)-1,3,4-thiadiazol-2-amine (50 mg, 0.152 mmol) and cyclopentanamine (0.2 mL, 2.025 mmol, Aldrich) in DMSO (0.9 mL). The mixture was stirred and heated in a Initiator microwave reactor (Personal Chemistry, Biotage AB, Inc., Uppsala, Sweden) at 160° C. for 75 min, then cooled to RT. The mixture was purified with RP-HPLC (5-40% ACN in water with 0.1% TFA) to give 5-(3-(6-(cyclopentylamino)pyrazin-2-yl)-1H-indol-5-yl)-1,3,4-thiadiazol-2-amine 2,2,2-trifluoroacetate (20.0 mg, 26.7%) as an orange solid MS (ESI, pos. ion) m/z: 378 (M+1). $^1$H NMR (400 MHz, DMSO-d$_6$) δ ppm 11.80 (1H, br. s.), 8.90 (1H, d, J=1.6 Hz), 8.15-8.26 (2H, m), 7.61-7.71 (2H, m), 7.52 (2H, d, J=8.6 Hz), 7.08 (1H, br. s.), 4.40-4.47 (2H, m), 2.02-2.24 (2H, m), 1.62-1.83 (4H, m), 1.47-1.62 (2H, m).

Example 18

4-(6-(5-(5-amino-1,3,4-thiadiazol-2-yl)-1H-indol-3-yl)pyrazin-2-yl)-1-methylpiperazin-2-one

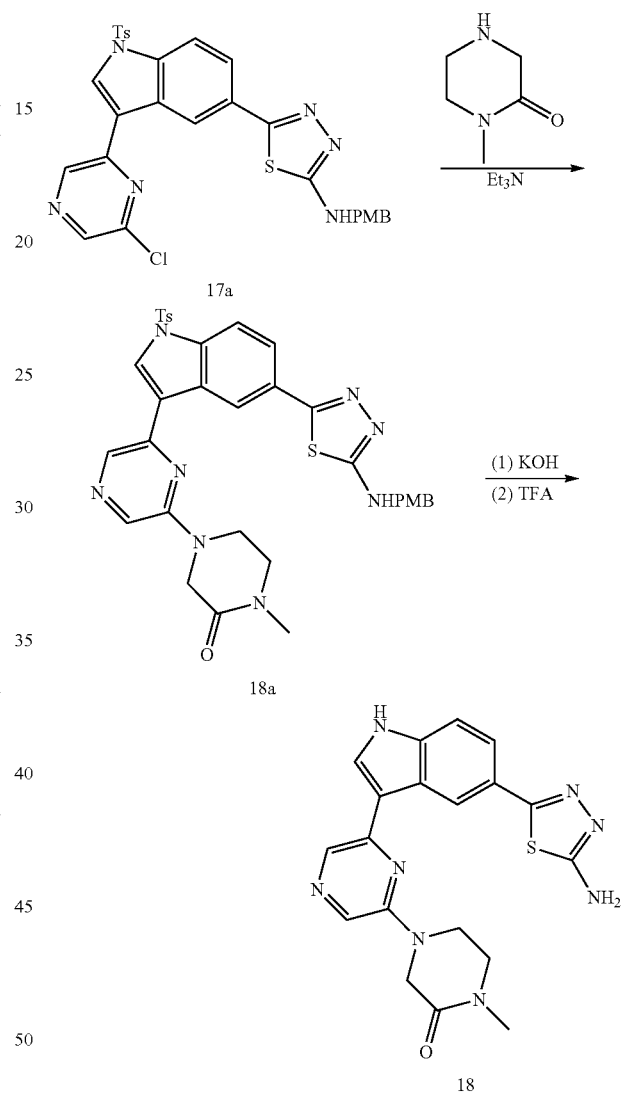

Preparation of compound 18a: 4-(6-(5-(5-(4-methoxybenzylamino)-1,3,4-thiadiazol-2-yl)-1-tosyl-1H-indol-3-yl)pyrazin-2-yl)-1-methylpiperazin-2-one To a solution of 5-(3-(6-chloropyrazin-2-yl)-1-tosyl-1H-indol-5-yl)-N-(4-methoxybenzyl)-1,3,4-thiadiazol-2-amine (100 mg, 0.166 mmol) in NMP (1 mL) was added 1-methylpiperazin-2-one (28.4 mg, 0.249 mmol) and Et$_3$N (69.2 µL, 0.497 mmol). The reaction was stirred at 155° C. for 18 h, then cooled to RT. H$_2$O was added and the resulting suspension was filtered to give the crude material. MS (ESI, pos. ion) m/z: 681 (M+1).

Preparation of compound 18: 4-(6-(5-(5-amino-1,3,4-thiadiazol-2-yl)-1H-indol-3-yl)pyrazin-2-yl)-1-methylpiperazin-2-one A glass microwave reaction vessel was charged with 4-(6-(5-(5-(4-methoxybenzylamino)-1,3,4-thiadiazol-2-yl)-1-tosyl-1H-indol-3-yl)pyrazin-2-yl)-1-methylpiperazin-2-one (70 mg, 0.103 mmol) in THF (2 mL) followed by 1 M KOH (500 µL, 0.500 mmol). The mixture was stirred and heated in a Initiator microwave reactor (Personal Chemistry, Biotage AB, Inc., Uppsala, Sweden) at 100° C. for 1 h, then cooled to RT. The mixture was diluted with H₂O, and extracted with DCM. The combined organic layers were dried, filtered and concentrated to give the crude 4-(6-(5-(5-(4-methoxybenzylamino)-1,3,4-thiadiazol-2-yl)-1H-indol-3-yl)pyrazin-2-yl)-1-methylpiperazin-2-one. MS (ESI, pos. ion) m/z: 527 (M+1). A glass microwave reaction vessel was charged with the above crude compound (54 mg, 0.103 mmol) in TFA (1 mL). The reaction was stirred and heated in a Initiator microwave reactor (Personal Chemistry, Biotage AB, Inc., Uppsala, Sweden) at 120° C. for 30 min, then solvent was removed. The residue was purified with RP-HPLC to give 4-(6-(5-(5-amino-1,3,4-thiadiazol-2-yl)-1H-indol-3-yl)pyrazin-2-yl)-1-methylpiperazin-2-one (10.0 mg, 0.025 mmol, 24%) as a light yellow solid. MS (ESI, pos. ion) m/z: 407 (M+1); $^1$H NMR (400 MHz, DMSO-$d_6$) δ ppm 11.86 (1H, br. s.), 8.73 (1H, s), 8.48 (1H, s), 8.28 (1H, d, J=2.5 Hz), 8.05 (1H, s), 7.74 (1H, dd, J=8.5, 1.5 Hz), 7.53 (1H, d, J=8.4 Hz), 7.26 (3H, s), 4.23 (2H, s), 4.06 (2H, t, J=5.4 Hz), 3.60 (2H, t, J=5.5 Hz), 3.28 (1H, s), 2.96 (3H, s)

Example 19

5-(3-(6-ethoxypyrazin-2-yl)-1H-indol-5-yl)-1,3,4-thiadiazol-2-amine

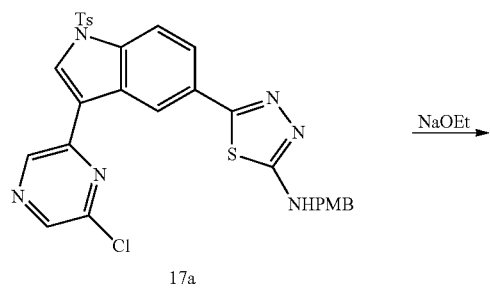

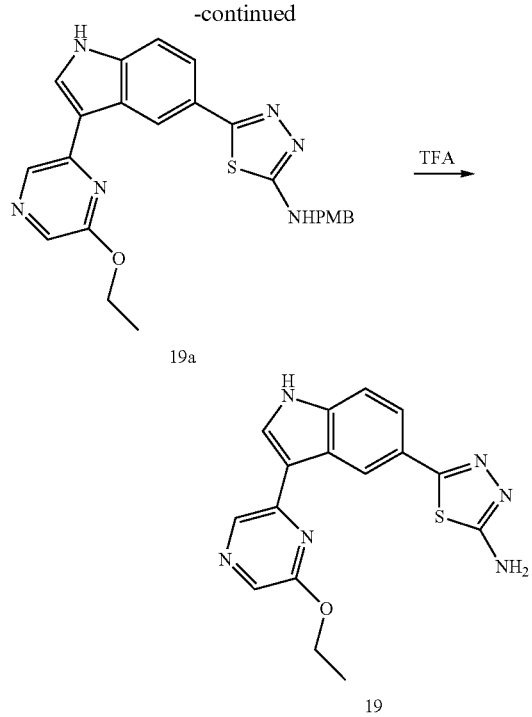

Preparation of compound 19a: 5-(3-(6-ethoxypyrazin-2-yl)-1H-indol-5-yl)-N-(4-methoxybenzyl)-1,3,4-thiadiazol-2-amine A glass microwave reaction vessel was charged with 5-(3-(6-chloropyrazin-2-yl)-1-tosyl-1H-indol-5-yl)-N-(4-methoxybenzyl)-1,3,4-thiadiazol-2-amine (90.0 mg, 0.149 mmol) and sodium ethoxide, 21 wt % solution in EtOH (0.152 mL, 0.448 mmol, Aldrich) in EtOH (1 mL). The reaction was stirred and heated in a Initiator microwave reactor (Personal Chemistry, Biotage AB, Inc., Uppsala, Sweden) at 120° C. for 1 h. Then the solvent was removed to give the crude material, which was used in the next step without further purification. MS (ESI, pos. ion) m/z: 459 (M+1).

Preparation of compound 19: 5-(3-(6-ethoxypyrazin-2-yl)-1H-indol-5-yl)-1,3,4-thiadiazol-2-amine A glass microwave reaction vessel was charged with 5-(3-(6-ethoxypyrazin-2-yl)-1H-indol-5-yl)-N-(4-methoxybenzyl)-1,3,4-thiadiazol-2-amine (68 mg, 0.148 mmol) in TFA (1 mL). The reaction was stirred and heated in a Initiator microwave reactor (Personal Chemistry, Biotage AB, Inc., Uppsala, Sweden) at 120° C. for 30 min, then the solvent was removed. The residue was purified with RP-HPLC (10-40% ACN in H₂O with 0.1% TFA) and the fractions were combined and MeCN was removed in vacuo. The mixture was treated with sat. NaHCO₃ and extracted with CHCl₃/iPrOH (4:1). The combined organic layers were dried, filtered and concentrated to give 5-(3-(6-ethoxypyrazin-2-yl)-1H-indol-5-yl)-1,3,4-thiadiazol-2-amine (18.5 mg, 0.055 mmol, 36.9% for two steps) as a yellow solid. MS (ESI, pos. ion) m/z: 339 (M+1); $^1$H NMR (400 MHz, DMSO-$d_6$) δ ppm 11.94 (1H, br. s.), 8.80 (1H, d, J=1.6 Hz), 8.76 (1H, s), 8.37 (1H, d, J=2.5

Hz), 8.00 (1H, s), 7.76 (1H, dd, J=8.5, 1.7 Hz), 7.54 (1H, d, J=8.4 Hz), 7.27 (2H, s), 4.61 (2H, q, J=7.0 Hz), 1.53 (3H, t, J=7.0 Hz).

Example 20

5-(3-(quinolin-3-yl)-1H-indol-5-yl)thiazol-2-amine

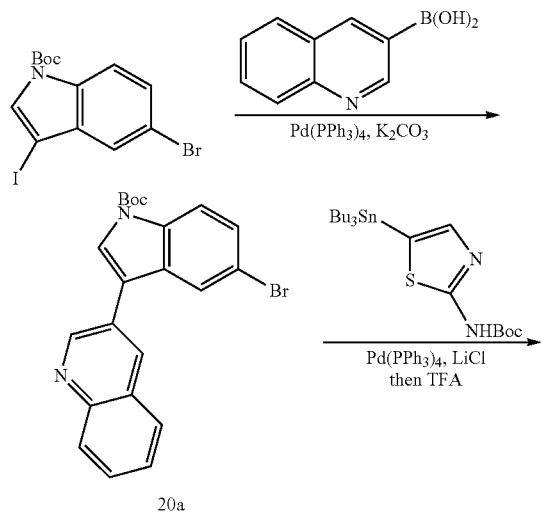

20a

20

Preparation of compound 20a: tert-butyl 5-bromo-3-(quinolin-3-yl)-1H-indole-1-carboxylate To a mixture of tert-butyl 5-bromo-3-iodo-1H-indole-1-carboxylate (1.750 g, 4.146 mmol, synchem), 3-quinolineboronic acid (1.076 g, 6.22 mmol), Pd(PPh$_3$)$_4$ (0.240 g, 0.207 mmol) and potassium carbonate ((1.719 g, 12.439 mmol) in dioxane (3.0 mL) was added H$_2$O (1.0 mL) and the reaction was heated at 60° C. for 42 h. Saturated NaHCO$_3$ solution (5.0 mL) was added to the mixture. The resulting mixture was extracted with EtOAc. The organic phases were combined, dried with sodium sulfate, filtered, and concentrated. The residue was purified by silica gel chromatography to give tert-butyl 5-bromo-3-(quinolin-3-yl)-1H-indole-1-carboxylate (642 mg, 36.6%) as a white foam. MS (ESI, pos. ion) m/z: 423 (M+1); $^1$H NMR (400 MHz, DMSO-d$_6$) δ ppm 1.68 (s, 9H), 7.62 (dd, J=8.8, 1.8 Hz, 1H), 7.67 (t, J=7.8 Hz, 1H), 7.79 (t, J=7.3 Hz, 1H), 8.07 (d, J=8.5 Hz, 1H), 8.13-8.20 (m, 3H), 8.30 (s, 1H), 8.74 (d, J=1.5 Hz, 1H), 9.26 (d, J=2.0 Hz, 1H)

Preparation of compound 20: 5-(3-(quinolin-3-yl)-1H-indol-5-yl)thiazol-2-amine

A mixture of tert-butyl 5-bromo-3-(quinolin-3-yl)-1H-indole-1-carboxylate (104 mg, 0.246 mmol), Pd(PPh$_3$)$_4$ (14 mg, 0.012 mmol), Lithium chloride (83 mg, 1.965 mmol) and DMF (2.0 ml, 0.246 mmol) in a microwave reaction vessel was sealed and heated at 100° C. for 5 min. A solution of tert-butyl 5-(tributylstannyl)thiazol-2-ylcarbamate (240 mg, 0.491 mmol) in DMF (1.0 mL) was then added and the reaction was heated at 100° C. for additional 17 h. The mixture was filtered through a pad of Celite and the filtrate was evaporated to dryness. The above crude product was dissolved in DCM (0.5 mL) followed by the addition of TFA (0.5 mL). The reaction was stirred at RT for 1 h then evaporated in vacuo to dryness. The residue was purified by silica gel chromatography to 5-(3-(quinolin-3-yl)-1H-indol-5-yl)thiazol-2-amine (6.7 mg, 8.0%) as a yellow solid. MS (ESI, pos. ion) m/z: 343 (M+1); $^1$H NMR (400 MHz, DMSO-d$_6$) δ ppm 6.98 (s, 2H), 7.32 (d, J=9.0 Hz, 1H), 7.38 (s, 1H), 7.48 (d, J=8.5 Hz, 1H), 7.62 (t, J=7.5 Hz, 1H), 7.70 (t, J=7.3 Hz, 1H), 7.98 (s, 1H), 8.00-8.05 (m, 2H), 8.10 (d, J=8.0 Hz, 1H), 8.62 (s, 1H), 9.29 (d, J=2.0 Hz, 1H), 11.65 (s, 1H).

Example 21

5-(3-(quinolin-3-yl)-1H-indol-5-yl)-1,3,4-thiadiazol-2-amine

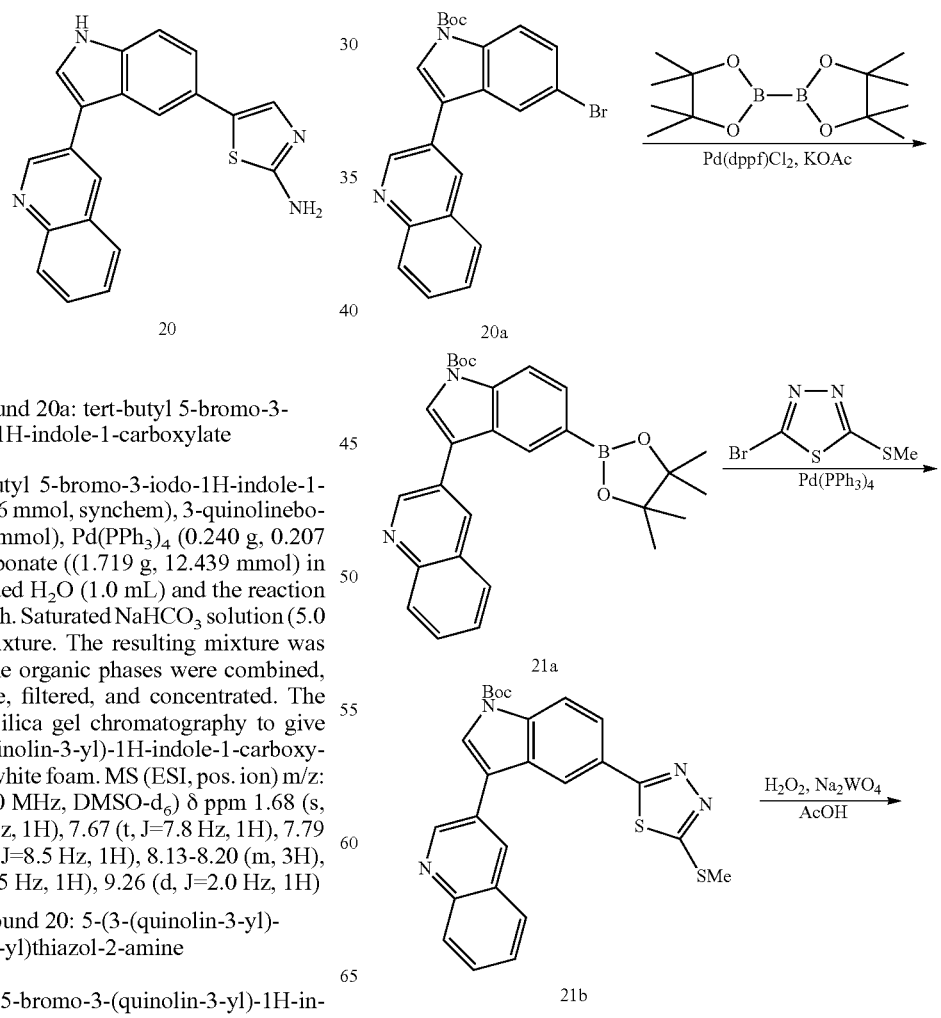

-continued

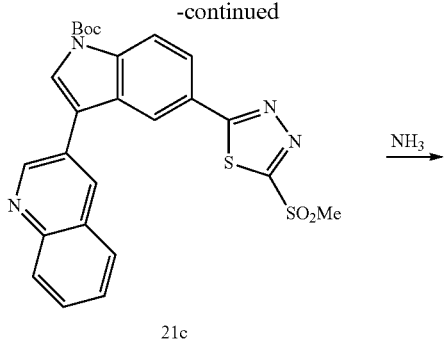

21c

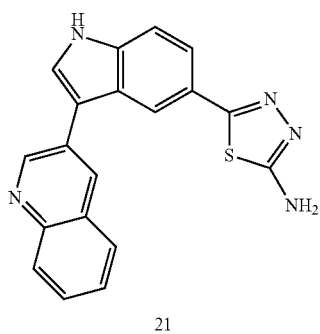

21

Preparation of compound 21a: tert-butyl 3-(quinolin-3-yl)-5-(4,4,5,5-tetramethyl-1,3,2-dioxaborolan-2-yl)-1H-indole-1-carboxylate A mixture of tert-butyl 5-bromo-3-(quinolin-3-yl)-1H-indole-1-carboxylate (217 mg, 513 µmol), bis(pinacolato)diboron (391 mg, 1538 µmol), potassium acetate (252 mg, 2563 µmol), and Pd(dppf)Cl$_2$ DCM adduct (23 mg, 31 µmol) in DMF (3.0 mL) was stirred at 90° C. for 18 h. The mixture was cooled to RT and ice was added. The resulting precipitates was collected by filtration, washed with H$_2$O and dried in the air. The solid was purified with flash chromatography to give tert-butyl 3-(quinolin-3-yl)-5-(4,4,5,5-tetramethyl-1,3,2-dioxaborolan-2-yl)-1H-indole-1-carboxylate (102 mg, 42%). MS (ESI, pos. ion) m/z: 471 (M+1); $^1$H NMR (400 MHz, CDCl3) δ ppm 1.36 (s, 12H), 1.72 (s, 9H), 7.57-7.65 (m, 1H), 7.71-7.79 (m, 1H), 7.83-7.90 (m, 2H), 7.94 (d, J=7.6 Hz, 1H), 8.17 (d, J=8.4 Hz, 1H), 8.26 (d, J=8.2 Hz, 1H), 8.32 (s, 1H), 8.41 (d, J=1.8 Hz, 1H), 9.25 (d, J=2.2 Hz, 1H)

Preparation of compound 21b: tert-butyl 5-(5-(methylthio)-1,3,4-thiadiazol-2-yl)-3-(quinolin-3-yl)-1H-indole-1-carboxylate A mixture of tert-butyl 3-(quinolin-3-yl)-5-(4,4,5,5-tetramethyl-1,3,2-dioxaborolan-2-yl)-1H-indole-1-carboxylate (80 mg, 170 µmol), 2-bromo-5-(methylthio)-1,3,4-thiadiazole (54 mg, 255 µmol), Pd(PPh$_3$)$_4$ (9.8 mg, 8.5 µmol) and potassium carbonate (71 mg, 510 µmol) in dioxane (1.0 mL) was added H$_2$O (0.2 mL). The reaction was heated in a microwave at 120° C. for 70 min. The solvent was then removed and the residue was purified with silica gel chromatography to give tert-butyl 5-(5-(methylthio)-1,3,4-thiadiazol-2-yl)-3-(quinolin-3-yl)-1H-indole-1-carboxylate (41 mg, 51%). MS (ESI, pos. ion) m/z: 475 (M+1).

Preparation of compound 21c: tert-butyl 5-(5-(methylsulfonyl)-1,3,4-thiadiazol-2-yl)-3-(quinolin-3-yl)-1H-indole-1-carboxylate To a stirred solution of tert-butyl 5-(5-(methylthio)-1,3,4-thiadiazol-2-yl)-3-(quinolin-3-yl)-1H-indole-1-carboxylate (38 mg, 80 µmol) in glacial HOAc (0.5 mL, 8659 µmol) with catalytic amount of NaWO$_4$ (0.0003 mL, 4 µmol) was added dropwise H$_2$O$_2$, 35 wt. % solution in H$_2$O (0.01 mL, 323 µmol) and the overall yellow mixture was stirred at RT for 1.5 h. The cloudy mixture was diluted with H$_2$O and the resulting precipitate was filtered, washed with H$_2$O and dried in vacuo to give tert-butyl 5-(5-(methylsulfonyl)-1,3,4-thiadiazol-2-yl)-3-(quinolin-3-yl)-1H-indole-1-carboxylate (38 mg, 94%) as a yellow solid. MS (ESI, pos. ion) m/z: 507 (M+1).

Preparation of compound 21: 5-(3-(quinolin-3-yl)-1H-indol-5-yl)-1,3,4-thiadiazol-2-amine A solution of tert-butyl 5-(5-(methylsulfonyl)-1,3,4-thiadiazol-2-yl)-3-(quinolin-3-yl)-1H-indole-1-carboxylate (15 mg, 30 µmol) in DMSO (1.5 mL) was bubbled with ammonia, anhydrous (50 mg, 2961 µmol) and heated in a microwave for 3 h. The mixture was concentrated in vacuo. The residue was purified by silica gel chromatography to give 5-(3-(quinolin-3-yl)-1H-indol-5-yl)-1,3,4-thiadiazol-2-amine (2.3 mg, 23%) as a yellow solid. MS (ESI, pos. ion) m/z: 344 (M+1). $^1$H NMR (400 MHz, DMSO-d$_6$) δ ppm 7.26 (s, 1H), 7.53-7.80 (m, 5H), 7.99-8.16 (m, 3H), 8.30 (s, 1H), 8.62 (d, J=1.4 Hz, 1H), 9.30 (d, J=2.0 Hz, 1H), 11.85 (s, 1H)

Example 22

5-(3-(biphenyl-3-yl)-1H-indol-5-yl)-N-methyl-1,3,4-thiadiazol-2-amine

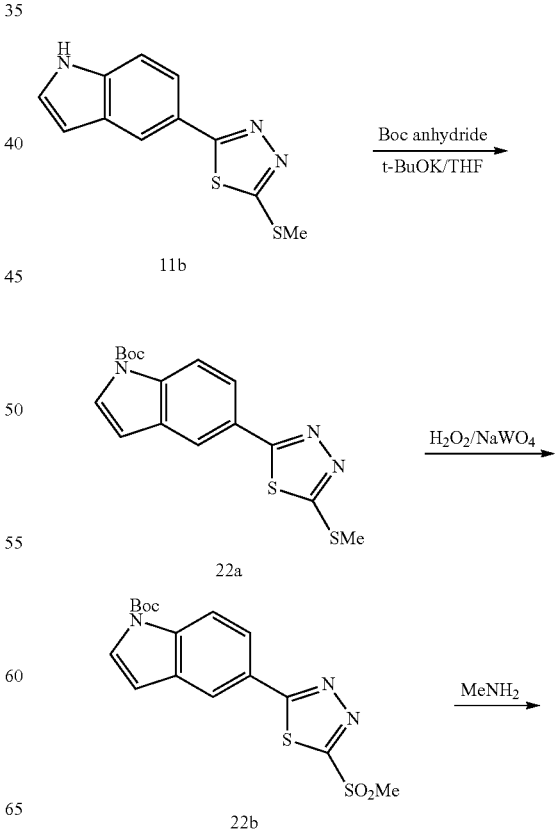

-continued

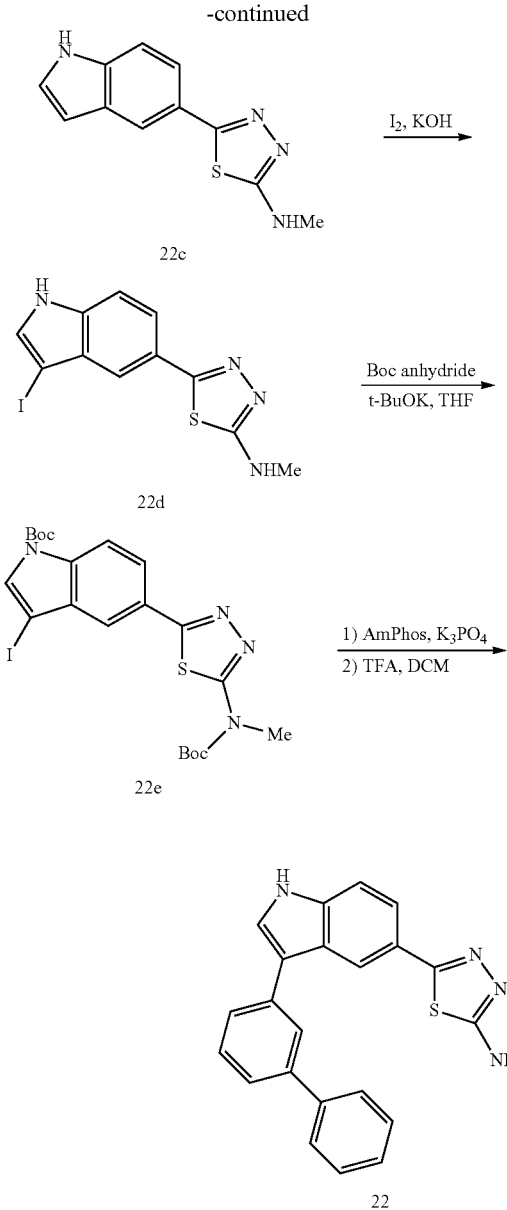

Preparation of compound 22a: tert-butyl 5-(5-(methylthio)-1,3,4-thiadiazol-2-yl)-1H-indole-1-carboxylate To a solution of 2-(1H-indol-5-yl)-5-(methylthio)-1,3,4-thiadiazole (2 g, 8 mmol) in THF (20 mL) at 0° C. was added KOtBu (2.33 g, 12 mmol) and Boc anhydride (2.6 g, 12 mmol). The reaction was stirred at RT for 2 h, then diluted with cold water and EtOAc. The organic layer was separated and the aqueous layer was extracted with EtOAc. The combined organic layers were dried, filtered and concentrated. The residue was purified with silica gel chromatography (eluting with 30% EtOAc in Hex) to give tert-butyl 5-(5-(methylthio)-1,3,4-thiadiazol-2-yl)-1H-indole-1-carboxylate (1.5 g, 53.5%). MS (ESI, pos. ion) m/z: 348 (M+1); $^1$H-NMR (DMSO-$d_6$, 300 MHz) δ ppm 1.6 (s, 9H), 2.8 (s, 3H), 6.8 (d, 1H) 7.8 (d, 1H) 7.95 (m, 1H), 8.2 (m, 2H),

Preparation of compound 22b: tert-butyl 5-(5-(methylsulfonyl)-1,3,4-thiadiazol-2-yl)-1H-indole-1-carboxylate To a solution of tert-butyl 5-(5-(methylthio)-1,3,4-thiadiazol-2-yl)-1H-indole-1-carboxylate (1.5 g, 4.32 mmol) in HOAc (15 ml) was added NaWO$_4$ (0.15 g, 0.64 mmol) and H$_2$O$_2$ (50% Sol., 6 ml). The reaction was stirred at RT for 4 h and HOAc was removed in vacuo. The residue was diluted with ice-cold water and EtOAc. The organic layer was separated and the aqueous layer was extracted with EtOAc. The combined organic layers were dried, filtered and concentrated. The residue was purified with silica gel chromatography (eluting with 40% EtOAc in Hex) to give tert-butyl 5-(5-(methylsulfonyl)-1,3,4-thiadiazol-2-yl)-1H-indole-1-carboxylate (0.5 g. 31%). MS (ESI, pos. ion) m/z: 380 (M+1). $^1$H-NMR (DMSO-$d_6$, 300 MHz) δ ppm 1.6 (s, 9H), 3.7 (s, 3H), 6.9 (d, 1H) 7.8 (d, 1H) 8.1 (m, 1H), 8.25 (m, 1H), 8.35 (m, 1H).

Preparation of compound 22c: 5-(1H-indol-5-yl)-N-methyl-1,3,4-thiadiazol-2-amine To a mixture of 5-(5-(methylsulfonyl)-1,3,4-thiadiazol-2-yl)-1H-indole-1-carboxylate (8 g, 21.11 mmol) in a sealed tube was added methylamine in DMSO (80 mL). The reaction was heated at 110° C. for 1 h and ice-cold water and EtOAc was added. The organic layer was separated and the aqueous layer was extracted with EtOAc. The combined organic layers were dried, filtered and concentrated. The residue was purified with silica gel chromatography (eluting with 40% EtOAc in Hex) to give 5-(1H-indol-5-yl)-N-methyl-1,3,4-thiadiazol-2-amine (3.8 g, 78%). MS (ESI, pos. ion) m/z: 231 (M+1); $^1$H-NMR (DMSO-$d_6$, 300 MHz): δ ppm 2.9 (s, 3H), 6.5 (d, 1H) 7.4 (d, 3H) 7.8 (m, 1H), 7.9 (s, 1H), 11.4 (s, 1H).

Preparation of compound 22d: 5-(3-iodo-1H-indol-5-yl)-N-methyl-1,3,4-thiadiazol-2-amine To a solution of 5-(1H-indol-5-yl)-N-methyl-1,3,4-thiadiazol-2-amine (0.5 g, 2.17 mmol) in DMF (5 mL) was added KOH (0.135 g, 2.39 mmol) followed by I$_2$ (0.6 g, 2.39 mmol). The mixture was stirred at RT for 2 h and 10% aq sodium bisulphite (2.5 mL) solution was added. The resulting precipitate was filtered and washed with H$_2$O, dried to give 5-(3-iodo-1H-indol-5-yl)-N-methyl-1,3,4-thiadiazol-2-amine (0.3 g, 39%). MS (ESI, pos. ion) m/z: 357 (M+1); $^1$HNMR (DMSO-$d_6$, 300 MHz): δ ppm 2.9 (s, 3H), 7.7 (m, 4H), 11.8 (s, 1H).

Preparation of compound 22e: tert-butyl 5-(5-(tert-butoxycarbonyl(methyl)amino)-1,3,4-thiadiazol-2-yl)-3-iodo-1H-indole-1-carboxylate To a solution of 5-(3-iodo-1H-indol-5-yl)-N-methyl-1,3,4-thiadiazol-2-amine (4.2 g, 11.8 mmol) in DMF (42 mL) at 0° C. was added KOtBu (1.4 g, 12.98 mmol) and Boc anhydride (2.82 g, 12.98 mmol). The reaction was stirred at RT for 2 h, then diluted with cold water and EtOAc. The organic layer was separated and the aqueous layer was extracted with EtOAc. The combined organic layers were dried, filtered and concentrated. The residue was purified with silica gel chromatography (eluting with 30% EtOAc in Hex) to give tert-butyl 5-(5-(tert-butoxycarbonyl(methyl)amino)-1,3,4-thiadiazol-2-yl)-3-iodo-1H-indole-1-carboxylate (4.8 g, 73%).

MS (ESI, pos. ion) m/z: 557 (M+1); $^1$H-NMR (DMSO-$d_6$, 300 MHz): δ ppm 1.6 (d, 18H), 3.6 (s, 3H), 7.9 (m, 3H), 8.2 (m, 1H), Preparation of compound 22: 5-(3-(biphenyl-3-yl)-1H-indol-5-yl)-N-methyl-1,3,4-thiadiazol-2-amine A mixture of potassium phosphate tribasic (80 mg, 0.378 mmol), AmPhos (2.7 mg, 0.00378 mmol), 5-(5-(tert-butoxycarbonyl(methyl)amino)-1,3,4-thiadiazol-2-yl)-3-iodo-1H-indole-1-carboxylate (70 mg, 0.126 mmol), biphenyl-3-ylboronic acid (0.05 g, 0.25 mmol) and 70% IPA/water (1.5 mL) was heated at 80° C. for 3 h. The mixture was concentrated in vacuo and the residue was diluted with 50% DCM/TFA (2 mL). The mixture was stirred at RT for 1 h and the solvent was removed. The residue was purified with RP-HPLC (10-90% MeCN in water with 0.1% TFA) to give 5-(3-(biphenyl-3-yl)-1H-indol-5-yl)-N-methyl-1,3,4-thiadiazol-2-amine (24 mg, 50%). MS (ESI, pos. ion) m/z: 383 (M+1).

Example 23

5-(3-(2,4-difluorophenyl)-1H-indol-5-yl)-N-methyl-1,3,4-thiadiazol-2-amine

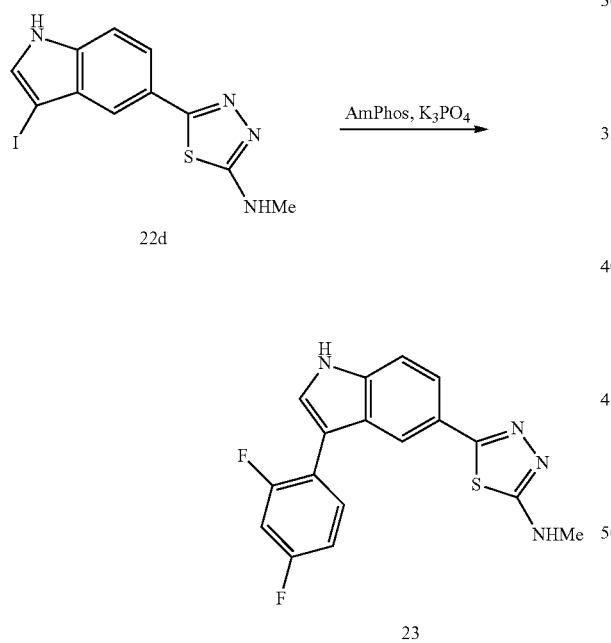

A mixture of potassium phosphate (0.089 g, 0.42 mmol), 2,4-difluorophenylboronic acid pinacol ester (0.040 g, 0.17 mmol, Aldrich), bis(di-tert-butyl(4-dimethylaminophenyl)phosphine)dichloropalladium(II) (5 mg, 7 µmol), 5-(3-iodo-1H-indol-5-yl)-N-methyl-1,3,4-thiadiazol-2-amine (0.05 g, 0.14 mmol), and IPA/H$_2$O (70%, 0.5 mL) was heated in a microwave at 120° C. for 10 min. The aqueous layer was removed and the organic layer was purified by preparative HPLC (10-90% MeCN/water/0.1% NH$_4$OH) to give 5-(3-(2,4-difluorophenyl)-1H-indol-5-yl)-N-methyl-1,3,4-thiadiazol-2-amine as a tan solid. MS (ESI, pos. ion) m/z: 343

(M+1). $^1$H NMR (400 MHz, CD$_3$OD) δ ppm 8.06 (1H, s), 7.64-7.73 (2H, m), 7.56-7.61 (2H, m), 7.06-7.14 (2H, m), 3.14 (3H, s).

Example 24

5-(3-(6-morpholinopyridin-2-yl)-1H-indol-5-yl)-1,3,4-thiadiazol-2-amine

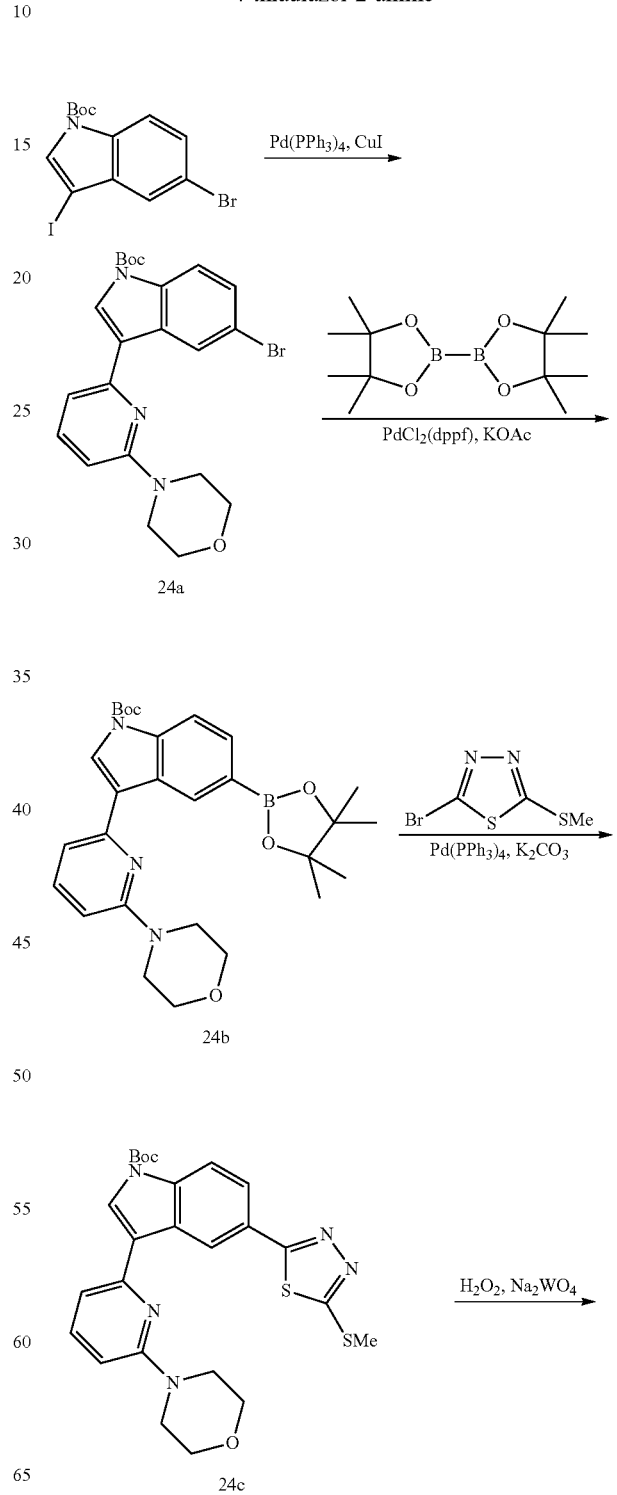

-continued

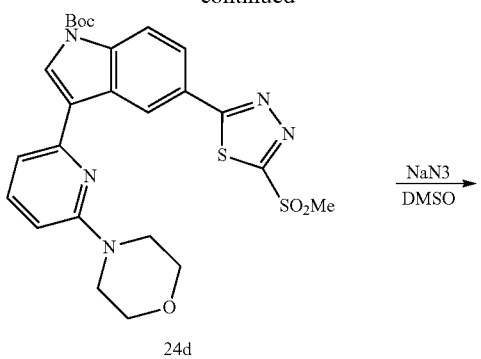

24d

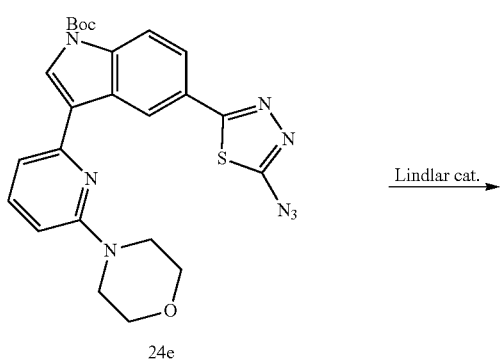

24e

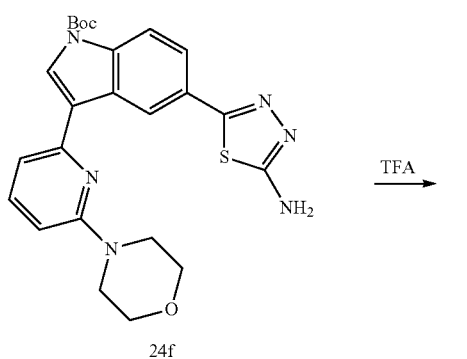

24f

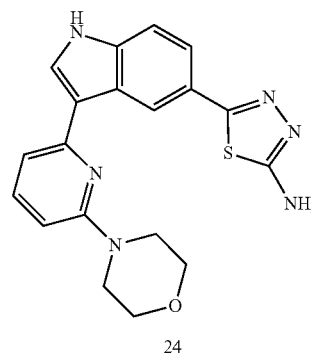

24

Preparation of compound 24a: tert-butyl 5-bromo-3-(6-morpholinopyridin-2-yl)-1H-indole-1-carboxylate To a mixture of Pd(PPh$_3$)$_4$ (255.0 mg, 220.6 μmol), tert-butyl 5-bromo-3-iodo-1H-indole-1-carboxylate (1000 mg, 2369 μmol) and CuI (546.2 mg, 2868 μmol) was added DMF (12 mL) followed by 4-(6-(tributylstannyl)pyridin-2-yl)morpholine (1000 mg, 2206 μmol). The mixture was heated at 100° C. for 20 min. After cooled to RT, the reaction was added H$_2$O (5 mL) and DCM (5 mL). The organic layer was separated. The aqueous layer was extracted with DCM (10 mL×2). The organic layers were combined, dried with sodium sulfate, filtered and evaporated to dryness. The brown crude oil was purified with silica gel chromatography (eluting with 100% DCM) to give tert-butyl 5-bromo-3-(6-morpholinopyridin-2-yl)-1H-indole-1-carboxylate (537.3 mg, 53.13%) as a white solid. MS (ESI, pos. ion) m/z: 458 (M+1). $^1$H NMR (400 MHz, DMSO-d$_6$) ppm 1.66 (s, 9H), 3.50-3.62 (m, 4H), 3.74-3.83 (m, 4H), 6.80 (d, J=8.4 Hz, 1H), 7.33 (d, J=7.4 Hz, 1H), 7.54 (dd, J=8.9, 2.1 Hz, 1H), 7.64 (dd, J=8.4, 7.6 Hz, 1H), 8.06 (d, J=9.0 Hz, 1H), 8.29 (s, 1H), 8.68 (d, J=2.2 Hz, 1H)

Preparation of compound 24b: tert-butyl 3-(6-morpholinopyridin-2-yl)-5-(4,4,5,5-tetramethyl-1,3,2-dioxaborolan-2-yl)-1H-indole-1-carboxylate A mixture of PdCl$_2$(dppf), complex with DCM (35.7 mg, 0.044 mmol), 4,4,4',4',5,5,5',5'-octamethyl-2,2'-bi(1,3,2-dioxaborolane) (278 mg, 1.093 mmol), tert-butyl 5-bromo-3-(6-morpholinopyridin-2-yl)-1H-indole-1-carboxylate (334 mg, 0.729 mmol) and potassium acetate (215 mg, 2.186 mmol) in 1 mL of p-dioxane and 1 mL of DMF in a sealed glass tube was heated in a microwave at 115° C. for 35 min. The residue was purified with silica gel chromatography (eluting with 25-50% EtOAc in Hex) to give tert-butyl 3-(6-morpholinopyridin-2-yl)-5-(4,4,5,5-tetramethyl-1,3,2-dioxaborolan-2-yl)-1H-indole-1-carboxylate (299 mg, 0.592 mmol, 81%) as an off white crystalline solid. MS (ESI, pos. ion) m/z: 506.1 (M+1).

Preparation of compound 24c: tert-butyl 5-(5-(methylthio)-1,3,4-thiadiazol-2-yl)-3-(6-morpholinopyridin-2-yl)-1H-indole-1-carboxylate A glass microwave reaction vessel was charged with tert-butyl 3-(6-morpholinopyridin-2-yl)-5-(4,4,5,5-tetramethyl-1,3,2-dioxaborolan-2-yl)-1H-indole-1-carboxylate (1.20 g, 2.374 mmol) and 2-bromo-5-(methylthio)-1,3,4-thiadiazole (1.002 g, 4.75 mmol) in p-dioxane/H$_2$O (4:1, 15 mL) followed by potassium carbonate (0.984 g, 7.12 mmol, Aldrich) and Pd(PPh$_3$)$_4$ (0.137 g, 0.119 mmol, Strem). The reaction was stirred and heated in an Initiator microwave reactor (Personal Chemistry, Biotage AB, Inc., Uppsala, Sweden) at 100° C. for 2 h. The mixture was diluted with DCM (150 mL) and washed with H$_2$O. The organic layer was dried, filtered and concentrated. The residue was purified with silica gel chromatography (eluting with 0-18% EtOAc in DCM) to give tert-butyl 5-(5-(methylthio)-1,3,4-thiadiazol-2-yl)-3-(6-morpholinopyridin-2-yl)-1H-indole-1-carboxylate (570 mg, 1.118 mmol, 47.1%) as a yellow solid. MS (ESI, pos. ion) m/z: 510 (M+1); $^1$H NMR (400 MHz, CDCl3) δ ppm 8.91 (1H, s), 8.17-8.32 (2H, m), 7.98 (1H, dd, J=8.7, 1.7 Hz), 7.65 (1H, t, J=8.0 Hz), 7.18 (1H, d, J=7.4 Hz), 6.70 (1H, d, J=8.4 Hz), 3.92-4.01 (4H, m), 3.68-3.77 (4H, m), 2.84 (3H, s), 1.72 (9H, s).

Preparation of compound 24d: tert-butyl 5-(5-(methylsulfonyl)-1,3,4-thiadiazol-2-yl)-3-(6-morpholinopyridin-2-yl)-1H-indole-1-carboxylate To a suspension of tert-butyl 5-(5-(methylthio)-1,3,4-thiadiazol-2-yl)-3-(6-morpholinopyridin-2-yl)-1H-indole-1-carboxylate (510 mg, 1.001 mmol) in HOAc (10 mL) was added disodium tungstate (3.52 µL, 0.050 mmol) and $H_2O_2$ 30% (204 µL, 2.001 mmol). The reaction was stirred at RT for 28 h, then solvent was removed. The residue was diluted in $H_2O$ and extracted with DCM. The combined organic layers were washed with 1 M $NaHCO_3$, dried, filtered and concentrated to give the crude material (600 mg). MS (ESI, pos. ion) m/z: 542 (M+1).

Preparation of compound 24e: tert-butyl 5-(5-azido-1,3,4-thiadiazol-2-yl)-3-(6-morpholinopyridin-2-yl)-1H-indole-1-carboxylate To a solution of tert-butyl 5-(5-(methylsulfonyl)-1,3,4-thiadiazol-2-yl)-3-(6-morpholinopyridin-2-yl)-1H-indole-1-carboxylate (300 mg, 0.554 mmol) in DMSO (3 mL) was added sodium azide (215.8 mg, 3.32 mmol). The reaction was heated at 55-65° C. for 4 h, then diluted with $H_2O$ and extracted with EtOAc (80 mL×3). The combined organic layers were washed with water (50 mL×4), dried, filtered and concentrated to give the crude material (240 mg). MS (ESI, pos. ion) m/z: 505 (M+1).

Preparation of compound 24f: tert-butyl 5-(5-amino-1,3,4-thiadiazol-2-yl)-3-(6-morpholinopyridin-2-yl)-1H-indole-1-carboxylate To a solution of tert-butyl 5-(5-azido-1,3,4-thiadiazol-2-yl)-3-(6-morpholinopyridin-2-yl)-1H-indole-1-carboxylate (224 mg, 0.444 mmol) in MeOH/THF (5 mL, 3:2) was added Lindlar catalyst (59.2 mg, 0.222 mmol). The mixture was stirred at RT under hydrogen for 15 h, then filtered through a plug of celite and washed with DCM/MeOH. The filtrated was concentrated to give the crude material. MS (ESI, pos. ion) m/z: 479 (M+1).

Preparation of compound 24: 5-(3-(6-morpholinopyridin-2-yl)-1H-indol-5-yl)-1,3,4-thiadiazol-2-amine A solution of tert-butyl 5-(5-amino-1,3,4-thiadiazol-2-yl)-3-(6-morpholinopyridin-2-yl)-1H-indole-1-carboxylate (212 mg, 0.443 mmol) in DCM/TFA (1:1, 4 mL) was stirred at RT for 1 h, then the solvent was removed. The residue was diluted with DCM and washed with sat. $NaHCO_3$. The organic layer was dried, filtered and concentrated. The residue was purified with silica gel chromatography (eluting with 0.5-4.5% MeOH in DCM) to give 5-(3-(6-morpholinopyridin-2-yl)-1H-indol-5-yl)-1,3,4-thiadiazol-2-amine (38.0 mg, 0.100 mmol, 22.7%) as a light brown solid. MS (ESI, pos. ion) m/z: 379 (M+1); $^1H$ NMR (400 MHz, DMSO-$d_6$) δ ppm 11.67 (1H, d, J=2.2 Hz), 8.82 (1H, d, J=1.6 Hz), 8.11 (1H, d, J=2.5 Hz), 7.74 (1H, dd, J=8.6, 1.8 Hz), 7.53-7.62 (1H, m), 7.48 (1H, d, J=8.6 Hz), 7.30 (1H, s), 7.22 (1H, d, J=7.4 Hz), 6.64 (1H, d, J=8.4 Hz), 3.79-3.93 (4H, m), 3.55-3.67 (4H, m).

Example 25

5-(3-(6-(3-methyl-5,6-dihydro-[1,2,4]triazolo[4,3-a]pyrazin-7(8H)-yl)-pyridin-2-yl)-1H-indol-5-yl)-1,3,4-thiadiazol-2-amine

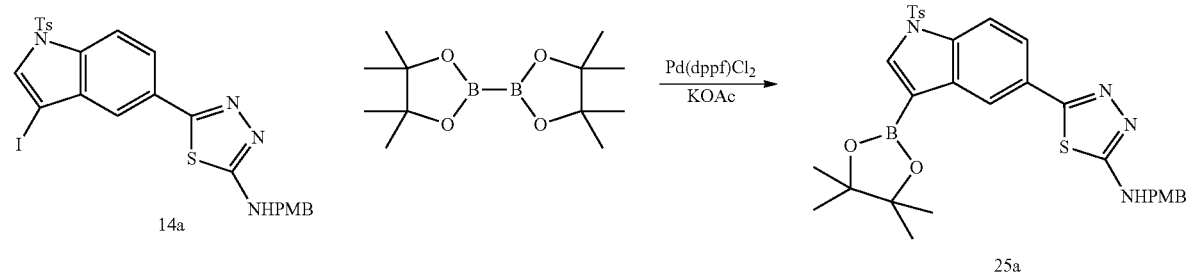

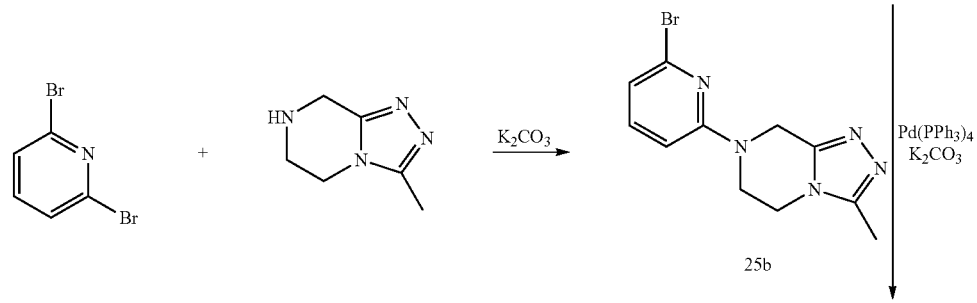

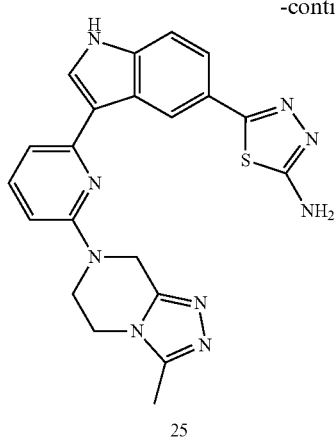

25

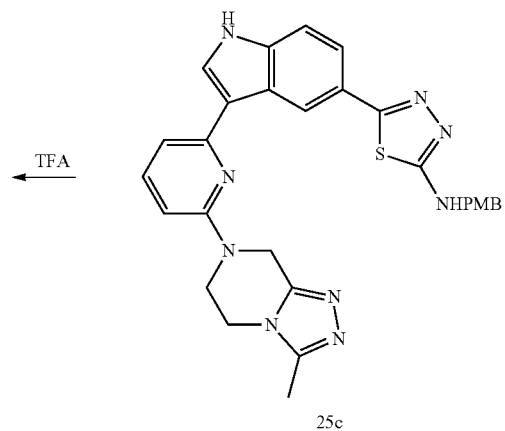

25c

Preparation of compound 25a: N-(4-methoxybenzyl)-5-(3-(4,4,5,5-tetramethyl-1,3,2-dioxaborolan-2-yl)-1-tosyl-1H-indol-5-yl)-1,3,4-thiadiazol-2-amine A mixture of 5-(3-iodo-1-tosyl-1H-indol-5-yl)-N-(4-methoxybenzyl)-1,3,4-thiadiazol-2-amine (240 mg, 0.389 mmol), bis(pinacolato)diboron (297 mg, 1.168 mmol), potassium acetate (191 mg, 1.946 mmol), PdCl$_2$(dppf), complex with DCM (47.7 mg, 0.058 mmol) and DMF (2.0 mL) was stirred at 90° C. in an oil bath for 1 h. The mixture was filtered through a plug of celite and washed with DCM. The filtrate was washed with H$_2$O (15 mL×3), dried, filtered and concentrated to give the crude material. MS (ESI, pos. ion) m/z: 430 (M+1).

Preparation of compound 25b: 7-(6-bromopyridin-2-yl)-3-methyl-5,6,7,8-tetrahydro-[1,2,4]triazolo[4,3-a]pyrazine A glass microwave reaction vessel was charged with 2,6-dibromopyridine (434 mg, 1.832 mmol, Aldrich), 3-methyl-5,6,7,8-tetrahydro-[1,2,4]triazolo[4,3-a]pyrazine (380 mg, 2.75 mmol, MolBridge) and potassium carbonate (253 mg, 1.832 mmol) in dioxane (1.8 mL). The reaction was stirred and heated in a Initiator microwave reactor (Personal Chemistry, Biotage AB, Inc., Uppsala, Sweden) at 140° C. for 4 h. The reaction was cooled to RT, H$_2$O was added and the resulting precipitate was collected by filtration, washed with H$_2$O and dried to give the crude product. MS (ESI, pos. ion) m/z: 294 (M+1).

Preparation of compound 25c: N-(4-methoxybenzyl)-5-(3-(6-(3-methyl-5,6-dihydro-[1,2,4]triazolo[4,3-a]pyrazin-7(8H)-yl)pyridin-2-yl)-1H-indol-5-yl)-1,3,4-thiadiazol-2-amine A glass microwave reaction vessel was charged with N-(4-methoxybenzyl)-5-(3-(4,4,5,5-tetramethyl-1,3,2-dioxaborolan-2-yl)-1-tosyl-1H-indol-5-yl)-1,3,4-thiadiazol-2-amine (90.0 mg, 0.146 mmol) and 7-(6-bromopyridin-2-yl)-3-methyl-5,6,7,8-tetrahydro-[1,2,4]triazolo[4,3-a]pyrazine (64.4 mg, 0.219 mmol) in p-dioxane/H$_2$O (3:1, 2.0 mL) followed by potassium carbonate (40.3 mg, 0.292 mmol) and Pd(PPh$_3$)$_4$ (8.43 mg, 7.30 μmol). The reaction was stirred and heated in a microwave at 100° C. for 15 min, then 120° C. for 15 min. The mixture was diluted with DCM and washed with brine, dried, filtered and concentrated to give the crude material. MS (ESI, pos. ion) m/z: 550 (M+1).

Preparation of compound 25: 5-(3-(6-(3-methyl-5,6-dihydro-[1,2,4]triazolo[4,3-a]pyrazin-7(8H)-yl)pyridin-2-yl)-1H-indol-5-yl)-1,3,4-thiadiazol-2-amine 2,2,2-trifluoroacetate A glass microwave reaction vessel was charged with N-(4-methoxybenzyl)-5-(3-(6-(3-methyl-5,6-dihydro-[1,2,4]triazolo[4,3-a]pyrazin-7(8H)-yl)pyridin-2-yl)-1H-indol-5-yl)-1,3,4-thiadiazol-2-amine (80.0 mg, 0.146 mmol) in TFA (1.0 mL). The reaction was heated in a microwave at 100° C. for 10 min, then solvent was removed. The residue was purified with RP-HPLC to give 5-(3-(6-(3-methyl-5,6-dihydro-[1,2,4]triazolo[4,3-a]pyrazin-7(8H)-yl)pyridin-2-yl)-1H-indol-5-yl)-1,3,4-thiadiazol-2-amine 2,2,2-trifluoroacetate (2.0 mg, 2.5%) as a light yellow solid. MS (ESI, pos. ion) m/z: 430 (M+1). 1H NMR (400 MHz, DMSO-d$_6$) δ ppm 11.73 (1H, br. s.), 8.80 (1H, s), 8.14 (1H, d, J=2.0 Hz), 7.61-7.72 (2H, m), 7.52 (1H, d, J=8.6 Hz), 7.22-7.43 (3H, m), 6.90 (1H, d, J=9.2 Hz), 5.07 (2H, br. s.), 4.15-4.37 (4H, m).

Example 26

5-(3-(2,4-difluorophenyl)-1H-indol-5-yl)-1,3,4-thiadiazol-2-ol

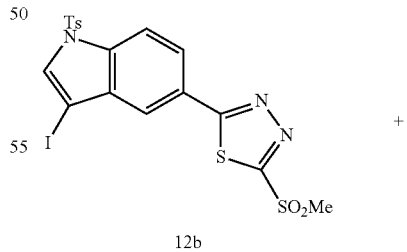

12b

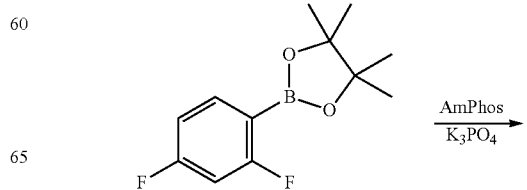

-continued

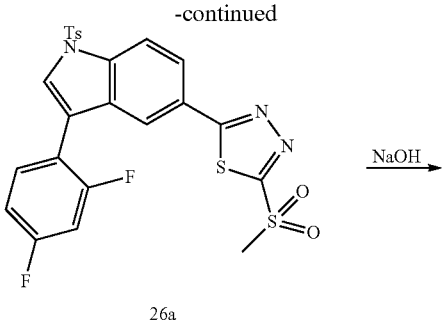

26a

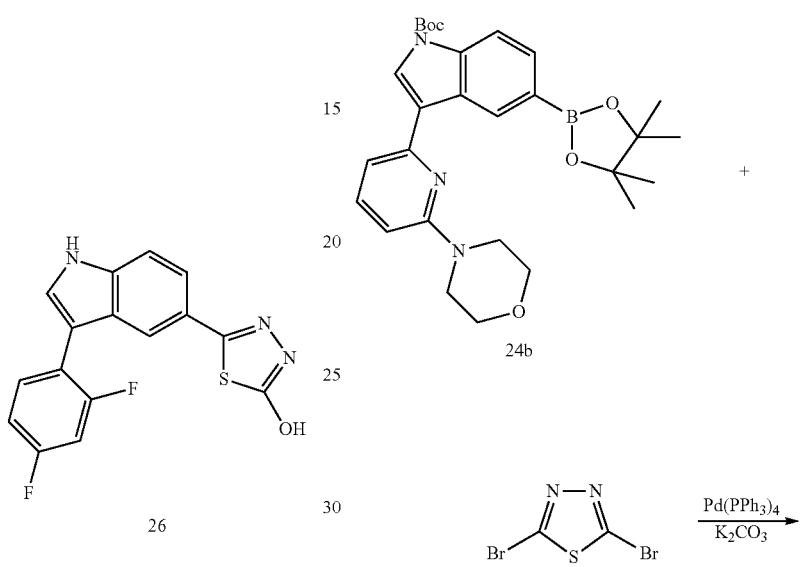

Example 27

4-(6-(5-(5-bromo-1,3,4-thiadiazol-2-yl)-1H-indol-3-yl)pyridin-2-yl)morpholine

Preparation of compound 26a: 2-(3-(2,4-difluorophenyl)-1-tosyl-1H-indol-5-yl)-5-(methylsulfonyl)-1,3,4-thiadiazole A mixture of potassium phosphate tribasic (1.309 g, 6.17 mmol, Aldrich), bis(di-tert-butyl(4-dimethylaminophenyl)phosphine)dichloropalladium(II) (0.044 g, 0.062 mmol, Aldrich), 2,4-difluorophenylboronic acid pinacol ester (0.740 g, 3.08 mmol, Aldrich), 2-(3-iodo-1-tosyl-1H-indol-5-yl)-5-(methylsulfonyl)-1,3,4-thiadiazole (1.15 g, 2.056 mmol), and IPA/H$_2$O (70%, 10 mL) was heated at 80° C. for 2 h. The mixture was partially concentrated to remove most IPA, and the aq. layer was extracted with DCM. The aq. layer was acidified with 2M HCl and extracted again with DCM. The combined DCM fractions were evaporated and purified by prep HPLC (50-95% AcCN/H$_2$O/0.1% TFA) to give 2-(3-(2,4-difluorophenyl)-1-tosyl-1H-indol-5-yl)-5-(methylsulfonyl)-1,3,4-thiadiazole (0.42 g, 0.770 mmol, 37.4%) as a light yellow solid. MS (ESI, pos. ion) m/z 546 (M+1).

Preparation of compound 26: 5-(3-(2,4-difluorophenyl)-1H-indol-5-yl)-1,3,4-thiadiazol-2-ol A solution of 2-(3-(2,4-difluorophenyl)-1-tosyl-1H-indol-5-yl)-5-(methylsulfonyl)-1,3,4-thiadiazole (0.010 g, 0.018 mmol), dioxane (0.5 mL), and NaOH (1 M, 0.1 mL) was heated in a Biotage microwave for 10 min at 100° C., then at 120° C. for an additional 10 min. The mixture was purified by preparative HPLC (20-90% AcCN/H$_2$O/0.1% TFA) to give 5-(3-(2,4-difluorophenyl)-1H-indol-5-yl)-1,3,4-thiadiazol-2-ol (1 mg, 2.068 μmol, 11.28%). MS (ESI, pos. ion) m/z: 330 (M+1). $^1$H NMR (400 MHz, CD$_3$OD) δ ppm 7.99 (1H, s), 7.67-7.75 (1H, m), 7.53-7.64 (3H, m), 7.07-7.15 (2H, m).

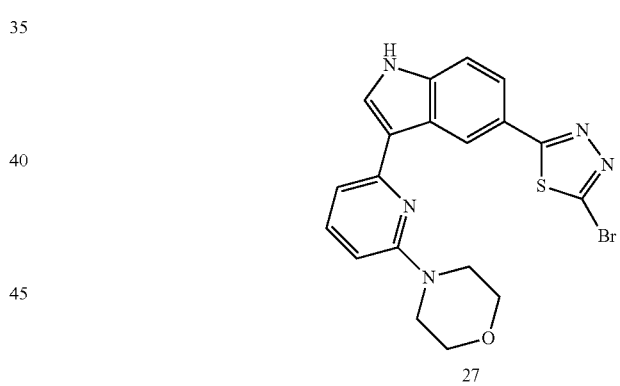

A glass microwave reaction vessel was charged with tert-butyl 3-(6-morpholinopyridin-2-yl)-5-(4,4,5,5-tetramethyl-1,3,2-dioxaborolan-2-yl)-1H-indole-1-carboxylate (250 mg, 0.495 mmol) and 2,5-dibromo-1,3,4-thiadiazole (133 mg, 0.544 mmol) in p-dioxane/H$_2$O (4:1, 4.5 mL) followed by potassium carbonate (205 mg, 1.484 mmol) and Pd(PPh$_3$)$_4$ (28.6 mg, 0.025 mmol). The reaction was stirred and heated in a Initiator microwave reactor (Personal Chemistry, Biotage AB, Inc., Uppsala, Sweden) at 100° C. for 75 min. The mixture was diluted with DCM, washed with H$_2$O, dried, filtered and concentrated. The residue was purified with silica gel chromatography (eluting with 2-10% EtOAc in DCM) to give 4-(6-(5-(5-bromo-1,3,4-thiadiazol-2-yl)-1H-indol-3-yl)pyridin-2-yl)morpholine (36.0 mg, 0.081 mmol, 16.45%) as a yellow solid. MS (ESI, pos. ion) 442 (M+1). $^1$H NMR (400 MHz, DMSO-d$_6$) δ ppm 11.85 (1H, br. s.), 9.11 (1H, d, J=1.6 Hz), 8.19 (1H, d, J=2.5 Hz), 7.80 (1H, dd, J=8.6, 1.8 Hz), 7.56-7.64 (2H, m), 7.24 (1H, d, J=7.4 Hz), 6.67 (1H, d, J=8.4 Hz), 3.79-3.86 (4H, m), 3.58-3.65 (4H, m).

Example 28

4-(6-(5-(1,3,4-thiadiazol-2-yl)-1H-indol-3-yl)pyridin-2-yl)morpholine

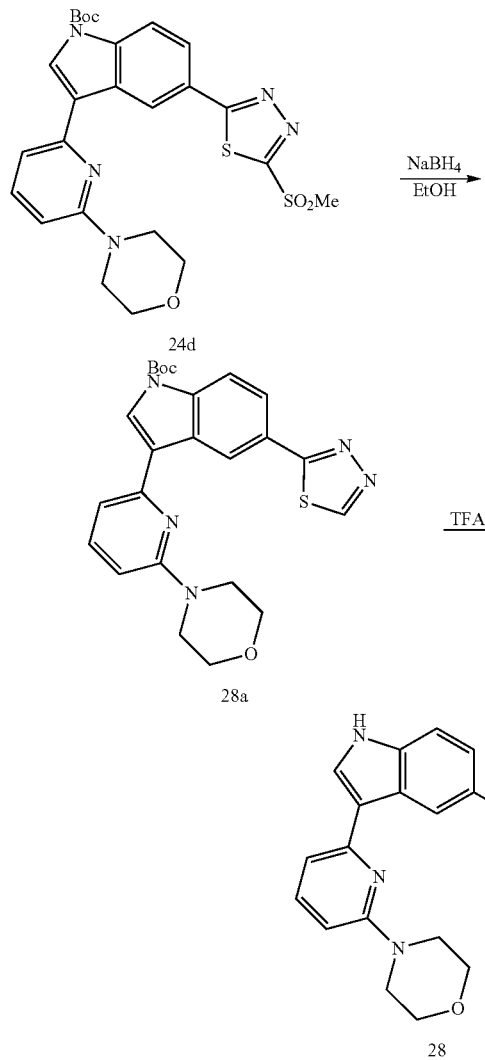

Preparation of compound 28a: tert-butyl 3-(6-morpholinopyridin-2-yl)-5-(1,3,4-thiadiazol-2-yl)-1H-indole-1-carboxylate To a solution of tert-butyl 5-(5-(methylsulfonyl)-1,3,4-thiadiazol-2-yl)-3-(6-morpholinopyridin-2-yl)-1H-indole-1-carboxylate (100 mg, 0.185 mmol) in EtOH was added sodium borohydride (20.95 mg, 0.554 mmol). The reaction was stirred for 2 h, neutralized with HOAc then the solvent was removed to give the crude material. MS (ESI, pos. ion) m/z: 464 (M+1).

Preparation of compound 28: 4-(6-(5-(1,3,4-thiadiazol-2-yl)-1H-indol-3-yl)pyridin-2-yl)morpholine To a solution of tert-butyl 3-(6-morpholinopyridin-2-yl)-5-(1,3,4-thiadiazol-2-yl)-1H-indole-1-carboxylate (86.0 mg, 0.186 mmol) in DCM (1.0 mL) was added TFA (1.0 mL) and the reaction was stirred at RT for 1 h, then solvent was removed. The residue was diluted with DCM (60 mL) and washed with sat. NaHCO$_3$, dried, filtered and concentrated. The residue was purified with RP-HPLC to give 4-(6-(5-(1,3,4-thiadiazol-2-yl)-1H-indol-3-yl)pyridin-2-yl)morpholine (34.0 mg, 0.094 mmol, 50.4%) as a yellow solid. MS (ESI, pos. ion) m/z: 364 (M+1). $^1$H NMR (400 MHz, DMSO-d$_6$) δ ppm 11.78 (1H, br. s.), 9.52 (1H, s), 9.17 (1H, d, J=1.4 Hz), 8.16 (1H, d, J=2.5 Hz), 7.92 (1H, dd, J=8.6, 1.6 Hz), 7.53-7.65 (2H, m), 7.24 (1H, d, J=7.6 Hz), 6.66 (1H, d, J=8.4 Hz), 3.78-3.90 (4H, m), 3.57-3.69 (4H, m).

Example 29

5-(3-(6-morpholinopyridin-2-yl)-1H-indol-5-yl)-1,3,4-thiadiazol-2-ol

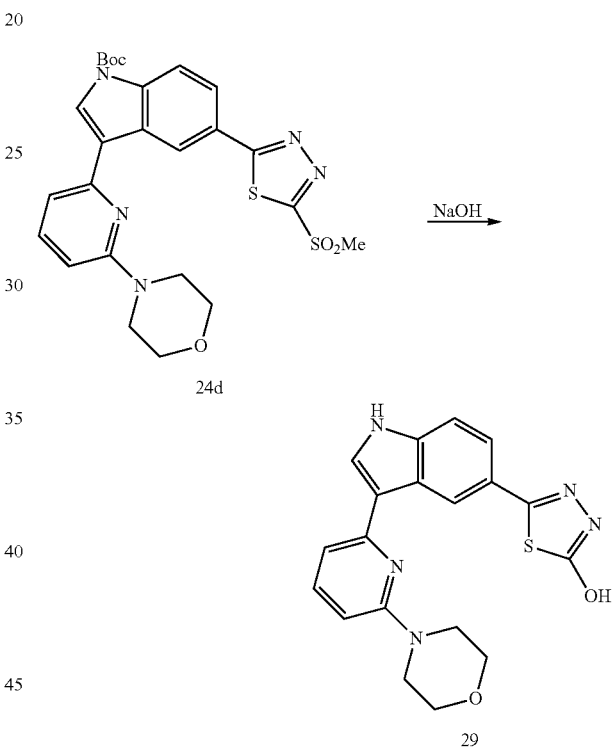

A glass microwave reaction vessel was charged with tert-butyl 5-(5-(methylsulfonyl)-1,3,4-thiadiazol-2-yl)-3-(6-morpholinopyridin-2-yl)-1H-indole-1-carboxylate (160.0 mg, 0.296 mmol) and aq. 10 M NaOH (1.5 mL, 15.0 mmol). The reaction was stirred and heated in a Initiator microwave reactor (Personal Chemistry, Biotage AB, Inc., Uppsala, Sweden) at 120° C. for 30 min. The mixture was neutralized with aq. 5 N HCl and the mixture was extracted with CHCl$_3$/iPrOH (4:1). The combined organic layers were dried, filtered and concentrated. The crude product was dissolved in MeOH/p-dioxane (2:1, 3 mL) and catalytic amount of Pd/C was added. The mixture was stirred under H$_2$ for 2 h, then filtered through a plug of celite. The filtrate was concentrated and the residue was purified with RP-HPLC to give 5-(3-(6-morpholinopyridin-2-yl)-1H-indol-5-yl)-1,3,4-thiadiazol-2-ol (16.0 mg, 0.042 mmol, 14%) as a pink solid. MS (ESI, pos. ion) m/z 380 (M+1). $^1$H NMR (400 MHz, DMSO-d$_6$) δ ppm 12.87 (1H, br. s.), 11.71 (1H, br. s.), 8.83 (1H, s), 8.12 (1H, d, J=2.5 Hz), 7.46-7.63 (3H, m), 7.20 (1H, d, J=7.6 Hz), 6.63 (1H, d, J=8.2 Hz), 3.76-3.87 (4H, m), 3.53-3.65 (4H, m).

Example 30

4-(6-(5-(5-amino-1,3,4-thiadiazol-2-yl)-1H-indol-3-yl)pyridin-2-yl)-1-methylpiperazin-2-one

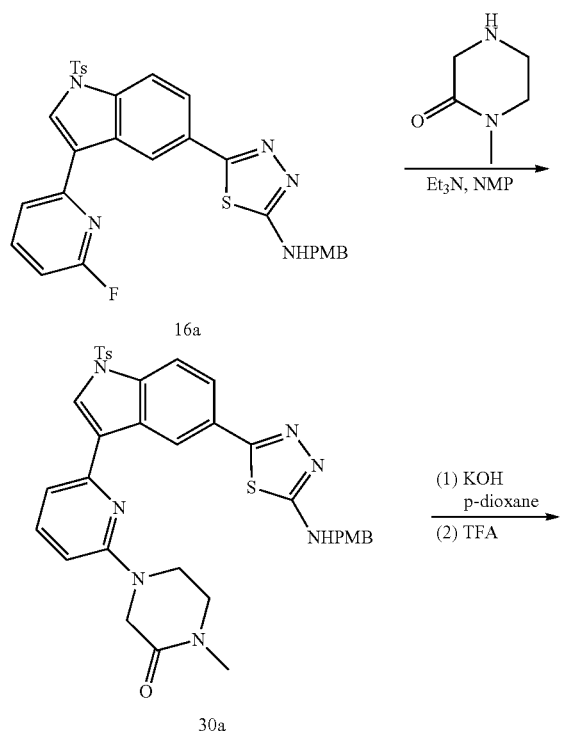

Preparation of compound 30a: 4-(6-(5-(5-(4-methoxybenzylamino)-1,3,4-thiadiazol-2-yl)-1-tosyl-1H-indol-3-yl)pyridin-2-yl)-1-methylpiperidin-2-one A glass microwave reaction vessel was charged with 5-(3-(6-fluoropyridin-2-yl)-1-tosyl-1H-indol-5-yl)-N-(4-methoxybenzyl)-1,3,4-thiadiazol-2-amine (300 mg, 0.512 mmol) and 1-methylpiperazin-2-one (117 mg, 1.024 mmol) in NMP (5 mL) followed by Et₃N (214 µL, 1.537 mmol). The reaction was stirred and heated in an oil bath at 150° C. for 60 h, and the mixture was diluted with DCM and washed with H₂O, brine, dried, filtered and concentrated to give the crude product. MS (ESI, pos. ion) m/z: 680 (M+1).

Preparation of compound 30: 4-(6-(5-(5-amino-1,3,4-thiadiazol-2-yl)-1H-indol-3-yl)pyridin-2-yl)-1-methylpiperazin-2-one A glass microwave reaction vessel was charged with 4-(6-(5-(5-(4-methoxybenzylamino)-1,3,4-thiadiazol-2-yl)-1-tosyl-1H-indol-3-yl)pyridin-2-yl)-1-methylpiperazin-2-one (350 mg, 0.515 mmol) in p-dioxane (6 mL) followed by aq. 1 M KOH (2.5 mL, 2.500 mmol). The reaction was stirred and heated in an Initiator microwave reactor (Personal Chemistry, Biotage AB, Inc., Uppsala, Sweden) at 80° C. for 15 min. The mixture was diluted with H₂O and extracted with DCM. The combined organic layers were dried, filtered and concentrated to give the crude product. MS (ESI, pos. ion) m/z: 526 (M+1). A glass microwave reaction vessel was charged with crude 4-(6-(5-(5-(4-methoxybenzylamino)-1,3,4-thiadiazol-2-yl)-1H-indol-3-yl)pyridin-2-yl)-1-methylpiperazin-2-one (271 mg, 0.516 mmol) and TFA (5.00 mL, 67.3 mmol). The reaction was stirred and heated in an Initiator microwave reactor (Personal Chemistry, Biotage AB, Inc., Uppsala, Sweden) at 120° C. for 40 min, then the solvent was removed. The residue was purified with RP-HPLC to give 4-(6-(5-(5-amino-1,3,4-thiadiazol-2-yl)-1H-indol-3-yl)pyridin-2-yl)-1-methylpiperazin-2-one (88.0 mg, 0.217 mmol, 42.1%). MS (ESI, pos. ion) m/z: 406 (M+1). ¹H NMR (400 MHz, DMSO-d₆) δ ppm 11.70 (1H, d, J=2.0 Hz), 8.79 (1H, d, J=1.6 Hz), 8.11 (1H, d, J=2.5 Hz), 7.71 (1H, dd, J=8.4, 1.8 Hz), 7.59 (1H, t, J=7.9 Hz), 7.50 (1H, d, J=8.6 Hz), 7.27 (2H, s), 7.22 (1H, d, J=7.4 Hz), 6.62 (1H, d, J=8.2 Hz), 4.12 (2H, s), 4.06 (2H, t, J=5.4 Hz), 3.58 (2H, t, J=5.3 Hz), 2.96 (3H, s).

Example 31

5-(3-(6-(4-chlorophenyl)pyridin-2-yl)-1H-indol-5-yl)-1,3,4-thiadiazol-2-amine

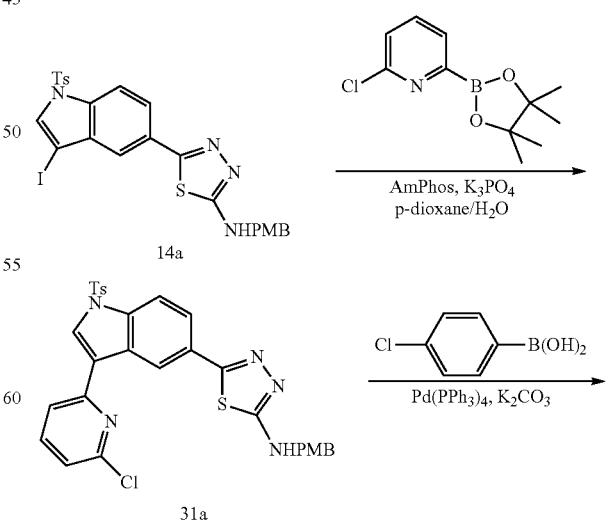

-continued

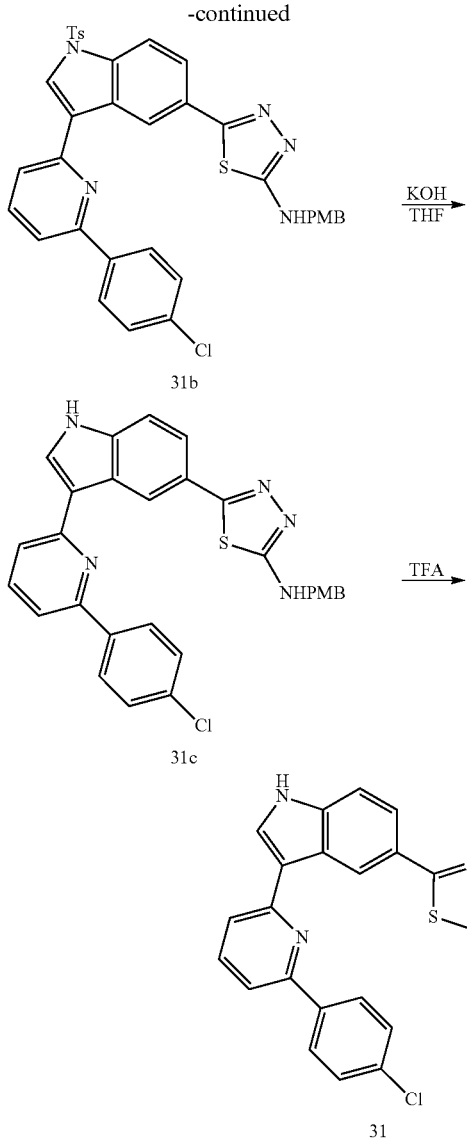

Preparation of compound 31a: 5-(3-(6-chloropyridin-2-yl)-1-tosyl-1H-indol-5-yl)-N-(4-methoxybenzyl)-1,3,4-thiadiazol-2-amine A glass microwave reaction vessel was charged with 5-(3-iodo-1-tosyl-1H-indol-5-yl)-N-(4-methoxybenzyl)-1,3,4-thiadiazol-2-amine (300 mg, 0.487 mmol) and 6-chloropyridine-2-boronic acid pinacol ester (175 mg, 0.730 mmol) in p-dioxane/H$_2$O (4:1, 5 mL) followed by bis(di-tert-butyl(4-dimethylaminophenyl)phosphine)dichloropalladium(II) (17.23 mg, 0.024 mmol) and potassium phosphate (310 mg, 1.460 mmol). The reaction was stirred and heated in a Initiator microwave reactor (Personal Chemistry, Biotage AB, Inc., Uppsala, Sweden) at 105° C. for 30 min. The mixture was diluted with DCM and washed with H$_2$O. The organic layer was dried, filtered and concentrated. The residue was purified with silica gel chromatography (eluting with 0-20% EtOAc in DCM) to give 5-(3-(6-chloropyridin-2-yl)-1-tosyl-1H-indol-5-yl)-N-(4-methoxybenzyl)-1,3,4-thiadiazol-2-amine (265 mg, 0.440 mmol, 90%) as a yellow solid. MS (ESI, pos. ion) m/z: 602 (M+1); $^1$H NMR (400 MHz, CDCl$_3$) δ ppm 8.73 (1H, d, J=1.4 Hz), 8.14 (1H, s), 8.05 (1H, d, J=8.8 Hz), 7.92 (1H, dd, J=8.7, 1.7 Hz), 7.81 (2H, d, J=8.2 Hz), 7.68-7.75 (1H, m), 7.59-7.66 (1H, m), 7.33 (2H, d, J=8.6 Hz), 7.24 (2H, d, J=3.7 Hz), 6.90 (2H, d, J=8.8 Hz), 4.54 (2H, s), 3.81 (3H, s), 2.35 (3H, s).

Preparation of compound 31b: 5-(3-(6-(4-chlorophenyl)pyridin-2-yl)-1-tosyl-1H-indol-5-yl)-N-(4-methoxybenzyl)-1,3,4-thiadiazol-2-amine A glass microwave reaction vessel was charged with 5-(3-(6-chloropyridin-2-yl)-1-tosyl-1H-indol-5-yl)-N-(4-methoxybenzyl)-1,3,4-thiadiazol-2-amine (245 mg, 0.407 mmol) and 4-chlorophenylboronic acid (95 mg, 0.610 mmol) in p-dioxane/H$_2$O (4:1, 4.5 mL) followed by potassium carbonate (168 mg, 1.221 mmol) and Pd(PPh$_3$)$_4$ (23.5 mg, 0.020 mmol). The reaction was stirred and heated in a Initiator microwave reactor (Personal Chemistry, Biotage AB, Inc., Uppsala, Sweden) at 105° C. for 30 min. The mixture was diluted with DCM and washed with H$_2$O and separated. The organic layer was dried, filtered and concentrated. The residue was purified with silica gel chromatography (eluting with 0-20% EtOAc in DCM) to give 5-(3-(6-(4-chlorophenyl)pyridin-2-yl)-1-tosyl-1H-indol-5-yl)-N-(4-methoxybenzyl)-1,3,4-thiadiazol-2-amine (230 mg, 0.339 mmol, 83%) as a light yellow solid. MS (ESI, pos. ion) m/z: 678 (M+1). $^1$H NMR (400 MHz, CDCl3) δ ppm 8.98 (1H, d, J=1.4 Hz), 8.15 (1H, s), 8.05-8.13 (3H, m), 7.98-8.03 (1H, m), 7.80-7.88 (3H, m), 7.66 (2H, d, J=8.2 Hz), 7.48 (2H, d, J=8.6 Hz), 7.33 (2H, d, J=8.6 Hz), 7.24 (2H, s), 6.89 (2H, d, J=8.6 Hz), 4.55 (2H, s), 3.80 (3H, s), 2.35 (3H, s).

Preparation of compound 31c: 5-(3-(6-(4-chlorophenyl)pyridin-2-yl)-1H-indol-5-yl)-N-(4-methoxybenzyl)-1,3,4-thiadiazol-2-amine A glass microwave reaction vessel was charged with 5-(3-(6-(4-chlorophenyl)pyridin-2-yl)-1-tosyl-1H-indol-5-yl)-N-(4-methoxybenzyl)-1,3,4-thiadiazol-2-amine (225 mg, 0.332 mmol) in THF (5 mL) followed by KOH (1.5 mL, 1.50 mmol, 1 M). The mixture was heated in microwave at 80° C. for 90 min, then cooled to RT. The mixture was diluted with water and extracted with DCM. The combined organic layers were dried, filtered and concentrated to give the crude material. MS (ESI, pos. ion) m/z: 524 (M+1).

Preparation of compound 31: 5-(3-(6-(4-chlorophenyl)pyridin-2-yl)-1H-indol-5-yl)-1,3,4-thiadiazol-2-amine A glass microwave reaction vessel was charged with 5-(3-(6-(4-chlorophenyl)pyridin-2-yl)-1H-indol-5-yl)-N-(4-methoxybenzyl)-1,3,4-thiadiazol-2-amine (174 mg, 0.332 mmol) in TFA (1.0 ml). The reaction was stirred and heated in an Initiator microwave reactor (Personal Chemistry, Biotage AB, Inc., Uppsala, Sweden) at 120° C. for 30 min, then solvent was removed. The residue was purified with RP-HPLC to give 5-(3-(6-(4-chlorophenyl)pyridin-2-yl)-1H-indol-5-yl)-1,3,4-thiadiazol-2-amine (60.0 mg, 0.149 mmol, 44.7%) as an off-white solid. MS (ESI, pos. ion) m/z: 404 (M+1). $^1$H NMR (400 MHz, DMSO-d$_6$) δ ppm 11.62 (1H, s), 8.90 (1H, s), 8.06-8.21 (3H, m), 7.70 (2H, d, J=4.1 Hz), 7.55-7.65 (2H, m), 7.50 (2H, d, J=8.4 Hz), 7.36 (1H, d, J=8.6 Hz), 7.16 (2H, s).

Example 32

5-(3-(6-Isopropoxypyridin-2-yl)-1H-indol-5-yl)-N-(piperidin-3-yl)-1,3,4-thiadiazol-2-amine 2,2,2-trifluoroacetate

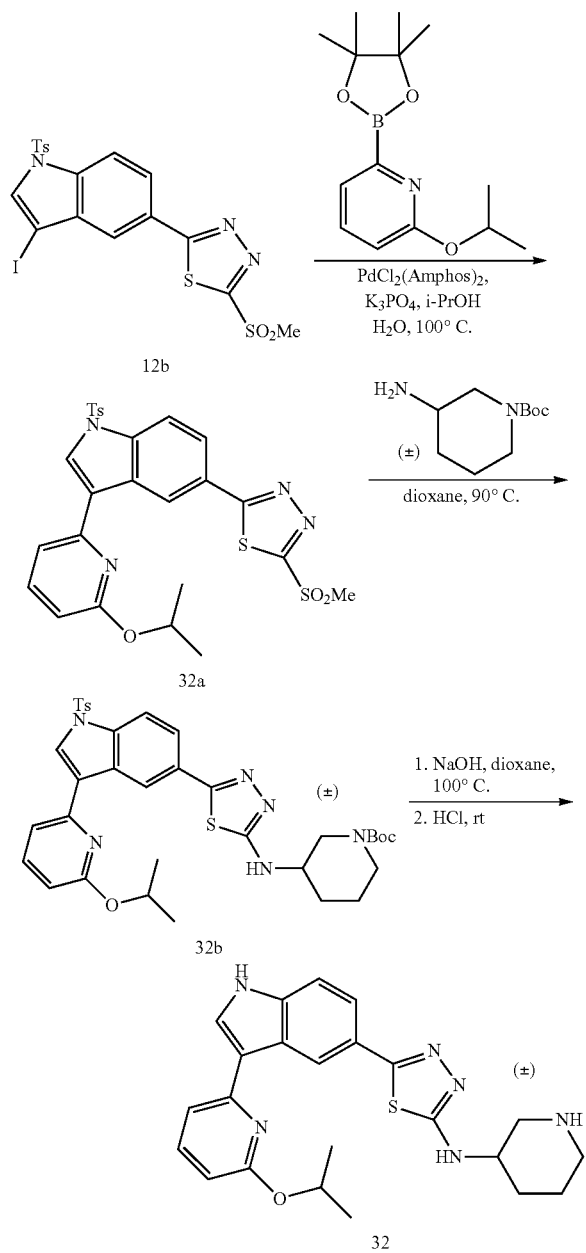

Preparation of compound 32a: 2-(3-(6-Isopropoxypyridin-2-yl)-1-tosyl-1H-indol-5-yl)-5-(methylsulfonyl)-1,3,4-thiadiazole A yellow suspension of 2-(3-iodo-1-tosyl-1H-indol-5-yl)-5-(methylsulfonyl)-1,3,4-thiadiazole (300 mg, 0.536 mmol), 2-isopropoxy-6-(4,4,5,5-tetramethyl-1,3,2-dioxaborolan-2-yl)pyridine (CombiPhos Catalysts, Inc., Princeton, N.J.; 198 mg, 0.751 mmol), bis(di-tert-butyl(4-dimethylaminophenyl)phosphine)-dichloropalladium(II) (Aldrich; 18.99 mg, 0.027 mmol), and potassium phosphate (341 mg, 1.609 mmol) in a mixture of IPA (3.5 mL) and H₂O (1.50 mL) was stirred at 100° C. for 10 min. The mixture was partitioned between EtOAc (80 mL) and H₂O (50 mL) and the organic layer was separated. The aqueous layer was extracted with EtOAc (2×50 mL), and the combined organic extracts were dried over sodium sulfate, filtered, and concentrated onto silica gel. Chromatographic purification (silica gel, 0-60% EtOAc/Hex) furnished 2-(3-(6-isopropoxypyridin-2-yl)-1-tosyl-1H-indol-5-yl)-5-(methylsulfonyl)-1,3,4-thiadiazole (89.3 mg, 0.157 mmol, 29%) as a colorless oil. MS (ESI, pos. ion) m/z: 569.1 (M+1).

Preparation of compound 32b: tert-Butyl 3-(5-(3-(6-isopropoxypyridin-2-yl)-1-tosyl-1H-indol-5-yl)-1,3,4-thiadiazol-2-ylamino)piperidine-1-carboxylate A yellow solution of 2-(3-(6-isopropoxypyridin-2-yl)-1-tosyl-1H-indol-5-yl)-5-(methylsulfonyl)-1,3,4-thiadiazole (89.3 mg, 0.115 mmol) and (±)-tert-butyl 3-aminopiperidine-1-carboxylate (Combi-Blocks, Inc., San Diego, Calif.; 0.110 mL, 0.573 mmol) in dioxane (1.0 mL) was heated in an open microwave vial at 90° C. for 3.5 d. Chromatographic purification of the resulting dry residue (silica gel, 0-100% EtOAc/Hex) furnished tert-butyl 3-(5-(3-(6-isopropoxypyridin-2-yl)-1-tosyl-1H-indol-5-yl)-1,3,4-thiadiazol-2-ylamino)piperidine-1-carboxylate (38.6 mg, 0.056 mmol, 49%) as a yellow oil: MS (ESI, pos. ion) m/z: 689.2 (M+1). ¹H NMR (400 MHz, CDCl3) δ ppm 8.79 (s, 1H), 8.07 (s, 2H), 7.92 (d, J=7.4 Hz, 1H), 7.82 (d, J=8.4 Hz, 4H), 7.59-7.64 (m, 2H), 7.29 (br. s., 1H), 6.61-6.65 (m, 1H), 5.55 (dt, J=12.5, 6.3 Hz, 1H), 3.69 (d, J=13.3 Hz, 2H), 3.48-3.59 (m, 1H), 3.41 (t, J=7.2 Hz, 2H), 2.36-2.39 (m, 2H), 2.35 (s, 3H), 1.55-1.57 (m, 2H), 1.46 (d, J=3.1 Hz, 6H), 1.44 (s, 9H).

Preparation of compound 32: 5-(3-(6-Isopropoxypyridin-2-yl)-1H-indol-5-yl)-N-(piperidin-3-yl)-1,3,4-thiadiazol-2-amine 2,2,2-trifluoroacetate An orange solution of tert-butyl 3-(5-(3-(6-isopropoxypyridin-2-yl)-1-tosyl-1H-indol-5-yl)-1,3,4-thiadiazol-2-ylamino)piperidine-1-carboxylate (38.6 mg, 0.056 mmol) and aq. NaOH (2.0 M, 0.1 mL, 0.200 mmol) in dioxane (1.0 mL) was heated at 100° C. for 30 min. Additional aq. NaOH (2.0 M, 0.1 mL, 0.200 mmol) was added, and the resulting mixture was stirred at 100° C. for 1.5 h. The mixture was then concentrated in vacuo, and the residue was taken up in HCl (4.0 M in dioxane; 1.0 mL, 4.00 mmol). The resulting yellow-orange mixture was stirred at 25° C. for 1 h, diluted with H₂O (4 mL) and 1 N aq NaOH (3.5 mL). The resulting mixture was partitioned between DCM (30 mL) and saturated aq NaHCO₃ (20 mL). The organic layer was separated, and the aqueous layer was extracted with DCM (20 mL). The combined organic extracts were dried over sodium sulfate, filtered, and concentrated in vacuo to provide crude 5-(3-(6-isopropoxypyridin-2-yl)-1H-indol-5-yl)-N-(piperidin-3-yl)-1,3,4-thiadiazol-2-amine as a light-yellow solid, which was taken up in DMSO (2.0 mL) and purified by reverse phase HPLC (10-100% AcCN/H₂O+0.1% TFA) to provide 5-(3-(6-isopropoxypyridin-2-yl)-1H-indol-5-yl)-N-(piperidin-3-yl)-1,3,4-thiadiazol-2-amine 2,2,2-trifluoroacetate (12.0 mg, 0.022 mmol, 39%) as a yellow oil: MS (ESI, pos. ion) m/z: 435.2 (M+1). ¹H NMR (400 MHz, MeOH-d₄) δ ppm 11.38 (br s, 1H), 8.80 (d, J=1.2 Hz, 1H), 7.98 (s, 1H), 7.75-7.79 (m, 1H), 7.71-7.75 (m, 1H), 7.54 (d, J=8.6 Hz, 1H), 7.43 (d, J=7.4 Hz, 1H), 6.66 (d, J=8.2 Hz, 1H), 5.53 (dt, J=12.2, 6.1 Hz, 1H), 4.07-4.16 (m, 1H), 3.68 (dd, J=12.2, 3.6 Hz, 1H), 3.34-3.35 (obsc m, 1H), 3.09-3.15 (m, 1H), 3.02-3.08 (m, 1H), 2.18-2.27 (m, 1H), 2.10 (dt, J=15.0, 5.1 Hz, 1H), 1.83-1.92 (m, 1H), 1.73-1.82 (m, 1H), 1.49-1.51 (m, 3H), 1.49 (s, 3H).

Example 33

(R)-1-(5-(3-(6-Isopropoxypyridin-2-yl)-1H-indol-5-yl)-1,3,4-thiadiazol-2-yl)pyrrolidin-3-amine 2,2,2-trifluoroacetate

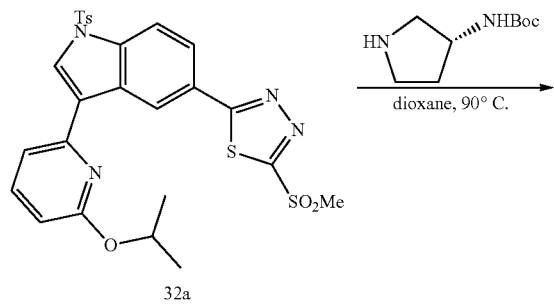

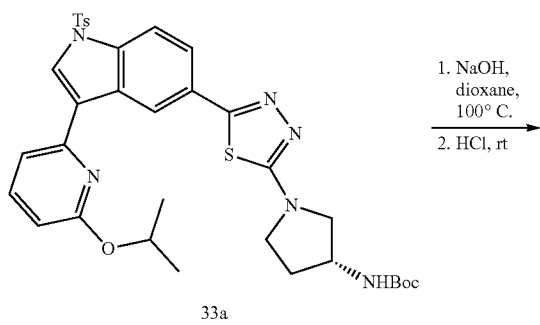

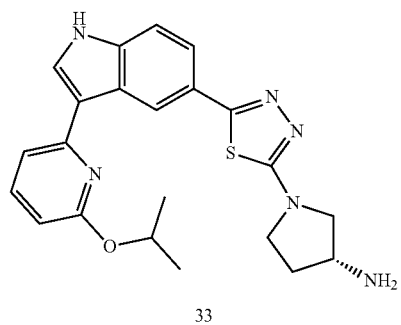

Preparation of compound 33a: (R)-tert-Butyl 1-(5-(3-(6-isopropoxypyridin-2-yl)-1-tosyl-1H-indol-5-yl)-1,3,4-thiadiazol-2-yl)pyrrolidin-3-ylcarbamate A yellow solution of 2-(3-(6-isopropoxypyridin-2-yl)-1-tosyl-1H-indol-5-yl)-5-(methylsulfonyl)-1,3,4-thiadiazole (107.4 mg, 0.189 mmol) and (3R)-(+)-3-(tert-butoxycarbonylamino)pyrrolidine (TCI America, Portland, Oreg.; 141 mg, 0.755 mmol) in dioxane (1.0 mL) was heated in an open microwave vial at 90° C. for 2 days. Chromatographic purification of the resulting dry residue (silica gel, 0-100% EtOAc/Hex) furnished (R)-tert-butyl 1-(5-(3-(6-isopropoxypyridin-2-yl)-1-tosyl-1H-indol-5-yl)-1,3,4-thiadiazol-2-yl)pyrrolidin-3-ylcarbamate (95 mg, 0.141 mmol, 75%) as an off-white solid: MS (ESI, pos. ion) m/z: 675.1 (M+1). $^1$H NMR (400 MHz, CDCl$_3$) δ ppm 8.78 (d, J=1.0 Hz, 1H), 8.02-8.08 (m, 2H), 7.94-7.99 (m, 1H), 7.82 (d, J=8.4 Hz, 2H), 7.61 (t, J=7.8 Hz, 1H), 7.28 (d, J=7.4 Hz, 1H), 7.24 (d, J=8.4 Hz, 2H), 6.63 (d, J=8.2 Hz, 1H), 5.57 (spt, J=6.2 Hz, 1H), 4.66-4.84 (m, 1H), 4.41 (br. s., 1H), 3.83 (dd, J=10.6, 6.1 Hz, 1H), 3.67-3.73 (m, 1H), 3.59-3.67 (m, 1H), 3.48-3.55 (m, 1H), 3.45 (dd, J=10.6, 4.1 Hz, 1H), 2.34 (s, 3H), 1.46 (s, 9H), 1.45 (br. s., 3H), 1.44 (br. s., 3H).

Preparation of compound 33: (R)-1-(5-(3-(6-Isopropoxypyridin-2-yl)-1H-indol-5-yl)-1,3,4-thiadiazol-2-yl)pyrrolidin-3-amine 2,2,2-trifluoroacetate A light-yellow solution of (R)-tert-butyl 1-(5-(3-(6-isopropoxypyridin-2-yl)-1-tosyl-1H-indol-5-yl)-1,3,4-thiadiazol-2-yl)pyrrolidin-3-ylcarbamate (105 mg, 0.156 mmol) and NaOH (2.0 M, aq; 0.6 mL, 1.800 mmol) in dioxane (3.0 mL) was heated at 100° C. for 3 h. The mixture was then concentrated in vacuo, and the residue was taken up in HCl (4.0 M in dioxane; 3.0 mL, 12.00 mmol). The resulting slurry was stirred at 25° C. for 40 min then concentrated in vacuo. The residue was sonicated with DMSO (2.0 mL), and the resulting suspension was filtered through Celite. The clear filtrate was purified by reverse phase HPLC (10-100% AcCN/H$_2$O+0.1% TFA) to provide (R)-1-(5-(3-(6-isopropoxypyridin-2-yl)-1H-indol-5-yl)-1,3,4-thiadiazol-2-yl)pyrrolidin-3-amine 2,2,2-trifluoroacetate (50.0 mg, 0.094 mmol, 60%) as a yellow solid: MS (ESI, pos. ion) m/z: 421.2 (M+1). $^1$H NMR (400 MHz, MeOH-d$_4$) δ ppm 8.87 (d, J=0.8 Hz, 1H), 7.99 (s, 1H), 7.76-7.79 (m, 1H), 7.72-7.76 (m, 1H), 7.55 (s, 1H), 7.45 (s, 1H), 6.66 (d, J=8.2 Hz, 1H), 5.56 (dt, J=12.3, 6.2 Hz, 1H), 4.10-4.18 (m, 1H), 3.97 (dd, J=11.6, 6.2 Hz, 1H), 3.75-3.84 (m, 1H), 3.73 (d, J=3.7 Hz, 1H), 3.67-3.71 (m, 1H), 2.55-2.64 (m, 1H), 2.24-2.33 (m, 1H), 1.50 (s, 3H), 1.49 (s, 3H).

Example 34

(S)-1-(5-(3-(6-Isopropoxypyridin-2-yl)-1H-indol-5-yl)-1,3,4-thiadiazol-2-yl)pyrrolidin-3-amine 2,2,2-trifluoroacetate

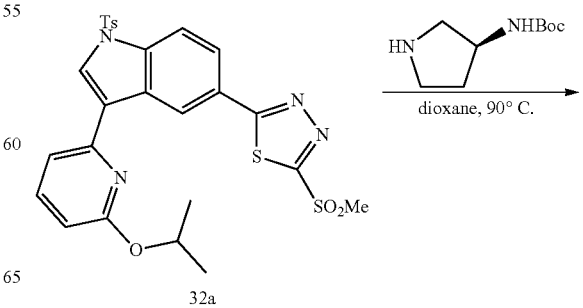

-continued

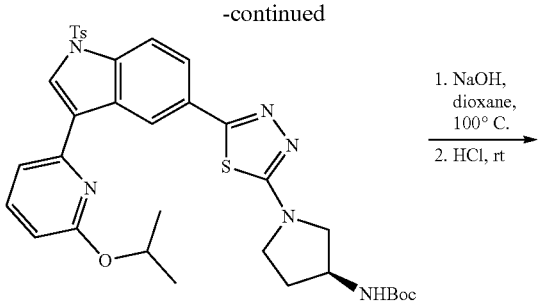

34a

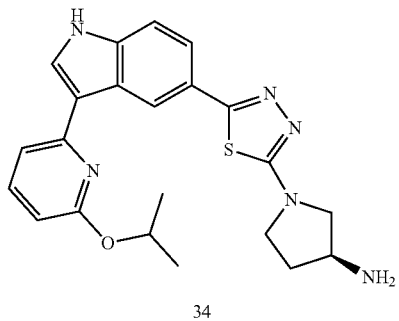

34

Preparation of compound 34a: (S)-tert-Butyl 1-(5-(3-(6-isopropoxypyridin-2-yl)-1-tosyl-1H-indol-5-yl)-1,3,4-thiadiazol-2-yl)pyrrolidin-3-ylcarbamate A yellow solution of 2-(3-(6-isopropoxypyridin-2-yl)-1-tosyl-1H-indol-5-yl)-5-(methylsulfonyl)-1,3,4-thiadiazole (168.4 mg, 0.296 mmol) and (3S)-(-)-3-(tert-butoxycarbonylamino)pyrrolidine (TCI America, Portland, Oreg.; 165 mg, 0.888 mmol) in dioxane (1.0 mL) was heated in an open microwave vial at 90° C. for 2 days. Chromatographic purification of the resulting dry residue (silica gel, 0-100% EtOAc/Hex) furnished (S)-tert-butyl 1-(5-(3-(6-isopropoxypyridin-2-yl)-1-tosyl-1H-indol-5-yl)-1,3,4-thiadiazol-2-yl)pyrrolidin-3-ylcarbamate (180 mg, 0.267 mmol, 90%) as a light-yellow solid: MS (ESI, pos. ion) m/z: 675.1 (M+1). $^1$H NMR (400 MHz, CDCl$_3$) δ ppm 8.80 (s, 1H), 8.07 (s, 2H), 7.94-7.99 (m, 1H), 7.82 (d, J=8.2 Hz, 2H), 7.62 (t, J=7.8 Hz, 1H), 7.28 (d, J=7.4 Hz, 1H), 7.22-7.25 (m, 2H), 6.63 (d, J=8.2 Hz, 1H), 5.57 (spt, J=6.2 Hz, 1H), 4.72 (br. s., 1H), 4.40 (br. s., 1H), 3.84 (dd, J=10.4, 5.9 Hz, 1H), 3.68-3.75 (m, 1H), 3.60-3.68 (m, 1H), 3.41-3.55 (m, 1H), 3.45 (m, J=10.4, 3.5 Hz, 1H), 2.35 (s, 3H), 1.46 (s, 9H), 1.45 (br. s., 6H).

Preparation of compound 34: (S)-1-(5-(3-(6-Isopropoxypyridin-2-yl)-1H-indol-5-yl)-1,3,4-thiadiazol-2-yl)pyrrolidin-3-amine 2,2,2-trifluoroacetate A solution of (S)-tert-butyl 1-(5-(3-(6-isopropoxypyridin-2-yl)-1-tosyl-1H-indol-5-yl)-1,3,4-thiadiazol-2-yl)pyrrolidin-3-ylcarbamate (170.5 mg, 0.253 mmol) and NaOH (3.0 M, aq; 1.0 mL, 3.00 mmol) in dioxane (5.0 mL) was heated at 100° C. for 3 h. Dioxane was then removed in vacuo, and the residue was taken up in HCl (4.0 M in dioxane; 5.0 mL, 20.0 mmol). The resulting solution was stirred at 25° C. for 10 min and concentrated in vacuo. The light-orange residue was sonicated with DMSO (2.0 mL), and the resulting suspension was filtered through Celite. The clear filtrate was purified by reverse phase HPLC (10-100% AcCN/H$_2$O+0.1% TFA) to provide (S)-1-(5-(3-(6-isopropoxypyridin-2-yl)-1H-indol-5-yl)-1,3,4-thiadiazol-2-yl)pyrrolidin-3-amine 2,2,2-trifluoroacetate (55.3 mg, 0.103 mmol, 41%) as a yellow solid: MS (ESI, pos. ion) m/z: 421.1 (M+1). $^1$H NMR (400 MHz, MeOH-d$_4$) δ ppm 8.85 (d, J=1.2 Hz, 1H), 8.03 (s, 1H), 7.86 (t, J=7.9 Hz, 1H), 7.76 (dd, J=8.6, 1.8 Hz, 1H), 7.58 (d, J=8.4 Hz, 1H), 7.49 (d, J=7.4 Hz, 1H), 6.76 (d, J=8.2 Hz, 1H), 5.54 (spt, J=6.2 Hz, 1H), 4.13-4.24 (m, 1H), 4.01 (dd, J=11.5, 6.3 Hz, 1H), 3.79-3.88 (m, 1H), 3.69-3.79 (m, 2H), 2.58-2.71 (m, 1H), 2.27-2.39 (m, 1H), 1.53 (s, 3H), 1.52 (s, 3H).

Example 35

(R)-5-(3-(6-Isopropoxypyridin-2-yl)-1H-indol-5-yl)-N-(piperidin-3-yl)-1,3,4-thiadiazol-2-amine 2,2,2-trifluoroacetate

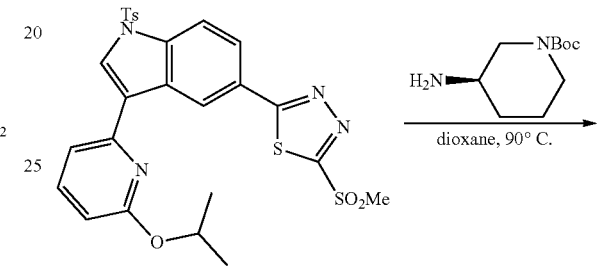

32a

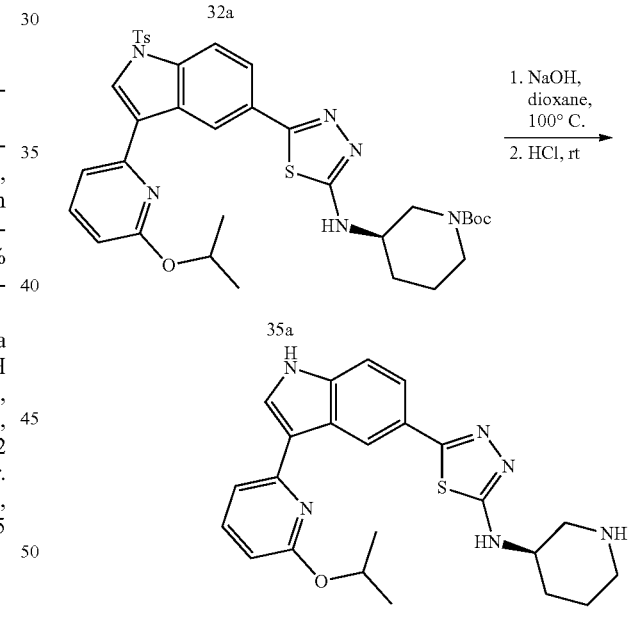

35

Preparation of compound 35a: (R)-tert-Butyl 3-(5-(3-(6-isopropoxypyridin-2-yl)-1-tosyl-1H-indol-5-yl)-1,3,4-thiadiazol-2-ylamino)piperidine-1-carboxylate A yellow solution of 2-(3-(6-isopropoxypyridin-2-yl)-1-tosyl-1H-indol-5-yl)-5-(methylsulfonyl)-1,3,4-thiadiazole (177.5 mg, 0.284 mmol) and (R)-tert-butyl 3-aminopiperidine-1-carboxylate (Small Molecules, Inc., Hoboken, N.J.; 0.251 mL, 1.296 mmol) in dioxane (2.0 mL) was heated in an open microwave vial at 90° C. for 2 d. The resulting solid residue was taken up in N-methyl-2-pyrrolidinone (0.4 mL) and heated under argon at 120° C. for 2.5 days. The mixture was then diluted with DCM (10 mL), concentrated onto silica gel, and chromatographically purified (silica gel, 0-100% EtOAc/Hex) to provide (R)-tert-butyl 3-(5-(3-(6-isopropoxy-pyridin-2-yl)-1-tosyl-1H-indol-5-yl)-1,3,4-thiadiazol-2-ylamino)piperidine-1-carboxylate (98.0 mg, 0.142 mmol, 50%) as a yellow oil: MS (ESI, pos. ion) m/z: 689.2 (M+1). $^1$H NMR (400 MHz, CDCl3) δ ppm 8.80 (1H, s), 8.07 (1H, s), 8.06 (1H, d, J=8.2 Hz), 7.93 (1H, d, J=8.7 Hz), 7.82 (2H, d, J=8.4 Hz), 7.62 (1H, t, J=7.8 Hz), 7.28 (2H, d, J=8.0 Hz), 7.24 (2H, s), 6.63 (1H, d, J=8.2 Hz), 5.55 (1H, dt, J=12.0, 5.9 Hz), 4.40 (1H, d, J=6.1 Hz), 3.61-3.74 (2H, m), 3.47-3.57 (2H, m), 3.36-3.45 (2H, m), 3.30 (2H, m), 2.35 (3H, s), 1.47 (9H, s), 1.44 (6H, br. s.).

Preparation of compound 35: (R)-5-(3-(6-Isopropoxypyridin-2-yl)-1H-indol-5-yl)-N-(piperidin-3-yl)-1,3,4-thiadiazol-2-amine 2,2,2-trifluoroacetate An orange-brown solution of (R)-tert-butyl 3-(5-(3-(6-isopropoxypyridin-2-yl)-1-tosyl-1H-indol-5-yl)-1,3,4-thiadiazol-2-ylamino)piperidine-1-carboxylate (98.0 mg, 0.142 mmol) and NaOH (3.0 M, aq; 0.6 mL, 1.80 mmol) in dioxane (3.0 mL) was heated at 100° C. for 4 h. Dioxane was then removed in vacuo, and the residue was taken up in HCl (4.0 M in dioxane; 3.0 mL, 12.00 mmol). The resulting solution was stirred at 25° C. for 10 min and concentrated in vacuo. The light-orange residue was sonicated with DMSO (2.0 mL), and the resulting suspension was filtered through Celite. The clear filtrate was purified by reverse phase HPLC (10-100% AcCN/H$_2$O+0.1% TFA) to provide (R)-5-(3-(6-isopropoxypyridin-2-yl)-1H-indol-5-yl)-N-(piperidin-3-yl)-1,3,4-thiadiazol-2-amine 2,2,2-trifluoroacetate (34.5 mg, 0.063 mmol, 44%) as a yellow solid: MS (ESI, pos. ion) m/z: 434.3 (M+1). $^1$H NMR (400 MHz, MeOH-d$_4$) δ ppm 8.79 (s, 1H), 7.96-8.01 (m, 1H), 7.75-7.79 (m, 1H), 7.71-7.75 (m, 1H), 7.54 (d, J=8.6 Hz, 1H), 7.43 (d, J=7.4 Hz, 1H), 6.66 (d, J=8.2 Hz, 1H), 5.53 (spt, J=6.1 Hz, 1H), 4.11 (spt, J=4.4 Hz, 1H), 3.67 (dd, J=12.5, 3.3 Hz, 1H), 3.32-3.37 (m, 1H), 3.09-3.15 (m, 1H), 3.02-3.09 (m, 1H), 2.18-2.27 (m, 1H), 2.05-2.15 (m, 1H), 1.82-1.95 (m, 1H), 1.70-1.82 (m, 1H), 1.49-1.52 (m, 3H), 1.49 (s, 3H).

Example 36

5-(3-(6-Cyclopropylpyrazin-2-yl)-1H-indol-5-yl)-N-(4-methoxybenzyl)-1,3,4-oxadiazol-2-amine 2,2,2-trifluoroacetate

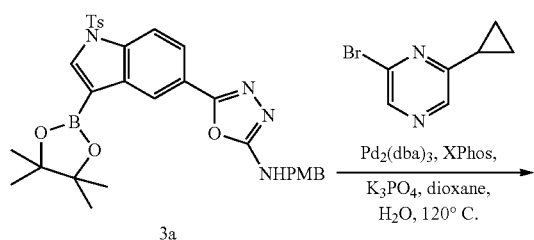

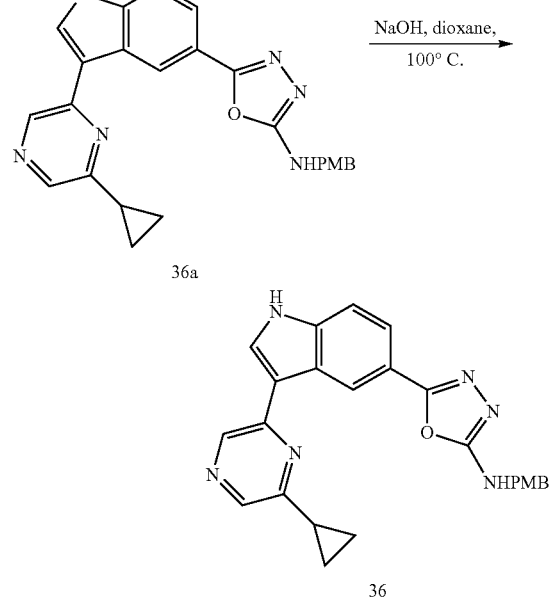

Preparation of compound 36a: 5-(3-(6-Cyclopropylpyrazin-2-yl)-1-tosyl-1H-indol-5-yl)-N-(4-methoxybenzyl)-1,3,4-oxadiazol-2-amine A mixture of N-(4-methoxybenzyl)-5-(3-(4,4,5,5-tetramethyl-1,3,2-dioxaborolan-2-yl)-1-tosyl-1H-indol-5-yl)-1,3,4-oxadiazol-2-amine (240 mg, 0.400 mmol), 2-bromo-6-cyclopropylpyrazine (CombiPhos Catalysts, Inc., Princeton, N.J.; 88 mg, 0.440 mmol), potassium phosphate (255 mg, 1.199 mmol), Pd$_2$(dba)$_3$ (10.98 mg, 0.012 mmol), and dicyclohexyl(2',4',6'-triisopropylbiphenyl-2-yl)phosphine (XPhos; 11.43 mg, 0.024 mmol) in dioxane (4.0 mL) and water (0.400 mL) was sparged with argon then heated at 120° C. (microwave) for 20 min. The reaction was cooled to RT, diluted with DCM (20 mL), and concentrated onto silica gel. Chromatographic purification (silica gel, 0-100% EtOAc/Hex) furnished 5-(3-(6-cyclopropylpyrazin-2-yl)-1-tosyl-1H-indol-5-yl)-N-(4-methoxybenzyl)-1,3,4-oxadiazol-2-amine (160 mg, 0.270 mmol, 68%) as a light-yellow solid: MS (ESI, pos. ion) m/z: 593.2 (M+1).

Preparation of compound 36: 5-(3-(6-Cyclopropylpyrazin-2-yl)-1H-indol-5-yl)-N-(4-methoxybenzyl)-1,3,4-oxadiazol-2-amine 2,2,2-trifluoroacetate A yellow solution of 5-(3-(6-cyclopropylpyrazin-2-yl)-1-tosyl-1H-indol-5-yl)-N-(4-methoxybenzyl)-1,3,4-oxadiazol-2-amine (69.5 mg, 0.117 mmol) and NaOH (3.0 M, aq; 0.5 mL, 1.500 mmol) in dioxane (2.0 mL) was heated at 100° C. for 2 h. The mixture was then concentrated in vacuo, and the residue was taken up in DMSO (2.0 mL) and filtered through Celite. The filtrate was purified by reverse phase HPLC (10-100% AcCN/H$_2$O+0.1% TFA) to provide 5-(3-(6-cyclopropylpyrazin-2-yl)-1H-indol-5-yl)-N-(4-methoxybenzyl)-1,3,4-oxadiazol-2-amine 2,2,2-trifluoroacetate (46.0 mg, 0.083 mmol, 71%) as a yellow solid: MS (ESI, pos. ion) m/z: 439.1 (M+1). $^1$H NMR (300 MHz, MeOH-d$_4$) δ ppm 11.58 (br. s., 1H), 9.04 (d, J=1.2 Hz, 1H), 8.75 (s, 1H), 8.23 (s, 1H), 8.12-8.17 (m, 1H), 7.79 (dd, J=8.6, 1.8 Hz, 1H), 7.58

(dd, J=8.6, 0.4 Hz, 1H), 7.39 (d, J=8.8 Hz, 2H), 6.91-6.98 (m, 2H), 4.59 (s, 2H), 3.79 (s, 3H), 2.14-2.25 (m, 1H), 1.25-1.33 (m, 2H), 1.04-1.14 (m, 2H).

Example 37

2-(3-(6-Cyclopropylpyrazin-2-yl)-1H-indol-5-yl)-5-(pyrrolidin-1-yl)-1,3,4-oxadiazole 2,2,2-trifluoroacetate

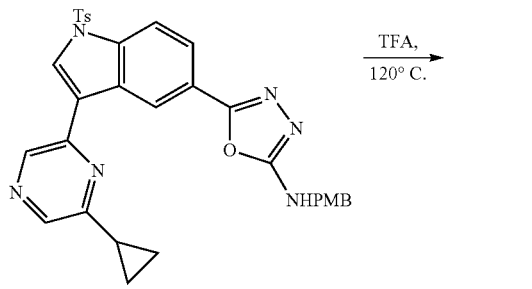

36

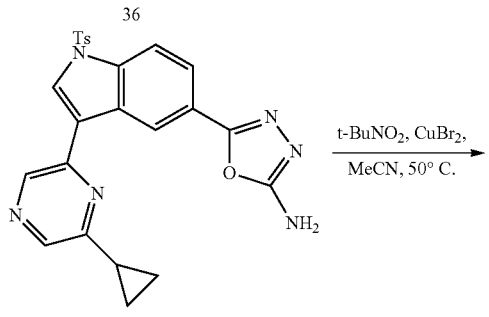

37a

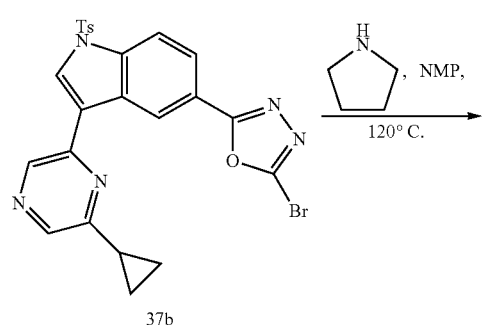

37b

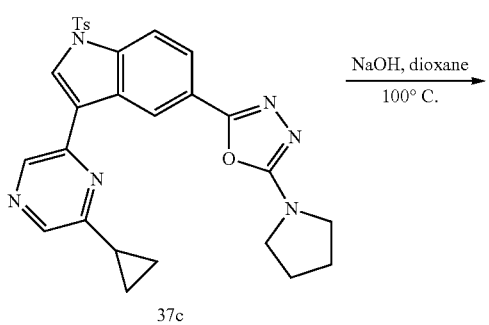

37c

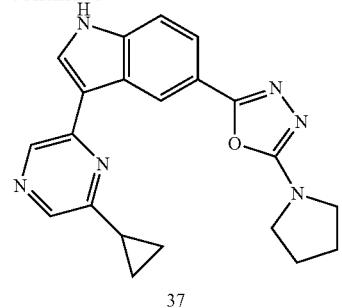

37

Preparation of compound 37a: 5-(3-(6-Cyclopropylpyrazin-2-yl)-1-tosyl-1H-indol-5-yl)-1,3,4-oxadiazol-2-amine An orange-brown solution of 5-(3-(6-cyclopropylpyrazin-2-yl)-1-tosyl-1H-indol-5-yl)-N-(4-methoxybenzyl)-1,3,4-oxadiazol-2-amine (69.7 mg, 0.118 mmol) in TFA (0.5 mL) was heated at 120° C. (microwave for 10 min. TFA was removed in vacuo, and the resulting brown oil was partitioned between DCM (30 mL) and 0.5 N NaOH (10 mL). The organic layer was separated and concentrated onto silica gel. Chromatographic purification (silica gel, 0-100% EtOAc/Hex) furnished 5-(3-(6-cyclopropylpyrazin-2-yl)-1-tosyl-1H-indol-5-yl)-1,3,4-oxadiazol-2-amine (38.3 mg, 0.081 mmol, 69%) as a white solid: MS (ESI, pos. ion) m/z: 473.1 (M+1).

Preparation of compound 37b: 2-Bromo-5-(3-(6-cyclopropylpyrazin-2-yl)-1-tosyl-1H-indol-5-yl)-1,3,4-oxadiazole tert-Butyl nitrite (0.017 mL, 0.144 mmol) was added to a dark green mixture of 5-(3-(6-cyclopropylpyrazin-2-yl)-1-tosyl-1H-indol-5-yl)-1,3,4-oxadiazol-2-amine (34.0 mg, 0.072 mmol) and copper(II) bromide (24.11 mg, 0.108 mmol) in ACN (1.0 mL) and the resulting mixture was stirred at 50° C. for 1 h. Additional tert-butyl nitrite (0.017 mL, 0.144 mmol) was added, and the reaction was stirred at 50° C. for 2 h. The reaction was cooled to RT and partitioned between EtOAc (80 mL) and water (30 mL). The organic layer was separated, sequentially washed with H₂O (30 mL) and brine (30 mL), dried over sodium sulfate, filtered, and concentrated in vacuo to provide crude 2-bromo-5-(3-(6-cyclopropylpyrazin-2-yl)-1-tosyl-1H-indol-5-yl)-1,3,4-oxadiazole (40.1 mg) as a yellow solid which was used without further purification: MS (ESI, pos. ion) m/z: 536.3 (M+1).

Preparation of compound 37c: 2-(3-(6-Cyclopropylpyrazin-2-yl)-1-tosyl-1H-indol-5-yl)-5-(pyrrolidin-1-yl)-1,3,4-oxadiazole A brown-orange solution of 2-bromo-5-(3-(6-cyclopropylpyrazin-2-yl)-1-tosyl-1H-indol-5-yl)-1,3,4-oxadiazole (35.0 mg, 0.065 mmol) and pyrrolidine (16.2 μL, 0.195 mmol) in NMP (1.0 mL) was heated in a sealed microwave process vial under argon at 120° C. for 18 h. The mixture was then diluted with DCM (5 mL), concentrated onto silica gel, and chromatographically purified (silica gel, 0-10% MeOH/DCM) to provide 2-(3-(6-cyclopropylpyrazin-2-yl)-1-tosyl-1H-indol-5-yl)-5-(pyrrolidin-1-yl)-1,3,4-oxadiazole (22.7 mg, 0.043 mmol, 66%) as a yellow oil: MS (ESI, pos. ion) m/z: 527.2 (M+1).

Preparation of compound 37: 2-(3-(6-Cyclopropylpyrazin-2-yl)-1H-indol-5-yl)-5-(pyrrolidin-1-yl)-1,3,4-oxadiazole 2,2,2-trifluoroacetate A yellow-orange solution of 2-(3-(6-cyclopropylpyrazin-2-yl)-1-tosyl-1H-indol-5-yl)-5-(pyrrolidin-1-yl)-1,3,4-oxadiazole (22.7 mg, 0.043 mmol) and NaOH (3.0 M, aq; 0.2 mL, 0.600 mmol) in dioxane (1.0 mL) was heated under argon at 100° C. for 2 h. The mixture was then concentrated in vacuo, and the residue was taken up in DMSO (2.0 mL) and filtered through Celite. The filtrate was purified by reverse phase HPLC (10-100% AcCN/H$_2$O+0.1% TFA) to provide 2-(3-(6-cyclopropylpyrazin-2-yl)-1H-indol-5-yl)-5-(pyrrolidin-1-yl)-1,3,4-oxadiazole 2,2,2-trifluoroacetate (6.3 mg, 0.013 mmol, 30%) as a yellow solid: MS (ESI, pos. ion) m/z: 373.3 (M+1). $^1$H NMR (400 MHz, MeOH-d$_4$) δ ppm 11.63 (1H, br. s.), 9.08-9.16 (1H, m), 8.74-8.84 (1H, m), 8.25-8.33 (1H, m), 8.16-8.22 (1H, m), 7.83 (1H, dd, J=8.7, 1.5 Hz), 7.60 (1H, d, J=8.6 Hz), 3.69-3.81 (4H, m), 2.21-2.29 (1H, m), 2.15-2.21 (4H, m), 1.31-1.37 (2H, m), 1.12-1.19 (2H, m).

Example 38

5-(3-(6-Cyclopropylpyrazin-2-yl)-1H-indol-5-yl)-1,3,4-oxadiazol-2(3H)-one 2,2,2-trifluoroacetate

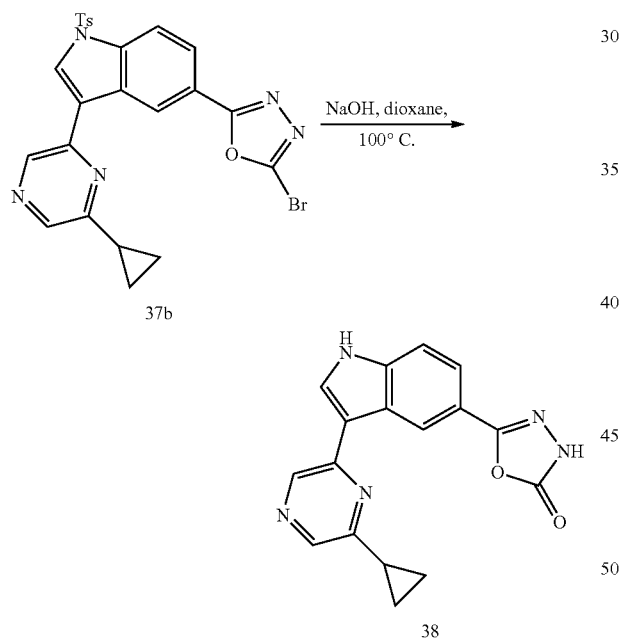

An orange-brown solution of 2-bromo-5-(3-(6-cyclopropylpyrazin-2-yl)-1-tosyl-1H-indol-5-yl)-1,3,4-oxadiazole (43.3 mg, 0.081 mmol) and NaOH (3.0 M, aq; 0.3 mL, 0.900 mmol) in dioxane (1.5 mL) was heated under argon at 100° C. for 3 h. The mixture was concentrated in vacuo, and the residue was taken up in DMSO (2.0 mL) and filtered through Celite. The filtrate was purified by reverse phase HPLC (25-100% AcCN/H$_2$O+0.1% TFA) to provide 5-(3-(6-cyclopropylpyrazin-2-yl)-1H-indol-5-yl)-1,3,4-oxadiazol-2(3H)-one 2,2,2-trifluoroacetate (10.0 mg, 0.023 mmol, 29%) as a yellow solid: MS (ESI, pos. ion) m/z: 320.3 (M+1). $^1$H NMR (400 MHz, MeOH-d$_4$) δ ppm 11.53 (1H, br. s.), 9.00 (1H, s), 8.77 (1H, br. s.), 8.26 (1H, br. s.), 8.14 (1H, d, J=2.7 Hz), 7.72 (1H, dd, J=8.6, 1.6 Hz), 7.55 (1H, d, J=8.6 Hz), 2.17-2.27 (1H, m), 1.27-1.36 (2H, m), 1.13-1.21 (2H, m).

Example 39

2-(3-(6-Cyclopropylpyrazin-2-yl)-1H-indol-5-yl)-5-(1H-pyrazol-5-yl)-1,3,4-oxadiazole 2,2,2-trifluoroacetate

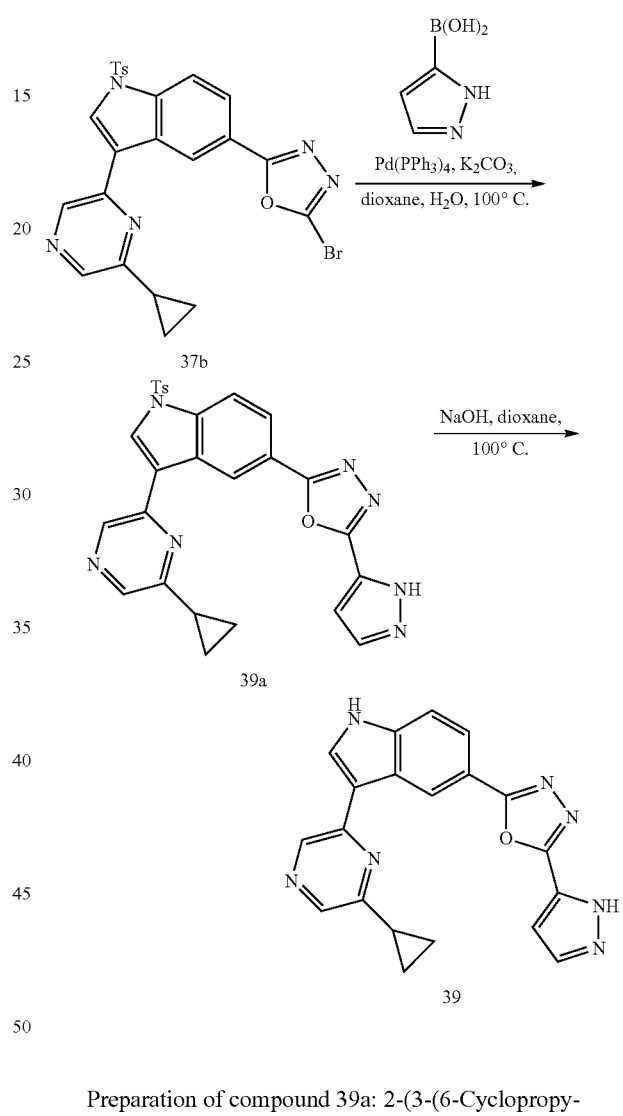

Preparation of compound 39a: 2-(3-(6-Cyclopropylpyrazin-2-yl)-1-tosyl-1H-indol-5-yl)-5-(1H-pyrazol-5-yl)-1,3,4-oxadiazole A brown mixture of 2-bromo-5-(3-(6-cyclopropylpyrazin-2-yl)-1-tosyl-1H-indol-5-yl)-1,3,4-oxadiazole (48.4 mg, 0.090 mmol), 1H-pyrazol-3-ylboronic acid (J&W Pharmlab, LLC, Levittown, Pa.; 30.3 mg, 0.271 mmol), Pd(PPh$_3$)$_4$ (20.85 mg, 0.018 mmol), and potassium carbonate (37.4 mg, 0.271 mmol) in a mixture of dioxane (1.0 mL) and H$_2$O (0.250 mL) was stirred under argon at 100° C. for 1.5 h. The mixture was cooled to RT, concentrated onto silica gel, and purified chromatographically (silica gel, 0-100% (10% MeOH-EtOAc)/Hex) to provide 2-(3-(6-cyclopropylpyrazin-2-yl)-1-tosyl-1H-indol-5-yl)-5-(1H-pyrazol-5-yl)-1,3,4- oxadiazole (19.6 mg, 0.037 mmol, 42%) as a light-yellow solid: MS (ESI, pos. ion) m/z: 524.2 (M+1).

Preparation of compound 39: 2-(3-(6-Cyclopropylpyrazin-2-yl)-1H-indol-5-yl)-5-(1H-pyrazol-5-yl)-1,3,4-oxadiazole 2,2,2-trifluoroacetate A yellow-orange solution of 2-(3-(6-cyclopropylpyrazin-2-yl)-1-tosyl-1H-indol-5-yl)-5-(1H-pyrazol-5-yl)-1,3,4-oxadiazole (19.6 mg, 0.037 mmol) and NaOH (3.0 M, aq; 0.2 mL, 0.600 mmol) in dioxane (1.0 mL) was heated under argon at 100° C. for 3 h. The mixture was concentrated in vacuo, and the residue was taken up in DMSO (2.0 mL) and filtered through Celite. The filtrate was purified by reverse phase HPLC (5-100% AcCN/H$_2$O+0.1% TFA) to provide 2-(3-(6-cyclopropylpyrazin-2-yl)-1H-indol-5-yl)-5-(1H-pyrazol-5-yl)-1,3,4-oxadiazole 2,2,2-trifluoroacetate (4.5 mg, 9.31 µmol, 25) as a yellow solid: MS (ESI, pos. ion) m/z: 370.2 (M+1). $^1$H NMR (400 MHz, MeOH-d$_4$) δ ppm 11.61 (1H, br. s.), 9.29 (1H, s), 8.82 (1H, br. s.), 8.30 (1H, br. s.), 8.18 (1H, s), 8.00 (1H, dd, J=8.6, 1.4 Hz), 7.90 (1H, d, J=2.2 Hz), 7.63 (1H, d, J=8.6 Hz), 7.07 (1H, d, J=2.3 Hz), 2.22-2.30 (1H, m), 1.37-1.43 (2H, m), 1.19-1.25 (2H, m Example 40

5-(3-(6-Cyclopropylpyrazin-2-yl)-1H-indol-5-yl)-N-phenyl-1,3,4-oxadiazol-2-amine

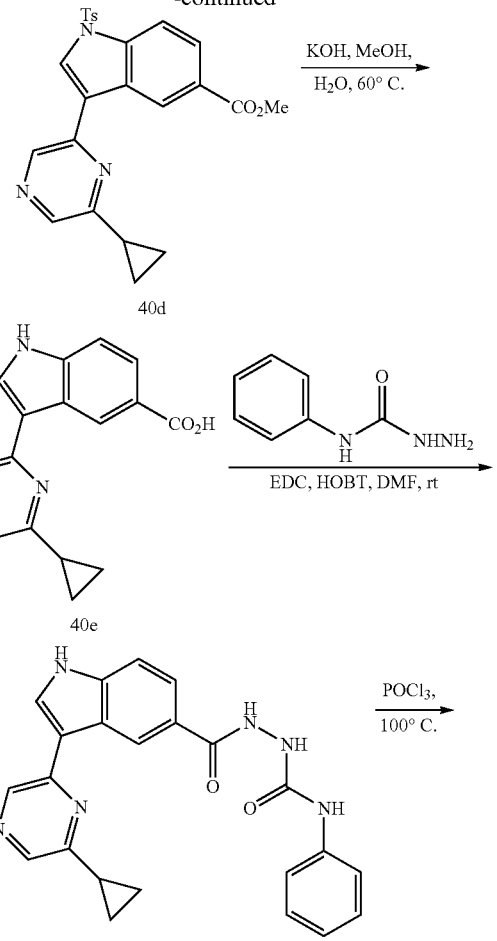

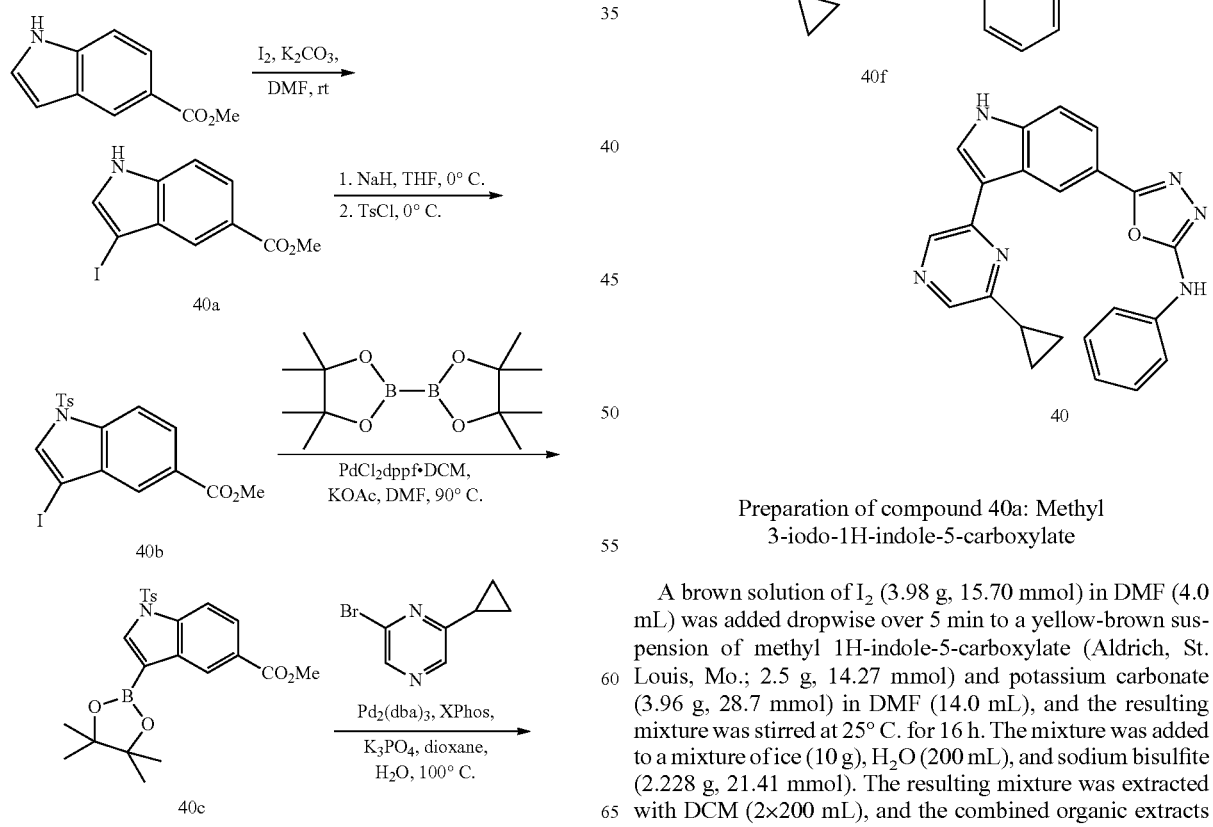

Preparation of compound 40a: Methyl 3-iodo-1H-indole-5-carboxylate

A brown solution of I$_2$ (3.98 g, 15.70 mmol) in DMF (4.0 mL) was added dropwise over 5 min to a yellow-brown suspension of methyl 1H-indole-5-carboxylate (Aldrich, St. Louis, Mo.; 2.5 g, 14.27 mmol) and potassium carbonate (3.96 g, 28.7 mmol) in DMF (14.0 mL), and the resulting mixture was stirred at 25° C. for 16 h. The mixture was added to a mixture of ice (10 g), H$_2$O (200 mL), and sodium bisulfite (2.228 g, 21.41 mmol). The resulting mixture was extracted with DCM (2×200 mL), and the combined organic extracts were dried over sodium sulfate, filtered, and concentrated in vacuo to provide methyl 3-iodo-1H-indole-5-carboxylate (3.87 g, 12.85 mmol, 90%) as a brown solid: MS (ESI, pos. ion) m/z: 301.9 (M+1). $^1$H NMR (400 MHz, CDCl3) δ ppm 8.22 (s, 1H), 8.00-8.03 (m, 1H), 7.96 (dd, J=8.6, 1.4 Hz, 1H), 7.39 (d, J=8.8 Hz, 1H), 7.37 (d, J=2.3 Hz, 1H), 3.96 (s, 3H).

Preparation of compound 40b: Methyl 3-iodo-1-tosyl-1H-indole-5-carboxylate

NaH (60% w/w in mineral oil; 0.532 g, 13.30 mmol) was added (portionwise, over 2 min) to a solution of methyl 3-iodo-1H-indole-5-carboxylate (3.64 g, 12.09 mmol) in THF (30 mL) at 0° C., and the resulting mixture was stirred at 0° C. for 5 min. p-Toluenesulfonyl chloride (2.54 g, 13.30 mmol) was then added (portionwise, over 2 min), and the resulting mixture was stirred at 0° C. for 1 h. H$_2$O (50 mL) was carefully added to the mixture at 0° C. and the reaction was warmed to 25° C. THF was removed in vacuo, and the resulting tan mixture was vacuum filtered. The collected solid was washed with H$_2$O (150 mL) and dried in vacuo to provide crude methyl 3-iodo-1-tosyl-1H-indole-5-carboxylate (5.94 g) as a tan solid: MS (ESI, pos. ion) m/z: 455.9 (M+1). $^1$H NMR (400 MHz, CDCl$_3$) δ ppm 8.03-8.11 (2H, m), 7.97-8.02 (1H, m), 7.79 (2H, d, J=8.2 Hz), 7.75 (1H, s), 7.26 (2H, d, J=8.2 Hz), 3.94 (3H, s), 2.36 (3H, s).

Preparation of compound 40c: Methyl 3-(4,4,5,5-tetramethyl-1,3,2-dioxaborolan-2-yl)-1-tosyl-1H-indole-5-carboxylate A brown mixture of methyl 3-iodo-1-tosyl-1H-indole-5-carboxylate (2.32 g, 5.10 mmol), 4,4,4',4',5,5,5',5'-octamethyl-2,2'-bi(1,3,2-dioxaborolane) (3.88 g, 15.29 mmol), PdCl$_2$(pddf).DCM (0.208 g, 0.255 mmol), and potassium acetate (2.501 g, 25.5 mmol) in DMF (25 mL) was sparged with argon and stirred at 90° C. for 1.5 h. The mixture was then cooled to RT and partitioned between EtOAc (500 mL) and H$_2$O (300 mL). The resulting mixture was filtered through Celite, and the organic layer was separated from the filtrate and sequentially washed with H$_2$O (2×300 mL), dried over sodium sulfate, filtered, and concentrated in vacuo to provide crude methyl 3-(4,4,5,5-tetramethyl-1,3,2-dioxaborolan-2-yl)-1-tosyl-1H-indole-5-carboxylate (5.52 g) as a brown solid, which was used without further purification: MS (ESI, pos. ion) m/z: 456.2 (M+1).

Preparation of compound 40d: Methyl 3-(6-cyclopropylpyrazin-2-yl)-1-tosyl-1H-indole-5-carboxylate A brown mixture of methyl 3-(4,4,5,5-tetramethyl-1,3,2-dioxaborolan-2-yl)-1-tosyl-1H-indole-5-carboxylate (2.32 g, 5.10 mmol), 2-bromo-6-cyclopropylpyrazine (CombiPhos Catalysts, Inc., Princeton, N.J.; 1.116 g, 5.60 mmol), Pd$_2$(dba)$_3$ (0.140 g, 0.153 mmol), dicyclohexyl(2',4',6'-triisopropylbiphenyl-2-yl)phosphine (XPhos; 0.146 g, 0.306 mmol), and potassium phosphate (3.24 g, 15.29 mmol) in a mixture of dioxane (45 mL) and H$_2$O (4.50 mL) was sparged with argon then heated at 100° C. for 3 h. Additional 2-bromo-6-cyclopropylpyrazine (CombiPhos Catalysts, Inc., Princeton, N.J.; 550 mg, 2.80 mmol) was added, and the resulting mixture was stirred at 100° C. for 2 h. The reaction was cooled to RT, diluted with DCM (50 mL), and concentrated onto silica gel. Chromatographic purification (silica gel, 0-80% EtOAc/Hex) furnished methyl 3-(6-cyclopropylpyrazin-2-yl)-1-tosyl-1H-indole-5-carboxylate (2.22 g, 4.96 mmol, 97%) as a light-yellow solid: MS (ESI, pos. ion) m/z: 448.1 (M+1).

Preparation of compound 40e: 3-(6-Cyclopropylpyrazin-2-yl)-1H-indole-5-carboxylic acid An orange-brown suspension of methyl 3-(6-cyclopropylpyrazin-2-yl)-1-tosyl-1H-indole-5-carboxylate (353.7 mg, 0.790 mmol) and KOH (310 mg, 5.53 mmol) in a mixture of MeOH (6.0 mL) and water (1.20 mL) was heated at 60° C. for 6 h. The mixture was subsequently cooled to RT and MeOH was removed in vacuo. 1.0 N aq HCl (4.0 mL) was added to the resulting slurry, and the precipitated solid was collected by vacuum filtration, washed with water (10 mL), and dried in vacuo to provide 3-(6-cyclopropylpyrazin-2-yl)-1H-indole-5-carboxylic acid (209.2 mg, 0.749 mmol, 95%) as a yellow solid: MS (ESI, pos. ion) m/z: 280.1 (M+1). $^1$H NMR (300 MHz, DMSO-d$_6$) δ ppm 11.96 (1H, br. s.), 9.12 (1H, s), 8.91 (1H, s), 8.33-8.40 (2H, m), 7.80 (1H, dd, J=8.3, 1.2 Hz), 7.51 (1H, d, J=8.5 Hz), 2.23 (1H, br. s.), 1.17 (2H, br. s.), 1.11 (2H, m, J=7.9 Hz).

Preparation of compound 40f: 2-(3-(6-Cyclopropylpyrazin-2-yl)-1H-indole-5-carbonyl)-N-phenylhydrazinecarboxamide A mixture of 3-(6-cyclopropylpyrazin-2-yl)-1H-indole-5-carboxylic acid (204.5 mg, 0.732 mmol), 4-phenylsemicarbazide (111 mg, 0.732 mmol), EDC (140 mg, 0.732 mmol), and HOBT (112 mg, 0.732 mmol) in DMF (3.5 mL) was stirred at 25° C. for 3 h. DIPEA (0.255 mL, 1.464 mmol) was added and the resulting mixture was stirred at 25° C. for 2 h. Additional 4-phenylsemicarbazide (111 mg, 0.732 mmol), HOBT (112 mg, 0.732 mmol), and EDC (140 mg, 0.732 mmol) were sequentially added, and the resulting mixture was stirred at 25° C. for 17 h. The mixture was diluted with H$_2$O (40 mL), and the precipitated solid was collected by vacuum filtration, sequentially washed with H$_2$O (2×30 mL) and Et$_2$O (2×15 mL), and dried in vacuo to provide 2-(3-(6-cyclopropylpyrazin-2-yl)-1H-indole-5-carbonyl)-N-phenylhydrazinecarboxamide (262 mg, 0.635 mmol, 87%) as a tan solid: MS (ESI, pos. ion) m/z: 413.2 (M+1). $^1$H NMR (400 MHz, DMSO-d$_6$) δ ppm 11.90-11.97 (1H, m), 10.19-10.25 (1H, m), 8.97-9.00 (1H, m), 8.94-8.97 (1H, m), 8.84 (1H, s), 8.36 (1H, s), 8.32 (1H, d, J=2.7 Hz), 8.15 (1H, s), 7.79 (1H, d, J=8.4 Hz), 7.51-7.55 (1H, m), 7.50 (2H, d, J=8.0 Hz), 7.27 (2H, t, J=7.7 Hz), 6.96 (1H, t, J=7.3 Hz), 2.18-2.27 (1H, m), 1.16-1.22 (2H, m), 1.04-1.13 (2H, m).

Preparation of compound 40: 5-(3-(6-Cyclopropylpyrazin-2-yl)-1H-indol-5-yl)-N-phenyl-1,3,4-oxadiazol-2-amine A brown solution of 2-(3-(6-cyclopropylpyrazin-2-yl)-1H-indole-5-carbonyl)-N-phenylhydrazinecarboxamide (118.5 mg, 0.287 mmol) and phosphorus oxychloride (3.5 mL, 37.56 mmol) was stirred at 100° C. for 13 h. The reaction was cooled to RT, and excess POCl$_3$ was removed in vacuo. The residue was partitioned between EtOAc (80 mL) and saturated aq NaHCO$_3$ (50 mL). The organic layer was separated, washed with brine (30 mL), dried over sodium sulfate, filtered, and concentrated in vacuo. Chromatographic purification of the residue (silica gel, 10-100% EtOAc/Hex) furnished 5-(3-(6-cyclopropylpyrazin-2-yl)-1H-indol-5-yl)-N-phenyl-1,3,4-oxadiazol-2-amine (36.0 mg, 0.091 mmol, 32%) as a tan solid: MS (ESI, pos. ion) m/z: 395.1 (M+1). $^1$H NMR (400 MHz, DMSO-d$_6$) δ ppm 12.01 (1H, br. s.), 10.53 (1H, s), 9.02 (1H, s), 8.91 (1H, s), 8.37 (1H, d, J=2.7 Hz), 8.36 (1H, s), 7.69-7.74 (1H, m), 7.63 (3H, dd, J=8.5, 1.7 Hz), 7.37 (2H, t, J=7.9 Hz), 7.02 (1H, t, J=7.3 Hz), 2.20-2.30 (1H, m), 1.16-1.21 (2H, m), 1.09-1.15 (2H, m).

Example 41

5-(3-(6-isopropoxypyridin-2-yl)-1H-indol-5-yl)-N-methyl-1,3,4-oxadiazol-2-amine

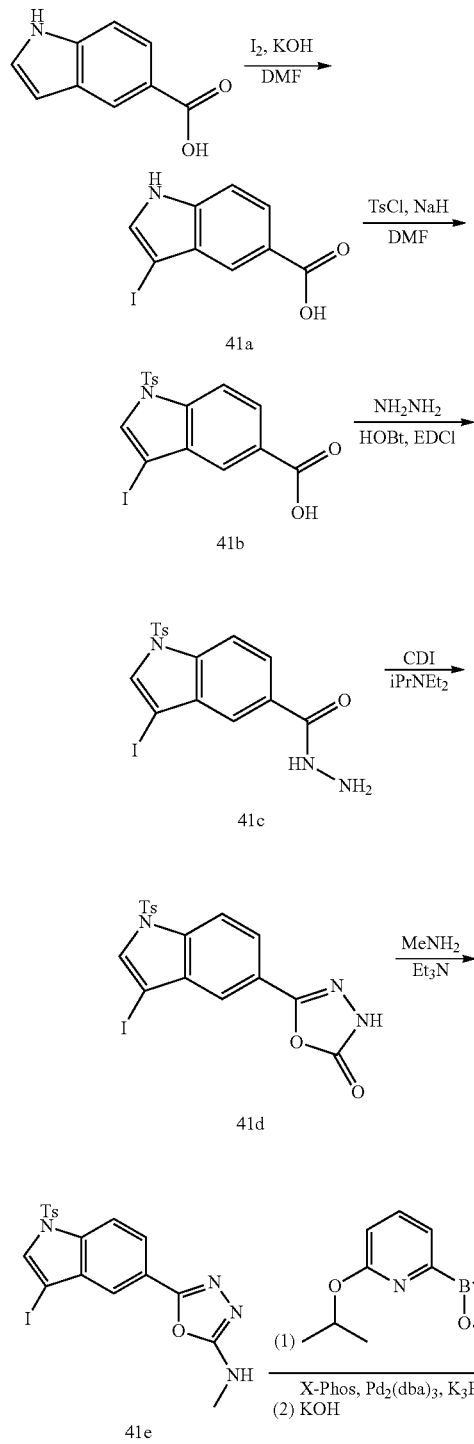

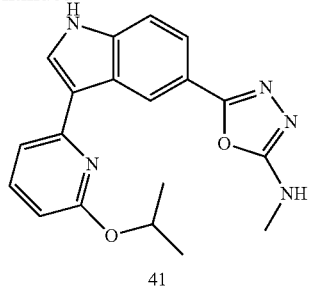

Preparation of compound 41a: 3-iodo-1H-indole-5-carboxylic acid

To a solution of 1H-indole-5-carboxylic acid (2.08 g, 12.89 mmol, Acros) in DMF (20 mL) was added $I_2$ (3.27 g, 12.89 mmol) and KOH (1.807 g, 32.2 mmol). The reaction was stirred at RT for 1 h then the mixture was poured into ice and $H_2O$ (120 mL) containing sodium bisulfite (1.341 g, 12.89 mmol). The mixture was treated with 5 M HCl to pH=4. The resulting yellow solid was collected by filtration, washed with water and dried to give crude 3-iodo-1H-indole-5-carboxylic acid (7.13 g) as a yellow amorphous solid. MS (ESI, pos. ion) m/z: 288.0 (M+1). $^1$H NMR (400 MHz, MeOH) δ ppm 8.09-8.14 (1H, m), 7.88 (1H, dd, J=8.6, 1.6 Hz), 7.48 (1H, s), 7.45 (1H, d, J=8.6 Hz).

Preparation of compound 41b: 3-iodo-1-tosyl-1H-indole-5-carboxylic acid

A solution of 3-iodo-1H-indole-5-carboxylic acid (3.70 g, 12.89 mmol) in DMF (9.5 mL) at 0° C. was treated with NaH (60% in mineral oil) (1.289 g, 32.2 mmol). After 15 min at 0° C., p-toluenesulfonyl chloride (2.95 g, 15.47 mmol) was added in 1 g portions at 0° C. every 15 min and the reaction was warmed slowly in the ice bath to 10° C. After 2 h, the mixture was dumped into $H_2O$ and the mixture was acidified with 5 M HCl. The precipitate was collected by filtration, washed with water and dried to afford crude 3-iodo-1-tosyl-1H-indole-5-carboxylic acid (5.72 g) as a tan solid. MS (ESI, pos. ion) m/z: 442 (M+1). $^1$H NMR (400 MHz, DMSO-$d_6$) δ ppm 8.20 (1H, s), 8.03-8.09 (1H, m), 7.93-8.02 (3H, m), 7.91 (1H, s), 7.42 (2H, d, J=8.0 Hz), 2.33 (3H, s)

Preparation of compound 41c: 3-iodo-1-tosyl-1H-indole-5-carbohydrazide 1H-benzo[d][1,2,3]triazol-1-ol hydrate (0.471 g, 3.07 mmol) (Aldrich), N1-((ethylimino)methylene)-N3,N3-dimethylpropane-1,3-diamine hydrochloride (0.589 g, 3.07 mmol) (Sigma-Aldrich), and 3-iodo-1-tosyl-1H-indole-5-carboxylic acid (1.13 g, 2.56 mmol) were weighed into a 100 mL round bottomed flask and dissolved in DMF (12 mL). The solution was stirred at RT for 30 min. Hydrazine (1.4 mL, 44.6 mmol) (Aldrich) was added, and the reaction was stirred at RT for 1.5 h. The solution was partially concentrated. The concentrate was diluted with $H_2O$ and a precipitate formed. The solid was collected by filtration, washed with $H_2O$, and dried to give 3-iodo-1-tosyl-1H-indole-5-carbohydrazide (0.802 g, 1.762 mmol, 68.8%) as a beige solid. MS (ESI, pos. ion) m/z: 455.9 (M+1). $^1$H NMR (400 MHz, DMSO-$d_6$) δ ppm 9.91 (s, 1H), 8.15 (s, 1H), 7.97-8.02 (m, 1H), 7.95 (d, J=8.4 Hz, 2H), 7.82-7.92 (m, 2H), 7.41 (d, J=8.2 Hz, 2H), 4.52 (br. s., 1H), 2.33 (s, 3H).

Preparation of compound 41d: 5-(3-iodo-1-tosyl-1H-indol-5-yl)-1,3,4-oxadiazol-2(3H)-one To a solution of 3-iodo-1-tosyl-1H-indole-5-carbohydrazide (2.00 g, 4.39 mmol) in DMF (10 mL) at RT was added N-ethyl-N-isopropylpropan-2-amine (1.68 mL, 9.66 mmol) and CDI (0.784 g, 4.83 mmol). The reaction was stirred at RT for 30 min, followed by 65° C. in an oil bath for 15 min. It was concentrated under reduced pressure and the residue was purified by flash chromatography on silica gel (eluted with 20-70% EtOAc in Hex) to afford 5-(3-iodo-1-tosyl-1H-indol-5-yl)-1,3,4-oxadiazol-2(3H)-one (1.7 g, 80%) as an off white crystalline solid. MS (ESI, pos. ion) m/z: 482.0 (M+1).

Preparation of compound 41e: 5-(3-iodo-1-tosyl-1H-indol-5-yl)-N-methyl-1,3,4-oxadiazol-2-amine To a mixture of 5-(3-iodo-1-tosyl-1H-indol-5-yl)-1,3,4-oxadiazol-2(3H)-one (585 mg, 1.216 mmol), methylamine (1.82 mL of 2 M in THF, 3.65 mmol) and diisopropylethylamine (0.42 mL, 2.43 mmol) in DMF (1.5 mL) was added 1H-benzo[d][1,2,3]triazol-1-yloxy)tris(dimethylamino)phosphonium hexafluorophosphate (V) (591 mg, 1.33 mmol). The reaction was stirred at RT for 18 h, then diluted with H$_2$O (5 mL) and extracted with EtOAc (2×15 mL). The combined organic solution was washed with brine, dried over MgSO$_4$, and concentrated. The residue was suspended in 5 mL of EtOAc, and filtered to 5-(3-iodo-1-tosyl-1H-indol-5-yl)-N-methyl-1,3,4-oxadiazol-2-amine (507 mg, 84%) as an off white crystalline solid. MS (ESI, pos. ion) m/z: 495.0 (M+1). $^1$H NMR (400 MHz, DMSO-d$_6$) δ ppm 8.21 (1H, s), 8.13 (1H, d, J=8.8 Hz), 7.98 (2H, d, J=8.4 Hz), 7.91 (1H, m), 7.71 (1H, m), 7.70 (1H, m), 7.44 (2H, d, J=8.0 Hz), 2.88 (3H, d, J=4.9 Hz), 2.35 (3H, s).

Preparation of compound 41: 5-(3-(6-isopropoxypyridin-2-yl)-1H-indol-5-yl)-N-methyl-1,3,4-oxadiazol-2-amine A mixture of 5-(3-iodo-1-tosyl-1H-indol-5-yl)-N-methyl-1,3,4-oxadiazol-2-amine (210 mg, 0.42 mmol), 2-isopropoxy-6-(4,4,5,5-tetramethyl-1,3,2-dioxaborolan-2-yl)pyridine (145 mg, 0.55 mmol) (CombiPhos Catalysts Inc., Cat#BE177), dicyclohexyl(2',4',6'-triisopropylbiphenyl-2-yl)phosphine (16 mg, 0.034 mmol, Strem), Pd$_2$(dba)$_3$ (15 mg, 0.017 mmol, Strem), and potassium phosphate (271 mg, 1.27 mmol) in dioxane (4 mL) and H$_2$O (1 mL) in a sealed glass tube was heated in a microwave reactor (Personal Chemistry, Biotage AB, Inc., Uppsala, Sweden) at 125° C. for 20 min. The mixture was partitioned between 2 mL of 0.5 N NaOH and 10 mL of EtOAc. The organic layer was filtered through a pad of Celite and concentrated to give crude 5-(3-(6-isopropoxypyridin-2-yl)-1-tosyl-1H-indol-5-yl)-N-methyl-1,3,4-oxadiazol-2-amine that was used in next step without further purification. MS (ESI, pos. ion) m/z: 504.1 (M+1). A mixture of 5-(3-(6-isopropoxypyridin-2-yl)-1-tosyl-1H-indol-5-yl)-N-methyl-1,3,4-oxadiazol-2-amine and KOH (49 mg, 0.88 mmol) in 2 mL of dioxane and 1 mL of H$_2$O was heated in a microwave at 105° C. for 15 min. It was partitioned between 15 mL of EtOAc and 3 mL of H$_2$O. The organic layer was concentrated and purified on a reverse phase HPLC, using a gradient of 10-90% [0.1% TFA in AcCN] in [0.1% TFA in H$_2$O] to afford 5-(3-(6-isopropoxypyridin-2-yl)-1H-indol-5-yl)-N-methyl-1,3,4-oxadiazol-2-amine 2,2,2-trifluoroacetate (51 mg, 27% overall for 2 steps) as a yellow crystalline solid. MS (ESI, pos. ion) m/z: 350.1 (M+1). $^1$H NMR (400 MHz, DMSO-d$_6$) δ ppm 11.81 (1H, br.), 8.99 (1H, s), 8.19 (1H, d, J=2.6 Hz,), 7.66 (2H, m), 7.56 (1H, d, J=8.6 Hz), 7.42 (1H, d, J=7.4 Hz), 6.52 (1H, d, J=8.0 Hz), 5.49 (1H, m), 4.06 (1H, br.), 2.89 (3H, s), 1.44 (6H, d, J=6.1 Hz).

Example 42

2-(3-(6-isopropoxypyridin-2-yl)-1H-indol-5-yl)-5-methyl-1,3,4-oxadiazole

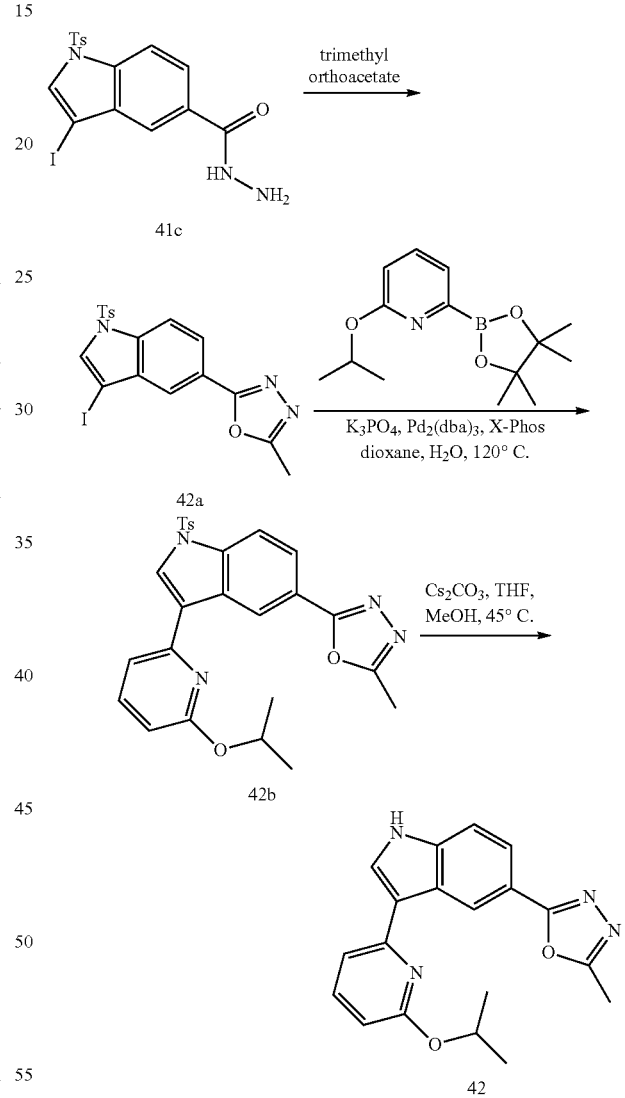

Preparation of compound 42a: 2-(3-iodo-1-tosyl-1H-indol-5-yl)-5-methyl-1,3,4-oxadiazole A mixture of 2-(3-iodo-1-tosyl-1H-indol-5-yl)-5-methyl-1,3,4-oxadiazole (0.113 g, 0.236 mmol) and trimethyl orthoacetate (2.0 mL, 15.91 mmol) (Aldrich) was heated in an Initiator microwave reactor (Personal Chemistry, Biotage AB, Inc., Uppsala, Sweden) at 160° C. for 45 min. The mixture was purified by flash chromatography (eluting with 5-50% EtOAc in Hex) to give 2-(3-iodo-1-tosyl-1H-indol-5-yl)-5-methyl-1,3,4-oxadiazole (0.113 g, 0.236 mmol, 53.9%) as a white solid. MS (ESI, pos. ion) m/z 480.0 (M+1).

Preparation of compound 42b: 2-(3-(6-isopropoxy-pyridin-2-yl)-1-tosyl-1H-indol-5-yl)-5-methyl-1,3,4-oxadiazole 2-(3-Iodo-1-tosyl-1H-indol-5-yl)-5-methyl-1,3,4-oxadiazole (113 mg, 0.236 mmol), 2-isopropoxy-6-(4,4,5,5-tetramethyl-1,3,2-dioxaborolan-2-yl)pyridine (74.4 mg, 0.283 mmol) (Combiphos Catalysts Inc.), dicyclohexyl(2',4',6'-triisopropylbiphenyl-2-yl)phosphine (6.74 mg, 0.014 mmol) (Strem), Pd$_2$(dba)$_3$ (6.48 mg, 7.07 μmol) (Strem), and potassium phosphate (150 mg, 0.707 mmol) (Reidel-de Haen) were weighed into a 20 mL glass microwave vial, which was then purged with argon. The solids were treated with dioxane (2.5 mL) and H$_2$O (0.25 mL), the tube was sealed, and the contents were heated in an Initiator microwave reactor (Personal Chemistry, Biotage AB, Inc., Uppsala, Sweden) at 120° C. for 15 min. The mixture was treated with 1N NaOH and extracted with EtOAc. The combined organic layers were dried, filtered and concentrated to give the crude product.

Preparation of compound 42: 2-(3-(6-isopropoxypyridin-2-yl)-1H-indol-5-yl)-5-methyl-1,3,4-oxadiazole 2-(3-(6-Isopropoxypyridin-2-yl)-1-tosyl-1H-indol-5-yl)-5-methyl-1,3,4-oxadiazole (214 mg, 0.438 mmol) in a round bottomed flask was dissolved in MeOH (1.500 mL) and THF (3.0 mL). Cesium carbonate (428 mg, 1.314 mmol) (Aldrich) was added, the flask was fitted with a reflux condenser and the contents of the flask were heated at 45° C. for 15 min. H$_2$O (30 mL) was added and the mixture was extracted with EtOAc (2×75 mL). The combined organic layers were dried, filtered and concentrated. The residue was purified with RP-HPLC (10-90% MeCN in H$_2$O with 0.01% TFA as additive) to give 2-(3-(6-isopropoxypyridin-2-yl)-1H-indol-5-yl)-5-methyl-1,3,4-oxadiazole (33.6 mg, 11.1%). MS (ESI, pos. ion) m/z 335.1 (M+1); $^1$H NMR (400 MHz, DMSO-d$_6$) δ ppm 11.89 (br. s., 1H), 9.20-9.29 (m, 1H), 8.25 (d, J=2.5 Hz, 1H), 7.82 (dd, J=8.5, 1.7 Hz, 1H), 7.57-7.72 (m, 2H), 7.46 (d, J=7.4 Hz, 1H), 6.53 (d, J=8.0 Hz, 1H), 5.58 (dt, J=12.3, 6.2 Hz, 1H), 2.59 (s, 3H), 1.47 (d, J=6.1 Hz, 6H).

Example 43

2-cyclopropyl-5-(3-(4-cyclopropylpyrimidin-2-yl)-1H-indol-5-yl)-1,3,4-oxadiazole

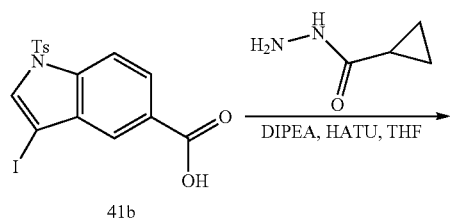

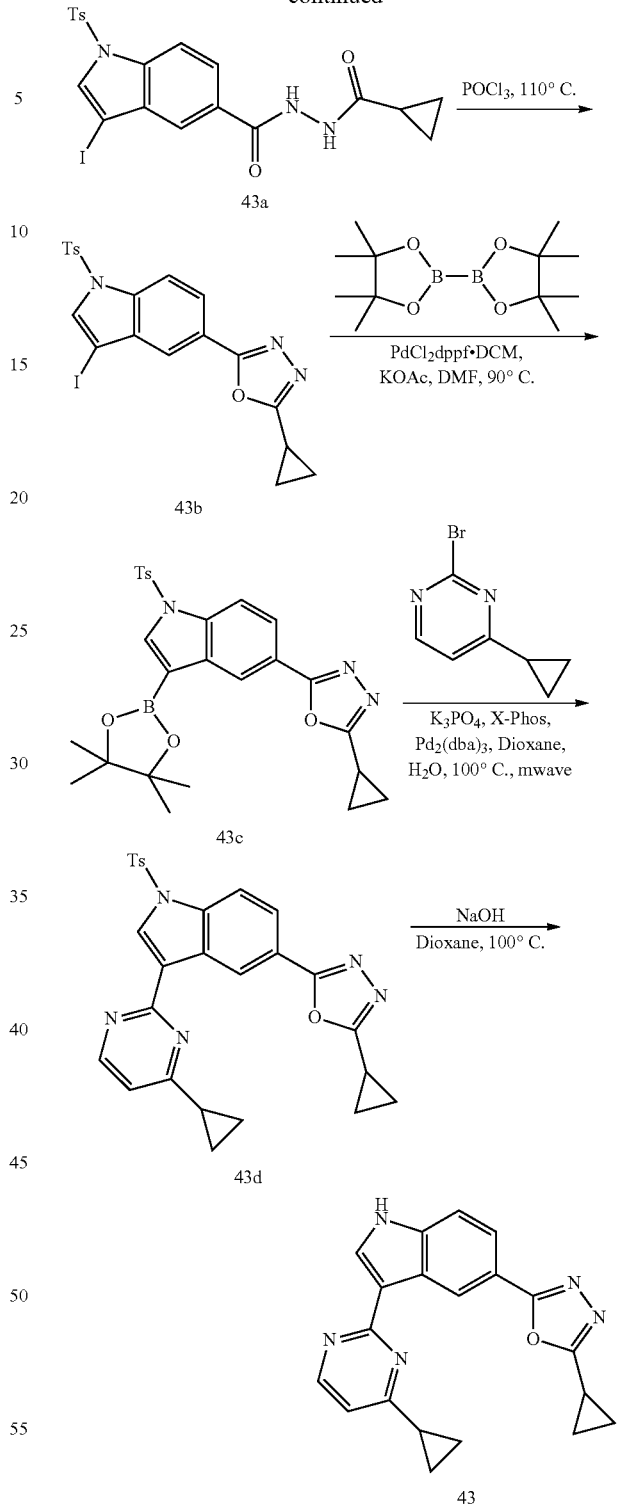

Preparation of compound 43a: N'-(cyclopropanecarbonyl)-3-iodo-1-tosyl-1H-indole-5-carbohydrazide To a stirring suspension of 3-iodo-1-tosyl-1H-indole-5-carboxylic acid (1.944 g, 4.41 mmol) and cyclopropanecarbohydrazide (0.441 g, 4.41 mmol) (Enamine) in THF (40 mL) was added N-ethyl-N-isopropylpropan-2-amine (1.919 mL, 11.01 mmol) (Sigma-Aldrich) followed by HATU (1.843 g, 4.85 mmol) (Oakwood Products) in one portion and the solution was stirred at RT for 45 min. Several ice chunks were added to the mixture followed by H$_2$O (75 mL). The mixture was extracted with EtOAc (2×100 mL). The organic layer was washed with 50 mL of sat. NaHCO$_3$, then brine, dried over MgSO$_4$, filtered, and concentrated to a volume of about 50 mL of EtOAc. A precipitate formed and was isolated by filtration. The filter cake was washed with EtOAc (2×10 mL) to give N'-(cyclopropanecarbonyl)-3-iodo-1-tosyl-1H-indole-5-carbohydrazide (1.13 g, 2.159 mmol, 49.0%) as an off-white solid. MS (ESI, pos. ion) m/z: 523.8 (M+1). $^1$H NMR (400 MHz, DMSO-d$_6$) δ ppm 10.49 (s, 1H), 10.14 (s, 1H), 8.14-8.21 (m, 1H), 8.01-8.09 (m, 1H), 7.89-8.01 (m, 4H), 7.41 (d, J=8.2 Hz, 2H), 2.32 (s, 3H), 1.63-1.74 (m, 1H), 0.63-0.87 (m, 4H).

Preparation of compound 43b: 2-cyclopropyl-5-(3-iodo-1-tosyl-1H-indol-5-yl)-1,3,4-oxadiazole In a 50 mL RBF, N'-(cyclopropanecarbonyl)-3-iodo-1-tosyl-1H-indole-5-carbohydrazide (1.13 g, 2.159 mmol) was treated with POCl$_3$ (5 mL, 53.6 mmol), under argon. The flask was fitted with a reflux condenser. The reaction was stirred and heated at 110° C. for 1.25 h. The crude material was treated with water and extracted with EtOAc. The organic layer was washed with brine, dried, filtered and concentrated to 20 mL of solvent. When about 20 mL of solvent remained, a brown solid precipitated and was collected by filtration. The mother liquor was purified with flash chromatography to give 2-cyclopropyl-5-(3-iodo-1-tosyl-1H-indol-5-yl)-1,3,4-oxadiazole (570 mg, 1.128 mmol, 52.2). MS (ESI, pos. ion) m/z: 506.0 (M+1). $^1$H NMR (400 MHz, DMSO-d$_6$) δ ppm 8.23 (s, 1H), 8.15 (d, J=8.6 Hz, 1H), 7.94-8.03 (m, 3H), 7.85 (s, 1H), 7.43 (d, J=8.0 Hz, 2H), 2.28-2.37 (m, 4H), 1.09-1.21 (m, 4H).

Preparation of compound 43c: 2-cyclopropyl-5-(3-(4,4,5,5-tetramethyl-1,3,2-dioxaborolan-2-yl)-1-tosyl-1H-indol-5-yl)-1,3,4-oxadiazole 2-Cyclopropyl-5-(3-iodo-1-tosyl-1H-indol-5-yl)-1,3,4-oxadiazole (340 mg, 0.673 mmol), bis(pinacolato)diboron (513 mg, 2.018 mmol) (Aldrich), potassium acetate (330 mg, 3.36 mmol) (Sigma-Aldrich), and PdCl$_2$(dppf), complex with DCM (82 mg, 0.101 mmol) (Strem) were weighed into a 5 mL glass microwave tube and the tube was purged with argon. The solids were suspended in DMF (2.5 mL), the tube was sealed and the contents were stirred and heated at 90° C. for 1 h using a hotplate and metal heating block. The mixture was treated with H$_2$O and extracted with EtOAc (2×40 mL). The organic layer was washed with brine (2×20 mL), dried over MgSO$_4$, filtered and concentrated to give 2-cyclopropyl-5-(3-(4,4,5,5-tetramethyl-1,3,2-dioxaborolan-2-yl)-1-tosyl-1H-indol-5-yl)-1,3,4-oxadiazole, MS (ESI, pos. ion) m/z: 506.0 (M+1).

Preparation of compound 43d: 2-cyclopropyl-5-(3-(4-cyclopropylpyrimidin-2-yl)-1-tosyl-1H-indol-5-yl)-1,3,4-oxadiazole To a 20 mL glass microwave tube containing 2-cyclopropyl-5-(3-(4,4,5,5-tetramethyl-1,3,2-dioxaborolan-2-yl)-1-tosyl-1H-indol-5-yl)-1,3,4-oxadiazole (340 mg, 0.673 mmol) was added 2-bromo-4-cyclopropylpyrimidine (154 mg, 0.774 mmol) (CombiPhos Catalysts Inc.), potassium phosphate (428 mg, 2.018 mmol) (Sigma-Aldrich), dicyclohexyl(2',4',6'-triisopropylbiphenyl-2-yl)phosphine (19.24 mg, 0.040 mmol) (Strem), and Pd$_2$(dba)$_3$ (18.48 mg, 0.020 mmol) (Strem). The tube was purged with argon, the solids were treated with dioxane (6.0 mL) and water (0.600 mL), the tube was sealed, and the contents were heated in an Initiator microwave reactor (Personal Chemistry, Biotage AB, Inc., Upssala, Sweden) at 100° C. for 20 min. The mixture was treated with water and extracted with EtOAc. The organic layer was washed with brine, dried over MgSO$_4$, filtered and concentrated. The crude material was purified by flash chromatography (20-70% EtOAc in Hex) affording 2-cyclopropyl-5-(3-(4-cyclopropylpyrimidin-2-yl)-1-tosyl-1H-indol-5-yl)-1,3,4-oxadiazole (78.6 mg, 0.158 mmol, 23.48%) as an amorphous, rust-coloured solid. MS (ESI, pos. ion) m/z: 498.1 (M+1).

Preparation of compound 43: 2-cyclopropyl-5-(3-(4-cyclopropylpyrimidin-2-yl)-1H-indol-5-yl)-1,3,4-oxadiazole 2-Cyclopropyl-5-(3-(4-cyclopropylpyrimidin-2-yl)-1-tosyl-1H-indol-5-yl)-1,3,4-oxadiazole (78.6 mg, 0.158 mmol) in a 5 mL glass microwave tube, was suspended in dioxane (1.5 mL). The suspension was treated with NaOH 1.000 n (2 mL, 2.000 mmol) (Fluka Analytical). The tube was sealed and the contents were stirred and heated in an Initiator microwave reactor (Personal Chemistry, Biotage AB, Inc., Upssala, Sweden) at 100° C. for 10 min. The mixture was diluted with H$_2$O (10 mL) and extracted with EtOAc (2×25 mL). The combined organic layers were washed with brine, dried over MgSO$_4$, filtered and concentrated. The crude material was purified by flash chromatography (0-10% MeOH in DCM) to give 2-cyclopropyl-5-(3-(4-cyclopropylpyrimidin-2-yl)-1H-indol-5-yl)-1,3,4-oxadiazole (19.2 mg, 0.056 mmol, 35.4%) as a pale yellow amorphous solid. MS (ESI, pos. ion) m/z: 344.0 (M+1). $^1$H NMR (400 MHz, DMSO-d$_6$) ppm 11.99 (br. s., 1H), 9.10 (s, 1H), 8.56 (d, J=5.3 Hz, 1H), 8.28 (s, 1H), 7.77-7.84 (m, 1H), 7.62 (d, J=8.6 Hz, 1H), 7.20 (d, J=5.1 Hz, 1H), 2.29-2.38 (m, 1H), 2.09-2.20 (m, 1H), 1.12-1.33 (m, 8H).

Example 44

2-Cyclopropyl-5-(3-(6-cyclopropylpyrazin-2-yl)-1H-indol-5-yl)-1,3,4-oxadiazole

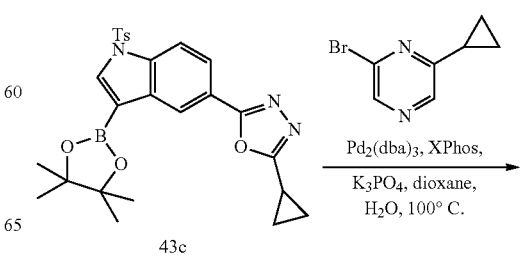

-continued

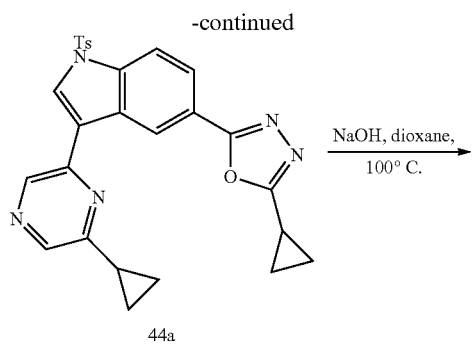

44a

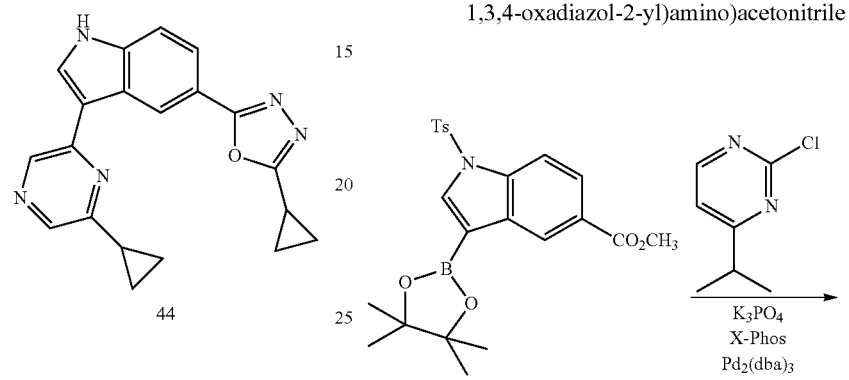

44

Preparation of compound 44a: 2-Cyclopropyl-5-(3-(6-cyclopropylpyrazin-2-yl)-1-tosyl-1H-indol-5-yl)-1,3,4-oxadiazole A brown mixture of 2-cyclopropyl-5-(3-(4,4,5,5-tetramethyl-1,3,2-dioxaborolan-2-yl)-1-tosyl-1H-indol-5-yl)-1,3,4-oxadiazole (298.4 mg, 0.590 mmol), 2-bromo-6-cyclopropylpyrazine (CombiPhos Catalysts, Inc., Princeton, N.J.; 129 mg, 0.649 mmol), Pd$_2$(dba)$_3$ (16.22 mg, 0.018 mmol), dicyclohexyl(2',4',6'-triisopropylbiphenyl-2-yl)phosphine (XPhos; 16.89 mg, 0.035 mmol), and potassium phosphate (376 mg, 1.771 mmol) in a mixture of dioxane (5.0 mL) and water (0.500 mL) was sparged with argon then heated at 100° C. for 2 h. The reaction was then cooled to RT, diluted with DCM (20 mL), and concentrated onto silica gel. Chromatographic purification (silica gel, 0-100% EtOAc/Hex) furnished 2-cyclopropyl-5-(3-(6-cyclopropylpyrazin-2-yl)-1-tosyl-1H-indol-5-yl)-1,3,4-oxadiazole (230 mg, 0.462 mmol, 78%) as a light-yellow solid: MS (ESI, pos. ion) m/z: 498.6 (M+1). $^1$H NMR (400 MHz, CDCl$_3$) δ ppm 8.99 (1H, s), 8.75 (1H, s), 8.43 (1H, s), 8.18 (1H, s), 8.12 (2H, s), 7.84 (2H, d, J=8.4 Hz), 7.28 (2H, s), 2.36 (3H, s), 2.24-2.32 (1H, m), 2.12-2.21 (1H, m), 1.25-1.31 (4H, m), 1.15-1.23 (4H, m).

Preparation of compound 44: 2-Cyclopropyl-5-(3-(6-cyclopropylpyrazin-2-yl)-1H-indol-5-yl)-1,3,4-oxadiazole A yellow solution of 2-cyclopropyl-5-(3-(6-cyclopropylpyrazin-2-yl)-1-tosyl-1H-indol-5-yl)-1,3,4-oxadiazole (206.8 mg, 0.416 mmol) and NaOH (3.0 M, aq; 2.0 mL, 6.00 mmol) in dioxane (5.0 mL) was heated at 100° C. for 40 min. The reaction was cooled to RT and partitioned between DCM (50 mL) and H$_2$O (30 mL). The organic layer was separated, and the aqueous layer was extracted with DCM (30 mL). The combined organic extracts were dried over sodium sulfate, filtered, and concentrated in vacuo. Chromatographic purification of the residue (silica gel, 0-100% (10% MeOH-EtOAc)/Hex) furnished 2-cyclopropyl-5-(3-(6-cyclopropy-lpyrazin-2-yl)-1H-indol-5-yl)-1,3,4-oxadiazole (71.0 mg, 0.207 mmol, 50%) as a yellow solid: MS (ESI, pos. ion) m/z: 344.2 (M+1). $^1$H NMR (400 MHz, DMSO-d$_6$) δ ppm 12.03 (1H, br. s.), 9.06 (1H, d, J=1.4 Hz), 8.93 (1H, s), 8.41 (1H, s), 8.38 (1H, s), 7.82 (1H, dd, J=8.5, 1.7 Hz), 7.61 (1H, d, J=8.6 Hz), 2.29-2.38 (1H, m), 2.20-2.29 (1H, m), 1.13-1.25 (8H, m).

Example 45

2-((5-(3-(4-isopropylpyrimidin-2-yl)-1H-indol-5-yl)-1,3,4-oxadiazol-2-yl)amino)acetonitrile

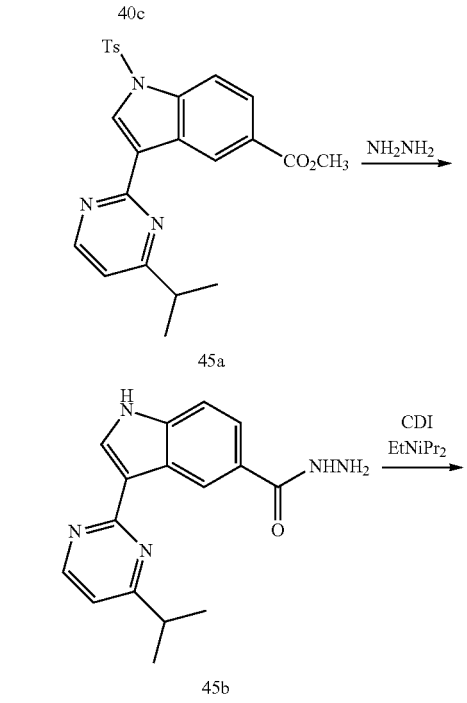

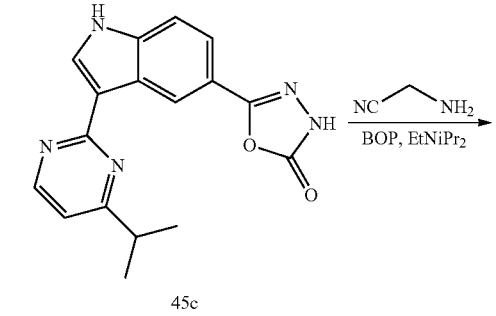

45c

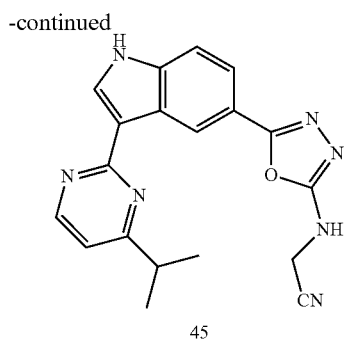

45

Preparation of compound 45a: Methyl 3-(4-isopropylpyrimidin-2-yl)-1-tosyl-1H-indole-5-carboxylate A brown mixture of methyl 3-(4,4,5,5-tetramethyl-1,3,2-dioxaborolan-2-yl)-1-tosyl-1H-indole-5-carboxylate (1.85 g, 4.06 mmol), 2-chloro-4-isopropylpyrimidine (0.700 g, 4.47 mmol) [CombiPhos Catalyst Inc.], potassium phosphate (2.59 g, 12.19 mmol), $Pd_2(dba)_3$ (0.15 g, 0.16 mmol), and dicyclohexyl(2',4',6'-triisopropylbiphenyl-2-yl)phosphine (X-Phos) (0.15 g, 0.32 mmol) in dioxane (15 mL) and $H_2O$ (3.00 mL) was purged with argon then heated in an oil bath at 100° C. for 3 h. The reaction was cooled to RT, diluted with EtOAc (100 mL), washed with NaOH (5 mL of 0.5 N) followed by brine (5 mL). The organic solution was dried and concentrated. Chromatographic purification of the brown residue (20-80% EtOAc/Hex) furnished methyl 3-(4-isopropylpyrimidin-2-yl)-1-tosyl-1H-indole-5-carboxylate (1.37 g, 75%) as a light-yellow solid. This material was used in next step without further purification. MS (ESI, pos. ion) m/z: 450.0 (M+1).

Preparation of compound 45b: 3-(4-Isopropylpyrimidin-2-yl)-1H-indole-5-carbohydrazide A light-yellow mixture of methyl 3-(4-isopropylpyrimidin-2-yl)-1-tosyl-1H-indole-5-carboxylate (1.37 g, 3.05 mmol) in anhydrous hydrazine (2.39 mL, 76 mmol) and dioxane (1 mL) was heated in an oil bath at 90° C. for 3 h. The mixture was cooled to RT, treated with 20 mL of ice cold $H_2O$. The precipitated pink solid was filtered, rinsed with 2×5 mL of water and 2×20 mL of EtOAc. The filtrate was transferred to a separatory funnel. The aqueous layer was discarded. The EtOAc layer was concentrated to half of its volume. The precipitated brown solid was filtered, rinsed with 2×2 mL of $Et_2O$. The above obtained pink solid and brown solid were combined and dried in a vacuum oven at 40° C. for 18 h to afford 3-(4-isopropylpyrimidin-2-yl)-1H-indole-5-carbohydrazide (400 mg). This material was used in next step without further purification. MS (ESI, pos. ion) m/z: 296.1 (M+1).

Preparation of compound 45c: 5-(3-(4-Isopropylpyrimidin-2-yl)-1H-indol-5-yl)-1,3,4-oxadiazol-2(3H)-one To a solution of 3-(4-isopropylpyrimidin-2-yl)-1H-indole-5-carbohydrazide (400 mg in about 60% pure) in DMF (3 mL) at RT was added N-ethyl-N-isopropylpropan-2-amine (0.47 mL, 2.71 mmol) followed by CDI (242 mg, 1.49 mmol). The mixture was stirred at RT for 5 min then heated in an oil bath at 65° C. for 1 h. It was cooled to RT, treated with 5 mL of $H_2O$ and extracted with 3×20 mL of EtOAc. The combine organic solution was washed with 3 mL of brine, dried and concentrated to afford 5-(3-(4-isopropylpyrimidin-2-yl)-1H-indol-5-yl)-1,3,4-oxadiazol-2(3H)-one (350 mg). This material was used in next step without further purification. MS (ESI, pos. ion) m/z: 322.0 (M+1).

Preparation of compound 45: 2-(5-(3-(4-Cyclopropylpyrimidin-2-yl)-1H-indol-5-yl)-1,3,4-oxadiazol-2-ylamino)acetonitrile To a solution of 5-(3-(4-isopropylpyrimidin-2-yl)-1H-indol-5-yl)-1,3,4-oxadiazol-2(3H)-one (350 mg, in about 60% pure) in DMF (4 mL) at RT was sequentially added 2-aminoacetonitrile hydrochloride (302 mg, 3.27 mmol) (Alfa Aesar), diisopropylethylamine (0.79 mL, 4.57 mmol) and BOP (530 mg, 1.20 mmol) (Aldrich). After the reaction was stirred at RT for 18 h, it was diluted with $H_2O$ (10 mL) and extracted with EtOAc (3×25 mL). The aqueous layer was discarded. The combined organic layers were washed with brine, dried over $MgSO_4$, filtered and concentrated. The crude material was purified on a silica gel column eluting with 25-100% EtOAc in Hex to give 2-(5-(3-(4-isopropylpyrimidin-2-yl)-1H-indol-5-yl)-1,3,4-oxadiazol-2-ylamino)-acetonitrile (45 mg) as a brown amorphous solid. MS (ESI, pos. ion) m/z: 360.0 (M+1). $^1$H-NMR (400 MHz, DMSO-$d_6$) δ ppm 11.99 (1H, br.), 9.16 (1H, s), 8.69 (1H, d, J=5.1 Hz), 8.49 (1H, t, J=5.7 Hz), 8.33 (1H, m), 7.73 (1H, d, J=8.2 Hz), 7.62 (1H, d, J=8.6 Hz), 7.16 (1H, d, J=5.1 Hz), 4.43 (2H, d, J=5.7 Hz), 3.06 (1H, dt, J=13.7, 6.8 Hz), 1.37 (6H, d, J=6.8 Hz).

Example 46

5-(3-(6-cyclopropylpyrazin-2-yl)-1H-indol-5-yl)-N-isopropyl-1,3,4-oxadiazol-2-amine

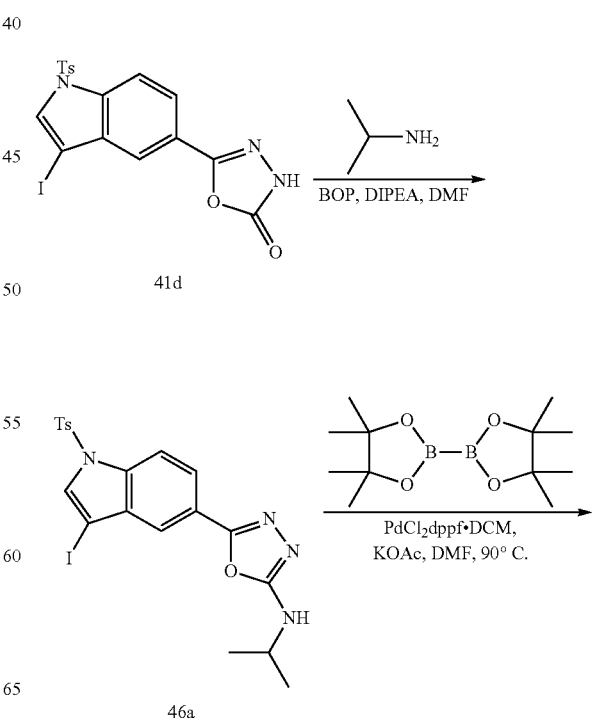

-continued

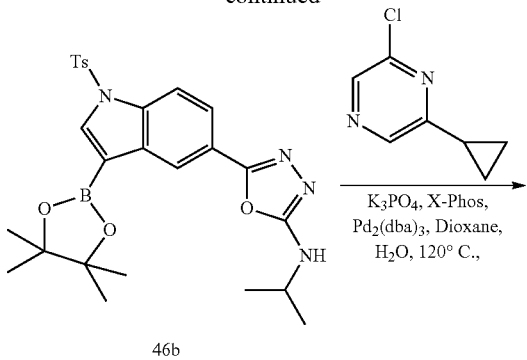

46b

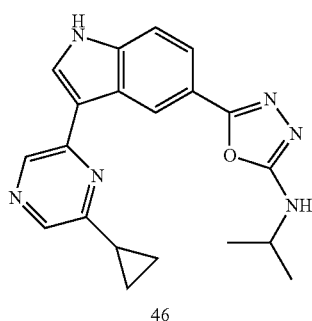

46c

46

Preparation of compound 46a: 5-(3-iodo-1-tosyl-1H-indol-5-yl)-N-isopropyl-1,3,4-oxadiazol-2-amine BOP (253 mg, 0.571 mmol) was added to a stirred mixture of 5-(3-iodo-1-tosyl-1H-indol-5-yl)-1,3,4-oxadiazol-2(3H)-one (250 mg, 0.519 mmol), propan-2-amine (0.13 mL, 1.56 mmol) and diisopropylethylamine (0.18 mL, 1.04 mmol) in DMF (1.5 mL). The reaction was stirred at RT for 14 h then diluted with water and extracted with EtOAc. The organic layer was washed with brine, dried over $MgSO_4$ and concentrated. Purification on the ISCO (12 g column, 20-70% EtOAc in Hex) afforded 5-(3-iodo-1-tosyl-1H-indol-5-yl)-N-isopropyl-1,3,4-oxadiazol-2-amine (199 mg, 73%) as a white amorphous solid. MS (ESI, pos. ion) m/z: 523.0 (M+1). $^1$H NMR (400 MHz, $CDCl_3$) δ ppm 8.02 (1H, d, J=8.6 Hz), 7.95 (1H, d, J=8.4 Hz), 7.86 (1H, s), 7.76-7.82 (2H, m), 7.71-7.76 (1H, m), 7.28 (2H, s), 4.54 (1H, d, J=7.6 Hz), 3.94-4.05 (1H, m), 2.37 (3H, s), 1.34 (6H, d, J=6.5 Hz).

Preparation of compound 46b: N-isopropyl-5-(3-(4,4,5,5-tetramethyl-1,3,2-dioxaborolan-2-yl)-1-tosyl-1H-indol-5-yl)-1,3,4-oxadiazol-2-amine In a 20 mL microwave tube, a mixture of 5-(3-iodo-1-tosyl-1H-indol-5-yl)-N-isopropyl-1,3,4-oxadiazol-2-amine (198 mg, 0.379 mmol), bis(pinacolato)diboron (289 mg, 1.137 mmol), potassium acetate (186 mg, 1.895 mmol), $PdCl_2$(dppf), complex with DCM (46.4 mg, 0.057 mmol) and DMF (4.0 mL) was stirred at 90° C. in an oil bath for 1 h. The reaction was cooled to RT, treated with EtOAc (20 mL) and rinsed with $H_2O$ (2×15 mL) and dried over $MgSO_4$, filtered and concentrated. The crude material was used in the next step without further purification.

Preparation of compound 46c: 5-(3-(6-cyclopropylpyrazin-2-yl)-1-tosyl-1H-indol-5-yl)-N-isopropyl-1,3,4-oxadiazol-2-amine To a 20 mL microwave vial was added N-isopropyl-5-(3-(4,4,5,5-tetramethyl-1,3,2-dioxaborolan-2-yl)-1-tosyl-1H-indol-5-yl)-1,3,4-oxadiazol-2-amine (167 mg, 0.379 mmol), 2-chloro-6-cyclopropylpyrazine (CombiPhos Catalyst Inc., 64.5 mg, 0.42 mmoles), dicyclohexyl(2',4',6'-triisopropylbiphenyl-2-yl)phosphine (10.9 mg, 0.023 mmol), $Pd_2(dba)_3$ (10.4 mg, 0.011 mmol), and $K_3PO_4$ (242 mg, 1.138 mmol) followed by purging with argon. The solids were treated with dioxane (4.0 mL) and $H_2O$ (0.4 mL) and heated in the microwave at 120° C. for 20 min. The mixture was treated with $H_2O$ and extracted with EtOAc, dried over $MgSO_4$, filtered and concentrated. Purification with flash chromatography (eluting with 5-100% EtOAc in Hex) afforded 5-(3-(6-cyclopropylpyrazin-2-yl)-1-tosyl-1H-indol-5-yl)-N-isopropyl-1,3,4-oxadiazol-2-amine (104.4 mg, 54%) as a pale yellow solid. MS (ESI, pos. ion) m/z: 515.2 (M+1). $^1$H NMR (400 MHz, $CDCl_3$) δ ppm 8.87 (1H, s), 8.74 (1H, s), 8.42 (1H, s), 8.16 (1H, s), 8.07-8.11 (1H, m), 7.98-8.03 (1H, m), 7.84 (2H, d, J=8.4 Hz), 7.28 (2H, s), 3.97-4.08 (1H, m), 2.36 (3H, s), 2.14 (1H, td, J=8.5, 4.2 Hz), 1.35 (6H, d, J=6.5 Hz), 1.24-1.30 (2H, m), 1.10-1.17 (2H, m).

Preparation of compound 46: 5-(3-(6-cyclopropylpyrazin-2-yl)-1H-indol-5-yl)-N-isopropyl-1,3,4-oxadiazol-2-amine 2,2,2-trifluoroacetate In a 20 mL glass microwave tube 5-(3-(6-cyclopropylpyrazin-2-yl)-1-tosyl-1H-indol-5-yl)-N-isopropyl-1,3,4-oxadiazol-2-amine (100 mg, 0.194 mmol) was treated with dioxane (1.5 mL) and 1N NaOH (0.5 mL) and heated in the microwave at 110° C. for 10 min. The mixture was diluted with $H_2O$ and extracted with EtOAc (2×25 mL) and concentrated under reduced pressure. The material was purified with reverse phase HPLC (5-100% gradient 0.1% TFA/AcCN in 0.1% TFA/$H_2O$) to give 5-(3-(6-cyclopropylpyrazin-2-yl)-1H-indol-5-yl)-N-isopropyl-1,3,4-oxadiazol-2-amine 2,2,2-trifluoroacetate (43.7 mg, 47%) as a bright yellow solid. MS (ESI, pos. ion) m/z: 361.1 (M+1). $^1$H NMR (400 MHz, MeOH-$d_4$) δ ppm 10.1 (1H, s), 7.60-7.66 (1H, m), 7.36 (1H, s), 6.85 (1H, s), 6.75 (1H, s), 6.38 (1H, dd, J=8.6, 1.6 Hz), 6.18

(1H, d, J=8.6 Hz), 2.60 (1H, dt, J=13.1, 6.5 Hz), 0.77-0.88 (1H, m), −0.01 (6H, d, J=6.5 Hz), −0.13--0.07 (2H, m), −0.30--0.21 (2H, m).

Example 47

6-cyclopropyl-2-(5-(5-(isopropylamino)-1,3,4-oxadiazol-2-yl)-1H-indol-3-yl)pyrimidine-4-carboxylic acid

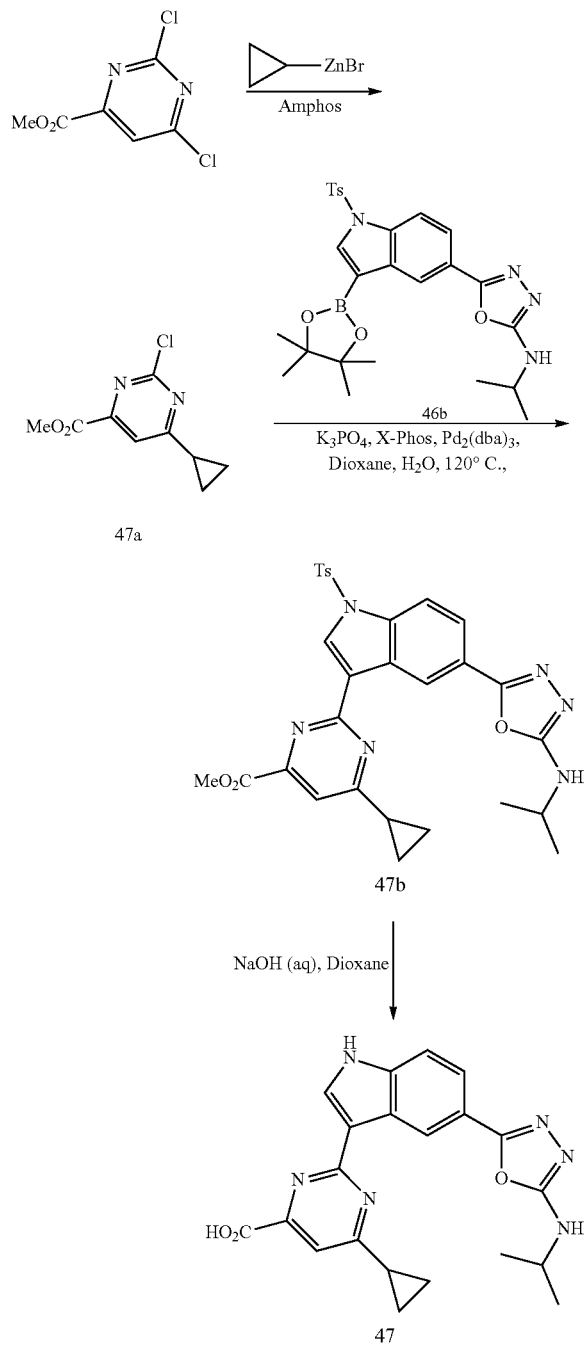

Preparation of compound 47a: methyl 2-chloro-6-cyclopropylpyrimidine-4-carboxylate In a 5 mL glass microwave tube methyl 2,4-dichloropyrimidine-6-carboxylate (621 mg, 3.00 mmol) (Astatech Inc.) and Amphos (53.1 mg, 0.075 mmol) were treated with cyclopropylzinc(II) bromide (Rieke, 0.5 M in THF) (1.2 mL, 6.00 mmol) via syringe under an atmosphere of argon. The solution was then heated in the microwave at 80° C. for 20 min. The mixture was treated with EtOAc and 1N NaOH resulting in a white suspension as the zinc hydroxide salts precipitated out. The suspension was extracted with EtOAc (50 mL) a second time and washed with brine and dried over $Na_2SO_4$, filtered and concentrated. The residue was purified with silica gel chromatography (eluting with 100% DCM) to give methyl 2-chloro-6-cyclopropylpyrimidine-4-carboxylate (254 mg, 40%) as a clear, colorless, viscous oil. MS (ESI, pos. ion) m/z: 213.1 (M+1). $^1$H NMR (400 MHz, $CDCl_3$) δ ppm 7.77 (1H, s), 3.99-4.04 (3H, m), 2.06-2.15 (1H, m), 1.20-1.31 (4H, m).

Preparation of compound 47b: methyl 6-cyclopropyl-2-(5-(5-(isopropylamino)-1,3,4-oxadiazol-2-yl)-1-tosyl-1H-indol-3-yl)pyrimidine-4-carboxylate To a 5 mL glass microwave tube containing N-isopropyl-5-(3-(4,4,5,5-tetramethyl-1,3,2-dioxaborolan-2-yl)-1-tosyl-1H-indol-5-yl)-1,3,4-oxadiazol-2-amine (120 mg, 0.230 mmol) was added methyl 2-chloro-6-cyclopropylpyrimidine-4-carboxylate (58.6 mg, 0.276 mmol), potassium phosphate (146 mg, 0.689 mmol), dicyclohexyl(2',4',6'-triisopropylbiphenyl-2-yl)phosphine (6.6 mg, 0.014 mmol), and $Pd_2(dba)_3$ (6.3 mg, 6.89 μmol). The tube was purged with argon, the solids were treated with dioxane (5 mL) and water (0.5 mL), the tube was sealed, and the contents were heated in an Initiator microwave reactor (Personal Chemistry, Biotage AB, Inc., Upssala, Sweden) at 130° C. for 25 min. The mixture was treated with $H_2O$ and extracted with EtOAc. The organic layer was washed with brine, dried over $MgSO_4$, filtered and concentrated. The crude material was purified by flash chromatography (eluting with 20-100% EtOAc in Hex) affording methyl 6-cyclopropyl-2-(5-(5-(isopropylamino)-1,3,4-oxadiazol-2-yl)-1-tosyl-1H-indol-3-yl)pyrimidine-4-carboxylate (16.4 mg, 13%) as a light yellow amorphous solid. MS (ESI, pos. ion) m/z: 397.1 (M+1).

Preparation of compound 47: 6-cyclopropyl-2-(5-(5-(isopropylamino)-1,3,4-oxadiazol-2-yl)-1H-indol-3-yl)pyrimidine-4-carboxylic acid In a 5 mL microwave tube methyl 6-cyclopropyl-2-(5-(5-(isopropylamino)-1,3,4-oxadiazol-2-yl)-1-tosyl-1H-indol-3-yl)pyrimidine-4-carboxylate (16 mg, 0.028 mmol) was treated with dioxane (1 mL) and 1N NaOH (0.5 mL) and heated in the microwave at 100° C. for 10 min. The mixture was concentrated and purified with reverse phase HPLC (20-95% 0.1% TFA/AcCN in 0.1% TFA/$H_2O$) affording 6-cyclopropyl-2-(5-(5-(isopropylamino)-1,3,4-oxadiazol-2-yl)-1H-indol-3-yl)pyrimidine-4-carboxylic acid (7.6 mg, 67%) as a yellow amorphous solid. MS (ESI, pos. ion) m/z: 405.2 (M+1). $^1$H NMR (400 MHz, DMSO-$d_6$) δ ppm 12.03 (1H, d, J=2.3 Hz), 9.04 (1H, s), 8.40 (1H, d, J=2.7 Hz), 7.65-7.72 (2H, m), 7.59-7.64 (1H, m), 7.57 (1H, d, J=7.8 Hz), 3.83 (1H, dd, J=13.8, 6.6 Hz), 2.34 (1H, dt, J=7.9, 3.9 Hz), 1.29-1.36 (2H, m), 1.27 (6H, d, J=6.5 Hz), 1.23 (3H, dt, J=7.9, 3.2 Hz).

Example 48

6-cyclopropyl-2-(5-(5-(isopropylamino)-1,3,4-oxadiazol-2-yl)-1H-indol-3-yl)pyrimidine-4-carboxamide

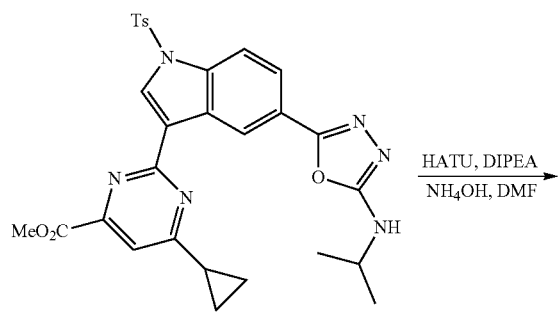

47b

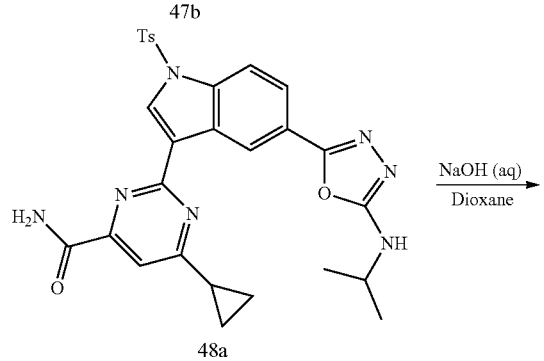

48a

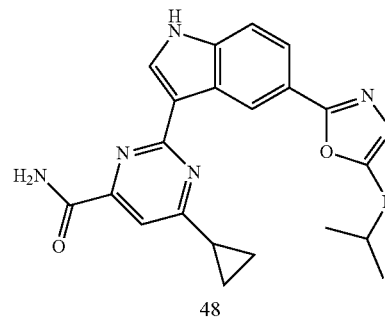

48

Preparation of compound 48a: 6-cyclopropyl-2-(5-(5-(isopropylamino)-1,3,4-oxadiazol-2-yl)-1-tosyl-1H-indol-3-yl)pyrimidine-4-carboxamide 6-Cyclopropyl-2-(5-(5-(isopropylamino)-1,3,4-oxadiazol-2-yl)-1-tosyl-1H-indol-3-yl)pyrimidine-4-carboxylic acid (50 mg) was treated with HATU (51.1 mg, 0.134 mmol) followed by DMF (3 mL) and Hunig's base (0.1 mL). The reaction was stirred for 30 min at RT then treated with NH$_4$OH (0.1 mL) and stirred for 30 min. The reaction was quenched with H$_2$O and extracted with EtOAc (50 mL) and washed with brine (3×20 mL), dried over MgSO$_4$, filtered and concentrated. The crude residue was used in the next step without further purification.

Preparation of compound 48: 6-cyclopropyl-2-(5-(5-(isopropylamino)-1,3,4-oxadiazol-2-yl)-1H-indol-3-yl)pyrimidine-4-carboxamide 2,2,2-trifluoroacetate In a 5 mL glass microwave tube 6-cyclopropyl-2-(5-(5-(isopropylamino)-1,3,4-oxadiazol-2-yl)-1-tosyl-1H-indol-3-yl)pyrimidine-4-carboxamide (50 mg, 0.090 mmol) was treated with dioxane (1 mL) and 1N NaOH (0.5 mL) and heated to 70° C. for 10 min. The mixture was treated with water and extracted with EtOAc (20 mL) and washed with brine and concentrated. Purification of the crude residue (20-95% 0.1% TFA/AcCN in 0.1% TFA/H$_2$O) afforded 6-cyclopropyl-2-(5-(5-(isopropylamino)-1,3,4-oxadiazol-2-yl)-1H-indol-3-yl)pyrimidine-4-carboxamide 2,2,2-trifluoroacetate (6.0 mg, 13%) as a yellow amorphous solid. MS (ESI, pos. ion) m/z: 404.0 (M+1). $^1$H NMR (400 MHz, DMSO-d$_6$) δ ppm 12.14-12.21 (1H, m), 9.04 (1H, s), 8.81 (1H, d, J=2.7 Hz), 8.58 (1H, br. s.), 7.98 (1H, br. s.), 7.84 (1H, d, J=7.6 Hz), 7.72-7.77 (2H, m), 7.64-7.69 (1H, m), 3.88-3.95 (1H, m), 2.35-2.44 (1H, m), 1.36-1.42 (2H, m), 1.33 (6H, d, J=6.5 Hz), 1.23-1.31 (2H, m).

Example 49

N-cyclopropyl-5-(3-(6-cyclopropylpyrazin-2-yl)-1H-indol-5-yl)-1,3,4-oxadiazol-2-amine

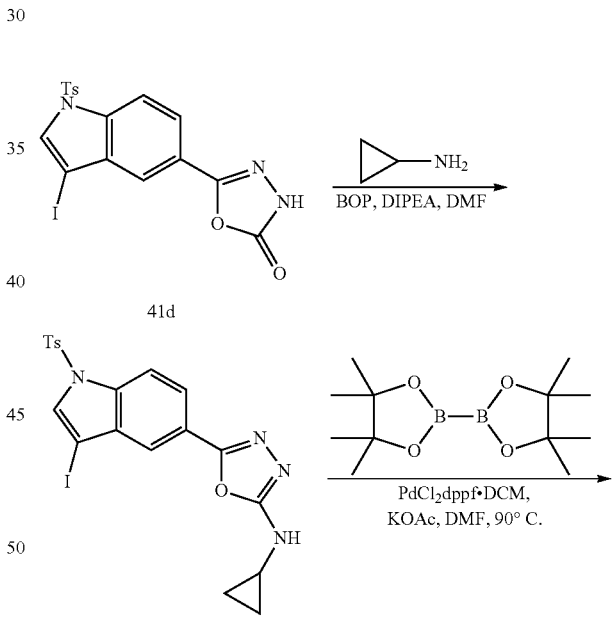

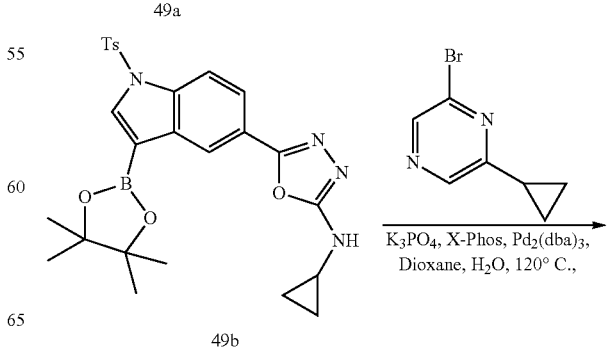

49b

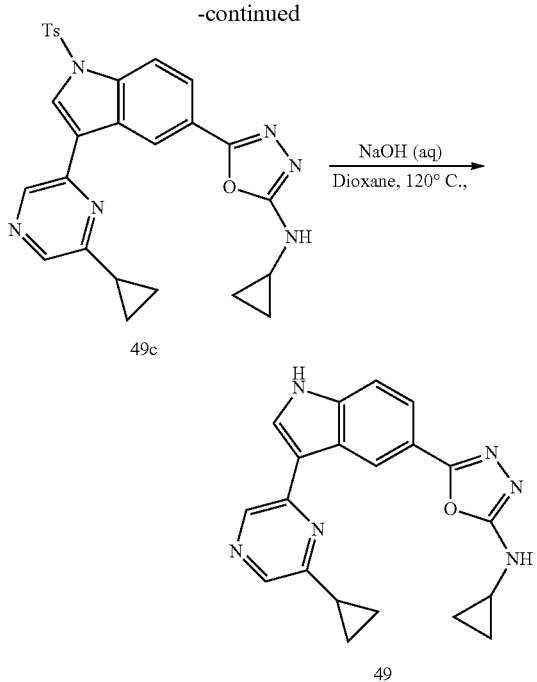

Preparation of compound 49a: N-cyclopropyl-5-(3-iodo-1-tosyl-1H-indol-5-yl)-1,3,4-oxadiazol-2-amine BOP (253 mg, 0.571 mmol) was added to a stirred mixture of 5-(3-iodo-1-tosyl-1H-indol-5-yl)-1,3,4-oxadiazol-2(3H)-one (250 mg, 0.519 mmol), cyclopropanamine (0.11 mL, 1.56 mmol) and diisopropylethylamine (0.18 mL, 1.04 mmol) in DMF (1.5 mL). The reaction was stirred at RT for 14 h. The mixture was diluted with H$_2$O and extracted with EtOAc, dried over MgSO$_4$ and concentrated resulting in a white amorphous solid. It was washed with a 1:1 mixture of EtOAc and Hex to give N-cyclopropyl-5-(3-iodo-1-tosyl-1H-indol-5-yl)-1,3,4-oxadiazol-2-amine (237 mg, 88%) MS (ESI, pos. ion) m/z: 521.1 (M+1). $^1$H NMR (400 MHz, CDCl$_3$) δ ppm 8.03 (1H, d, J=8.8 Hz), 7.96 (1H, d, J=8.8 Hz), 7.84-7.91 (1H, m), 7.76-7.83 (2H, m), 7.74 (1H, s), 7.28 (2H, d, J=8.8 Hz), 5.14 (1H, s), 2.80-2.87 (1H, m), 2.37 (3H, s), 0.84-0.92 (2H, m), 0.68-0.76 (2H, m).

Preparation of compound 49b: N-cyclopropyl-5-(3-(4,4,5,5-tetramethyl-1,3,2-dioxaborolan-2-yl)-1-tosyl-1H-indol-5-yl)-1,3,4-oxadiazol-2-amine In a 20 mL microwave tube, a mixture of N-cyclopropyl-5-(3-iodo-1-tosyl-1H-indol-5-yl)-1,3,4-oxadiazol-2-amine (237 mg, 0.455 mmol), bis(pinacolato)diboron (347 mg, 1.366 mmol), potassium acetate (224 mg, 2.277 mmol), PdCl$_2$(dppf) complex with DCM (55.8 mg, 0.068 mmol) and DMF (4.0 mL) was stirred at 90° C. in the oil bath for 1 h. The mixture was cooled to RT, treated with EtOAc (20 mL) and rinsed with water (2×15 mL) and dried over MgSO$_4$, filtered and concentrated. The crude material was used in the next step without further purification.

Preparation of compound 49c: N-cyclopropyl-5-(3-(6-cyclopropylpyrazin-2-yl)-1-tosyl-1H-indol-5-yl)-1,3,4-oxadiazol-2-amine To a 20 mL microwave vial was added N-cyclopropyl-5-(3-(4,4,5,5-tetramethyl-1,3,2-dioxaborolan-2-yl)-1-tosyl-1H-indol-5-yl)-1,3,4-oxadiazol-2-amine (200 mg, 0.456 mmol), 2-chloro-6-cyclopropylpyrazine (CombiPhos Catalysts Inc., 78 mg, 0.502 mmol), dicyclohexyl(2',4',6'-triisopropylbiphenyl-2-yl)phosphine (13.05 mg, 0.027 mmol), Pd$_2$(dba)$_3$ (12.5 mg, 0.014 mmol), and potassium phosphate (291 mg, 1.369 mmol) followed by purging with argon. The solids were treated with dioxane (4.0 mL) and water (0.4 mL) and heated in the microwave at 130° C. for 20 min. The mixture was treated with H$_2$O and extracted with EtOAc, dried over MgSO$_4$, filtered and concentrated. Purification (0-100% EtOAc in Hex) afforded N-cyclopropyl-5-(3-(6-cyclopropylpyrazin-2-yl)-1-tosyl-1H-indol-5-yl)-1,3,4-oxadiazol-2-amine (45.6 mg, 19%) as a pale yellow solid. MS (ESI, pos. ion) m/z: 513.1 (M+1).

Preparation of compound 49: N-cyclopropyl-5-(3-(6-cyclopropylpyrazin-2-yl)-1H-indol-5-yl)-1,3,4-oxadiazol-2-amine 2,2,2-trifluoroacetate In a 20 mL glass microwave tube N-cyclopropyl-5-(3-(6-cyclopropylpyrazin-2-yl)-1-tosyl-1H-indol-5-yl)-1,3,4-oxadiazol-2-amine (100 mg, 0.195 mmol) was treated with dioxane (1.5 mL) and 1N NaOH (0.5 mL) and heated in the microwave at 110° C. for 10 min. The crude material was then purified with reverse phase HPLC (5-100% gradient 0.1% TFA/MeCN in 0.1% TFA/water) affording N-cyclopropyl-5-(3-(6-cyclopropylpyrazin-2-yl)-1H-indol-5-yl)-1,3,4-oxadiazol-2-amine 2,2,2-trifluoroacetate (3.8 mg, 4%) as a bright yellow solid. MS (ESI, pos. ion) m/z: 359.1 (M+1). $^1$H NMR (400 MHz, MeOH-d$_4$) δ ppm 10.33 (1H, s), 7.76 (1H, s), 7.47 (1H, br. s.), 6.97 (1H, br. s.), 6.88 (1H, s), 6.48 (1H, dd, J=8.6, 1.6 Hz), 6.28-6.33 (1H, m), 1.57 (1H, tt, J=6.8, 3.4 Hz), 0.89-0.98 (1H, m), −0.03-0.03 (2H, m), −0.18--0.10 (2H, m), −0.37--0.31 (2H, m), −0.52--0.45 (2H, m).

Example 50

5-(3-(6-cyclopropylpyrazin-2-yl)-1H-indol-5-yl)-N-(2-phenylpropan-2-yl)-1,3,4-oxadiazol-2-amine

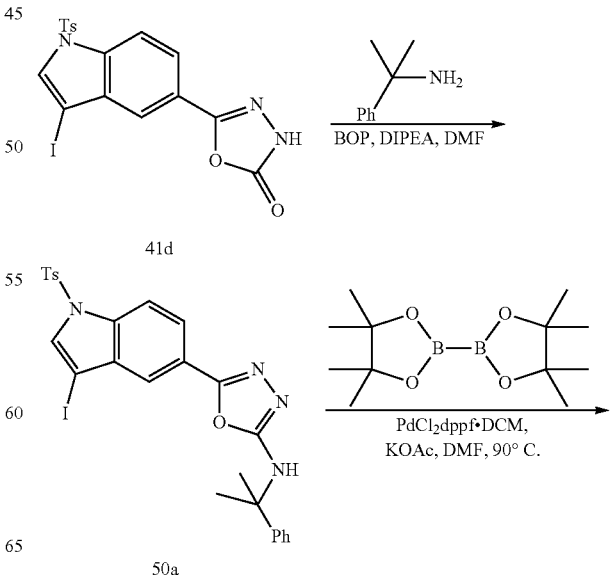

-continued

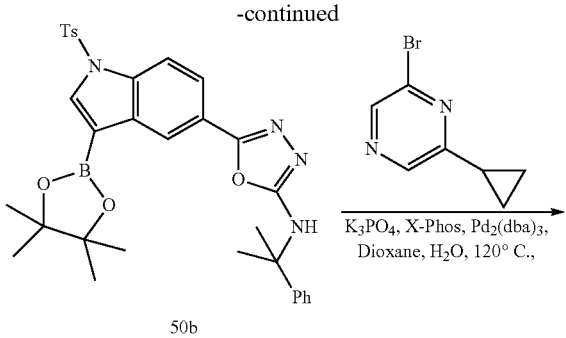

50b

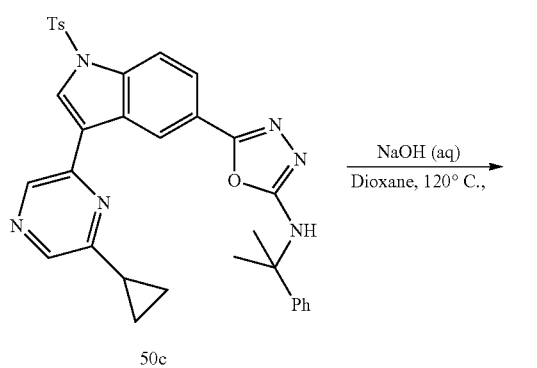

50c

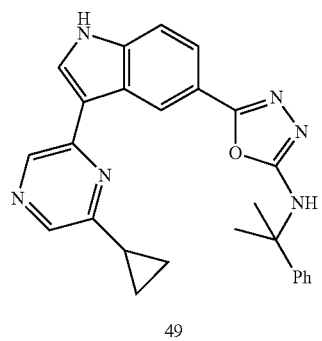

49

Preparation of compound 50a: 5-(3-iodo-1-tosyl-1H-indol-5-yl)-N-(2-phenylpropan-2-yl)-1,3,4-oxadiazol-2-amine BOP (455 mg, 1.029 mmol) was added to a stirred mixture of 5-(3-iodo-1-tosyl-1H-indol-5-yl)-1,3,4-oxadiazol-2(3H)-one (450 mg, 0.935 mmol), 2-phenylpropan-2-amine (0.442 mL, 3.27 mmol) and diisopropylethylamine (0.33 mL, 1.87 mmol) in DMF (5.0 mL). The mixture was stirred at RT for 14 h. It was treated with BOP (300 mg) and 2-phenylpropan-2-amine (0.3 mL) and heated to 65° C. for 3 h. The mixture was diluted with water and extracted with EtOAc (50 mL). The organic layer was washed with brine, dried over MgSO₄, and concentrated. Purification (eluting with 20-70% EtOAc in Hex) afforded 5-(3-iodo-1-tosyl-1H-indol-5-yl)-N-(2-phenylpropan-2-yl)-1,3,4-oxadiazol-2-amine (103.6 mg, 19%) as a white amorphous solid. MS (ESI, pos. ion) m/z: 601.0 (M+1).

Preparation of compound 50b: N-(2-phenylpropan-2-yl)-5-(3-(4,4,5,5-tetramethyl-1,3,2-dioxaborolan-2-yl)-1-tosyl-1H-indol-5-yl)-1,3,4-oxadiazol-2-amine In a 20 mL microwave tube, a mixture of 5-(3-iodo-1-tosyl-1H-indol-5-yl)-N-(2-phenylpropan-2-yl)-1,3,4-oxadiazol-2-amine (100 mg, 0.167 mmol), bis(pinacolato)diboron (127 mg, 0.501 mmol), potassium acetate (82 mg, 0.835 mmol), PdCl₂(dppf), complex with DCM (20.5 mg, 0.025 mmol) and DMF (2.0 mL) was stirred at 90° C. in the oil bath for 1 h. The reaction was purged with argon and treated with another 15 mg of catalyst and stirred for another 30 min at 90° C. The mixture was cooled to RT, treated with EtOAc (20 mL) and rinsed with water (2×15 mL) and dried over MgSO₄, filtered and concentrated. The crude residue was used in the next step without further purification.

Preparation of compound 50c: 5-(3-(6-cyclopropylpyrazin-2-yl)-1-tosyl-1H-indol-5-yl)-N-(2-phenylpropan-2-yl)-1,3,4-oxadiazol-2-amine To a 20 mL microwave vial was added N-(2-phenylpropan-2-yl)-5-(3-(4,4,5,5-tetramethyl-1,3,2-dioxaborolan-2-yl)-1-tosyl-1H-indol-5-yl)-1,3,4-oxadiazol-2-amine (86 mg, 0.167 mmol), dicyclohexyl(2',4',6'-triisopropylbiphenyl-2-yl)phosphine (4.8 mg, 9.99 µmol), Pd₂(dba)₃ (4.6 mg, 5.00 µmol), 2-bromo-6-cyclopropylpyrazine (CombiPhos Catalyst Inc., 36.5 mg, 0.183 mmol) and potassium phosphate (106 mg, 0.500 mmol) followed by purging with argon. The solids were treated with dioxane (3.0 mL) and water (0.3 mL) and heated in the microwave at 120° C. for 20 min. The mixture was treated with water and extracted with EtOAc, dried over MgSO₄, filtered and concentrated. Purification (10-100% EtOAc in Hex) afforded 5-(3-(6-cyclopropylpyrazin-2-yl)-1-tosyl-1H-indol-5-yl)-N-(2-phenylpropan-2-yl)-1,3,4-oxadiazol-2-amine (28.1 mg, 29%) as a pale yellow solid. MS (ESI, pos. ion) m/z: 591.2 (M+1). ¹H NMR (400 MHz, CDCl₃) δ ppm 8.64-8.71 (2H, m), 8.39 (1H, s), 8.13 (1H, s), 8.03 (1H, d, J=8.8 Hz), 7.81 (2H, d, J=8.4 Hz), 7.78 (1H, dd, J=8.7, 1.5 Hz), 7.54 (2H, d, J=7.6 Hz), 7.35 (2H, t, J=7.7 Hz), 7.22-7.29 (3H, m), 6.01 (1H, s), 2.35 (3H, s), 2.09-2.16 (1H, m), 1.86 (6H, s), 1.20-1.24 (2H, m), 1.08-1.14 (2H, m).

Preparation of compound 50: 5-(3-(6-cyclopropylpyrazin-2-yl)-1H-indol-5-yl)-N-(2-phenylpropan-2-yl)-1,3,4-oxadiazol-2-amine 2,2,2-trifluoroacetate In a 5 mL glass microwave tube 5-(3-(6-cyclopropylpyrazin-2-yl)-1-tosyl-1H-indol-5-yl)-N-(2-phenylpropan-2-yl)-1,3,4-oxadiazol-2-amine (28 mg, 0.047 mmol) was treated with dioxane (1.5 mL) and 1N NaOH (0.5 mL) and heated in the microwave at 110° C. for 10 min. The mixture was diluted with water and extracted with EtOAc (2×20 mL) and concentrated. It was purified with reverse phase HPLC (5-100% 0.1% TFA/AcCN in 0.1% TFA/H₂O) to give 5-(3-(6-cyclopropylpyrazin-2-yl)-1H-indol-5-yl)-N-(2-phenylpropan-2-yl)-1,3,4-oxadiazol-2-amine 2,2,2-trifluoroacetate (4.6 mg, 18%) as a bright yellow amorphous solid. MS (ESI, pos. ion) m/z: 437.1 (M+1). ¹H NMR (400 MHz, CDCl₃) δ ppm 11.03 (1H, br. s.), 8.43 (1H, s), 8.37 (1H, br. s.), 7.92 (1H, br. s.), 7.67 (1H, s), 7.35 (1H, d, J=8.6 Hz), 7.19-7.26 (3H, m), 7.06 (2H, t, J=7.7 Hz), 6.91-6.98 (1H, m), 1.84-1.93 (1H, m), 1.56 (6H, s), 0.94-1.01 (2H, m), 0.81-0.88 (2H, m).

Example 51

2-(3-(4-cyclopropylpyrimidin-2-yl)-1H-indol-5-yl)-5-isobutyl-1,3,4-oxadiazole

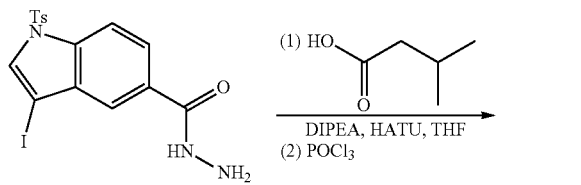

41c

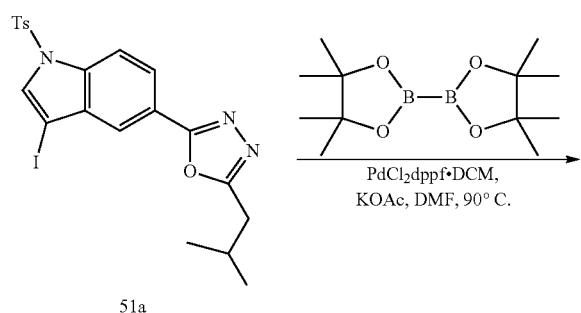

51a

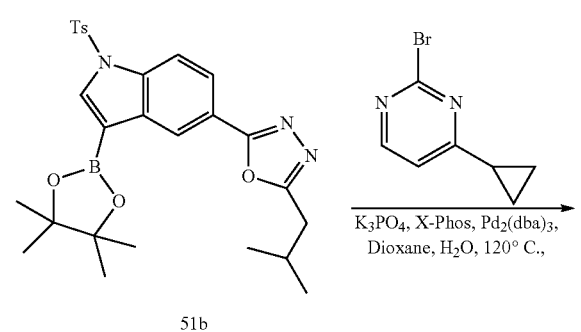

51b

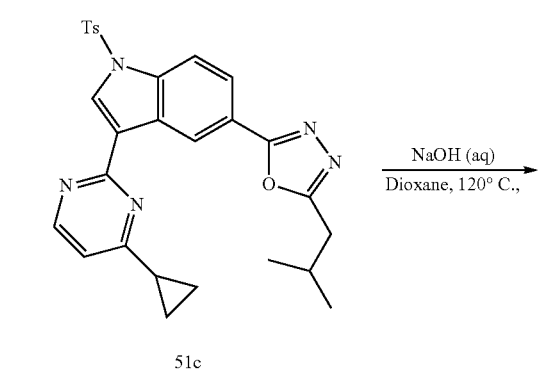

51c

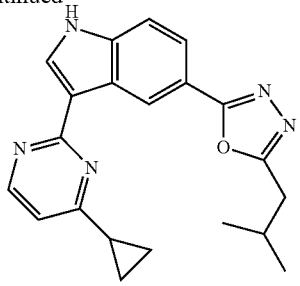

51

Preparation of compound 51a: 2-(3-iodo-1-tosyl-1H-indol-5-yl)-5-isobutyl-1,3,4-oxadiazole In a 150 mL RBF was weighed 3-iodo-1-tosyl-1H-indole-5-carbohydrazide (1.16 g, 2.55 mmol) followed by THF (20 mL), isovalerianic acid (0.29 mL, 2.55 mmol) (TCI America) and N-ethyl-N-isopropylpropan-2-amine (1.11 mL, 6.37 mmol). To this stirring suspension was added HATU (1.07 g, 2.80 mmol) in one portion and the solution was stirred at RT for 2 h. The mixture was concentrated and treated with $POCl_3$ (10 mL, 107 mmol) under argon. The flask was fitted with a reflux condenser and the reaction was heated to 110° C. for 14 h. The excess $POCl_3$ was removed under reduced pressure and the crude residue was treated with EtOAc and a saturated solution of $NaHCO_3$. It was extracted with EtOAc (50 mL) and washed with brine and dried over $MgSO_4$, filtered and concentrated. The crude material was purified by flash chromatography (0-50% EtOAc in Hex) affording 2-(3-iodo-1-tosyl-1H-indol-5-yl)-5-isobutyl-1,3,4-oxadiazole (277 mg, 35%) as a white amorphous solid. MS (ESI, pos. ion) m/z: 522.0 $(M+H)^1$. $^1H$ NMR (400 MHz, DMSO-$d_6$) δ ppm 8.24 (s, 1H), 8.17 (d, J=8.6 Hz, 1H), 8.03 (d, J=8.8 Hz, 1H), 7.97 (m, J=8.2 Hz, 2H), 7.87 (s, 1H), 7.43 (m, J=8.2 Hz, 2H), 2.84 (d, J=7.0 Hz, 2H), 2.33 (s, 3H), 2.15 (dt, J=13.5, 6.8 Hz, 1H), 0.99 (d, J=6.7 Hz, 6H).

Preparation of compound 51b: 2-isobutyl-5-(3-(4,4,5,5-tetramethyl-1,3,2-dioxaborolan-2-yl)-1-tosyl-1H-indol-5-yl)-1,3,4-oxadiazole In a 20 mL microwave tube, a mixture of 2-(3-iodo-1-tosyl-1H-indol-5-yl)-5-isobutyl-1,3,4-oxadiazole (276 mg, 0.529 mmol), bis(pinacolato)diboron (403 mg, 1.59 mmol), potassium acetate (260 mg, 2.65 mmol), $PdCl_2$(dppf), complex with DCM (64.8 mg, 0.079 mmol) and DMF (2.5 mL) was stirred at 90° C. in the oil bath for 1 h. The mixture was treated with water, extracted with EtOAc (50 mL) and washed with brine (2×20 mL), dried over $MgSO_4$, filtered and concentrated affording a viscous brown oil. It was used in the next step without further purification.

Preparation of compound 51c: 2-(3-(4-cyclopropylpyrimidin-2-yl)-1-tosyl-1H-indol-5-yl)-5-isobutyl-1,3,4-oxadiazole To a 20 mL microwave vial was added 2-isobutyl-5-(3-(4,4,5,5-tetramethyl-1,3,2-dioxaborolan-2-yl)-1-tosyl-1H-indol-5-yl)-1,3,4-oxadiazole (233 mg, 0.530 mmol), dicyclohexyl(2',4',6'-triisopropylbiphenyl-2-yl)phosphine (15.2 mg, 0.032 mmol), $Pd_2$(dba)$_3$ (14.6 mg, 0.016 mmol), 2-bromo-4-cyclopropylpyrimidine (CombiPhos Catalysts Inc., 121 mg, 0.610 mmol) and potassium phosphate (338 mg, 1.59 mmol) followed by purging with argon. The solids were treated with dioxane (4.0 mL) and water (0.4 mL) and heated in the microwave at 130° C. for 20 min. The mixture was treated with $H_2O$ and extracted with EtOAc, dried over $MgSO_4$, filtered and concentrated. Purification (eluting with 10-60% EtOAc in Hex) afforded 2-(3-(4-cyclopropylpyrimidin-2-yl)-1-tosyl-1H-indol-5-yl)-5-isobutyl-1,3,4-oxadiazole (108 mg, 40%) as a light yellow viscous oil. MS (ESI, pos. ion) m/z: 514.1 (M+1). $^1$H NMR (400 MHz, $CDCl_3$) δ ppm 9.27 (1H, s), 8.50-8.58 (2H, m), 8.09-8.13 (2H, m), 7.86 (2H, d, J=8.4 Hz), 7.24 (2H, s), 7.07 (1H, d, J=5.1 Hz), 2.84 (2H, d, J=7.2 Hz), 2.35 (3H, s), 2.29 (1H, s), 1.91 (1H, br. s.), 1.34-1.40 (2H, m), 1.17 (2H, dd, J=7.8, 2.9 Hz), 1.07 (6H, d, J=6.7 Hz).

Preparation of compound 51: 2-(3-(4-cyclopropylpyrimidin-2-yl)-1H-indol-5-yl)-5-isobutyl-1,3,4-oxadiazole 2,2,2-trifluoroacetate In a 5 mL microwave tube 2-(3-(4-cyclopropylpyrimidin-2-yl)-1-tosyl-1H-indol-5-yl)-5-isobutyl-1,3,4-oxadiazole (108 mg, 0.210 mmol) was treated with dioxane (2.0 mL) and 1N NaOH (0.5 mL) and heated at 110° C. for 10 min. The mixture was treated with water and extracted with EtOAc (2×25 mL) and washed with brine (20 mL) and concentrated. Purification with reverse phase HPLC (10-90% 0.1% TFA/AcCN in 0.1% TFA/$H_2O$) afforded 2-(3-(4-cyclopropylpyrimidin-2-yl)-1H-indol-5-yl)-5-isobutyl-1,3,4-oxadiazole 2,2,2-trifluoroacetate (37.7 mg, 38%) as a light yellow amorphous solid. MS (ESI, pos. ion) m/z: 360.2 (M+1). $^1$H NMR (400 MHz, DMSO-$d_6$) δ ppm 12.07 (1H, br. s.), 9.16 (1H, s), 8.59 (1H, d, J=5.1 Hz), 8.33 (1H, d, J=2.7 Hz), 7.84 (1H, dd, J=8.5, 1.7 Hz), 7.65 (1H, d, J=8.4 Hz), 7.25 (1H, d, J=5.3 Hz), 2.86 (2H, d, J=7.0 Hz), 2.14-2.26 (2H, m), 1.26-1.32 (2H, m), 1.15-1.22 (2H, m), 1.04 (6H, d, J=6.7 Hz).

Example 52

N-(2-phenylpropan-2-yl)-5-(3-(pyrimidin-2-yl)-1H-indol-5-yl)-1,3,4-oxadiazol-2-amine 2,2,2-trifluoroacetate

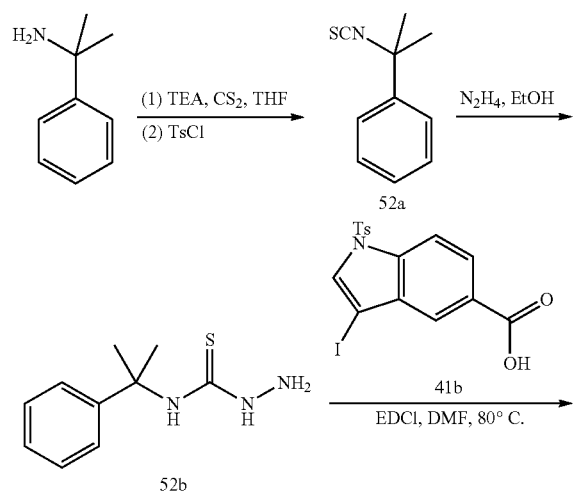

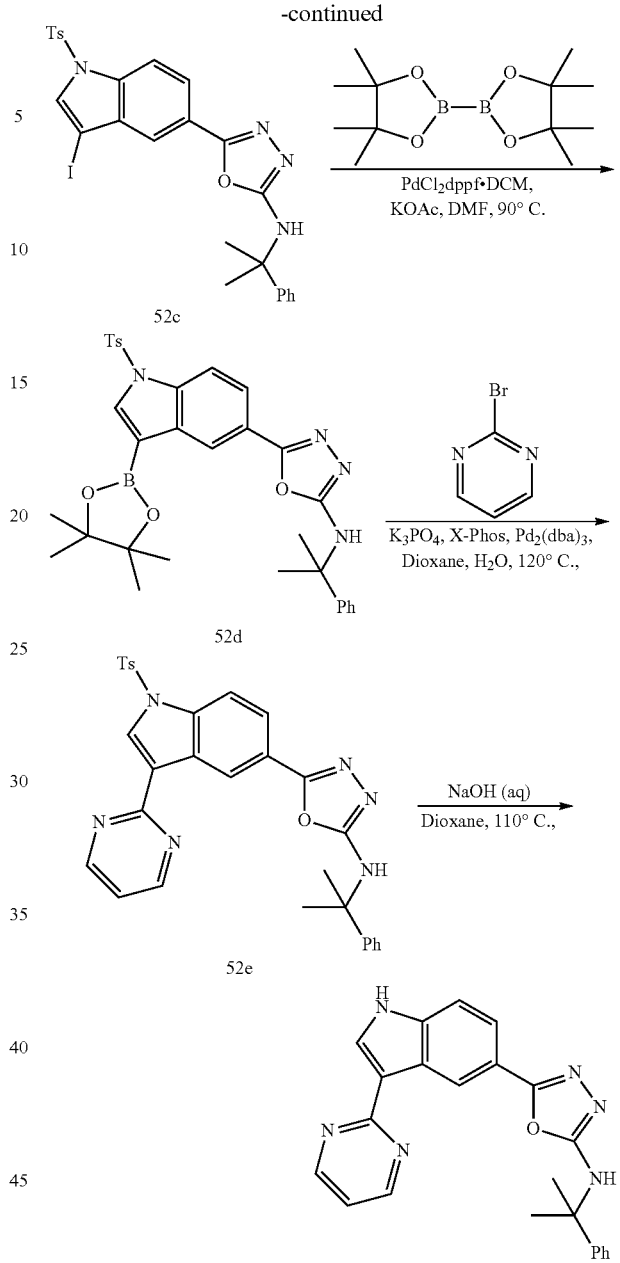

Preparation of compound 52a: (2-isothiocyanatopropan-2-yl)benzene

Cumylamine (5.32 mL, 37.0 mmol) (TCI America) and $Et_3N$ (16.97 mL, 122 mmol) (Aldrich) were mixed in THF (40 mL) at 0° C. under a nitrogen atmosphere. Carbon disulfide (2.224 mL, 37.0 mmol) (J.T.Baker) was added dropwise via syringe over the course of 10 min. The reaction was stirred at 0° C. for 1 h before being warmed to RT and stirred for 1 h. p-Toluenesulfonyl chloride (7.76 g, 40.7 mmol) (Fluka) was added, and the reaction was stirred at RT for 1 h. The mixture was quenched with 1 M HCl and extracted with EtOAc. The organic layer was washed with brine, dried over $MgSO_4$, and concentrated to give (2-isothiocyanatopropan-2-yl)benzene.

Preparation of compound 52b: N-(2-phenylpropan-2-yl)hydrazinecarbothioamide

Anhydrous hydrazine (1.161 mL, 37.0 mmol) (Sigma-Aldrich) was added to a stirring solution of (2-isothiocyanatopropan-2-yl)benzene (6.56 g, 37.0 mmol) in EtOH (150 mL). The reaction was stirred at RT for 2 h to give N-(2-phenylpropan-2-yl)hydrazinecarbothioamide. MS (ESI, pos. ion) m/z: 210.2 (M+1). The material was used without purification.

Preparation of compound 52c: 5-(3-iodo-1-tosyl-1H-indol-5-yl)-N-(2-phenylpropan-2-yl)-1,3,4-oxadiazol-2-amine A solution of 3-iodo-1-tosyl-1H-indole-5-carboxylic acid (1.330 g, 3.01 mmol), N-(2-phenylpropan-2-yl)hydrazinecarbothioamide (0.631 g, 3.01 mmol), and N1-((ethylimino)methylene)-N3,N3-dimethylpropane-1,3-diamine hydrochloride (1.156 g, 6.03 mmol) (Sigma-Aldrich) in DMF (5.0 mL) was heated at 80° C. for 2 h. The solution was cooled to RT. Water (precipitate formed), EtOAc and Celite were added, and the solids were removed by filtration and washed with EtOAc (3×). The organic layer was evaporated to reduce solvent volume. The aqueous layer was then extracted with EtOAc (2×50 mL). The combined organic layers were concentrated in vacuo and the crude material was purified by flash chromatography (20-100% EtOAc in Hex) to give 5-(3-iodo-1-tosyl-1H-indol-5-yl)-N-(2-phenylpropan-2-yl)-1,3,4-oxadiazol-2-amine (408.1 mg, 0.682 mmol, 22.62%). MS (ESI, pos. ion) m/z: 599.0 (M+1).

Preparation of compound 52d: N-(2-phenylpropan-2-yl)-5-(3-(4,4,5,5-tetramethyl-1,3,2-dioxaborolan-2-yl)-1-tosyl-1H-indol-5-yl)-1,3,4-oxadiazol-2-amine 5-(3-Iodo-1-tosyl-1H-indol-5-yl)-N-(2-phenylpropan-2-yl)-1,3,4-oxadiazol-2-amine (0.4081 g, 0.682 mmol), bis(pinacolato)diboron (0.519 g, 2.046 mmol) (Aldrich), potassium acetate (0.335 g, 3.41 mmol) (Sigma-Aldrich), and PdCl$_2$(dppf), complex with DCM (0.084 g, 0.102 mmol) (Strem Chemicals) were weighed into a 20 mL glass microwave tube. The tube was purged with argon and the solids were dissolved in DMF (7.0 mL). The tube was sealed and heated at 90° C. for 3 h using a metal block and hotplate. The reaction was cooled to RT, treated with EtOAc (100 mL) and rinsed with water (2×40 mL). The combined organic layers were dried over MgSO$_4$, filtered and concentrated to give N-(2-phenylpropan-2-yl)-5-(3-(4,4,5,5-tetramethyl-1,3,2-dioxaborolan-2-yl)-1-tosyl-1H-indol-5-yl)-1,3,4-oxadiazol-2-amine. MS (ESI, pos. ion) m/z: 600.0 (M+1).

Preparation of compound 52e: N-(2-phenylpropan-2-yl)-5-(3-(pyrimidin-2-yl)-1-tosyl-1H-indol-5-yl)-1,3,4-oxadiazol-2-amine N-(2-Phenylpropan-2-yl)-5-(3-(4,4,5,5-tetramethyl-1,3,2-dioxaborolan-2-yl)-1-tosyl-1H-indol-5-yl)-1,3,4-oxadiazol-2-amine (757.3 mg, 1.265 mmol), 2-bromopyrimidine (221 mg, 1.392 mmol) (Aldrich), potassium phosphate (806 mg, 3.80 mmol) (Sigma-Aldrich), dicyclohexyl(2',4',6'-triisopropylbiphenyl-2-yl)phosphine (36.2 mg, 0.076 mmol) (Strem Chemicals), and Pd$_2$(dba)$_3$ (34.8 mg, 0.038 mmol) (Strem Chemicals) were weighed into a 20 mL glass microwave tube, and the tube was purged with argon. The solids were treated with dioxane (8 mL) and water (0.800 mL), the tube was sealed and the contents were heated in an Initiator microwave reactor (Personal Chemistry, Biotage AB, Inc., Upssala, Sweden) at 120° C. for 20 min. The mixture was treated with water, extracted with EtOAc (3×50 mL), dried over MgSO$_4$, filtered and concentrated. The crude material was purified by flash chromatography (30-100% EtOAc in Hex) to give N-(2-phenylpropan-2-yl)-5-(3-(pyrimidin-2-yl)-1-tosyl-1H-indol-5-yl)-1,3,4-oxadiazol-2-amine (297.4 mg, 0.540 mmol, 42.7%). MS (ESI, pos. ion) m/z: 551.2 (M+1).

Preparation of compound 52: N-(2-phenylpropan-2-yl)-5-(3-(pyrimidin-2-yl)-1H-indol-5-yl)-1,3,4-oxadiazol-2-amine 2,2,2-trifluoroacetate N-(2-Phenylpropan-2-yl)-5-(3-(pyrimidin-2-yl)-1-tosyl-1H-indol-5-yl)-1,3,4-oxadiazol-2-amine (297.4 mg, 0.540 mmol) in a 20 mL glass microwave tube was suspended in dioxane (10 mL) and treated with NaOH 1.00 normal (5.40 mL, 5.40 mmol) (Fluka Analytical). The tube was sealed and the contents were heated in an Initiator microwave reactor (Personal Chemistry, Biotage AB, Inc., Upssala, Sweden) at 110° C. for 10 min. The mixture was diluted with water (20 mL) and extracted with EtOAc (2×75 mL). The combined organic layers were dried over MgSO$_4$, filtered and concentrated. The residue was dissolved in 2.1 mL of DMSO. Purification by reverse phase chromatography (10-90% MeCN in H$_2$O with 0.01% TFA as additive to each solvent by volume) afforded N-(2-phenylpropan-2-yl)-5-(3-(pyrimidin-2-yl)-1H-indol-5-yl)-1,3,4-oxadiazol-2-amine 2,2,2-trifluoroacetate (21.3 mg, 0.042 mmol, 7.73%) as an amorphous yellow solid. MS (ESI, pos. ion) m/z: 397.1 (M+1). $^1$H NMR (400 MHz, MeOH-d$_4$) δ ppm 9.13 (d, J=1.2 Hz, 1H), 8.81 (d, J=4.9 Hz, 2H), 8.29 (s, 1H), 7.71 (dd, J=8.6, 1.8 Hz, 1H), 7.57 (dd, J=7.9, 1.9 Hz, 3H), 7.39 (t, J=7.7 Hz, 2H), 7.22-7.31 (m, 2H), 1.84 (s, 6H).

Example 53

5-(3-(4-cyclopropylpyrimidin-2-yl)-1H-indol-5-yl)-N-(2,2,2-trifluoroethyl)-1,3,4-oxadiazol-2-amine

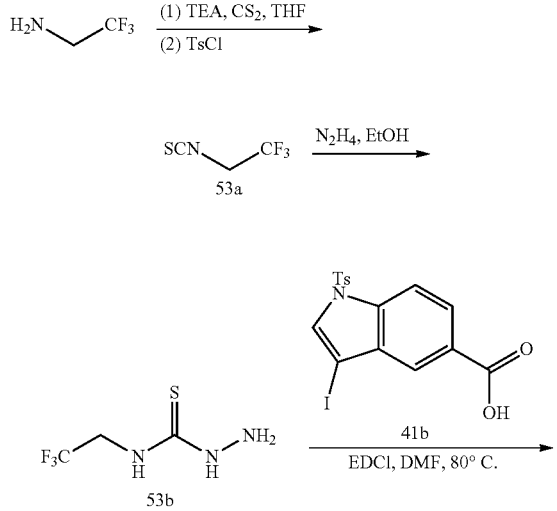

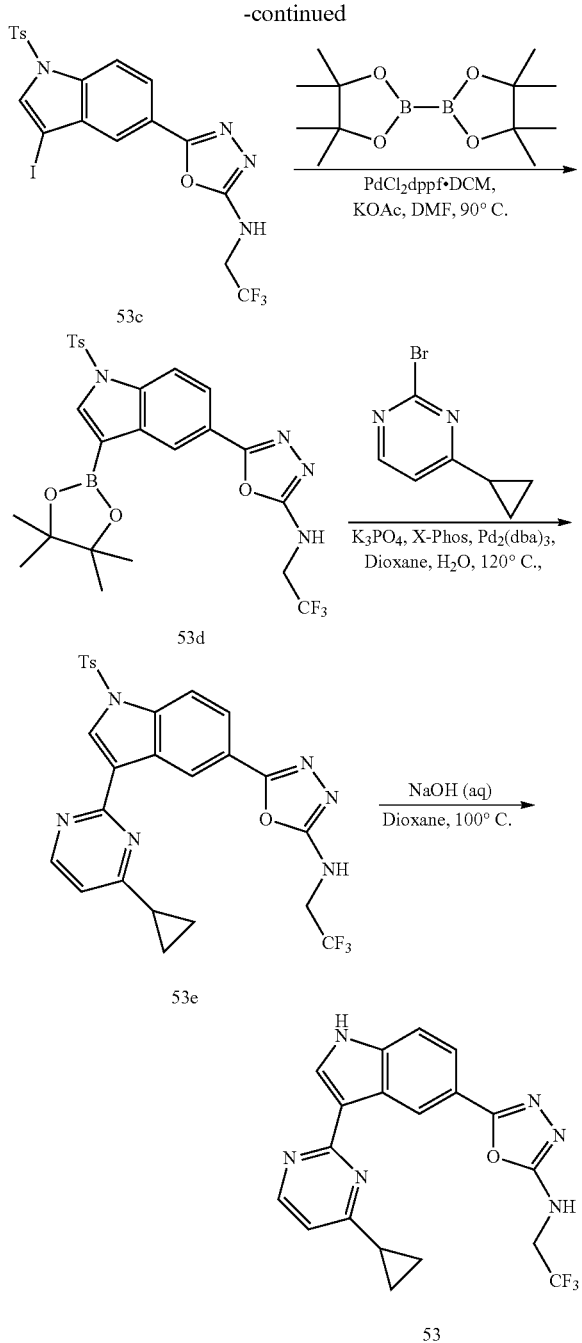

concentrated to give 1,1,1-trifluoro-2-isothiocyanatoethane. The product was used without purification.

Preparation of compound 53b: N-(2,2,2-trifluoroethyl)hydrazinecarbothioamide

Anhydrous hydrazine (0.634 mL, 20.20 mmol) (Sigma-Aldrich) was added to a stirring solution of 1,1,1-trifluoro-2-isothiocyanatoethane (2.85 g, 20.20 mmol) in EtOH (80 mL). The reaction was stirred at RT for 2 h. The solvent was removed in vacuo to give N-(2,2,2-trifluoroethyl)hydrazinecarbothioamide, and the material was used without purification.

Preparation of compound 53c: 5-(3-iodo-1-tosyl-1H-indol-5-yl)-N-(2,2,2-trifluoroethyl)-1,3,4-oxadiazol-2-amine A solution of 3-iodo-1-tosyl-1H-indole-5-carboxylic acid (1.996 g, 4.52 mmol), N-(2,2,2-trifluoroethyl)hydrazinecarbothioamide (0.783 g, 4.52 mmol), and N1-((ethylimino)methylene)-N3,N3-dimethylpropane-1,3-diamine hydrochloride (2.60 g, 13.57 mmol) (Sigma-Aldrich) in DMF (8.0 mL) was heated at 80° C. for 21.25 h, then at 90° C. for 24 h. The solution was cooled to RT. $H_2O$ was added and the solution was extracted with EtOAc (3×75 mL). The combined organic layers were washed with brine, dried over $MgSO_4$, filtered and concentrated to give the crude material. The crude material was purified by flash chromatography (10-60% EtOAc in Hex). The fractions were combined and DCM was added to the residue. A solid was present and was removed by filtration to give 5-(3-iodo-1-tosyl-1H-indol-5-yl)-N-(2,2,2-trifluoroethyl)-1,3,4-oxadiazol-2-amine (180 mg, 0.320 mmol, 7.08%) as an off white solid. MS (ESI, pos. ion) m/z: 562.9 (M+1). $^1$H NMR (400 MHz, DMSO-$d_6$) δ ppm 8.65 (t, J=6.6 Hz, 1H), 8.21 (s, 1H), 8.10-8.16 (m, 1H), 7.89-7.99 (m, 3H), 7.73 (s, 1H), 7.43 (d, J=8.2 Hz, 2H), 4.06-4.20 (m, 2H), 2.33 (s, 3H).

Preparation of compound 53d: 5-(3-(4,4,5,5-tetramethyl-1,3,2-dioxaborolan-2-yl)-1-tosyl-1H-indol-5-yl)-N-(2,2,2-trifluoroethyl)-1,3,4-oxadiazol-2-amine 5-(3-Iodo-1-tosyl-1H-indol-5-yl)-N-(2,2,2-trifluoroethyl)-1,3,4-oxadiazol-2-amine (180 mg, 0.320 mmol), bis(pinacolato)diboron (244 mg, 0.960 mmol) (Aldrich), potassium acetate (157 mg, 1.601 mmol) (Sigma-Aldrich), and $PdCl_2$(dppf) complex with DCM (39.2 mg, 0.048 mmol) (Strem) were weighed into a 5 mL glass microwave tube and the tube was purged with argon. The solids were suspended in DMF (1.6 mL), the tube was sealed and the contents were stirred and heated at 90° C. for 1.5 h using a hotplate and metal heating block. The mixture was treated with $H_2O$ and extracted with EtOAc (50 mL). The organic layer was washed with brine (2×20 mL), dried over $MgSO_4$, filtered and concentrated affording 5-(3-(4,4,5,5-tetramethyl-1,3,2-dioxaborolan-2-yl)-1-tosyl-1H-indol-5-yl)-N-(2,2,2-trifluoroethyl)-1,3,4-oxadiazol-2-amine. MS (ESI, pos. ion) m/z: 563.2 (M+1), and 1-tosyl-5-(5-(2,2,2-trifluoroethylamino)-1,3,4-oxadiazol-2-yl)-1H-indol-3-ylboronic acid as a viscous brown oil. MS (ESI, pos. ion) m/z: 481.1 (M+1).

Preparation of compound 53e: 5-(3-(4-cyclopropylpyrimidin-2-yl)-1-tosyl-1H-indol-5-yl)-N-(2,2,2-trifluoroethyl)-1,3,4-oxadiazol-2-amine To a 5 mL glass microwave tube containing 5-(3-(4,4,5,5-tetramethyl-1,3,2-dioxaborolan-2-yl)-1-tosyl-1H-indol-5- yl)-N-(2,2,2-trifluoroethyl)-1,3,4-oxadiazol-2-amine (180 mg, 0.320 mmol) was added 2-bromo-4-cyclopropylpyrimidine (73.3 mg, 0.368 mmol) (CombiPhos Catalysts Inc.), potassium phosphate (204 mg, 0.960 mmol) (Sigma-Aldrich), dicyclohexyl(2',4',6'-triisopropylbiphenyl-2-yl)phosphine (9.16 mg, 0.019 mmol) (Strem), and Pd$_2$(dba)$_3$ (8.79 mg, 9.60 µmol) (Strem). The tube was purged with argon, the solids were treated with dioxane (2.0 mL) and water (0.200 mL), the tube was sealed, and the contents were heated in an Initiator microwave reactor (Personal Chemistry, Biotage AB, Inc., Upssala, Sweden) at 100° C. for 20 min. The mixture was treated with H$_2$O and extracted with EtOAc. The organic layer was washed with brine, dried over MgSO$_4$, filtered and concentrated. The crude material was purified by flash chromatography (20-100% EtOAc in Hex) affording 5-(3-(4-cyclopropylpyrimidin-2-yl)-1-tosyl-1H-indol-5-yl)-N-(2,2,2-trifluoroethyl)-1,3,4-oxadiazol-2-amine as an amorphous beige solid. MS (ESI, pos. ion) m/z: 554.9 (M+1). $^1$H NMR (400 MHz, DMSO-d$_6$) δ ppm 9.03 (s, 1H), 8.63-8.71 (m, 2H), 8.53 (s, 1H), 8.16 (d, J=8.8 Hz, 1H), 8.04 (m, J=8.4 Hz, 2H), 7.92 (d, J=7.2 Hz, 1H), 7.43 (m, J=8.2 Hz, 2H), 7.37 (d, J=5.1 Hz, 1H), 4.06-4.21 (m, 2H), 2.33 (s, 3H), 2.16-2.27 (m, 1H), 1.24 (br. s., 2H), 1.18 (d, J=6.7 Hz, 2H).

Preparation of compound 53: 5-(3-(4-cyclopropylpyrimidin-2-yl)-1H-indol-5-yl)-N-(2,2,2-trifluoroethyl)-1,3,4-oxadiazol-2-amine 5-(3-(4-Cyclopropylpyrimidin-2-yl)-1-tosyl-1H-indol-5-yl)-N-(2,2,2-trifluoroethyl)-1,3,4-oxadiazol-2-amine (117 mg, 0.211 mmol) in a 5 mL glass microwave tube, was suspended in dioxane (1.5 mL). The suspension was treated with NaOH 1.000 n (2 mL, 2.000 mmol) (Fluka Analytical). The tube was sealed and the contents were stirred and heated in an Initiator microwave reactor (Personal Chemistry, Biotage AB, Inc., Upssala, Sweden) at 100° C. for 10 min. The mixture was diluted with H$_2$O (10 mL) and extracted with EtOAc (2×25 mL). The combined organic layers were washed with brine, dried over MgSO$_4$, filtered and concentrated. The crude material was purified by flash chromatography (eluting with 0-8% MeOH in DCM) to give 5-(3-(4-cyclopropylpyrimidin-2-yl)-1H-indol-5-yl)-N-(2,2,2-trifluoroethyl)-1,3,4-oxadiazol-2-amine (19.1 mg, 0.048 mmol, 22.61%) as a pale yellow amorphous solid. MS (ESI, pos. ion) m/z: 401.1 (M+1). $^1$H NMR (400 MHz, DMSO-d$_6$) δ ppm 11.95 (br. s., 1H), 9.01 (s, 1H), 8.50-8.59 (m, 2H), 8.27 (d, J=2.3 Hz, 1H), 7.70 (dd, J=8.5, 1.5 Hz, 1H), 7.60 (d, J=8.4 Hz, 1H), 7.16 (d, J=5.3 Hz, 1H), 4.05-4.21 (m, 2H), 2.08-2.20 (m, 1H), 1.20-1.29 (m, 2H), 1.07-1.16 (m, 2H).

Example 54

N-tert-butyl-5-(3-(4-cyclopropylpyrimidin-2-yl)-1H-indol-5-yl)-1,3,4-oxadiazol-2-amine 2,2,2-trifluoroacetate

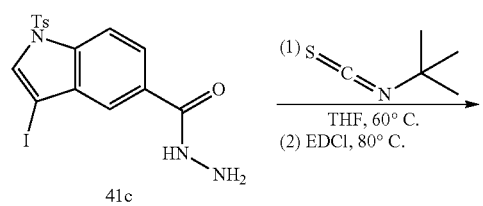

41c

Preparation of compound 54a: N-tert-butyl-5-(3-iodo-1-tosyl-1H-indol-5-yl)-1,3,4-oxadiazol-2-amine 3-Iodo-1-tosyl-1H-indole-5-carbohydrazide (625 mg, 1.373 mmol) in a 250 mL RBF was treated with THF (25 mL) and 2-isothiocyanato-2-methylpropane (0.871 mL, 6.86 mmol) (Aldrich). The flask was fitted with a reflux condenser and heated at 60° C. for 2.5 h. The reaction was cooled to RT, the THF was removed in vacuo and replaced with DMF (10.00 mL). The solution was treated with N1-((ethylimino)methylene)-N3,N3-dimethylpropane-1,3-diamine hydrochloride (395 mg, 2.059 mmol), fitted with a reflux condenser and heated to 80° C. for 2 h. The mixture was treated with H$_2$O and extracted with EtOAc (2×50 mL), washed with brine

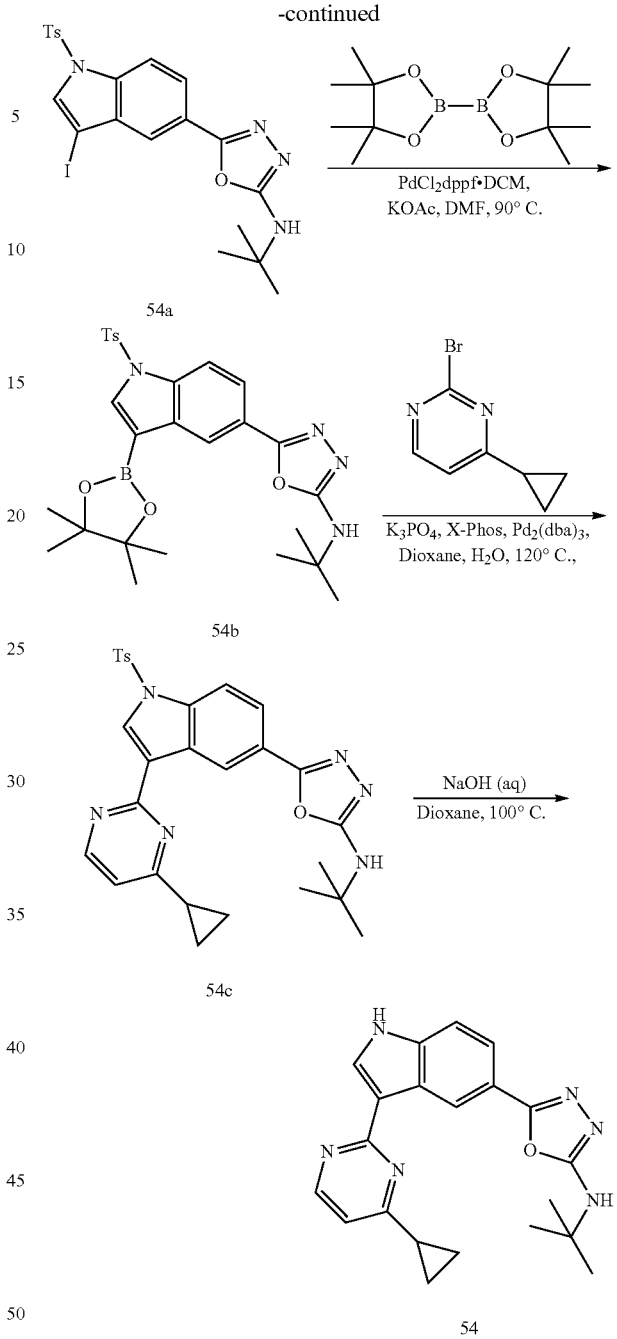

and dried over MgSO₄, filtered and concentrated. The crude material was purified by flash chromatography (eluting with 0-100% EtOAc in Hex) to give N-tert-butyl-5-(3-iodo-1-tosyl-1H-indol-5-yl)-1,3,4-oxadiazol-2-amine (378.7 mg, 0.706 mmol, 51.4) as a white amorphous solid. MS (ESI, pos. ion) m/z: 536.9 (M+1). ¹H NMR (400 MHz, DMSO-d₆) δ ppm 8.19 (s, 1H), 8.12 (d, J=8.8 Hz, 1H), 7.98 (s, 1H), 7.90 (dd, J=8.7, 1.5 Hz, 1H), 7.69 (s, 2H), 7.43 (d, J=8.2 Hz, 2H), 2.33 (s, 3H), 1.37 (s, 9H).

Preparation of compound 54b: N-tert-butyl-5-(3-(4,4,5,5-tetramethyl-1,3,2-dioxaborolan-2-yl)-1-tosyl-1H-indol-5-yl)-1,3,4-oxadiazol-2-amine N-tert-Butyl-5-(3-iodo-1-tosyl-1H-indol-5-yl)-1,3,4-oxadiazol-2-amine (350 mg, 0.653 mmol), 4,4,4',4',5,5,5',5'-octamethyl-2,2'-bi(1,3,2-dioxaborolane) (497 mg, 1.958 mmol) (Aldrich), potassium acetate (320 mg, 3.26 mmol) (Sigma-Aldrich), and PdCl₂(dppf) complex with DCM (80 mg, 0.098 mmol) (Strem) were weighed into a 20 mL glass microwave tube and the tube was purged with argon. The solids were suspended in DMF (2.5 mL), the tube was sealed and the contents were stirred and heated at 90° C. for 1 h using a hotplate and metal heating block. The mixture was treated with H₂O and extracted with EtOAc (50 mL). A solid was present in the organic layer. The organic layer was washed with brine (2×20 mL) and filtered to remove the solid. The filtrate was dried over MgSO₄, filtered and concentrated affording crude N-tert-butyl-5-(3-(4,4,5,5-tetramethyl-1,3,2-dioxaborolan-2-yl)-1-tosyl-1H-indol-5-yl)-1,3,4-oxadiazol-2-amine (711 mg)

Preparation of compound 54c: N-tert-butyl-5-(3-(4-cyclopropylpyrimidin-2-yl)-1-tosyl-1H-indol-5-yl)-1,3,4-oxadiazol-2-amine To a 5 mL glass microwave tube containing N-tert-butyl-5-(3-(4,4,5,5-tetramethyl-1,3,2-dioxaborolan-2-yl)-1-tosyl-1H-indol-5-yl)-1,3,4-oxadiazol-2-amine (357.8 mg, 0.667 mmol) was added 2-bromo-4-cyclopropylpyrimidine (153 mg, 0.767 mmol) (CombiPhos Catalysts Inc.), potassium phosphate (425 mg, 2.001 mmol) (Sigma-Aldrich), dicyclohexyl(2',4',6'-triisopropylbiphenyl-2-yl)phosphine (19.08 mg, 0.040 mmol) (Strem), and Pd₂(dba)₃ (18.32 mg, 0.020 mmol) (Strem). The tube was purged with argon, the solids were treated with Dioxane (3.0 mL) and Water (0.300 mL), the tube was sealed, and the contents were heated in an Initiator microwave reactor (Personal Chemistry, Biotage AB, Inc., Upssala, Sweden) at 120° C. for 20 min. The mixture was treated with H₂O and extracted with EtOAc. The organic layer was washed with brine, dried over MgSO₄, filtered and concentrated. The crude material was purified by flash chromatography (eluting with 5-60% EtOAc in Hex) affording N-tert-butyl-5-(3-(4-cyclopropylpyrimidin-2-yl)-1-tosyl-1H-indol-5-yl)-1,3,4-oxadiazol-2-amine (86.2 mg, 0.163 mmol, 24.45) as an off-white foam. MS (ESI, pos. ion) m/z: 529.0 (M+1).

Preparation of compound 54: N-tert-butyl-5-(3-(4-cyclopropylpyrimidin-2-yl)-1H-indol-5-yl)-1,3,4-oxadiazol-2-amine 2,2,2-trifluoroacetate N-tert-Butyl-5-(3-(4-cyclopropylpyrimidin-2-yl)-1-tosyl-1H-indol-5-yl)-1,3,4-oxadiazol-2-amine (86.2 mg, 0.163 mmol) in a 5 mL glass microwave tube, was suspended in dioxane (1.5 mL). The suspension was treated with NaOH 1.000 n (1.0 mL, 53.3 mmol) (Fluka Analytical). The tube was sealed and the contents were stirred and heated in an Initiator microwave reactor (Personal Chemistry, Biotage AB, Inc., Upssala, Sweden) at 100° C. for 10 min. The mixture was diluted with water (20 mL) and extracted with EtOAc (2×75 mL). The combined organic layers were washed with brine, dried over MgSO₄, filtered and concentrated. The residue was dissolved in 0.9 mL of DMSO. Purification by reverse phase chromatography (20-95% MeCN in H₂O with 0.01% TFA as additive to each solvent by volume) afforded N-tert-butyl-5-(3-(4-cyclopropylpyrimidin-2-yl)-1H-indol-5-yl)-1,3,4-oxadiazol-2-amine 2,2,2-trifluoroacetate (24.9 mg, 0.051 mmol, 31.3%) as a pale yellow amorphous solid. MS (ESI, pos. ion) m/z: 375.0 (M+1). ¹H NMR (400 MHz, DMSO-d₆) δ ppm 11.96 (br. s., 1H), 8.98 (s, 1H), 8.57 (d, J=5.1 Hz, 1H), 8.28 (d, J=2.7 Hz, 1H), 7.63-7.70 (m, 1H), 7.59 (d, J=8.6 Hz, 2H), 7.17 (d, J=5.3 Hz, 1H), 2.11-2.21 (m, 1H), 1.40 (s, 9H), 1.10-1.26 (m, 4H).

Example 55

N-tert-butyl-5-(3-(5-fluoro-4-methoxypyrimidin-2-yl)-1-tosyl-1H-indol-5-yl)-1,3,4-oxadiazol-2-amine

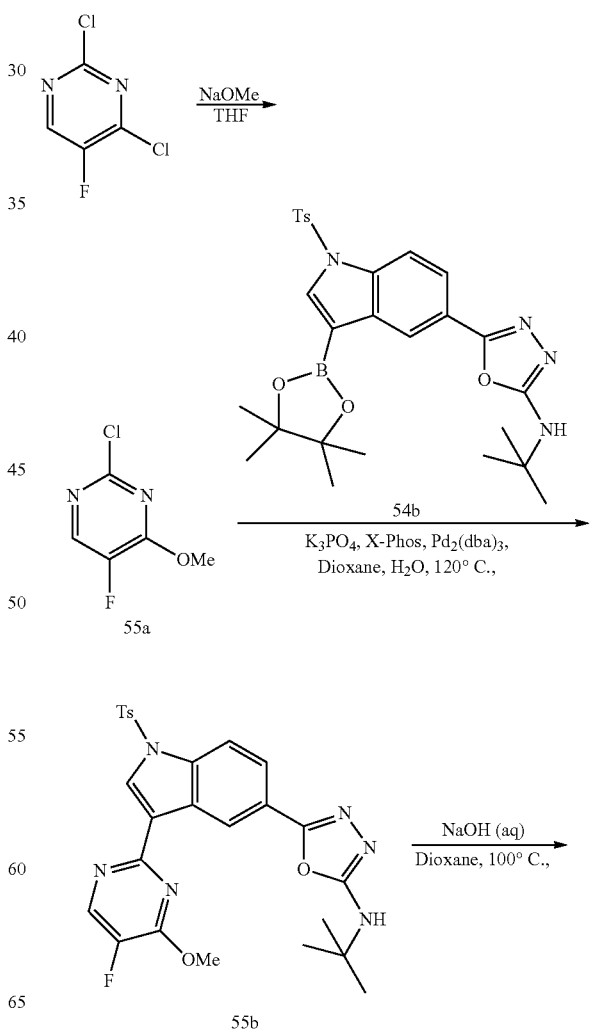

-continued

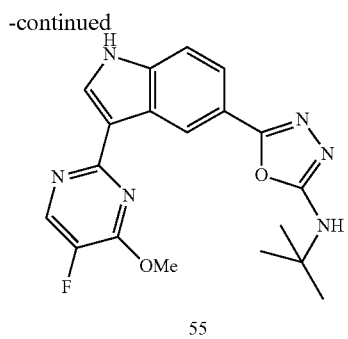

55

Preparation of compound 55a:
2-chloro-5-fluoro-4-methoxypyrimidine 2,4-Dichloro-5-fluoropyrimidine (515 mg, 3.08 mmol) was weighed into a 150 mL RBF, and was suspended in THF (5.0 mL). The stirring suspension was cooled to −10° C. NaOMe (250 mg, 4.63 mmol) was added in one portion at −10° C. An additional 0.5 eq of NaOMe were added and the suspension was stirred at RT for 21 h. The suspension was diluted with MeOH, and the solvents were removed in vacuo. The crude material was purified by flash chromatography (eluting with 100% DCM) to give 2-chloro-5-fluoro-4-methoxypyrimidine (37 mg, 0.228 mmol, 7.38%) as an amorphous white solid. MS (ESI, pos. ion) m/z: 162.9 (M+1). $^1$H NMR (400 MHz, DMSO-$d_6$) δ ppm 8.60 (d, J=2.7 Hz, 1H), 4.04 (s, 3H).

Preparation of compound 55b: N-tert-butyl-5-(3-(5-fluoro-4-methoxypyrimidin-2-yl)-1-tosyl-1H-indol-5-yl)-1,3,4-oxadiazol-2-amine N-tert-Butyl-5-(3-(4,4,5,5-tetramethyl-1,3,2-dioxaborolan-2-yl)-1-tosyl-1H-indol-5-yl)-1,3,4-oxadiazol-2-amine (166 mg, 0.309 mmol), dicyclohexyl(2',4',6'-triisopropylbiphenyl-2-yl)phosphine (6.63 mg, 0.014 mmol) (Strem), Pd$_2$(dba)$_3$ (6.37 mg, 6.96 μmol) (Strem), potassium phosphate (148 mg, 0.696 mmol) (Sigma-Aldrich) and 2-chloro-5-fluoro-4-methoxypyrimidine (37.7 mg, 0.232 mmol) were weighed into a 5 mL glass microwave tube. The tube was purged with argon and the solids were treated with dioxane (2 mL) and water (0.200 mL). The tube was sealed, and the contents were heated an Initiator microwave reactor (Personal Chemistry, Biotage AB, Inc., Upssala, Sweden) at 130° C. for 20 min. The mixture was treated with H$_2$O and extracted with EtOAc. The organic layer was washed with brine, dried over MgSO$_4$, filtered and concentrated. The crude material was purified by flash chromatography (eluting with 5-60% EtOAc in Hex) to give N-tert-butyl-5-(3-(5-fluoro-4-methoxypyrimidin-2-yl)-1-tosyl-1H-indol-5-yl)-1,3,4-oxadiazol-2-amine (75.5 mg, 0.141 mmol, 60.7%) as an off white solid. MS (ESI, pos. ion) m/z: 537.0 (M+1). $^1$H NMR (400 MHz, DMSO-$d_6$) δ ppm 8.98-9.03 (m, 1H), 8.72 (d, J=3.1 Hz, 1H), 8.56 (s, 1H), 8.16 (d, J=8.8 Hz, 1H), 8.02-8.07 (m, 2H), 7.86-7.92 (m, 1H), 7.64 (s, 1H), 7.40-7.48 (m, 2H), 4.22 (s, 3H), 2.33 (s, 3H), 1.35-1.41 (m, 9H).

Preparation of compound 55: N-tert-butyl-5-(3-(5-fluoro-4-methoxypyrimidin-2-yl)-1H-indol-5-yl)-1,3,4-oxadiazol-2-amine 2,2,2-trifluoroacetate N-tert-Butyl-5-(3-(5-fluoro-4-methoxypyrimidin-2-yl)-1-tosyl-1H-indol-5-yl)-1,3,4-oxadiazol-2-amine (75.5 mg, 0.141 mmol) was weighed into a 5 mL glass microwave tube, and was treated with dioxane (1.5 mL) and 1N NaOH (0.75 mL). The solution was heated in an Initiator microwave reactor (Personal Chemistry, Biotage AB, Inc., Upssala, Sweden) at 100° C. for 10 min. The mixture was treated with water, extracted with EtOAc, and concentrated. The crude residue was purified with reverse phase HPLC (20-95% 0.1% TFA/AcCN in 0.1% TFA/H$_2$O by volume) to give N-tert-butyl-5-(3-(5-fluoro-4-methoxypyrimidin-2-yl)-1H-indol-5-yl)-1,3,4-oxadiazol-2-amine 2,2,2-trifluoroacetate (29.9 mg, 0.060 mmol, 42.8%) as a light yellow amorphous solid. MS (ESI, pos. ion) m/z: 383.0 (M+1). $^1$H NMR (400 MHz, DMSO-$d_6$) δ ppm 12.01 (br. s., 1H), 8.97 (s, 1H), 8.59 (d, J=3.1 Hz, 1H), 8.28 (d, J=2.5 Hz, 1H), 7.65-7.73 (m, 1H), 7.54-7.64 (m, 2H), 4.19 (s, 3H), 1.39 (s, 9H).

Example 56

N-tert-butyl-5-(3-(4-cyclopropyl-5-fluoropyrimidin-2-yl)-1H-indol-5-yl)-1,3,4-oxadiazol-2-amine

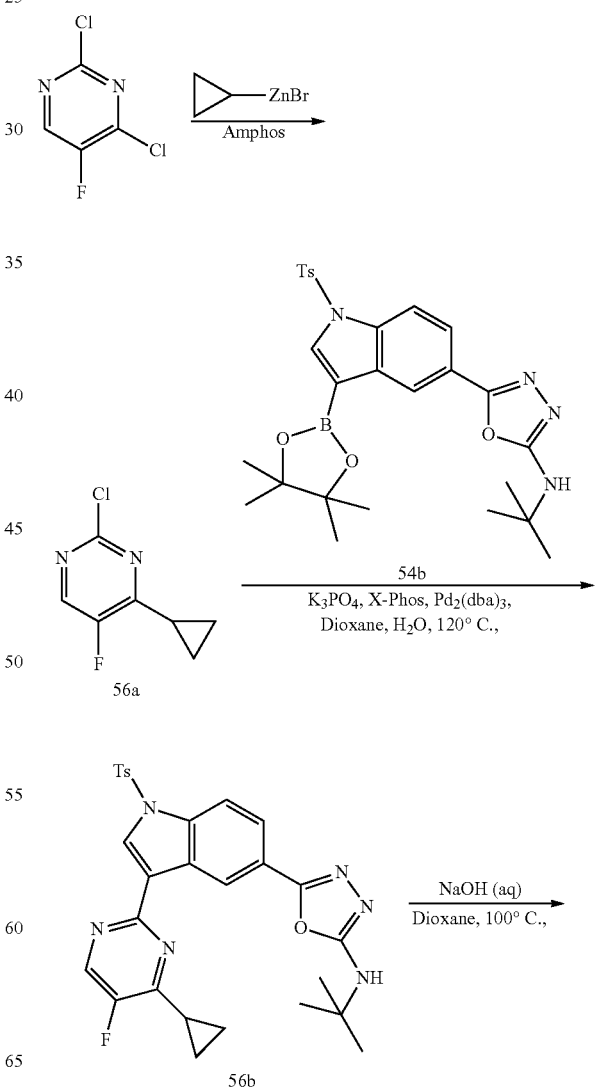

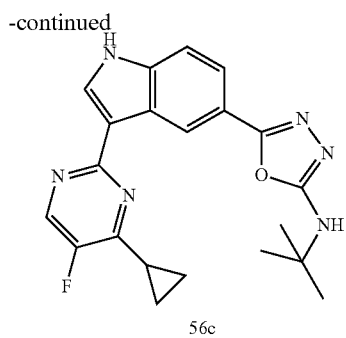

56c

Preparation of compound 56a: 2-chloro-4-cyclopropyl-5-fluoropyrimidine

In a 20 mL glass microwave tube 2,4-dichloro-5-fluoropyrimidine (500 mg, 2.99 mmol) and Amphos (53.0 mg, 0.075 mmol) were treated with 0.5 M cyclopropylzinc(II) bromide (7786 µL, 3.89 mmol) via syringe under an atmosphere of argon. The solution was then heated in the microwave at 70° C. for 20 min. The mixture was treated with 1N NaOH and extracted with EtOAc (25 mL), dried over MgSO$_4$, filtered and concentrated. Purification with flash chromatography (eluting with 100% DCM) afforded 2-chloro-4-cyclopropyl-5-fluoropyrimidine (263 mg, 51%) as a pale yellow viscous oil. MS (ESI, pos. ion) m/z: 173.0 (M+1). $^1$H NMR (400 MHz, CDCl$_3$) δ ppm 8.21-8.28 (1H, m), 2.24-2.34 (1H, m), 1.27-1.34 (2H, m), 1.17-1.27 (2H, m).

Preparation of compound 56b: N-tert-butyl-5-(3-(4-cyclopropyl-5-fluoropyrimidin-2-yl)-1-tosyl-1H-indol-5-yl)-1,3,4-oxadiazol-2-amine To a 5 mL glass microwave tube containing N-tert-butyl-5-(3-(4,4,5,5-tetramethyl-1,3,2-dioxaborolan-2-yl)-1-tosyl-1H-indol-5-yl)-1,3,4-oxadiazol-2-amine (166 mg, 0.309 mmol) was added 2-chloro-4-cyclopropyl-5-fluoropyrimidine (69.4 mg, 0.402 mmol), potassium phosphate (197 mg, 0.928 mmol), dicyclohexyl(2',4',6'-triisopropylbiphenyl-2-yl)phosphine (8.9 mg, 0.019 mmol), and Pd$_2$(dba)$_3$ (8.5 mg, 9.28 µmol). The tube was purged with argon, the solids were treated with dioxane (3 mL) and Water (0.3 mL), the tube was sealed, and the contents were heated in an Initiator microwave reactor (Personal Chemistry, Biotage AB, Inc., Upssala, Sweden) at 130° C. for 30 min. The mixture was treated with H$_2$O and extracted with EtOAc. The organic layer was washed with brine, dried over MgSO$_4$, filtered and concentrated. The crude material was purified by flash chromatography (eluting with 5-60% EtOAc in Hex) affording N-tert-butyl-5-(3-(4-cyclopropyl-5-fluoropyrimidin-2-yl)-1-tosyl-1H-indol-5-yl)-1,3,4-oxadiazol-2-amine (129 mg, 76%) as a light yellow viscous oil. MS (ESI, pos. ion) m/z: 547.1 (M+1).

Preparation of compound 56: N-tert-butyl-5-(3-(4-cyclopropyl-5-fluoropyrimidin-2-yl)-1H-indol-5-yl)-1,3,4-oxadiazol-2-amine 2,2,2-trifluoroacetate In a 5 mL glass microwave tube was weighed N-tert-butyl-5-(3-(4-cyclopropyl-5-fluoropyrimidin-2-yl)-1-tosyl-1H-indol-5-yl)-1,3,4-oxadiazol-2-amine (125 mg, 0.229 mmol) followed by dioxane (2 mL) and 1N NaOH (1.0 mL). The solution was heated in the microwave at 100° C. for 10 min. The mixture was treated with H$_2$O and extracted with EtOAc, washed with brine and concentrated. The crude residue was purified with reverse phase HPLC (20-95% 0.1% TFA/AcCN in 0.1% TFA/H$_2$O) affording N-tert-butyl-5-(3-(4-cyclopropyl-5-fluoropyrimidin-2-yl)-1H-indol-5-yl)-1,3,4-oxadiazol-2-amine 2,2,2-trifluoroacetate (42 mg, 36%) as a light yellow amorphous solid after drying in the genevac overnight. MS (ESI, pos. ion) m/z: 393.2 (M+1). $^1$H NMR (400 MHz, DMSO-d$_6$) δ ppm 11.91-11.99 (1H, m), 8.92 (1H, s), 8.66 (1H, d, J=2.2 Hz), 8.23 (1H, d, J=2.7 Hz), 7.65-7.71 (1H, m), 7.61 (2H, d, J=8.6 Hz), 2.33-2.44 (1H, m), 1.39-1.48 (9H, m), 1.31-1.36 (2H, m), 1.22-1.30 (2H, m).

Example 57

N-tert-butyl-5-(3-(4-ethyl-5-fluoropyrimidin-2-yl)-1H-indol-5-yl)-1,3,4-oxadiazol-2-amine

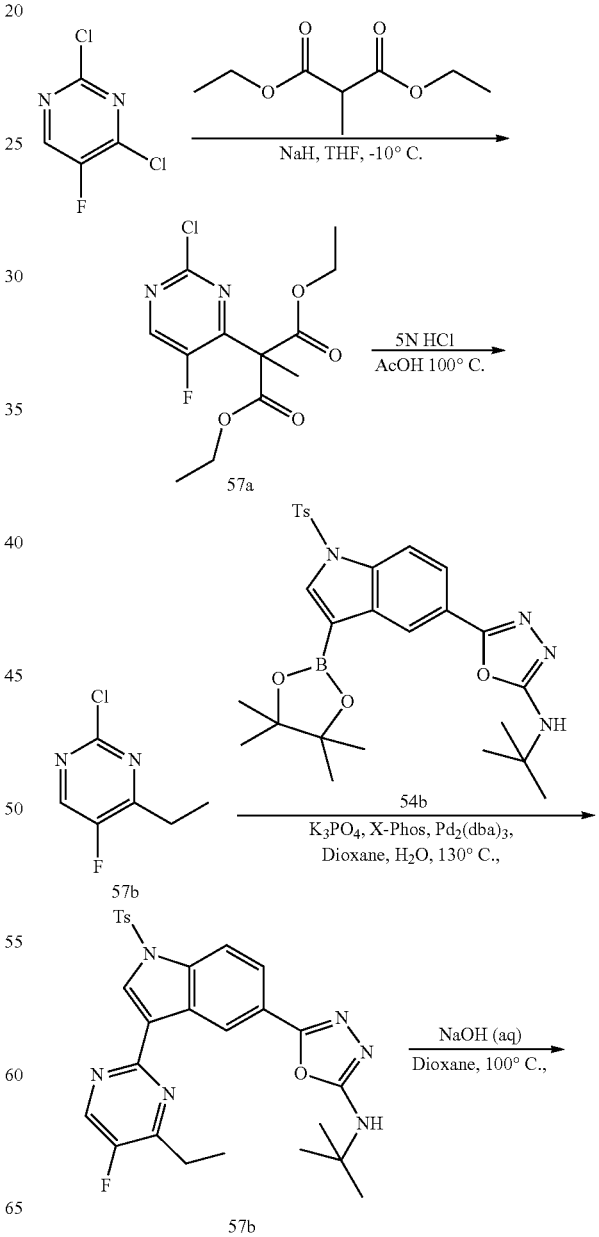

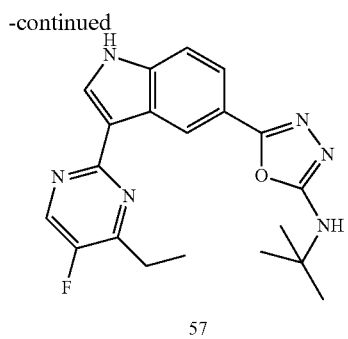

57

Preparation of compound 57a: diethyl 2-(2-chloro-5-fluoropyrimidin-4-yl)-2-methylmalonate (Prepared according to Butters, M. et al. *Org. Proc. Res. Dev.* 2001, 5, 28-36). Diethyl 2-methylmalonate (2.35 mL, 13.78 mmol) was treated with THF (80 mL) and cooled to −10° C. in a brine/ice bath. It was then treated with NaH (60 wt % suspension in mineral oil, 1.10 g, 27.6 mmol) and stirred at this temperature for 30 min. 2,4-Dichloro-5-fluoropyrimidine (2.00 g, 11.98 mmol) was suspended in THF (20 mL) and added to the cooled solution via pipette over 10 min. The solution turned an opaque yellow color. After stirring 20 min at −10° C. it was quenched by the addition of $H_2O$ (100 mL), DCM (150 mL) and glacial HOAc (ca. 1 mL to pH 6). The DCM layer was then separated and dried over $MgSO_4$, filtered and concentrated affording a viscous oil. Purification with flash chromatography (eluting with 100% DCM) afforded diethyl 2-(2-chloro-5-fluoropyrimidin-4-yl)-2-methylmalonate (3.04 g, 83%) as a pale yellow viscous oil. MS (ESI, pos. ion) m/z: 305.1 (M+1). $^1$H NMR (400 MHz, $CDCl_3$) δ ppm 8.44 (1H, d, J=2.0 Hz), 4.24-4.33 (4H, m), 1.90 (3H, s), 1.24-1.33 (9H, m).

Preparation of compound 57b: 2-chloro-4-ethyl-5-fluoropyrimidine

Diethyl 2-(2-chloro-5-fluoropyrimidin-4-yl)-2-methylmalonate (3.00 g, 9.85 mmol) was treated with glacial HOAc (25 mL) and 5N HCl (10 mL) and fitted with a reflux condenser and heated to 100° C. for 18 h. The reaction was cooled to RT and treated with $H_2O$ (30 mL) and DCM (45 mL) and the DCM layer separated and dried over $MgSO_4$, filtered and concentrated. The crude residue was purified with flash chromatography (eluting with 100% DCM) affording 2-chloro-4-ethyl-5-fluoropyrimidine (328 mg, 21%) as a viscous pale yellow oil. MS (ESI, pos. ion) m/z: 161.0 (M+1). $^1$H NMR (400 MHz, $CDCl_3$) δ ppm 8.34 (1H, s), 2.87 (2H, qd, J=7.6, 2.0 Hz), 1.29-1.37 (3H, t).

Preparation of compound 57c: N-tert-butyl-5-(3-(4-ethyl-5-fluoropyrimidin-2-yl)-1-tosyl-1H-indol-5-yl)-1,3,4-oxadiazol-2-amine To a 5 mL glass microwave tube containing N-tert-butyl-5-(3-(4,4,5,5-tetramethyl-1,3,2-dioxaborolan-2-yl)-1-tosyl-1H-indol-5-yl)-1,3,4-oxadiazol-2-amine (166 mg, 0.309 mmol) was added 2-chloro-4-ethyl-5-fluoropyrimidine (78 mg, 0.402 mmol), potassium phosphate (197 mg, 0.928 mmol), dicyclohexyl(2',4',6'-triisopropylbiphenyl-2-yl)phosphine (8.9 mg, 0.019 mmol), and $Pd_2(dba)_3$ (8.5 mg, 9.28 μmol). The tube was purged with argon, the solids were treated with dioxane (2.5 mL) and water (0.25 mL), the tube was sealed, and the contents were heated in an Initiator microwave reactor (Personal Chemistry, Biotage AB, Inc., Upssala, Sweden) at 130° C. for 30 min. The mixture was treated with $H_2O$ and extracted with EtOAc and the organic layer was washed with brine, dried over $MgSO_4$, filtered and concentrated. The crude material was purified by flash chromatography (eluting with 5-60% EtOAc in Hex) affording N-tert-butyl-5-(3-(4-ethyl-5-fluoropyrimidin-2-yl)-1-tosyl-1H-indol-5-yl)-1,3,4-oxadiazol-2-amine (124 mg, 75%) as a light yellow foam. MS (ESI, pos. ion) m/z: 535.1 (M+1). $^1$H NMR (400 MHz, $CDCl_3$) δ ppm 9.16 (1H, s), 8.46-8.53 (2H, m), 8.09 (1H, d, J=8.4 Hz), 7.94-8.00 (1H, m), 7.86 (2H, d, J=8.6 Hz), 7.25 (2H, d, J=8.6 Hz), 4.71 (1H, s), 2.89-2.99 (2H, m), 2.35 (3H, s), 1.50 (9H, s), 1.44 (3H, t, J=7.5 Hz).

Preparation of compound 57: N-tert-butyl-5-(3-(4-ethyl-5-fluoropyrimidin-2-yl)-1H-indol-5-yl)-1,3,4-oxadiazol-2-amine 2,2,2-trifluoroacetate In a 5 mL glass microwave tube was weighed N-tert-butyl-5-(3-(4-ethyl-5-fluoropyrimidin-2-yl)-1-tosyl-1H-indol-5-yl)-1,3,4-oxadiazol-2-amine (123 mg, 0.230 mmol) followed by dioxane (2 mL) and 1N NaOH (1 mL). The solution was heated in the microwave at 100° C. for 10 min. The mixture was treated with $H_2O$ and extracted with EtOAc, washed with brine and concentrated. The crude residue was purified with reverse phase HPLC (20-95% 0.1% TFA/AcCN in 0.1% TFA/$H_2O$) affording N-tert-butyl-5-(3-(4-ethyl-5-fluoropyrimidin-2-yl)-1H-indol-5-yl)-1,3,4-oxadiazol-2-amine 2,2,2-trifluoroacetate (40 mg, 35%) as a light yellow amorphous solid. MS (ESI, pos. ion) m/z: 381.2 (M+1). $^1$H NMR (400 MHz, DMSO-$d_6$) δ ppm 11.97 (1H, br. s.), 9.02 (1H, s), 8.67-8.72 (1H, m), 8.26 (1H, d, J=2.7 Hz), 7.69 (1H, d, J=8.4 Hz), 7.60 (2H, d, J=8.6 Hz), 2.89 (2H, q, J=7.4 Hz), 1.40 (9H, s), 1.34-1.39 (3H, t).

Example 58

2-(3-(6-cyclopropylpyrazin-2-yl)-1H-indol-5-yl)-5-phenyl-1,3,4-thiadiazole

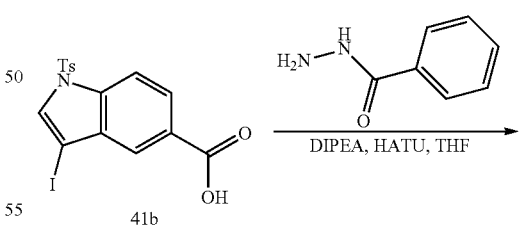

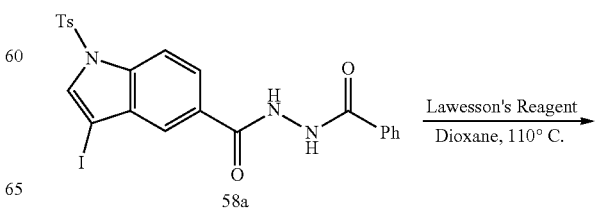

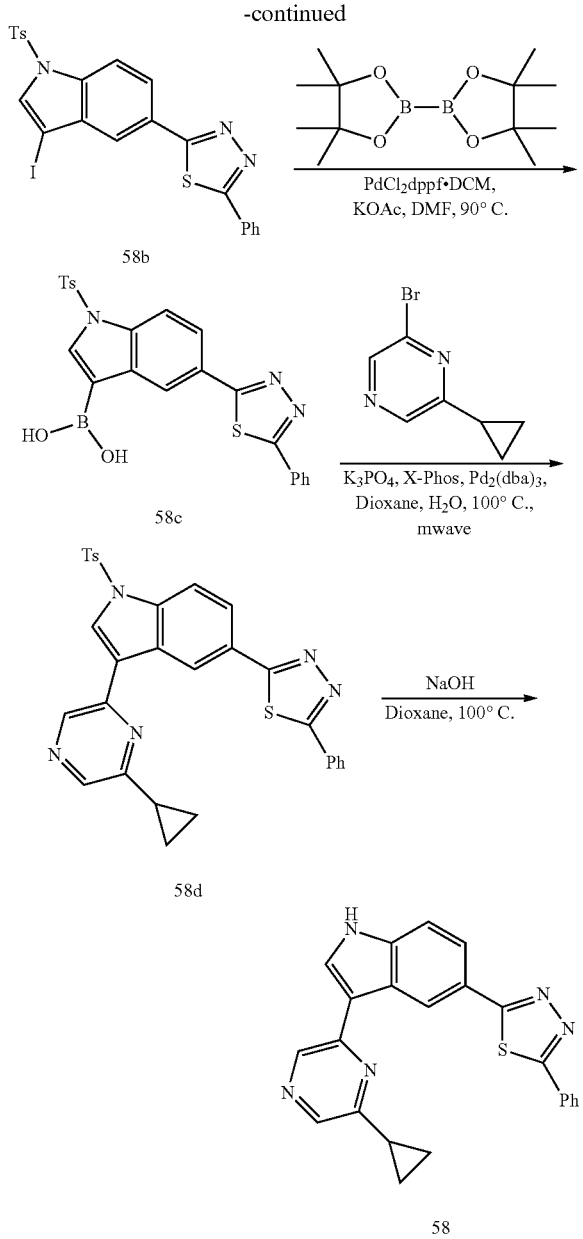

Preparation of compound 58a: N'-benzoyl-3-iodo-1-tosyl-1H-indole-5-carbohydrazide To a stirring suspension of 3-iodo-1-tosyl-1H-indole-5-carboxylic acid (515 mg, 1.17 mmol) and benzohydrazide (159 mg, 1.167 mmol) in THF (10 mL) was added N-ethyl-N-isopropylpropan-2-amine (0.51 mL, 2.92 mmol) followed by HATU (488 mg, 1.28 mmol) in one portion and the solution was stirred at RT for 2 h. The reaction was quenched with 20 mL of ice cold $H_2O$ and extracted with EtOAc (2×50 mL). The organic layer was washed with 10 mL of sat. $NaHCO_3$ followed by brine, and dried over $Na_2SO_4$. It was concentrated to about 5 mL and the precipitated solid was filtered, rinsed with EtOAc (2×2 mL). The white solid was collected and dried in a vacuum oven for 5 h at 40° C. affording N'-benzoyl-3-iodo-1-tosyl-1H-indole-5-carbohydrazide (305 mg, 47%) as an off-white crystalline solid. MS (ESI, pos. ion) m/z: 560.0 (M+1). $^1H$ NMR (400 MHz, DMSO-$D_6$) δ ppm 10.67 (1H, s), 10.52 (1H, s), 8.19 (1H, s), 8.08 (1H, d, J=8.4 Hz), 78.03-7.88 (6H, m), 7.67-7.49 (3H, m), 7.42 (2H, d, J=8.2 Hz), 2.33 (3H, s).

Preparation of compound 58b: 2-(3-iodo-1-tosyl-1H-indol-5-yl)-5-phenyl-1,3,4-thiadiazole To a suspension of N'-benzoyl-3-iodo-1-tosyl-1H-indole-5-carbohydrazide (1.29 g, 2.31 mmol) in dioxane (24 mL) at RT was added Lawesson's Reagent (1.40 g, 3.46 mmol) (Aldrich). The solution was heated to 110° C. for 3 h. The mixture was concentrated and the residue was purified with flash chromatography (eluting with 0-60% EtOAc in Hex) to give 2-(3-iodo-1-tosyl-1H-indol-5-yl)-5-phenyl-1,3,4-thiadiazole (518 mg, 40%) as a light yellow-orange crystalline solid after washing with $Et_2O$. MS (ESI, pos. ion) m/z: 557.9 (M+1). $^1H$ NMR (400 MHz, $CDCl_3$) δ ppm 7.96-8.10 (5H, m), 7.81 (2H, d, J=8.4 Hz), 7.77 (1H, s), 7.48-7.55 (3H, m), 7.28 (2H, d, J=8.2 Hz), 2.37 (3H, s).

Preparation of compound 58c: 5-(5-phenyl-1,3,4-thiadiazol-2-yl)-1-tosyl-1H-indol-3-ylboronic acid In a 20 mL microwave tube, a mixture of 2-(3-iodo-1-tosyl-1H-indol-5-yl)-5-phenyl-1,3,4-thiadiazole (493 mg, 0.884 mmol), bis(pinacolato)diboron (674 mg, 2.65 mmol), potassium acetate (434 mg, 4.42 mmol), $PdCl_2$(dppf), complex with DCM (108 mg, 0.133 mmol) and DMF (4.0 mL) was stirred at 90° C. in the oil bath for 1 h. The mixture was treated with $H_2O$, extracted with EtOAc (50 mL) and washed with brine (2×20 mL), dried over $MgSO_4$, filtered and concentrated affording a brown oil which crystallized upon standing. It was used in the next step without further purification.

Preparation of compound 58d: 2-(3-(6-cyclopropylpyrazin-2-yl)-1-tosyl-1H-indol-5-yl)-5-phenyl-1,3,4-thiadiazole To a 20 mL microwave vial was added 5-(5-phenyl-1,3,4-thiadiazol-2-yl)-1-tosyl-1H-indol-3-ylboronic acid (245 mg, 0.515 mmol), dicyclohexyl(2',4',6'-triisopropylbiphenyl-2-yl)phosphine (14.7 mg, 0.031 mmol), $Pd_2(dba)_3$ (14.2 mg, 0.015 mmol), 2-bromo-6-cyclopropylpyrazine (118 mg, 0.593 mmol) (CombiPhos Catalysts Inc.) and potassium phosphate (328 mg, 1.55 mmol) followed by purging with argon. The solids were treated with dioxane (4.0 mL) and $H_2O$ (0.4 mL) and heated in the microwave at 130° C. for 20 min. The mixture was treated with $H_2O$ and extracted with EtOAc, dried over $MgSO_4$, filtered and concentrated. The residue was purified with silica gel chromatography (eluting with 10-80% EtOAc in Hex) to give 2-(3-(6-cyclopropylpyrazin-2-yl)-1-tosyl-1H-indol-5-yl)-5-phenyl-1,3,4-thiadiazole (191 mg, 67%) as a light yellow amorphous solid. (ESI, pos. ion) m/z: 550.1 (M+1). $^1H$ NMR (400 MHz, $CDCl_3$) δ ppm 9.01 (1H, s), 8.77 (1H, s), 8.43 (1H, s), 8.17-8.22 (2H, m), 8.11-8.16 (1H, m), 8.03 (1H, dd, J=6.6, 2.8 Hz), 7.86 (2H, d, J=8.4 Hz), 7.48-7.55 (3H, m), 7.28 (2H, d, J=8.4 Hz), 2.36 (3H, s), 2.14-2.22 (1H, m), 1.29-1.34 (2H, m), 1.17-1.24 (2H, m).

Preparation of compound 58: 2-(3-(6-cyclopropylpyrazin-2-yl)-1H-indol-5-yl)-5-phenyl-1,3,4-thiadiazole In a 20 mL glass microwave tube 2-(3-(6-cyclopropylpyrazin-2-yl)-1-tosyl-1H-indol-5-yl)-5-phenyl-1,3,4-thiadiazole (190 mg, 0.346 mmol) was treated with dioxane (2.5 mL) and 1N NaOH (0.75 mL) and heated in the microwave to 100° C. for 10 min. The mixture was treated with H₂O, extracted with EtOAc (2×15 mL), washed with brine, dried over MgSO₄, filtered and concentrated affording 2-(3-(6-cyclopropylpyrazin-2-yl)-1H-indol-5-yl)-5-phenyl-1,3,4-thiadiazole (89 mg, 65%) as a yellow amorphous solid. (ESI, pos. ion) m/z: 396.0 (M+1). ¹H NMR (400 MHz, DMSO-d₆) δ ppm 12.06 (1H, br. s.), 9.13 (1H, s), 8.96 (1H, s), 8.43 (1H, d, J=2.5 Hz), 8.40 (1H, s), 7.99-8.08 (2H, m), 7.89-7.96 (1H, m), 7.58-7.69 (4H, m), 2.23-2.32 (1H, m), 1.17-1.30 (4H, m).

Example 59

N-isopropyl-5-(3-(4-methoxypyrimidin-2-yl)-1H-indol-5-yl)-1,3,4-oxadiazol-2-amine

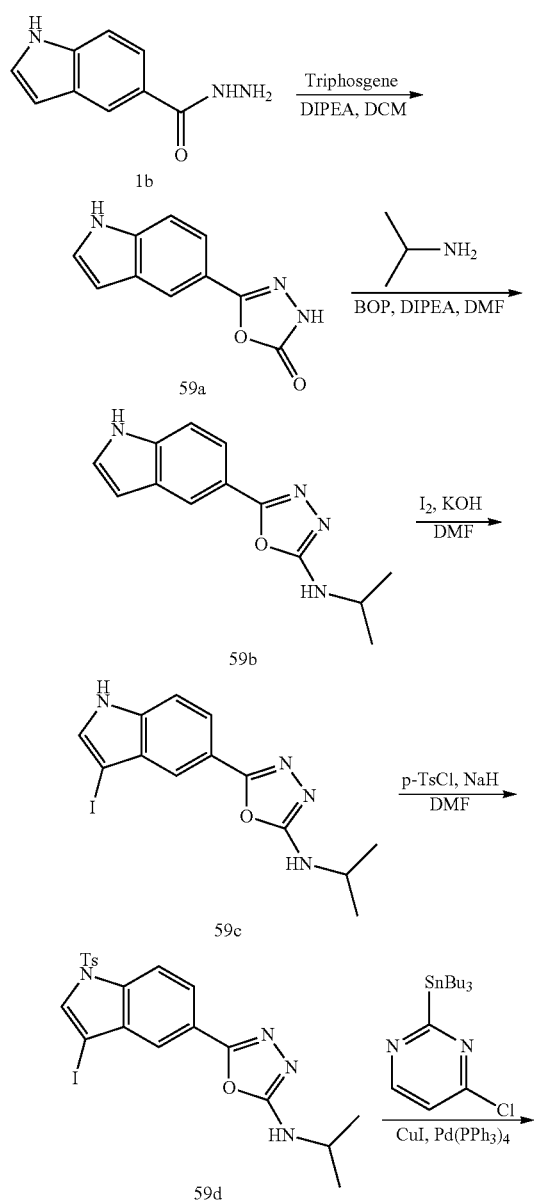

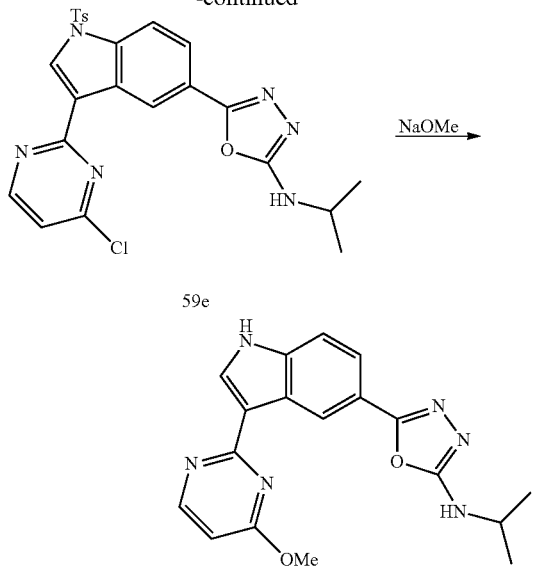

Preparation of compound 59a: 5-(1H-indol-5-yl)-1,3,4-oxadiazol-2(3H)-one

To a suspension of 1H-indole-5-carbohydrazide (200 mg, 1.142 mmol) in DCM (10 mL) was added DIPEA (0.39 mL, 2.285 mmol) drop wise at RT and the reaction was stirred for 5 min. To the reaction was added a solution of triphosgene (338 mg, 1.142 mmol) in DCM (10 mL) drop wise and the reaction was further stirred for 1 h. Then the reaction was concentrated and quenched with 10M aq.NaHCO₃ (10 mL) to get off white precipitate. The precipitate was filtered, washed with H₂O (10 mL) and dried. The solid was triturated with petroleum ether (3×10 mL) to afford 5-(1H-indol-5-yl)-1,3, 4-oxadiazol-2(3H)-one (30 mg, 13%) as off white colored solid. MS (ESI, pos. ion) m/z: 202.2 (M+1).

Preparation of compound 59b: 5-(1H-indol-5-yl)-N-isopropyl-1,3,4-oxadiazol-2-amine To a solution of 5-(1H-indol-5-yl)-1,3,4-oxadiazol-2(3H)-one (200 mg, 0.995 mmol) in DMF (2 mL) was added isopropyl amine (0.169 mL, 1.99 mmol), diphenyl ether (161 mg, 0.995 mmol), and DIPEA (0.34 mL, 1.99 mmol) and the reaction was stirred at RT for 5 min. To the above mixture at RT was added BOP reagent (461 mg, 1.045 mmol) and the reaction was further stirred for 18 h at RT. The mixture was treated with H₂O (10 mL) to get off white precipitate. The precipitate was filtered, washed with H₂O (10 mL) and dried. The solid was further triturated with petroleum ether (2×5 mL) to afford 5-(1H-indol-5-yl)-N-isopropyl-1,3,4-oxadiazol-2-amine (150 mg, 62%) as an off white solid. MS (ESI, pos. ion) m/z: 243.1 (M+1); ¹H NMR (400 MHz, DMSO-d₆): δ 11.40 (brs, 1H), 7.98 (s, 1H), 7.59 (dd, J=6.8, 1.6 Hz, 1H), 7.51 (t, J=7.2 Hz, 2H), 7.44 (m, 1H), 3.70-3.75 (m, 1H), 1.22 (d, J=6.4 Hz, 6H).

Preparation of compound 59c: 5-(3-iodo-1H-indol-5-yl)-N-isopropyl-1,3,4-oxadiazol-2-amine To a solution of 5-(1H-indol-5-yl)-N-isopropyl-1,3,4-oxadiazol-2-amine (150 mg, 0.6148 mmol) in DMF (1.5 mL) was added 1.2M aq. KOH (1.5 mL) and the reaction was stirred at 0° C. for 5 min. I₂ (234 mg, 0.9297 mmol) was added and the mixture was stirred for additional 1 h. The reaction was quenched with H₂O (10 mL) to get a pink precipitate. The precipitate was filtered, washed with H₂O (6 mL) and dried. The crude product was purified with silica-gel column chromatography (eluent: 50% EtOAc in petroleum ether) to give 5-(3-iodo-1H-indol-5-yl)-N-isopropyl-1,3,4-oxadiazol-2-amine (140 mg, 61%) as a pink solid. MS (ESI, pos. ion) m/z: 369.1 (M+1); ¹H NMR (400 MHz, DMSO-d₆): δ 11.85 (brs, 1H), 7.68 (m, 2H), 7.65 (m, 1H), 7.62 (d, J=7.2 Hz, 1H), 7.55 (d, J=8.4 Hz, 1H), 3.70-3.75 (m, 1H), 1.20 (d, J=6.4 Hz, 6H).

Preparation of compound 59d: 5-(3-iodo-1-tosyl-1H-indol-5-yl)-N-isopropyl-1,3,4-oxadiazol-2-amine To a solution of 5-(3-iodo-1H-indol-5-yl)-N-isopropyl-1,3,4-oxadiazol-2-amine (14 g, 38.04 mmol) in THF (140 mL) was added 60% NaH in mineral oil (4.5 g, 114.12 mmol) at 10° C. and the mixture was stirred for 5 min. To the mixture at 10° C. was added p-TsCl (10.84 g, 57.06 mmol) and the reaction was further stirred for 1 h. The reaction was quenched with H₂O (200 mL) to get an off white precipitate. The precipitate was filtered, washed with H₂O (2×100 mL) and dried. The crude was purified with silica-gel column chromatography (eluent: 50% EtOAc in petroleum ether) to afford 5-(3-iodo-1-tosyl-1H-indol-5-yl)-N-isopropyl-1,3,4-oxadiazol-2-amine (11.2 g, 56%) as an off white colored solid. MS (ESI, pos. ion) m/z: 523.2 (M+1); ¹H-NMR (400 MHz, DMSO-d₆): δ 8.21 (brs, 1H), 8.13 (d, J=12 Hz, 1H), 7.98 (s, 1H), 7.95 (s, 1H), 7.91 (dd, J=12, 4 Hz, 1H), 7.81 (d, J=8 Hz, 1H), 7.69 (d, J=4 Hz, 1H), 7.44 (d, J=12 Hz, 2H), 3.82 (m, 1H), 2.33 (s, 3H), 1.22 (d, J=8.4 Hz, 6H).

Preparation of compound 59e: 5-(3-(4-chloropyrimidin-2-yl)-1-tosyl-1H-indol-5-yl)-N-isopropyl-1,3,4-oxadiazol-2-amine A glass microwave reaction vessel was charged with 5-(3-iodo-1-tosyl-1H-indol-5-yl)-N-isopropyl-1,3,4-oxadiazol-2-amine (1.00 g, 1.914 mmol) and 4-chloro-2-(tributylstannyl)pyrimidine (0.966 g, 2.393 mmol) in DMF (5 mL) followed by Pd(PPh₃)₄ (0.111 g, 0.096 mmol, Strem) and CuI (0.072 g, 0.383 mmol, Aldrich). The reaction was stirred and heated in a Initiator microwave reactor at 100° C. for 1 h. The mixture was then diluted with DCM and washed with H₂O, brine. The organic layer was dried (MgSO₄), filtered and concentrated. The residue was purified with flash chromatography (eluent: 25%-60% EtOAc in Hexanes) to give 5-(3-(4-chloropyrimidin-2-yl)-1-tosyl-1H-indol-5-yl)-N-isopropyl-1,3,4-oxadiazol-2-amine (550 mg, 1.081 mmol, 56.4%) as a green solid. MS (ESI, pos. ion) m/z: 508.9 (M+1).

Preparation of compound 59: N-isopropyl-5-(3-(4-methoxypyrimidin-2-yl)-1H-indol-5-yl)-1,3,4-oxadiazol-2-amine A glass microwave reaction vessel was charged with 5-(3-(4-chloropyrimidin-2-yl)-1-tosyl-1H-indol-5-yl)-N-isopropyl-1,3,4-oxadiazol-2-amine (50 mg, 0.098 mmol) and sodium methoxide (18.57 mg, 0.344 mmol, Alfa Aesar) in MeOH (1 mL). The reaction was stirred and heated in a Initiator microwave reactor at 85° C. for 30 min and 100° C. for 1 h. The solvent was removed and the residue was purified with RP-HPLC (eluent: 10-50% MeCN in water with 0.1% TFA). The fractions containing the product were combined and concentrated to remove AcCN. The remaining mixture was neutralized with NH₄OH and filtered and dried to give N-isopropyl-5-(3-(4-methoxypyrimidin-2-yl)-1H-indol-5-yl)-1,3,4-oxadiazol-2-amine (21.0 mg, 0.060 mmol, 61.0%) as an off-white solid. MS (ESI, pos. ion) m/z: 351.0 (M+1). ¹H NMR (400 MHz, DMSO-d₆) δ ppm 11.98 (1H, br. s.), 9.04 (1H, s), 8.52 (1H, d, J=5.7 Hz), 8.32 (1H, s), 7.69 (1H, d, J=8.6 Hz), 7.58 (2H, dd, J=13.4, 7.9 Hz), 6.68 (1H, d, J=5.7 Hz), 4.09 (3H, s), 3.66-3.82 (1H, m), 1.23 (6H, d, J=6.5 Hz)

Example 60

5-(3-(4-isopropoxypyrimidin-2-yl)-1H-indol-5-yl)-N-isopropyl-1,3,4-oxadiazol-2-amine

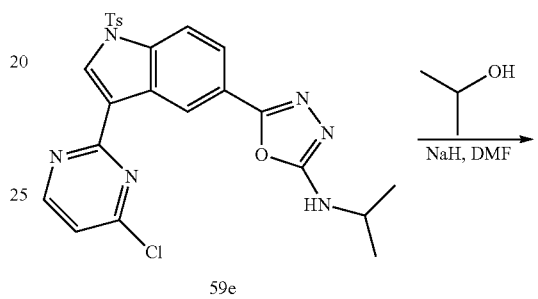

59e

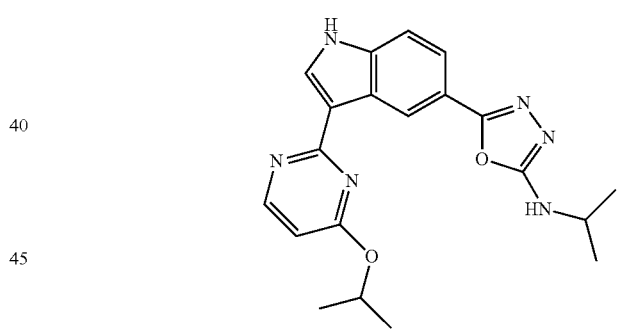

60

A glass microwave reaction vessel was charged with IPA (1 mL, 13.06 mmol) and 5-(3-(4-chloropyrimidin-2-yl)-1-tosyl-1H-indol-5-yl)-N-isopropyl-1,3,4-oxadiazol-2-amine (80 mg, 0.157 mmol), followed by the addition of 60% of NaH in mineral oil (15.72 mg, 0.393 mmol, Aldrich). The reaction was stirred and heated in a Initiator microwave reactor at 100° C. for 30 min, then the solvent was removed. The residue was purified with RP-HPLC (eluent: 10-50% MeCN in water with 0.1% TFA). The fractions containing the product were combined and concentrated to remove AcCN. The remaining mixture was neutralized with NH₄OH and filtered and dried to give 5-(3-(4-isopropoxypyrimidin-2-yl)-1H-indol-5-yl)-N-isopropyl-1,3,4-oxadiazol-2-amine (6.0 mg, 0.016 mmol, 10.09%) as an off-white solid. MS (ESI, pos. ion) m/z: 379.1 (M+1); ¹H NMR (400 MHz, DMSO-d₆) δ ppm 11.99 (1H, br. s.), 9.00 (1H, s), 8.50 (1H, d, J=5.7 Hz), 8.30 (1H, s), 7.52-

7.72 (3H, m), 6.60 (1H, d, J=5.9 Hz), 5.47-5.62 (1H, m), 3.67-3.81 (1H, m), 1.42 (6H, d, J=6.1 Hz), 1.23 (6H, d, J=6.5 Hz).

Example 61

4-(2-(5-(5-(isopropylamino)-1,3,4-oxadiazol-2-yl)-1H-indol-3-yl)pyrimidin-4-yl)-1-methylpiperazin-2-one

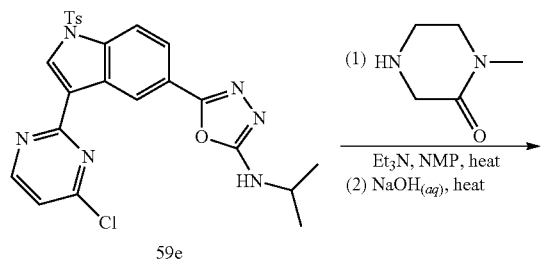

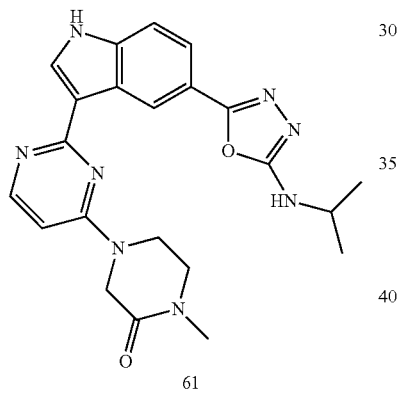

A glass microwave reaction vessel was charged with 5-(3-(4-chloropyrimidin-2-yl)-1-tosyl-1H-indol-5-yl)-N-isopropyl-1,3,4-oxadiazol-2-amine (80 mg, 0.157 mmol) and 1-methylpiperazin-2-one (17.94 mg, 0.157 mmol) in NMP (1.0 mL), followed by Et₃N (65.6 µL, 0.472 mmol, Aldrich). The reaction was stirred and heated in a Initiator microwave reactor at 100° C. for 30 min. Then aq. NaOH (5 M, 0.3 mL) was added and the reaction was heated in microwave at 100° C. for 20 min. The mixture was purified with RP-HPLC (eluent: 10-60% MeCN in water with 0.1% TFA) and the fractions containing the product were combined and concentrated to remove AcCN. The remaining mixture was neutralized with sat. NaHCO₃ and extracted with CHCl₃/iPrOH (4:1). The combined organic layers were dried, filtered and concentrated to give 4-(2-(5-(5-(isopropylamino)-1,3,4-oxadiazol-2-yl)-1H-indol-3-yl)pyrimidin-4-yl)-1-methylpiperazin-2-one (30.0 mg, 0.069 mmol, 44.1%) as a light yellow solid. MS (ESI, pos. ion) m/z: 433.1 (M+1); ¹H NMR (400 MHz, DMSO-d₆) δ ppm 11.88 (1H, br. s.), 9.10 (1H, s), 8.30 (1H, d, J=6.1 Hz), 8.23 (1H, d, J=2.7 Hz), 7.60-7.73 (2H, m), 7.56 (1H, d, J=8.4 Hz), 6.69 (1H, d, J=6.1 Hz), 4.40 (2H, br. s.), 3.93 (2H, br. s.), 3.75 (1H, dq, J=13.3, 6.5 Hz), 3.51 (2H, t, J=5.2 Hz), 2.97 (3H, s), 1.25 (6H, d, J=6.8 Hz), 1.24 (3H, s).

Example 62

N-isopropyl-5-(3-(4-((1-methylpiperidin-3-yl)oxy)pyrimidin-2-yl)-1H-indol-5-yl)-1,3,4-oxadiazol-2-amine 2,2,2-trifluoroacetate

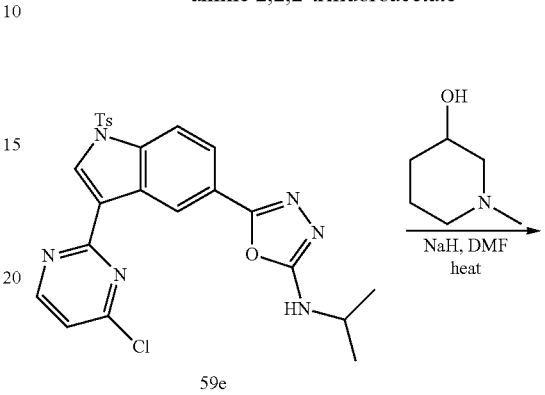

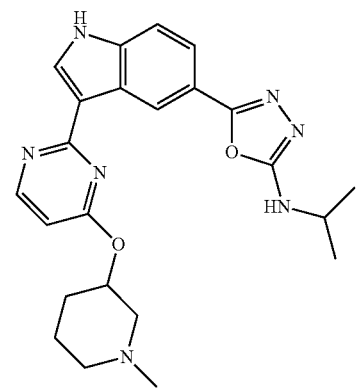

A glass microwave reaction vessel was charged with 1-methylpiperidin-3-ol (67.9 mg, 0.589 mmol, Aldrich) and NaH, 60% dispersion in mineral oil (23.57 mg, 0.589 mmol) in DMF (2 mL). The mixture was stirred 10 min at RT and a solution of 5-(3-(4-chloropyrimidin-2-yl)-1-tosyl-1H-indol-5-yl)-N-isopropyl-1,3,4-oxadiazol-2-amine (100 mg, 0.196 mmol) in DMF (2 mL) was added. The reaction was stirred in an oil bath at 85° C. for 2 h. The mixture was purified with RP-HPLC (eluent: 5-40% MeCN in water with 0.1% TFA) to give the TFA salt of N-isopropyl-5-(3-(4-(1-methylpiperidin-3-yloxy)pyrimidin-2-yl)-1H-indol-5-yl)-1,3,4-oxadiazol-2-amine 2,2,2-trifluoroacetate (43.5 mg, 41%) as a white solid. MS (ESI, pos. ion) m/z: 434.0 (M+1); ¹H NMR (400 MHz, DMSO-d₆) δ ppm 12.00-12.15 (1H, m), 9.43 (1H, br. s.), 9.01 (1H, s), 8.57-8.68 (1H, m), 8.32-8.45 (1H, m), 7.59-7.75 (3H, m), 6.67-6.77 (1H, m), 5.78 (1H, br. s.), 3.70-3.92 (2H, m), 3.36-3.51 (1H, m), 2.98-3.20 (1H, m), 2.91 (1H, d, J=4.3 Hz), 2.83 (2H, d, J=4.5 Hz), 1.80-2.25 (4H, m), 1.26 (6H, d, J=6.5 Hz), 1.25 (3H, s).

Example 63

5-(3-(6-isopropoxypyridin-2-yl)-1H-indol-5-yl)-1,2,4-thiadiazol-3-amine

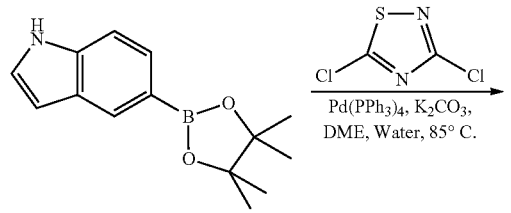

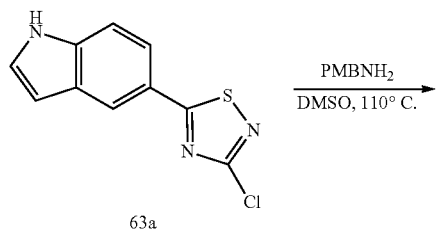

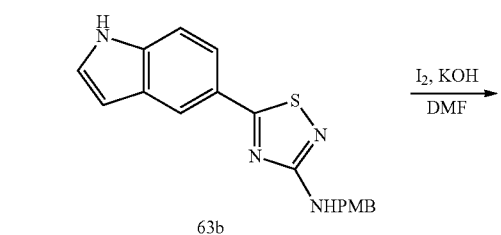

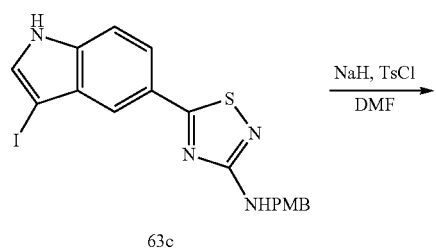

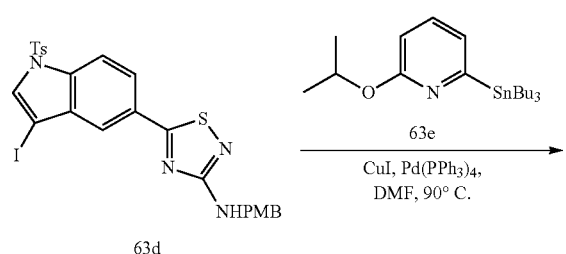

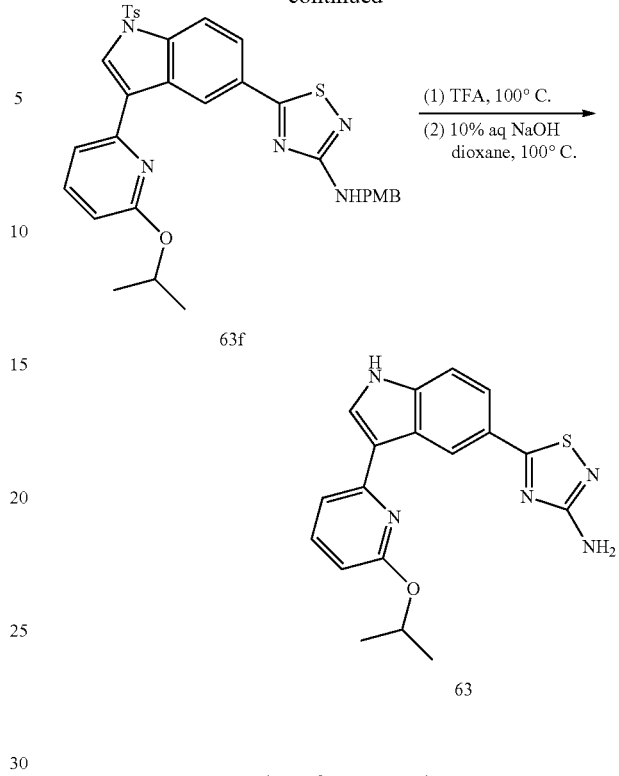

Preparation of compound 63a: 3-chloro-5-(1H-indol-5-yl)-1,2,4-thiadiazole

To a mixture of 5-(4,4,5,5-tetramethyl-1,3,2-dioxaborolan-2-yl)-1H-indole (2 g, 8.23 mmol, Aldrich) and 3,5-dichloro-1,2,4-thiadiazole (1.27 g, 8.23 mmol, Aldrich) in 1,2-dimethoxy ethane (30 mL)/H$_2$O (10 mL) was added K$_2$CO$_3$ (2.27 g, 16.46 mmol) and Pd(PPh$_3$)$_4$ (0.95 g, 0.82 mmol). N$_2$ gas was purged for 15 min through the mixture. The reaction was heated at reflux at 85° C. for 6 h. The mixture was cooled to RT and quenched with H$_2$O (100 mL) and was extracted with EtOAc (2×100 mL). The organic layer was dried over anhydrous Na$_2$SO$_4$ and concentrated. The residue was purified by silica-gel column chromatography (eluent: 5% EtOAc in petroleum ether) to give 3-chloro-5-(1H-indol-5-yl)-1,2,4-thiadiazole (680 mg, 35.5%) as an off white solid. MS (ESI, pos. ion) m/z: 236 (M+1); $^1$H-NMR (300 MHz, CDCl$_3$): δ 8.5 (brs, 1H), 8.29 (d, J=0.8 Hz, 1H), 7.78 (dd, J=8.4, 1.8 Hz, 1H), 7.49 (d, J=8.7 Hz, 1H), 7.32-7.31 (m, 1H), 6.67 (t, J=2.1 Hz, 1H).

Preparation of compound 63b: 5-(1H-indol-5-yl)-N-(4-methoxybenzyl)-1,2,4-thiadiazol-3-amine A mixture of 3-chloro-5-(1H-indol-5-yl)-1,2,4-thiadiazole (0.67 g, 2.85 mmol) and 4-methoxybenzylamine (1.95 g, 14.25 mmol, Aldrich) in DMSO (7 mL) was stirred for 12 h at 110° C. The reaction was cooled to RT and quenched with ice cold water (50 mL) and extracted into EtOAc (20 mL). The aqueous layer was back extracted with EtOAc (20 mL). The combined organic layers were dried over anhydrous Na$_2$SO$_4$ and concentrated in vacuo. The residue was purified by using silica-gel column chromatography (eluent: 30-40% EtOAc and petroleum ether) to give 5-(1H-indol-5-yl)-N-(4-methoxybenzyl)-1,2,4-thiadiazol-3-amine (670 mg, 70.5%) as a off brown solid. MS (ESI, pos. ion) m/z: 337.1 (M+1); $^1$H-NMR (300 MHz, CDCl$_3$): δ 8.44 (brs, 1H), 8.21 (d, J=9

Hz, 1H), 7.73 (dd, J=8.4, 1.8 Hz, 1H), 7.45 (d, J=8.4 Hz, 1H), 7.35 (d, J=8.7 Hz, 2H), 7.28-7.26 (m, 1H), 6.90 (dd, J=6.9, 2.1 Hz, 2H), 6.64 (m, 1H), 5.42 (m, 1H), 4.62 (d, J=7.6 Hz, 1H), 3.80 (s, 3H).

Preparation of compound 63c: 5-(3-iodo-1H-indol-5-yl)-N-(4-methoxybenzyl)-1,2,4-thiadiazol-3-amine To a solution of 5-(1H-indol-5-yl)-N-(4-methoxybenzyl)-1,2,4-thiadiazol-3-amine (0.67 g, 1.99 mmol) in DMF (7 mL) was added KOH pellets (0.325 g, 5.95 mmol) followed by $I_2$ (1 g, 3.98 mmol) in portions at 0° C. The reaction was stirred for 1 h at RT. 10% aq sodium bisulphite solution was added to the mixture and solid precipitate was obtained. The suspension was filtered and washed with $H_2O$ (2×20 mL) and dried under vacuum to give 5-(3-iodo-1H-indol-5-yl)-N-(4-methoxybenzyl)-1,2,4-thiadiazol-3-amine (800 mg, 87%) as an off brown solid. MS (ESI, pos. ion) m/z: 463.0 (M+1); $^1$H-NMR (300 MHz, CDCl$_3$): δ 8.72 (brs, 1H), 8.02 (d, J=6 Hz, 1H), 7.77 (d, J=8.4 Hz, 1H), 7.43 (d, J=8.7 Hz, 1H), 7.36-7.33 (m, 2H), 6.90 (d, J=8.4 Hz, 1H), 5.43 (m, 1H), 4.63 (d, J=5.7 Hz, 2H), 3.80 (s, 3H).

Preparation of compound 63d: 5-(3-iodo-1-tosyl-1H-indol-5-yl)-N-(4-methoxybenzyl)-1,2,4-thiadiazol-3-amine To a solution of 5-(3-iodo-1H-indol-5-yl)-N-(4-methoxybenzyl)-1,2,4-thiadiazol-3-amine (0.8 g, 1.73 mmol) in DMF (8 mL) was added 60% NaH (0.067 g, 2.77 mmol) portion wise and the reaction was stirred at 0° C. for 10 min. To the above mixture, p-TsCl (0.53 g, 2.59 mmol) in DMF (1 mL) was added in one portion and the reaction was stirred for additional 2 h at RT. The reaction mixture was treated with ice water to generate off white precipitate. The precipitate was filtered, washed with $H_2O$ (2×20 mL) and vacuum dried. The solid was further re-crystallized with 20% EtOAc in petroleum ether to give 5-(3-iodo-1-tosyl-1H-indol-5-yl)-N-(4-methoxybenzyl)-1,2,4-thiadiazol-3-amine (0.78 g, 73.5%) as an off brown solid. MS (ESI, pos. ion) m/z: 617.0 (M+1); $^1$H-NMR (400 MHz, CDCl$_3$): δ 8.04 (d, J=8.4 Hz, 1H), 7.88-7.84 (m, 2H), 7.43 (d, J=8.4 Hz, 2H), 7.34 (d, J=8.4 Hz, 7.6 Hz, 1H), 4.61 (s, 2H), 3.80 (s, 3H), 2.37 (s, 3H).

Preparation of compound 63e: 2-isopropoxy-6-(tributylstannyl)pyridine

Sodium pieces (200 mg) was added portion wise to 2-propanol (0.521 g, 6.35 mmol) and the reaction was stirred for 12 h at RT. To the above thick solution, 2,6-dibromo pyridine (1 g, 4.23 mmol, Aldrich) was added and the reaction was heated to 90° C. for 2 h. The mixture was cooled to RT and the solvent was removed. The crude residue was treated with ice water (10 mL) and extracted with EtOAc (2×25 mL). The combined organic layers were dried over anhydrous $Na_2SO_4$ and concentrated. The residue was purified with silica gel column chromatography (Eluent: 0.5% EtOAc in petroleum ether) to give 2-bromo-6-isopropoxypyridine (600 mg, 66.5%) as a colorless liquid. MS (ESI, pos. ion) m/z: 216.0 (M+1); $^1$H-NMR (400 MHz, CDCl$_3$): δ 7.38-7.34 (m, 1H), 6.99 (dd, J=7.2 Hz, J=4 Hz 1H), 6.60 (dd, J=8.0 Hz, J=4 Hz 1H). 5.28-5.25 (m, 1H), 1.32 (d, J=4.4 Hz, 6H). A solution of 2-bromo-6-isopropoxypyridine (1 g, 4.67 mmol) in dry THF (10 mL) was treated with n-BuLi (1.6M in hexane) (3.2 mL, 5.14 mmol) dropwise at −78° C. and the reaction was stirred at the same temperature for 30 min. Tributyl tin chloride (1.8 mL, 5.60 mmol, Aldrich) was added to the reaction at −78° C. and the reaction was stirred at the same temperature for 30 min. The mixture was treated with saturated $NH_4Cl$ solution (10 mL) and extracted with EtOAc (25 mL). The organic layer was dried over anhydrous $Na_2SO_4$, concentrated in vacuo. The residue was purified with silica gel column chromatography using (eluent: 100% petroleum ether) to give 2-isopropoxy-6-(tributylstannyl)pyridine (1 g, 50%) as a colorless liquid. $^1$H-NMR (300 MHz, CDCl$_3$): δ 7.40-7.35 (m, 1H), 6.99 (dd, J=5.4, 4.5 Hz, 1H), 6.65 (dd, J=7.2, 0.6 Hz, 1H). 5.32-5.24 (m, 1H), 1.34-1.32 (m, 10H), 1.31-1.25 (m, 13H), 0.87-0.84 (m, 10H).

Preparation of compound 63f: 5-(3-(6-isopropoxypyridin-2-yl)-1-tosyl-1H-indol-5-yl)-N-(4-methoxybenzyl)-1,2,4-thiadiazol-3-amine A solution of 5-(3-iodo-1-tosyl-1H-indol-5-yl)-N-(4-methoxybenzyl)-1,2,4-thiadiazol-3-amine (0.8 g, 1.29 mmol) and 2-isopropoxy-6-(tributylstannyl)pyridine (0.83 g, 1.95 mmol) in DMF (8 mL) was bubbled with Argon for 15 min. To the above mixture was added CuI (0.124 g, 0.65 mmol) and Pd(PPh$_3$)$_4$ (0.15 g, 0.13 mmol) and argon gas was purged for another 15 min. The reaction was heated at 90° C. for 1 h. The mixture was treated with ice cold water (20 mL) to obtain off white precipitate. The precipitate was filtered, washed with $H_2O$ (20 mL) and dried. The solid was purified by basic alumina chromatography (eluent: 20% EtOAc in petroleum ether) to give 5-(3-(6-isopropoxypyridin-2-yl)-1-tosyl-1H-indol-5-yl)-N-(4-methoxybenzyl)-1,2,4-thiadiazol-3-amine (0.35 g, 43%) as a white solid. MS (ESI, pos. ion) m/z: 625.2 (M+1); $^1$H-NMR (400 MHz, CDCl$_3$): δ 9.02 (d, J=1.2 Hz, 1H), 8.10-8.08 (m, 2H), 7.96 (dd, J=8.8, 2.0 Hz, 1H), 7.83 (d, J=8.4 Hz, 2H), 7.64 (t, J=8.0 Hz, 1H), 7.34-7.24 (m, 2H) 4.62 (d, J=5.6 Hz, 2H), 3.80 (s, 3H), 2.35 (s, 3H), 1.46 (d, J=5.6 Hz, 6H).

Preparation of compound 63: 5-(3-(6-isopropoxypyridin-2-yl)-1H-indol-5-yl)-1,2,4-thiadiazol-3-amine A solution of 5-(3-(6-isopropoxypyridin-2-yl)-1-tosyl-1H-indol-5-yl)-N-(4-methoxybenzyl)-1,2,4-thiadiazol-3-amine (0.35 g, 0.56 mmol) in TFA (3.5 mL) was heated in a Biotage microwave at 100° C. for 30 min. The reaction was cooled to RT. TFA was removed in vacuo and the residue was washed with Et$_2$O (7 mL) to get the crude product (250 mg), which was used in next step without further purification. MS (ESI, pos. ion) m/z: 506.1 (M+1). To a solution of crude 5-(3-(6-isopropoxypyridin-2-yl)-1-tosyl-1H-indol-5-yl)-1,2,4-thiadiazol-3-amine (0.25 g, 0.442 mmol) in 1,4-dioxane (2.5 mL) was added 10% aq NaOH (1.3 mL) and the reaction was heated at 100° C. for 2 h. The mixture was treated with ice cold water (10 mL), resulting a white precipitate. The precipitate was filtered and washed with ice cold water (~10 mL) and dried under vacuum. The solid was purified by preparative HPLC (eluent: 10-70% MeCN:MeOH (1:1) in H$_2$O with 0.01% TFA) to give 5-(3-(6-isopropoxypyridin-2-yl)-1H-indol-5-yl)-1,2,4-thiadiazol-3-amine (30 mg, 17.5%). MS (ESI, pos. ion) m/z: 352.1 (M+1); $^1$H-NMR (400 MHz, DMSO-d$_6$): δ 11.96 (s, 1H), 9.05 (d, J=1.2 Hz, 1H), 8.25 (d, J=2.8 Hz, 1H), 7.76 (dd, J=8.4, 1.6 Hz, 1H), 7.69-7.65 (m, 2H), 7.64 (d, J=8.4 Hz, 1H), 7.46 (t, J=7.2 Hz, 2H), 6.70 (s, 2H), 6.54 (d, J=8 Hz, 1H), 5.61-5.55 (m, 1H), 1.52 (d, J=5.6 Hz, 6H).

Example 64

5-(3-(6-(isopropylamino)pyrazin-2-yl)-1H-indol-5-yl)-1,2,4-thiadiazol-3-amine

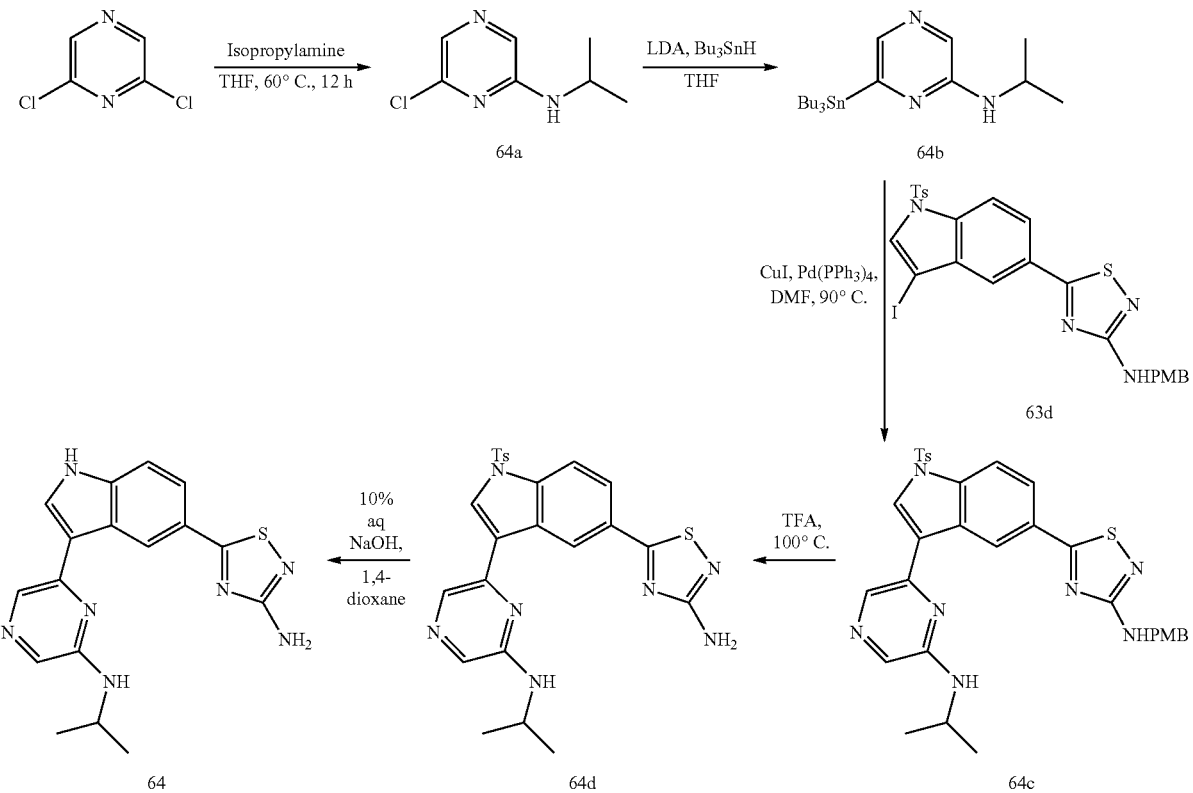

Preparation of compound 64a: 6-chloro-N-isopropylpyrazin-2-amine

To a mixture of 2,6-dichloropyrazine (5 g, 33.78 mmolm, Aldrich) and isopropyl amine (2.4 g, 50.67 mmol, Aldrich) in dry THF (5 mL) was added Et$_3$N (2.5 mL) and the reaction was stirred at 60° C. for 12 h. The reaction was cooled to RT, treated with ice cold water (~25 mL) and extracted with EtOAc (2×25 mL). The combined organic layers were dried over anhydrous Na$_2$SO$_4$ and concentrated. The residue was triturated with n-pentane to give 6-chloro-N-isopropylpyrazin-2-amine (3 g, 52.5%) as a white solid. MS (ESI, pos. ion) m/z: 172.0 (M+1); $^1$H-NMR (400 MHz, DMSO-d$_6$): δ 7.81 (s, 1H), 7.64 (s, 1H), 7.46 (d, J=7.2 Hz, 1H), 3.93-3.88 (m, 1H), 1.15 (d, J=5.6 Hz, 6H).

Preparation of compound 64b: N-isopropyl-6-(tributylstannyl)pyrazin-2-amine

To a solution of tributyl tin hydride (8.5 mL, 29.23 mmol, Aldrich) in THF (50 mL) was added LDA (2.0 M) (THF/heptane/ethyl benzene) (18.3 mL, 29.23 mmol, Aldrich) at 0° C. and the mixture was stirred for 10 min at RT. To the mixture at 0-5° C. was added 6-chloro-N-isopropylpyrazin-2-amine (2.5 g, 14.61 mmol) and the mixture was stirred for an additional 3 h at RT. The reaction was quenched with 10% aq KF (25 mL) and extracted with EtOAc (2×25 mL). The combined organic layers were dried over anhydrous Na$_2$SO$_4$ and concentrated. The residue was further purified with basic alumina column chromatography (eluent: 10% EtOAc in petroleum ether) to give N-isopropyl-6-(tributylstannyl)pyrazin-2-amine (2 g, 26.5%) as a colorless liquid. MS (ESI, pos. ion) m/z: 428.2 (M+1); $^1$H-NMR (400 MHz, CDCl$_3$): δ 7.77 (s, 1H), 7.64 (s, 1H), 4.28-4.23 (m, 1H), 4.09-3.98 (m, 1H), 1.63-1.54 (m, 7H), 1.39-1.23 (m, 14H), 1.12-1.08 (m, 6H), 0.91-0.88 (q, 6H).

Preparation of compound 64c: 5-(3-(6-(isopropylamino)pyrazin-2-yl)-1-tosyl-1H-indol-5-yl)-N-(4-methoxybenzyl)-1,2,4-thiadiazol-3-amine A solution of 5-(3-iodo-1-tosyl-1H-indol-5-yl)-N-(4-methoxybenzyl)-1,2,4-thiadiazol-3-amine (0.78 g, 1.26 mmol) and N-isopropyl-6-(tributylstannyl)pyrazin-2-amine ((0.65 g, 1.52 mmol) in DMF (8 mL) was purged with argon for 15 min. To the above mixture, CuI (0.289 g, 1.52 mmol) and Pd(PPh$_3$)$_4$ (0.146 g, 0.126 mmol) was added and argon gas was purged for another 15 min. The reaction was heated at 90° C. for 1 h, then cooled to RT. The mixture was treated with ice cold H$_2$O to obtain off brown precipitate. The precipitate was filtered and washed with H$_2$O and dried. The crude was purified by neutral alumina column chromatography (eluent: 20% EtOAc in petroleum ether) to give 5-(3-(6-(isopropylamino)pyrazin-2-yl)-1-tosyl-1H-indol-5-yl)-N-(4-methoxybenzyl)-1,2,4-thiadiazol-3-amine (0.5 g, 63.5%) as an off brown solid. MS (ESI, pos. ion) m/z: 626.2 (M+1); $^1$H-NMR (300 MHz, DMSO-d$_6$): δ 9.02 (brs, 1H), 8.70 (s, 1H), 8.18-8.16 (m, 1H), 7.99 (m, 2H), 7.65-7.75 (m, 3H), 7.44-7.40 (m, 3H), 7.30-7.28 (m, 2H), 1.70-7.68 (m, 1H), 6.88 (m, 1H), 4.42 (m, 2H), 3.71 (s, 3H), 2.31 (s, 3H), 1.56 (m, 6H).

Preparation of compound 64d: 5-(3-(6-(isopropylamino)pyrazin-2-yl)-1-tosyl-1H-indol-5-yl)-1,2,4-thiadiazol-3-amine A solution of 5-(3-(6-(isopropylamino)pyrazin-2-yl)-1-tosyl-1H-indol-5-yl)-N-(4-methoxybenzyl)-1,2,4-thiadiazol-3-amine (0.5 g, 0.80 mmol) in TFA (5 mL) was heated in Biotage microwave at 100° C. for 30 min. TFA was removed in vacuo and the residue was washed with Et₂O (10 mL) to give the crude 5-(3-(6-(isopropylamino)pyrazin-2-yl)-1-tosyl-1H-indol-5-yl)-1,2,4-thiadiazol-3-amine (0.5 g) as an off yellow solid, which was used for next step without any purification. MS (ESI, pos. ion) m/z: 506.0 (M+1).

Preparation of compound 64: 5-(3-(6-(isopropylamino)pyrazin-2-yl)-1H-indol-5-yl)-1,2,4-thiadiazol-3-amine To a solution of 5-(3-(6-(isopropylamino)pyrazin-2-yl)-1-tosyl-1H-indol-5-yl)-1,2,4-thiadiazol-3-amine (0.5 g, 0.99 mmol) in 1,4-dioxane (5 mL) was added 10% aq NaOH (2.5 mL) and the reaction was heated at 100° C. for 2 hr. The mixture was cooled to RT and was treated with ice cold water to give off white precipitate. The precipitate was filtered and washed with ice cold water and further purified by preparative HPLC (eluent: 10-70% MeCN:MeOH (1:1) in water with 0.01% TFA) to give 5-(3-(6-(isopropylamino)pyrazin-2-yl)-1-tosyl-1H-indol-5-yl)-N-(4-methoxybenzyl)-1,2,4-thiadiazol-3-amine (70 mg, 20%). MS (ESI, pos. ion) m/z: 352.1 (M+1); ¹H-NMR (400 MHz, DMSO-$d_6$): δ 11.96 (s, 1H), 9.05 (d, J=1.2 Hz, 1H), 8.27 (m, 2H), 7.78 (d, J=8.4 Hz, 1H), 7.67 (m, 2H), 7.59 (d, J=8.4 Hz, 1H), 7.20 (m, 1H), 4.61 (m, 1H), 1.32 (d, J=6.4 Hz, 6H).

Example 65

3-(3-(6-isopropoxypyridin-2-yl)-1H-indol-5-yl)-1,2,4-thiadiazol-5-amine

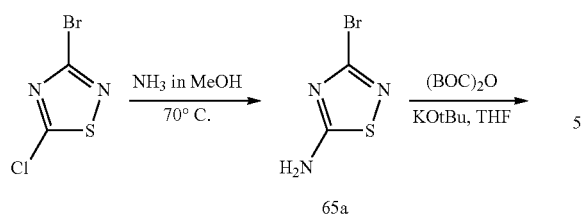

65a

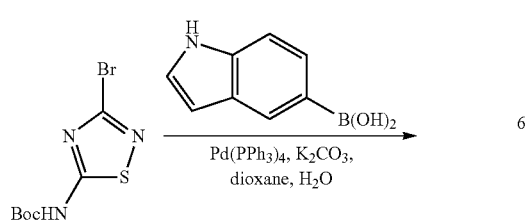

65b

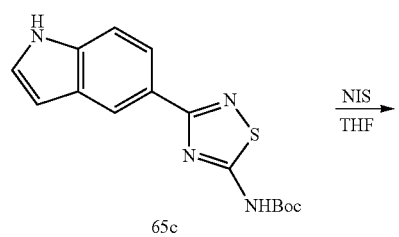

65c

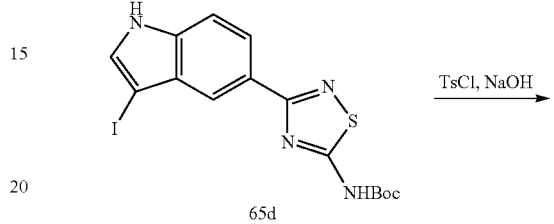

65d

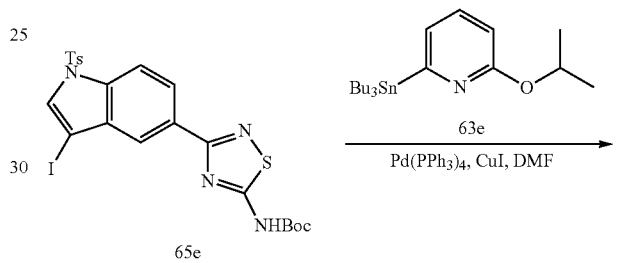

65e

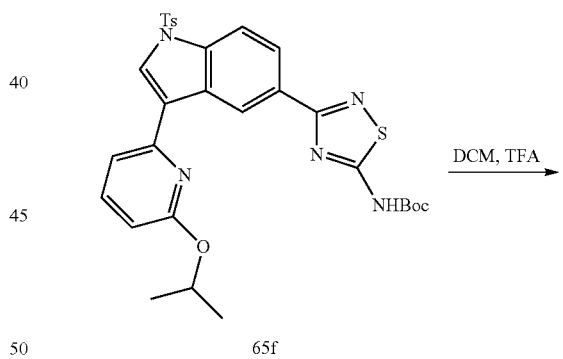

65f

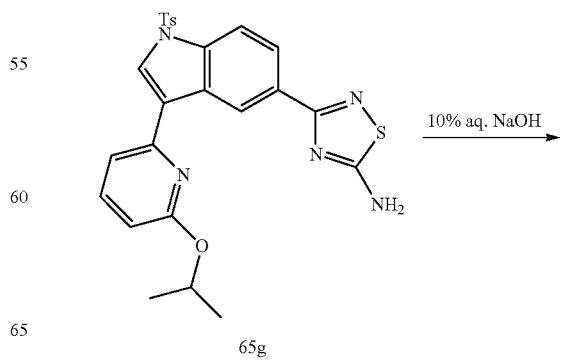

65g

-continued

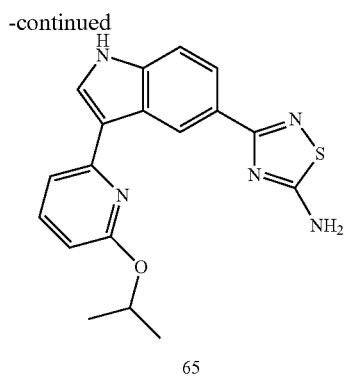

65

Preparation of compound 65a:
3-bromo-1,2,4-thiadiazol-5-amine

To a sealed tube containing a solution of saturated ammonia in MeOH (1 mL) was added 3-bromo-5-chloro-1,2,4-thiadiazole (100 mg, 0.5 mmol, Oakwood). The reaction was heated to 70° C. for 30 min. During the progress of reaction, a white precipitate was obtained. The resulting suspension was cooled to RT for 1 h and MeOH was evaporated. The crude was treated with $H_2O$ (10 mL) and extracted with EtOAc (2×25 mL). The organic layer was dried over anhydrous $Na_2SO_4$ and concentrated. The residue was triturated with petroleum ether to give 3-bromo-1,2,4-thiadiazol-5-amine (20 mg, 22.4%) as a white solid. $^1$H NMR (400 MHz, DMSO-$d_6$): δ 8.42 (s, 2H).

Preparation of compound 65b: tert-butyl
(3-bromo-1,2,4-thiadiazol-5-yl)carbamate To a solution of 3-bromo-1,2,4-thiadiazol-5-amine (5 g, 28.0 mmol) in THF (50 mL) was added KOtBu (6.30 g, 56.0 mmol) in one portion and the reaction was stirred for 10 min at 0° C. Boc$_2$O (6.74 g, 30.89 mmol) was added at 0° C. and the reaction was stirred for 1 h at RT. The mixture was treated $H_2O$ (50 mL) and extracted with EtOAc (50 mL). The aqueous layer was back extracted with EtOAc (50 mL). The combined organic layers were dried over anhydrous $Na_2SO_4$ and concentrated under reduced pressure. The crude was further purified by silica gel column chromatography (eluent: 10% EtOAc in petroleum ether) to give tert-butyl (3-bromo-1,2,4-thiadiazol-5-yl)carbamate (2.83 g, 36.2%) as an off white solid. MS (ESI, pos. ion) m/z: 279.2 (M+1); $^1$H NMR (400 MHz, DMSO-$d_6$): δ 9.81 (s, 1H), 1.57 (s, 9H).

Preparation of compound 65c: tert-butyl (3-(1H-indol-5-yl)-1,2,4-thiadiazol-5-yl)carbamate To a mixture of tert-butyl (3-bromo-1,2,4-thiadiazol-5-yl) carbamate (100 mg, 0.359 mmol) and indole-5-boronic acid (57.9 mg, 0.359 mmol) in 1,4-dioxane (5 mL) was added Pd(PPh$_3$)$_4$ (20.77 mg, 0.017 mmol) and 1M aq K$_2$CO$_3$ solution (0.539 mL, 0.539 mmol). N$_2$ gas was purged for 15 min. After 15 min, the reaction was heated at reflux for 4 h. The reaction mixture was cooled to RT and treated with $H_2O$ (5 mL), extracted with EtOAc (25 mL). The aqueous layer was back extracted with EtOAc (25 mL). The combined organic layers were dried over anhydrous Na$_2$SO$_4$ and concentrated. The crude was further purified by silica gel column chromatography (eluent: 10% EtOAc in petroleum ether) to afford tert-butyl (3-(1H-indol-5-yl)-1,2,4-thiadiazol-5-yl)carbamate (50 mg, 44.2%) as an off white solid. MS (ESI, pos. ion) m/z: 261 (M+1); $^1$H NMR (400 MHz, DMSO-$d_6$): δ 12.40 (s, 1H), 11.31 (s, 1H), 8.35 (s, 1H), 7.91 (dd, J=1.2 Hz & 8.4 Hz, 1H), 7.46 (d, J=8.4 Hz, 1H), 7.41-7.40 (m, 1H), 6.35 (s, 1H), 1.52 (s, 9H).

Preparation of compound 65d: tert-butyl (3-(3-iodo-1H-indol-5-yl)-1,2,4-thiadiazol-5-yl)carbamate To a solution of tert-butyl (3-(1H-indol-5-yl)-1,2,4-thiadiazol-5-yl)carbamate (100 mg, 0.316 mmol) in THF (5 mL) at 0° C. was added N-iodosuccinimide (78 mg; 0.348 mmol) and the reaction was stirred for 1 h at RT. The mixture was treated with saturated aq. NaHSO$_3$ solution (5 mL). The volatile solvent were evaporated and the crude residue was further treated with ice-cold water and petroleum ether to give tert-butyl (3-(3-iodo-1H-indol-5-yl)-1,2,4-thiadiazol-5-yl)carbamate (80 mg, 58.8%) as an off white solid. MS (ESI, pos. ion) m/z: 386.9 (M+1) (carbamic acid mass); $^1$H NMR (400 MHz, DMSO-$d_6$): δ 12.42 (brs, 1H), 11.76 (brs, 1H), 8.15 (s, 1H), 8.00-7.98 (m, 1H), 7.62 (d, J=2.4 Hz, 1H), 7.49 (d, J=8.8 Hz, 1H), 1.51 (s, 9H).

Preparation of compound 65e: tert-butyl (3-(3-iodo-1-tosyl-1H-indol-5-yl)-1,2,4-thiadiazol-5-yl)carbamate To a solution of tert-butyl (3-(3-iodo-1H-indol-5-yl)-1,2,4-thiadiazol-5-yl)carbamate (80 mg, 0.18 mmol) in DMF (2.5 mL) at 0° C. was added 60% NaH (80 mg, 0.199 mmol) at 0° C. and the reaction was stirred at RT. After 5 min, the mixture was again cooled to 0° C. and 4-methylbenzene sulfonyl chloride (38 mg, 0.199 mmol) in DMF (2.5 mL) was added dropwise. The reaction was stirred at RT for 1 h, then treated with ice cold water (5 mL) and extracted with EtOAc (10 mL). The aqueous layer was back extracted with EtOAc (10 mL). The combined organic layers were dried over anhydrous Na$_2$SO$_4$ and concentrated. The crude was purified by silica-gel column Chromatography (eluent: 15% EtOAc in petroleum ether) to give tert-butyl (3-(3-iodo-1-tosyl-1H-indol-5-yl)-1,2,4-thiadiazol-5-yl)carbamate (50 mg, 46.7%) as an off white solid. MS (ESI, pos. ion) m/z: 540.9 (M+1) (carbamic acid mass). $^1$H NMR (400 MHz, DMSO-$d_6$) δ 12.45 (brs, 1H), 8.22-8.19 (m, 1H), 8.15 (s, 1H), 8.11-8.07 (m, 2H), 7.95 (d, J=8.4 Hz, 2H), 7.41 (d, J=8 Hz, 2H), 2.31 (s, 3H), 1.51 (s, 9H).

Preparation of compound 65f: tert-butyl (3-(3-(6-isopropoxypyridin-2-yl)-1-tosyl-1H-indol-5-yl)-1,2,4-thiadiazol-5-yl)carbamate A mixture of tert-butyl (3-(3-iodo-1-tosyl-1H-indol-5-yl)-1,2,4-thiadiazol-5-yl)carbamate (0.6 g, 1.0 mmol) and 2-isopropoxy-6-(tributylstannyl)pyridine (0.429 g, 1.0 mmol) in DMF (10 mL) was bubbled N$_2$ gas for 15 min. To the above mixture, CuI (95 mg, 0.5 mmol.) and Pd(PPh$_3$)$_4$ (12 mg, 0.1 mmol) were added and N$_2$ gas was bubbled for another 15 min. The reaction was heated at 90° C. for 1 h. The reaction mixture was quenched with H$_2$O (10 mL) and extracted with CHCl$_3$ (2×25 mL). The organic layer was dried over anhydrous Na$_2$SO$_4$ and concentrated under reduced pressure. The crude was purified by neutral alumina column chromatography (eluent: 20% EtOAc in petroleum ether) to give tert-butyl (3-(3-(6-isopropoxypyridin-2-yl)-1-tosyl-1H-indol-5-yl)-1,2,4-thiadiazol-5-yl)carbamate (0.35 g, 57.4%). MS (ESI, pos. ion) m/z: 606.4 (M+1); $^1$H NMR (DMSO-$d_6$, 400 MHz): δ 9.33 (s, 1H), 8.52 (s, 1H), 8.16-8.08 (m, 2H), 7.97 (d, J=8 Hz, 2H), 7.76 (t, J=7.6 Hz, 1H), 7.63 (d, J=7.6 Hz, 2H), 7.40 (d, J=8.4 Hz, 1H), 6.69 (d, J=8 Hz, 1H), 5.52-5.49 (m, 1H), 2.30 (s, 3H), 1.40 (d, J=6 Hz, 6H).

195

Preparation of compound 65g: 3-(3-(6-isopropoxy-pyridin-2-yl)-1-tosyl-1H-indol-5-yl)-1,2,4-thiadiazol-5-amine To a mixture of tert-butyl (3-(3-(6-isopropoxypyridin-2-yl)-1-tosyl-1H-indol-5-yl)-1,2,4-thiadiazol-5-yl)carbamate (0.35 g, 0.577 mmol) in DCM (10 mL) was added TFA (4 mL) at 0° C. The reaction was stirred for 2 h at RT. The solvent was then removed in vacuo and the residue was triturated with Et₂O to give 3-(3-(6-isopropoxypyridin-2-yl)-1-tosyl-1H-indol-5-yl)-1,2,4-thiadiazol-5-amine (0.25 g, 85.6%). MS (ESI, pos. ion) m/z: 506.1 (M+1).

Preparation of compound 65: 3-(3-(6-isopropoxypyridin-2-yl)-1H-indol-5-yl)-1,2,4-thiadiazol-5-amine To a solution of 3-(3-(6-isopropoxypyridin-2-yl)-1-tosyl-1H-indol-5-yl)-1,2,4-thiadiazol-5-amine (0.25 g, 0.49 mmol) in 1,4-dioxane (10 mL) was added 10% aq NaOH (5 mL) and the reaction was heated at 100° C. for 2 h. The reaction was quenched with ice cold H₂O to give a pale yellow precipitate. The precipitate was filtered, washed with ice cold H₂O and dried under vacuum. The crude product was purified with preparative HPLC (eluent: 30-100% MeCN in H₂O with 5 mM NH₄OAc) to give 3-(3-(6-isopropoxypyridin-2-yl)-1H-indol-5-yl)-1,2,4-thiadiazol-5-amine (35 mg, 20.2%). MS (ESI, pos. ion) m/z: 352.3 (M+1); ¹H NMR (DMSO-d₆, 400 MHz): δ 11.65 (brs, 1H), 8.11 (d, J=2.4 Hz, 1H), 7.91 (dd, J=8.4, 1.6 Hz, 1H) 7.85 (brs, 2H), 7.66 (t, J=8, 1H) 7.46 (d, J=8.8, 1H), 7.39 (d, J=7.6, 1H), 6.50 (d, J=8, 1H), 5.58-5.55 (m, 1H), 1.42 (d, J=6 Hz, 6H).

Example 66

3-(3-(6-isopropoxypyridin-2-yl)-1H-indol-5-yl)-1,2,4-thiadiazol-5-amine

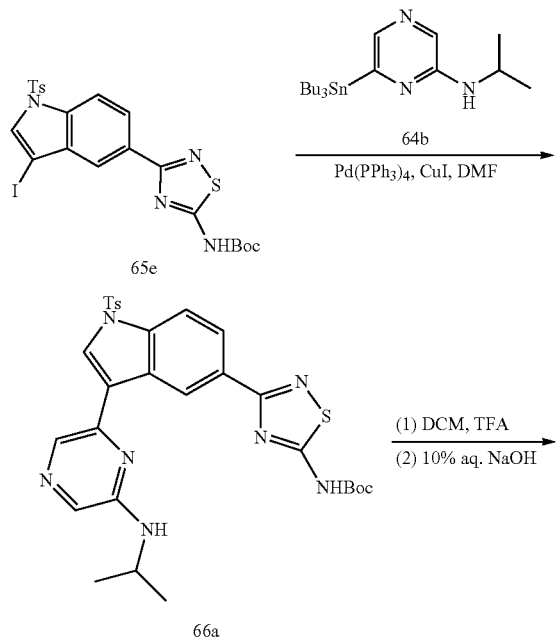

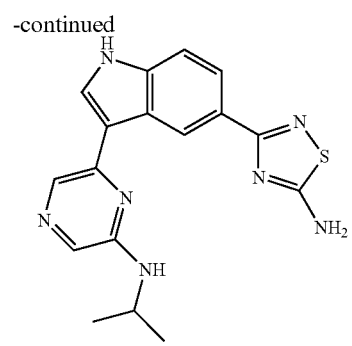

Preparation for compound 66a: tert-butyl (3-(3-(6-(isopropylamino)pyrazin-2-yl)-1-tosyl-1H-indol-5-yl)-1,2,4-thiadiazol-5-yl)carbamate A mixture of tert-butyl (3-(3-iodo-1-tosyl-1H-indol-5-yl)-1,2,4-thiadiazol-5-yl)carbamate (0.6 g, 1.0 mmol) and N-isopropyl-6-(tributylstannyl)pyrazin-2-amine (0.429 g, 1.0 mmol) in DMF (10 mL) was bubbled N₂ gas for 15 min. To the mixture was added CuI (95 mg, 0.5 mmol.) and Pd(PPh₃)₄ (12 mg, 0.1 mmol) and N₂ gas was bubbled for another 15 min. The reaction was heated at 90° C. for 1 h. The mixture was quenched with H₂O (10 mL) and extracted with CHCl₃ (2×25 mL). The organic layer was dried over anhydrous Na₂SO₄ and concentrated under reduced pressure. The crude was purified by neutral alumina column chromatography (eluent: 20% EtOAc in petroleum ether) to give tert-butyl (3-(3-(6-(isopropylamino)pyrazin-2-yl)-1-tosyl-1H-indol-5-yl)-1,2,4-thiadiazol-5-yl)carbamate (0.49 g, 81%). MS (ESI, pos. ion) m/z: 606.1 (M+1).

Preparation of compound 66: 3-(3-(6-(isopropylamino)pyrazin-2-yl)-1H-indol-5-yl)-1,2,4-thiadiazol-5-amine To a mixture of tert-butyl (3-(3-(6-(isopropylamino)pyrazin-2-yl)-1-tosyl-1H-indol-5-yl)-1,2,4-thiadiazol-5-yl)carbamate (0.49 g, 0.8 mmol) in DCM (10 mL) was added TFA (4 mL) at 0° C. The reaction was stirred for 2 h at RT. The solvent was then removed in vacuo and the residue was triturated with Et₂O to give 3-(3-(6-(isopropylamino)pyrazin-2-yl)-1-tosyl-1H-indol-5-yl)-1,2,4-thiadiazol-5-amine (0.23 g, 56.2%). MS (ESI, pos. ion) m/z: 506.1 (M+1). To a solution of 3-(3-(6-(isopropylamino)pyrazin-2-yl)-1-tosyl-1H-indol-5-yl)-1,2,4-thiadiazol-5-amine (0.23 g, 0.45 mmol) in 1-4-dioxane (10 mL) was added 10% aq NaOH (5 mL) and the reaction was heated at 100° C. for 2 h. The reaction was quenched with ice cold H₂O to give a pale yellow precipitate. The precipitate was filtered, washed with ice cold H₂O and dried under vacuum. The crude product was purified with preparative HPLC (eluent: 20-80% AcCN in H₂O with 0.1% TFA) to give 3-(3-(6-(isopropylamino)pyrazin-2-yl)-1H-indol-5-yl)-1,2,4-thiadiazol-5-amine (45 mg, 28.3%). MS (ESI, pos. ion) m/z: 352.1 (M+1); ¹H NMR (DMSO-d₆, 400 MHz): δ 11.81 (s, 1H), 9.19 (s, 1H), 8.20-8.18 (m, 2H), 7.92

(dd, J=8.4, 1.2 Hz, 1H) 7.86 (brs, 2H), 7.63 (s, 1H), 7.47 (d, J=8.4 Hz, 1H), 4.32-4.29 (m, 1H), 1.29 (d, J=6.4 Hz, 6H).

Example 67

5-(3-(6-(isopropylamino)pyrazin-2-yl)-1H-indol-5-yl)-1,2,4-oxadiazol-3-amine

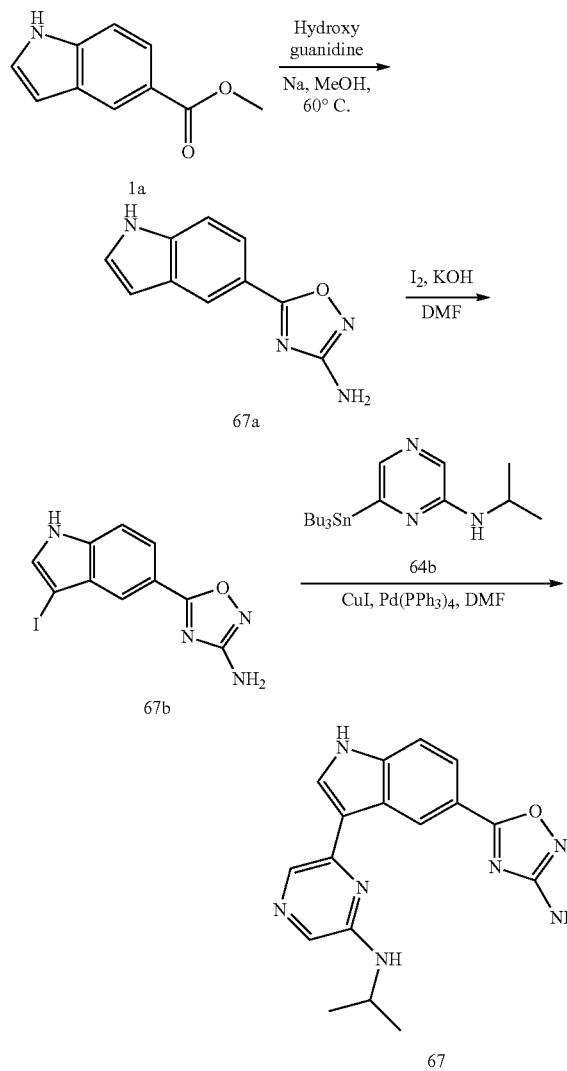

Preparation of compound 67a: 5-(1H-Indol-5-yl)-[1,2,4]oxadiazol-3-ylamine

To a stirred solution of NaOMe [prepared in-situ from sodium metal (0.261 g, 11.36 mmol) in MeOH (10 mL) at 60° C.] was added hydroxyguanidine (0.863 g, 11.36 mmol) and the resulting mixture was stirred at 60° C. for 30 min. To the above mixture, methyl 1H-indole-5-carboxylate (1 g, 5.68 mmol) was added and the reaction was stirred at 60° C. for 12 h. The reaction was cooled to RT and quenched with H₂O (100 mL). The aqueous layer was extracted in EtOAc (2×100 mL). The combined organic layers were dried over anhydrous Na₂SO₄ and concentrated. The residue was purified by triturating with pentane to give 5-(1H-indol-5-yl)-[1,2,4]oxadiazol-3-ylamine (0.1 g, 8.6%) as an off-white solid. MS (ESI, pos. ion) m/z: 201.1 (M+1). ¹H-NMR (400 MHz DMSO-d₆): δ 11.53 (s, —1H), 8.24 (s, 1H), 7.73 (dd, J=11.6, 2.4 Hz, 1H), 7.56 (m, 2H), 6.61 (s, 1H), 6.29 (s, 2H).

Preparation of compound 67b: 5-(3-iodo-1H-indol-5-yl)-1,2,4-oxadiazol-3-amine

To a solution of 5-(1H-indol-5-yl)-[1,2,4]oxadiazol-3-ylamine (0.225 g, 1.12 mmol) in DMF (1 mL) was added KOH pellets (0.189 g, 3.36 mmol) at 0-5° C. The reaction was stirred for 10 min then I₂ (0.567 g, 2.24 mmol) was added portionwise. The reaction was stirred another 2 h at RT then treated with saturated aq sodium thiosulphate (100 mL) to obtain a brownish precipitate. The precipitate was filtered and dried under vacuum. The crude was further treated with petroleum ether to give 5-(3-iodo-1H-indol-5-yl)-1,2,4-oxadiazol-3-amine (0.2 g, 54%) as off white solid. MS (ESI, pos. ion) m/z: 326.9 (M+1).

Preparation of compound 67: 5-(3-(6-(isopropylamino)pyrazin-2-yl)-1H-indol-5-yl)-1,2,4-oxadiazol-3-amine To a solution of 5-(3-iodo-1H-indol-5-yl)-1,2,4-oxadiazol-3-amine (0.15 g, 0.460 mmol) and isopropyl-(6-tributylstannanyl-pyrazin-2-yl)-amine (0.235 g, 0.549 mmol) was bubbled N₂ gas for 15 min. To the mixture was added CuI (0.070 g, 0.366 mmol) and Pd(PPh₃)₄ (0.053 g, 0.043 mmol) and N₂ gas was bubbled for another 15 min. The reaction was heated at 90° C. for 1 h. The mixture was cooled to RT, quenched with H₂O (100 mL) and extracted with EtOAc (2×100 mL). The organic layer was dried over anhydrous Na₂SO₄ and concentrated. The residue was purified with preparative HPLC (eluent: 10-60% AcCN in H₂O with 0.01% TFA) to give 5-(3-(6-(isopropylamino)pyrazin-2-yl)-1H-indol-5-yl)-1,2,4-oxadiazol-3-amine (0.015 g, 10%) as a pale yellow solid. MS (ESI, pos. ion) m/z: 336.2 (M+1); ¹H-NMR (400 MHz, CD₃OD): δ 9.34 (s, 1H), 8.09 (s, 1H), 8.04 (d, J=0.8 Hz, 1H), 7.88 (d, J=8.4 Hz, 1H), 7.56 (d, J=8.8 Hz, 1H), 4.39 (m, 1H), 1.38 (dd, J=6.8, 1.2 Hz, 6H).

Example 68

5-(3-(6-isopropoxypyridin-2-yl)-1H-indol-5-yl)-1,2,4-oxadiazol-3-amine

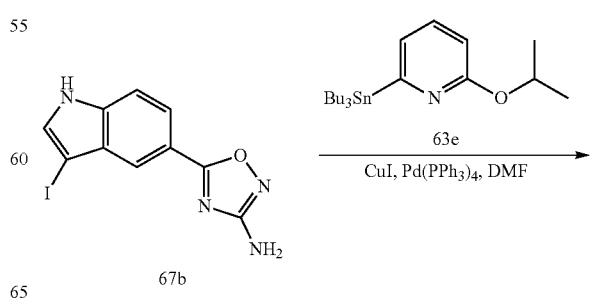

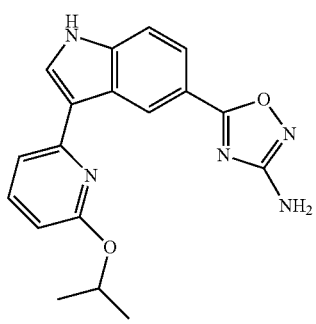

68

To a solution of 5-(3-iodo-1H-indol-5-yl)-1,2,4-oxadiazol-3-amine (0.3 g, 0.92 mmol) and 2-isopropoxy-6-(tributylstannyl)pyridine (0.471 g, 1.1 mmol) in DMF (10 mL) was bubbled with $N_2$ gas for 15 min. To the mixture was added CuI (0.140 g, 0.73 mmol) and $Pd(PPh_3)_4$ (0.100 g, 0.092 mmol) and $N_2$ gas was bubbled for another 15 min. The reaction was heated at 90° C. for 1 h. The reaction mixture was cooled to RT, and quenched with water (100 mL) and extracted in EtOAc (2×100 mL). The organic layer was dried over anhydrous $Na_2SO_4$ and concentrated. The residue was purified with preparative HPLC (eluent: 30-70% MeCN in water with 0.01% TFA) to afford 5-(3-(6-isopropoxypyridin-2-yl)-1H-indol-5-yl)-1,2,4-oxadiazol-3-amine (0.01 g, 7%) as a white solid. MS (ESI, pos. ion) m/z: 336.2 (M+1); $^1$H-NMR (400 MHz, $CD_3OD$): δ 9.36 (s, 1H), 7.99 (s, 1H), 7.89 (d, J=8.4 Hz, 1H), 7.64 (m, 2H), 7.37 (d, J=7.6 Hz, 1H), 6.52 (d, J=8.4 Hz, 1H), 5.65 (m, 1H), 1.51 (d, J=6.0 Hz, 6H).

Example 69

3-(3-(6-isopropoxypyridin-2-yl)-1H-indol-5-yl)-1,2,4-oxadiazol-5-amine

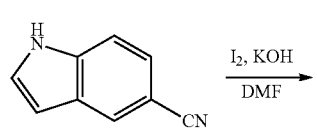

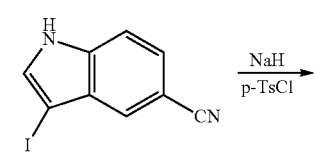

69a

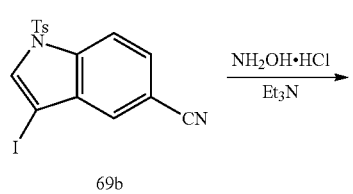

69b

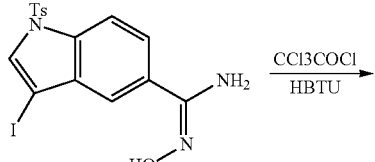

69c

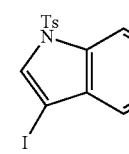

69d

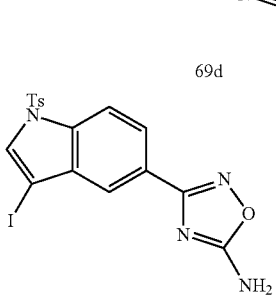 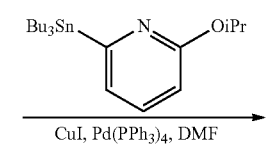

69e

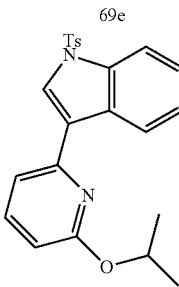

69f

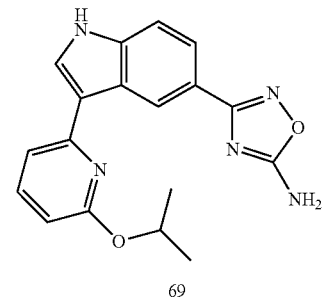

69

Preparation of compound 69a:
3-iodo-1H-indole-5-carbonitrile

To a solution of 1H-indole-5-carbonitrile (1 g, 7.048 mmol) in DMF (10 mL) was added KOH pellets (1.15 g, 21.14 mmol), followed by $I_2$ (3.57 g, 14.08 mmol) portionwise. The reaction was stirred for 1 h at RT. 10% aq sodium bisulphite solution (10 mL) was added to the mixture and an off-white solid precipitate was formed. The suspension was filtered and the solid was washed with $H_2O$ (10 mL) and dried under vacuum to give 3-iodo-1H-indole-5-carbonitrile (1.7 g, 94.5%) as an off white solid. $^1$H NMR (400 MHz, DMSO-$d_6$): δ 12.18 (brs, 1H), 7.78 (s, 1H), 7.75 (d, J=1.2 Hz, 1H), 7.59 (dd, J=8.4, 0.4 Hz, 1H), 7.52 (dd, J=8.4, 1.6 Hz, 1H).

Preparation of compound 69b: 3-iodo-1-tosyl-1H-indole-5-carbonitrile

To a solution of 3-iodo-1H-indole-5-carbonitrile (2 g, 7.40 mmol) in DMF (20 mL) was added 60% NaH (538 mg, 22.38 mmol) portion wise at 0° C. and the reaction was stirred for 10 min RT. To the above mixture at 0° C., p-TsCl (2.2 g, 11.19 mmol) solution in DMF (4 mL) was added and stirred for further 2 h at RT. The reaction was quenched with ice cold H$_2$O (20 mL). The resulting suspension was filtered and the solid was washed with H$_2$O (10 mL) and dried. The crude was purified with silica gel chromatography (eluent: 20% EtOAc in petroleum ether) to afford 3-iodo-1-tosyl-1H-indole-5-carbonitrile (3.0 g, 95.5%) as an off brown solid. $^1$H NMR (400 MHz, DMSO-d$_6$): δ 8.30 (s, 1H), 8.13 (d, J=8.8 Hz, 1H), 7.98 (d, J=8.4 Hz, 2H), 7.87-7.81 (m, 2H), 7.43 (d, J=8.0 Hz, 2H), 2.32 (s, 3H).

Preparation of compound 69c: N'-hydroxy-3-iodo-1-tosyl-1H-indole-5-carboximidamide To a suspension of 3-iodo-1-tosyl-1H-indole-5-carbonitrile (1 g, 2.37 mmol) in EtOH (10 mL) was added Et$_3$N (1.65 mL, 11.87 mmol) followed by NH$_2$OH.HCl (410 mg, 5.93 mmol) and the reaction was stirred for 48 h at RT. The solvent was removed in vacuo and the residue was treated with H$_2$O (10 mL) and extracted with EtOAc (25 mL). The aqueous layer was extracted with EtOAc (25 mL). The combined organic layers were dried over anhydrous Na$_2$SO$_4$, filtered and concentrated. The residue was further triturated with n-pentane to give N'-hydroxy-3-iodo-1-tosyl-1H-indole-5-carboximidamide (950 mg, 88.7%) as an off brown solid. MS (ESI, pos. ion) m/z: 455.8; $^1$H NMR (400 MHz, CDCl$_3$): δ 7.99 (d, J=8.8 Hz, 1H), 7.84-7.73 (m, 4H), 7.68 (d, J=8.4 Hz, 1H), 7.63-7.61 (m, 1H), 7.31-7.24 (m, 1H), 4.92 (brs, 2H), 3.14-3.09 (m, 1H), 2.36 (s, 3H).

Preparation of compound 69d: 3-(3-iodo-1-tosyl-1H-indol-5-yl)-5-(trichloromethyl)-1,2,4-oxadiazole To a suspension of N'-hydroxy-3-iodo-1-tosyl-1H-indole-5-carboximidamide (950 mg, 2.09 mmol) in dry THF (10 mL) was added Et$_3$N (1.4 mL, 10.10 mmol) and O-benzotriazole-N,N,N',N'-tetramethyl-uronium-hexafluoro-phosphate (HBTU) (1.6 g, 4.18 mmol) at 0° C. Trichloroacetyl chloride (0.48 mL, 2.51 mmol) was added portion wise at 0° C. and the reaction was stirred for 16 h at RT. The mixture was treated with H$_2$O (10 mL) and extracted with EtOAc (2×25 mL). The combined organic layers were dried over anhydrous Na$_2$SO$_4$, filtered and concentrated in vacuo. The residue was further with basic alumina chromatography (eluent: 5% EtOAc in petroleum ether) to afford 3-(3-iodo-1-tosyl-1H-indol-5-yl)-5-(trichloromethyl)-1,2,4-oxadiazole (250 mg, 20.8%) as an off white solid. $^1$H NMR (400 MHz, DMSO-d$_6$): δ 8.26 (s, 1H), 8.21 (d, J=8.8 z, 1H), 8.10 (t, J=1.2 Hz, 1H), 7.99-7.95 (m, 3H), 7.44 (d, J=8.4 Hz, 1H), 2.32 (s, 3H).

Preparation of compound 69e: 3-(3-iodo-1-tosyl-1H-indol-5-yl)-1,2,4-oxadiazol-5-amine In a sealed tube equipped with magnetic stir bar, 2M NH$_3$ in MeOH (2.5 mL) was added. To the above solution was added 3-(3-iodo-1-tosyl-1H-indol-5-yl)-5-(trichloromethyl)-1,2,4-oxadiazole (50 mg, 0.086 mmol) and the tube was sealed and heated to 90° C. for 24 h. The reaction was cooled to RT. The solvent was removed and the residue was treated with H$_2$O (20 mL) and extracted with EtOAc (2×20 mL). The organic layer was dried over anhydrous Na$_2$SO$_4$ and concentrated. The residue was triturated with Et$_2$O (10 mL) to give 3-(3-iodo-1-tosyl-1H-indol-5-O-1,2,4-oxadiazol-5-amine (15 mg, 36.3%). MS (ESI, pos. ion) m/z: 481.1 (M+1); $^1$H NMR (400 MHz, DMSO-d$_6$): δ 8.88 (brs, 1H), 8.45 (s, 1H), 8.23-8.17 (m, 2H), 8.11 (d, J=1.2 Hz, 1H), 8.02-7.97 (m, 3H), 7.43 (d, J=8.4 Hz, 1H), 2.32 (s, 3H).

Preparation of compound 69f: 3-(3-(6-isopropoxypyridin-2-yl)-1-tosyl-1H-indol-5-yl)-1,2,4-oxadiazol-5-amine Argon gas was bubbled through a solution of 3-(3-iodo-1-tosyl-1H-indol-5-yl)-1,2,4-oxadiazol-5-amine (350 mg, 0.73 mmol) and 2-isopropoxy-6-(tributylstannyl)pyridine (374 mg, 0.87 mmol) in dry DMF (3.5 mL) for 15 min. To the mixture was added CuI (139 mg, 0.73 mmol) and Pd(PPh$_3$)$_4$ (84 mg, 0.073 mmol) and argon gas was further bubbled for additional 15 min. The reaction was heated at 90° C. for 1 h then cooled to RT. The reaction was quenched with ice cold water. The resulting suspension was filtered and washed with water. The solid was purified with basic alumina column chromatography (eluent: 20% EtOAc in petroleum ether) to give 3-(3-(6-isopropoxypyridin-2-yl)-1-tosyl-1H-indol-5-yl)-1,2,4-oxadiazol-5-amine (220 mg, 61.5%). MS (ESI, pos. ion) m/z: 490.1 (M+1).

Preparation of compound 69: 3-(3-(6-isopropoxypyridin-2-yl)-1H-indol-5-yl)-1,2,4-oxadiazol-5-amine To a solution of 3-(3-(6-isopropoxypyridin-2-yl)-1-tosyl-1H-indol-5-yl)-1,2,4-oxadiazol-5-amine (220 mg, 0.44 mmol) in 1,4-dioxane (2.2 mL) was added 10% aq NaOH (1.1 mL) and the reaction was heated at 100° C. for 2 h. The mixture was cooled to RT and treated with ice cold water (2.2 mL). The precipitate was collected through filtration and the crude product was purified with preparative HPLC (eluent: 20-100% MeCN in water with 0.01% TFA) to give 3-(3-(6-isopropoxypyridin-2-yl)-1H-indol-5-yl)-1,2,4-oxadiazol-5-amine (25 mg, 17%). MS (ESI, pos. ion) m/z: 336.1 (M+1); $^1$H NMR (400 MHz, DMSO-d$_6$): δ 11.75 (s, 1H), 9.10 (s, 1H), 8.16 (s, 1H), 7.75-7.64 (m, 4H), 7.52 (d, J=8.4 Hz, 1H), 7.41 (d, J=7.2 Hz, 1H), 6.51 (d, J=8.4 Hz, 1H), 5.54-5.52 (m, 1H), 1.44 (d, J=6.0 Hz, 6H).

Example 70

3-(3-(6-(isopropylamino)pyrazin-2-yl)-1H-indol-5-yl)-1,2,4-oxadiazol-5-amine

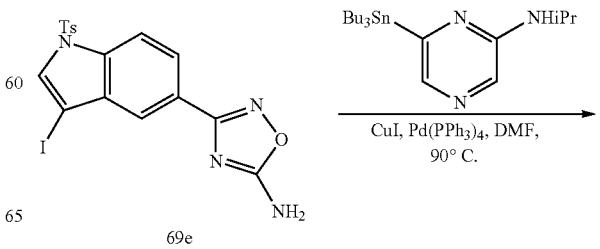

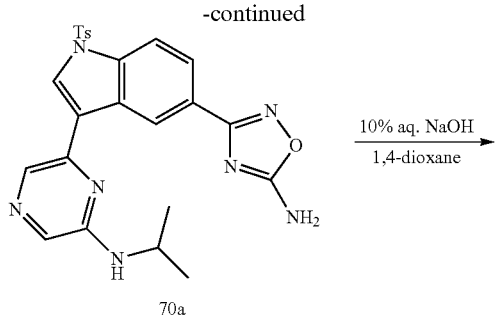

Preparation of compound 70a: 3-(3-(6-(isopropylamino)pyrazin-2-yl)-1-tosyl-1H-indol-5-yl)-1,2,4-oxadiazol-5-amine Argon gas was bubbled through a solution of 3-(3-iodo-1-tosyl-1H-indol-5-yl)-1,2,4-oxadiazol-5-amine (350 mg, 0.73 mmol) and N-isopropyl-6-(tributylstannyl)pyrazin-2-amine (374.5 mg, 0.87 mmol) in dry DMF (3.5 mL) for 15 min. To the mixture was added CuI (139 mg, 0.73 mmol) and Pd(PPh$_3$)$_4$ (84 mg, 0.073 mmol) and argon gas was further bubbled for additional 15 min. The reaction was heated at 90° C. for 1 h then cooled to RT. The reaction was quenched with ice cold H$_2$O. The resulting suspension was filtered and washed with H$_2$O. The solid was purified with basic alumina column chromatography (eluent: 20% EtOAc in petroleum ether) to give 34346-(isopropylamino)pyrazin-2-yl)-1-tosyl-1H-indol-5-yl)-1,2,4-oxadiazol-5-amine (200 mg, 55.8%). MS (ESI, pos. ion) m/z: 490.2 (M+1).

Preparation of compound 70: 3-(3-(6-(isopropylamino)pyrazin-2-yl)-1H-indol-5-yl)-1,2,4-oxadiazol-5-amine To a solution of 3-(3-(6-(isopropylamino)pyrazin-2-yl)-1-tosyl-1H-indol-5-yl)-1,2,4-oxadiazol-5-amine (200 mg, 0.41 mmol) in 1,4-dioxane (2.0 mL) was added 10% aq NaOH (1.0 mL) and the reaction was heated at 100° C. for 2 h. The mixture was cooled to RT and treated with ice cold H$_2$O (2.0 mL). The precipitate was collected through filtration and the crude product was purified with preparative HPLC (eluent: 10-60% AcCN in H$_2$O with 0.01% TFA) to give 3-(3-(6-(isopropylamino)pyrazin-2-yl)-1H-indol-5-yl)-1,2,4-oxadiazol-5-amine (40 mg, 24.5%). MS (ESI, pos. ion) m/z: 336.1 (M+1); $^1$H NMR (400 MHz, DMSO-d$_6$): δ 11.96 (s, 1H), 9.07 (s, 1H), 8.25-8.22 (m, 2H), 7.76 (s, 2H), 7.72 (dd, J=6.8, 1.6 Hz, 1H), 7.64 (s, 1H), 7.54 (d, J=8.4 Hz, 1H), 4.30-4.27 (m, 1H), 1.32 (d, J=6.4 Hz, 6H).

Example 71

3-(3-(6-isopropoxypyrazin-2-yl)-1H-indol-5-yl)-1,2,4-oxadiazol-5-amine

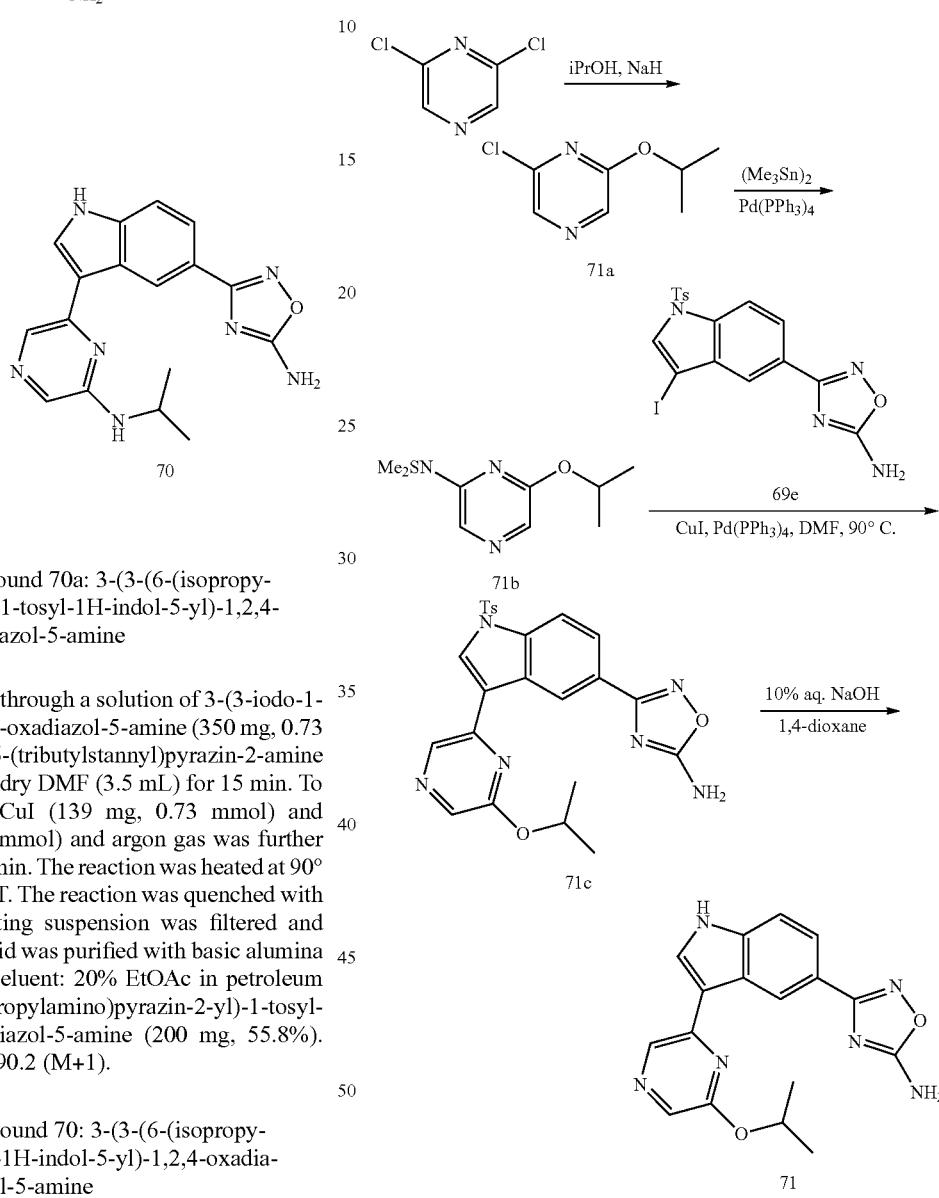

Preparation of compound 71a: 2-chloro-6-isopropoxypyrazine

To a solution of 2-propanol (2.26 mL, 31.99 mmol) in dry THF (40 mL) was added 60% NaH (960 mg, 39.90 mmol) at 0° C. and the reaction was stirred for 15 min. To the mixture at 0° C. was added 2,6-dichloropyrazine (4 g, 26.66 mmol, Aldrich) and the reaction was stirred for 2 h at RT. The reaction was quenched with ice cold H$_2$O (20 mL) and extracted with EtOAc. The organic layer was dried over anhydrous Na$_2$SO$_4$, filtered and concentrated. The residue was purified with silica gel column chromatography (eluent: 100% petroleum ether) to afford 2-chloro-6-isopropoxypyrazine (4.0 g, 86%) as an off brown liquid. MS (ESI, pos. ion) m/z: 173.0 (M+1); $^1$H NMR (400 MHz, CDCl$_3$): δ 8.28 (s, 1H), 8.14 (s, 1H), 5.31-5.25 (m, 1H), 1.37-1.36 (m, 6H).

Preparation of compound 71b: 2-isopropoxy-6-(trimethylstannyl)pyrazine

To a solution of 2-chloro-6-isopropoxypyrazine (4 g, 23.39 mmol) in toluene (40 mL) was added hexamethylditin (3.86 mL, 46.78 mmol) followed by Pd(PPh$_3$)$_4$ (13.5 g, 11.69 mmol) at RT. The mixture was purged with argon for 15 min, and heated at 115° C. for 3 h. The reaction was cooled to RT and quenched with ice cold water (25 mL). The aqueous layer was extracted with EtOAc (2×50 mL) and the organic layer was dried over Na$_2$SO$_4$, and concentrated. The residue was purified with silica gel column chromatography (eluent: 3% EtOAc in petroleum ether) to give 2-isopropoxy-6-(trimethylstannyl)-pyrazine (3.2 g, 45.7%) as a colorless solid. MS (ESI, pos. ion) m/z: 302.9 (M+1); $^1$H NMR (400 MHz, CDCl$_3$): δ 8.07 (s, 1H), 7.96 (s, 1H), 5.34-5.25 (m, 1H), 1.37-1.35 (m, 6H), 0.35 (s, 9H).

Preparation of compound 71c: 3-(3-(6-isopropoxy-pyrazin-2-yl)-1-tosyl-1H-indol-5-yl)-1,2,4-oxadiazol-5-amine Argon gas was bubbled through a solution of 3-(3-iodo-1-tosyl-1H-indol-5-yl)-1,2,4-oxadiazol-5-amine (250 mg, 0.52 mmol) and 2-isopropoxy-6-(trimethylstannyl)pyrazine (188 mg, 0.62 mmol) in dry DMF (2.5 mL) for 15 min. To the mixture was added CuI (99 mg, 0.52 mmol) and Pd(PPh$_3$)$_4$ (60 mg, 0.052 mmol) and argon gas was further bubbled for additional 15 min. The reaction was heated at 90° C. for 1 h then cooled to RT. The reaction was quenched with ice cold water. The resulting suspension was filtered and washed with water. The solid was purified with basic alumina column chromatography (eluent: 20% EtOAc in petroleum ether) to give 3-(3-(6-isopropoxypyrazin-2-yl)-1-tosyl-1H-indol-5-yl)-1,2,4-oxadiazol-5-amine (150 mg, 59%). MS (ESI, pos. ion) m/z: 491.1 (M+1).

Preparation of compound 71: 3-(3-(6-isopropoxy-pyrazin-2-yl)-1H-indol-5-yl)-1,2,4-oxadiazol-5-amine To a solution of 3-(3-(6-isopropoxypyrazin-2-yl)-1-tosyl-1H-indol-5-yl)-1,2,4-oxadiazol-5-amine (150 mg, 0.30 mmol) in 1,4-dioxane (1.5 mL) was added 10% aq NaOH (0.75 mL) and the reaction was heated at 100° C. for 2 h. The mixture was cooled to RT and treated with ice cold water (1.5 mL). The precipitate was collected through filtration and the crude product was purified with preparative HPLC (eluent: 30-70% AcCN in H$_2$O with 0.01% TFA) to give 3-(3-(6-isopropoxypyrazin-2-yl)-1H-indol-5-yl)-1,2,4-oxadiazol-5-amine (35 mg, 34%). MS (ESI, pos. ion) m/z: 337.1 (M+1); $^1$H NMR (400 MHz, DMSO-d$_6$): δ 11.75 (s, 1H), 9.10 (s, 1H), 8.72 (s, 1H), 8.37 (d, J=2.8 Hz, 1H), 7.94 (s, 1H), 7.77-7.71 (m, 3H), 7.56 (d, J=8.4 Hz, 1H), 5.51-5.48 (m, 1H), 1.49 (d, J=6.4 Hz, 6H).

Example 72

3-(3-(6-isopropoxypyrazin-2-yl)-1H-indol-5-yl)-N-methyl-1,2,4-oxadiazol-5-amine

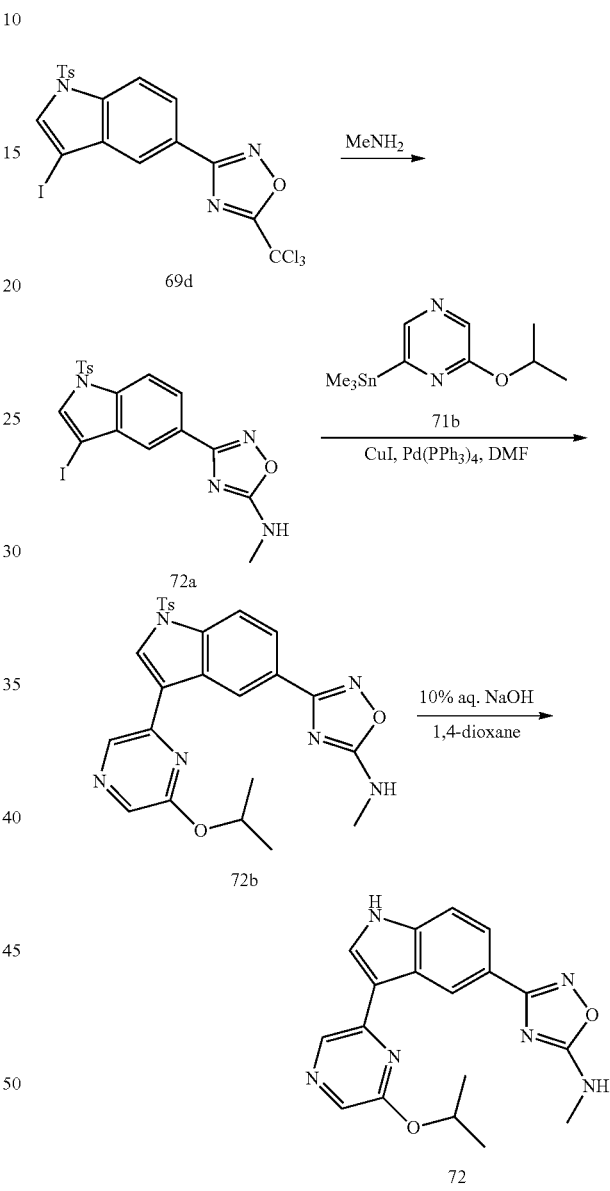

Preparation of compound 72a: 3-(3-iodo-1-tosyl-1H-indol-5-yl)-N-methyl-1,2,4-oxadiazol-5-amine N-Methylamine (1M in THF) (5 mL) was added to a sealed tube equipped with magnetic stir bar followed by the addition of 3-(3-iodo-1-tosyl-1H-indol-5-yl)-5-(trichloromethyl)-1,2,4-oxadiazole (250 mg, 0.43 mmol). The tube was sealed and heated at 90° C. in oil bath for 12 h. After completion of the reaction, it was cooled to RT. The mixture was treated with water and extracted with EtOAc (2×20 mL). The organic layer was dried over anhydrous Na$_2$SO$_4$, and concentrated in vacuo. The residue was purified with basic alumina column chromatography (eluent: 40% EtOAc in petroleum ether) to give 3-(3-iodo-1-tosyl-1H-indol-5-yl)-N-methyl-1,2,4-oxadiazol-5-amine (200 mg, 94.3%) as an off white solid. MS (ESI, pos. ion) m/z: 495.0 (M+1).

Preparation of compound 72b: 3-(3-(6-isopropoxy-pyrazin-2-yl)-1-tosyl-1H-indol-5-yl)-N-methyl-1,2,4-oxadiazol-5-amine Argon gas was bubbled through a solution of 3-(3-iodo-1-tosyl-1H-indol-5-yl)-N-methyl-1,2,4-oxadiazol-5-amine (250 mg, 0.50 mmol) and 2-isopropoxy-6-(trimethylstannyl)-pyrazine (168 mg, 0.55 mmol) in dry DMF (2.5 mL) for 15 min. To the mixture was added CuI (95 mg, 0.50 mmol) and Pd(PPh$_3$)$_4$ (59 mg, 0.050 mmol) and argon gas was further bubbled for additional 15 min. The reaction was heated at 90° C. for 1 h then cooled to RT. The reaction was quenched with ice cold water. The resulting suspension was filtered and washed with H$_2$O. The solid was purified with basic alumina column chromatography (eluent: 20% EtOAc in petroleum ether) to give 3-(3-(6-isopropoxypyrazin-2-yl)-1-tosyl-1H-indol-5-yl)-N-methyl-1,2,4-oxadiazol-5-amine (80 mg, 31.5%). MS (ESI, pos. ion) m/z: 505.1 (M+1).

Preparation of compound 72: 3-(3-(6-isopropoxy-pyrazin-2-yl)-1H-indol-5-yl)-N-methyl-1,2,4-oxadiazol-5-amine To a solution of 3-(3-(6-isopropoxypyrazin-2-yl)-1-tosyl-1H-indol-5-yl)-N-methyl-1,2,4-oxadiazol-5-amine (160 mg, 0.32 mmol) in 1,4-dioxane (1.6 mL) was added 10% aq NaOH (0.8 mL) and the reaction was heated at 100° C. for 2 h. The mixture was cooled to RT and treated with ice cold water (1.5 mL). The precipitate was collected through filtration and the crude product was purified with preparative HPLC (eluent: 20-70% AcCN in H$_2$O with 0.01% TFA) to give 3-(3-(6-isopropoxypyrazin-2-yl)-1H-indol-5-yl)-N-methyl-1,2,4-oxadiazol-5-amine (23 mg, 20.7%). MS (ESI, pos. ion) m/z: 351.1 (M+1); $^1$H NMR (400 MHz, DMSO-d$_6$): δ 11.96 (s, 1H), 9.15 (s, 1H), 8.74 (s, 1H), 8.38 (d, J=1.6 Hz, 1H), 8.18 (dd, J=8.8, 4.4 Hz, 1H), 7.94 (s, 1H), 7.77 (dd, J=8.4, 1.2 Hz, 1H), 7.55 (d, J=8.8 Hz, 1H), 5.56-5.53 (m, 1H), 2.96 (d, J=4.0 Hz, 3H), 1.49 (d, J=6.0 Hz, 6H).

Example 73

3-(3-(6-isopropoxypyrazin-2-yl)-1H-indol-5-yl)-N-isopropyl-1,2,4-oxadiazol-5-amine

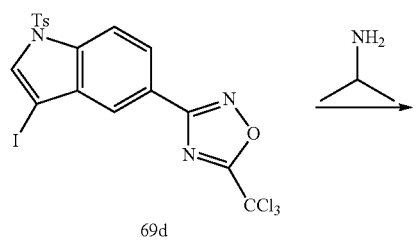

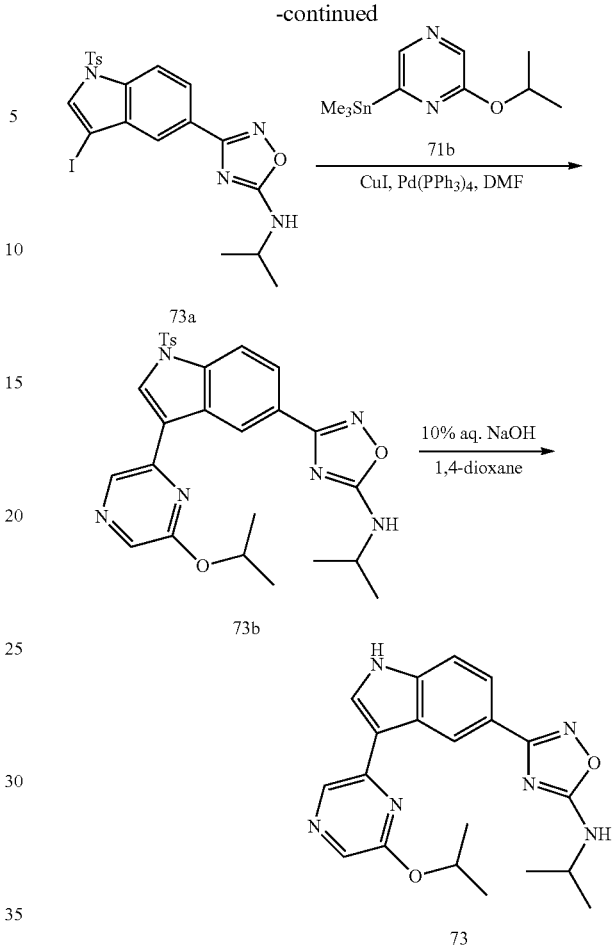

Preparation of compound 73a: 3-(3-iodo-1-tosyl-1H-indol-5-yl)-N-isopropyl-1,2,4-oxadiazol-5-amine To a solution of 3-(3-iodo-1-tosyl-1H-indol-5-yl)-5-(trichloromethyl)-1,2,4-oxadiazole (600 mg, 1.03 mmol) in DMSO (6 mL) was added isopropyl amine (1.2 mL). The reaction was heated to 90° C. in a sealed tube for 12 h then cooled to RT. The mixture was treated with water and extracted with EtOAc (2×20 mL). The organic layer was dried over anhydrous Na$_2$SO$_4$, and concentrated in vacuo. The residue was purified with basic alumina column chromatography (eluent: 35% EtOAc in petroleum ether) to give 3-(3-iodo-1-tosyl-1H-indol-5-yl)-N-isopropyl-1,2,4-oxadiazol-5-amine (450 mg, 83.3%) as an off brown solid. MS (ESI, pos. ion) m/z: 523.0 (M+1); $^1$H NMR (400 MHz, DMSO-d$_6$): δ 9.44 (d, J=7.6 Hz, 1H), 8.18 (s, 1H), 8.09-8.07 (m, 1H), 7.96-7.93 (m, 3H), 7.83 (d, J=1.2 Hz, 1H), 7.42 (d, J=8.0 Hz, 1H), 3.88-3.83 (m, 1H), 2.32 (s, 3H), 1.22 (d, J=6.4 Hz, 6H).

Preparation of compound 73b: 3-(3-(6-isopropoxy-pyrazin-2-yl)-1-tosyl-1H-indol-5-yl)-N-isopropyl-1,2,4-oxadiazol-5-amine Argon gas was bubbled through a solution of 3-(3-iodo-1-tosyl-1H-indol-5-yl)-N-isopropyl-1,2,4-oxadiazol-5-amine (450 mg, 0.86 mmol) and 2-isopropoxy-6-(trimethylstannyl)pyrazine (311 mg, 1.03 mmol) in dry DMF (4.5 ml) for 15 min. To the mixture was added CuI (163 mg, 0.86 mmol) and Pd(PPh$_3$)$_4$ (99 mg, 0.086 mmol) and argon gas was further bubbled for additional 15 min. The reaction was heated at 90° C. for 1 h then cooled to RT. The reaction was quenched with ice cold water. The resulting suspension was filtered and washed with water. The solid was purified with basic alumina column chromatography (eluent: 20% EtOAc in petroleum ether) to give 3-(3-(6-isopropoxypyrazin-2-yl)-1-tosyl-1H-indol-5-yl)-N-isopropyl-1,2,4-oxadiazol-5-amine (200 mg, 43.5%). MS (ESI, pos. ion) m/z: 533.3 (M+1).

Preparation of compound 73: 3-(3-(6-isopropoxy-pyrazin-2-yl)-1H-indol-5-yl)-N-isopropyl-1,2,4-oxa-diazol-5-amine To a solution of 3-(3-(6-isopropoxypyrazin-2-yl)-1-tosyl-1H-indol-5-yl)-N-isopropyl-1,2,4-oxadiazol-5-amine (200 mg, 0.375 mmol) in 1,4-dioxane (2.0 mL) was added 10% aq NaOH (1.0 mL) and the reaction was heated at 100° C. for 2 h. The mixture was cooled to RT and treated with ice cold water (2.0 mL). The precipitate was collected through filtration and the crude product was purified with preparative HPLC (eluent: 60-90% MeCN in water with 0.01% TFA) to give 3-(3-(6-isopropoxypyrazin-2-yl)-1H-indol-5-yl)-N-isopropyl-1,2,4-oxadiazol-5-amine (40 mg, 28.0%). MS (ESI, pos. ion) m/z: 379.1 (M+1); $^1$H NMR (400 MHz, DMSO-d$_6$): δ 11.96 (s, 1H), 9.11 (s, 1H), 8.73 (s, 1H), 8.34 (d, J=2.0 Hz, 1H), 8.24 (d, J=7.6 Hz, 1H), 7.93 (s, 1H), 7.76 (d, J=8.4 Hz, 1H), 7.55 (d, J=8.4 Hz, 1H), 5.55-5.49 (m, 1H), 3.93-3.85 (m, 1H), 1.47 (d, J=6.0 Hz, 6H), 1.25 (d, J=6.4 Hz, 6H).

Example 74

N-(3-(3-(6-isopropoxypyrazin-2-yl)-1H-indol-5-yl)-1,2,4-oxadiazol-5-yl)acetamide

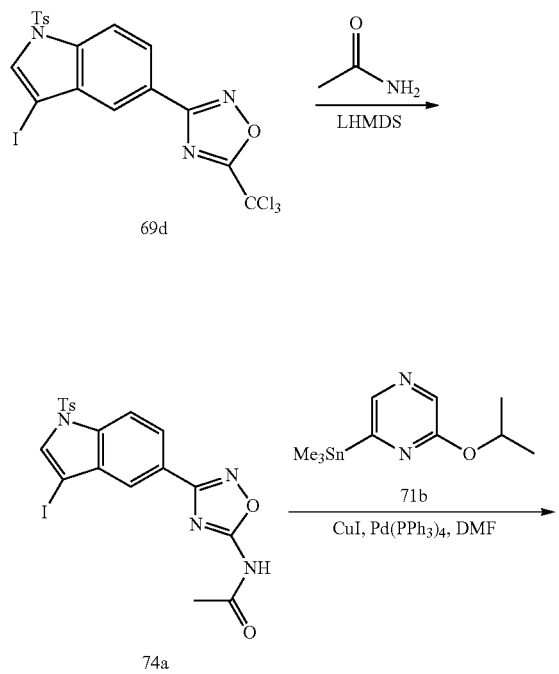

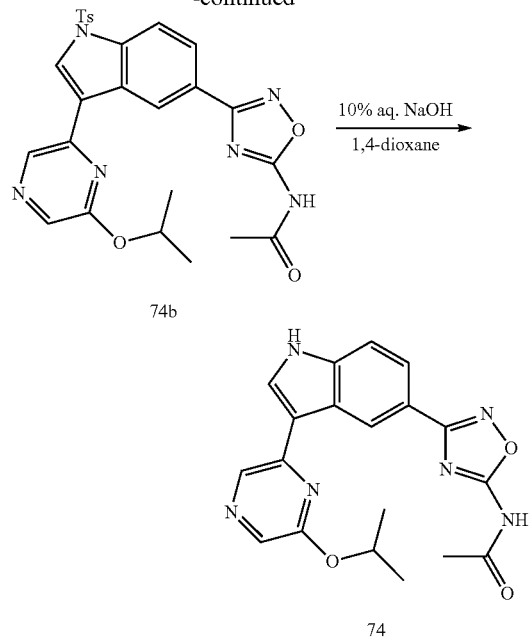

Preparation of compound 74a: N-(3-(3-iodo-1-tosyl-1H-indol-5-yl)-1,2,4-oxadiazol-5-yl)acetamide To a solution of acetamide (91.5 mg, 1.54 mmol in dry THF (10 mL) was added 1.0M lithium bis(trimethylsilyl)amide (LHMDS) (1.2 mL, 1.54 mmol) at −78° C. and the mixture was stirred for 45 min at −78° C. and 10 min at −10° C. Again the reaction was cooled back to −78° C. To the mixture at −78° C. was added 3-(3-iodo-1-tosyl-1H-indol-5-yl)-5-(trichloromethyl)-1,2,4-oxadiazole (600 mg, 1.03 mmol) and the reaction was stirred at RT for 12 h. The solvent was then removed in vacuo and the residue was diluted with water (10 mL) and extracted with EtOAc (2×20 mL). The combined organic layers were dried over anhydrous Na$_2$SO$_4$, and concentrated in vacuo. The residue was purified with basic alumina column chromatography (eluent: 35% EtOAc in petroleum ether) to give N-(3-(3-iodo-1-tosyl-1H-indol-5-yl)-1,2,4-oxadiazol-5-yl)acetamide (300 mg, 55.5%) as an off brown solid. MS (ESI, pos. ion) m/z: 523.0 (M+1); $^1$H-NMR (400 MHz, DMSO-d$_6$): δ 12.22 (brs, 1H), 8.22 (s, 1H), 8.15 (d, J=8.8 Hz, 1H), 8.02-7.90 (m, 4H), 7.44 (d, J=8.0 Hz, 2H), 2.33 (m, 3H), 2.19 (s, 3H).

Preparation of compound 74: N-(3-(3-(6-isopropoxy-pyrazin-2-yl)-1H-indol-5-yl)-1,2,4-oxadiazol-5-yl) acetamide To a solution of N-(3-(3-(6-isopropoxypyrazin-2-yl)-1-tosyl-1H-indol-5-yl)-1,2,4-oxadiazol-5-yl)acetamide (220 mg, 0.47 mmol) in 1,4-dioxane (2.0 mL) was added 10% aq NaOH (1.0 mL) and the reaction was stirred at RT for 48 h. The mixture was treated with ice cold water (5.0 mL) and the precipitate was filtered and washed with water. The crude product was purified with preparative HPLC (eluent: 50-80% MeCN in water with 0.01% TFA) to give N-(3-(3-(6-isopropoxypyrazin-2-yl)-1H-indol-5-yl)-1,2,4-oxadiazol-5-yl)acetamide (10 mg, 5.6%). MS (ESI, pos. ion) m/z: 379.2 (M+1); $^1$H NMR (400 MHz, DMSO-d$_6$): δ 12.10 (brs, 2H), 9.17 (s, 1H), 8.74 (s, 1H), 8.42 (d, J=2.4 Hz, 1H), 7.96 (s, 1H), 7.82

(dd, J=8.4, 1.2 Hz, 1H), 7.62 (d, J=8.4 Hz, 1H), 5.53-5.47 (m, 1H), 2.23 (s, 3H), 1.51 (d, J=6.4 Hz, 6H).

The compounds of examples 75-274 were made in accordance with exemplary methods 1-58. The compound examples were named according to the ACD naming convention, as associated with ISIS software. The mass spectral data is recorded M+1, which is the positive ion as measured by an electrospray ionization method.

TABLE 1

| Ex# | IUPAC Name | M + 1 | Method | Structures |
|---|---|---|---|---|
| 75 | 5-(3-(6-(4-methyl-1-piperazinyl)-2-pyridinyl)-1H-indol-5-yl)-1,3,4-oxadiazol-2-amine | 376 | Ex. 1 | 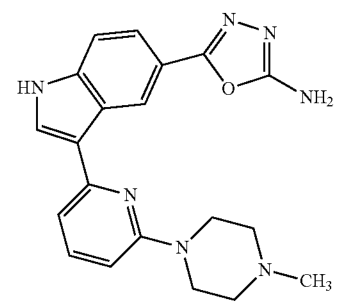 [SMILES: CN1CCN(c2cccc(-c3c[nH]c4ccc(-c5nnc(N)o5)cc34)n2)CC1] |
| 76 | 5-(3-(6-(1-methylethoxy)-2-pyrazinyl)-1H-indol-5-yl)-1,3,4-oxadiazol-2-amine | 337 | Ex. 1 | 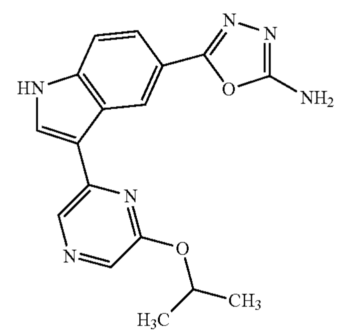 [SMILES: CC(C)Oc1cncc(-c2c[nH]c3ccc(-c4nnc(N)o4)cc23)n1] |
| 77 | 5-(3-(6-(1H-pyrazol-1-yl)-2-pyridinyl)-1H-indol-5-yl)-1,3,4-oxadiazol-2-amine | 344 | Ex. 1 | 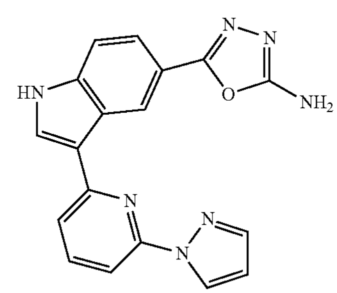 [SMILES: Nc1nnc(-c2ccc3[nH]cc(-c4cccc(-n5cccn5)n4)c3c2)o1] |
| 78 | 5-(3-(2,3-difluorophenyl)-1H-indol-5-yl)-1,3,4-oxadiazol-2-amine | 313 | Ex. 1 | 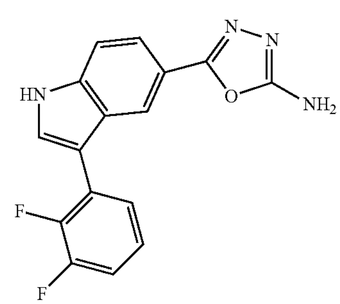 [SMILES: Nc1nnc(-c2ccc3[nH]cc(-c4cccc(F)c4F)c3c2)o1] |

TABLE 1-continued

| Ex# | IUPAC Name | M + 1 | Method | Structures |
|---|---|---|---|---|
| 79 | 5-(3-(3-fluoro-5-(1-methylethoxy)phenyl)-1H-indol-5-yl)-1,3,4-oxadiazol-2-amine | 353 | Ex. 1 | 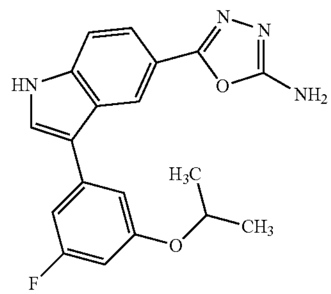 [SMILES: CC(C)Oc1cc(F)cc(-c2c[nH]c3ccc(-c4nnc(N)o4)cc23)c1] |
| 80 | 5-(3-(1-(2-methylpropyl)-1H-pyrazol-4-yl)-1H-indol-5-yl)-1,3,4-oxadiazol-2-amine | 323 | Ex. 1 | 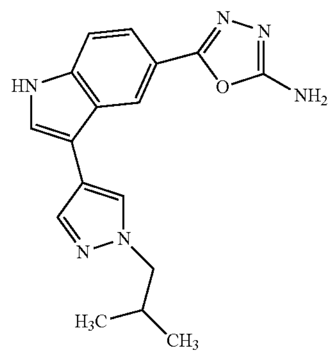 [SMILES: CC(C)Cn1cc(-c2c[nH]c3ccc(-c4nnc(N)o4)cc23)cn1] |
| 81 | 5-(3-(1-(2-(4-morpholinyl)ethyl)-1H-pyrazol-4-yl)-1H-indol-5-yl)-1,3,4-oxadiazol-2-amine | 380 | Ex. 1 | 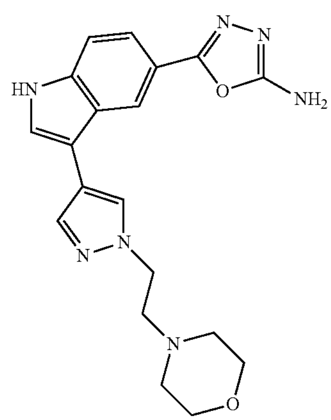 [SMILES: Nc1nnc(-c2ccc3[nH]cc(-c4cnn(CCN5CCOCC5)c4)c3c2)o1] |
| 82 | 5-(3-(5-(4-morpholinylcarbonyl)-3-pyridinyl)-1H-indol-5-yl)-1,3,4-oxadiazol-2-amine | 391 | Ex. 1 | 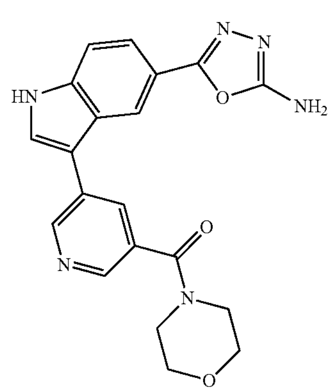 [SMILES: Nc1nnc(-c2ccc3[nH]cc(-c4cncc(C(=O)N5CCOCC5)c4)c3c2)o1] |

TABLE 1-continued
| Ex# | IUPAC Name | M + 1 | Method | Structures |
|---|---|---|---|---|
| 83 | 5-(3-(2-fluoro-5-(1-methylethoxy)phenyl)-1H-indol-5-yl)-1,3,4-oxadiazol-2-amine | 353 | Ex. 1 | 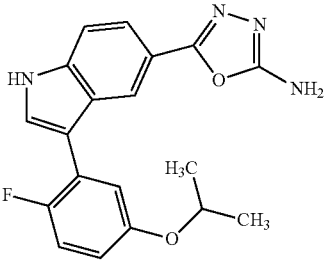 [SMILES: CC(C)Oc1ccc(F)c(-c2c[nH]c3ccc(-c4nnc(N)o4)cc23)c1] |
| 84 | 5-(3-(2-fluorophenyl)-1H-indol-5-yl)-1,3,4-oxadiazol-2-amine | 295 | Ex. 1 | 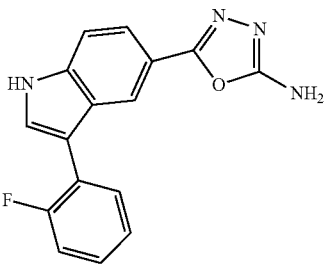 [SMILES: Nc1nnc(-c2ccc3[nH]cc(-c4ccccc4F)c3c2)o1] |
| 85 | 5-(3-(3-(1-methylethoxy)phenyl)-1H-indol-5-yl)-1,3,4-oxadiazol-2-amine | 335 | Ex. 1 | 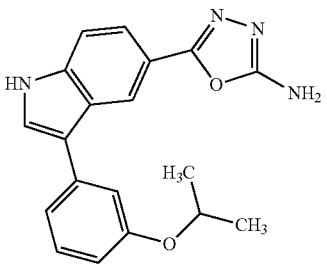 [SMILES: CC(C)Oc1cccc(-c2c[nH]c3ccc(-c4nnc(N)o4)cc23)c1] |
| 86 | 5-(3-(5-ethoxy-2-pyrazinyl)-1H-indol-5-yl)-1,3,4-oxadiazol-2-amine | 323 | Ex. 1 | 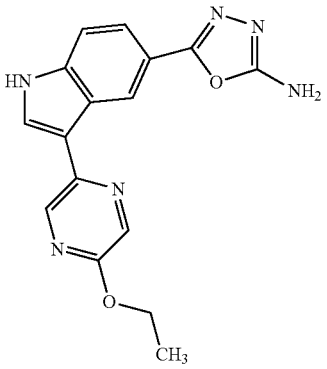 [SMILES: CCOc1cnc(-c2c[nH]c3ccc(-c4nnc(N)o4)cc23)cn1] |
| 87 | 5-(3-(6-(1-methylethoxy)-2-pyridinyl)-1H-indol-5-yl)-1,3,4-oxadiazol-2-amine | 336 | Ex. 1 | 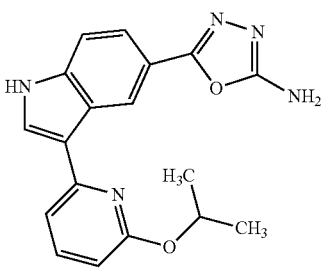 [SMILES: CC(C)Oc1cccc(-c2c[nH]c3ccc(-c4nnc(N)o4)cc23)n1] |

TABLE 1-continued

| Ex# | IUPAC Name | M + 1 | Method | Structures |
|---|---|---|---|---|
| 88 | 5-(3-(6-(3,3-difluoro-1-pyrrolidinyl)-2-pyrazinyl)-1H-indol-5-yl)-1,3,4-oxadiazol-2-amine | 384 | Ex. 2 | 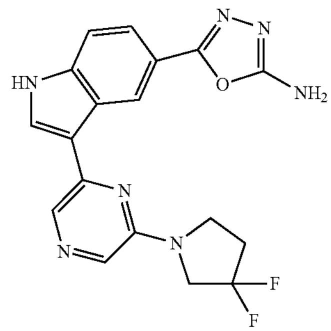 [SMILES: Nc1nnc(-c2ccc3[nH]cc(-c4cncc(N5CCC(F)(F)C5)n4)c3c2)o1] |
| 89 | 5-(3-(6-(1-piperidinyl)-2-pyrazinyl)-1H-indol-5-yl)-1,3,4-oxadiazol-2-amine | 362 | Ex. 2 | 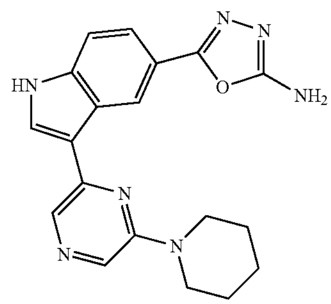 |
| 90 | 5-(3-(6-(4-morpholinyl)-2-pyrazinyl)-1H-indol-5-yl)-1,3,4-oxadiazol-2-amine | 364 | Ex. 2 | 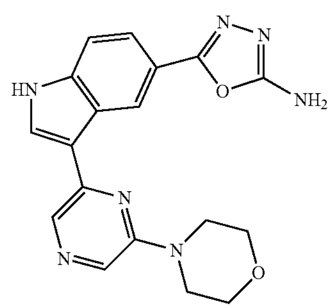 [SMILES: Nc1nnc(-c2ccc3[nH]cc(-c4cncc(N5CCOCC5)n4)c3c2)o1] |
| 91 | 5-(3-(4-((3S)-3-methyl-4-morpholinyl)-2-pyrimidinyl)-1H-indol-5-yl)-1,3,4-oxadiazol-2-amine | 378 | Ex. 3 | 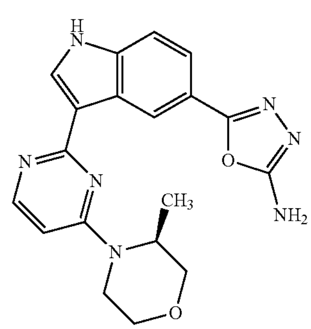 [SMILES: C[C@H]1COCCN1c1ccnc(-c2c[nH]c3ccc(-c4nnc(N)o4)cc23)n1] |

TABLE 1-continued
| Ex# | IUPAC Name | M + 1 | Method | Structures |
|---|---|---|---|---|
| 92 | 5-(3-(6-phenoxy-2-pyrazinyl)-1H-indol-5-yl)-1,3,4-oxadiazol-2-amine | 371 | Ex. 3 | 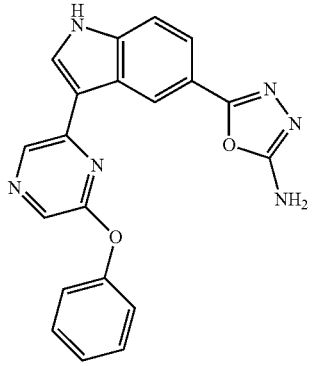 [SMILES: Nc1nnc(-c2ccc3[nH]cc(-c4cncc(Oc5ccccc5)n4)c3c2)o1] |
| 93 | 5-(3-(2-pyrimidinyl)-1H-indol-5-yl)-1,3,4-oxadiazol-2-amine | 279 | Ex. 3 | 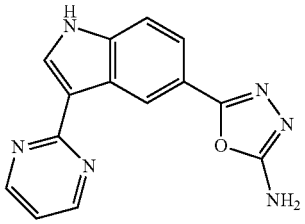 [SMILES: Nc1nnc(-c2ccc3[nH]cc(-c4ncccn4)c3c2)o1] |
| 94 | 5-(3-(4-cyclopropyl-2-pyrimidinyl)-1H-indol-5-yl)-1,3,4-oxadiazol-2-amine | 319 | Ex. 3 | 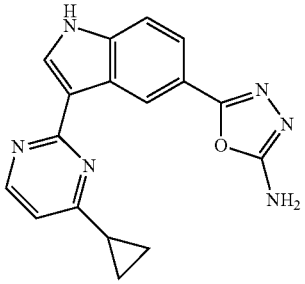 [SMILES: Nc1nnc(-c2ccc3[nH]cc(-c4nccc(C5CC5)n4)c3c2)o1] |
| 95 | 5-(3-(6-(trifluoromethyl)-4-pyrimidinyl)-1H-indol-5-yl)-1,3,4-oxadiazol-2-amine | 347 | Ex. 3 | 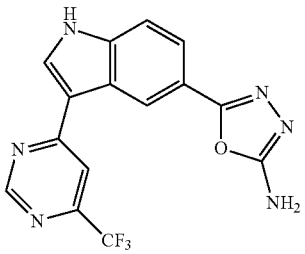 |
| 96 | 5-(3-(4-(trifluoromethyl)-2-pyrimidinyl)-1H-indol-5-yl)-1,3,4-oxadiazol-2-amine | 347 | Ex. 3 | 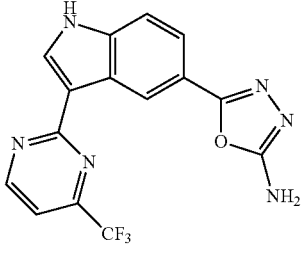 [SMILES: Nc1nnc(-c2ccc3[nH]cc(-c4nccc(C(F)(F)F)n4)c3c2)o1] |

TABLE 1-continued
| Ex# | IUPAC Name | M + 1 | Method | Structures |
|---|---|---|---|---|
| 97 | 5-(3-(4-(2-methyl-1-pyrrolidinyl)-2-pyrimidinyl)-1H-indol-5-yl)-1,3,4-oxadiazol-2-amine | 362 | Ex. 3 | 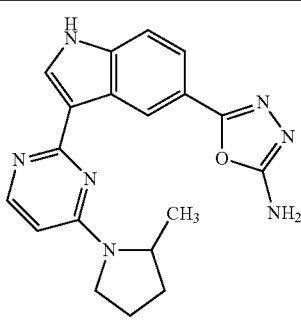 |
| 98 | 5-(3-(6-cyclopropyl-2-pyrazinyl)-1H-indol-5-yl)-1,3,4-oxadiazol-2-amine | 319 | Ex. 3 | 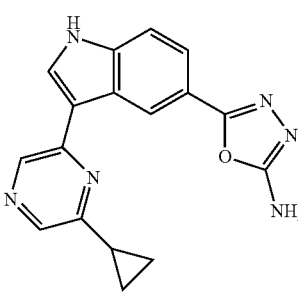 |
| 99 | 5-(3-(6-((3R)-3-piperidinyloxy)-2-pyrazinyl)-1H-indol-5-yl)-1,3,4-oxadiazol-2-amine | 378 | Ex. 3 | 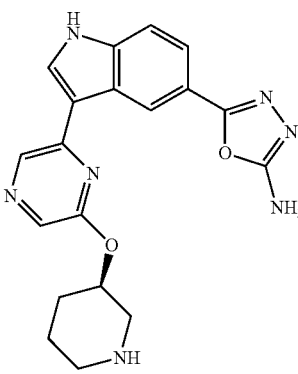 |
| 100 | 6-(5-(5-amino-1,3,4-oxadiazol-2-yl)-1H-indol-3-yl)-N-(cyclopropylmethyl)-2-pyrazinamine | 348 | Ex. 4 | 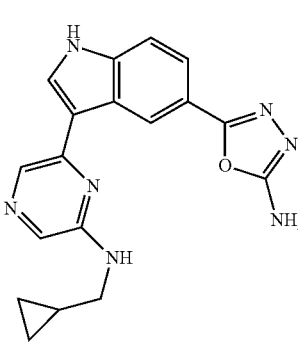 |

TABLE 1-continued
| Ex# | IUPAC Name | M + 1 | Method | Structures |
|---|---|---|---|---|
| 101 | 6-(5-(5-amino-1,3,4-oxadiazol-2-yl)-1H-indol-3-yl)-N-(1-methylethyl)-2-pyrazinamine | 336 | Ex. 4 | 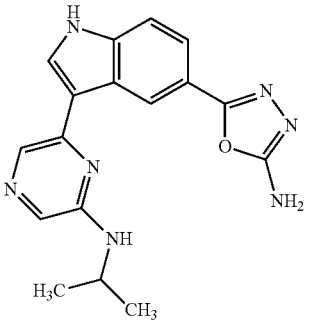 [SMILES: CC(C)Nc1cncc(-c2c[nH]c3ccc(-c4nnc(N)o4)cc23)n1] |
| 102 | 5-(3-(6-chloro-2-pyrazinyl)-1H-indol-5-yl)-1,3,4-oxadiazol-2-amine | 313 | Ex. 4 | 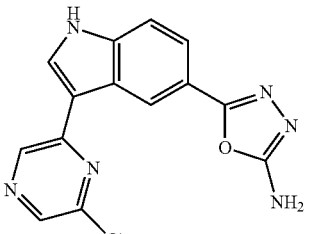 |
| 103 | 2-(5-(5-amino-1,3,4-oxadiazol-2-yl)-1H-indol-3-yl)-N-(1-methylethyl)-4-pyrimidinamine | 336 | Ex. 5 | 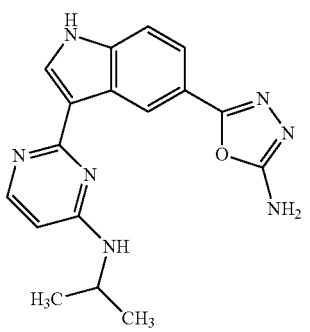 [SMILES: CC(C)Nc1ccnc(-c2c[nH]c3ccc(-c4nnc(N)o4)cc23)n1] |
| 104 | 1-(2-(5-(5-amino-1,3,4-oxadiazol-2-yl)-1H-indol-3-yl)-4-pyrimidinyl)-3-piperidinol | 378 | Ex. 5 | 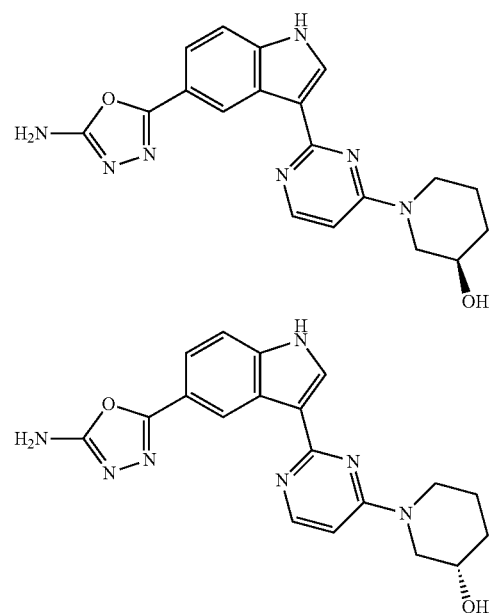 |

TABLE 1-continued
| Ex# | IUPAC Name | M + 1 | Method | Structures |
|---|---|---|---|---|
| 105 | 5-(3-(4-(3-methyl-1-piperidinyl)-2-pyrimidinyl)-1H-indol-5-yl)-1,3,4-oxadiazol-2-amine | 376 | Ex. 5 | 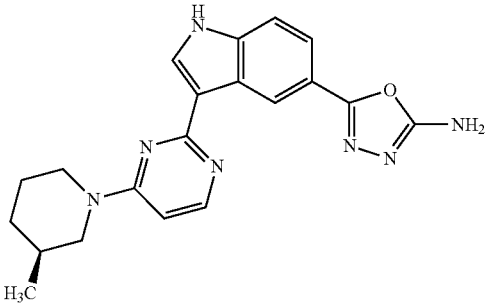 [SMILES: C[C@H]1CCCN(c2ccnc(-c3c[nH]c4ccc(-c5nnc(N)o5)cc34)n2)C1] |
| 106 | 5-(3-(4-phenoxy-2-pyrimidinyl)-1H-indol-5-yl)-1,3,4-oxadiazol-2-amine | 371 | Ex. 5 | 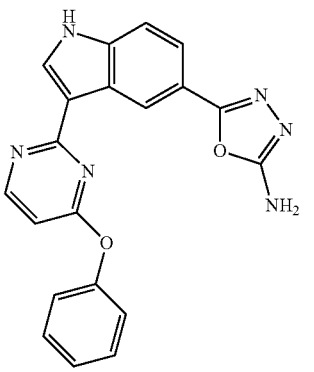 [SMILES: Nc1nnc(-c2ccc3[nH]cc(-c4nccc(Oc5ccccc5)n4)c3c2)o1] |

TABLE 1-continued
| Ex# | IUPAC Name | M + 1 | Method | Structures |
|---|---|---|---|---|
| 107 | 1-(2-(5-(5-amino-1,3,4-oxadiazol-2-yl)-1H-indol-3-yl)-4-pyrimidinyl)-N,N-dimethyl-3-piperidinamine | 405 | Ex. 5 | 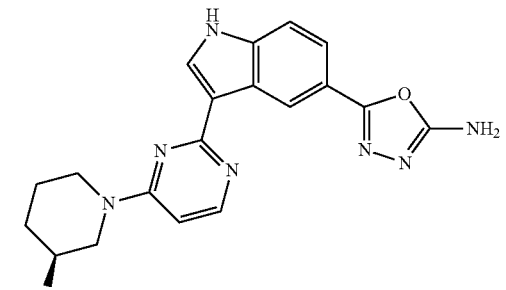 |
| 108 | 2-(5-(5-amino-1,3,4-oxadiazol-2-yl)-1H-indol-3-yl)-N-phenyl-4-pyrimidinamine | 370 | Ex. 5 | 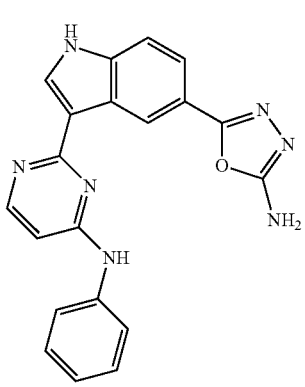 [SMILES: Nc1nnc(-c2ccc3[nH]cc(-c4nccc(Nc5ccccc5)n4)c3c2)o1] |
| 109 | 5-(3-(4-((2S)-2-(methoxymethyl)-1-pyrrolidinyl)-2-pyrimidinyl)-1H-indol-5-yl)-1,3,4-oxadiazol-2-amine | 392 | Ex. 5 | 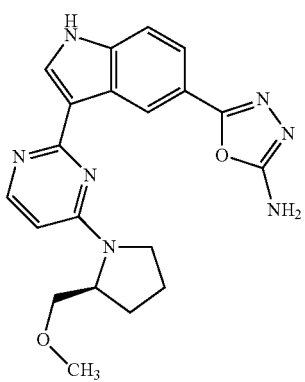 [SMILES: COC[C@@H]1CCCN1c1ccnc(-c2c[nH]c3ccc(-c4nnc(N)o4)cc23)n1] |

TABLE 1-continued
| Ex# | IUPAC Name | M + 1 | Method | Structures |
|---|---|---|---|---|
| 110 | 5-(3-(4-(2,2,2-trifluoroethoxy)-2-pyrimidinyl)-1H-indol-5-yl)-1,3,4-oxadiazol-2-amine | 377 | Ex. 5 | 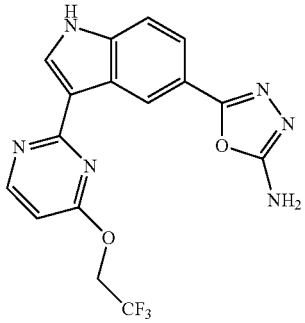 [SMILES: Nc1nnc(-c2ccc3[nH]cc(-c4nccc(OCC(F)(F)F)n4)c3c2)o1] |
| 111 | 2-(5-(5-amino-1,3,4-oxadiazol-2-yl)-1H-indol-3-yl)-N-(1-methyl-3-piperidinyl)-4-pyrimidinamine | 391 | Ex. 5 | 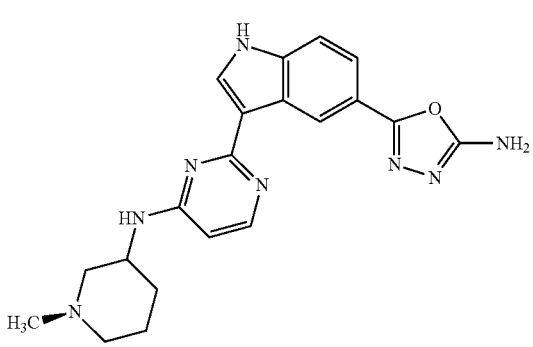 |
| 112 | 5-(3-(4-((1-methyl-3-piperidinyl)oxy)-2-pyrimidinyl)-1H-indol-5-yl)-1,3,4-oxadiazol-2-amine | 392 | Ex. 5 | 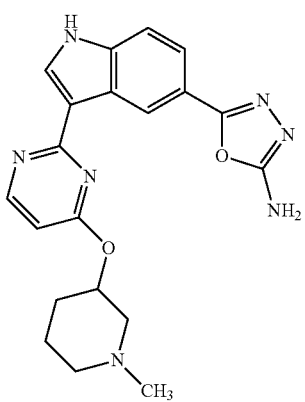 [SMILES: CN1CCCC(Oc2ccnc(-c3c[nH]c4ccc(-c5nnc(N)o5)cc34)n2)C1] |

TABLE 1-continued

| Ex# | IUPAC Name | M + 1 | Method | Structures |
|---|---|---|---|---|
| 113 | 5-(3-(4-((2R)-2-(methoxymethyl)-1-pyrrolidinyl)-2-pyrimidinyl)-1H-indol-5-yl)-1,3,4-oxadiazol-2-amine | 392 | Ex. 5 | 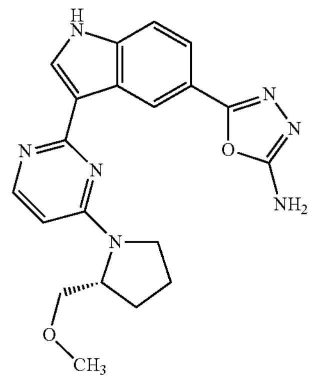 [SMILES: COC[C@H]1CCCN1c1ccnc(-c2c[nH]c3ccc(-c4nnc(N)o4)cc23)n1] |
| 114 | 5-(3-(6-(4-chlorophenyl)-2-pyrazinyl)-1H-indol-5-yl)-1,3,4-oxadiazol-2-amine | 389 | Ex. 07 | 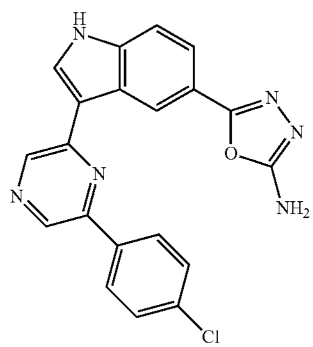 [SMILES: Nc1nnc(-c2ccc3[nH]cc(-c4cncc(-c5ccc(Cl)cc5)n4)c3c2)o1] |
| 115 | 5-(3-(6-phenyl-2-pyrazinyl)-1H-indol-5-yl)-1,3,4-oxadiazol-2-amine | 355 | Ex. 07 | 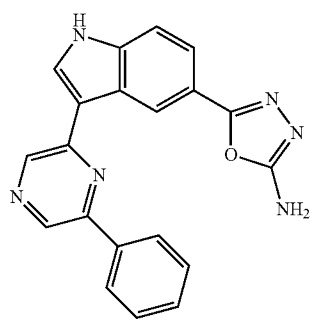 [SMILES: Nc1nnc(-c2ccc3[nH]cc(-c4cncc(-c5ccccc5)n4)c3c2)o1] |
| 116 | 5-(3-(6-(2-fluorophenyl)-2-pyrazinyl)-1H-indol-5-yl)-1,3,4-oxadiazol-2-amine | 373 | Ex. 07 | 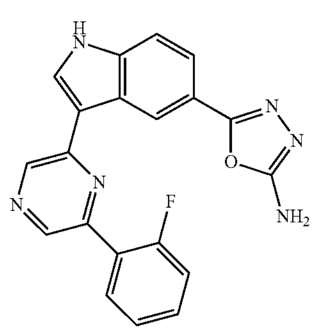 [SMILES: Nc1nnc(-c2ccc3[nH]cc(-c4cncc(-c5ccccc5F)n4)c3c2)o1] |

TABLE 1-continued

| Ex# | IUPAC Name | M + 1 | Method | Structures |
|---|---|---|---|---|
| 117 | 5-(3-(6-(2-chlorophenyl)-2-pyrazinyl)-1H-indol-5-yl)-1,3,4-oxadiazol-2-amine | 389 | Ex. 07 | 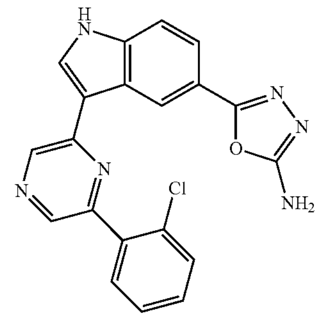 [SMILES: Nc1nnc(-c2ccc3[nH]cc(-c4cncc(-c5ccccc5Cl)n4)c3c2)o1] |
| 118 | 5-(3-(4-(2-chlorophenyl)-2-pyrimidinyl)-1H-indol-5-yl)-1,3,4-oxadiazol-2-amine | 389 | Ex. 07 | 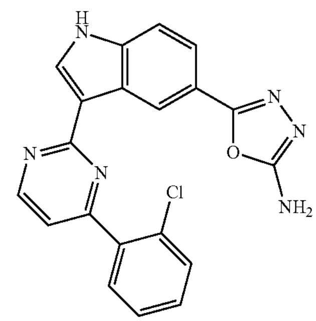 [SMILES: Nc1nnc(-c2ccc3[nH]cc(-c4nccc(-c5ccccc5Cl)n4)c3c2)o1] |
| 119 | 5-(3-(6-(3-fluorophenyl)-2-pyrazinyl)-1H-indol-5-yl)-1,3,4-oxadiazol-2-amine | 373 | Ex. 07 | 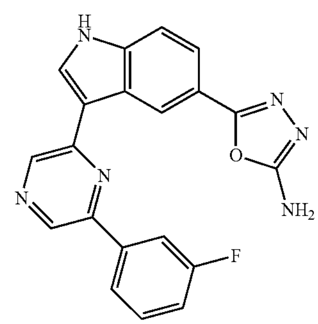 [SMILES: Nc1nnc(-c2ccc3[nH]cc(-c4cncc(-c5cccc(F)c5)n4)c3c2)o1] |
| 120 | 5-(3-(6-(3-chlorophenyl)-2-pyrazinyl)-1H-indol-5-yl)-1,3,4-oxadiazol-2-amine | 389 | Ex. 07 | 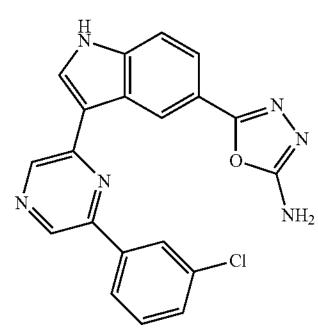 [SMILES: Nc1nnc(-c2ccc3[nH]cc(-c4cncc(-c5cccc(Cl)c5)n4)c3c2)o1] |

TABLE 1-continued

| Ex# | IUPAC Name | M + 1 | Method | Structures |
|---|---|---|---|---|
| 121 | 5-(3-(6-(1-methyl-1H-pyrazol-4-yl)-2-pyrazinyl)-1H-indol-5-yl)-1,3,4-oxadiazol-2-amine | 359 | Ex. 07 | 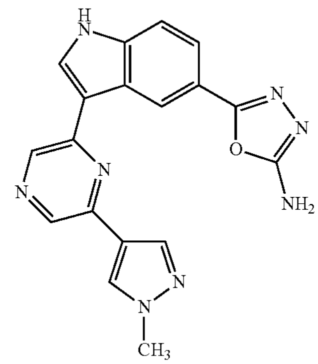 [SMILES: Cn1cc(-c2cncc(-c3c[nH]c4ccc(-c5nnc(N)o5)cc34)n2)cn1] |
| 122 | 5-(3-(4-phenyl-2-pyrimidinyl)-1H-indol-5-yl)-1,3,4-oxadiazol-2-amine | 355 | Ex. 08 | 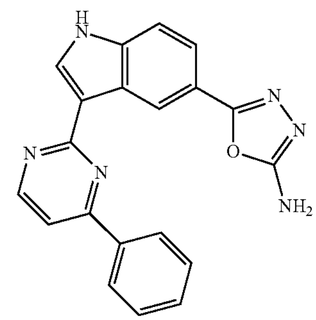 [SMILES: Nc1nnc(-c2ccc3[nH]cc(-c4nccc(-c5ccccc5)n4)c3c2)o1] |
| 123 | 5-(3-(4-(2-fluorophenyl)-2-pyrimidinyl)-1H-indol-5-yl)-1,3,4-oxadiazol-2-amine | 373 | Ex. 08 | 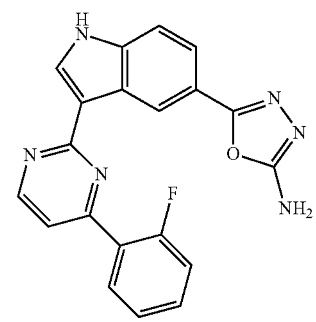 [SMILES: Nc1nnc(-c2ccc3[nH]cc(-c4nccc(-c5ccccc5F)n4)c3c2)o1] |
| 124 | 5-(3-(4-(2-methylphenyl)-2-pyrimidinyl)-1H-indol-5-yl)-1,3,4-oxadiazol-2-amine | 369 | Ex. 08 | 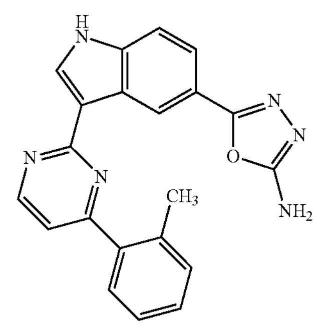 [SMILES: Cc1ccccc1-c1ccnc(-c2c[nH]c3ccc(-c4nnc(N)o4)cc23)n1] |
| 125 | 5-(3-(2-fluoro-5-(1-methylethoxy)phenyl)-1H-pyrrolo[3,2-b]pyridin-5-yl)-1,3,4-oxadiazol-2-amine | 354 | Ex. 09 | 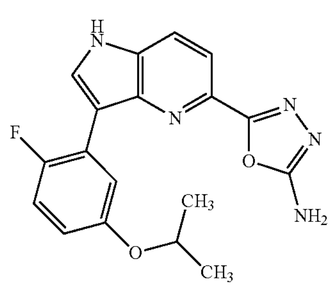 [SMILES: CC(C)Oc1ccc(F)c(-c2c[nH]c3ccc(-c4nnc(N)o4)nc23)c1] |

TABLE 1-continued

| Ex# | IUPAC Name | M + 1 | Method | Structures |
|---|---|---|---|---|
| 126 | 5-(3-(3-(1-methylethoxy)phenyl)-1H-pyrrolo[3,2-b]pyridin-5-yl)-1,3,4-oxadiazol-2-amine | 336 | Ex. 09 | 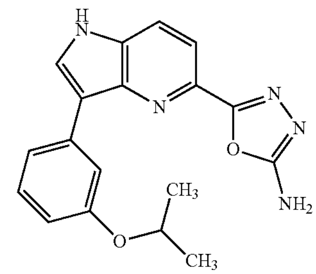 [SMILES: CC(C)Oc1cccc(-c2c[nH]c3ccc(-c4nnc(N)o4)nc23)c1] |
| 127 | 5-(3-(1-(2-methylpropyl)-1H-pyrazol-4-yl)-1H-pyrrolo[3,2-b]pyridin-5-yl)-1,3,4-oxadiazol-2-amine | 324 | Ex. 09 | 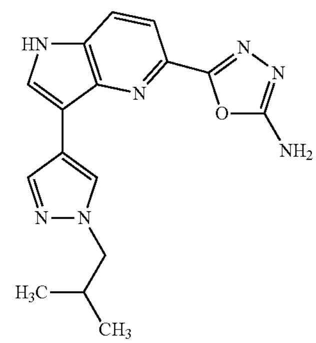 [SMILES: CC(C)Cn1cc(-c2c[nH]c3ccc(-c4nnc(N)o4)nc23)cn1] |
| 128 | (3S)-1-(2-(5-(5-(methylamino)-1,3,4-thiadiazol-2-yl)-1H-indol-3-yl)-4-pyrimidinyl)-3-piperidinamine | 407 | Ex. 11 | 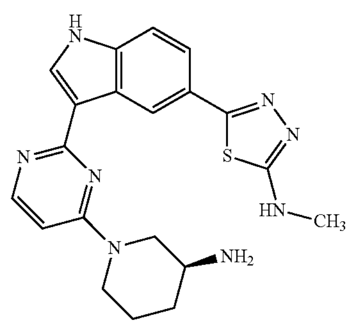 [SMILES: CNc1nnc(-c2ccc3[nH]cc(-c4nccc(N5CCC[C@H](N)C5)n4)c3c2)s1] |
| 129 | N-methyl-5-(3-(2-(4-morpholinyl)-4-pyrimidinyl)-1H-indol-5-yl)-1,3,4-thiadiazol-2-amine | 394 | Ex. 11 | 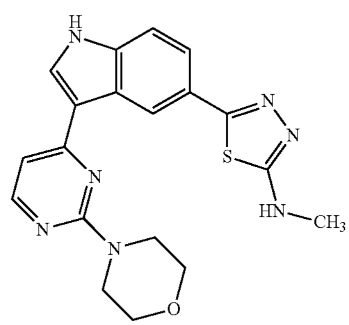 [SMILES: CNc1nnc(-c2ccc3[nH]cc(-c4ccnc(N5CCOCC5)n4)c3c2)s1] |
| 130 | 5-(3-(6-phenyl-2-pyridinyl)-1H-indol-5-yl)-1,3,4-thiadiazol-2-amine | 370 | Ex. 11 | 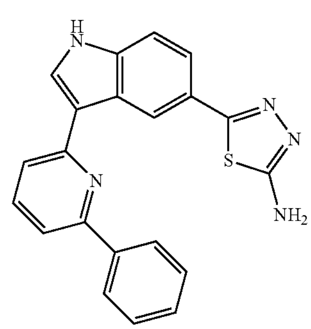 [SMILES: Nc1nnc(-c2ccc3[nH]cc(-c4cccc(-c5ccccc5)n4)c3c2)s1] |

TABLE 1-continued

| Ex# | IUPAC Name | M + 1 | Method | Structures |
|---|---|---|---|---|
| 131 | N-methyl-5-(3-(4-phenyl-2-pyrimidinyl)-1H-indol-5-yl)-1,3,4-thiadiazol-2-amine | 385 | Ex. 11 | 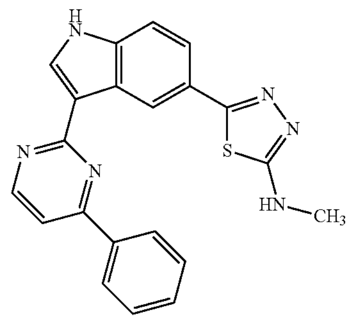 [SMILES: CNc1nnc(-c2ccc3[nH]cc(-c4nccc(-c5ccccc5)n4)c3c2)s1] |
| 132 | N-methyl-5-(3-(4-(4-methyl-1-piperazinyl)-2-pyrimidinyl)-1H-indol-5-yl)-1,3,4-thiadiazol-2-amine | 407 | Ex. 11 | 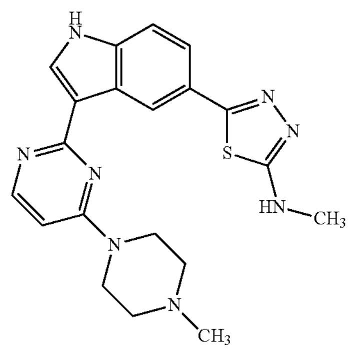 [SMILES: CNc1nnc(-c2ccc3[nH]cc(-c4nccc(N5CCN(C)CC5)n4)c3c2)s1] |
| 133 | 5-(3-(2-(4-morpholinyl)-4-pyrimidinyl)-1H-indol-5-yl)-1,3,4-thiadiazol-2-amine | 380 | Ex. 11 | 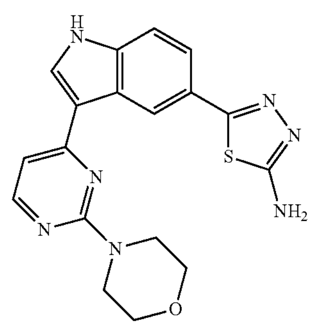 |
| 134 | N-methyl-5-(3-(4-(4-morpholinyl)-2-pyrimidinyl)-1H-indol-5-yl)-1,3,4-thiadiazol-2-amine | 394 | Ex. 11 | 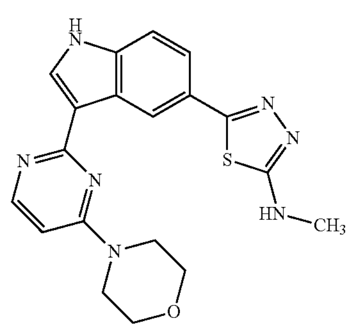 [SMILES: CNc1nnc(-c2ccc3[nH]cc(-c4nccc(N5CCOCC5)n4)c3c2)s1] |

TABLE 1-continued

| Ex# | IUPAC Name | M + 1 | Method | Structures |
|---|---|---|---|---|
| 135 | N-methyl-5-(3-(4-(1-piperidinyl)-2-pyrimidinyl)-1H-indol-5-yl)-1,3,4-thiadiazol-2-amine | 392 | Ex. 11 | 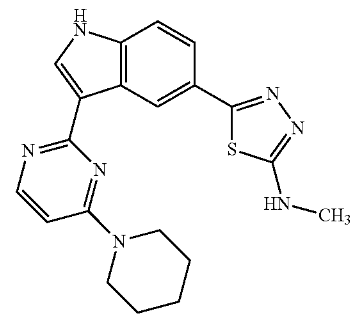 [SMILES: CNc1nnc(-c2ccc3[nH]cc(-c4nccc(N5CCCCC5)n4)c3c2)s1] |
| 136 | 5-(3-(2-fluorophenyl)-1H-indol-5-yl)-1,3,4-thiadiazol-2-amine | 311 | Ex. 12 | 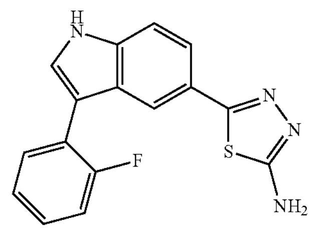 [SMILES: Nc1nnc(-c2ccc3[nH]cc(-c4ccccc4F)c3c2)s1] |
| 137 | 3-(5-(5-amino-1,3,4-thiadiazol-2-yl)-1H-indol-3-yl)-4-fluoro-N-phenylbenzamide | 430 | Ex. 12 | 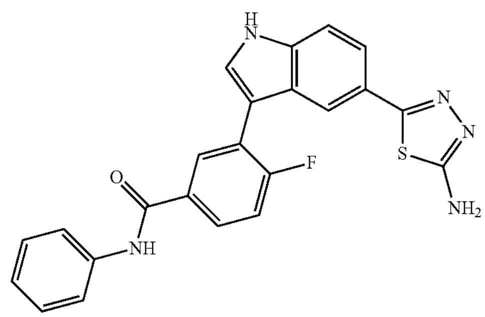 [SMILES: Nc1nnc(-c2ccc3[nH]cc(-c4cc(C(=O)Nc5ccccc5)ccc4F)c3c2)s1] |
| 138 | 5-(3-(2,6-difluorophenyl)-1H-indol-5-yl)-1,3,4-thiadiazol-2-amine | 329 | Ex. 12 | 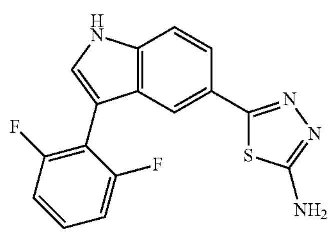 [SMILES: Nc1nnc(-c2ccc3[nH]cc(-c4c(F)cccc4F)c3c2)s1] |
| 139 | N-(5-(3-(2-fluorophenyl)-1H-indol-5-yl)-1,3,4-thiadiazol-2-yl)-3-piperidinamine | 394 | Ex. 12 | |

TABLE 1-continued
| Ex# | IUPAC Name | M + 1 | Method | Structures |
|---|---|---|---|---|
| 140 | 1-(5-(3-(2-fluorophenyl)-1H-indol-5-yl)-1,3,4-thiadiazol-2-yl)-3-pyrrolidinamine | 380 | Ex. 12 | 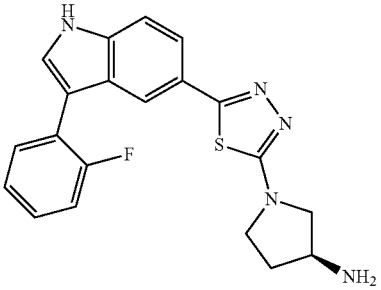 [SMILES: N[C@H]1CCN(c2nnc(-c3ccc4[nH]cc(-c5ccccc5F)c4c3)s2)C1] |
| 141 | 5-(3-(2-fluorophenyl)-1H-indol-5-yl)-N-(2-(2-piperidinyl)ethyl)-1,3,4-thiadiazol-2-amine | 422 | Ex. 12 | 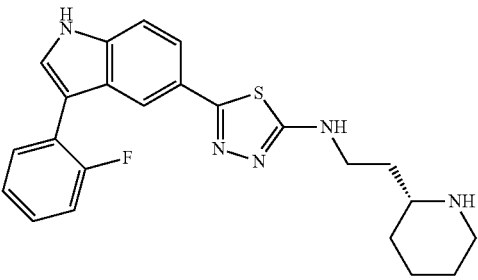 [SMILES: Fc1ccccc1-c1c[nH]c2ccc(-c3nnc(NCC[C@H]4CCCCN4)s3)cc12] |
| 142 | 5-(3-(2-fluorophenyl)-1H-indol-5-yl)-N-(1H-indol-5-ylmethyl)-1,3,4-thiadiazol-2-amine | 440 | Ex. 12 | 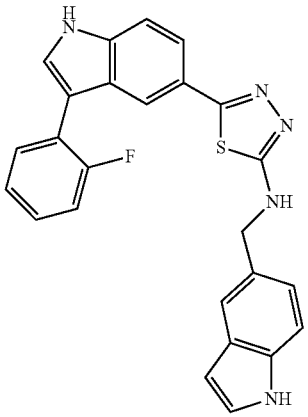 [SMILES: Fc1ccccc1-c1c[nH]c2ccc(-c3nnc(NCc4ccc5[nH]ccc5c4)s3)cc12] |

TABLE 1-continued
| Ex# | IUPAC Name | M + 1 | Method | Structures |
|---|---|---|---|---|
| 143 | 5-(3-(2-fluorophenyl)-1H-indol-5-yl)-N-(1H-indol-4-ylmethyl)-1,3,4-thiadiazol-2-amine | 440 | Ex. 12 | 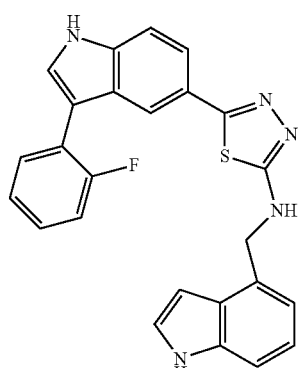 |
| 144 | 1-(5-(3-(2-fluorophenyl)-1H-indol-5-yl)-1,3,4-thiadiazol-2-yl)-4-piperidinamine | 394 | Ex. 12 | 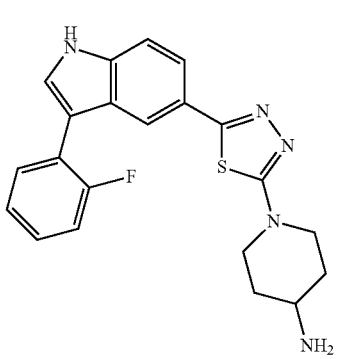 [SMILES: NC1CCN(c2nnc(-c3ccc4[nH]cc(-c5ccccc5F)c4c3)s2)CC1] |
| 145 | N-(3-(((5-(3-(2-fluorophenyl)-1H-indol-5-yl)-1,3,4-thiadiazol-2-yl)amino)methyl)phenyl)acetamide | 458 | Ex. 12 | 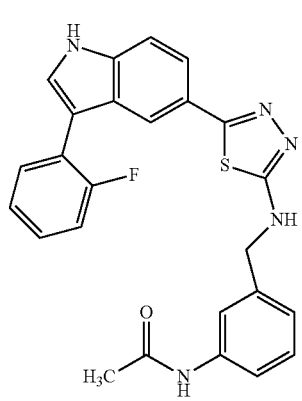 [SMILES: CC(=O)Nc1cccc(CNc2nnc(-c3ccc4[nH]cc(-c5ccccc5F)c4c3)s2)c1] |
| 146 | N-(3-(((5-(3-(2-fluorophenyl)-1H-indol-5-yl)-1,3,4-thiadiazol-2-yl)amino)methyl)phenyl)-2-methoxyacetamide | 488 | Ex. 12 | 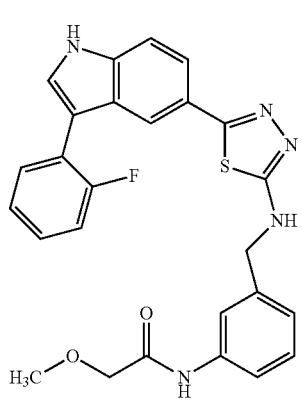 [SMILES: COCC(=O)Nc1cccc(CNc2nnc(-c3ccc4[nH]cc(-c5ccccc5F)c4c3)s2)c1] |

TABLE 1-continued
| Ex# | IUPAC Name | M + 1 | Method | Structures |
|---|---|---|---|---|
| 147 | 5-(3-(2,4-difluorophenyl)-1H-indol-5-yl)-N-((2,3-dimethyl-1H-indol-5-yl)methyl)-1,3,4-thiadiazol-2-amine | 486 | Ex. 12 | 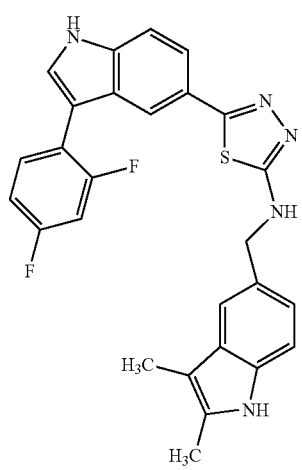 [SMILES: Cc1[nH]c2ccc(CNc3nnc(-c4ccc5[nH]cc(-c6ccc(F)cc6F)c5c4)s3)cc2c1C] |
| 148 | N-(4-(((5-(3-(2,4-difluorophenyl)-1H-indol-5-yl)-1,3,4-thiadiazol-2-yl)amino)methyl)phenyl)acetamide | 476 | Ex. 12 | 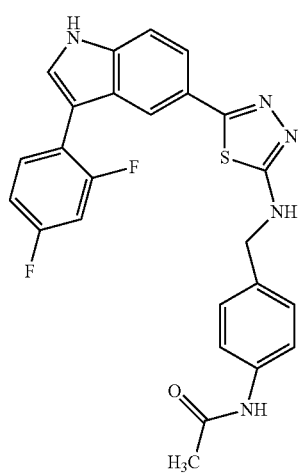 [SMILES: CC(=O)Nc1ccc(CNc2nnc(-c3ccc4[nH]cc(-c5ccc(F)cc5F)c4c3)s2)cc1] |
| 149 | N-benzyl-5-(3-(2-fluorophenyl)-1H-indol-5-yl)-1,3,4-thiadiazol-2-amine | 401 | Ex. 12 | 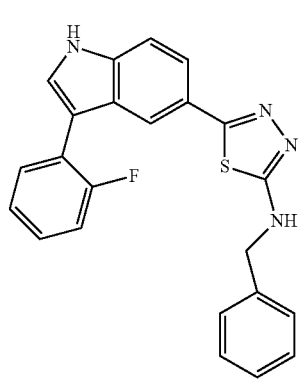 [SMILES: Fc1ccccc1-c1c[nH]c2ccc(-c3nnc(NCc4ccccc4)s3)cc12] |

TABLE 1-continued

| Ex# | IUPAC Name | M + 1 | Method | Structures |
|---|---|---|---|---|
| 150 | 5-(3-(2,4-difluorophenyl)-1H-indol-5-yl)-N-(3-(methylamino)benzyl)-1,3,4-thiadiazol-2-amine | 448 | Ex. 12 | 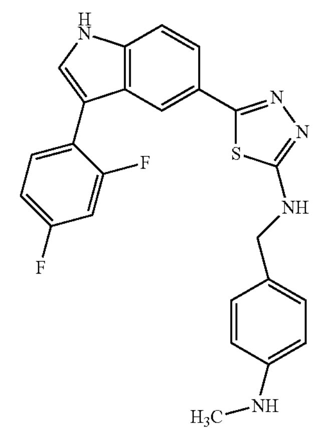 [SMILES: CNc1ccc(CNc2nnc(-c3ccc4[nH]cc(-c5ccc(F)cc5F)c4c3)s2)cc1] |
| 151 | 5-(3-(6-quinoxalinyl)-1H-indol-5-yl)-1,3,4-thiadiazol-2-amine | 345 | Ex. 12 | 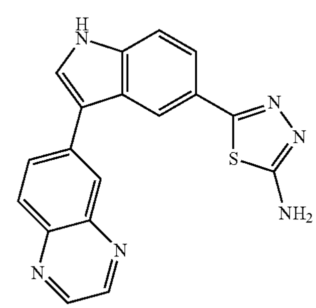 [SMILES: Nc1nnc(-c2ccc3[nH]cc(-c4ccc5nccnc5c4)c3c2)s1] |
| 152 | (3S)-1-(6-(5-(5-amino-1,3,4-thiadiazol-2-yl)-1H-indol-3-yl)-2-pyridinyl)-3-piperidinamine | 392 | Ex. 13 | 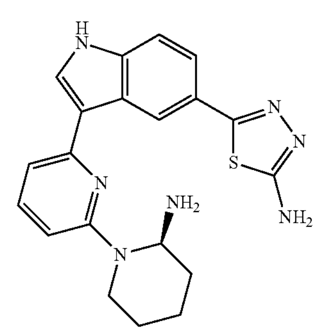 [SMILES: Nc1nnc(-c2ccc3[nH]cc(-c4cccc(N5CCCC[C@@H]5N)n4)c3c2)s1] |

TABLE 1-continued
| Ex# | IUPAC Name | M + 1 | Method | Structures |
|---|---|---|---|---|
| 153 | 5-(3-(6-(2-methyl-1-piperidinyl)-2-pyrazinyl)-1H-indol-5-yl)-1,3,4-thiadiazol-2-amine | 392 | Ex. 14 | 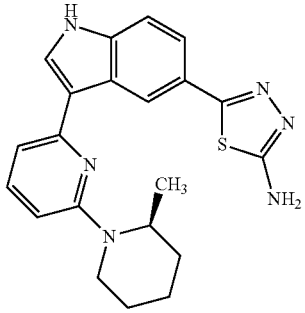 [SMILES: C[C@H]1CCCCN1c1cccc(-c2c[nH]c3ccc(-c4nnc(N)s4)cc23)n1]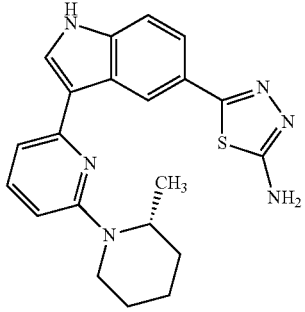 [SMILES: C[C@@H]1CCCCN1c1cccc(-c2c[nH]c3ccc(-c4nnc(N)s4)cc23)n1] |
| 154 | 6-(5-(5-amino-1,3,4-thiadiazol-2-yl)-1H-indol-3-yl)-N,N-diethyl-2-pyrazinamine | 366 | Ex. 14 | 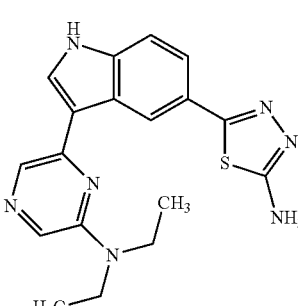 |
| 155 | 5-(3-(6-(4-methyl-1H-imidazol-1-yl)-2-pyridinyl)-1H-indol-5-yl)-1,3-4-thiadiazol-2-amine | 374 | Ex. 14 | 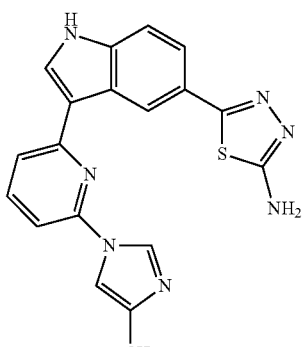 |

TABLE 1-continued

| Ex# | IUPAC Name | M + 1 | Method | Structures |
|-----|------------|-------|--------|------------|
| 156 | 5-(3-(6-(4-morpholinyl)-2-pyrazinyl)-1H-indol-5-yl)-1,3,4-thiadiazol-2-amine | 380 | Ex. 14 | 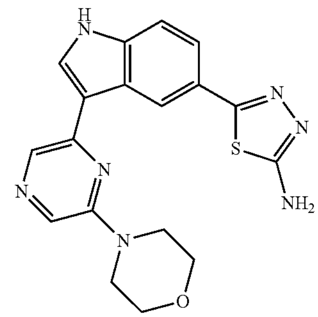 [SMILES: Nc1nnc(-c2ccc3[nH]cc(-c4cncc(N5CCOCC5)n4)c3c2)s1] |
| 157 | 5-(3-(6-(1-methylethoxy)-2-pyridinyl)-1H-indol-5-yl)-1,3,4-thiadiazol-2-amine | 352 | Ex. 14 | 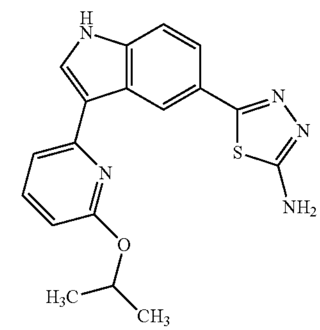 [SMILES: CC(C)Oc1cccc(-c2c[nH]c3ccc(-c4nnc(N)s4)cc23)n1] |
| 158 | 6-(5-(5-amino-1,3,4-thiadiazol-2-yl)-1H-indol-3-yl)-N,N-dimethyl-2-pyrazinamine | 338 | Ex. 14 | 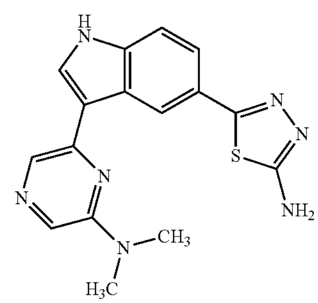 [SMILES: CN(C)c1cncc(-c2c[nH]c3ccc(-c4nnc(N)s4)cc23)n1] |
| 159 | 5-(3-(6-(1-methylethoxy)-2-pyrazinyl)-1H-indol-5-yl)-1,3,4-thiadiazol-2-amine | 353 | Ex. 14 | 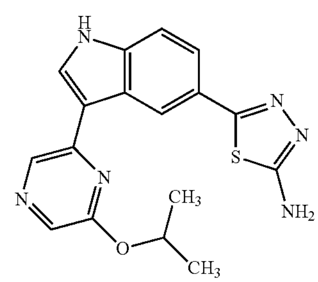 [SMILES: CC(C)Oc1cncc(-c2c[nH]c3ccc(-c4nnc(N)s4)cc23)n1] |
| 160 | 5-(3-(6-(cyclopentyloxy)-2-pyrazinyl)-1H-indol-5-yl)-1,3,4-thiadiazol-2-amine | 379 | Ex. 14 | 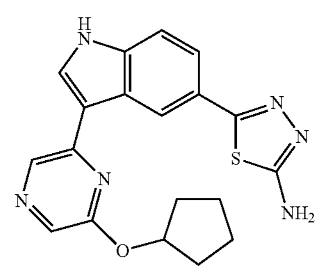 [SMILES: Nc1nnc(-c2ccc3[nH]cc(-c4cncc(OC5CCCC5)n4)c3c2)s1] |

TABLE 1-continued
| Ex# | IUPAC Name | M + 1 | Method | Structures |
|---|---|---|---|---|
| 161 | 5-(3-(6-(cyclobutyloxy)-2-pyridinyl)-1H-indol-5-yl)-1,3,4-thiadiazol-2-amine | 364 | Ex. 14 | 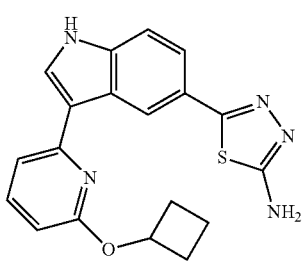 [SMILES: Nc1nnc(-c2ccc3[nH]cc(-c4cccc(OC5CCC5)n4)c3c2)s1] |
| 162 | 5-(3-(6-(4-methyl-1-piperidinyl)-2-pyrazinyl)-1H-indol-5-yl)-1,3,4-thiadiazol-2-amine | 392 | Ex. 14 | 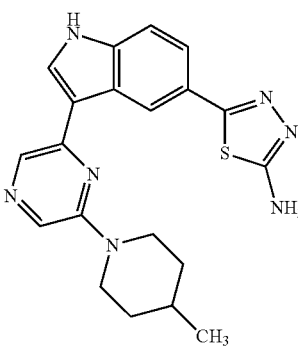 |
| 163 | 5-(3-(6-(cyclopentyloxy)-2-pyridinyl)-1H-indol-5-yl)-1,3,4-thiadiazol-2-amine | 378 | Ex. 14 | 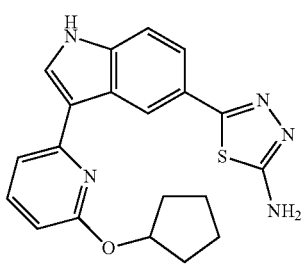 [SMILES: Nc1nnc(-c2ccc3[nH]cc(-c4cccc(OC5CCCC5)n4)c3c2)s1] |
| 164 | 5-(3-(6-ethoxy-2-pyridinyl)-1H-indol-5-yl)-1,3,4-thiadiazol-2-amine | 338 | Ex. 14 | 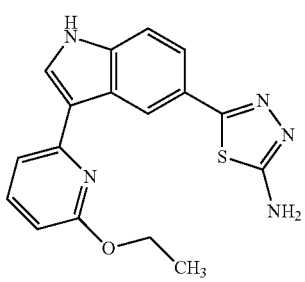 [SMILES: CCOc1cccc(-c2c[nH]c3ccc(-c4nnc(N)s4)cc23)n1] |
| 165 | 5-(3-(6-propoxy-2-pyridinyl)-1H-indol-5-yl)-1,3,4-thiadiazol-2-amine | 352 | Ex. 14 | 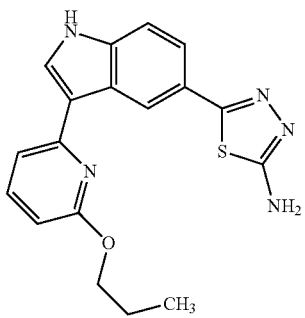 [SMILES: CCCOc1cccc(-c2c[nH]c3ccc(-c4nnc(N)s4)cc23)n1] |

TABLE 1-continued

| Ex# | IUPAC Name | M + 1 | Method | Structures |
|---|---|---|---|---|
| 166 | 1-(6-(5-(5-amino-1,3,4-thiadiazol-2-yl)-1H-indol-3-yl)-2-pyridinyl)-2-pyrrolidinone | 377 | Ex. 14 | 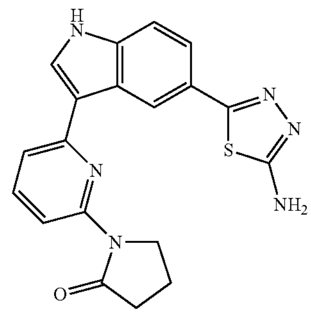 [SMILES: Nc1nnc(-c2ccc3[nH]cc(-c4cccc(N5CCCC5=O)n4)c3c2)s1] |
| 167 | 5-(3-(6-(2-methyl-1-piperidinyl)-2-pyridinyl)-1H-indol-5-yl)-1,3,4-thiadiazol-2-amine | 391 | Ex. 14 | |
| 168 | 5-(3-(5,6-dimethoxy-2-pyridinyl)-1H-indol-5-yl)-1,3,4-thiadiazol-2-amine | 354 | Ex. 14 | 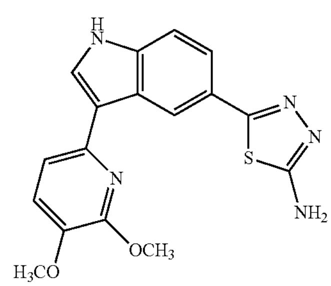 [SMILES: COc1ccc(-c2c[nH]c3ccc(-c4nnc(N)s4)cc23)nc1OC] |
| 169 | 5-(3-(6-(2-methyl-1H-imidazol-1-yl)-2-pyridinyl)-1H-indol-5-yl)-1,3,4-thiadiazol-2-amine | 374 | Ex. 14 | 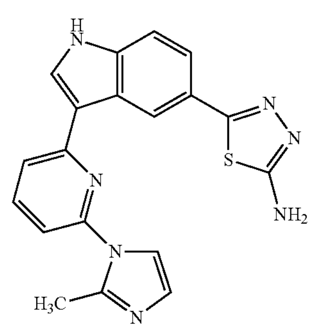 [SMILES: Cc1nccn1-c1cccc(-c2c[nH]c3ccc(-c4nnc(N)s4)cc23)n1] |

TABLE 1-continued

| Ex# | IUPAC Name | M + 1 | Method | Structures |
|---|---|---|---|---|
| 170 | 5-(3-(2-(4-methyl-1H-imidazol-1-yl)-1,3-thiazol-4-yl)-1H-indol-5-yl)-1,3,4-thiadiazol-2-amine | 380 | Ex. 14 | 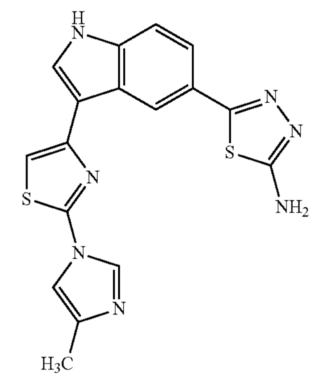 [SMILES: Cc1cn(-c2nc(-c3c[nH]c4ccc(-c5nnc(N)s5)cc34)cs2)cn1] |
| 171 | 5-(3-(1H-indazol-6-yl)-1H-indol-5-yl)-1,3,4-thiadiazol-2-amine | 333 | Ex. 14 | 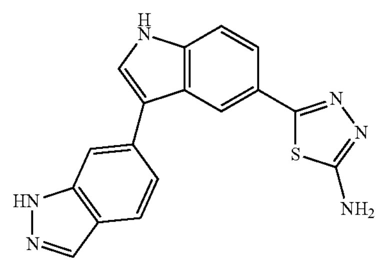 [SMILES: Nc1nnc(-c2ccc3[nH]cc(-c4ccc5cn[nH]c5c4)c3c2)s1] |
| 172 | 5-(3-(6-(1-piperidinyl)-2-pyridinyl)-1H-indol-5-yl)-1,3,4-thiadiazol-2-amine | 377 | Ex. 14 | 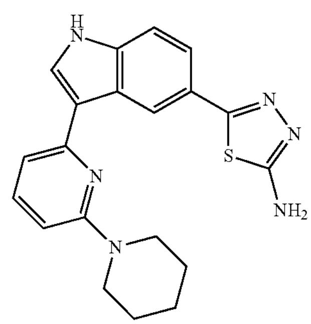 [SMILES: Nc1nnc(-c2ccc3[nH]cc(-c4cccc(N5CCCCC5)n4)c3c2)s1] |
| 173 | 5-(3-(6-(cyclohexyloxy)-2-pyridinyl)-1H-indol-5-yl)-1,3,4-thiadiazol-2-amine | 392 | Ex. 14 | 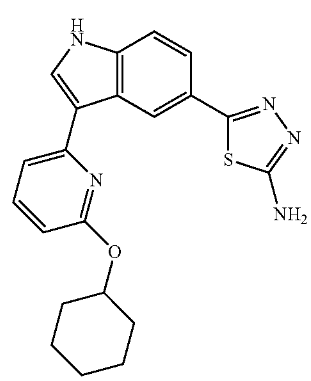 [SMILES: Nc1nnc(-c2ccc3[nH]cc(-c4cccc(OC5CCCCC5)n4)c3c2)s1] |

TABLE 1-continued

| Ex# | IUPAC Name | M + 1 | Method | Structures |
|---|---|---|---|---|
| 174 | 5-(3-(6-(3-methyl-1-piperidinyl)-2-pyridinyl)-1H-indol-5-yl)-1,3,4-thiadiazol-2-amine | 391 | Ex. 14 | |
| 175 | 5-(3-(6-(4-methyl-1-piperidinyl)-2-pyridinyl)-1H-indol-5-yl)-1,3,4-thiadiazol-2-amine | 391 | Ex. 14 | 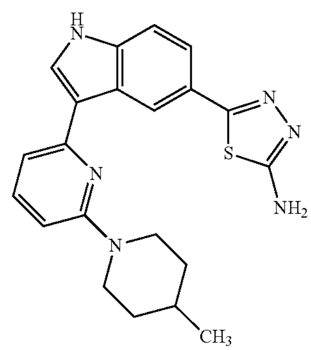 [SMILES: CC1CCN(c2cccc(-c3c[nH]c4ccc(-c5nnc(N)s5)cc34)n2)CC1] |
| 176 | 5-(3-(6-(1-pyrrolidinyl)-2-pyridinyl)-1H-indol-5-yl)-1,3,4-thiadiazol-2-amine | 363 | Ex. 14 | 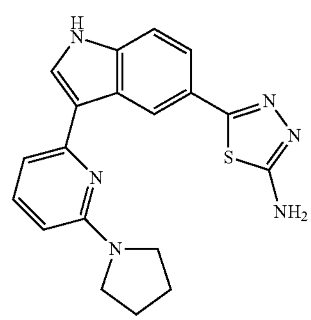 [SMILES: Nc1nnc(-c2ccc3[nH]cc(-c4cccc(N5CCCC5)n4)c3c2)s1] |
| 177 | 1-(4-(5-(5-amino-1,3,4-thiadiazol-2-yl)-1H-indol-3-yl)-1,3-thiazol-2-yl)-2(1H)-pyridinone | 393 | Ex. 14 | 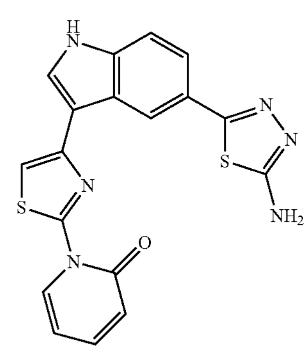 [SMILES: Nc1nnc(-c2ccc3[nH]cc(-c4csc(-n5ccccc5=O)n4)c3c2)s1] |

TABLE 1-continued

| Ex# | IUPAC Name | M + 1 | Method | Structures |
|---|---|---|---|---|
| 178 | 5-(3-(5-(4-methyl-1-piperazinyl)-2-pyrazinyl)-1H-indol-5-yl)-1,3,4-thiadiazol-2-amine | 393 | Ex. 14 | 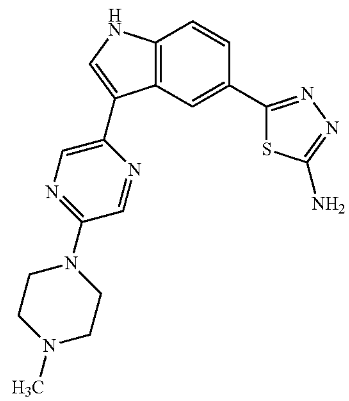 [SMILES: CN1CCN(c2cnc(-c3c[nH]c4ccc(-c5nnc(N)s5)cc34)cn2)CC1] |
| 179 | 5-(3-(6-(3-methyl-1H-pyrazol-1-yl)-2-pyridinyl)-1H-indol-5-yl)-1,3,4-thiadiazol-2-amine | 374 | Ex. 14 | 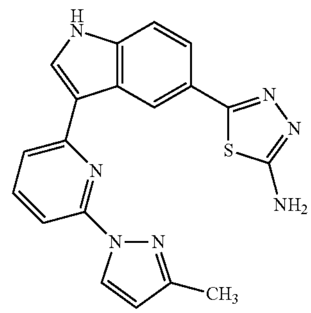 [SMILES: Cc1ccn(-c2cccc(-c3c[nH]c4ccc(-c5nnc(N)s5)cc34)n2)n1] |
| 180 | 5-(3-(6-(1H-pyrazol-1-yl)-2-pyridinyl)-1H-indol-5-yl)-1,3,4-thiadiazol-2-amine | 360 | Ex. 14 | 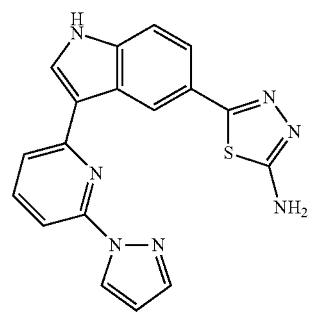 [SMILES: Nc1nnc(-c2ccc3[nH]cc(-c4cccc(-n5cccn5)n4)c3c2)s1] |
| 181 | 1-(6-(5-(5-amino-1,3,4-thiadiazol-2-yl)-1H-indol-3-yl)-2-pyridinyl)-2-piperidinone | 391 | Ex. 14 | 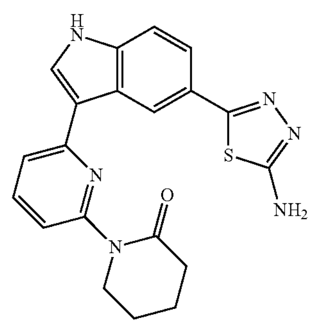 [SMILES: Nc1nnc(-c2ccc3[nH]cc(-c4cccc(N5CCCCC5=O)n4)c3c2)s1] |
| 182 | 5-(3-(6-(trifluoromethyl)-2-pyridinyl)-1H-indol-5-yl)-1,3,4-thiadiazol-2-amine | 362 | Ex. 14 | 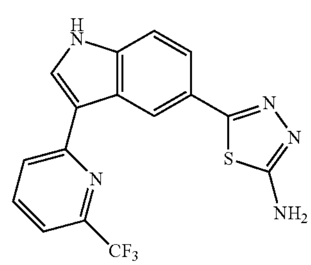 [SMILES: Nc1nnc(-c2ccc3[nH]cc(-c4cccc(C(F)(F)F)n4)c3c2)s1] |

TABLE 1-continued

| Ex# | IUPAC Name | M + 1 | Method | Structures |
|---|---|---|---|---|
| 183 | 6-(5-(5-amino-1,3,4-thiadiazol-2-yl)-1H-indol-3-yl)-2-pyridinecarbonitrile | 319 | Ex. 14 | 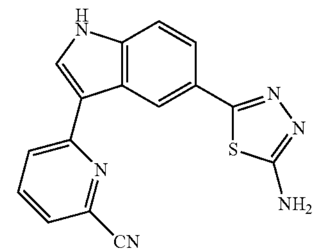 [SMILES: N#Cc1cccc(-c2c[nH]c3ccc(-c4nnc(N)s4)cc23)n1] |
| 184 | 5-(3-(2-(2-methyl-1-piperidinyl)-1,3-thiazol-4-yl)-1H-indol-5-yl)-1,3,4-thiadiazol-2-amine | 397 | Ex. 14 | |
| 185 | 1-(6-(5-(5-amino-1,3,4-thiadiazol-2-yl)-1H-indol-3-yl)-2-pyridinyl)-2-piperidinone 6'-(5-(5-amino-1,3,4-thiadiazol-2-yl)-1H-indol-3-yl)-2H-1,2'-bipyridin-2-one | 387 | Ex. 14 | 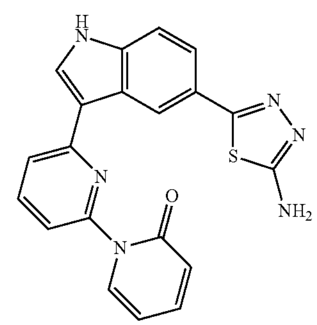 [SMILES: Nc1nnc(-c2ccc3[nH]cc(-c4cccc(-n5ccccc5=O)n4)c3c2)s1] |
| 186 | 4-(5-(5-amino-1,3,4-thiadiazol-2-yl)-1H-indol-3-yl)-2-pyridinamine | 309 | Ex. 14 | 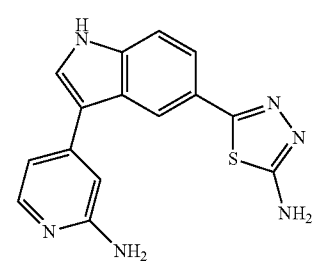 [SMILES: Nc1cc(-c2c[nH]c3ccc(-c4nnc(N)s4)cc23)ccn1] |

TABLE 1-continued
| Ex# | IUPAC Name | M + 1 | Method | Structures |
|---|---|---|---|---|
| 187 | 5-(3-(5-(1-methylethoxy)-2-pyrazinyl)-1H-indol-5-yl)-1,3,4-thiadiazol-2-amine | 353 | Ex. 14 | 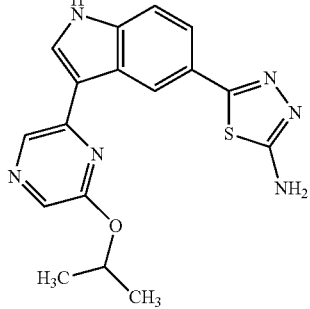 |
| 188 | 5-(5-(5-amino-1,3,4-thiadiazol-2-yl)-1H-indol-3-yl)-N-ethyl-N-methyl-2-pyrazinamine | 352 | Ex. 14 | 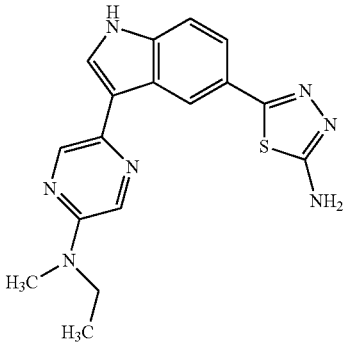 [SMILES: CCN(C)c1cnc(-c2c[nH]c3ccc(-c4nnc(N)s4)cc23)cn1] |
| 189 | 5-(3-(5-(1-pyrrolidinyl)-2-pyrazinyl)-1H-indol-5-yl)-1,3,4-thiadiazol-2-amine | 364 | Ex. 14 | 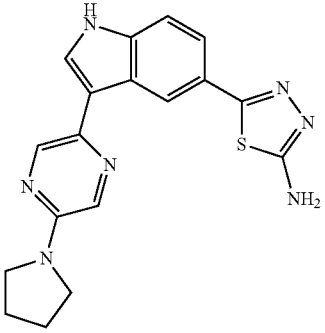 [SMILES: Nc1nnc(-c2ccc3[nH]cc(-c4cnc(N5CCCC5)cn4)c3c2)s1] |
| 190 | 6-(5-(5-amino-1,3,4-thiadiazol-2-yl)-1H-indol-3-yl)-2-pyridinamine | 309 | Ex. 14 | 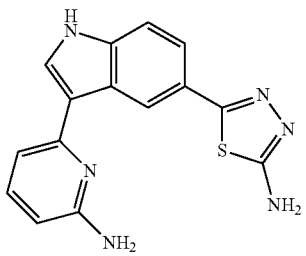 |
| 191 | 5-(3-(5-fluoro-6-methyl-2-pyridinyl)-1H-indol-5-yl)-1,3,4-thiadiazol-2-amine | 326 | Ex. 14 | 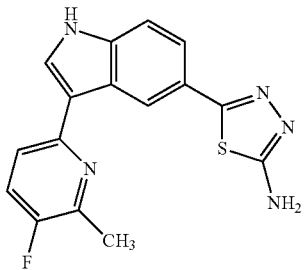 [SMILES: Cc1nc(-c2c[nH]c3ccc(-c4nnc(N)s4)cc23)ccc1F] |

TABLE 1-continued
| Ex# | IUPAC Name | M + 1 | Method | Structures |
|---|---|---|---|---|
| 192 | 5-(3-(5-(4-morpholinyl)-2-pyrazinyl)-1H-indol-5-yl)-1,3,4-thiadiazol-2-amine | 380 | Ex. 14 | 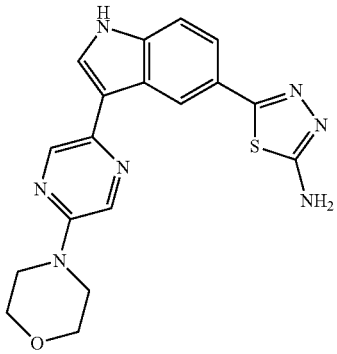 [SMILES: Nc1nnc(-c2ccc3[nH]cc(-c4cnc(N5CCOCC5)cn4)c3c2)s1] |
| 193 | 5-(3-(5-butoxy-2-pyrazinyl)-1H-indol-5-yl)-1,3,4-thiadiazol-2-amine | 367 | Ex. 14 | 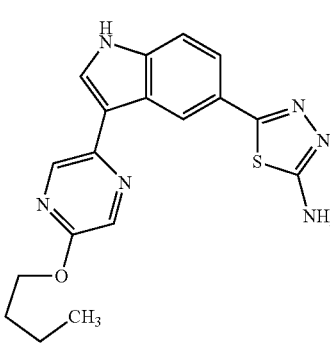 |
| 194 | 1-(5-(5-(5-amino-1,3,4-thiadiazol-2-yl)-1H-indol-3-yl)-2-pyrazinyl)-2-pyrrolidinone | 378 | Ex. 14 | 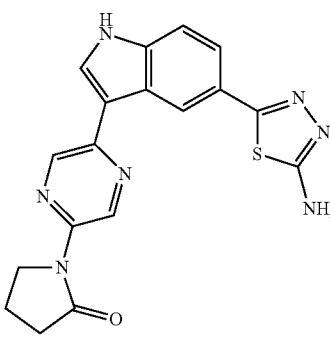 |
| 195 | 5-(3-(5-(cyclopentyloxy)-2-pyrazinyl)-1H-indol-5-yl)-1,3,4-thiadiazol-2-amine | 379 | Ex. 14 | 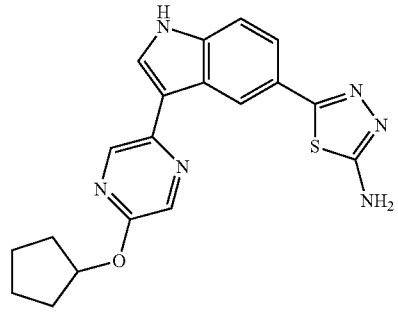 [SMILES: Nc1nnc(-c2ccc3[nH]cc(-c4cnc(OC5CCCC5)cn4)c3c2)s1] |
| 196 | 6-(5-(5-amino-1,3,4-thiadiazol-2-yl)-1H-indol-3-yl)-2-pyridinol | 310 | Ex. 14 | 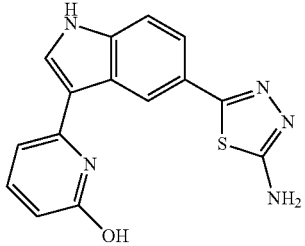 |

TABLE 1-continued
| Ex# | IUPAC Name | M + 1 | Method | Structures |
|---|---|---|---|---|
| 197 | 5-(3-(5-(3-methyl-1H-pyrazol-1-yl)-2-pyrazinyl)-1H-indol-5-yl)-1,3,4-thiadiazol-2-amine | 375 | Ex. 14 | 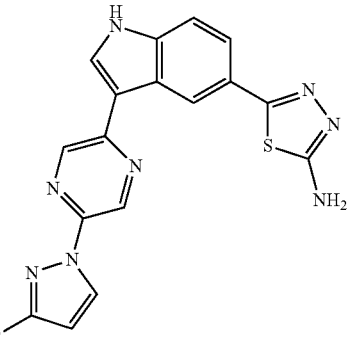 |
| 198 | 5-(3-(6-(1-piperidinyl)-2-pyrazinyl)-1H-indol-5-yl)-1,3,4-thiadiazol-2-amine | 378 | Ex. 14 | 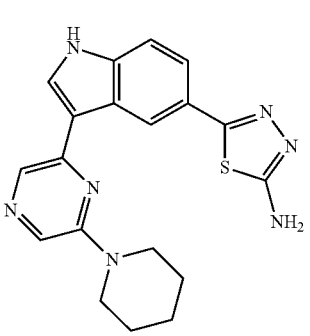 [SMILES: Nc1nnc(-c2ccc3[nH]cc(-c4cncc(N5CCCCC5)n4)c3c2)s1] |
| 199 | 5-(3-(5-methoxy-3-pyridinyl)-1H-indol-5-yl)-1,3,4-thiadiazol-2-amine | 324 | Ex. 14 | 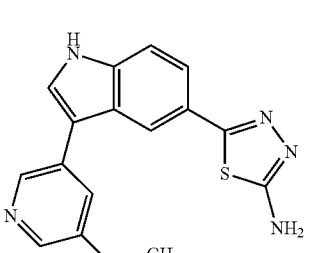 |
| 200 | 5-(3-(6-methoxy-2-(1-methylethoxy)-4-pyrimidinyl)-1H-indol-5-yl)-1,3,4-thiadiazol-2-amine | 383 | Ex. 15 | 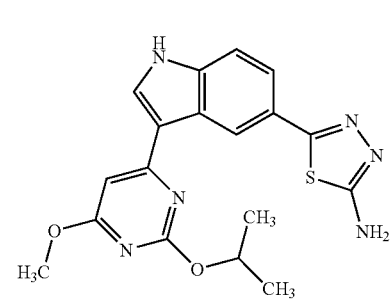 [SMILES: COc1cc(-c2c[nH]c3ccc(-c4nnc(N)s4)cc23)nc(OC(C)C)n1] |
| 201 | 5-(3-(7,7-dimethyl-6,7-dihydro-5H-pyrrolo[2,3-b]pyrazin-2-yl)-1H-indol-5-yl)-1,3,4-thiadiazol-2-amine | 364 | Ex. 15 | 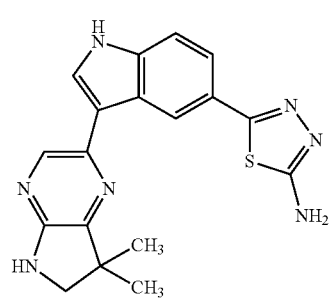 [SMILES: CC1(C)CNc2ncc(-c3c[nH]c4ccc(-c5nnc(N)s5)cc34)nc21] |

TABLE 1-continued

| Ex# | IUPAC Name | M + 1 | Method | Structures |
|---|---|---|---|---|
| 202 | 5-(3-(2,6-dimethoxy-4-pyrimidinyl)-1H-indol-5-yl)-1,3,4-thiadiazol-2-amine | 355 | Ex. 15 | 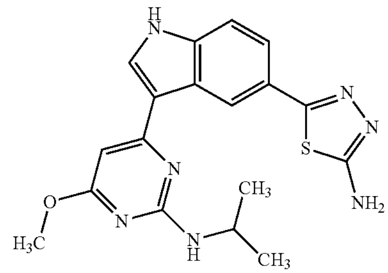 [SMILES: COc1cc(-c2c[nH]c3ccc(-c4nnc(N)s4)cc23)nc(NC(C)C)n1] |
| 203 | 6-(5-(5-amino-1,3,4-thiadiazol-2-yl)-1H-indol-3-yl)-N-(1-methylethyl)-2-pyridinamine | 351 | Ex. 16 | 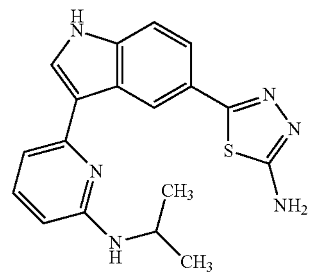 [SMILES: CC(C)Nc1cccc(-c2c[nH]c3ccc(-c4nnc(N)s4)cc23)n1] |
| 204 | 6-(5-(5-amino-1,3,4-thiadiazol-2-yl)-1H-indol-3-yl)-N-(cyclopropylmethyl)-2-pyridinamine | 363 | Ex. 16 | 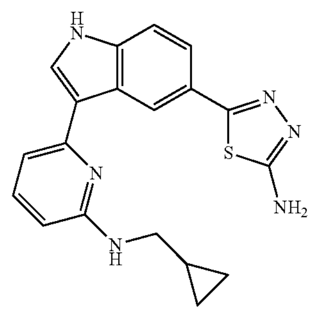 [SMILES: Nc1nnc(-c2ccc3[nH]cc(-c4cccc(NCC5CC5)n4)c3c2)s1] |
| 205 | 6-(5-(5-amino-1,3,4-thiadiazol-2-yl)-1H-indol-3-yl)-N-cyclohexyl-2-pyridinamine | 391 | Ex. 16 | 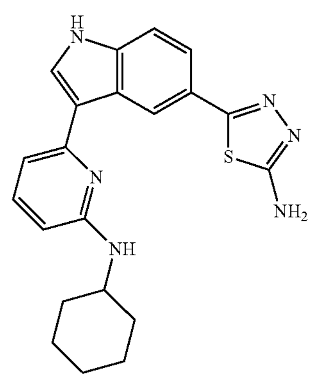 [SMILES: Nc1nnc(-c2ccc3[nH]cc(-c4cccc(NC5CCCCC5)n4)c3c2)s1] |
| 206 | 6-(5-(5-amino-1,3,4-thiadiazol-2-yl)-1H-indol-3-yl)-N-(1-methylethyl)-2-pyrazinamine | 352 | Ex. 17 | 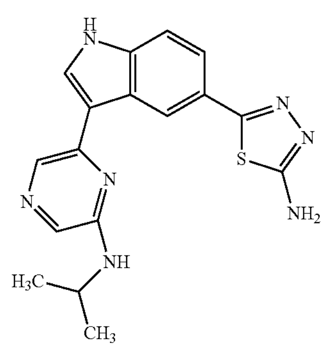 [SMILES: CC(C)Nc1cncc(-c2c[nH]c3ccc(-c4nnc(N)s4)cc23)n1] |

TABLE 1-continued
| Ex# | IUPAC Name | M + 1 | Method | Structures |
|---|---|---|---|---|
| 207 | 6-(5-(5-amino-1,3,4-thiadiazol-2-yl)-1H-indol-3-yl)-N-(cyclopropylmethyl)-2-pyrazinamine | 364 | Ex. 17 | 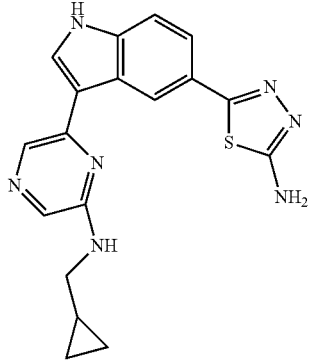 [SMILES: Nc1nnc(-c2ccc3[nH]cc(-c4cncc(NCC5CC5)n4)c3c2)s1] |
| 208 | 6-(5-(5-amino-1,3,4-thiadiazol-2-yl)-1H-indol-3-yl)-N-cyclohexyl-2-pyrazinamine | 392 | Ex. 17 | 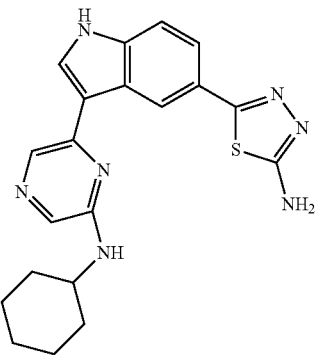 [SMILES: Nc1nnc(-c2ccc3[nH]cc(-c4cncc(NC5CCCCC5)n4)c3c2)s1] |
| 209 | 5-(3-(6-fluoro-2-pyridinyl)-1H-indol-5-yl)-1,3,4-thiadiazol-2-amine | 312 | Ex. 17 | 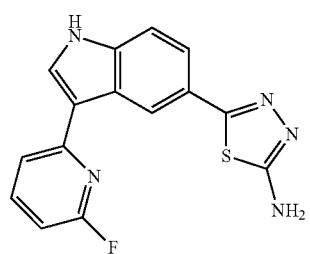 [SMILES: Nc1nnc(-c2ccc3[nH]cc(-c4cccc(F)n4)c3c2)s1] |
| 210 | 6-(5-(5-amino-1,3,4-thiadiazol-2-yl)-1H-indol-3-yl)-2-pyrazinamine | 310 | Ex. 17 | 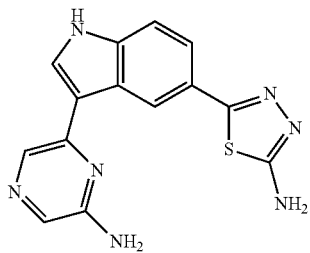 [SMILES: Nc1cncc(-c2c[nH]c3ccc(-c4nnc(N)s4)cc23)n1] |
| 211 | 5-(3-(6-(2,2,2-trifluoro-1-methylethoxy)-2-pyrazinyl)-1H-indol-5-yl)-1,3,4-thiadiazol-2-amine | 407 | Ex. 19 | 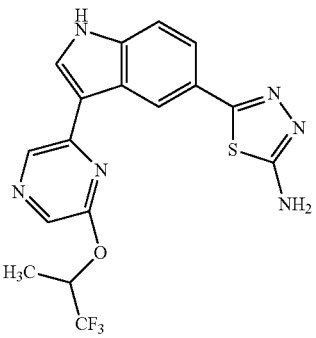 [SMILES: CC(Oc1cncc(-c2c[nH]c3ccc(-c4nnc(N)s4)cc23)n1)C(F)(F)F] |

TABLE 1-continued
| Ex# | IUPAC Name | M + 1 | Method | Structures |
|---|---|---|---|---|
| 212 | 5-(3-(6-methoxy-2-pyrazinyl)-1H-indol-5-yl)-1,3,4-thiadiazol-2-amine | 325 | Ex. 19 | 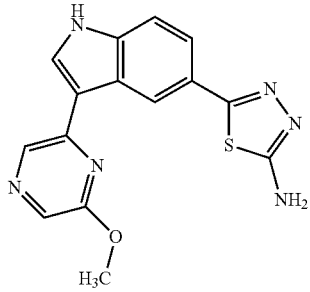 [SMILES: COc1cncc(-c2c[nH]c3ccc(-c4nnc(N)s4)cc23)n1] |
| 213 | 5-(3-(6-(4-morpholinyl)-2-pyridinyl)-1H-indol-5-yl)-1,3-thiazol-2-amine | 378 | Ex. 20 | 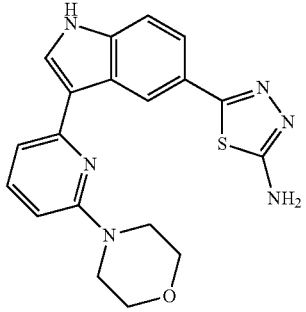 [SMILES: Nc1nnc(-c2ccc3[nH]cc(-c4cccc(N5CCOCC5)n4)c3c2)s1] |
| 214 | N-methyl-5-(3-(6-(4-morpholinyl)-2-pyridinyl)-1H-indol-5-yl)-1,3,4-thiadiazol-2-amine | 393 | Ex. 21 | 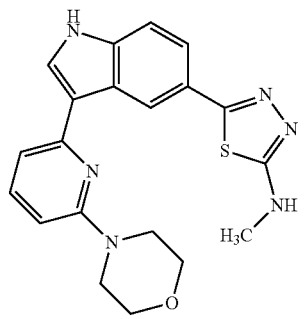 [SMILES: CNc1nnc(-c2ccc3[nH]cc(-c4cccc(N5CCOCC5)n4)c3c2)s1] |
| 215 | 5-(5-(methylsulfonyl)-1,3,4-thiadiazol-2-yl)-3-(6-(4-morpholinyl)-2-pyridinyl)-1H-indole | 442 | Ex. 21 | 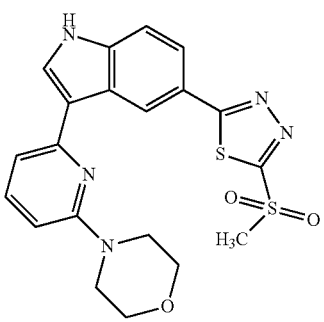 [SMILES: CS(=O)(=O)c1nnc(-c2ccc3[nH]cc(-c4cccc(N5CCOCC5)n4)c3c2)s1] |
| 216 | 5-(3-(2,2-dimethyl-2,3-dihydro-1-benzofuran-6-yl)-1H-indol-5-yl)-N-methyl-1,3,4-thiadiazol-2-amine | 377 | Ex. 22 | 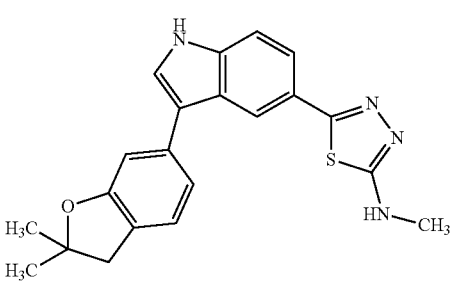 |

TABLE 1-continued

| Ex# | IUPAC Name | M + 1 | Method | Structures |
|---|---|---|---|---|
| 217 | N-methyl-5-(3-(3-quinolinyl)-1H-indol-5-yl)-1,3,4-thiadiazol-2-amine | 358 | Ex. 22 | 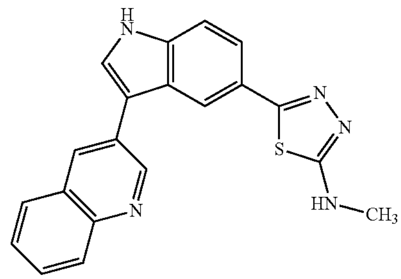 [SMILES: CNc1nnc(-c2ccc3[nH]cc(-c4cnc5ccccc5c4)c3c2)s1] |
| 218 | N-methyl-5-(3-(1H-pyrazol-4-yl)-1H-indol-5-yl)-1,3,4-thiadiazol-2-amine | 297 | Ex. 22 | 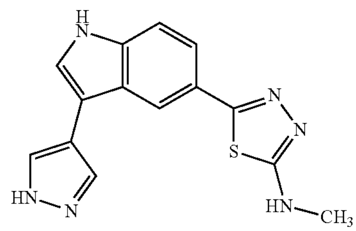 [SMILES: CNc1nnc(-c2ccc3[nH]cc(-c4cn[nH]c4)c3c2)s1] |
| 219 | N-methyl-5-(3-(4-pyridinyl)-1H-indol-5-yl)-1,3,4-thiadiazol-2-amine | 308 | Ex. 22 | 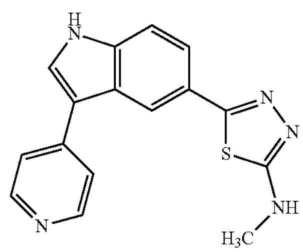 |
| 220 | N-methyl-5-(3-(3-pyridinyl)-1H-indol-5-yl)-1,3,4-thiadiazol-2-amine | 308 | Ex. 22 | 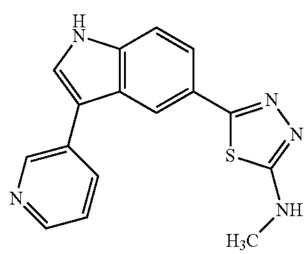 [SMILES: CNc1nnc(-c2ccc3[nH]cc(-c4cccnc4)c3c2)s1] |
| 221 | 5-(3-(3-aminophenyl)-1H-indol-5-yl)-N-methyl-1,3,4-thiadiazol-2-amine | 322 | Ex. 22 | 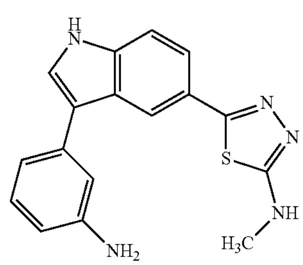 [SMILES: CNc1nnc(-c2ccc3[nH]cc(-c4cccc(N)c4)c3c2)s1] |
| 222 | N-methyl-5-(3-(1H-pyrazol-5-yl)-1H-indol-5-yl)-1,3,4-thiadiazol-2-amine | 297 | Ex. 22 | 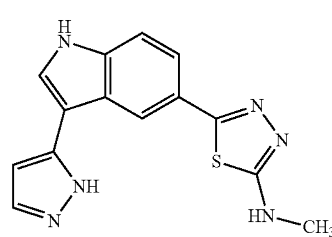 [SMILES: CNc1nnc(-c2ccc3[nH]cc(-c4ccn[nH]4)c3c2)s1] |

| Ex# | IUPAC Name | M + 1 | Method | Structures |
|---|---|---|---|---|
| 223 | N-methyl-5-(3-phenyl-1H-indol-5-yl)-1,3,4-thiadiazol-2-amine | 307 | Ex. 22 | 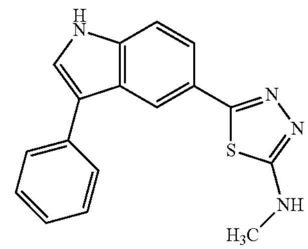 [SMILES: CNc1nnc(-c2ccc3[nH]cc(-c4ccccc4)c3c2)s1] |
| 224 | N-methyl-5-(3-(3-(trifluoromethyl)phenyl)-1H-indol-5-yl)-1,3,4-thiadiazol-2-amine | 375 | Ex. 22 | 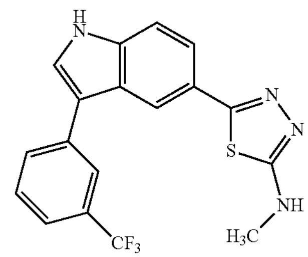 [SMILES: CNc1nnc(-c2ccc3[nH]cc(-c4cccc(C(F)(F)F)c4)c3c2)s1] |
| 225 | N-methyl-5-(3-(3-(trifluoromethoxy)phenyl)-1H-indol-5-yl)-1,3,4-thiadiazol-2-amine | 391 | Ex. 22 | 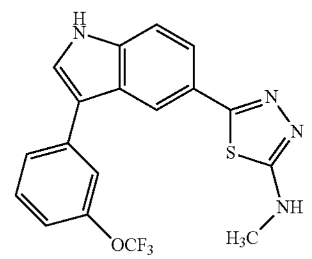 [SMILES: CNc1nnc(-c2ccc3[nH]cc(-c4cccc(OC(F)(F)F)c4)c3c2)s1] |
| 226 | 5-(3-(3-methoxyphenyl)-1H-indol-5-yl)-N-methyl-1,3,4-thiadiazol-2-amine | 337 | Ex. 22 | 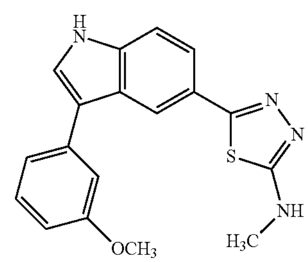 |
| 227 | N-methyl-5-(3-(6-(1-piperidinyl)-2-pyrazinyl)-1H-indol-5-yl)-1,3,4-thiadiazol-2-amine | 392 | Ex. 23 | 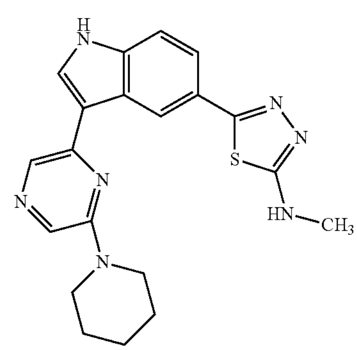 [SMILES: CNc1nnc(-c2ccc3[nH]cc(-c4cncc(N5CCCCC5)n4)c3c2)s1] |

TABLE 1-continued

| Ex# | IUPAC Name | M + 1 | Method | Structures |
|---|---|---|---|---|
| 228 | N-methyl-5-(3-(6-(4-methyl-1H-imidazol-1-yl)-2-pyridinyl)-1H-indol-5-yl)-1,3,4-thiadiazol-2-amine | 388 | Ex. 23 | 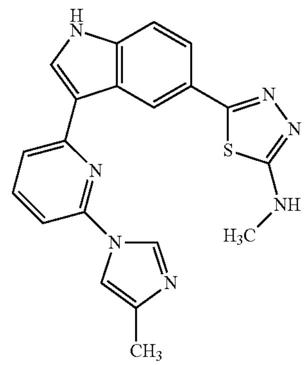 [SMILES: CNc1nnc(-c2ccc3[nH]cc(-c4cccc(-n5cnc(C)c5)n4)c3c2)s1] |
| 229 | 1-(6-(5-(5-(methylamino)-1,3,4-thiadiazol-2-yl)-1H-indol-3-yl)-2-pyridinyl)-2-pyrrolidinone | 391 | Ex. 23 | 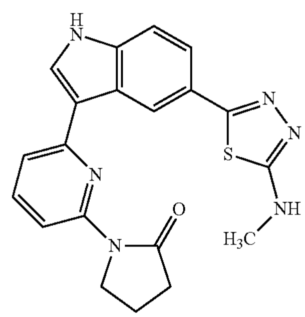 [SMILES: CNc1nnc(-c2ccc3[nH]cc(-c4cccc(N5CCCC5=O)n4)c3c2)s1] |
| 230 | 5-(3-(6-ethoxy-2-pyridinyl)-1H-indol-5-yl)-N-methyl-1,3,4-thiadiazol-2-amine | 352 | Ex. 23 | 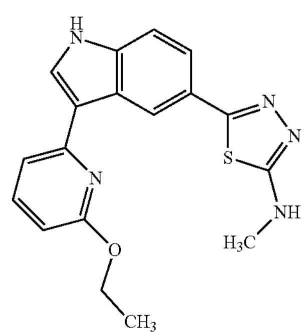 [SMILES: CCOc1cccc(-c2c[nH]c3ccc(-c4nnc(NC)s4)cc23)n1] |
| 231 | N,N-dimethyl-6-(5-(5-(methylamino)-1,3,4-thiadiazol-2-yl)-1H-indol-3-yl)-2-pyrazinamine | 352 | Ex. 23 | 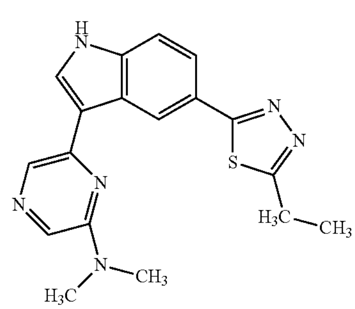 [SMILES: CCc1nnc(-c2ccc3[nH]cc(-c4cncc(N(C)C)n4)c3c2)s1] |

TABLE 1-continued

| Ex# | IUPAC Name | M + 1 | Method | Structures |
|---|---|---|---|---|
| 232 | 5-(3-(6-(cyclobutyloxy)-2-pyridinyl)-1H-indol-5-yl)-N-methyl-1,3,4-thiadiazol-2-amine | 378 | Ex. 23 | 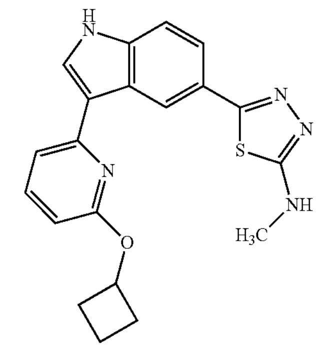 [SMILES: CNc1nnc(-c2ccc3[nH]cc(-c4cccc(OC5CCC5)n4)c3c2)s1] |
| 233 | N-methyl-5-(3-(2-(4-methyl-1H-imidazol-1-yl)-1,3-thiazol-4-yl)-1H-indol-5-yl)-1,3,4-thiadiazol-2-amine | 394 | Ex. 23 | 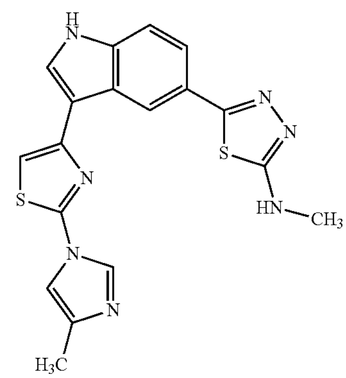 [SMILES: CNc1nnc(-c2ccc3[nH]cc(-c4csc(-n5cnc(C)c5)n4)c3c2)s1] |
| 234 | N-methyl-5-(3-(6-(2-methyl-1H-imidazol-1-yl)-2-pyridinyl)-1H-indol-5-yl)-1,3,4-thiadiazol-2-amine | 388 | Ex. 23 | 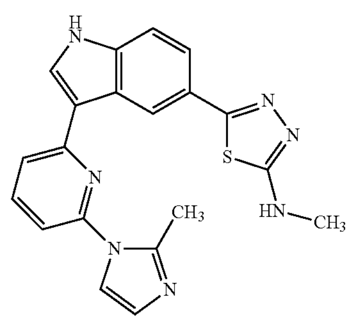 [SMILES: CNc1nnc(-c2ccc3[nH]cc(-c4cccc(-n5ccnc5C)n4)c3c2)s1] |
| 235 | 5-(3-(2-fluorophenyl)-1H-indol-5-yl)-N-methyl-1,3,4-thiadiazol-2-amine | 325 | Ex. 23 | 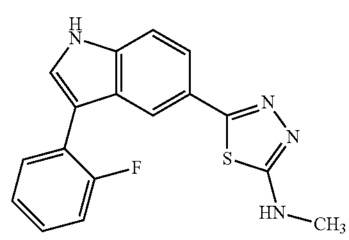 [SMILES: CNc1nnc(-c2ccc3[nH]cc(-c4ccccc4F)c3c2)s1] |
| 236 | 1-(6-(5-(5-(methylamino)-1,3,4-thiadiazol-2-yl)-1H-indol-3-yl)-2-pyridinyl)-2-piperidinone | 405 | Ex. 23 | 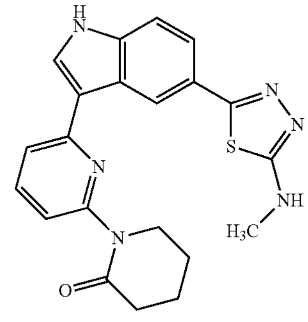 [SMILES: CNc1nnc(-c2ccc3[nH]cc(-c4cccc(N5CCCCC5=O)n4)c3c2)s1] |

TABLE 1-continued

| Ex# | IUPAC Name | M + 1 | Method | Structures |
|---|---|---|---|---|
| 237 | 5-(3-(2,6-difluorophenyl)-1H-indol-5-yl)-N-methyl-1,3,4-thiadiazol-2-amine | 343 | Ex. 23 | 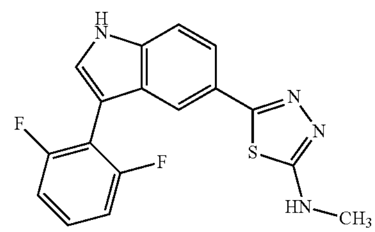 [SMILES: CNc1nnc(-c2ccc3[nH]cc(-c4c(F)cccc4F)c3c2)s1] |
| 238 | 6'-(5-(5-(methylamino)-1,3,4-thiadiazol-2-yl)-1H-indol-3-yl)-2H-1,2'-bipyridin-2-one | 401 | Ex. 23 | 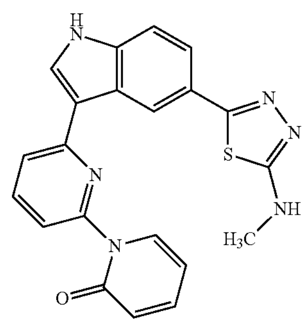 [SMILES: CNc1nnc(-c2ccc3[nH]cc(-c4cccc(-n5ccccc5=O)n4)c3c2)s1] |
| 239 | 5-(3-(6-fluoro-2-pyridinyl)-1H-indol-5-yl)-N-methyl-1,3,4-thiadiazol-2-amine | 326 | Ex. 23 | 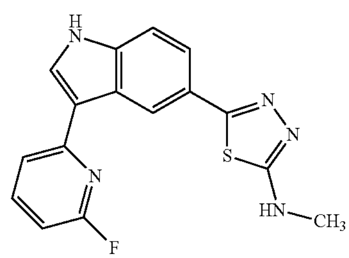 [SMILES: CNc1nnc(-c2ccc3[nH]cc(-c4cccc(F)n4)c3c2)s1] |
| 240 | 5-(3-(2-(3-furanyl)-1,3-thiazol-4-yl)-1H-indol-5-yl)-N-methyl-1,3,4-thiadiazol-2-amine | 380 | Ex. 23 | 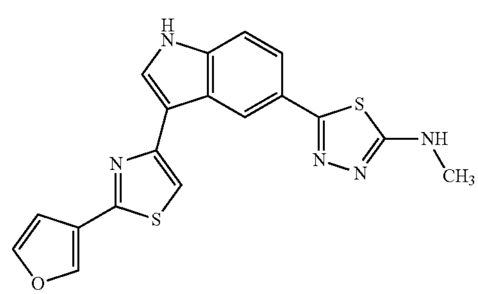 [SMILES: CNc1nnc(-c2ccc3[nH]cc(-c4csc(-c5ccoc5)n4)c3c2)s1] |
| 241 | 5-(3-(2,2'-bithiophen-5-yl)-1H-indol-5-yl)-N-methyl-1,3,4-thiadiazol-2-amine | 395 | Ex. 23 | 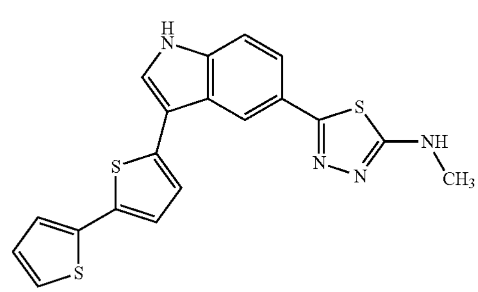 [SMILES: CNc1nnc(-c2ccc3[nH]cc(-c4ccc(-c5cccs5)s4)c3c2)s1] |

TABLE 1-continued

| Ex# | IUPAC Name | M + 1 | Method | Structures |
|---|---|---|---|---|
| 242 | 5-(3-(6-(4-morpholinyl)-2-pyridinyl)-1H-indol-5-yl)-1,3,4-thiadiazole-2-carboxamide | 407 | Ex. 24 | 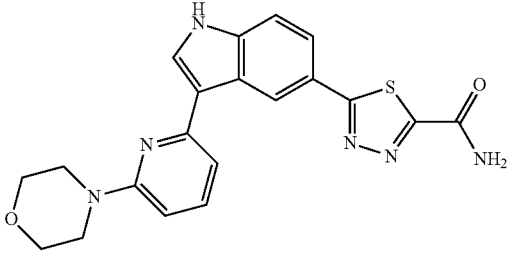 [SMILES: NC(=O)c1nnc(-c2ccc3[nH]cc(-c4cccc(N5CCOCC5)n4)c3c2)s1] |
| 243 | 5-(5-(methylsulfanyl)-1,3,4-thiadiazol-2-yl)-3-(6-(4-morpholinyl)-2-pyridinyl)-1H-indole | 410 | Ex. 24 | 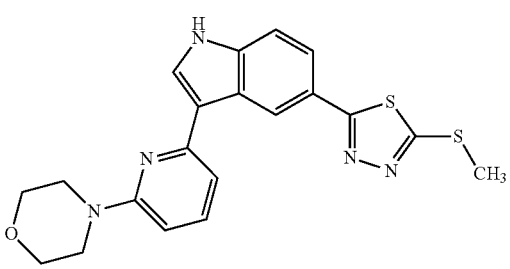 [SMILES: CSc1nnc(-c2ccc3[nH]cc(-c4cccc(N5CCOCC5)n4)c3c2)s1] |
| 244 | 3-(6-(1-methylethoxy)-2-pyridinyl)-5-(1,3,4-oxadiazol-2-yl)-1H-indole | 321 | Ex. 33 | 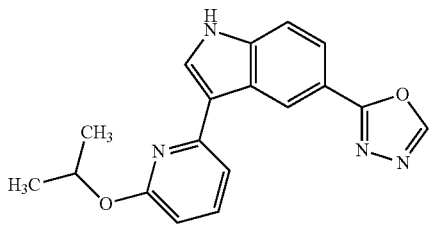 [SMILES: CC(C)Oc1cccc(-c2c[nH]c3ccc(-c4nnco4)cc23)n1] |
| 245 | 3-(6-cyclopropyl-2-pyrazinyl)-5-(5-(4-morpholinyl)-1,3,4-oxadiazol-2-yl)-1H-indole | 389 | Ex. 37 | 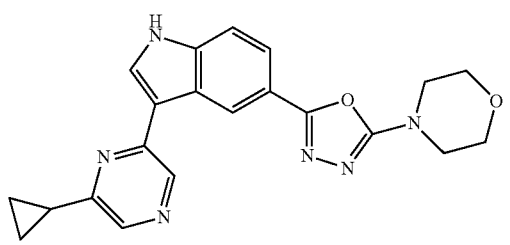 [SMILES: c1cc2[nH]cc(-c3cncc(C4CC4)n3)c2cc1-c1nnc(N2CCOCC2)o1] |
| 246 | 3-(6-cyclopropyl-2-pyrazinyl)-5-(5-(1-piperazinyl)-1,3,4-oxadiazol-2-yl)-1H-indole | 388 | Ex. 37 | 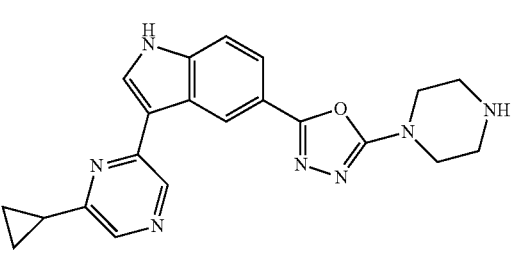 [SMILES: c1cc2[nH]cc(-c3cncc(C4CC4)n3)c2cc1-c1nnc(N2CCNCC2)o1] |
| 247 | N-3-azetidinyl-5-(3-(6-cyclopropyl-2-pyrazinyl)-1H-indol-5-yl)-1,3,4-oxadiazol-2-amine | 374 | Ex. 37 | 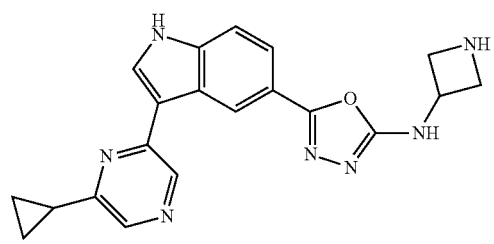 [SMILES: c1cc2[nH]cc(-c3cncc(C4CC4)n3)c2cc1-c1nnc(NC2CNC2)o1] |

TABLE 1-continued

| Ex# | IUPAC Name | M + 1 | Method | Structures |
|-----|------------|-------|--------|------------|
| 248 | 3-(6-cyclopropyl-2-pyrazinyl)-5-(5-((3S)-3-methyl-4-morpholinyl)-1,3,4-oxadiazol-2-yl)-1H-indole | 403 | Ex. 37 | 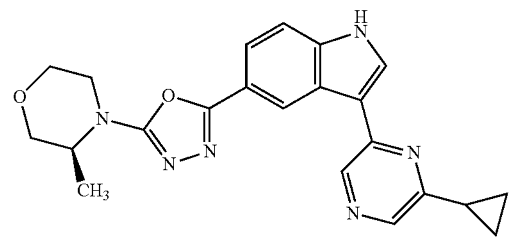 [SMILES: C[C@H]1COCCN1c1nnc(-c2ccc3[nH]cc(-c4cncc(C5CC5)n4)c3c2)o1] |
| 249 | 3-(6-cyclopropyl-2-pyrazinyl)-5-(5-((3R)-3-methyl-4-morpholinyl)-1,3,4-oxadiazol-2-yl)-1H-indole | 403 | Ex. 37 | 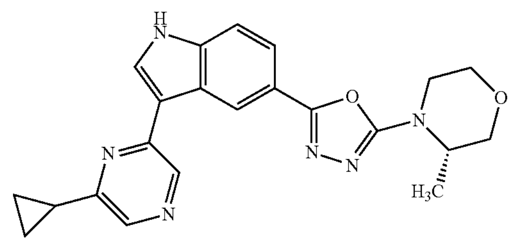 [SMILES: C[C@H]1COCCN1c1nnc(-c2ccc3[nH]cc(-c4cncc(C5CC5)n4)c3c2)o1] |
| 250 | 3-(6-cyclopropyl-2-pyrazinyl)-5-(5-((2S)-2-methyl-4-morpholinyl)-1,3,4-oxadiazol-2-yl)-1H-indole | 403 | Ex. 37 | 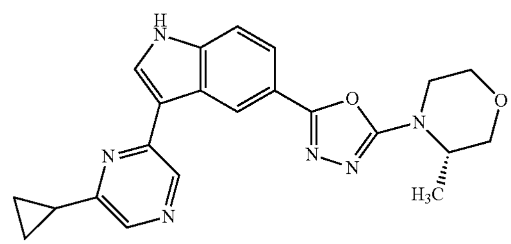 [SMILES: C[C@H]1COCCN1c1nnc(-c2ccc3[nH]cc(-c4cncc(C5CC5)n4)c3c2)o1] |
| 251 | 5-(3-(6-cyclopropyl-2-pyrazinyl)-1H-indol-5-yl)-N-3-oxetanyl-1,3,4-oxadiazol-2-amine | 375 | Ex. 37 | 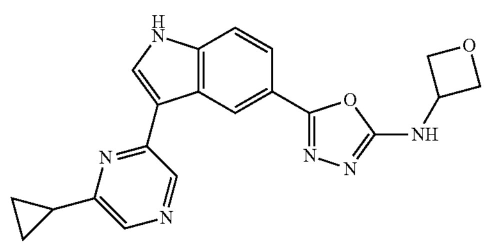 [SMILES: c1cc2[nH]cc(-c3cncc(C4CC4)n3)c2cc1-c1nnc(NC2COC2)o1] |
| 252 | 3-(6-cyclopropyl-2-pyrazinyl)-5-(5-(3-ethyl-4-morpholinyl)-1,3,4-oxadiazol-2-yl)-1H-indole | 417 | Ex. 37 | |

TABLE 1-continued

| Ex# | IUPAC Name | M + 1 | Method | Structures |
|---|---|---|---|---|
| 253 | 3-(6-cyclopropyl-2-pyrazinyl)-5-(5-(3,3-dimethyl-4-morpholinyl)-1,3,4-oxadiazol-2-yl)-1H-indole | 417 | Ex. 37 | 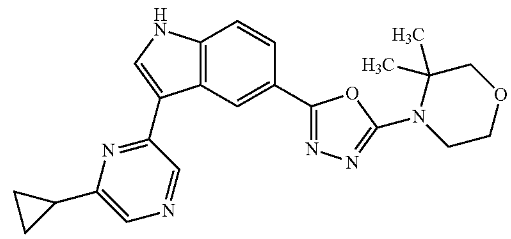 [SMILES: CC1(C)COCCN1c1nnc(-c2ccc3[nH]cc(-c4cncc(C5CC5)n4)c3c2)o1] |
| 254 | 3-(6-cyclopropyl-2-pyrazinyl)-5-(5-phenyl-1,3,4-oxadiazol-2-yl)-1H-indole | 380 | Ex. 39 | 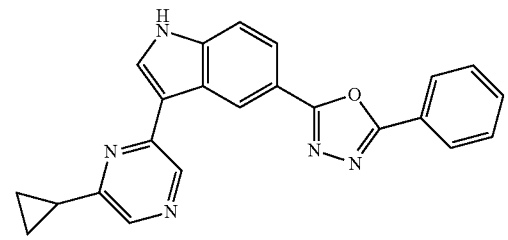 [SMILES: c1ccc(-c2nnc(-c3ccc4[nH]cc(-c5cncc(C6CC6)n5)c4c3)o2)cc1] |
| 255 | 3-(4-cyclopropyl-2-pyrimidinyl)-5-(5-phenyl-1,3,4-oxadiazol-2-yl)-1H-indole | 380 | Ex. 43 | 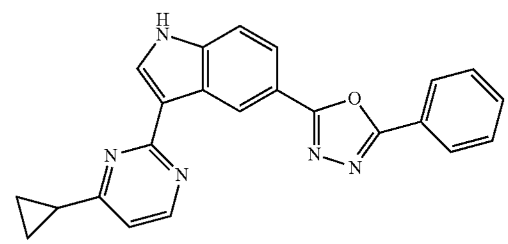 [SMILES: c1ccc(-c2nnc(-c3ccc4[nH]cc(-c5nccc(C6CC6)n5)c4c3)o2)cc1] |
| 256 | 5-(3-(4-cyclopropyl-2-pyrimidinyl)-1H-indol-5-yl)-N-3-oxetanyl-1,3,4-oxadiazol-2-amine | 375 | Ex. 46 | 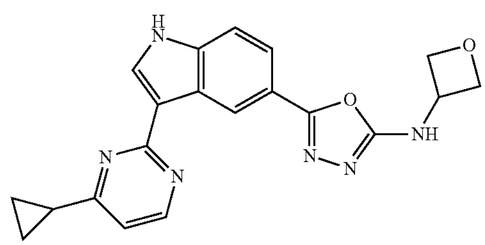 [SMILES: c1cc(C2CC2)nc(-c2c[nH]c3ccc(-c4nnc(NC5COC5)o4)cc23)n1] |
| 257 | N-cyclopropyl-5-(3-(4-cyclopropyl-2-pyrimidinyl)-1H-indol-5-yl)-1,3,4-oxadiazol-2-amine | 359 | Ex. 46 | 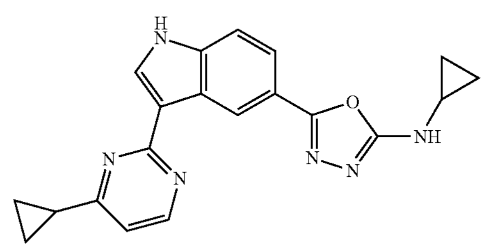 [SMILES: c1cc(C2CC2)nc(-c2c[nH]c3ccc(-c4nnc(NC5CC5)o4)cc23)n1] |
| 258 | N-(1-methylethyl)-5-(3-(4-(trifluoromethyl)-2-pyrimidinyl)-1H-indol-5-yl)-1,3,4-oxadiazol-2-amine | 389 | Ex. 46 | 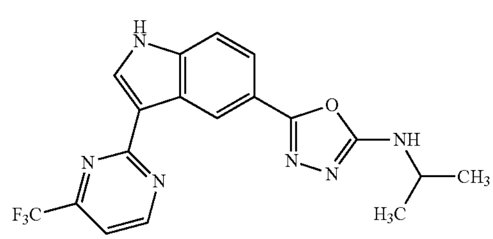 [SMILES: CC(C)Nc1nnc(-c2ccc3[nH]cc(-c4nccc(C(F)(F)F)n4)c3c2)o1] |

TABLE 1-continued

| Ex# | IUPAC Name | M + 1 | Method | Structures |
|---|---|---|---|---|
| 259 | 5-(3-(4-ethoxy-5-fluoro-2-pyrimidinyl)-1H-indol-5-yl)-N-(1-methylethyl)-1,3,4-oxadiazol-2-amine | 383 | Ex. 46 | 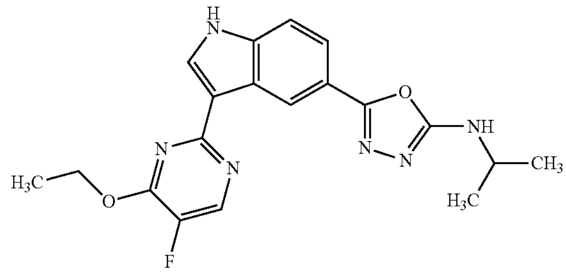 [SMILES: CCOc1nc(-c2c[nH]c3ccc(-c4nnc(NC(C)C)o4)cc23)ncc1F] |
| 260 | 5-(3-(5-fluoro-4-methoxy-6-methyl-2-pyrimidinyl)-1H-indol-5-yl)-N-(1-methylethyl)-1,3,4-oxadiazol-2-amine | 383 | Ex. 46 | 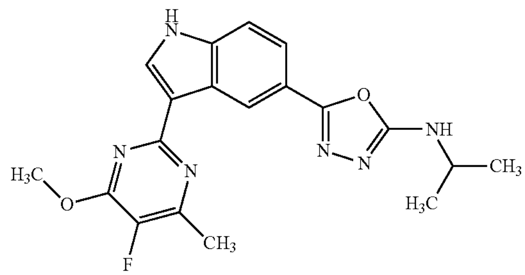 [SMILES: COc1nc(-c2c[nH]c3ccc(-c4nnc(NC(C)C)o4)cc23)nc(C)c1F] |
| 261 | 2-(5-(5-((1-methylethyl)amino)-1,3,4-oxadiazol-2-yl)-1H-indol-3-yl)-4-pyrimidinecarboxamide | 364 | Ex. 46 | 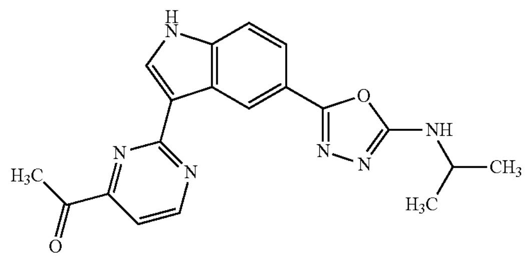 [SMILES: CC(=O)c1ccnc(-c2c[nH]c3ccc(-c4nnc(NC(C)C)o4)cc23)n1] |
| 262 | 5-(3-(4-cyclopropyl-5-fluoro-2-pyrimidinyl)-1H-indol-5-yl)-N-(1-methylethyl)-1,3,4-oxadiazol-2-amine | 379 | Ex. 46 | 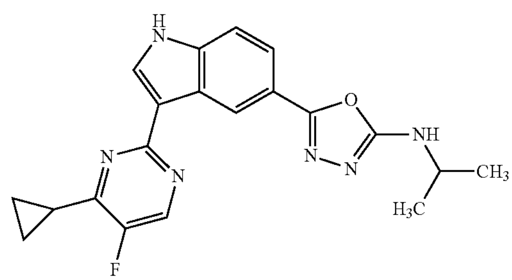 [SMILES: CC(C)Nc1nnc(-c2ccc3[nH]cc(-c4ncc(F)c(C5CC5)n4)c3c2)o1] |
| 263 | 5-(3-(3-cyclopropyl-1H-1,2,4-triazol-5-yl)-1H-indol-5-yl)-N-(1-methylethyl)-1,3,4-oxadiazol-2-amine | 350 | Ex. 46 | 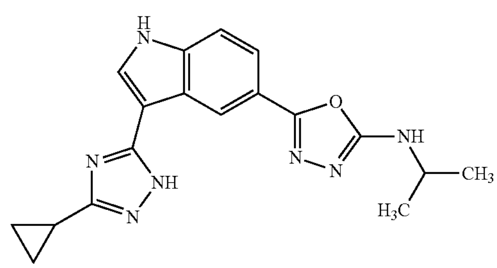 [SMILES: CC(C)Nc1nnc(-c2ccc3[nH]cc(-c4nc(C5CC5)n[nH]4)c3c2)o1] |
| 264 | 5-(3-(4-cyclopropyl-2-pyrimidinyl)-1H-indol-5-yl)-N-(1-methylethyl)-1,3,4-oxadiazol-2-amine | 361 | Ex. 46 | 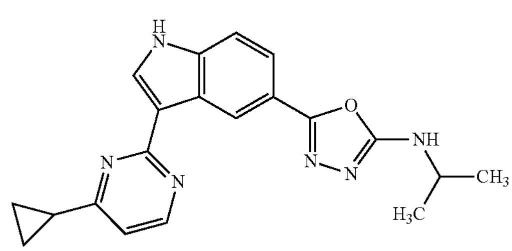 [SMILES: CC(C)Nc1nnc(-c2ccc3[nH]cc(-c4nccc(C5CC5)n4)c3c2)o1] |

TABLE 1-continued

| Ex# | IUPAC Name | M + 1 | Method | Structures |
|---|---|---|---|---|
| 265 | 3-(6-cyclopropyl-2-pyrazinyl)-5-(5-(2-methylpropyl)-1,3,4-oxadiazol-2-yl)-1H-indole | 360 | Ex. 51 | 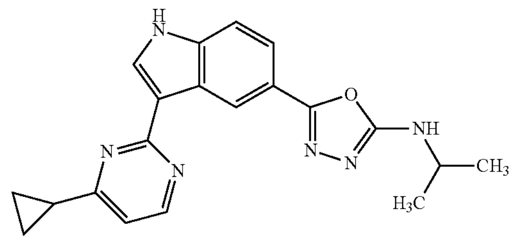 [SMILES: CC(C)Nc1nnc(-c2ccc3[nH]cc(-c4nccc(C5CC5)n4)c3c2)o1] |
| 266 | N-(1-phenylethyl)-5-(3-(2-pyrimidinyl)-1H-indol-5-yl)-1,3,4-oxadiazol-2-amine | 383 | Ex. 52 | 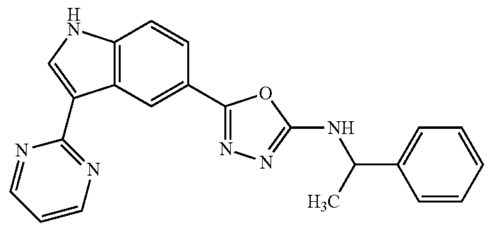 [SMILES: CC(Nc1nnc(-c2ccc3[nH]cc(-c4ncccn4)c3c2)o1)c1ccccc1] |
| 267 | N-(1-phenylethyl)-5-(3-(2-pyridinyl)-1H-indol-5-yl)-1,3,4-oxadiazol-2-amine | 382 | Ex. 52 | 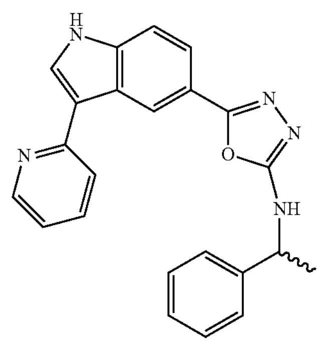 [SMILES: CC(Nc1nnc(-c2ccc3[nH]cc(-c4ccccn4)c3c2)o1)c1ccccc1] |
| 268 | N-(1-phenylethyl)-5-(3-(2-pyrazinyl)-1H-indol-5-yl)-1,3,4-oxadiazol-2-amine | 383 | Ex. 52 | 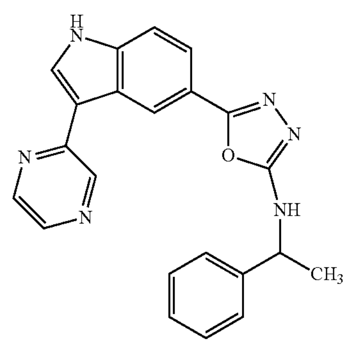 [SMILES: CC(Nc1nnc(-c2ccc3[nH]cc(-c4cnccn4)c3c2)o1)c1ccccc1] |
| 269 | 5-(3-(4-cyclopropyl-2-pyrimidinyl)-1H-indol-5-yl)-N-(3-fluorophenyl)-1,3,4-oxadiazol-2-amine | 413 | Ex. 54 | 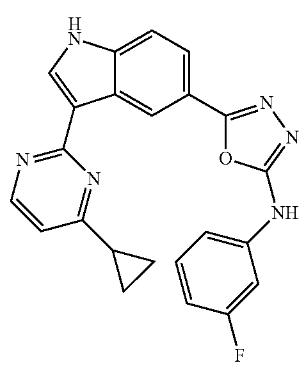 [SMILES: Fc1cccc(Nc2nnc(-c3ccc4[nH]cc(-c5nccc(C6CC6)n5)c4c3)o2)c1] |

TABLE 1-continued

| Ex# | IUPAC Name | M + 1 | Method | Structures |
|---|---|---|---|---|
| 270 | N-tert-butyl-5-(3-(4-methyl-2-pyrimidinyl)-1H-indol-5-yl)-1,3,4-oxadiazol-2-amine | 349 | Ex. 54 | 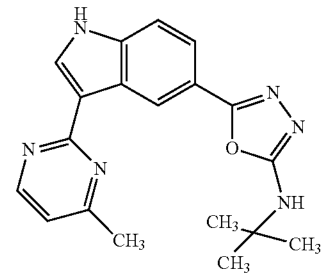 [SMILES: Cc1ccnc(-c2c[nH]c3ccc(-c4nnc(NC(C)(C)C)o4)cc23)n1] |
| 271 | N-tert-butyl-5-(3-(3,6-dihydro-2H-pyran-4-yl)-1H-indol-5-yl)-1,3,4-oxadiazol-2-amine | 339 | Ex. 54 | 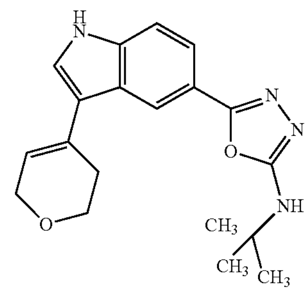 |
| 272 | 2-(5-(5-(tert-butylamino)-1,3-4-oxadiazol-2-yl)-1H-indol-3-yl)-6-methyl-4-pyrimidinamine | 364 | Ex. 54 | 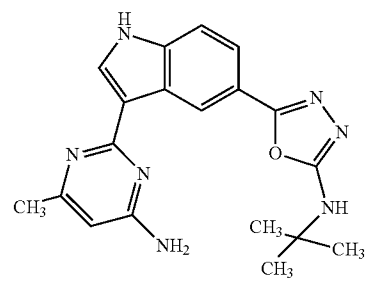 [SMILES: Cc1cc(N)nc(-c2c[nH]c3ccc(-c4nnc(NC(C)(C)C)o4)cc23)n1] |
| 273 | 2-(5-(5-(tert-butylamino)-1,3-4-oxadiazol-2-yl)-1H-indol-3-yl)-4-pyrimidinecarboxamide | 378 | Ex. 55 | 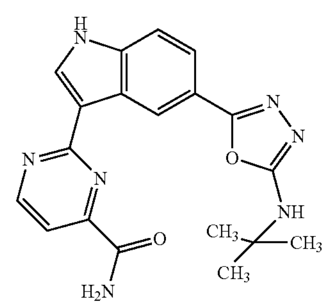 [SMILES: CC(C)(C)Nc1nnc(-c2ccc3[nH]cc(-c4nccc(C(N)=O)n4)c3c2)o1] |
| 274 | 3-(6-methyl-2-pyrazinyl)-5-(5-phenyl-1,3,4-thiadiazol-2-yl)-1H-indole | 370 | Ex. 58 | 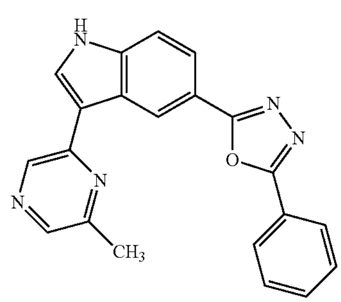 [SMILES: Cc1cncc(-c2c[nH]c3ccc(-c4nnc(-c5ccccc5)o4)cc23)n1] |

Example 275

N-cyclopropyl-2-(5-(5-((1-methylethyl)amino)-1,3,4-oxadiazol-2-yl)-1H-indol-3-yl)-1,3-thiazole-5-carboxamide

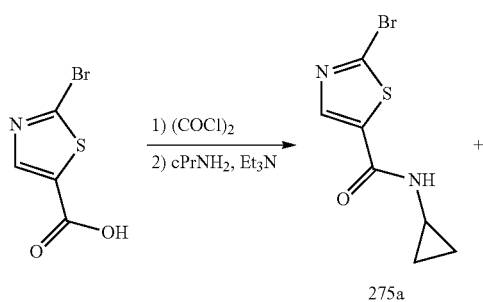

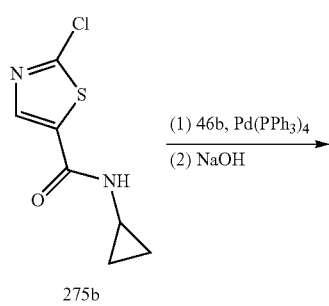

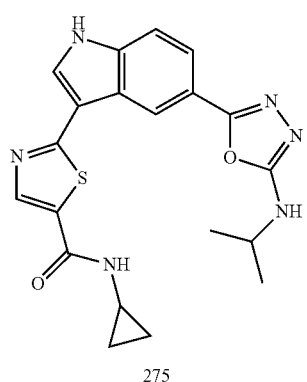

Preparation of compound 275a and 275b: 2-Bromo-N-cyclopropylthiazole-5-carboxamide and 2-chloro-N-cyclopropylthiazole-5-carboxamide A suspension of 2-bromothiazole-5-carboxylic acid (Aldrich, cat #642487, 1.07 g, 5.14 mmol) in 25 mL of DCM at 0° C. was treated with oxalyl chloride (0.64 mL, 7.20 mmol) followed by 3 drops of DMF. The mixture was stirred at RT for 1 h. It was concentrated under reduced pressure. The remaining white solid was suspended in 25 mL of DCM, cooled with an ice bath and treated with Et$_3$N (0.72 mL, 5.14 mmol) followed by cyclopropylamine (Aldrich, 0.54 mL, 7.72 mmol). After the mixture was stirred at 0° C. for 15 min followed by RT for 15 min, it was diluted with 100 mL of DCM, washed with 30 mL of 1 N NaOH followed by 10 mL of brine. The DCM layer was dried and concentrated to give 0.93 g of an off white crystalline solid, as a 1:1 mixture of 2-bromo-N-cyclopropylthiazole-5-carboxamide and 2-chloro-N-cyclopropylthiazole-5-carboxamide, which was used as crude in the next step without further purification. MS (ESI, pos. ion) m/z: 203.0 (M+1), and 246.9/248.9 (M+1).

Preparation of compound 275: N-cyclopropyl-2-(5-(5-((1-methylethyl)amino)-1,3,4-oxadiazol-2-yl)-1H-indol-3-yl)-1,3-thiazole-5-carboxamide A mixture of N-isopropyl-5-(3-(4,4,5,5-tetramethyl-1,3,2-dioxaborolan-2-yl)-1-tosyl-1H-indol-5-yl)-1,3,4-oxadiazol-2-amine (150 mg, 0.287 mmol), 78 mg of the 1:1 mixture of 2-bromo-N-cyclopropylthiazole-5-carboxamide and 2-chloro-N-cyclopropylthiazole-5-carboxamide, Pd$_2$(dba)$_3$ (Strem Chemicals, 8 mg, 8.6 μmol), Xphos (Stem Chemicals, cat #15-1152, 9 mg, 17 μmol), potassium phosphate (183 mg, 0.861 mmol) in dioxane (2.5 mL) and water (0.5 mL) was heated in an Initiator microwave reactor (Personal Chemistry, Biotage AB, Inc., Upssala, Sweden) at 130° C. for 25 min. LCMS indicated the presence of desired product (M+1=563.0), as well as a significant amount of the starting N-isopropyl-5-(3-(4,4,5,5-tetramethyl-1,3,2-dioxaborolan-2-yl)-1-tosyl-1H-indol-5-yl)-1,3,4-oxadiazol-2-amine. To the reaction mixture was added Pd(PPh$_3$)$_4$ (Strem Chemicals, cat #46-2150, 10 mg) and 50 mg of the 1:1 mixture of 2-bromo-N-cyclopropylthiazole-5-carboxamide and 2-chloro-N-cyclopropylthiazole-5-carboxamide. It was heated again at 130° C. for 15 min in an Initiator microwave reactor. The reaction mixture was treated with water (5 mL) and extracted with EtOAc (2×25 mL). The organic extracts were washed with brine, dried over MgSO$_4$, filtered and concentrated. The crude material was purified by silica gel flash chromatography using a gradient of 20-100% EtOAc in hexanes to give N-cyclopropyl-2-(5-(5-(isopropylamino)-1,3,4-oxadiazol-2-yl)-1-tosyl-1H-indol-3-yl)thiazole-5-carb oxamide (60 mg, in 75% purity) as a brown amorphous solid. MS (ESI, pos. ion) m/z: 563.0 (M+1).

A solution of the above obtained N-cyclopropyl-2-(5-(5-(isopropylamino)-1,3,4-oxadiazol-2-yl)-1-tosyl-1H-indol-3-yl)thiazole-5-carboxamide (60 mg, in 75% purity) in 1 mL of dioxane and 1 mL of 1 N NaOH was heated in an oil bath at 100° C. for 15 min. It was cooled to RT, diluted with 15 mL of EtOAc and 1 mL of water. The organic layer was separated, and concentrated. The brown residue was dissolved in 2 mL of DMSO and purified on a reversed phase HPLC using a gradient of 10-90% [0.1% TFA in CH$_3$CN] in [0.1% TFA in water]. The desired fraction was concentrated, then basified with 1 N NaOH and extracted with EtOAc. The organic solution was dried over Na$_2$SO$_4$ and concentrated to give N-cyclopropyl-2-(5-(5-(isopropylamino)-1,3,4-oxadiazol-2-yl)-1H-indol-3-yl)thiazole-5-carboxamide (28 mg, 24% overall yield for 2 steps) as an off white crystalline solid. $^1$H NMR (400 MHz, DMSO-d$_6$) δ ppm 12.11 (1H, br.), 8.59 (2H, m), 8.26 (1H, s), 8.29 (1H, s), 7.69 (2H, m), 7.60 (1H, d, J=8.6

Hz), 3.69 (1H, m), 2.81 (1H, m), 1.23 (6H, d, J=6.5 Hz), 0.69 (2H, m), 0.58 (2H, m). MS (ESI, pos. ion) m/z: 409.0 (M+1).

Example 276

2-(5-(5-((1-methylethyl)amino)-1,3,4-oxadiazol-2-yl)-1H-indol-3-yl)-1,3-thiazole-5-carboxamide

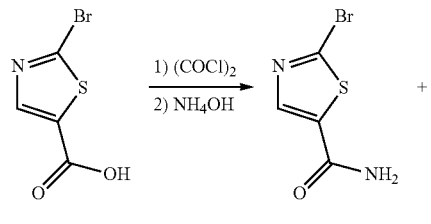

276a

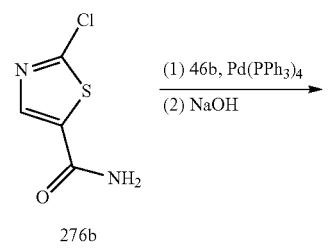

276b

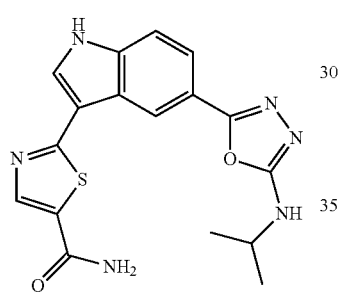

276

Preparation of compound 276a and 276b: 2-Bromothiazole-5-carboxamide and 2-chlorothiazole-5-carboxamide A suspension of 2-bromothiazole-5-carboxylic acid (Aldrich, 1.07 g, 5.14 mmol) in 25 mL of DCM at 0° C. was treated with oxalyl chloride (0.64 mL, 7.20 mmol) followed by 3 drops of DMF. The mixture was stirred at RT for 1 h. It was concentrated under reduced pressure. The remaining white solid was suspended in 25 mL of THF, cooled with an ice bath and treated with NH$_4$OH (Aldrich, 28-30% wt, 3.58 mL, 25.7 mmol). After the mixture was stirred at 0° C. for 15 min followed by RT for 15 min, it was diluted with 100 mL of EtOAc, washed with 30 mL of water followed by 10 mL of brine. The EtOAc layer was dried and concentrated to give 779 mg of an off white crystalline solid, as a 1:1 mixture of 2-bromothiazole-5-carboxamide and 2-chlorothiazole-5-carboxamide, which was used as crude in the next step without further purification. MS (ESI, pos. ion) m/z: 162.9 (M+1), and 206.9/208.9 (M+1).

Preparation of compound 276: 2-(5-(5-((1-methylethyl)amino)-1,3,4-oxadiazol-2-yl)-1H-indol-3-yl)-1,3-thiazole-5-carboxamide The title compound (55 mg, 40% yield) as a yellow crystalline solid was prepared according to compound 275, using N-isopropyl-5-(3-(4,4,5,5-tetramethyl-1,3,2-dioxaborolan-2-yl)-1-tosyl-1H-indol-5-yl)-1,3,4-oxadiazol-2-amine (150 mg, 0.287 mmol), 125 mg of the 1:1 mixture of 2-bromothiazole-5-carboxamide and 2-chlorothiazole-5-carboxamide, and Pd(PPh$_3$)$_4$ (Strem Chemicals, 17 mg) as the starting materials and reagent. $^1$H NMR (400 MHz, DMSO-d$_6$) δ ppm 12.19 (1H, d, J=2.3 Hz), 8.66 (1H, s), 8.38 (1H, s), 8.31 (1H, d, J=2.7 Hz), 8.13 (1H, br.), 8.01 (1H, d, J=6.8 Hz), 7.77 (1H, dd, J=8.5, 1.7 Hz), 7.64 (1H, d, J=8.6 Hz), 7.56 (1H, br.), 3.77 (1H, m), 1.25 (6H, d, J=6.5 Hz). MS (ESI, pos. ion) m/z: 369.0 (M+H)$^+$.

Example 277

2-(5-(5-(tert-butylamino)-1,3,4-oxadiazol-2-yl)-1H-indol-3-yl)-1,3-thiazole-5-carboxamide

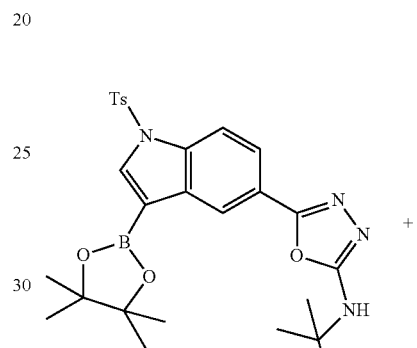

54b

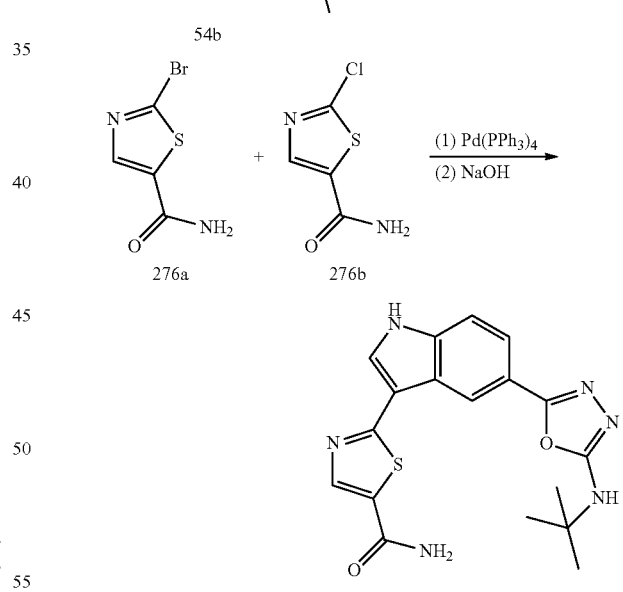

277

The title compound (49 mg, 52% yield) as a yellow crystalline solid was prepared similar to that described in Example 275, using N-tert-butyl-5-(3-(4,4,5,5-tetramethyl-1,3,2-dioxaborolan-2-yl)-1-tosyl-1H-indol-5-yl)-1,3,4-oxadiazol-2-amine (131 mg, 0.244 mmol), 106 mg of the 1:1 mixture of 2-bromothiazole-5-carboxamide and 2-chlorothiazole-5-carboxamide, and Pd(PPh$_3$)$_4$ (Strem Chemicals, 14 mg) as the starting materials and reagent. $^1$H NMR (400 MHz, DMSO-d$_6$) δ ppm 12.21 (1H, br.), 8.63 (1H, s), 8.38 (s, 1H), 8.28 (1H, s), 8.14 (1H, br.), 7.75 (1H, d, J=8.80 Hz), 7.66 (2H, m), 7.53 (1H, br.), 1.40 (9H, s). MS (ESI, pos. ion) m/z: 383.0 (M+H)+.

Example 278

N-cyclopropyl-2-(5-(5-((1-methylethyl)amino)-1,3,4-oxadiazol-2-yl)-1H-indol-3-yl)-1,3-thiazole-4-carboxamide

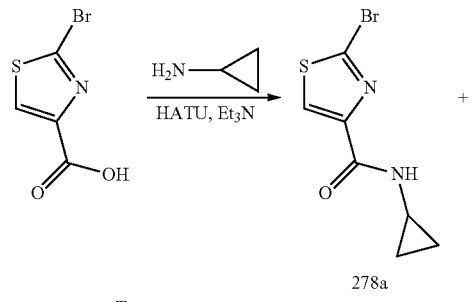

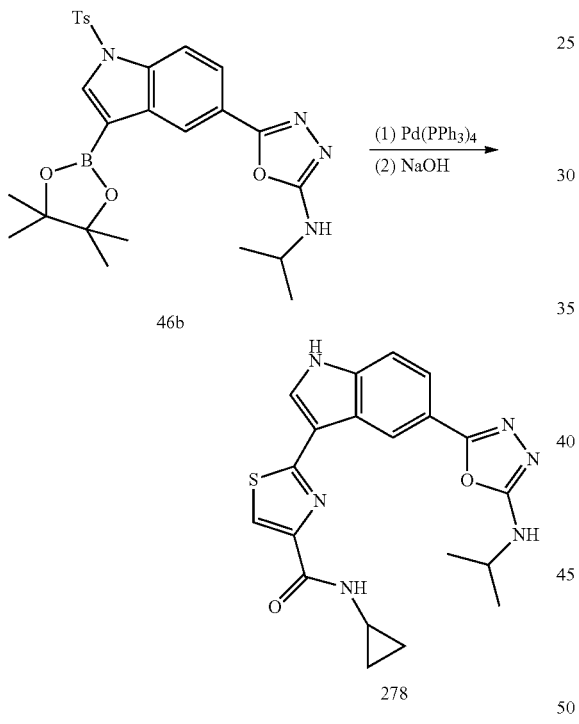

Preparation of compound 278a:
2-Bromo-N-cyclopropylthiazole-4-carboxamide

At RT, to a solution of 2-bromothiazole-4-carboxylic acid (Synthonix, 600 mg, 2.88 mmol) in 8 mL of THF and 2 mL of DMF was added HATU (Aldrich, 1.2 g, 3.17 mmol). The mixture was stirred for 30 min, and cyclopropanamine (0.3 mL, 4.33 mmol) was added followed by Et$_3$N (0.4 mL, 2.88 mmol). After the reaction mixture was stirred for 1 h at RT, additional HATU (150 mg) was added and the mixture stirred for another 1 h. It was diluted with 100 mL of EtOAc, washed sequentially with 5 mL of 1 N NaOH, 5 mL of water and 5 ml of brine. The EtOAc layer was concentrated and the residue was purified on a silica gel column (25-50% EtoAc in hexanes) to give 2-bromo-N-cyclopropylthiazole-4-carboxamide (300 mg, 42% yield) as an off white crystalline solid. $^1$H NMR (400 MHz, DMSO-D$_6$) δ ppm 8.50 (1H, m), 8.28 (1H, s), 2.87 (1H, m), 0.67 (4H, m). MS (ESI, pos. ion) m/z: 246.9/248.9 (M+1).

Preparation of compound 278: N-cyclopropyl-2-(5-(5-((1-methylethyl)amino)-1,3,4-oxadiazol-2-yl)-1H-indol-3-yl)-1,3-thiazole-4-carboxamide The title compound (34 mg, 30% yield) as a yellow crystalline solid was prepared according to Example 275, using N-isopropyl-5-(3-(4,4,5,5-tetramethyl-1,3,2-dioxaborolan-2-yl)-1-tosyl-1H-indol-5-yl)-1,3,4-oxadiazol-2-amine (145 mg, 0.278 mmol), 2-bromo-N-cyclopropylthiazole-4-carboxamide (75 mg, 0.305 mmol), and Pd(PPh$_3$)$_4$ (Strem Chemicals, 16 mg) as the starting materials and reagent. $^1$H NMR (400 MHz, DMSO-d$_6$) δ ppm 12.15 (1H, br.), 8.57 (1H, s), 8.29 (2H, m), 8.15 (1H, s), 7.74 (1H, d, J=7.4 Hz), 7.65 (2H, d, J=8.6 Hz), 3.77 (1H, m), 2.90 (1H, m), 1.25 (6H, d, J=6.1 Hz), 0.75 (2H, m.), 0.69 (2H, m). MS (ESI, pos. ion) m/z 409.1 (M+H)+.

Example 279

5-(3-(4-cyclopropyl-2-pyrimidinyl)-6-fluoro-1H-indol-5-yl)-N-(1-methylethyl)-1,3,4-oxadiazol-2-amine

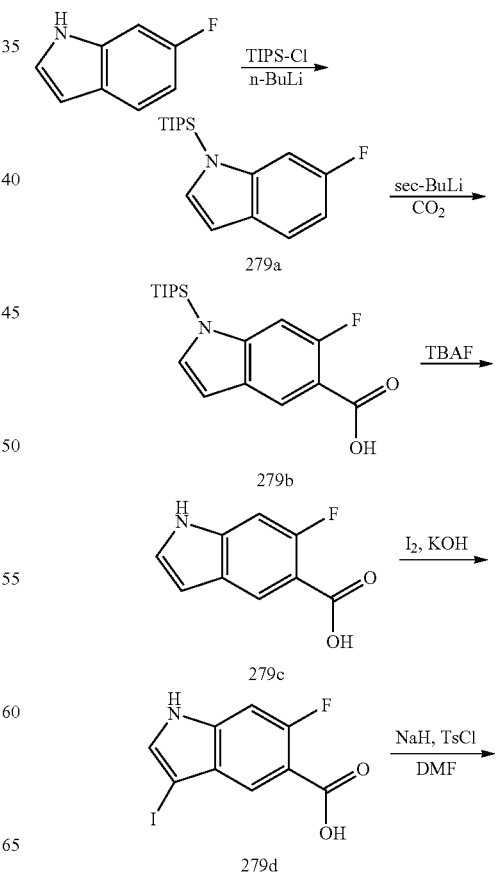

-continued

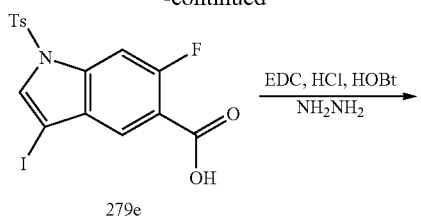

279e

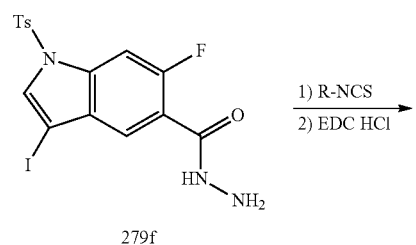

279f

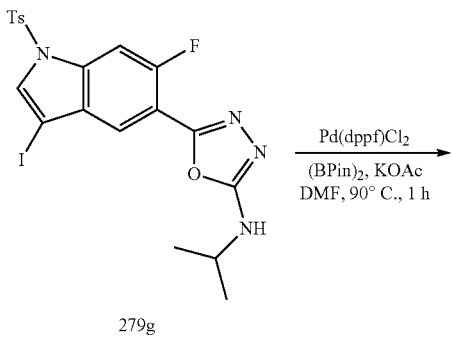

279g

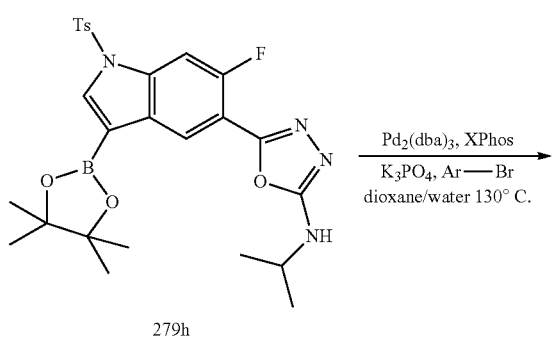

279h

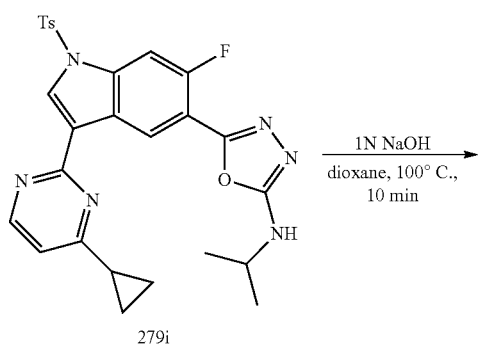

279i

-continued

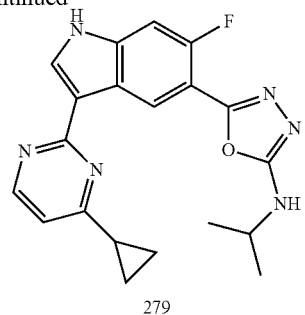

279

Preparation of compound 279a:
6-fluoro-1-(triisopropylsilyl)-1H-indole

Prepared according to: Schlosser, M.; Ginanneschi, A.; Leroux, F. *Eur. J. Org. Chem.* 2006, 2956-2969. In a 500 mL round bottomed flask, THF (75 mL) was cooled to −78° C. and treated with a butyllithium solution, 1.6 M in hexane (23.12 mL, 37.0 mmol), 6-fluoroindole (5.00 g, 37.0 mmol) and triisopropylsilyl chloride (7.92 mL, 37.0 mmol). The solution was then removed from the cooling bath and warmed to RT and stirred for 1 h. The reaction mixture was concentrated on the rotovap and the crude residue was purified on the ISCO Combiflash Companion (40 g Redisep column, using a gradient of 0-10% EtOAc in hexanes) affording 6-fluoro-1-(triisopropylsilyl)-1H-indole (9.78 g, 33.6 mmol, 91% yield) as a clear, viscous colorless oil. MS (ESI, pos. ion) m/z 292.1 (M+H)$^+$. $^1$H NMR (400 MHz, CDCl$_3$) δ ppm 7.51 (1H, dd, J=8.4, 5.9 Hz), 7.13-7.23 (2H, m), 6.83-6.92 (1H, m), 6.59 (1H, d, J=2.3 Hz), 1.68 (3H, quin, J=7.5 Hz), 1.14 (18H, d, J=7.6 Hz).

Preparation of compound 279b: 6-fluoro-1-(triisopropylsilyl)-1H-indole-5-carboxylic acid In a 250 mL round bottomed flask, 6-fluoro-1-(triisopropylsilyl)-1H-indole (5.12 g, 17.57 mmol) was treated with THF (35 mL), cooled to −75° C. and treated with sec-butyllithium, 1.4 M in cyclohexane (12.55 mL, 17.57 mmol) and stirred at −75° C. for 2 h. The reaction mixture was treated with crushed dry ice and was warmed to RT over 30 min. The reaction mixture was treated with 10 mL water and the organic layer was washed with 1 M citric acid (2×20 mL) in an extraction funnel. The organic layer was then concentrated under reduced pressure (rotary evaporator) and recrystallized from a 9:1 mixture of hexanes:Et$_2$O (100 mL) overnight in the freezer affording 6-fluoro-1-(triisopropylsilyl)-1H-indole-5-carboxylic acid (4.36 g, 13.00 mmol, 74.0% yield) as a white crystalline solid. MS (ESI, pos. ion) m/z: 336.0 (M+H)$^+$. $^1$H NMR (400 MHz, CDCl$_3$) δ ppm 8.25 (1H, d, J=7.4 Hz), 7.26 (1H, d, J=3.1 Hz), 7.20 (1H, d, J=12.9 Hz), 6.65 (1H, d, J=2.9 Hz), 1.68 (3H, quin, J=7.5 Hz), 1.14 (18H, d, J=7.6 Hz).

Preparation of compound 279c:
6-fluoro-1H-indole-5-carboxylic acid

6-Fluoro-1-(triisopropylsilyl)-1H-indole-5-carboxylic acid (4.36 g, 13.00 mmol) was treated with THF (30 mL) and tetra-n-butylammonium fluoride (1.0 M in THF, 13.0 mL, 13.00 mmol) and stirred at RT for 15 min. The reaction mixture was diluted with Et$_2$O (30 mL) resulting in a suspension which was collected by filtration affording 6-fluoro-1H- indole-5-carboxylic acid (2.41 g) as a white crystalline solid. MS (ESI, pos. ion) m/z: 180.1 (M+H)+. The crude material was used in the subsequent reaction without further purification.

Preparation of compound 279d:
6-fluoro-3-iodo-1H-indole-5-carboxylic acid

To a solution of 6-fluoro-1H-indole-5-carboxylic acid (2.32 g, 12.95 mmol) in DMF (15 mL) was added iodine (3.45 g, 13.60 mmol) and potassium hydroxide (1.60 g, 28.5 mmol). After stirring 20 min at RT, the reaction mixture was poured into ice water (40 mL) containing sodium hydrogensulfite (1.35 g, 12.95 mmol). The reaction mixture was stirred for 5 min, treated with 2 N HCl to adjust the pH to about pH=6 and filtered. The resulting orange solid was washed with water (2×25 mL) and transferred to a 250 mL round bottomed flask and dried overnight using a lyophilizer to afford 6-fluoro-3-iodo-1H-indole-5-carboxylic acid (3.63 g, 11.90 mmol, 92% yield) as an orange amorphous solid. MS (ESI, pos. ion) m/z: 305.9 (M+H)+.

Preparation of compound 279e:
6-fluoro-3-iodo-1-tosyl-1H-indole-5-carboxylic acid A solution of 6-fluoro-3-iodo-1H-indole-5-carboxylic acid (650 mg, 2.13 mmol) in DMF (5 mL) at 0° C. was treated with NaH (60% dispersion in mineral oil, 0.213 g, 5.33 mmol). After 30 minutes at 0° C., TsCl (0.447 g, 2.34 mmol) was added in 1 portion and the reaction mixture was warmed slowly in the ice bath (reached ca. 10° C.). After 1.5 h, the reaction mixture was poured onto ice, and the pH adjusted to pH 5 with 2 N HCl causing precipitation of the product. It was then collected by filtration, washing with water on a sintered glass frit, transferred to a flask and dried on a lyopholizer for 5 h affording 6-fluoro-3-iodo-1-tosyl-1H-indole-5-carboxylic acid (858 mg, 1.87 mmol, 88% yield) as an off-white amorphous solid. MS (ESI, pos. ion) m/z: 459.8 (M+H)+. The crude material was used in the subsequent step without further purification.

Preparation of compound 279f:
6-fluoro-3-iodo-1-tosyl-1H-indole-5-carbohydrazide HOBt (Aldrich, St. Louis, Mo., 303 mg, 2.24 mmol), EDC HCl (430 mg, 2.242 mmol) and 6-fluoro-3-iodo-1-tosyl-1H-indole-5-carboxylic acid (858 mg, 1.87 mmol) were weighed into a 250 mL round bottomed flask and treated with DMF (7 mL). The resulting solution was stirred at RT for 30 min. The reaction mixture was then treated with anhydrous hydrazine (0.29 mL, 9.34 mmol) and stirred at RT for 30 min. The reaction mixture was diluted with water resulting in precipitate formation. The solid was collected by filtration, washed with water, and dried under high vacuum for 3 h at 50° C., affording crude 6-fluoro-3-iodo-1-tosyl-1H-indole-5-carbohydrazide (2.17 g) as a light yellow amorphous solid. MS (ESI, pos. ion) m/z: 473.9 (M+H)+. $^1$H NMR (400 MHz, DMSO-d$_6$) δ ppm 9.59 (1H, br. s.), 8.17 (1H, s), 8.01 (2H, d, J=8.4 Hz), 7.97 (5H, s), 7.82 (1H, d, J=10.8 Hz), 7.50 (1H, d, J=6.5 Hz), 7.45 (3H, d, J=8.2 Hz), 4.56 (2H, br. s.), 4.11 (3H, br. s.), 2.36 (4H, s).

Preparation of compound 279g: 5-(6-fluoro-3-iodo-1-tosyl-1H-indol-5-yl)-N-isopropyl-1,3,4-oxadiazol-2-amine In a 250 mL round bottomed flask, 6-fluoro-3-iodo-1-tosyl-1H-indole-5-carbohydrazide (880 mg, 1.86 mmol) was treated with THF (10 mL) and 2-isothiocyanatopropane (0.56 mL, 5.58 mmol) and heated to 60° C. for 1 h. The THF was removed under reduced pressure (rotary evaporator) and replaced with DMF (5.0 mL) and the solution was treated with EDC HCl (Aldrich, St. Louis, Mo., 535 mg, 2.79 mmol) and heated at 90° C. for 30 min. The reaction mixture was cooled to RT and treated with water and extracted with EtOAc (2×50 mL), washed with brine (2×50 mL) and dried over MgSO$_4$, filtered and concentrated. Purification of the crude residue on the ISCO Combiflash Rf (40 g Redisep column, using a gradient of 0-100% EtOAc in hexanes) afforded 5-(6-fluoro-3-iodo-1-tosyl-1H-indol-5-yl)-N-isopropyl-1,3,4-oxadiazol-2-amine (407 mg, 0.75 mmol, 40.5% yield) as an off-white amorphous solid. MS (ESI, pos. ion) m/z: 540.8 (M+H)+. $^1$H NMR (400 MHz, DMSO-d$_6$) δ ppm 8.20 (1H, s), 8.03 (2H, m, J=8.4 Hz), 7.95 (1H, d, J=11.2 Hz), 7.81 (1H, d, J=7.4 Hz), 7.71 (1H, d, J=6.7 Hz), 7.44 (2H, m, J=8.2 Hz), 3.74 (1H, dq, J=13.4, 6.6 Hz), 2.35 (3H, s), 1.21 (6H, d, J=6.5 Hz).

Preparation of compound 279h: 5-(6-fluoro-3-(4,4,5,5-tetramethyl-1,3,2-dioxaborolan-2-yl)-1-tosyl-1H-indol-5-yl)-N-isopropyl-1,3,4-oxadiazol-2-amine A 20 mL microwave tube was charged with a mixture of 5-(6-fluoro-3-iodo-1-tosyl-1H-indol-5-yl)-N-isopropyl-1,3,4-oxadiazol-2-amine (375 mg, 0.694 mmol), bis(pinacolato)diboron (Aldrich, St. Louis, Mo., 529 mg, 2.08 mmol), potassium acetate (341 mg, 3.47 mmol), Pd(dppf)Cl$_2$, complex with DCM (Strem Chemicals, Newburyport, Mass., 85 mg, 0.104 mmol) and DMF (5.0 mL) and stirred at 90° C. in the oil bath for 1 h. The reaction mixture was cooled to RT, treated with EtOAc (50 mL) and washed with brine (2×25 mL) and dried over MgSO$_4$, filtered and concentrated. MS (ESI, pos. ion) m/z: 459.0 and 541.1 (M+H)+ corresponding to the boronic acid and pinacol boronic ester in ca. a 1:1 mixture. The crude residue was used in the next step without further purification.

Preparation of compound 279i: 5-(3-(4-cyclopropylpyrimidin-2-yl)-6-fluoro-1-tosyl-1H-indol-5-yl)-N-isopropyl-1,3,4-oxadiazol-2-amine A 20 mL microwave vial was charged with 5-(6-fluoro-3-(4,4,5,5-tetramethyl-1,3,2-dioxaborolan-2-yl)-1-tosyl-1H-indol-5-yl)-N-isopropyl-1,3,4-oxadiazol-2-amine (185 mg, 0.342 mmol), Xphos (Strem Chemicals, Newburyport, Mass., 9.8 mg, 0.021 mmol), Pd$_2$(dba)$_3$ (Strem Chemicals, Newburyport, Mass., 9.4 mg, 10.27 µmol), 2-bromo-4-cyclopropylpyrimidine (CombiPhos Catalysts Inc., Princeton, N.J., 82 mg, 0.411 mmol) and potassium phosphate (218 mg, 1.03 mmol) followed by purging with argon. The solids were treated with dioxane (4.0 mL) and water (1.0 mL) and heated in the microwave at 130° C. for 20 min. The reaction mixture was treated with water and extracted with EtOAc, dried over MgSO$_4$, filtered and concentrated. Purification of the crude residue on the ISCO Combiflash Rf (12 g Redisep column, using a gradient of 0-100% EtOAc in hexanes) afforded 5-(3-(4-cyclopropylpyrimidin-2-yl)-6-fluoro-1-tosyl-1H-indol-5-yl)-N-isopropyl-1,3,4-oxadiazol-2-amine (186.7 mg, 0.351 mmol, 102% yield) as a viscous yellow oil in ca. 90% purity. MS (ESI, pos. ion) m/z: 533.0 (M+H)+. The material was used in the subsequent step without further purification.

Preparation of compound 279: 5-(3-(4-cyclopropyl-2-pyrimidinyl)-6-fluoro-1H-indol-5-yl)-N-(1-methylethyl)-1,3,4-oxadiazol-2-amine A 5 mL glass microwave tube was charged with 5-(3-(4-cyclopropylpyrimidin-2-yl)-6-fluoro-1-tosyl-1H-indol-5- yl)-N-isopropyl-1,3,4-oxadiazol-2-amine (180 mg, 0.338 mmol) and treated with dioxane (2 mL) and 1 N NaOH (1 mL) and heated at 100° C. for 10 min in the microwave. The reaction mixture was treated with brine and extracted with EtOAc (2×20 mL), concentrated and purified by reverse phase using a Gilson automated platform (Silicycle Silichrome XT $C_{18}$ column; 30×150 mm, 5 μm, 10-95% 0.1% TFA/$CH_3$CN in 0.1% TFA/water by volume over 10 min), then dried in a Genevac Series II Evaporator affording the title compound (48.2 mg, 0.098 mmol, 29.0% yield) as a yellow amorphous solid. LC-MS (ESI, pos. ion) m/z: 379.2 (M+1). $^1$H NMR (400 MHz, DMSO-$d_6$) δ ppm 11.93-12.03 (1H, m), 8.98 (1H, d, J=7.4 Hz), 8.59 (1H, d, J=5.1 Hz), 8.29 (1H, d, J=2.7 Hz), 7.85 (1H, d, J=7.4 Hz), 7.45 (1H, d, J=11.3 Hz), 7.21 (1H, d, J=5.3 Hz), 3.82 (1H, dq, J=13.2, 6.5 Hz), 2.13-2.22 (1H, m), 1.27 (6H, d, J=6.5 Hz), 1.20-1.25 (2H, m), 1.12-1.20 (2H, m). $^{19}$F NMR (377 MHz, DMSO-$d_6$) δ ppm −74.90 (3F, s), −119.9 (1F, s).

Example 280

5-(3-(6-cyclopropyl-2-pyrazinyl)-6-fluoro-1H-indol-5-yl)-N-(1-methylethyl)-1,3,4-oxadiazol

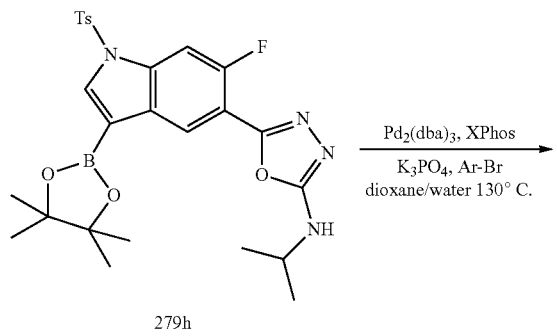

279h

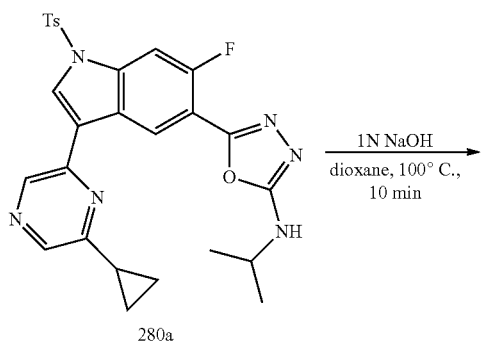

280a

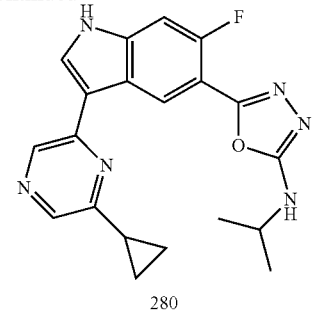

280

Preparation of compound 280a: 5-(3-(6-cyclopropylpyrazin-2-yl)-6-fluoro-1-tosyl-1H-indol-5-yl)-N-isopropyl-1,3,4-oxadiazol-2-amine A 20 mL microwave vial was charged with 5-(6-fluoro-3-(4,4,5,5-tetramethyl-1,3,2-dioxaborolan-2-yl)-1-tosyl-1H-indol-5-yl)-N-isopropyl-1,3,4-oxadiazol-2-amine (185 mg, 0.342 mmol), Xphos (Strem Chemicals, Newburyport, Mass., 9.8 mg, 0.021 mmol), $Pd_2$(dba)$_3$ (Strem Chemicals, Newburyport, Mass., 9.4 mg, 10.27 μmol), 2-bromo-6-cyclopropylpyrazine (CombiPhos Catalyst Inc., Princeton, N.J., 82 mg, 0.411 mmol) and potassium phosphate (218 mg, 1.03 mmol) followed by purging with argon. The solids were then treated with dioxane (4.0 mL) and water (1.0 mL) and heated in the microwave at 130° C. for 20 min. The reaction mixture was treated with water and extracted with EtOAc, dried over $MgSO_4$, filtered and concentrated. Purification of the crude residue on the ISCO Combiflash Rf (12 g Redisep column, using a gradient of 0-100% EtOAc in hexanes) afforded 5-(3-(6-cyclopropylpyrazin-2-yl)-6-fluoro-1-tosyl-1H-indol-5-yl)-N-isopropyl-1,3,4-oxadiazol-2-amine (65.8 mg, 0.124 mmol, 36.1% yield) as an off-white solid. MS (ESI, pos. ion) m/z: 533.0 (M+H)$^+$. The material was used in the subsequent step without further purification.

Preparation of compound 280: 5-(3-(6-cyclopropyl-2-pyrazinyl)-6-fluoro-1H-indol-5-yl)-N-(1-methylethyl)-1,3,4-oxadiazol A 5 mL glass microwave tube was charged with 5-(3-(6-cyclopropylpyrazin-2-yl)-6-fluoro-1-tosyl-1H-indol-5-yl)-N-isopropyl-1,3,4-oxadiazol-2-amine (65 mg, 0.122 mmol) then treated with dioxane (2 mL) and 1 N NaOH (1 mL) and heated at 100° C. for 10 min in the microwave. The reaction mixture was treated with brine and extracted with EtOAc (25 mL), concentrated and purified on a Gilson automated platform (Silicycle Silichrome XT $C_{18}$ column; 30×150 mm, 5 μm, 10-95% 0.1% TFA/$CH_3$CN in 0.1% TFA/water by volume over 10 min), affording enriched product after drying in the genevac overnight. The material was then repurified on an Agilent mass-triggered LC (Silicycle Silichrome XT $C_{18}$ column; 30×150 mm, 5 μm, 20-45% 0.1% TFA/$CH_3$CN in 0.1% TFA/water by volume over 10 min) affording the title compound (3.2 mg, 6.9% yield) as a yellow amorphous solid after drying in the genevac overnight. MS (ESI, pos. ion) m/z: 379.1 (M+H)$^+$. $^1$H NMR (400 MHz, MeOH-d4 and CDCl$_3$ for solubility) δ ppm 8.93 (1H, d, J=7.0 Hz), 8.71 (1H, s), 8.23 (1H, s), 8.03 (1H, s), 7.31 (1H, d, J=11.2 Hz), 3.98 (1H, dt, J=13.1, 6.5 Hz), 2.16-2.25 (1H, m), 1.35 (6H, d, J=6.7 Hz), 1.25-1.34 (4H, m), 1.11-1.19 (2H, m). $^{19}$F NMR (377 MHz, MeOH) δ ppm −119.8 (1F, s).

Example 281

4-cyclopropyl-2-(5-(5-((1-methylethyl)amino)-1,3,4-oxadiazol-2-yl)-1H-indol-3-yl)-5-pyrimidinecarboxamide

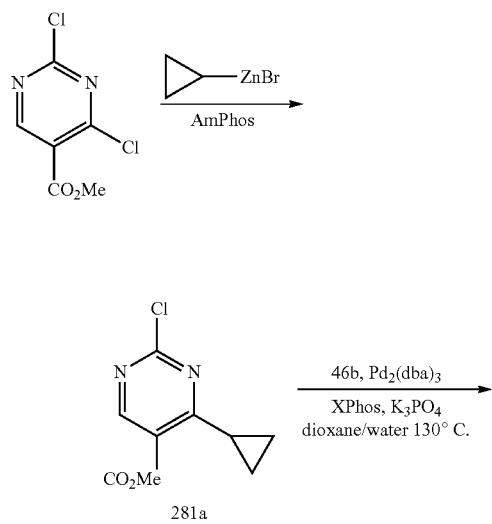

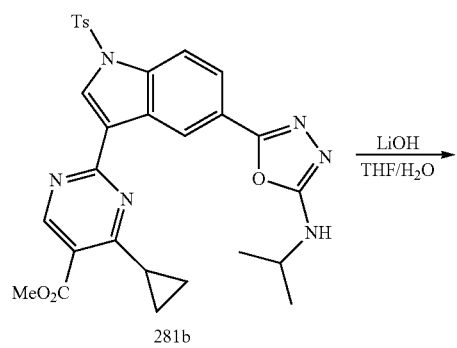

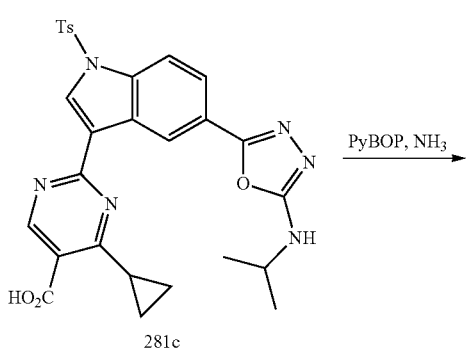

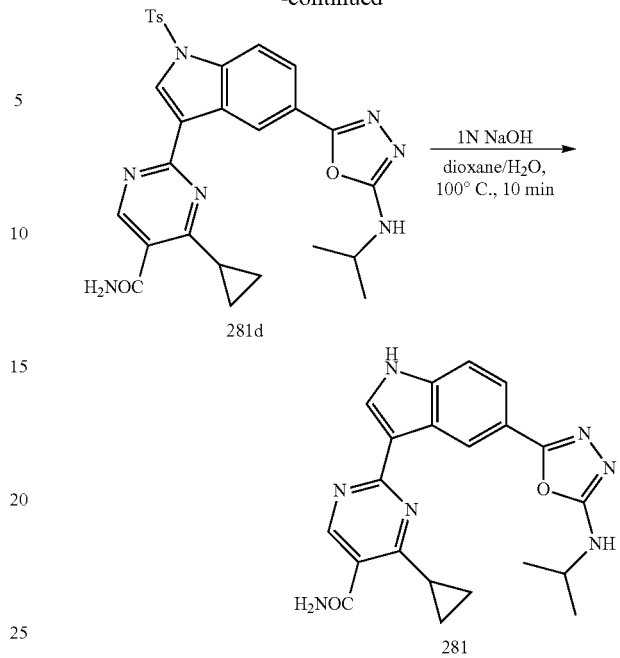

Preparation of compound 281a: methyl 2-chloro-4-cyclopropylpyrimidine-5-carboxylate A 20 mL glass microwave tube was charged with methyl 2,4-dichloropyrimidine-5-carboxylate (Aldrich, St. Louis, Mo., 831 mg, 4.01 mmol and Amphos (Aldrich, St. Louis, Mo., 71.1 mg, 0.100 mmol) were treated with cyclopropylzinc(II) bromide (Rieke Metals, Lincoln, Nebr., 0.5 M in THF, 16.1 mL, 8.03 mmol) via syringe under an atmosphere of argon. The solution was then heated in the microwave at 80° C. for 20 min. The reaction mixture was treated with EtOAc and then with 1 N NaOH resulting in a white suspension as the zinc hydroxide salts precipitated. It was extracted with EtOAc (50 mL) a second time and washed with brine and dried over anhydrous Na$_2$SO$_4$, filtered and concentrated. Purification of the crude residue on the ISCO Combiflash Rf (40 g Redisep column, using 100% DCM) afforded two readily separable peaks. The first eluting peak was found to be methyl 2-chloro-4-cyclopropylpyrimidine-5-carboxylate (269 mg, 1.26 mmol, 31.5% yield) as a white amorphous solid upon concentration. MS (ESI, pos. ion) m/z: 213.1 (M+H)$^+$. $^1$H NMR (400 MHz, CDCl$_3$) δ ppm 8.91 (1H, s), 3.97 (3H, s), 3.12-3.20 (1H, m), 1.34-1.40 (2H, m), 1.20-1.27 (2H, m).

Preparation of compound 281b: methyl 4-cyclopropyl-2-(5-(5-(isopropylamino)-1,3,4-oxadiazol-2-yl)-1-tosyl-1H-indol-3-yl)pyrimidine-5-carboxylate A 20 mL microwave vial was charged with N-isopropyl-5-(3-(4,4,5,5-tetramethyl-1,3,2-dioxaborolan-2-yl)-1-tosyl-1H-indol-5-yl)-1,3,4-oxadiazol-2-amine (300 mg, 0.574 mmol), Xphos (Stem Chemicals, Newburyport, Mass., 16.4 mg, 0.034 mmol), Pd$_2$(dba)$_3$ (Strem Chemicals, Newburyport, Mass., 15.8 mg, 0.017 mmol), methyl 2-chloro-4-cyclopropylpyrimidine-5-carboxylate (147 mg, 0.689 mmol) and potassium phosphate (366 mg, 1.723 mmol) followed by purging with argon. The solids were treated with dioxane (3 mL) and water (1.0 mL) and heated in the microwave at 130° C. for 20 min. The reaction mixture was treated with water and extracted with EtOAc, dried over MgSO₄, filtered and concentrated. Purification of the crude residue on the ISCO (12 g Redisep column, using a gradient of 0-100% EtOAc in hexanes) afforded methyl 4-cyclopropyl-2-(5-(5-(isopropylamino)-1,3,4-oxadiazol-2-yl)-1-tosyl-1H-indol-3-yl)pyrimidine-5-carboxylate (132.4 mg, 0.231 mmol, 40.3% yield) as light yellow amorphous solid. MS (ESI, pos. ion) m/z: 573.2 (M+H)⁺. ¹H NMR (400 MHz, CDCl₃) δ ppm 9.11 (1H, s), 9.04 (1H, d, J=1.2 Hz), 8.59 (1H, s), 8.08 (1H, d, J=8.8 Hz), 8.01 (1H, dd, J=8.8, 1.6 Hz), 7.86 (2H, d, J=8.4 Hz), 7.28 (2H, s), 4.55 (1H, br. s.), 4.00-4.08 (1H, m), 3.98 (3H, s), 3.24-3.34 (1H, m), 2.36 (3H, s), 1.32-1.39 (6H, m), 1.21-1.30 (4H, m).

Preparation of compound 281c: 4-cyclopropyl-2-(5-(5-(isopropylamino)-1,3,4-oxadiazol-2-yl)-1-tosyl-1H-indol-3-yl)pyrimidine-5-carboxylic acid Methyl 4-cyclopropyl-2-(5-(5-(isopropylamino)-1,3,4-oxadiazol-2-yl)-1-tosyl-1H-indol-3-yl)pyrimidine-5-carboxylate (110 mg, 0.192 mmol) was treated with THF (2 mL), water (1.0 mL) and lithium hydroxide monohydrate (20 mg, 0.48 mmol) and stirred at RT for 1.5 h. The reaction mixture was treated with a 5 N HCl (0.5 mL) and concentrated on the rotovap. It was then dried further by azeotroping with toluene and drying under high vacuum at 50° C. for 3 h. MS (ESI, pos. ion) m/z: 559.0 (M+H)⁺. It was then used in the subsequent step with further purification.

Preparation of compound 281d: 4-cyclopropyl-2-(5-(5-(isopropylamino)-1,3,4-oxadiazol-2-yl)-1-tosyl-1H-indol-3-yl)pyrimidine-5-carboxamide 4-Cyclopropyl-2-(5-(5-(isopropylamino)-1,3,4-oxadiazol-2-yl)-1-tosyl-1H-indol-3-yl)pyrimidine-5-carboxylic acid (107 mg, 0.192 mmol) was treated with PyBOP (169 mg, 0.326 mmol) and 1,4-dioxane (5 mL) and DMF (1.0 mL) and stirred at RT for 10 min. The reaction was then cooled in an ice bath and treated with NH₃, 0.5 M solution in 1,4-dioxane (1.9 mL, 0.96 mmol) and stirred at 0° C. for 1.5 h. The reaction was quenched with water, extracted with EtOAc (25 mL), washed with brine (2×25 mL), dried over MgSO₄, filtered and concentrated affording 261 mg of the crude amide. MS (ESI, pos. ion) m/z: 558.2 (M+H)⁺. The crude material was used without further purification.

Preparation of compound 281: 4-cyclopropyl-2-(5-(5-((1-methylethyl)amino)-1,3,4-oxadiazol-2-yl)-1H-indol-3-yl)-5-pyrimidinecarboxamide 2,2,2-trifluoroacetate A 5 mL microwave tube was charged with 4-cyclopropyl-2-(5-(5-(isopropylamino)-1,3,4-oxadiazol-2-yl)-1-tosyl-1H-indol-3-yl)pyrimidine-5-carboxamide (107 mg, 0.192 mmol) and treated with dioxane (2 mL) and 1 N NaOH (0.5 mL) and heated in the microwave at 80° C. for 10 min. The reaction mixture was treated with brine and extracted with EtOAc (2×25 mL), washed with brine and concentrated. The crude residue was purified on the Gilson (Silicycle Silichrome XT C₁₈ column; 30×150 mm, 5 μm, 10-95% 0.1% TFA/CH₃CN in 0.1% TFA/water by volume over 10 min) affording the title compound (48.4 mg, 0.094 mmol, 48.7% yield) as a yellow amorphous solid after drying in the genevac overnight. MS (ESI, pos. ion) m/z: 404.1 (M+H)⁺. ¹H NMR (400 MHz, DMSO-d₆) δ ppm 12.08 (1H, d, J=2.3 Hz), 8.97 (1H, s), 8.69 (1H, s), 8.35 (1H, d, J=2.7 Hz), 8.10 (1H, br. s.), 8.03 (1H, d, J=6.5 Hz), 7.69-7.74 (1H, m), 7.67 (1H, br. s.), 7.60-7.65 (1H, m), 3.79-3.91 (1H, m), 2.73-2.82 (1H, m), 1.32-1.38 (2H, m), 1.28 (6H, d, J=6.5 Hz), 1.14-1.22 (2H, m). ¹⁹F NMR (377 MHz, DMSO-d₆) δ ppm −74.96 (1F, s) TFA present.

Example 282

N-methyl-2-(5-(5-((1-methylethyl)amino)-1,3,4-oxadiazol-2-yl)-1H-indol-3-yl)-4-pyrimidinecarboxamide 2,2,2-trifluoroacetate

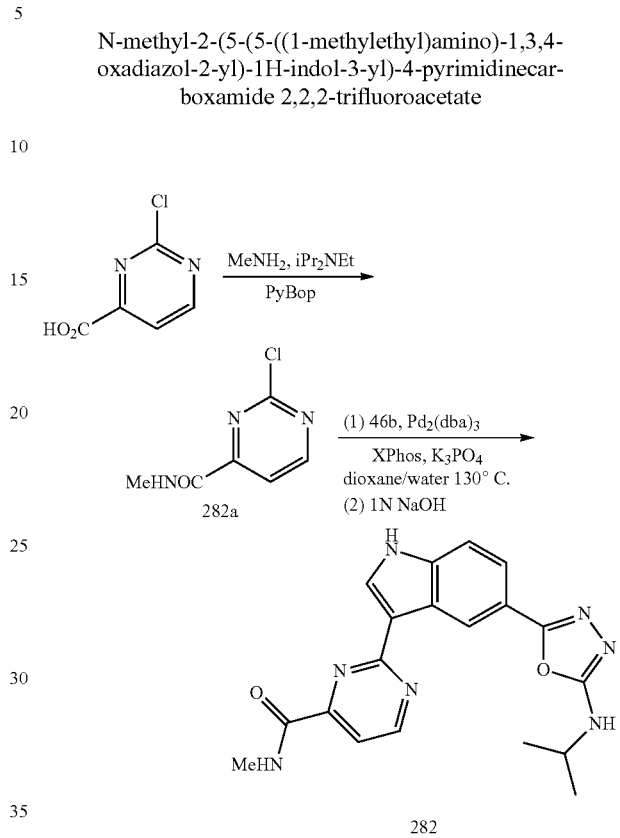

Preparation of compound 282a: 2-chloro-N-methylpyrimidine-4-carboxamide

2-Chloropyrimidine-4-carboxylic acid (Maybridge Chemicals, Maybridge, UK, 0.523 g, 3.30 mmol), DIPEA (0.48 mL, 2.75 mmol) and PyBop (1.717 g, 3.30 mmol) were weighed into a 150 mL round bottomed flask and dissolved in dioxane (15 mL). The solution was stirred at RT, then cooled to 0° C., and stirred for 5 min. Methylamine, 2.0 M in THF (2.75 mL, 5.50 mmol) was added, and the solution became a thick suspension. The suspension was stirred at 0° C. for 2.5 h. No further progression was seen, so an additional equivalent of MeNH₂ was added, and the mixture was stirred for another 4 h. EtOAc was added and the mixture was washed with water (50 mL), 1 N NaOH (2×50 mL) and brine (50 mL). The material was dried over MgSO₄, filtered and concentrated and used without purification. MS (ESI, pos. ion) m/z: 171.9 (M+H)⁺.

Preparation of compound 282: N-methyl-2-(5-(5-((1-methylethyl)amino)-1,3,4-oxadiazol-2-yl)-1H-indol-3-yl)-4-pyrimidinecarboxamide 2,2,2-trifluoroacetate N-Isopropyl-5-(3-(4,4,5,5-tetramethyl-1,3,2-dioxaborolan-2-yl)-1-tosyl-1H-indol-5-yl)-1,3,4-oxadiazol-2-amine (0.300 g, 0.574 mmol), Xphos (Stem Chemicals, Newburyport, Mass., 16 mg, 0.034 mmol), Pd₂(dba)₃ (Strem Chemicals, Newburyport, Mass., 16 mg, 0.017 mmol), potassium phosphate (0.366 g, 1.723 mmol) and 2-chloro-N-methylpyrimidine-4-carboxamide (0.099 g, 0.574 mmol) were weighed into a 5 mL glass microwave tube. The tube was purged with argon, the solids were treated with dioxane (3 mL) and water (0.30 mL) and the tube was heated at 130° C. for 20 min in an Initiator microwave reactor (Personal Chemistry, Biotage AB, Inc., Upssala, Sweden). Very little product was seen. Additional 2-chloro-N-methylpyrimidine-4-carboxamide (0.099 g, 0.574 mmol), Xphos (16 mg, 0.034 mmol) and $Pd_2(dba)_3$ (16 mg, 0.017 mmol) were added, the tube was sealed, and the contents were again heated in the microwave at 130° C. for 20 min. Little conversion was seen. Heating again at 145° C. for 20 min. resulted in an increase in product. The tube was heated at 145° C. for 30 min, resulting in little change in the reaction mixture composition. $Pd(PPh_3)_4$ (10 mg) and 2 M $Na_2CO_3$ (1.5 mL) were added and the materials were heated in the microwave at 160° C. for 20 min. Some additional conversion to the desired product was observed by LCMS (M+1=532.0). The reaction mixture was treated with water and extracted with EtOAc. The organic layer was washed with brine, dried over $MgSO_4$, filtered and concentrated. The crude material was purified by flash chromatography using an ISCO Combiflash $R_f$ (25 g Thomson Single Step silica gel column; 20-100% EtOAc in hexanes) to give 2-(5-(5-(isopropylamino)-1,3,4-oxadiazol-2-yl)-1-tosyl-1H-indol-3-yl)-N-methylpyrimidine-4-carboxamide (56.1 mg, 0.106 mmol, 18.3% yield) as a light brown oil. MS (ESI, pos. ion) m/z: 532.1 $(M+H)^+$. 2-(5-(5-(Isopropylamino)-1,3,4-oxadiazol-2-yl)-1-tosyl-1H-indol-3-yl)-N-methylpyrimidine-4-carboxamide (56.1 mg, 0.106 mmol) was weighed into a 5 mL glass microwave tube, and was treated with dioxane (1.5 mL) and 1 N NaOH (0.5 mL). The solution was heated in an Initiator microwave reactor (Personal Chemistry, Biotage AB, Inc., Upssala, Sweden) at 100° C. for 10 min. The reaction mixture was treated with water and extracted with EtOAc. The organic layer was concentrated in vacuo. The crude residue was dissolved in DMSO (2.0 mL) and purified using a Gilson automated platform (Silicycle Silichrome XT $C_{18}$ column; 30×150 mm, 5 μm, 20-95% 0.1% $TFA/CH_3CN$ in 0.1% TFA/water by volume over 10 min), then dried in a Genevac Personal Evaporator affording the title compound (16.1 mg, 0.033 mmol, 31.0% yield) as a yellow amorphous solid. MS (ESI, pos. ion) m/z: 378.0 $(M+H)^+$. $^1H$ NMR (400 MHz, DMSO-$d_6$) δ ppm 12.12-12.24 (m, 1H), 9.08-9.16 (m, 1H), 9.05 (d, J=4.9 Hz, 1H), 8.95-8.99 (m, 1H), 8.82 (d, J=2.9 Hz, 1H), 7.70-7.79 (m, 2H), 7.68 (d, J=5.1 Hz, 1H), 7.59-7.66 (m, 1H), 3.76 (dq, J=13.2, 6.5 Hz, 1H), 2.91 (d, J=4.9 Hz, 3H), 1.24 (d, J=6.7 Hz, 6H). $^{19}F$ NMR (377 MHz, DMSO-$d_6$) δ ppm −74.70 (s, 3F)—TFA present.

Example 283

N-cyclopropyl-2-(5-(5-((1-methylethyl)amino)-1,3,4-oxadiazol-2-yl)-1H-indol-3-yl)-4-pyrimidinecarboxamide 2,2,2-trifluoroacetate

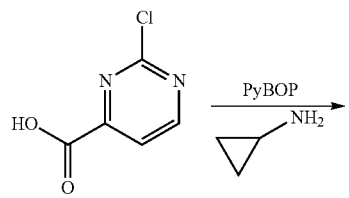

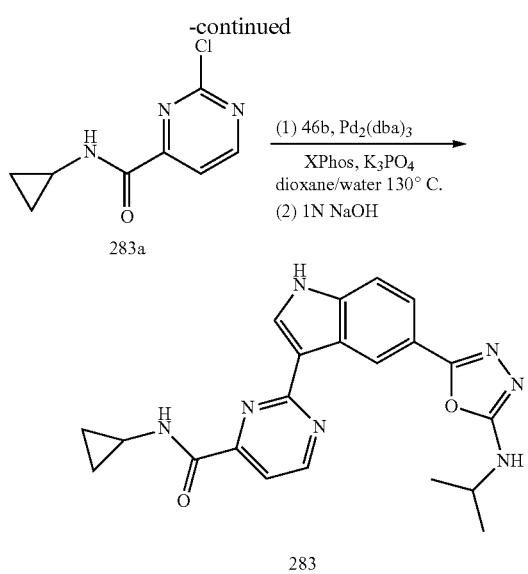

Preparation of compound 283a:
2-chloro-N-cyclopropylpyrimidine-4-carboxamide

2-Chloropyrimidine-4-carboxylic acid (0.516 g, 3.25 mmol) (Maybridge Chemicals, Maybridge, UK), DIPEA (0.94 mL, 5.42 mmol) and PyBop (1.69 g, 3.25 mmol) were weighed into a 150 mL RBF and dissolved in dioxane (15 mL). The solution was stirred at RT, then cooled to 0° C., and stirred for 5 min. Cyclopropylamine (0.38 mL, 5.42 mmol) was added, and the solution was stirred at 0° C. for 1 h. The mixture became solid. Additional dioxane was added (6 mL), the flask was removed from the ice bath and the contents were stirred at RT for 68 h. EtOAc was added and the mixture was washed with water (75 mL), 1 N NaOH (75 mL) and brine (75 mL). The crude material was purified by flash chromatography using an ISCO Combiflash $R_f$(25 g Thomson Single Step silica gel column; 20-100% EtOAc in hexanes) to afford 2-chloro-N-cyclopropylpyrimidine-4-carboxamide (0.139 g, 0.703 mmol, 25.9% yield) as a yellow oil. MS (ESI, pos. ion) m/z: 197.9 $(M+H)^+$.

Preparation of compound 283: N-cyclopropyl-2-(5-(5-((1-methylethyl)amino)-1,3,4-oxadiazol-2-yl)-1H-indol-3-yl)-4-pyrimidinecarboxamide 2,2,2-trifluoroacetate N-Isopropyl-5-(3-(4,4,5,5-tetramethyl-1,3,2-dioxaborolan-2-yl)-1-tosyl-1H-indol-5-yl)-1,3,4-oxadiazol-2-amine (0.300 g, 0.574 mmol), Xphos (Strem Chemicals, Newburyport, Mass., 16 mg, 0.034 mmol), $Pd_2(dba)_3$ (Strem Chemicals, Newburyport, Mass., 16 mg, 0.017 mmol), potassium phosphate (0.366 g, 1.723 mmol) and 2-chloro-N-cyclopropylpyrimidine-4-carboxamide (0.136 g, 0.689 mmol) were weighed into a 5 mL glass microwave tube. The tube was purged with argon, the solids were treated with dioxane (3 mL) and water (0.30 mL) and the tube was heated at 130° C. for 20 min in an Initiator microwave reactor (Personal Chemistry, Biotage AB, Inc., Upssala, Sweden). The reaction mixture was treated with water and extracted with EtOAc. The organic layer was washed with brine, dried over $MgSO_4$, filtered and concentrated. The crude material was purified by flash chromatography using an ISCO Combiflash $R_f$(25 g Thomson Single Step silica gel column; 0-10% MeOH in DCM) to give N-cyclopropyl-2-(5-(5-(isopropylamino)-1,3,4-oxadiazol-2-yl)-1-tosyl-1H-indol-3-yl)pyrimidine-4-carboxamide (284 mg, 0.509 μmol, 89% yield) as a light brown tar. MS (ESI, pos. ion) m/z: 558.0 (M+H)⁺. N-Cyclopropyl-2-(5-(5-(isopropylamino)-1,3,4-oxadiazol-2-yl)-1-tosyl-1H-indol-3-yl)pyrimidine-4-carboxamide (284 mg, 0.509 mmol) was weighed into a 20 mL glass microwave tube, and was treated with dioxane (5.0 mL) and 1 N NaOH (1.5 mL). The solution was heated in an Initiator microwave reactor (Personal Chemistry, Biotage AB, Inc., Upssala, Sweden) at 100° C. for 10 min. The reaction mixture was treated with water (20 mL) and extracted with EtOAc (30 mL). The organic layer was concentrated in vacuo. The crude residue was dissolved in DMSO (4.0 mL) and purified using a Gilson automated platform (Silicycle Silichrome XT $C_{18}$ column; 30×150 mm, 5 μm, 20-95% 0.1% TFA/CH₃CN in 0.1% TFA/water by volume over 10 min), then dried in a Genevac Series II Evaporator affording the title compound (31.5 mg, 0.061 mmol, 11.95% yield) as a light yellow amorphous solid. MS (ESI, pos. ion) m/z: 404.0 (M+H)⁺. ¹H NMR (400 MHz, DMSO-d₆) δ ppm 12.12-12.22 (m, 1H), 9.04 (d, J=5.1 Hz, 1H), 8.98 (s, 1H), 8.93 (d, J=4.5 Hz, 1H), 8.84 (d, J=2.9 Hz, 1H), 7.83 (d, J=7.0 Hz, 1H), 7.71 (dd, J=8.5, 1.7 Hz, 1H), 7.67 (d, J=4.9 Hz, 1H), 7.63 (d, J=8.4 Hz, 1H), 3.76 (dq, J=13.2, 6.4 Hz, 1H), 2.87-3.00 (m, 1H), 1.24 (d, J=6.5 Hz, 6H), 0.73-0.84 (m, 4H). ¹⁹F NMR (376 MHz, DMSO-d₆) δ ppm −74.84 (s, 3F).

Example 284

5-(3-(5-(methylsulfonyl)-2-pyridinyl)-1H-indol-5-yl)-1,3,4-oxadiazol-2-amine 2,2,2-trifluoroacetate

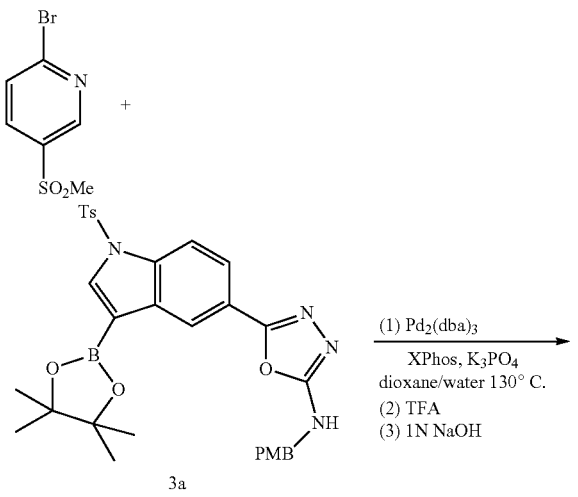

3a

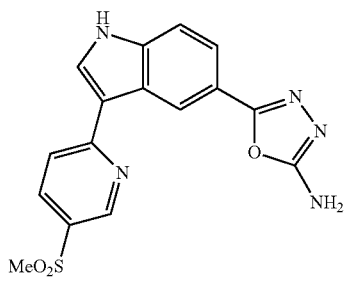

284

N-(4-Methoxybenzyl)-5-(3-(4,4,5,5-tetramethyl-1,3,2-dioxaborolan-2-yl)-1-tosyl-1H-indol-5-yl)-1,3,4-oxadiazol-2-amine (0.200 g, 0.333 mmol), 2-bromo-5-(methylsulfonyl)pyridine (0.118 g, 0.500 mmol) (Acme Bioscience Inc., Palo Alto, Calif.), Xphos (Strem Chemicals, Newburyport, Mass., 9.5 mg, 0.020 mmol), Pd₂(dba)₃ (Strem Chemicals, Newburyport, Mass., 9.2 mg, 9.99 μmol) and potassium phosphate (0.212 g, 0.999 mmol) were weighed into a 5 mL glass microwave tube. The tube was purged with argon and the solids were treated with dioxane (2.0 mL) and water (0.20 mL). The tube was sealed, and the contents heated at 130° C. for 20 min using an Initiator microwave reactor (Personal Chemistry, Biotage AB, Inc., Upssala, Sweden). The reaction mixture was treated with water (40 mL) and extracted with EtOAc (75 mL). The organic layer was washed with brine, dried over MgSO₄, filtered and concentrated. The crude material was purified by flash chromatography using an ISCO Combiflash $R_f$ (12 g Thomson Single Step silica gel column; 30-100% EtOAc in hexanes) to afford N-(4-methoxybenzyl)-5-(3-(5-(methylsulfonyl)pyridin-2-yl)-1-tosyl-1H-indol-5-yl)-1,3,4-oxadiazol-2-amine (0.113 g, 0.179 mmol, 53.9% yield) as a brown amorphous solid. MS (ESI, pos. ion) m/z: 629.9 (M+H)⁺. ¹H NMR (400 MHz, DMSO-d₆) δ ppm 9.15 (d, J=2.2 Hz, 1H), 9.02 (d, J=1.4 Hz, 1H), 8.95 (s, 1H), 8.43 (s, 1H), 8.39 (d, J=2.3 Hz, 1H), 8.37 (s, 1H), 8.28-8.31 (m, 1H), 8.16 (d, J=8.8 Hz, 1H), 7.91 (d, J=1.6 Hz, 1H), 7.44 (d, J=8.6 Hz, 3H), 7.33 (m, J=8.6 Hz, 2H), 6.90 (m, J=8.8 Hz, 2H), 4.38 (d, J=5.9 Hz, 2H), 3.72 (s, 3H), 3.37 (s, 3H), 2.33 (s, 3H). A solution of N-(4-methoxybenzyl)-5-(3-(5-(methylsulfonyl)pyridin-2-yl)-1-tosyl-1H-indol-5-yl)-1,3,4-oxadiazol-2-amine (0.113 g, 0.179 mmol) in TFA (2.0 mL) was heated in an Initiator microwave reactor (Personal Chemistry, Biotage AB, Inc., Upssala, Sweden) at 100° C. for 20 min. The residual TFA was removed in vacuo. The residue was treated with 1 N NaOH (20 mL) and extracted with EtOAc (50 mL). The organic layer was washed with water (20 mL) then brine (20 mL), dried over MgSO₄, filtered and concentrated to give 5-(3-(5-(methylsulfonyl)pyridin-2-yl)-1-tosyl-1H-indol-5-yl)-1,3,4-oxadiazol-2-amine as a beige solid. The material was used in the next step without purification, assuming the theoretical yield. MS (ESI, pos. ion) m/z: 509.9 (M+H)⁺. 5-(3-(5-(Methylsulfonyl)pyridin-2-yl)-1-tosyl-1H-indol-5-yl)-1,3,4-oxadiazol-2-amine (91 mg, 0.179 mmol) was weighed into a 5 mL glass microwave tube, and was treated with dioxane (1.5 mL) and 1 N NaOH (0.5 mL). The solution was heated in an Initiator microwave reactor (Personal Chemistry, Biotage AB, Inc., Upssala, Sweden) at 100° C. for 10 min. The reaction mixture was treated with water, extracted with EtOAc, and the organic layer was concentrated. The crude residue was dissolved in DMSO (2.5 mL) and purified by reverse phase using a Gilson automated platform (Silicycle Silichrome XT $C_{18}$ column; 30×150 mm, 5 μm, 20-95% 0.1% TFA/CH₃CN in 0.1% TFA/water by volume over 10 min), then dried in a Genevac Series II Evaporator affording 5-(3-(5-(methylsulfonyl)pyridin-2-yl)-1H-indol-5-yl)-1,3,4-oxadiazol-2-amine 2,2,2-trifluoroacetate (12.1 mg, 0.026 mmol, 14.43% yield) as an orange amorphous solid.). MS (ESI, pos. ion) m/z: 356.0 (M+H)⁺. ¹H NMR (400 MHz, DMSO-d₆) δ ppm 12.15 (br. s., 1H), 9.02 (s, 1H), 9.05 (s, 1H), 8.49 (d, J=2.5 Hz, 1H), 8.23 (dd, J=8.6, 2.3 Hz, 1H), 8.13 (d, J=8.6 Hz, 1H), 7.71 (d, J=8.4 Hz, 1H), 7.61 (d, J=8.6 Hz, 1H), 7.34 (br. s., 2H), 3.33 (s, 3H). $^{19}$F NMR (376 MHz, DMSO-$d_6$) δ ppm −74.66 (br. s., 3F) TFA present.

Example 285

6-(5-(5-(isopropylamino)-1,3,4-oxadiazol-2-yl)-1H-indol-3-yl)-N-methylpicolinamide

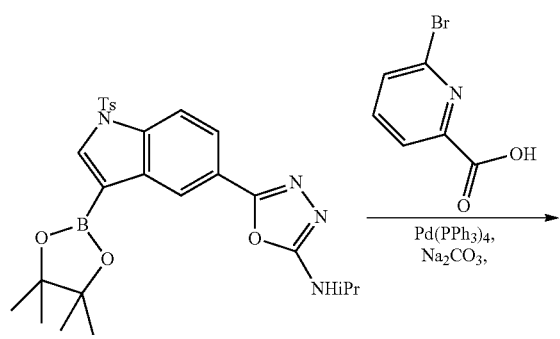

46b

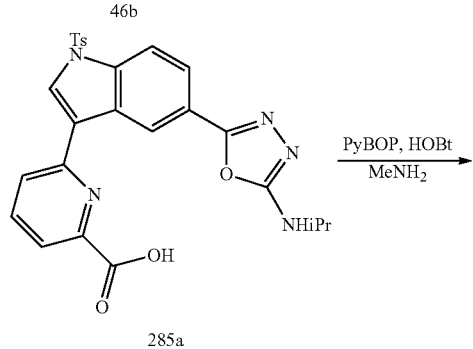

285a

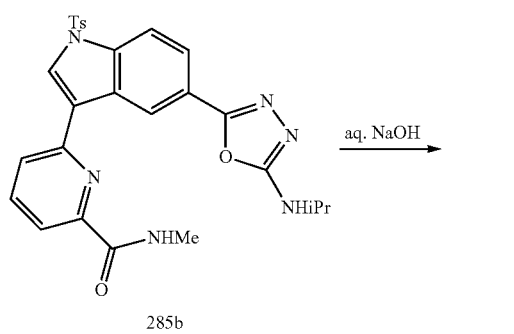

285b

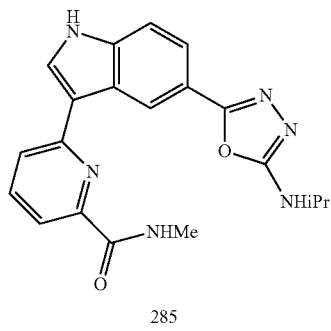

285

Preparation of compound 285a: 6-(5-(5-(isopropylamino)-1,3,4-oxadiazol-2-yl)-1-tosyl-1H-indol-3-yl)picolinic acid To a solution of N-isopropyl-5-(3-(4,4,5,5-tetramethyl-1,3,2-dioxaborolan-2-yl)-1-tosyl-1H-indol-5-yl)-1,3,4-oxadiazol-2-amine (500 mg, 0.957 mmol) and 6-bromopicolinic acid (280 mg, 1.436 mmol, Sigma-Aldrich) in DME (10 mL)/water (2.5 mL) was added Na$_2$CO$_3$ (304 mg, 2.871 mmol) and Pd(PPh$_3$)$_4$ (111 mg, 0.096 mmol) and Ar gas was bubbled for 5 min. The reaction mixture was heated at 90° C. for 4 h. The reaction was quenched with water (200 mL) to get a brown precipitate. The precipitate was filtered, washed with water (2×100 mL) and dried to give crude product, which was used in the next step without further purification. MS (ESI, pos. ion) m/z: 518.2 (M+1).

Preparation of compound 285b: 6-(5-(5-(isopropylamino)-1,3,4-oxadiazol-2-yl)-1-tosyl-1H-indol-3-yl)-N-methylpicolinamide To a solution of 6-(5-(5-(isopropylamino)-1,3,4-oxadiazol-2-yl)-1-tosyl-1H-indol-3-yl)picolinic acid (150 mg, 0.29 mmol) in DMF (3 mL) was added PyBOP (226 mg, 0.439 mmol), HOBt (59 mg, 0.435 mmol) and DIPEA (0.15 mL, 0.87 mmol). Methylamine hydrochloride (23 mg, 0.348 mmol) was added and the reaction was stirred for 2 h under Ar at RT. The reaction was quenched with water (200 mL) to get a brown precipitate. The precipitate was filtered, washed with water (2×100 mL) and dried. The crude product was purified with basic alumina chromatography (eluting with EtOAc) to give 6-(5-(5-(isopropylamino)-1,3,4-oxadiazol-2-yl)-1-tosyl-1H-indol-3-yl)-N-methylpicolinamide (150 mg, 98%). MS (ESI, pos. ion) m/z: 531.2 (M+1).

Preparation of compound 285: 6-(5-(5-(isopropylamino)-1,3,4-oxadiazol-2-yl)-1H-indol-3-yl)-N-methylpicolinamide To a solution of 6-(5-(5-(isopropylamino)-1,3,4-oxadiazol-2-yl)-1-tosyl-1H-indol-3-yl)-N-methylpicolinamide (100 mg, 0.189 mmol) in 1,4-dioxane (2 mL) was added aq.NaOH (7 M, 2 mL) and the reaction was heated at 90° C. for 1 h. The reaction was then quenched with water to get a precipitate. The precipitate was filtered and washed with water (2×100 mL) and dried. The crude product was crystallized from 20% EtOAc in petroleum ether (3×10 mL) to give 6-(5-(5-(isopropylamino)-1,3,4-oxadiazol-2-yl)-1H-indol-3-yl)-N-methylpicolinamide (16 mg, 23%). MS (ESI, pos. ion) m/z: 377.2 (M+1); $^1$H NMR (400 MHz, DMSO-d6) δ 12.21 (s, 1H), 8.67-8.69 (m, 2H), 8.48 (s, 1H), 8.00 (d, 2H, J=4.0 Hz), 7.80-7.82 (m, 1H), 7.69 (dd, 1H, J=8.4, 1.6 Hz), 7.63 (d, 1H, J=8.4 Hz), 7.59 (d, 1H, J=7.6 Hz), 3.71-3.78 (m, 1H), 2.93 (d, 3H, J=4.8 Hz), 1.23 (d, 6H, J=6.4 Hz).

Example 286

5-(5-(5-(isopropylamino)-1,3,4-oxadiazol-2-yl)-1H-indol-3-yl)-N-methylnicotinamide

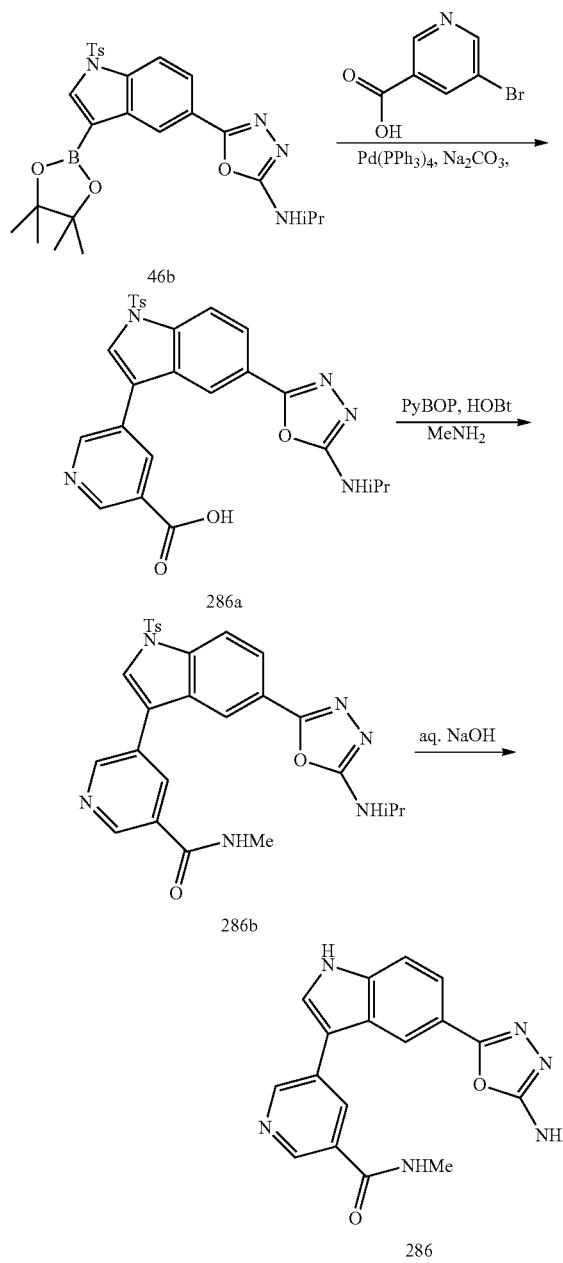

Preparation of compound 286a: 5-(5-(5-(isopropylamino)-1,3,4-oxadiazol-2-yl)-1-tosyl-1H-indol-3-yl)nicotinic acid To a solution of N-isopropyl-5-(3-(4,4,5,5-tetramethyl-1,3,2-dioxaborolan-2-yl)-1-tosyl-1H-indol-5-yl)-1,3,4-oxadiazol-2-amine (4.0 g, 7.662 mmol) and 5-bromonicotinic acid (2.3 g, 11.49 mmol, Sigma-Aldrich) in DME (75 mL)/ water (18 mL) was added Na₂CO₃ (2.7 g, 22.98 mmol) and Pd(PPh₃)₄ (878 mg, 0.76 mmol) and Ar gas was bubbled for 5 min. The reaction mixture was heated at 90° C. for 4 h. The reaction was quenched with water (200 mL) to get a brown precipitate. The precipitate was filtered, washed with water (2×100 mL) and dried to give crude product (3.0 g), which was used in the next step without further purification. MS (ESI, pos. ion) m/z: 518.2 (M+1).

Preparation of compound 286b: 5-(5-(5-(isopropylamino)-1,3,4-oxadiazol-2-yl)-1-tosyl-1H-indol-3-yl)-N-methylnicotinamide To a solution of 5-(5-(5-(isopropylamino)-1,3,4-oxadiazol-2-yl)-1-tosyl-1H-indol-3-yl)nicotinic acid (500 mg, 0.967 mmol) in DMF (10 mL) was added PyBOP (755 mg, 1.45 mmol), HOBt (196 mg, 1.45 mmol) and DIPEA (0.50 mL, 2.9 mmol). Methylamine hydrochloride (77.7 mg, 1.160 mmol) was added and the reaction was stirred for 2 h under Ar at RT. The reaction was quenched with water (200 mL) to get a brown precipitate. The precipitate was filtered, washed with water (2×100 mL) and dried. The crude product was purified with basic alumina chromatography (eluting with EtOAc) to give 5-(5-(5-(isopropylamino)-1,3,4-oxadiazol-2-yl)-1-tosyl-1H-indol-3-yl)-N-methylnicotinamide (150 mg, 29%). MS (ESI, pos. ion) m/z: 531.2 (M+1).

Preparation of compound 286: 5-(5-(5-(isopropylamino)-1,3,4-oxadiazol-2-yl)-1H-indol-3-yl)-N-methylnicotinamide To a solution of 5-(5-(5-(isopropylamino)-1,3,4-oxadiazol-2-yl)-1-tosyl-1H-indol-3-yl)-N-methylnicotinamide (150 mg, 0.283 mmol) in 1,4-dioxane (3 mL) was added aq.NaOH (7 M, 3 mL) and the reaction was heated at 90° C. for 1 h. The reaction was then quenched with water to get a precipitate. The precipitate was filtered and washed with water (2×100 mL) and dried. The crude product was purified with preparative HPLC (eluting with 30-70% MeCN in water with 0.1% TFA in each solvent) to give 5-(5-(5-(isopropylamino)-1,3,4-oxadiazol-2-yl)-1H-indol-3-yl)-N-methylnicotinamide (30 mg, 28%). MS (ESI, pos. ion) m/z: 377.1 (M+1); ¹H NMR (400 MHz, DMSO-d6) δ 11.95 (s, 1H), 9.04 (d, 1H, J=2.0 Hz), 8.89 (d, 1H, J=2.0 Hz), 8.74-8.76 (m, 1H), 8.44-8.45 (m, 1H), 8.24 (s, 1H), 8.02 (d, 1H, J=2.0 Hz), 7.73 (dd, 1H, J=8.8, 2.0 Hz), 7.62-7.66 (m, 2H), 3.71-3.76 (m, 1H), 2.85 (d, 3H, J=4.4 Hz), 1.22 (d, 6H, J=6.4 Hz).

Example 287

N-isopropyl-5-(3-(2-(isopropylamino)pyrimidin-4-yl)-1H-indol-5-yl)-1,3,4-oxadiazol-2-amine

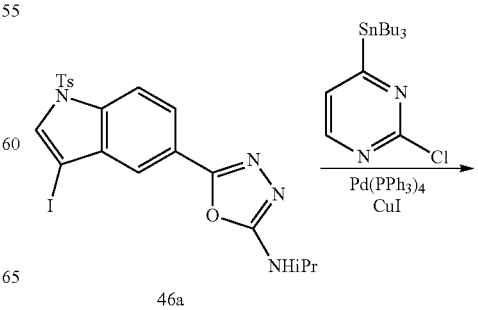

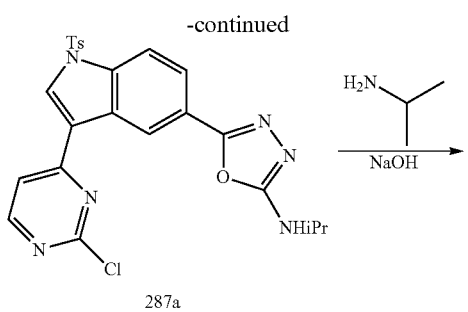

pyl-5-(3-(2-(isopropylamino)pyrimidin-4-yl)-1H-indol-5-yl)-1,3,4-oxadiazol-2-amine (29 mg, 0.077 mmol, 39.1% yield) as a yellow solid. MS (ESI, pos. ion) m/z: 378.0 (M+1); $^1$H NMR (400 MHz, DMSO-$d_6$) δ ppm 11.95 (1H, s), 8.99 (1H, br. s.), 8.30 (1H, s), 8.17 (1H, d, J=5.1 Hz), 7.64 (1H, dd, J=8.5, 1.5 Hz), 7.57 (1H, d, J=8.6 Hz), 7.45 (1H, d, J=7.2 Hz), 7.00 (1H, d, J=5.3 Hz), 6.70 (1H, br. s.), 4.17-4.29 (1H, m), 3.71-3.83 (1H, m), 1.20-1.30 (12H, m).

Example 288

2-(isopropylamino)-6-(5-(5-(isopropylamino)-1,3,4-oxadiazol-2-yl)-1H-indol-3-yl)pyrimidin-4(3H)-one

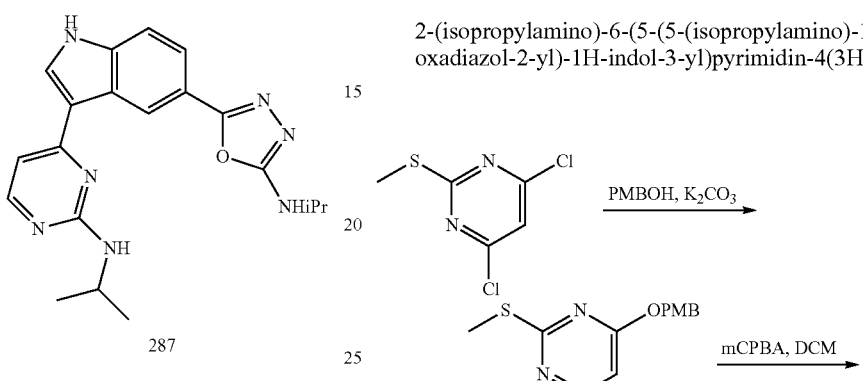

Preparation of compound 287a: 5-(3-(2-chloropyrimidin-4-yl)-1-tosyl-1H-indol-5-yl)-N-isopropyl-1,3,4-oxadiazol-2-amine A glass microwave reaction vessel was charged with 5-(3-iodo-1-tosyl-1H-indol-5-yl)-N-isopropyl-1,3,4-oxadiazol-2-amine (1.00 g, 1.914 mmol) and 2-chloro-4-(tributylstannyl)pyrimidine (0.966 g, 2.393 mmol) in DMF (5 mL) followed by tetrakis(triphenylphosphine)palladium (0.111 g, 0.096 mmol) and CuI (0.016 mL, 0.479 mmol). The reaction mixture was stirred and heated in an Initiator microwave reactor (Personal Chemistry, Biotage AB, Inc., Upssala, Sweden) at 100° C. for 1 h. The mixture was diluted with DCM and washed with water (3×50 mL) and brine. The organic layer was dried, filtered and concentrated. The residue was purified with silica gel chromatography (eluting with 5-40% EtOAc in Hexanes) to give 5-(3-(2-chloropyrimidin-4-yl)-1-tosyl-1H-indol-5-yl)-N-isopropyl-1,3,4-oxadiazol-2-amine (672 mg, 1.320 mmol, 69.0% yield) as a brown solid. MS (ESI, pos. ion) m/z: 509.0 (M+1).

Preparation of compound 287: N-isopropyl-5-(3-(2-(isopropylamino)pyrimidin-4-yl)-1H-indol-5-yl)-1,3,4-oxadiazol-2-amine A glass microwave reaction vessel was charged with 5-(3-(2-chloropyrimidin-4-yl)-1-tosyl-1H-indol-5-yl)-N-isopropyl-1,3,4-oxadiazol-2-amine (100 mg, 0.196 mmol) and isopropylamine (16.88 μl, 0.196 mmol) in NMP (2.0 mL). The reaction mixture was stirred and heated in an Initiator microwave reactor (Personal Chemistry, Biotage AB, Inc., Upssala, Sweden) at 135° C. for 1 h. aq. NaOH (0.5 mL, 5 M) was added to the mixture and the reaction was heated in the microwave at 100° C. for 20 min. The mixture was purified with preparative HPLC (eluting with 10-50% MeCN in water with 0.1% TFA in each solvent) and the fractions containing the product were combined and concentrated in vacuo to remove MeCN. The resulting mixture was extracted with $CHCl_3$/iPrOH (4:1) and the combined organic layers were dried (MgSO$_4$), filtered and concentrated to give N-isopro-

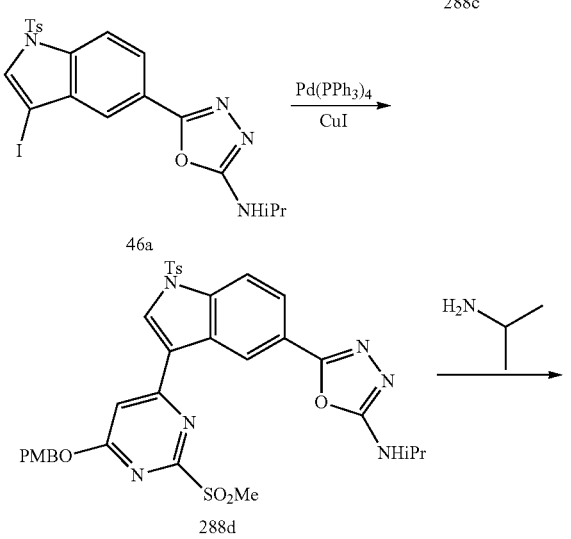

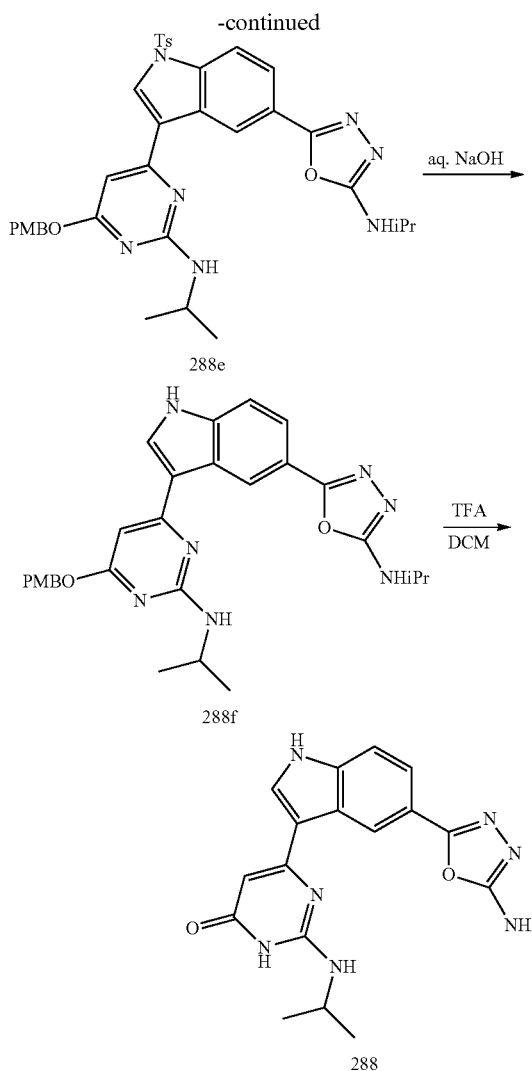

Preparation of compound 288a: 4-chloro-6-((4-methoxybenzyl)oxy)-2-(methylthio)pyrimidine To a solution of 4,6-dichloro-2-(methyl thio)pyrimidine (75 g, 38.4 mmol, Sigma-Aldrich) in DMF (750 mL) was added p-methoxybenzyl alcohol (58.38 g, 42.1 mmol) and $K_2CO_3$ (212.3 g, 1538 mmol). The reaction was stirred at 60° C. for 12 h, then cooled to RT. Water (500 mL) was added to get a white solid and the mixture was filtered. The resulting solid was triturated with hexanes to give 4-chloro-6-((4-methoxybenzyl)oxy)-2-(methylthio)pyrimidine (75 g, 66.4%) as white solid. MS (ESI, pos. ion) m/z: 297 (M+1).

Preparation of compound 288b: 4-chloro-6-((4-methoxybenzyl)oxy)-2-(methylsulfonyl)pyrimidine To a solution of 4-chloro-6-(4-methoxy-benzyloxy)-2-methylsulfanyl-pyrimidine (75 g, 253 mmol) in DCM (750 mL) was added 3-chloro peroxybenzoic acid (130 g, 760 mmol) and the mixture was stirred at RT for 2 h. The reaction was quenched with sat $NaHCO_3$ and extracted with DCM. The combined organic layers were dried over $Na_2SO_4$, filtered and concentrated in vacuo. The residue was purified with silica gel chromatography (eluting with 12% EtOAc in petroleum ether) to give 4-chloro-6-((4-methoxybenzyl)oxy)-2-(methylsulfonyl)pyrimidine (75 g, 90.3%) as a white solid. $^1$H NMR (400 MHz, DMSO-$d_6$): δ 7.54 (s, 1H), 7.45 (d, J=8.4 Hz, 2H), 6.96 (d, J=8.4 Hz, 2H), 5.44 (s, 2H), 3.75 (s, 3H), 3.43 (s, 3H).

Preparation of compound 288c: 4-((4-methoxybenzyl)oxy)-2-(methylsulfonyl)-6-(trimethylstannyl)pyrimidine A glass microwave reaction vessel was charged with 4-chloro-6-(4-methoxybenzyloxy)-2-(methylsulfonyl)pyrimidine (500 mg, 1.521 mmol) and hexamethylditin (473 μL, 2.281 mmol, Sigma-Aldrich) in p-dioxane (3 mL). The reaction mixture was stirred and heated in a Initiator microwave reactor (Personal Chemistry, Biotage AB, Inc., Upssala, Sweden) at 100° C. for 1 h, then the solvent was removed in vacuo. The residue was purified through a plug of neutral alumina and eluted with Hex:EtOAc (4:1) to give 4-(4-methoxybenzyloxy)-2-(methylsulfonyl)-6-(trimethylstannyl)pyrimidine (388 mg, 0.849 mmol, 55.8% yield) as a colorless oil. $^1$H NMR (400 MHz, CDCl$_3$): δ 7.42 (dd, J=6.8, 2.0 Hz, 2H), 7.08 (s, 1H), 6.91 (dd, J=6.8, 2.0 Hz, 2H), 5.43 (s, 2H), 3.82 (s, 3H), 3.37 (s, 3H), 0.38 (s, 9H)

Preparation of compound 288d: N-isopropyl-5-(3-(6-((4-methoxybenzyl)oxy)-2-(methylsulfonyl)pyrimidin-4-yl)-1-tosyl-1H-indol-5-yl)-1,3,4-oxadiazol-2-amine A glass microwave reaction vessel was charged with 5-(3-iodo-1-tosyl-1H-indol-5-yl)-N-isopropyl-1,3,4-oxadiazol-2-amine (800 mg, 1.532 mmol) and 4-((4-methoxybenzyl)oxy)-2-(methylsulfonyl)-6-(trimethylstannyl)pyrimidine (875 mg, 1.914 mmol) in DMF (5 mL) followed by Pd(PPh$_3$)$_4$ (88 mg, 0.077 mmol) and CuI (72.9 mg, 0.383 mmol). The reaction mixture was stirred and heated in an Initiator microwave reactor (Personal Chemistry, Biotage AB, Inc., Upssala, Sweden) at 100° C. for 1 h. The mixture was filtered through a plug of celite and washed with DCM. The filtrate was washed with water (25 mL×3) and the organic layer was dried, filtered and concentrated. The residue was purified with silica gel chromatography (eluting with 10-20% EtOAc in DCM with 1% MeOH) to give N-isopropyl-5-(3-(6-((4-methoxybenzyl)oxy)-2-(methylsulfonyl)pyrimidin-4-yl)-1-tosyl-1H-indol-5-yl)-1,3,4-oxadiazol-2-amine (660 mg, 0.958 mmol, 62.6% yield) as a brown solid. MS (ESI, pos. ion) m/z: 688.8 (M+1).

Preparation of compound 288e: N-isopropyl-5-(3-(2-(isopropylamino)-6-((4-methoxybenzyl)oxy)pyrimidin-4-yl)-1-tosyl-1H-indol-5-yl)-1,3,4-oxadiazol-2-amine A glass microwave reaction vessel was charged with N-isopropyl-5-(3-(6-((4-methoxybenzyl)oxy)-2-(methylsulfonyl)pyrimidin-4-yl)-1-tosyl-1H-indol-5-yl)-1,3,4-oxadiazol-2-amine (120 mg, 0.174 mmol) and isopropylamine (0.075 mL, 0.871 mmol) in NMP (1.0 mL). The reaction mixture was stirred and heated in an Initiator microwave reactor (Personal Chemistry, Biotage AB, Inc., Upssala, Sweden) at 120° C. for 1 h. The mixture was diluted with water and filtered. The remaining solid was dried to give the crude product (100 mg), which was used in the next step without further purification. MS (ESI, pos. ion) m/z: 668.0 (M+1).

Preparation of compound 288f: N-isopropyl-5-(3-(2-(isopropylamino)-6-((4-methoxybenzyl)oxy)pyrimidin-4-yl)-1H-indol-5-yl)-1,3,4-oxadiazol-2-amine A glass microwave reaction vessel was charged with N-isopropyl-5-(3-(2-(isopropylamino)-6-((4-methoxybenzyl)oxy)pyrimidin-4-yl)-1-tosyl-1H-indol-5-yl)-1,3,4-oxadiazol-2-amine (100 mg, 0.150 mmol) and NaOH (0.3 mL, 3.00 mmol) in p-dioxane (1.0 mL). The reaction mixture was stirred and heated in a Initiator microwave reactor (Personal Chemistry, Biotage AB, Inc., Upssala, Sweden) at 100° C. for 1 h. The mixture was diluted with $CHCl_3$/iPrOH (4:1) and washed with water. The organic layer was dried, filtered and concentrated to give the crude N-isopropyl-5-(3-(2-(isopropylamino)-6-((4-methoxybenzyl)oxy)pyrimidin-4-yl)-1H-indol-5-yl)-1,3,4-oxadiazol-2-amine (70 mg, 0.136 mmol, 91% yield), which was used in the next step without further purification. MS (ESI, pos. ion) m/z: 514.1 (M+1).

Preparation of compound 288: 2-(isopropylamino)-6-(5-(5-(isopropylamino)-1,3,4-oxadiazol-2-yl)-1H-indol-3-yl)pyrimidin-4(3H)-one To a 15-mL round-bottomed flask was added N-isopropyl-5-(3-(2-(isopropylamino)-6-((4-methoxybenzyl)oxy)pyrimidin-4-yl)-1H-indol-5-yl)-1,3,4-oxadiazol-2-amine (77 mg, 0.150 mmol) and TFA (0.3 mL, 4.04 mmol) in DCM (1 mL). The reaction was stirred at RT for 15 min and then the solvent was removed. The residue was purified with preparative HPLC (10-50% MeCN in water with 0.1% TFA in each solvent) and the fractions containing the product were combined and concentrated in vacuo to remove MeCN. The resulting mixture was extracted with $CHCl_3$/iPrOH (4:1) and the combined organic layers were dried ($MgSO_4$), filtered and concentrated to give 2-(isopropylamino)-6-(5-(5-(isopropylamino)-1,3,4-oxadiazol-2-yl)-1H-indol-3-yl)pyrimidin-4(3H)-one (20.0 mg, 0.051 mmol, 33.9% yield) as a light yellow solid. MS (ESI, pos. ion) m/z: 394.1 (M+1); $^1$H NMR (400 MHz, DMSO-$d_6$) δ ppm 11.90 (1H, br. s.), 10.14-10.38 (1H, m), 8.75 (1H, s), 8.15 (1H, s), 7.63-7.70 (1H, m), 7.48-7.62 (2H, m), 6.23-6.40 (1H, m), 6.03 (1H, s), 4.24 (1H, dq, J=13.3, 6.5 Hz), 3.75 (1H, dq, J=13.6, 6.6 Hz), 1.29 (6H, d, J=6.5 Hz), 1.24 (6H, d, J=6.7 Hz).

Example 289

4-fluoro-3-(5-(5-(isopropylamino)-1,3,4-oxadiazol-2-yl)-1H-indol-3-yl)-N-methylbenzamide

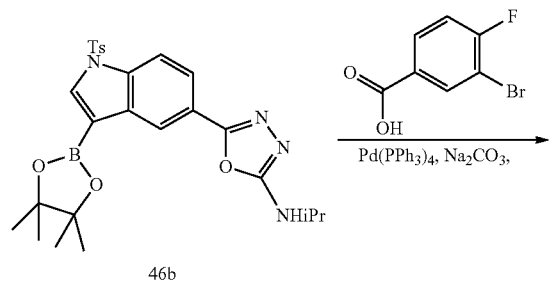

46b

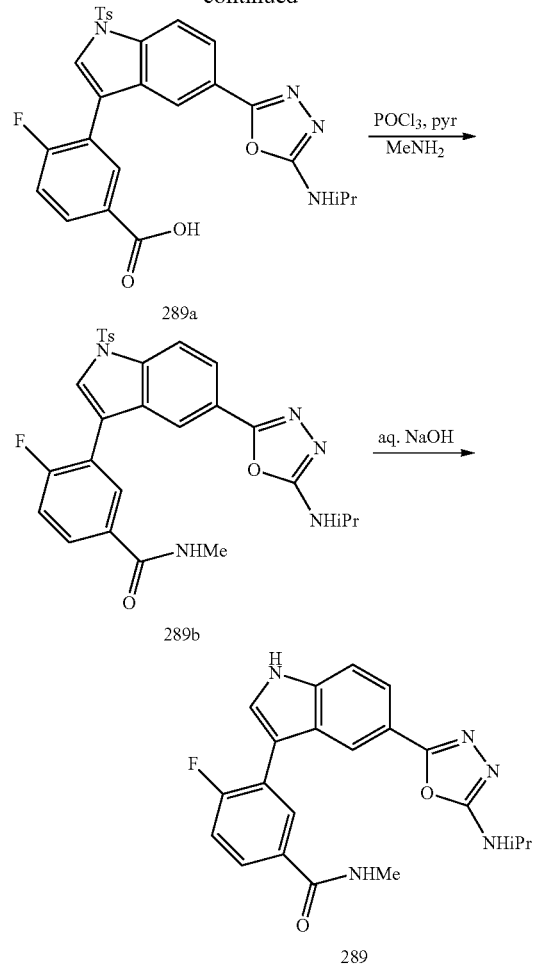

Preparation of compound 289a: 4-fluoro-3-(5-(5-(isopropylamino)-1,3,4-oxadiazol-2-yl)-1-tosyl-1H-indol-3-yl)benzoic acid To a solution of N-isopropyl-5-(3-(4,4,5,5-tetramethyl-1,3,2-dioxaborolan-2-yl)-1-tosyl-1H-indol-5-yl)-1,3,4-oxadiazol-2-amine (2.0 g, 3.831 mmol) and 5-bromonicotinic acid (1.2 g, 5.74 mmol, Sigma-Aldrich) in DME (38 mL)/water (9 mL) was added $Na_2CO_3$ (1.35 g, 11.5 mmol) and $Pd(PPh_3)_4$ (439 mg, 0.38 mmol) and Ar gas was bubbled for 5 min. The reaction mixture was heated at 90° C. for 4 h. The reaction was quenched with water (200 mL) to get a brown precipitate. The precipitate was filtered, washed with water (2×100 mL) and dried to give crude product (2.0 g), which was used in the next step without further purification. MS (ESI, pos. ion) m/z: 534.2 (M+1).

Preparation of compound 289b: 4-fluoro-3-(5-(5-(isopropylamino)-1,3,4-oxadiazol-2-yl)-1-tosyl-1H-indol-3-yl)-N-methylbenzamide To a solution of 4-fluoro-3-(5-(5-(isopropylamino)-1,3,4-oxadiazol-2-yl)-1-tosyl-1H-indol-3-yl)benzoic acid (500 mg, 0.936 mmol) and methylamine hydrochloride (97 mg, 1.40 mmol) in pyridine (10 mL) was added $POCl_3$ (0.13 mL, 1.40 mmol). The reaction was stirred at RT for 1 h, then quenched with ice cold water (20 mL) to get a precipitate. The precipitate was filtered, washed with water (2×100 mL) and dried. The crude product was purified with basic alumina chromatography (eluting with EtOAc) to give 4-fluoro-3-(5-(5-(isopropylamino)-1,3,4-oxadiazol-2-yl)-1-tosyl-1H-indol-3-yl)-N-methylbenzamide (250 mg, 48%). MS (ESI, pos. ion) m/z: 548.2 (M+1).

Preparation of compound 289: 4-fluoro-3-(5-(5-(isopropylamino)-1,3,4-oxadiazol-2-yl)-1H-indol-3-yl)-N-methylbenzamide To a solution of 4-fluoro-3-(5-(5-(isopropylamino)-1,3,4-oxadiazol-2-yl)-1-tosyl-1H-indol-3-yl)-N-methylbenzamide (250 mg, 0.457 mmol) in 1,4-dioxane (5 mL) was added aq. NaOH (7 M, 5 mL) and the reaction was heated at 90° C. for 1 h. The reaction was then quenched with water to get a precipitate. The precipitate was filtered and washed with water (2×100 mL) and dried. The crude product was purified with preparative HPLC (eluted with 20-80% MeCN in water with 0.1% TFA in each solvent) to give 4-fluoro-3-(5-(5-(isopropylamino)-1,3,4-oxadiazol-2-yl)-1H-indol-3-yl)-N-methylbenzamide (23 mg, 12%). MS (ESI, pos. ion) m/z: 394.1 (M+1); $^1$H NMR (400 MHz, DMSO-d6) δ 11.90 (s, 1H), 8.56 (d, 1H, J=4.8 Hz), 8.16 (dd, 1H, J=7.2, 2.4 Hz), 8.01 (s, 1H), 7.81-7.84 (m, 2H), 7.70 (dd, 1H, J=8.8, 1.2 Hz), 7.60-7.63 (m, 2H), 7.46 (dd, 1H, J=10.4, 8.8 Hz), 3.68-3.76 (m, 1H), 2.81 (d, 3H, J=4.4 Hz), 1.20 (d, 6H, J=6.8 Hz).

Example 290

3-fluoro-4-(5-(5-(isopropylamino)-1,3,4-oxadiazol-2-yl)-1H-indol-3-yl)benzamide

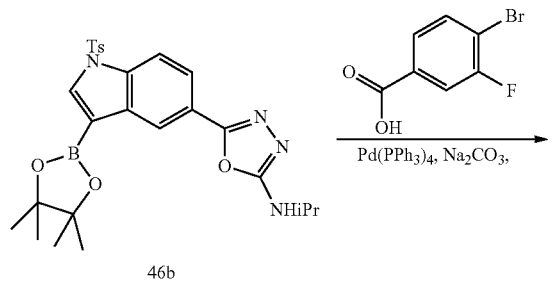

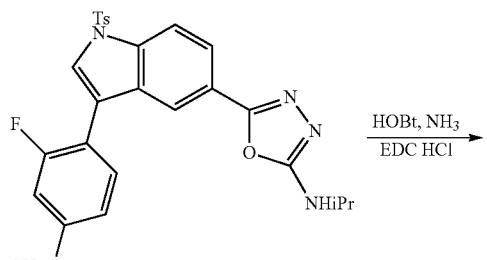

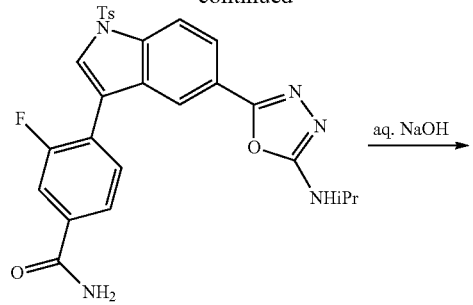

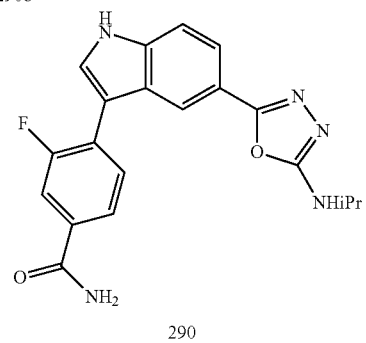

Preparation of compound 290a: 3-fluoro-4-(5-(5-(isopropylamino)-1,3,4-oxadiazol-2-yl)-1-tosyl-1H-indol-3-yl)benzoic acid To a solution of N-isopropyl-5-(3-(4,4,5,5-tetramethyl-1,3,2-dioxaborolan-2-yl)-1-tosyl-1H-indol-5-yl)-1,3,4-oxadiazol-2-amine (2.0 g, 3.831 mmol) and 4-bromo-3-fluorobenzoic acid (1.2 g, 5.74 mmol, Sigma-Aldrich) in DME (38 mL)/water (9 mL) was added Na$_2$CO$_3$ (1.35 g, 11.5 mmol) and Pd(PPh$_3$)$_4$ (439 mg, 0.38 mmol) and Ar gas was bubbled for 5 min. The reaction mixture was heated at 90° C. for 4 h. The reaction was quenched with water (200 mL) to get a brown precipitate. The precipitate was filtered, washed with water (2×100 mL) and dried to give crude product (1.0 g), which was used in the next step without further purification. MS (ESI, pos. ion) m/z: 535.1 (M+1).

Preparation of compound 290b: 3-fluoro-4-(5-(5-(isopropylamino)-1,3,4-oxadiazol-2-yl)-1-tosyl-1H-indol-3-yl)benzamide To a solution of 3-fluoro-4-(5-(5-(isopropylamino)-1,3,4-oxadiazol-2-yl)-1-tosyl-1H-indol-3-yl)benzoic acid (500 mg, 0.936 mmol) in DMF (10 mL) was added EDC HCl (269 mg, 1.40 mmol) followed by HOBt and NH$_3$ (284 mg, 1.87 mmol). The reaction was stirred at RT for 1 h, then quenched with ice cold water (20 mL) to get a precipitate. The precipitate was filtered, washed with water (2×100 mL) and dried to give the crude product (250 mg). MS (ESI, pos. ion) m/z: 534.1 (M+1).

Preparation of compound 290: 3-fluoro-4-(5-(5-(isopropylamino)-1,3,4-oxadiazol-2-yl)-1H-indol-3-yl)benzamide To a solution of 3-fluoro-4-(5-(5-(isopropylamino)-1,3,4-oxadiazol-2-yl)-1-tosyl-1H-indol-3-yl)benzamide (200 mg, 0.375 mmol) in 1,4-dioxane (3.75 mL) was added aq. NaOH (7 M, 3.75 mL) and the reaction was heated at 90° C. for 1 h. The reaction was then quenched with water to get a precipitate. The precipitate was filtered and washed with water (2×100 mL) and dried. The crude product was purified with preparative HPLC (eluting with 20-80% ACN in water with 0.1% TFA in each solvent) to give 3-fluoro-4-(5-(5-(isopropylamino)-1,3,4-oxadiazol-2-yl)-1H-indol-3-yl)benzamide (65 mg, 46%). MS (ESI, pos. ion) m/z: 380.1 (M+1); $^1$H NMR (300 MHz, DMSO-d6) δ 11.98 (s, 1H), 8.07 (brs, 2H), 7.74-7.83 (m, 4H), 7.51-7.69 (m, 4H), 3.65-3.75 (m, 1H), 1.19 (d, 6H, J=6.6 Hz).

Example 291

N-(5-(5-(isopropylamino)-1,3,4-oxadiazol-2-yl)-1H-indol-3-yl)cyclopropanecarboxamide

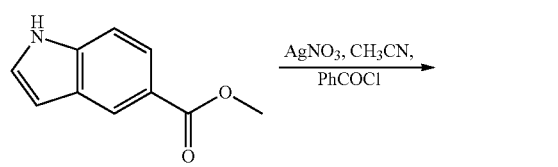

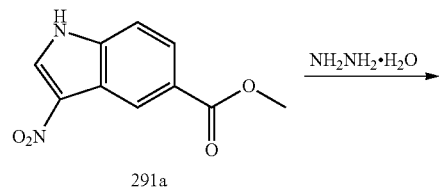

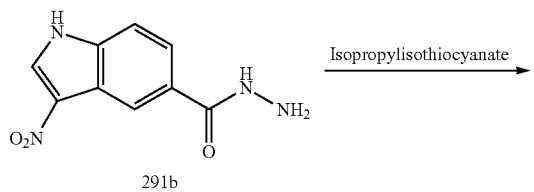

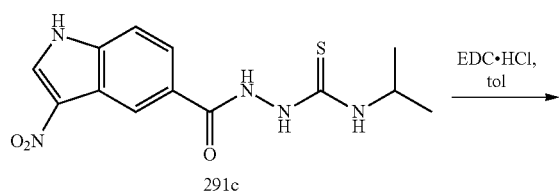

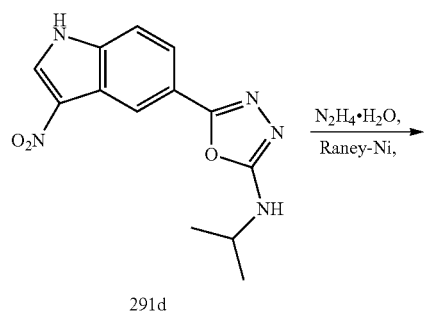

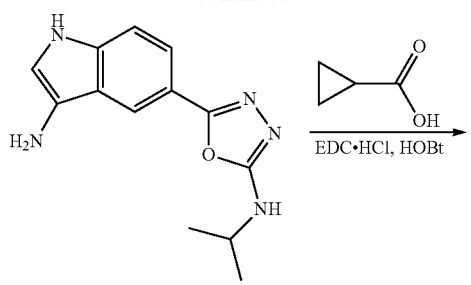

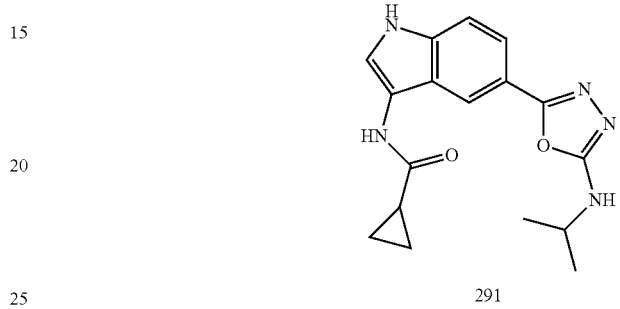

Preparation of compound 291a: methyl 3-nitro-1H-indole-5-carboxylate

To a stirred solution of AgNO$_3$ (531.1 mg, 3.14 mmol, Sigma-Aldrich) in ACN (10 mL) was added benzoyl chloride (440 mg, 3.14 mmol, Sigma-Aldrich) dropwise at 0° C. The mixture was stirred for 10 min, then a solution of 1H-indole-5-carboxylic acid methyl ester (500 mg, 2.85 mmol) in ACN (5 mL) was added at 0° C. and stirred for 1 h at RT. The reaction mixture was then poured onto ice to get a dark brown precipitate. The precipitate was filtered, washed with water and dried. The crude intermediate was further purified by using 5% activated charcoal to afford methyl 3-nitro-1H-indole-5-carboxylate (350 mg, 56%) as dark brown solid. MS (ESI, Neg. ion) m/z: 219.0 (M−1); $^1$H NMR (400 MHz, DMSO-d$_6$): δ 13.0 (brs, 1H) 8.80 (s, 1H), 8.73 (d, J=1.6 Hz, 1H), 7.94 (dd, 1H, J=8.4, 1.6 Hz), 7.67 (d, 1H, J=8.4 Hz), 3.90 (s, 3H).

Preparation of compound 291b: 3-nitro-1H-indole-5-carbohydrazide

To a suspension of methyl 3-nitro-1H-indole-5-carboxylate (2.0 g, 9.09 mmol) in EtOH (40 mL) was added hydrazine hydrate (6 mL) and the reaction mixture was heated to reflux for 30 h. The mixture was cooled to RT and EtOH was removed in vacuo. Petroleum ether was added to the residue to get a yellow precipitate. The precipitate was filtered, washed with petroleum ether (3×40 mL) and dried to afford 3-nitro-1H-indole-5-carbohydrazide (1.0 g, 50%) as a yellow solid. MS (ESI, pos. ion) m/z: 221.0 (M+1); $^1$H NMR (300 MHz, DMSO-d$_6$): δ 9.83 (s, 1H), 8.71 (s, 1H), 8.57 (s, 1H), 7.77 (dd, 1H, J=8.7, 1.2 Hz), 7.58 (d, 1H, J=8.7 Hz), 4.49 (brs, 2H).

Preparation of compound 291c: N-isopropyl-2-(3-nitro-1H-indole-5-carbonyl)hydrazinecarbothioamide To a suspension of 3-nitro-1H-indole-5-carbohydrazide (1.2 g, 5.454 mmol) in DMF (5 mL) was added isopropyl isothiocyanate (661 mg, 6.545 mmol) in one lot and the reaction was heated to reflux for 4 h. The mixture was quenched with water (20 mL) to get a pale yellow precipitate. The precipitate was filtered, washed with water (2×10 mL) and dried. The crude product was treated with 20% EtOAc in petroleum ether (2×20 mL) to afford N-isopropyl-2-(3-nitro-1H-indole-5-carbonyl)hydrazinecarbothioamide (1.5 g, 88%) as pale yellow solid. MS (ESI, pos. ion) m/z: 322.1 (M+1); $^1$H-NMR (300 MHz, DMSO-$d_6$): δ 12.90 (brs, 1H), 10.43 (brs, 1H), 9.19 (s, 1H), 8.75 (s, 1H), 8.71 (s, 1H), 7.87-7.93 (m, 1H), 7.76 (d, 1H, J=8.4 Hz), 7.62 (d, 1H, J=8.4 Hz), 4.40-4.53 (m, 1H), 1.11 (d, 6H, J=6.6 Hz).

Preparation of compound 291d: N-isopropyl-5-(3-nitro-1H-indol-5-yl)-1,3,4-oxadiazol-2-amine To a suspension of N-isopropyl-2-(3-nitro-1H-indole-5-carbonyl)hydrazinecarbothioamide (1.5 g, 4.672 mmol) in toluene (15 mL) was added EDC HCl (1.3 g, 7.009 mmol) in one lot and the reaction was heated to reflux for 16 h. After completion, toluene was removed in vacuo and the residue was treated with water (25 mL) to get a precipitate. The precipitate was filtered washed and dried. The crude product was washed with 10% EtOAc in petroleum ether to afford N-isopropyl-5-(3-nitro-1H-indol-5-yl)-1,3,4-oxadiazol-2-amine (1.2 g, 92%) as pale yellow colored solid. MS (ESI, pos. ion) m/z: 288.1 (M+1); $^1$H-NMR (300 MHz, DMSO-$d_6$): δ 12.88 (brs, 1H), 8.75 (s, 1H), 8.47 (s, 1H), 7.67-7.84 (m, 3H), 3.69-3.76 (m, 1H), 1.21 (d, 6H, J=6.6 Hz).

Preparation of compound 291e: 5-(3-amino-1H-indol-5-yl)-N-isopropyl-1,3,4-oxadiazol-2-amine To a suspension of Raney-Ni (100 mg) in MeOH (2 mL) was added N-isopropyl-5-(3-nitro-1H-indol-5-yl)-1,3,4-oxadiazol-2-amine (200 mg, 0.698 mmol) followed by addition of $NH_2NH_2$ (0.2 mL). The reaction mixture was stirred at RT for 1 h. The mixture was then filtered through a plug of Celite and the filtrate was concentrated. The residue was treated with water and the resulting suspension was filtered, washed with water and dried. The crude product was purified by washing with petroleum ether (2×5 mL) to afford 5-(3-amino-1H-indol-5-yl)-N-isopropyl-1,3,4-oxadiazol-2-amine (50 mg, 27%) as a brown solid. MS (ESI, pos. ion) m/z: 258.2 (M+1); $^1$H-NMR (400 MHz, DMSO-$d_6$): δ 10.43 (s, 1H), 8.02 (s, 1H), 7.46-7.49 (m, 2H), 7.30 (d, 1H, J=8.4 Hz), 6.67 (brs, 1H), 4.27 (s, 2H), 3.70-3.76 (m, 1H), 1.23 (d, 6H, J=6.4 Hz).

Preparation of compound 291: N-(5-(5-(isopropylamino)-1,3,4-oxadiazol-2-yl)-1H-indol-3-yl)cyclopropanecarboxamide To a solution of cyclopropanecarboxylic acid (55 mg, 0.642 mmol) in DMF (6 mL) was added EDC.HCl (167 mg, 0.875 mmol), HOBt (118 mg, 0.875 mmol) and triethylamine (0.244 mL, 1.75 mmol). The mixture was stirred for 15 min, then 5-(3-amino-1H-indol-5-yl)-N-isopropyl-1,3,4-oxadiazol-2-amine (150 mg, 0.583 mmol) was added and the mixture was stirred for 16 h at RT. The reaction was quenched with water and extracted with EtOAc. The organic layer was dried over anhydrous $Na_2SO_4$, filtered and concentrated. The residue was purified with basic alumina chromatography to give N-(5-(5-(isopropylamino)-1,3,4-oxadiazol-2-yl)-1H-indol-3-yl)cyclopropane carboxamide (21 mg, 11%). MS (ESI, pos. ion) m/z: 326.2 (M+1); $^1$H-NMR (300 MHz, DMSO-$d_6$): δ 11.13 (s, 1H), 10.43 (s, 1H), 8.37 (brs, 1H), 7.75 (d, 1H, J=2.1 Hz), 7.41-7.55 (m, 3H), 3.70-3.76 (m, 1H), 1.92-1.97 (m, 1H), 1.21 (d, 6H, J=6.6 Hz), 0.77-0.79 (m, 4H).

The compounds of examples 292-304 shown in Table 3 were made in accordance with exemplary methods above. The compound examples were named according to the ACD naming convention, as associated with ISIS software. The mass spectral data is recorded M+1, which is the positive ion as measured by an electrospray ionization method.

TABLE 3

| Ex# | Name | M + 1 | Method | NMR | Structure |
|---|---|---|---|---|---|
| 292 | N,N-dimethyl-6-(5-(5-((1-methylethyl)amino)-1,3,4-oxadiazol-2-yl)-1H-indol-3-yl)-2-pyridinecarboxamide | 391.4 | Ex 285 | 1H NMR (400 MHz, DMSO-d6) δ 11.90 (s, 1H), 8.96 (s, 1H), 8.29 (d, 1H, J = 2.0 Hz), 7.88-7.96 (m, 2H), 7.65 (dd, 1H, J = 8.4, 1.6 Hz), 7.54-7.59 (m, 2H), 7.35 (d, 1H, J = 6.8 Hz), 3.72-3.79 (m, 1H), 3.16 (s, 3H), 3.10 (s, 3H), 1.25 (d, 6H, J = 6.8 Hz). | 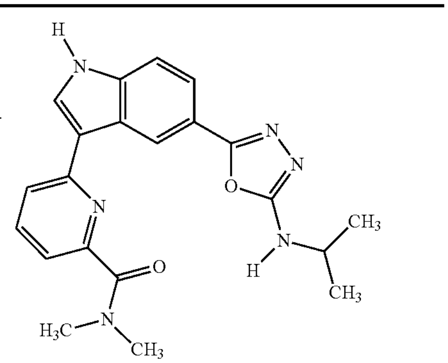 |

TABLE 3-continued

| Ex# | Name | M + 1 | Method | NMR | Structure |
|---|---|---|---|---|---|
| 293 | N-(1-methylethyl)-6-(5-(5-((1-methylethyl)amino)-1,3,4-oxadiazol-2-yl)-1H-indol-3-yl)-2-pyridinecarboxamide | 405.2 | Ex 285 | 1H NMR (400 MHz, DMSO-d6) δ 11.97 (brs, 1H), 8.86 (s, 1H), 8.41 (s, 1H), 8.19-8.22 (m, 1H), 7.97-8.06 (m, 2H), 7.83 (d, 1H, J = 6.8 Hz), 7.61-7.66 (m, 2H), 7.50-7.48 (d, 1H, J = 7.2 Hz), 4.14-4.18 (m, 1H), 3.73-3.78 (m, 1H), 1.29 (d, 6H, J = 6.4 Hz), 1.23 (d, 6H, J = 6.4 Hz). | 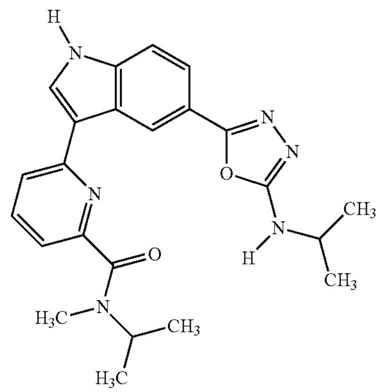 [SMILES: CC(C)Nc1nnc(-c2ccc3[nH]cc(-c4cccc(C(=O)N(C)C(C)C)n4)c3c2)o1] |
| 294 | N-cyclopropyl-6-(5-(5-((1-methylethyl)amino)-1,3,4-oxadiazol-2-yl)-1H-indol-3-yl)-2-pyridinecarboxamide | 403.3 | Ex 285 | 1H NMR (400 MHz, DMSO-d6) δ 11.99 (s, 1H), 8.78 (s, 1H), 8.42-8.46 (m, 2H), 7.97-8.05 (m, 2H), 7.81 (d, 1H, J = 7.2 Hz), 7.61-7.67 (m, 2H), 7.54 (d, 1H, J = 7.6 Hz), 3.75-3.80 (m, 1H), 2.95-3.01 (m, 1H), 1.24 (d, 6H, J = 6.4 Hz), 0.75-0.81 (m, 4H). | 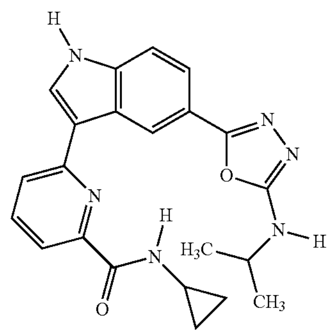 [SMILES: CC(C)Nc1nnc(-c2ccc3[nH]cc(-c4cccc(C(=O)NC5CC5)n4)c3c2)o1] |
| 295 | N-methyl-6-(5-(5-((1-methylethyl)amino)-1,3,4-oxadiazol-2-yl)-1H-indol-3-yl)-3-pyridinecarboxamide | 377.2 | Ex 285 | 1H NMR (400 MHz, DMSO-d6) δ 11.97 (s, 1H), 9.05 (d, 1H, J = 2.0 Hz), 9.01 (d, 1H, J = 1.2 Hz), 8.55-8.58 (m, 1H), 8.35 (s, 1H), 8.16 (dd, 1H, J = 8.4, 2.0 Hz), 7.97 (d, 1H, J = 8.4 Hz), 7.70 (dd, 1H, J = 8.4, 1.6 Hz), 7.57-7.63 (m, 2H), 3.72-3.77 (m, 1H), 2.83 (d, 3H, J = 4.4 Hz), 1.24 (d, 6H, J = 6.4 Hz). | 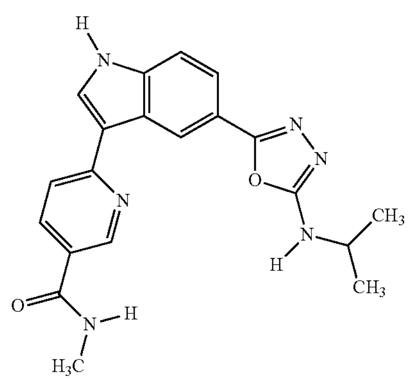 [SMILES: CNC(=O)c1ccc(-c2c[nH]c3ccc(-c4nnc(NC(C)C)o4)cc23)nc1] |
| 296 | N,N-dimethyl-5-(5-(5-((1-methylethyl)amino)-1,3,4-oxadiazol-2-yl)-1H-indol-3-yl)-3-pyridinecarboxamide | 391.2 | Ex 286 | 1H NMR (400 MHz, DMSO-d6) δ 11.94 (d, 1H, J = 1.6 Hz), 8.99 (d, 1H, J = 2.0 Hz), 8.51 (d, 1H, J = 2.0 Hz), 8.23 (s, 1H), 8.10 (t, 1H, J = 2.0 Hz), 8.03 (d, 1H, J = 2.4 Hz), 7.72 (dd, 1H, J = 8.8, 1.2 Hz), 7.61-7.63 (m, 2H), 3.70-3.78 (m, 1H), 3.05 (s, 3H), 3.01 (s, 3H), 1.22 (d, 6H, J = 6.4 Hz). | 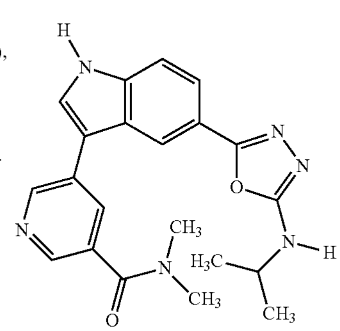 |

| Ex# | Name | M + 1 | Method | NMR | Structure |
|---|---|---|---|---|---|
| 297 | 5-(3-(2-methoxy-4-pyrimidinyl)-1H-indol-5-yl)-N-(1-methylethyl)-1,3,4-oxadiazol-2-amine | 351 | Ex 287 | 1H NMR (400 MHz, DMSO-d6) δ ppm 12.16 (1 H, br. s.), 9.04 (1 H, s), 8.51 (1 H, s), 8.45 (1 H, d, J = 5.3 Hz), 7.71 (1 H, dd, J = 8.6, 1.0 Hz), 7.52-7.65 (3 H, m), 4.05 (3 H, s), 3.74 (1 H, dq, J = 13.4, 6.6 Hz), 1.24 (6 H, d, J = 6.3 Hz). | 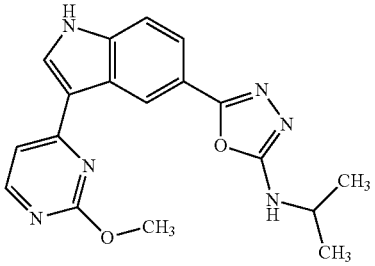 [SMILES: COc1nccc(-c2c[nH]c3ccc(-c4nnc(NC(C)C)o4)cc23)n1] |
| 298 | 2-methoxy-6-(5-(5-((1-methylethyl)amino)-1,3,4-oxadiazol-2-yl)-1H-indol-3-yl)-4(3H)-pyrimidinone | 367 | Ex 288 | 1H NMR (400 MHz, DMSO-d6) δ ppm 12.00 (1 H, br. s.), 8.77 (1 H, br. s.), 8.25 (1 H, br. s.), 7.69 (1 H, s), 7.59 (2 H, s), 6.36 (1 H, br. s.), 4.05 (3 H, s), 3.72 (1 H, dq, J = 13.6, 7.1 Hz), 1.22 (6 H, d, J = 6.5 Hz); | 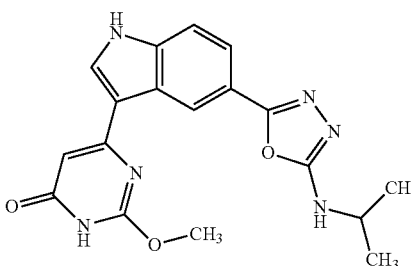 |
| 299 | N-cyclopropyl-5-(5-(5-((1-methylethyl)amino)-1,3,4-oxadiazol-2-yl)-1H-indol-3-yl)-3-pyridinecarboxamide | 403.2 | Ex 286 | 1H NMR (400 MHz, DMSO-d6) δ 11.95 (brs, 1H), 9.03 (d, 1H, J = 2.0 Hz), 8.86 (d, 1H, J = 2.0 Hz), 8.72 (d, 1H, J = 4.0 Hz), 8.41 (s, 1H), 8.21 (s, 1H), 8.01 (d, 1H, J = 2.4 Hz), 7.72 (d, 1H, J = 8.8 Hz), 7.60-7.65 (m, 2H), 3.70-3.76 (m, 1H), 2.88-2.91(m, 1H), 1.21 (d, 6H, J = 6.4 Hz), 0.71-0.75 (m, 2H), 0.60-0.63 (m, 2H). | 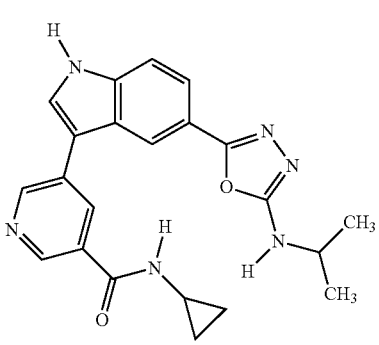 [SMILES: CC(C)Nc1nnc(-c2ccc3[nH]cc(-c4cncc(C(=O)NC5CC5)c4)c3c2)o1] |
| 300 | 2-cyclopropyl-6-(5-(5-((1-methylethyl)amino)-1,3,4-oxadiazol-2-yl)-1H-indol-3-yl)-4(3H)-pyrimidinone | 377 | Ex 288 | 1H NMR (400 MHz, DMSO-d6) δ ppm 12.41 (1 H, br. s.), 11.97 (1 H, br. s.), 8.66 (1 H, s), 8.20 (1 H, d, J = 2.7 Hz), 7.60-7.69 (2 H, m), 7.56 (1 H, d, J = 8.4 Hz), 6.47 (1 H, s), 3.74-3.85 (1 H, m), 1.92-2.03 (1 H, m), 1.20-1.27 (8 H, m), 1.07-1.16 (2 H, m). | 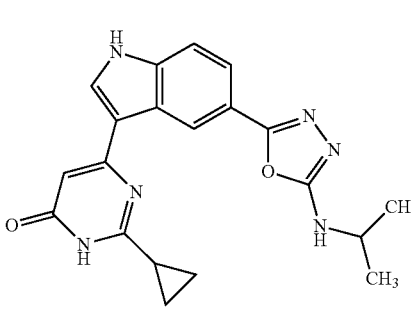 |
| 301 | 5-(3-(2-cyclopropyl-4-pyrimidinyl)-1H-indol-5-yl)-N-(1-methylethyl)-1,3,4-oxadiazol-2-amine | 361.1 | Ex 287 | 1H NMR (400 MHz, DMSO-d6) δ ppm 12.32 (1 H, br. s.), 9.00 (1 H, s), 8.57-8.64 (1 H, m), 8.54 (1 H, d, J = 5.9 Hz), 7.79 (1 H, d, J = 5.9 Hz), 7.70-7.74 (1 H, m), 7.60-7.67 (2 H, m), 2.25-2.32 (1 H, m), 1.18-1.32 (10 H, m). | 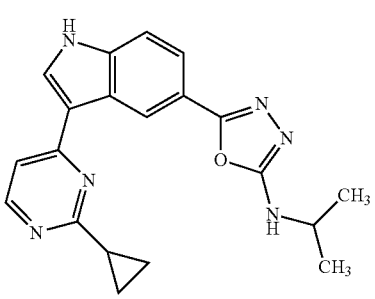 [SMILES: CC(C)Nc1nnc(-c2ccc3[nH]cc(-c4ccnc(C5CC5)n4)c3c2)o1] |

TABLE 3-continued

| Ex# | Name | M + 1 | Method | NMR |
|---|---|---|---|---|
| 302 | 4-fluoro-N,N-dimethyl-3-(5-(5-((1-methylethyl)amino)-1,3,4-oxadiazol-2-yl)-1H-indol-3-yl)benzamide | 408.2 | Ex 289 | 1H NMR (300 MHz, DMSO-d6) δ 11.87 (s, 1H), 8.00 (s, 1H), 7.79 (s, 1H), 7.66 (d, 2H, J = 8.1 Hz), 7.58 (d, 2H, J = 8.1 Hz), 7.40 (d, 2H, J = 8.1 Hz), 3.63-3.73 (m, 1H), 2.98 (s, 6H), 1.19 (d, 6H, J = 6.6 Hz). |
| 303 | 6-(5-(5-((1-methylethyl)amino)-1,3,4-oxadiazol-2-yl)-1H-indol-3-yl)-3-pyridinecarboxamide | 363.1 | Ex 285 | 1H NMR (400 MHz, DMSO-d6) δ 11.99 (s, 1H), 9.09 (d, 1H, J = 1.6 Hz), 9.01 (d, 1H, J = 1.6 Hz), 8.37 (d, 1H, J = 2.8 Hz), 8.18-8.22 (m, 1H), 8.14 (brs, 1H), 7.97 (d, 1H, J = 8.4 Hz), 7.62-7.74 (m, 7.52 (s, 1H), 3.71-3.81 (m, 1H), 1.24 (d, 6H, J = 6.4 Hz). |
| 304 | N-(5-(5-((1-methylethyl)amino)-1,3,4-oxadiazol-2-yl)-1H-indol-3-yl)-4-pyridinecarboxamide | 363.1 | Ex 291 | 1H-NMR (300 MHz, DMSO-d6): δ 11.28 (s, 1H), 10.69 (s, 1H), 8.77-8.79 (m, 2H), 8.42 (s, 1H), 7.91 (brs, 2H), 7.47-7.60 (m, 2H), 3.68-3.76 (m, 1H), 1.20 (d, 6H, J = 6.0 Hz). |

Biological Activity
Pim-1 and Pim-2
Cloning and Expression:

Full-length human cDNAs encoding Pim-1 (MGC ID 3913552) or Pim-2 (IMAGE ID 5092935) were purchased from Invitrogen, Carlsbad, Calif. These cDNAs were used as templates in PCR reactions to produce full-length DNA clones of the PIMs. Oligonucleotide PCR primers for Pim-1 were 5'-TGGCTGATCAATGCTCTTGTCCAAAATC-3' and 5'-ATTAGAATTCTATTTGCTGGGCCCCGGC-3'. Oligonucleotide PCR primers for Pim-2 were 5'-TGCAGGATC-CATGTTGACCAAGCCTCTAC-3' and 5'-ACGTGAATTC-TATCCCTGTGACATGGCC-3'. PCR products were digested with BclI and EcoRI for Pim-1 and BamHI and EcoRI for Pim-2 and ligated into a modified baculovirus transfer vector (pFastBac1) cleaved with BamHI and EcoRI. For bacterial expression, the same cleaved PCR products encoding Pim-1 or Pim-2 were ligated into a modified E. coli expression vector pET28(a) cleaved with BamHI and EcoRI Amino-terminal hexahistidine tags followed by a thrombin cleavage site were previously added to the vectors using standard methods of molecular biology. Recombinant baculoviruses expressing Pim-1 or Pim-2 were made using standard methods (Fastbac manual, Invitrogen, Carlsbad, Calif.). Infection of Sf9 cells was done at an m.o.i. of greater than 5 for 24-48 h. Cells were harvested by centrifugation and frozen at −80 C. For E. coli expression, cells carrying pET28-His6-Th-Pim-1 or pET28-His6-Th-Pim-2 were picked from a single colony and grown o/n in LB media. The o/n culture was used to inoculate a 2 liter flask with 500 mL media. This was grown o/n and used to inoculate 15-20 liters of Terrific Broth in a New Brunswick Scientific fermentor. The E. coli were grown at 37° C. to and OD600>1.6. The temperature was dropped to 18° C. and o/n expression was induced with 0.5 mM IPTG. Cells were harvested by centrifugation and frozen at −80° C.

Purification

The frozen cell pellets were thawed by stirring in chilled lysis buffer (0.05 M HEPES, pH 8.0, 0.25 M NaCl, 0.01 M 2-mercaptoethanol, 10% (w/v) glycerol, 0.5% (v/v) protease inhibitor cocktail (Sigma P-8340) at a ratio of 1 L/200 g cells until homogeneous. The thawed suspension was applied to a microfluidizer at 10,000 PSI to disrupt the cells and the whole lysates were clarified by centrifugation at 50,000×g for 90 min, 4° C. Imidazole was added to the clarified lysate to a final concentration of 2.5 mM and the lysate was mixed with 10 mL of Talon resin (Clontech) and the slurry rocked gently overnight at 4° C. The slurry was centrifuged at 1,000×g for 5 min, the supernatant decanted, and the resin suspended in 40 mL of lysis wash buffer (lysis buffer at 0.75 M NaCl). This step was repeated 3× and the resin was transferred to a 2.5 cm glass column. Ten column volumes of wash buffer (0.05 M HEPES, pH 8.0, 0.1 M NaCl, 0.01 M 2-mercaptoethanol, 10% (w/v) glycerol) were applied to the resin followed by 10 column volumes of elution buffer (0.05 M HEPES, pH 8.0, 0.25 M NaCl, 0.01 M 2-mercaptoethanol, 10% (w/v) glycerol, 0.1 M imidazole). Fractions were analyzed by SDS-PAGE and those containing the protein of interest were pooled and concentrated. The concentrated protein was applied to an Amersham Superdex 75 (XK 26/60) column equilibrated in 0.025 M Tris-HCl, pH 7.5, 0.1 M NaCl, 0.01 M 2-mercaptoethanol, 10% (w/v) glycerol. The protein eluted at a retention time indicative of it being monomeric and fractions were analyzed by SDS-PAGE. Fractions containing the monomeric protein of interest were pooled, concentrated to 2 mg/mL, and stored at −80° C.

Pim-3

Pim-3 was purchased from Millipore (UK).

Pim Enzyme Assays

The assay for the determination of Pim activity is based on the formation of phosphorylated biotinylated-BAD peptide at the Serine 112 residue (S112) and employs HTRF® (homogeneous time resolved fluorescence) technology to detect the product in a 96-well plate format. The phosphorylation of biotinylated-BAD (S112) peptide by full length recombinant Pim-1, Pim-2, or Pim-3 protein was detected with streptavidin:Allophycocyanin (APC) conjugate and a europium (Eu) labeled antibody directed against phosphorylated-BAD (S112). Excitation of Eu by a high energy laser light (337 nm) leads to a transfer of energy to the APC molecule, and results in an emission at 665 nm. The fluorescence is directly proportional to the amount of phosphorylated BAD peptide present in the reaction.

Compounds were prepared in DMSO by conducting 3-fold serial dilutions to give a 10-point dosing curve having a high dose of 1 uM. A reference compound was included on each assay plate in order to validate that plate; on one plate of every assay run, two additional reference compounds were included.

The final buffer conditions were as follows: 60 mM Hepes, pH 7.0, 0.05% BSA, 2 mM DTT. Incubations were carried out at RT (22° C.) for 2 h for Pim-1, 1 h and 30 min for Pim-3, and 45 min for Pim-2. The reaction was then stopped by the addition of 3 mM EDTA, and fluorescence was measured by an HTRF® Rubystar microplate reader. For each plate, percent of control (POC) values were calculated for each well. Values for the $IC_{50}$ IP were estimated using a standard 4-parameter logistic model.

Pim Cell Assay

U2OS

The cell lines used in the assay were generated by the stable transfection of either Pim-1 or Pim-2 into the U2OS human osteogenic sarcoma line. The assay for determination of the Pim activity in the engineered U2OS cell lines measures levels of phospho-BAD normalized against total BAD protein levels. It was conducted as follows:

The adherent cells were dissociated from the flasks using non-enzymatic cell dissociation solution (Sigma #C5914). Cells were then plated out to 96-well plates at an initial density of 40,000 cells/well in 100 µL of complete growth medium (McCoy's 5A—Invitrogen #16600-082, 10% FBS—Gibco #10099-141, Geneticin/G418 at 500 ug/mL—Invitrogen #10131-027). The cells were then incubated overnight at 37° C., 5% $CO_2$.

Compounds were initially diluted in DMSO by conducting 3-fold serial dilutions to give a 10-point dosing curve having a high dose of 31.6 uM. In addition to the 10-point dosing curve of the test compound, DMSO alone was run as the high control.

This dilution in DMSO was then diluted again into cell growth medium. Aliquots (12 µL) of the compound diluted in growth medium were then transferred to the appropriate wells of the 96-well plates containing cells to a final DMSO concentration of 0.3%. The cell plates were then incubated with compound for 29 min at 37° C., 5% $CO_2$.

After a 29 minute incubation, the cell plates had the compound-containing medium removed, and were washed with 150 µL of PBS (Gibco #14040). Following the wash, the cell plates were placed on ice and given 50 µL of ice-cold complete lysis buffer (MSD kit components, Protease Inhibitor Cocktail Tablets—Roche #04 693 116 001). The cell plates containing lysis buffer were then immediately stored at −70° C.

These prepared lysates were then assayed for phospho and total BAD according to the manufacturer's protocols (Meso Scale Diagnostics, Cat#K15103C-3 & #K15103D-3). The plates were read on the MSD Sector Imager 6000, and results were calculated according to the assay protocols ((% Phosphoprotein=((2×Phospho signal)/(Phospho signal+Total signal))×100)).

Pim Cell Assay

KMS12

The assay for determination of the antiproliferative activity of multiple Pim inhibitors in the KMS-12-BM myeloma cells measures levels of phospho-BAD and total BAD. It was conducted as follows:

The suspension cells were plated out onto 96-well, V-bottom plates at an initial density of 80,000 cells/well in 100 µL of complete growth medium (RPMI Medium 1640—Invitrogen #11875, 10% Heat inactivated FBS—Hyclone #SH 30070.03HI, 1×L-glutamine—Invitrogen #25030). The cells were then incubated overnight at 37° C., 5% $CO_2$.

Compounds were initially diluted in DMSO by conducting 3-fold serial dilutions to give a 10-point dosing curve having a high dose of 31.6 uM. In addition to the 10-point dosing curve of the test compound, DMSO alone was run as the high control and 7.9 uM 2510883 as the low control.

This dilution in DMSO was then diluted again into cell growth medium. Aliquots (11.1 uL) of the compound diluted in growth medium were then transferred to the appropriate wells of the 96-well plates containing cells to yield a final DMSO concentration of 0.3%. The cell plates were then incubated with compound for 2 hours at 37° C., 5% $CO_2$.

After a two h incubation, the compound-containing medium was removed. The cell plates were placed on ice and given 50 µL of ice-cold complete lysis buffer (MSD kit components, Protease Inhibitor Cocktail Tablets—Roche #04 693

116 001). The cell plates containing lysis buffer were then immediately stored at −70° C.

These prepared lysates were then assayed for phospho and total BAD according to the manufacturer's protocols (Meso Scale Diagnostics, Cat#K15103C-3 & #K15103D-3). The plates were read on the MSD Sector Imager 6000, and results were calculated according to the assay protocols ((% Phosphoprotein=((2×Phospho signal)/(Phospho signal+Total signal))×100)).

IC$_{50}$ Activity of Compounds of the Invention

TABLE 2

| Ex# | Pim_1_IC50 (uM) | Pim2_IC50 (uM) | Pim3 IC50 (uM) | U2OS Pim1_Cell_IC50 (uM) | U2OS Pim2_Cell_IC50 (uM) |
|---|---|---|---|---|---|
| 1 | 0.000714 | 0.002063 | 0.001061 | 0.011865 | 0.43486 |
| 2 | 0.00194 | 0.002256 | 0.001083 | 0.029354 | 0.41914 |
| 3 | 0.005949 | 0.002186 | 0.000974 | 0.054611 | 0.234604 |
| 4 | 0.001009 | 0.001997 | 0.000586 | 0.026959 | 0.341924 |
| 5 | 0.006905 | 0.002236 | 0.001674 | 0.739165 | 1.222709 |
| 6 | 0.005913 | 0.020769 | 0.005743 | 0.061902 | 2.107847 |
| 7 | 0.028762 | 0.042476 | 0.019719 | | |
| 8 | 0.010594 | 0.007002 | 0.004967 | 0.147463 | 1.345653 |
| 9 | 0.643509 | 0.717262 | 0.175836 | | |
| 10 | 1.134542 | 0.569603 | 0.64219 | | |
| 11 | 0.019721 | 0.008613 | 0.007686 | 0.910618 | 2.204954 |
| 12 | 0.051643 | 0.154614 | 0.013688 | 3.17414 | |
| 13 | 0.002019 | 0.010897 | 0.000625 | 0.197979 | 3.011141 |
| 14 | 0.011054 | 0.041983 | 0.008912 | 0.159374 | 12.0816 |
| 15 | 0.004572 | 0.020071 | 0.003394 | 0.107857 | 2.044254 |
| 16 | 0.012431 | 0.021109 | 0.005067 | 0.111089 | 3.094044 |
| 17 | 0.001502 | 0.005923 | 0.000763 | 0.056633 | 1.217665 |
| 18 | 0.015761 | 0.089205 | 0.007406 | >31.600000 | >31.600000 |
| 19 | 0.019735 | 0.027785 | 0.007803 | 0.204721 | 2.746634 |
| 20 | 0.2811 | 2.708963 | 0.267022 | | |
| 21 | 0.177539 | 1.006029 | 0.178727 | | |
| 22 | 2.799345 | >3.000000 | 1.474539 | | |
| 23 | 0.423144 | 1.552408 | 0.136061 | | |
| 24 | 0.017422 | 0.058685 | 0.005587 | 0.232009 | 7.572486 |
| 25 | 0.017462 | 0.088684 | 0.003024 | >31.600000 | >31.600000 |
| 26 | 2.002468 | >3.000000 | 0.795025 | | |
| 27 | 1.309976 | >3.000000 | 0.3994 | | |
| 28 | 0.04068 | 0.156647 | 0.026955 | 1.073051 | >31.600000 |
| 29 | 0.121115 | 0.253572 | 0.028857 | 6.864828 | >31.600000 |
| 30 | 0.013285 | 0.052679 | 0.002504 | 1.165632 | 5.059012 |
| 31 | 0.037431 | 0.075509 | 0.013649 | 1.090488 | 28.34562 |
| 32 | 0.012247 | 0.019998 | 0.003456 | 0.573249 | 6.849202 |
| 33 | 0.00884 | 0.016713 | 0.001321 | 0.328042 | 19.50487 |
| 34 | 0.01046 | 0.024798 | 0.001511 | 0.279692 | >31.600000 |
| 35 | 0.009228 | 0.012136 | 0.00184 | 1.151273 | 10.93655 |
| 36 | 0.042961 | 0.211593 | 0.011371 | | |
| 37 | 0.009142 | 0.080051 | 0.006777 | 0.236548 | |
| 38 | 0.065523 | 0.054541 | 0.037655 | | |
| 39 | 0.051411 | 0.158312 | 0.019849 | | |
| 40 | 0.105162 | 0.214684 | | | |
| 41 | 0.00648 | 0.019579 | 0.002256 | 0.124087 | 1.321199 |
| 42 | 0.021177 | 0.038604 | 0.010004 | 0.273392 | 15.58233 |
| 43 | 0.007578 | 0.004317 | | 0.247088 | 3.385434 |
| 44 | 0.009921 | 0.02601 | | 0.628277 | >31.600000 |
| 45 | 0.00383 | 0.002826 | | | |
| 46 | 0.001393 | 0.004252 | 0.000498 | 0.032063 | 0.826923 |
| 47 | 0.020069 | 0.001156 | | | |
| 48 | 0.002531 | 0.002959 | | | |
| 49 | 0.003432 | 0.007641 | 0.001818 | 0.083449 | 2.684258 |
| 50 | 0.057743 | 0.302102 | 0.014357 | | |
| 51 | 0.092542 | 0.030789 | 0.048224 | | |
| 52 | 0.070129 | 0.2711 | 0.040319 | | |
| 53 | 0.000407 | 0.000638 | | 0.034503 | 0.475453 |
| 54 | 0.001578 | 0.002395 | | | |
| 55 | 0.008767 | 0.028681 | | | |
| 56 | 0.002531 | 0.008813 | | | |
| 57 | 0.005795 | 0.020951 | | | |
| 58 | >1.000000 | >1.000000 | | | |
| 59 | 0.030364 | 0.016673 | | | |
| 60 | 0.020069 | 0.013459 | | | |
| 61 | 0.04594 | 0.046752 | | | |
| 62 | 0.069507 | 0.206538 | | | |
| 63 | 0.551039 | 0.400037 | | | |
| 64 | 0.004263 | 0.058701 | | 0.200234 | >10.000000 |
| 65 | 0.335493 | Undefined | | | |
| 66 | 0.020069 | 0.649232 | | | |
| 67 | 0.005795 | 0.058884 | | | |
| 68 | 0.042737 | 0.079744 | | | |
| 69 | 0.240724 | 0.668036 | | | |

TABLE 2-continued

| Ex# | Pim_1_IC50 (uM) | Pim2_IC50 (uM) | Pim3 IC50 (uM) | U2OS Pim1_Cell_IC50 (uM) | U2OS Pim2_Cell_IC50 (uM) |
|---|---|---|---|---|---|
| 70 | 0.030364 | 0.361743 | | | |
| 71 | 0.069507 | 0.53827 | | | |
| 72 | 0.069507 | 0.242326 | | | |
| 73 | 0.04594 | 0.504197 | | | |
| 74 | 0.186166 | >1.000000 | | | |
| 75 | 0.003824 | 0.006871 | 0.00254 | 0.17255 | 2.35462 |
| 76 | 0.005589 | 0.005177 | 0.002466 | 0.035811 | 0.635809 |
| 77 | 0.011927 | 0.013744 | 0.004132 | 0.112341 | 1.894038 |
| 78 | 0.102757 | 0.164405 | 0.054315 | 1.11349 | 18.73612 |
| 79 | 0.154373 | 0.184887 | 0.0858 | | |
| 80 | 0.046952 | 0.077984 | 0.067148 | 0.142456 | 3.65878 |
| 81 | 0.101477 | 0.272784 | 0.146618 | | |
| 82 | 2.35295 | 1.77729 | 2.376642 | | |
| 83 | 0.059274 | 0.193387 | 0.036191 | 0.725497 | 18.52213 |
| 84 | 0.092614 | 0.139925 | 0.026042 | | |
| 85 | 0.225308 | 0.384935 | 0.081788 | | |
| 86 | 0.279205 | 0.324238 | 0.121965 | | |
| 87 | 0.004147 | 0.005458 | 0.001114 | 0.045092 | 0.822601 |
| 88 | 0.001923 | 0.006435 | 0.001604 | 0.040716 | 0.464302 |
| 89 | 0.00211 | 0.004765 | 0.001831 | 0.059874 | 0.691993 |
| 90 | 0.008914 | 0.013445 | 0.006455 | 0.374478 | 5.423101 |
| 91 | 0.001955 | 0.001069 | 0.002211 | 0.220771 | 1.048476 |
| 92 | 0.025889 | 0.046563 | 0.012292 | | |
| 93 | 0.269143 | 0.110993 | 0.139676 | | |
| 94 | 0.005189 | 0.000984 | 0.000998 | 0.075196 | 0.279648 |
| 95 | >1.000000 | 0.83803 | 0.116208 | | |
| 96 | 0.067021 | 0.03188 | 0.01203 | | |
| 97 | 0.006419 | 0.0017 | 0.001218 | 0.100473 | 0.314646 |
| 98 | 0.004344 | 0.004849 | 0.001587 | 0.085746 | 0.720584 |
| 99 | 0.006771 | 0.012915 | 0.012358 | 12.17806 | >31.600000 |
| 100 | 0.001161 | 0.002067 | 0.000668 | 0.041719 | 0.551494 |
| 101 | 0.001501 | 0.004025 | 0.000901 | 0.066353 | 0.809161 |
| 102 | 0.157405 | 0.146123 | 0.02924 | | |
| 103 | 0.006905 | 0.002236 | 0.001674 | 0.739165 | 1.222709 |
| 104 | 0.011376 | 0.007727 | 0.005099 | 2.131342 | 15.24937 |
| 105 | 0.0055 | 0.004807 | 0.001785 | 0.103683 | 0.920019 |
| 106 | 0.015168 | 0.006391 | 0.005689 | 0.154595 | 1.186123 |
| 107 | 0.005982 | 0.003243 | 0.003743 | 3.855742 | >31.600000 |
| 108 | 0.009409 | 0.003099 | 0.002066 | 0.71141 | 1.405396 |
| 109 | 0.032203 | 0.026776 | 0.01298 | | |
| 110 | 0.004681 | 0.002378 | | 0.219404 | 1.627463 |
| 111 | 0.01861 | 0.006595 | | >31.600000 | >31.600000 |
| 112 | 0.005795 | 0.002853 | | 0.17959 | 1.162128 |
| 113 | 0.013685 | 0.025652 | | 0.379854 | >10.000000 |
| 114 | 0.012555 | 0.025149 | 0.00702 | 0.136697 | >31.600000 |
| 115 | 0.009232 | 0.014024 | 0.005357 | 0.10545 | >31.600000 |
| 116 | 0.015186 | 0.019602 | 0.007814 | 0.224404 | >31.600000 |
| 117 | 0.016459 | 0.057257 | 0.02184 | 0.226904 | |
| 118 | 0.016733 | 0.019167 | 0.015703 | 0.217341 | >31.600000 |
| 119 | 0.006067 | 0.010731 | 0.002145 | 0.084994 | >31.600000 |
| 120 | 0.009406 | 0.022908 | 0.004228 | 0.241916 | >31.600000 |
| 121 | 0.018993 | 0.034593 | 0.005542 | 3.137333 | >31.600000 |
| 122 | 0.006846 | 0.003866 | 0.002397 | 0.1317 | 0.830785 |
| 123 | 0.010594 | 0.007002 | 0.004967 | 0.147463 | 1.345653 |
| 124 | 0.027945 | 0.033396 | 0.017185 | | |
| 125 | 0.022808 | 0.057029 | 0.007683 | 0.109053 | 4.428729 |
| 126 | 0.272057 | 0.243694 | 0.084753 | | |
| 127 | 0.388787 | 0.289382 | 0.308916 | | |
| 128 | 0.002913 | 0.001527 | 0.000734 | 13.75712 | 15.869 |
| 129 | 0.031342 | 0.082389 | 0.01229 | 0.981821 | >31.600000 |
| 130 | 0.039553 | 0.039005 | 0.020522 | 7.881001 | >31.600000 |
| 131 | 0.088151 | 0.035771 | 0.016391 | >10.000000 | >31.600000 |
| 132 | 0.010969 | 0.033607 | 0.003981 | 1.472073 | 6.909496 |
| 133 | 0.013412 | 0.019407 | 0.003999 | 0.534977 | 8.056722 |
| 134 | 0.038009 | 0.01631 | 0.012259 | 1.443717 | 6.114657 |
| 135 | 0.086089 | 0.059704 | 0.032716 | 8.443666 | >31.600000 |
| 136 | 0.067319 | 0.059994 | 0.030949 | 3.411295 | >31.600000 |
| 137 | 0.175874 | 0.236817 | 0.090268 | | |
| 138 | 0.199143 | 0.347647 | 0.096651 | | |
| 139 | 0.029346 | 0.105803 | 0.01838 | 0.578322 | |
| 140 | 0.073168 | 0.244472 | 0.01341 | 0.871155 | |
| 141 | 0.073959 | 0.480061 | 0.049585 | 1.109598 | |
| 142 | 0.108823 | 1.478127 | 0.059532 | | |
| 143 | 0.145083 | 3.021023 | 0.084466 | 5.203945 | |
| 144 | 0.266583 | 1.697159 | 0.163433 | | |
| 145 | 0.307769 | 2.167722 | 0.308428 | | |

TABLE 2-continued

| Ex# | Pim_1_IC50 (uM) | Pim2_IC50 (uM) | Pim3 IC50 (uM) | U2OS Pim1_Cell_IC50 (uM) | U2OS Pim2_Cell_IC50 (uM) |
|---|---|---|---|---|---|
| 146 | 0.365409 | 2.51375 | 0.539889 | | |
| 147 | 0.513145 | >3.000000 | 0.633558 | | |
| 148 | 0.776723 | >3.000000 | 1.267849 | | |
| 149 | 1.053026 | >3.000000 | 0.522207 | | |
| 150 | 1.253755 | >3.000000 | 0.901284 | | |
| 151 | 0.102676 | 0.144172 | 0.017506 | 0.925255 | >31.600000 |
| 152 | 0.001789 | 0.003702 | 0.000307 | 3.09422 | 19.60609 |
| 153 | 0.001766 | 0.009735 | 0.001696 | 0.051896 | 1.662447 |
| 154 | 0.002004 | 0.020026 | 0.001447 | 0.043417 | 2.297682 |
| 155 | 0.004424 | 0.002254 | 0.000425 | 0.258563 | >31.600000 |
| 156 | 0.005588 | 0.012314 | 0.004383 | 0.162751 | 1.898648 |
| 157 | 0.007772 | 0.010073 | 0.001579 | 0.10635 | 2.217043 |
| 158 | 0.008178 | 0.028224 | 0.00386 | 0.132993 | 3.036659 |
| 159 | 0.008204 | 0.016581 | 0.002999 | 0.09189 | 2.220602 |
| 160 | 0.010481 | 0.024633 | 0.010661 | 0.175836 | 6.5417 |
| 161 | 0.010852 | 0.016833 | 0.002984 | 0.205174 | 3.477539 |
| 162 | 0.012722 | 0.049388 | 0.008537 | 0.214004 | 5.678768 |
| 163 | 0.014684 | 0.040791 | 0.004579 | 0.479465 | 6.904077 |
| 164 | 0.014711 | 0.021562 | 0.003252 | 0.140502 | 3.732176 |
| 165 | 0.015228 | 0.03527 | 0.00573 | 0.230926 | 4.231178 |
| 166 | 0.018187 | 0.038334 | 0.005335 | >31.600000 | >31.600000 |
| 167 | 0.01904 | 0.064403 | 0.005874 | 0.420833 | 24.99225 |
| 168 | 0.023158 | 0.044071 | 0.006339 | 0.110983 | >3.164557 |
| 169 | 0.026366 | 0.023773 | 0.011806 | 1.805164 | >31.600000 |
| 170 | 0.034786 | 0.100419 | 0.009468 | 0.876497 | >31.600000 |
| 171 | 0.036598 | 0.058333 | 0.01391 | 2.65913 | >31.600000 |
| 172 | 0.040453 | 0.068807 | 0.013853 | 0.413966 | >31.600000 |
| 173 | 0.040545 | 0.114434 | 0.017784 | 1.01657 | |
| 174 | 0.041016 | 0.158913 | 0.023609 | 0.997587 | |
| 175 | 0.041357 | 0.117311 | 0.017653 | 0.682174 | |
| 176 | 0.043541 | 0.104384 | 0.01447 | 0.525836 | |
| 177 | 0.045752 | 0.091216 | 0.030473 | 0.537776 | >31.600000 |
| 178 | 0.061269 | 0.459372 | 0.054062 | 2.250443 | |
| 179 | 0.076964 | 0.064601 | 0.024127 | 0.815551 | >31.600000 |
| 180 | 0.082141 | 0.049459 | 0.026642 | 0.925541 | 5.458986 |
| 181 | 0.098139 | 0.22297 | 0.046951 | 2.255718 | |
| 182 | 0.120753 | 0.13476 | 0.022497 | | |
| 183 | 0.155982 | 0.174198 | 0.048175 | | |
| 184 | 0.161309 | 0.601866 | 0.094661 | | |
| 185 | 0.224083 | 0.243747 | 0.068157 | | |
| 186 | 0.259975 | 0.270032 | 0.083828 | | |
| 187 | 0.297229 | 1.294157 | 0.18531 | | |
| 188 | 0.39789 | 1.218571 | 0.125815 | | |
| 189 | 0.56408 | 0.689915 | 0.07318 | | |
| 190 | 0.705172 | 0.977359 | 0.185635 | | |
| 191 | 0.792332 | 0.821737 | 0.144194 | | |
| 192 | 0.908354 | 2.404779 | 0.266402 | | |
| 193 | 0.930678 | 1.546829 | 0.391697 | | |
| 194 | 0.9452 | 1.042567 | 0.509155 | | |
| 195 | 0.956226 | 1.34313 | 0.506324 | | |
| 196 | 2.066546 | >3.000000 | 0.918346 | | |
| 197 | 2.266922 | 2.903676 | 0.836274 | | |
| 198 | 0.002506 | 0.010897 | 0.002785 | 0.03685 | 1.717565 |
| 199 | 0.267548 | 0.61848 | 0.164854 | | |
| 200 | 0.015415 | 0.030092 | 0.002165 | 0.112381 | 3.801255 |
| 201 | 0.017868 | 0.032392 | 0.004928 | 0.387242 | 3.833025 |
| 202 | 0.073156 | 0.087466 | 0.011095 | 0.238301 | >31.600000 |
| 203 | 0.020896 | 0.037164 | 0.005419 | 0.384482 | 2.191155 |
| 204 | 0.082882 | 0.144668 | 0.018247 | 0.465674 | 7.715706 |
| 205 | 0.109726 | 0.226694 | 0.021562 | | |
| 206 | 0.001754 | 0.009654 | 0.001153 | 0.040207 | 0.945422 |
| 207 | 0.001767 | 0.007705 | 0.001676 | 0.0374 | 1.089628 |
| 208 | 0.00315 | 0.01807 | 0.001988 | 0.056263 | 2.604346 |
| 209 | 0.705348 | 0.557988 | 0.149327 | | |
| 210 | 0.142179 | 0.192339 | 0.028702 | | |
| 211 | 0.024482 | 0.053742 | 0.01322 | 0.191782 | 2.802098 |
| 212 | 0.038318 | 0.030178 | 0.014893 | 0.1767 | >31.600000 |
| 213 | 0.094917 | 0.7298 | 0.044358 | 1.515513 | |
| 214 | 0.025671 | 0.091896 | 0.010084 | 0.587414 | 15.21945 |
| 215 | 0.20791 | 8.78 | 0.168305 | >31.600000 | >31.600000 |
| 216 | 0.187333 | 1.841035 | 0.091511 | 1.771941 | >31.600000 |
| 217 | 0.234405 | 1.632168 | 0.181018 | | |
| 218 | 0.241266 | 0.622523 | 0.1231 | | |
| 219 | 0.551479 | 0.686352 | 0.203855 | | |
| 220 | 0.635635 | 1.231235 | 0.274281 | | |
| 221 | 0.744149 | 1.491218 | 0.15756 | | |

TABLE 2-continued

| Ex# | Pim_1_IC50 (uM) | Pim2_IC50 (uM) | Pim3 IC50 (uM) | U2OS Pim1_Cell_IC50 (uM) | U2OS Pim2_Cell_IC50 (uM) |
|---|---|---|---|---|---|
| 222 | 1.005769 | 1.436727 | 0.268342 | | |
| 223 | 1.144447 | 1.94812 | 0.304871 | | |
| 224 | 1.890203 | >3.000000 | 0.206902 | | |
| 225 | 2.361147 | >3.000000 | 0.416034 | | |
| 226 | 2.446276 | >3.000000 | 0.353915 | | |
| 227 | 0.005069 | 0.040974 | 0.00142 | 0.120811 | 9.953391 |
| 228 | 0.013239 | 0.008279 | 0.001498 | >31.600000 | >31.600000 |
| 229 | 0.028843 | 0.080438 | 0.006728 | 0.312386 | >31.600000 |
| 230 | 0.03091 | 0.063115 | 0.007131 | 0.912042 | >31.600000 |
| 231 | 0.038246 | 0.137462 | 0.009888 | 0.376656 | >31.600000 |
| 232 | 0.056981 | 0.10413 | 0.016265 | 1.715257 | >31.600000 |
| 233 | 0.100488 | 0.502395 | 0.028044 | 1.40373 | >31.600000 |
| 234 | 0.107878 | 0.122625 | 0.018468 | | |
| 235 | 0.227596 | 0.781823 | 0.062835 | 5.390473 | >31.600000 |
| 236 | 0.324654 | 0.538316 | 0.114277 | | |
| 237 | 0.538481 | 1.219163 | 0.227142 | | |
| 238 | 0.711897 | 0.855584 | 0.197159 | | |
| 239 | 1.032586 | 0.739487 | 0.170393 | | |
| 240 | 1.518466 | 2.635252 | 0.409296 | | |
| 241 | 2.183246 | >10.000000 | 0.413716 | | |
| 242 | 0.982522 | >3.000000 | 0.351299 | | |
| 243 | 0.222872 | 2.818316 | 0.085233 | 6.327893 | >31.600000 |
| 244 | 0.024805 | 0.085392 | 0.015126 | 0.309735 | 12.1502 |
| 245 | 0.020281 | 0.035769 | 0.00794 | 0.216675 | >31.600000 |
| 246 | 0.004192 | 0.021526 | 0.007106 | 0.449665 | >31.600000 |
| 247 | 0.001339 | 0.001051 | 0.000346 | 1.936104 | >31.600000 |
| 248 | 0.013864 | 0.020864 | | 0.19204 | >31.600000 |
| 249 | 0.016121 | 0.048948 | | 0.374999 | >31.600000 |
| 250 | 0.023024 | 0.060938 | | 0.609584 | >31.600000 |
| 251 | 0.003201 | 0.005842 | | 0.107446 | 2.007647 |
| 252 | 0.009659 | 0.029819 | | 0.310001 | >31.600000 |
| 253 | 0.026732 | 0.140902 | | | |
| 254 | 0.174541 | >1.000000 | 0.137928 | >15.800000 | 0.807936 |
| 255 | 0.322812 | 0.67686 | 0.123303 | | |
| 256 | 0.007693 | 0.003204 | 0.001208 | 0.068113 | 0.734198 |
| 257 | 0.001994 | 0.00141 | | 0.099993 | 0.942594 |
| 258 | 0.013716 | 0.025247 | | 0.229184 | 3.717153 |
| 259 | 0.030364 | 0.036949 | | | |
| 260 | 0.159107 | 0.106121 | | | |
| 261 | 0.105162 | 0.070778 | | | |
| 262 | 0.002531 | 0.00277 | | | |
| 263 | 0.240724 | 0.383178 | | | |
| 264 | 0.001396 | 0.001394 | 0.000435 | 0.025756 | 0.238397 |
| 265 | 0.028639 | 0.050995 | | | |
| 266 | 0.06483 | 0.228802 | 0.043588 | | |
| 267 | 0.097189 | 0.230511 | 0.056115 | | |
| 268 | 0.170919 | 0.559298 | 0.081229 | | |
| 269 | 0.364209 | 0.44978 | | | |
| 270 | 0.008767 | 0.034834 | | | |
| 271 | 0.04594 | 0.737904 | | | |
| 272 | 0.105162 | 0.350994 | | | |
| 273 | 0.011766 | 0.028508 | | | |
| 274 | >1.000000 | >1.000000 | | | |

TABLE 4

| EX# | Pim_1_IC50 (uM) | Pim2_IC50 (uM) | KMS12_IC50 (uM) |
|---|---|---|---|
| 275 | 0.259 | 0.705 | |
| 276 | 0.111 | 0.315 | |
| 277 | 0.0582 | 0.393 | |
| 278 | 0.186 | 0.408 | |
| 279 | 0.00238 | 0.00188 | 0.746 |
| 280 | 0.00471 | 0.00804 | 3.83 |
| 281 | 0.00119 | 0.00215 | 1.28 |
| 282 | 0.509 | 0.652 | |
| 283 | 0.517 | 0.453 | |
| 284 | 0.515 | 0.555 | |
| 285 | 0.401 | 0.76 | |
| 286 | 0.713 | 0.843 | |
| 287 | 0.00415 | 0.0111 | 1.56 |
| 288 | 0.00244 | 0.0143 | 4.2 |
| 289 | 0.233 | 0.301 | |
| 290 | 0.0696 | 0.238 | |
| 291 | 0.0531 | 0.0256 | 1.44 |
| 292 | 0.496 | 0.541 | |
| 293 | Undefined | Undefined | |
| 294 | 0.664 | Undefined | |
| 295 | 0.578 | Undefined | |
| 296 | >1.0 | >1.0 | |
| 297 | 0.0392 | 0.0738 | |
| 298 | 0.0159 | 0.0244 | Undefined |
| 299 | 0.767 | 0.299 | |
| 300 | 0.0012 | 0.00224 | 1.44 |
| 301 | 0.00254 | 0.00465 | 0.945 |
| 302 | 0.291 | Undefined | |

TABLE 4-continued

| EX# | Pim_1_IC50 (uM) | Pim2_IC50 (uM) | KMS12_IC50 (uM) |
|---|---|---|---|
| 303 | 0.268 | Undefined | |
| 304 | 0.07 | 0.115 | |

The compounds of the present invention may be administered orally, parentally, by inhalation spray, rectally, or topically in dosage unit formulations containing conventional pharmaceutically acceptable carriers, adjuvants, and vehicles.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment.

The dosage regimen for using these compounds diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as HCl acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$)alkyloxy) ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed:
1. A compound of Formula IIa

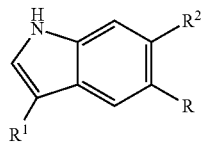

wherein R is optionally substituted thiadiazolyl or optionally substituted oxadiazolyl;
wherein $R^1$ is $C_{3-6}$ cycloalkylcarbonylamino, optionally substituted 6-membered heterocyclylcarbonylamino, optionally substituted phenyl or optionally substituted 5-membered heterocyclyl, optionally substituted 6-membered heterocyclyl, optionally substituted 9 membered heterocyclyl or optionally substituted 10 membered heterocyclyl; and
wherein $R^2$ is H or halo;
provided R is not 2-[4-(1-piperdinyl)butylamino]-1,3,4-oxadiazolyl, when $R^1$ is phenyl, and $R^2$ is H;
and a pharmaceutically acceptable salt thereof.

2. The compound of claim 1, wherein $R^1$ is unsubstituted or substituted phenyl, unsubstituted or substituted biphenyl, unsubstituted or substituted pyrazinyl, unsubstituted or substituted pyridyl, unsubstituted or substituted pyrimidinyl, unsubstituted or substituted pyridazinyl, unsubstituted or substituted quinolyl, unsubstituted or substituted dihydrobenzofuryl, unsubstituted or substituted quinoxalinyl, unsubstituted or substituted indazolyl, unsubstituted or substituted 6,7-dihydro-5H-pyrrolo[2,3-b]pyrazinyl, unsubstituted or substituted triazolyl, unsubstituted or substituted dihydro-2H-pyranyl, unsubstituted or substituted thiazolyl, unsubstituted or substituted pyrazolyl, or unsubstituted or substituted thienyl and a pharmaceutically acceptable salt thereof.

3. The compound of claim 1, wherein R is oxadiazolyl optionally substituted with amino, $C_{1-6}$ alkylamino, $C_{1-6}$ haloalkylamino, cyano-$C_{1-6}$ alkylamino, amino-$C_{1-6}$ alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$alkylamino, optionally substituted 9-10-membered nitrogen containing heterocyclyl substituted amino, optionally substituted 9-10-membered nitrogen containing heterocyclyl-$C_{1-4}$alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

4. The compound of claim 1, wherein R is thiadiazolyl optionally substituted with amino, $C_{1-6}$ alkylamino, $C_{1-6}$ haloalkylamino, cyano-$C_{1-6}$ alkylamino, amino-$C_{1-6}$ alkylamino, hydroxy, $C_{1-6}$ alkoxy, halo, $C_{1-6}$ alkyl, $C_{3-6}$ cycloalkyl, optionally substituted phenyl, aminocarbonyl, $C_{1-6}$ alkylcarbonylamino, $C_{1-6}$ alkylsulphonyl, $C_{1-6}$ alkylthio, $C_{3-6}$ cycloalkylamino, optionally substituted 4-6-membered nitrogen containing heterocyclyl substituted amino, optionally substituted 4-6-membered nitrogen containing heterocyclyl-$C_{1-4}$alkylamino, optionally substituted 9-10-membered nitrogen containing heterocyclyl substituted amino, optionally substituted 9-10-membered nitrogen containing heterocyclyl-$C_{1-4}$alkylamino, optionally substituted phenylamino, optionally substituted phenyl-$C_{1-4}$ alkylamino, optionally substituted 4-6 membered nitrogen containing heterocyclyl, or optionally substituted 4-6-membered oxygen containing heterocyclylamino; and a pharmaceutically acceptable salt thereof.

5. The compound of claim 1, wherein R is

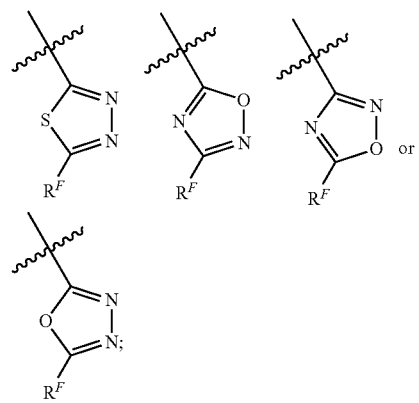

wherein $R^F$ is H, amino, methylamino, propylamino, isopropylamino, tert-butylamino, cyanomethylamino, aminopropylamino, 1,1,1-trifluoroethylamino, methylcarbonylamino, hydroxy, methoxy, ethoxy, propoxy, isopropoxy, butoxy, isobutoxy, tert-butoxy, hexyloxy, methylthio, bromo, methyl, ethyl, n-propyl, isopropyl, n-butyl, isobutyl, sec-butyl, tert-butyl, pentyl, isoamyl, hexyl, cyclopropyl, cyclobutyl, cyclopentyl, cyclohexyl, aminocarbonyl, cyclopropylamino, piperidylamino, piperidylmethylamino, piperidylethylamino, indolylmethylamino, 2,3-dimethylaminoindolylmethylamino, phenylamino, 3-fluorophenylamino, benzylamino, 3-(methylcarbonylamino)benzylamino, 3-(methylamino)benzylamino, 3-(methoxymethylcarbonylamino)benzylamino, 4-(methylcarbonylamino)benzylamino, 2-methyl-2-phenylethylamino, phenyl, pyrrolidinyl, 3-amino-1-pyrrolidinyl, piperidyl, 4-amino-1-piperidyl, pyrazolyl, morpholinyl, 2-methylmorpholinyl, 3-methylmorpholinyl, 3,3-dimethylmorpholinyl, 3-ethylmorpholinyl, piperazinyl, oxetanyl, or azetidinyl; and a pharmaceutically acceptable salt thereof.

6. The compound of claim 1, wherein $R^1$ is optionally substituted phenyl or optionally substituted biphenyl; and a pharmaceutically acceptable salt thereof.

7. The compound of claim 1, wherein $R^1$ is optionally substituted pyrazinyl, optionally substituted pyridyl, or optionally substituted pyrimidinyl, or optionally substituted pyridazinyl; and a pharmaceutically acceptable salt thereof.

8. The compound of claim 1, wherein $R^1$ is optionally substituted quinolyl, optionally substituted dihydrobenzofuryl, optionally substituted quinoxalinyl, optionally substituted indazolyl, or optionally substituted 6,7-dihydro-5H-pyrrolo[2,3-b]pyrazinyl; and a pharmaceutically acceptable salt thereof.

9. The compound of claim 1, wherein $R^1$ is unsubstituted or substituted triazolyl, unsubstituted or substituted dihydro-2H-pyranyl, unsubstituted or substituted thiazolyl, unsubstituted or substituted pyrazolyl, or unsubstituted or substituted thienyl; and a pharmaceutically acceptable salt thereof.

10. The compound of claim 1, wherein $R^1$ is
pyrimidinyl unsubstituted or substituted with one or more amino, halo, cyano, hydroxy, oxo, $C_{1-6}$ alkyl, $C_{1-3}$ haloalkyl, $C_{1-6}$ alkylamino, (optionally substituted 5-6-membered nitrogen containing heterocyclyl)amino, phenylamino, $C_{3-6}$ cycloalkyl-$C_{1-3}$-alkylamino, $C_{3-6}$ cycloalkylamino, carboxy, aminocarbonyl, $C_{1-6}$ alkylaminocarbonyl, $C_{3-6}$ cycloalkylaminocarbonyl, phenylaminocarbonyl, optionally substituted 5-6-membered nitrogen containing heterocyclyl)carbonyl, $C_{1-6}$ alkoxy, $C_{1-6}$ haloalkoxy, $C_{3-6}$ cycloalkoxy, optionally substituted phenyloxy, (optionally substituted 5-6-membered nitrogen containing heterocyclyl)oxy, optionally substituted phenyl, optionally substituted 6-membered nitrogen containing heterocyclyl, optionally substituted 5-membered nitrogen containing heterocyclyl, optionally substituted 9-10-membered nitrogen containing heterocyclyl, or $C_{3-6}$ cycloalkyl, pyrazinyl unsubstituted or substituted with one or more amino, halo, cyano, hydroxy, $C_{1-6}$ alkyl, $C_{1-3}$ haloalkyl, $C_{1-6}$ alkylamino, (optionally substituted 5-6-membered nitrogen containing heterocyclyl)amino, phenylamino, $C_{3-6}$ cycloalkyl-$C_{1-3}$-alkylamino, $C_{3-6}$ cycloalkylamino, carboxy, aminocarbonyl, phenylaminocarbonyl, $C_{3-6}$ cycloalkylaminocarbonyl, optionally substituted 5-6-membered nitrogen containing heterocyclyl)carbonyl, $C_{1-6}$ alkoxy, $C_{1-6}$ haloalkoxy, $C_{3-6}$ cycloalkoxy, optionally substituted phenyloxy, (optionally substituted 5-6-membered nitrogen containing heterocyclyl)oxy, optionally substituted phenyl, optionally substituted 6-membered nitrogen containing heterocyclyl, optionally substituted 5-membered nitrogen containing heterocyclyl, optionally substituted 9-10-membered nitrogen containing heterocyclyl, or $C_{3-6}$ cycloalkyl, pyridinyl unsubstituted or substituted with one or more amino, halo, cyano, hydroxy, oxo, $C_{1-6}$ alkyl, $C_{1-3}$ haloalkyl, $C_{1-6}$ alkylamino, (optionally substituted 5-6-membered nitrogen containing heterocyclyl)amino, phenylamino, $C_{3-6}$ cycloalkyl-$C_{1-3}$-alkylamino, $C_{3-6}$ cycloalkylamino, carboxy, aminocarbonyl, $C_{1-6}$ alkylaminocarbonyl, $C_{3-6}$ cycloalkylaminocarbonyl, phenylaminocarbonyl, (optionally substituted 5-6-membered nitrogen containing heterocyclyl)carbonyl, $C_{1-6}$ alkylsulfonyl, $C_{1-6}$ alkoxy, $C_{1-6}$ haloalkoxy, $C_{3-6}$ cycloalkoxy, optionally substituted phenyloxy, (optionally substituted 5-6-membered nitrogen containing heterocyclyl)oxy, optionally substituted phenyl, optionally substituted 6-membered nitrogen containing heterocyclyl, optionally substituted 5-membered nitrogen containing heterocyclyl, optionally substituted 9-10-membered nitrogen containing heterocyclyl, or $C_{3-6}$ cycloalkyl, phenyl unsubstituted or substituted with one or more amino, halo, cyano, hydroxy, $C_{1-6}$ alkyl, $C_{1-3}$ haloalkyl, $C_{1-6}$ alkylamino, (optionally substituted 5-6-membered nitrogen containing heterocyclyl)amino, phenylamino, $C_{3-6}$ cycloalkyl-$C_{1-3}$-alkylamino, $C_{3-6}$ cycloalkylamino, carboxy, aminocarbonyl, $C_{1-6}$ alkylaminocarbonyl, phenylaminocarbonyl, optionally substituted 5-6-membered nitrogen containing heterocyclyl)carbonyl, $C_{1-6}$ alkoxy, $C_{1-6}$ haloalkoxy, $C_{3-6}$ cycloalkoxy, optionally substituted phenyloxy, (optionally substituted 5-6-membered nitrogen containing heterocyclyl)oxy, optionally substituted phenyl, optionally substituted 6-membered nitrogen containing heterocyclyl, optionally substituted 5-membered nitrogen containing heterocyclyl, optionally substituted 9-10-membered nitrogen containing heterocyclyl, or $C_{3-6}$ cycloalkyl, 3-quinolinyl, 1H-indazolyl, 2,2-dimethyl-2,3-dihydro-1-benzofuranyl, 6-quinoxalinyl, 7,7-dimethyl-6,7-dihydro-5H-pyrrolo[2,3-b]pyrazinyl, thiazolyl unsubstituted or substituted with aminocarbonyl, $C_{3-6}$ cycloalkylaminocarbonyl, 4-methyl-1H-imidazolyl, 2-oxo-pyridinyl, furyl, or methylpiperidinyl, triazolyl unsubstituted or substituted with $C_{3-6}$ cyclopropyl, dihydro-2H-pyranyl, pyrazolyl unsubstituted or substituted with 2-methylpropyl, or 2-(4-morpholinyl)ethyl, or thiophenyl unsubstituted or substituted with thienyl;
and a pharmaceutically acceptable salt thereof.

11. The compound of claim 1, wherein $R^1$ is
2-pyrimidinyl, 4-methyl-2-pyrimidinyl, 4-ethyl-5-fluoro-6-methyl-2-pyrimidinyl, 4-methoxy-5-fluoro-6-methyl-2-pyrimidinyl, 4-amino-6-methyl-2-pyrimidinyl, 4-isopropyl-2-pyrimidinyl, 4-trifluoromethyl-6-pyrimidinyl, 4-trifluoromethyl-2-pyrimidinyl, 4-trifluoromethoxy-2-pyrimidinyl, 4-(1-methylethylamino)-2-pyrimidinyl, 2-isopropylamino-4-pyrimidinyl, 4-(1-methyl-3-piperidinyl)amino-2-pyrimidinyl,
4-methoxy-2-pyrimidinyl, 2-methoxy-4-pyrimidinyl, 4-isopropoxy-2-pyrimidinyl, 2,4-dimethoxy-6-pyrimidinyl, 6-methoxy-2-(1-methylethoxy)-4-pyrimidinyl, 5-fluoro-4-methoxy-2-pyrimidinyl, 4-ethoxy-5-fluoro-2-pyrimidinyl, 5-fluoro-4-methoxy-2-pyrimidinyl, 4-phenyloxy-2-pyrimidinyl, 4-(1-methyl-3-piperidinyl)oxy-2-pyrimidinyl, 4-phenylamino-2-pyrimidinyl, 4-cyclopropyl-2-pyrimidinyl, 4-carboxy-6-cyclopropyl-2-pyrimidinyl, 5-aminocarbonyl-4-cyclopropyl-2-pyrimidinyl, 4-aminocarbonyl-2-pyrimidinyl, 4-methylaminocarbonyl-2-pyrimidinyl,
4-cyclopropylaminocarbonyl-2-pyrimidinyl, 2-(4-morpholinyl)-4-pyrimidinyl, 4-(4-morpholinyl)-2-pyrimidinyl, 4-(3-methyl-4-morpholinyl)-2-pyrimidinyl, 4-(1-piperidinyl)-2-pyrimidinyl, 4-(2-methyl-1-piperidinyl)-2-pyrimidinyl, 4-(1-methyl-3-piperidinyl)-2-pyrimidinyl, 4-(3-methyl-1-piperidinyl)-2-pyrimidinyl, 4-(3-amino-1-piperidinyl)-2-pyrimidinyl, 4-(3-dimethyl-amino-1-piperidinyl)-2-pyrimidinyl, 4-(3-hydroxy-1-piperidinyl)-2-pyrimidinyl, 4-(2-methyl-1-pyrrolidinyl)-2-pyrimidinyl, 4-(2-methoxymethyl-1-pyrrolidinyl)-2-pyrimidinyl, 4-(2-methoxy-1-pyrrolidinyl)-2-pyrimidinyl, 4-(4-methyl-1-piperazinyl)-2-pyrimidinyl, 4-(4-methyl-3-oxo-1-piperazinyl)-2-pyrimidinyl, 4-(3-amino-piperidinyl)-2-pyrimidinyl, 4-(1-methyl-3-piperidinyl)oxy-2-pyrimidinyl, 4-cyclopropyl-2-pyrimidinyl, 2-cyclopropyl-4-pyrimidinyl, 5-fluoro-4-cyclopropyl-2-pyrimidinyl, 4-(2-chlorophenyl)-2-pyrimidinyl, 4-(2-fluorophenyl)-2-pyrimidinyl, 4-(2-methylphenyl)-2-pyrimidinyl, 4-phenyl-2-pyrimidinyl, 2-isopropylamino-4-oxo-6-pyrimidinyl, 2-cyclopropyl-4-oxo-6-pyrimidinyl, 2-methoxy-4-oxo-6-pyrimidinyl, 2-cyclopropyl-4-oxo-6-pyrimidinyl, 2-pyrazinyl, 6-amino-2-pyrazinyl, 6-chloro-2-pyrazinyl, 6-methyl-2-pyrazinyl, 6-cyclopropylmethyl-amino-2-pyrazinyl, 6-(1-methylethylamino)-2-pyrazinyl, 5-(N-ethyl-N-methyl-amino)-2-pyrazinyl, 2-(N,N-dimethylamino)-6-pyrazinyl, 6-(N,N-diethylamino)-2-pyrazinyl, 6-cyclopropyl-amino-2-pyrazinyl, 6-cyclopentylamino-2-pyrazinyl, 6-cyclohexylamino-2-pyrazinyl, 5-ethoxy-2-pyrazinyl, 2-isopropoxy-6-pyrazinyl, 6-(2,2,2-trifluoro-1-methylethoxy)-2-pyrazinyl, 6-methoxy-2-pyrazinyl, 6-ethoxy-2-pyrazinyl, 5-(1-methylethoxy)-2-pyrazinyl, 6-(1-methylethoxy)-2-pyrazinyl, 5-butoxy-2-pyrazinyl, 6-(cyclopentyloxy)-2-pyrazinyl, 5-(cyclopentyloxy)-2-pyrazinyl, 6-(phenyloxy)-2-pyrazinyl, 6-(3-piperidinyloxy)-2-pyrazinyl, 5-(1-pyrrolidinyl)-2-pyrazinyl, 6-(1-pyrrolidinyl)-2-pyrazinyl, 5-(2-oxo-1-pyrrolidinyl)-2-pyrazinyl, 6-(3,3-difluoro-1-pyrrolidinyl)-2-pyrazinyl, 4-(1-methyl-2-oxo-piperazinyl)-2-pyrazinyl, 5-(4-methyl-1-piperazinyl)-2-pyrazinyl, 6-(1-piperidinyl)-2-pyrazinyl, 6-(2-methyl-1-piperidinyl)-2-pyrazinyl, 6-(4,4-difluoro-1-piperidinyl)-2-pyrazinyl, 6-(4-methyl-1-piperidinyl)-2-pyrazinyl, 6-(4-morpholinyl)-2-pyrazinyl, 5-(4-morpholinyl)-2-pyrazinyl, 6-(1-methyl-1H-pyrazol-4-yl)-2-pyrazinyl, 5-(3-methyl-1H-pyrazol-1-yl)-2-pyrazinyl, 6-cyclopropyl-2-pyrazinyl, 6-phenyl-2-pyrazinyl, 6-(4-fluorophenyl)-2-pyrazinyl, 6-(3-fluorophenyl)-2-pyrazinyl, 6-(2-fluorophenyl)-2-pyrazinyl, 6-(3-chlorophenyl)-2-pyrazinyl, 6-(2-chlorophenyl)-2-pyrazinyl, 6-(4-chlorophenyl)-2-pyrazinyl, 2-pyridinyl, 4-pyridinyl, 3-pyridinyl, 2-amino-4-pyridinyl, 6-amino-2-pyridinyl, 5-amino-4-pyridinyl, 6-(1-methylethyl-amino)-2-pyridinyl, 6-(cyclopropylmethylamino)-2-pyridinyl, 6-cyclopentylamino-2-pyridinyl, 6-(cyclohexylamino)-2-pyridinyl, 6-trifluoromethyl-2-pyridinyl, 5-fluoro-6-methyl-2-pyridinyl, 6-fluoro-2-pyridinyl, 6-cyano-2-pyridinyl, 6-hydroxy-2-pyridinyl, 3-methylsulphonyl-6-pyridinyl, 5,6-dimethoxy-2-pyridinyl, 5-methoxy-3-pyridinyl, 6-ethoxy-2-pyridinyl, 6-propoxy-2-pyridinyl, 2-(1-methylethoxy)-6-pyridinyl, 6-(cyclobutyloxy)-2-pyridinyl, 6-(cyclopentyloxy)-2-pyridinyl, 6-(cyclohexyloxy)-2-pyridinyl, 3-aminocarbonylpyridin-6-yl, 2-methylaminocarbonylpyridin-6-yl, 3-methylaminocarbonylpyridin-6-yl, 3-(N,N-dimethylamino)carbonylpyridin-5-yl, 2-(N,N-dimethylamino)carbonylpyridin-6-yl, 3-methylaminocarbonylpyridin-5-yl, 3-isopropylaminocarbonylpyridin-5-yl, 2-isopropylaminocarbonylpyridin-6-yl, 3-cyclopropylaminocarbonylpyridin-5-yl, 2-cyclopropylaminocarbonylpyridin-6-yl, 5-(4-morpholinylcarbonyl)-3-pyridinyl, 3-(4-morpholinylcarbonyl)-6-pyridinyl, 6-(1-pyrrolidinyl)-2-pyridinyl, 6-(2-oxo-1-pyrrolidinyl)-2-pyridinyl, 6-(4-methyl-1-piperazinyl)-2-pyridinyl, 4-(1-methyl-2-oxo-piperazinyl)-2-pyridinyl, 6-(4-morpholinyl)-2-pyridinyl, 6-(1-piperidinyl)-2-pyridinyl, 6-(3-methylpiperidin-1-yl)pyridin-2-yl, 6-(4-methyl-1-piperidinyl)-2-pyridinyl, 6-(2-methylpiperidin-1-yl)pyridin-2-yl, 6-(3-amino-piperidinyl)-2-pyridinyl, 6-(2-oxo-1-piperidinyl)-2-pyridinyl, 6-(2-methyl-1H-imidazol-1-yl)-2-pyridinyl, 6-(4-methyl-1H-imidazol-1-yl)-2-pyridinyl, 6-(1H-pyrazol-1-yl)-2-pyridinyl, 6-(3-methyl-1H-pyrazol-1-yl)-2-pyridinyl, 6-(2-oxo-1-pyridinyl)-2-pyridinyl, 6-(3-methyl-5,6-dihydro[1,2,4]triazolo[4,3-a]pyrazin-7(8H)-yl)-2-pyridinyl, 6-phenyl-2-pyridinyl, 6-(4-chlorophenyl)-2-pyridinyl, phenyl, 2-fluorophenyl, 2,3-difluorophenyl, 2,4-difluorophenyl, 2,6-difluorophenyl, 2-fluoro-5-(1-methylethoxy)phenyl, 3-(1-methylethoxy)phenyl, 3-fluoro-5-(1-methylethoxy)phenyl, 2-fluoro-5-(N-phenylaminocarbonyl)phenyl, 2-fluoro-5-(N, N-dimethylaminocarbonyl)phenyl, 2-fluoro-5-(N-methylaminocarbonyl)phenyl, 4-aminocarbonyl-2-fluorophenyl, 3-aminophenyl, 3-(trifluoromethyl)phenyl, 3-(trifluoromethoxy)phenyl, 3-methoxyphenyl, 3-quinolinyl, 3-biphenyl, 1H-indazol-6-yl, 2,2-dimethyl-2,3-dihydro-1-benzofuran-6-yl, 6-quinoxalinyl, 7,7-dimethyl-6,7-dihydro-5H-pyrrolo[2,3-b]pyrazin-2-yl, 5-aminocarbonyl-1,3-thiazol-2-yl, 4-cyclopropylaminocarbonyl-1,3-thiazol-2-yl, 5-cyclopropylaminocarbonyl-1,3-thiazol-2-yl, 2-(4-methyl-1H-imidazol-1-yl)-1,3-thiazol-4-yl, 2-(2-oxo-1-pyridinyl)-1,3-thiazol-4-yl, 2-(3-furyl)-1,3-thiazol-4-yl, 2-(2-methylpiperidin-1-yl)thiazol-4-yl, 1H-pyrazol-4-yl, 1H-pyrazol-5-yl, 1-(2-methylpropyl)-1H-pyrazol-4-yl, 1-(2-(4-morpholinyl)ethyl)-1H-pyrazol-4-yl, 3-cyclopropyl-1H-1,2,4-triazol-5-yl, 3,6-dihydro-2H-pyran-4-yl or 2,2'-bithiophen-5-yl;

and a pharmaceutically acceptable salt thereof.

12. The compound of claim 1, wherein $R^2$ is H or fluoro; and a pharmaceutically acceptable salt thereof.

13. The compound of claim 1, wherein $R^1$ is cyclopropylcarbonylamino, cyclobutylcarbonylamino, pyrmindinylcarbonylamino, or pyridylcarbonylamino; and a pharmaceutically acceptable salt thereof.

14. A compound selected from 5-(3-(4-cyclopropyl-2-pyrimidinyl)-1H-indol-5-yl)-N-(2,2,2-trifluoroethyl)-1,3,4-oxadiazol-2-amine;

5-(3-(4-cyclopropyl-2-pyrimidinyl)-1H-indol-5-yl)-1,3,4-oxadiazol-2-amine;

6-cyclopropyl-2-(5-(5-((1-methylethyl)amino)-1,3,4-oxadiazol-2-yl)-1H-indol-3-yl)-4-pyrimidinecarboxamide;

5-(3-(4-cyclopropyl-2-pyrimidinyl)-1H-indol-5-yl)-N-(1-methylethyl)-1,3,4-oxadiazol-2-amine;

((5-(3-(4-(1-methylethyl)-2-pyrimidinyl)-1H-indol-5-yl)-1,3,4-oxadiazol-2-yl)amino)acetonitrile;

5-(3-(6-cyclopropyl-2-pyrazinyl)-1H-indol-5-yl)-N-(1-methylethyl)-1,3,4-oxadiazol-2-amine;

N-tert-butyl-5-(3-(4-cyclopropyl-2-pyrimidinyl)-1H-indol-5-yl)-1,3,4-oxadiazol-2-amine;

N-cyclopropyl-5-(3-(4-cyclopropyl-2-pyrimidinyl)-1H-indol-5-yl)-1,3,4-oxadiazol-2-amine;

5-(3-(4-cyclopropyl-2-pyrimidinyl)-6-fluoro-1H-indol-5-yl)-N-(1-methylethyl)-1,3,4-oxadiazol-2-amine;

5-(3-(6-cyclopropyl-2-pyrazinyl)-1H-indol-5-yl)-1,3,4-oxadiazol-2-amine;

5-(3-(2-cyclopropyl-4-pyrimidinyl)-1H-indol-5-yl)-N-(1-methylethyl)-1,3,4-oxadiazol-2-amine;

5-(3-(6-(1-methylethoxy)-2-pyrazinyl)-1H-indol-5-yl)-1,3,4-oxadiazol-2-amine;

2-(5-(5-(tert-butylamino)-1,3,4-oxadiazol-2-yl)-1H-indol-3-yl)-4-pyrimidinecarboxamide;

4-cyclopropyl-2-(5-(5-((1-methylethyl)amino)-1,3,4-oxadiazol-2-yl)-1H-indol-3-yl)-5-pyrimidinecarboxamide;

5-(3-(4-(2-methyl-1-piperidinyl)-2-pyrimidinyl)-1H-indol-5-yl)-1,3,4-oxadiazol-2-amine;

5-(3-(4-(2-methyl-1-pyrrolidinyl)-2-pyrimidinyl)-1H-indol-5-yl)-1,3,4-oxadiazol-2-amine;

6-(5-(5-amino-1,3,4-oxadiazol-2-yl)-1H-indol-3-yl)-N-cyclopentyl-2-pyrazinamine;

5-(3-(6-(4,4-difluoro-1-piperidinyl)-2-pyrazinyl)-1H-indol-5-yl)-1,3,4-oxadiazol-2-amine;

5-(3-(6-(2-methyl-1-piperidinyl)-2-pyrazinyl)-1H-indol-5-yl)-1,3,4-oxadiazol-2-amine;

5-(3-(6-(3,3-difluoro-1-pyrrolidinyl)-2-pyrazinyl)-1H-indol-5-yl)-1,3,4-oxadiazol-2-amine;

6-(5-(5-amino-1,3,4-oxadiazol-2-yl)-1H-indol-3-yl)-N-(cyclopropylmethyl)-2-pyrazinamine;

5-(3-(4-cyclopropyl-2-pyrimidinyl)-1H-indol-5-yl)-N-3-oxetanyl-1,3,4-oxadiazol-2-amine;

6-(5-(5-amino-1,3,4-oxadiazol-2-yl)-1H-indol-3-yl)-N-(1-methyl ethyl)-2-pyrazinamine;

5-(3-(6-(1-piperidinyl)-2-pyrazinyl)-1H-indol-5-yl)-1,3,4-oxadiazol-2-amine; and 5-(3-(4-phenyl-2-pyrimidinyl)-1H-indol-5-yl)-1,3,4-oxadiazol-2-amine; or a pharmaceutically acceptable salt thereof.

15. A composition comprising a therapeutically effective amount of the compound of claim 1, or a stereoisomer, tautomer, or pharmaceutically acceptable salt thereof, together with a pharmaceutically acceptable carrier.

16. A composition comprising a therapeutically effective amount of the compound of claim 14, or the pharmaceutically acceptable salt thereof, together with a pharmaceutically acceptable carrier.

* * * * *